(12) United States Patent
Cheng et al.

(10) Patent No.: US 11,384,066 B1
(45) Date of Patent: Jul. 12, 2022

(54) HETEROCYCLIC COMPOUNDS USEFUL AS AURORA A SELECTIVE INHIBITORS

(71) Applicant: Jacobio Pharmaceuticals Co., Ltd., Beijing (CN)

(72) Inventors: Dai Cheng, Beijing (CN); Mingming Chen, Beijing (CN); Amin Li, Beijing (CN); Haijun Li, Beijing (CN); Guiqun Yang, Beijing (CN)

(73) Assignee: Jacobio Pharmaceuticals Co., Ltd., Beijing (CN)

( * ) Notice: Subject to any disclaimer, the term of this patent is extended or adjusted under 35 U.S.C. 154(b) by 0 days.

(21) Appl. No.: 17/484,456

(22) Filed: Sep. 24, 2021

Related U.S. Application Data

(63) Continuation of application No. PCT/CN2021/073169, filed on Jan. 22, 2021.

(30) Foreign Application Priority Data

| Jan. 22, 2020 | (WO) | PCT/CN2020/073786 |
| Feb. 21, 2020 | (WO) | PCT/CN2020/076159 |
| Apr. 21, 2020 | (WO) | PCT/CN2020/085922 |

(51) Int. Cl.
  *C07D 401/14* (2006.01)
(52) U.S. Cl.
  CPC ............... *C07D 401/14* (2013.01)
(58) Field of Classification Search
  CPC .................................................. C07D 401/14
  See application file for complete search history.

(56) References Cited

FOREIGN PATENT DOCUMENTS

| CN | 101528731 A | 9/2009 |
| CN | 104159893 A | 11/2014 |
| CN | 107108567 A | 8/2017 |
| WO | 2008/026768 A1 | 3/2008 |
| WO | 2009/104802 A1 | 8/2009 |
| WO | 2020/112514 A1 | 6/2020 |
| WO | 2021/008338 A1 | 1/2021 |

OTHER PUBLICATIONS

International Search Report and Written Opinion for Application No. PCT/CN2021/073169, dated Apr. 20, 2021, 15 pages.

*Primary Examiner* — Brian E McDowell
(74) *Attorney, Agent, or Firm* — McCarter & English, LLP; Steven G. Davis; Wei Song

(57) ABSTRACT

Provided are compounds of formula (I), or pharmaceutically acceptable salts thereof, which can be used for inhibiting the activity of Aurora A and treating cancer mediated by Aurora A.

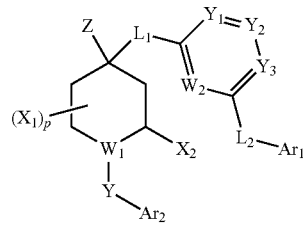

(1)

4 Claims, No Drawings

HETEROCYCLIC COMPOUNDS USEFUL AS AURORA A SELECTIVE INHIBITORS

CROSS-REFERENCE TO RELATED APPLICATIONS

This application is a continuation application of International Application No. PCT/CN2021/073169, filed Jan. 22, 2021, which claims priority to International Application No. PCT/CN2020/073786, filed on Jan. 22, 2021; International Application No. PCT/CN2020/076159, filed on Feb. 21, 2020; and International Application No. PCT/CN2020/085922, filed on Apr. 21, 2020. The entire contents of each of which are incorporated herein by reference.

TECHNICAL FIELD

The present invention relates to novel heterocyclic compounds useful as an Aurora A selective inhibitor, their synthesis, pharmaceutical compositions thereof, and use of compounds and pharmaceutical compositions for the treatment of cancer and cancer occurrence-related diseases.

BACKGROUND ART

Aurora kinases are a family of serine/threonine kinases and are key regulators of mitosis. There are three human homologs of Aurora kinases, A, B, and C, of which Aurora A has been implicated in cancers of diverse histological origin and may possess oncogenic properties when overexpressed.

Aurora-A localizes to centrosomes/spindle poles and is required for spindle assembly, whereas Aurora-B is a chromosome passenger protein required for phosphorylation of histone H3, chromosome segregation and cytokinesis. Aurora-A and —B are both overexpressed in a wide range of different human tumours. Additionally, certain Aurora B inhibitors and Aurora A/B dual inhibitors in clinical development have been reported as presenting neutropenia and bone marrow cytotoxicity in patients while certain relatively selective Aurora A inhibitors in clinical development did not show these disorders. Therefore, it is desirable to selectively inhibit Aurora A and reduce or avoid Aurora B or Aurora A/B dual inhibition. As such, selective Aurora A inhibition may be useful for cancer therapy.

Therefore, there remains a need to provide alternative Aurora A inhibitors for treatment of cancer. Also, there remains a need to provide selective Aurora A inhibitors that reduce or avoid Aurora B or Aurora A/B dual inhibition. Accordingly, the present invention provides certain inhibitors of Aurora A which may be useful for treating cancer. The compounds of the present invention fulfill the need of small molecules in order to inhibit the activity of Aurora A.

SUMMARY OF INVENTION

The present invention relates to novel heterocyclic compounds useful as Aurora A selective inhibitors and for the treatment of conditions mediated by Aurora A. The compounds of the invention have the general structure as Formula I or a pharmaceutically acceptable salt thereof:

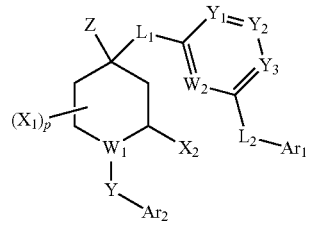

I and

Z is selected from —H, deuterium, halogen, —NH$_2$, —CN, —OH, —N$_3$, —NO$_2$, carboxyl, C$_{1-6}$alkyl, C$_{1-6}$alkoxy, C$_{2-6}$alkenyl, C$_{2-6}$alkynyl, —C$_{6-10}$aryl; —C$_{5-10}$heteroaryl, C$_{3-10}$heterocyclic ring or C$_{3-10}$carbocyclic ring, and each of the heteroaryl and heterocyclic ring contains at least one heteroatoms selected from N, O or S; and each of which is independently optionally substituted with deuterium, halogen, —NH$_2$, —CN, —OH, —NO$_2$, carbonyl, =O, oxo, carboxyl, C$_{1-6}$alkoxy, or C$_{1-6}$alkyl;

L$_1$ and L$_2$ is independently O, CR$_{2a}$R$_{2b}$, or NR$_{2a}$;

each of R$_{2a}$ and R$_{2b}$ is independently —H, deuterium, —NH$_2$, —CN, —OH, oxo, carboxyl, —CO—C$_{1-6}$alkyl, —COOC$_{1-6}$alkyl, —C$_{1-6}$alkylene-CO—C$_{1-6}$alkyl, —C$_{1-6}$alkoxy, —C$_{1-6}$alkyl, —C$_{2-6}$alkenyl, or —C$_{2-6}$alkynyl, and each of which is independently optionally substituted deuterium, halogen, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, or —SO$_2$C$_{1-6}$alkyl;

Y$_1$ is independently CH, CR$_{Y1}$ or N;
Y$_2$, is independently CH, CR$_{Y2}$ or N;
Y$_3$ is independently CH, CR$_{Y3}$ or N; provided, however Y$_1$, Y$_2$, Y$_3$ are not all N;

R$_{Y1}$, R$_{Y2}$ and R$_{Y3}$ is independently deuterium, halogen, —CN, —OH, —NH$_2$, —NO$_2$, —NH(C$_{1-6}$alkyl), —N(C$_{1-6}$alkyl)$_2$, —CO—C$_{1-6}$alkyl, —S—C$_{1-6}$alkyl, —SO—C$_{1-6}$alkyl, —SO$_2$, —SO$_2$C$_{1-6}$alkyl, C$_{1-6}$alkyl, C$_{1-6}$alkoxy, C$_{3-10}$carbocyclic ring, C$_{6-10}$aryl, C$_{3-10}$heterocyclic ring or C$_{5-10}$heteroaryl, and each of the heterocyclic ring and heteroaryl contains 1, 2 or 3 heteroatoms selected from N, O or S; and each of which is independently optionally substituted with deuterium, halogen, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, or —SO$_2$C$_{1-6}$alkyl;

W$_1$ is CR$_w$ or N;
W$_2$ is CR$_w$ or N;

R$_w$ is independently —H; halogen; —NH$_2$; —CN; —OH; —NO$_2$; carboxyl; —C$_{1-6}$alkyl; —C$_{1-6}$alkoxy; —C$_{1-6}$alkyl or —C$_{1-6}$alkoxy substituted with deuterium, halogen, —NH$_2$, —CN, —OH, —NO$_2$, carboxyl, —C$_{1-6}$alkyl or —C$_{1-6}$alkoxy;

Each X$_1$ and X$_2$ is independently —H, deuterium, —CN, —OH, —NH$_2$, carboxyl, C$_{1-6}$alkyl, C$_{1-6}$alkoxy, —C$_{1-6}$alkylene-NR$_2$R$_3$, —C$_{1-6}$alkylene-O—C$_{1-6}$alkyl, —C$_{1-6}$alkylene-CO—OR$_2$, —C$_{1-6}$alkylene-CO—NR$_2$R$_3$, —C$_{1-6}$alkylene-NR$_2$CO—NR$_2$R$_3$, —C$_{1-6}$alkylene-NR$_2$—COC$_{1-6}$alkyl, —C$_{1-6}$alkylene-C$_{3-10}$heterocyclic ring, —C$_{1-6}$alkylene-C$_{5-10}$heteroaryl, —CO—C$_{1-6}$alkylene-NR$_2$R$_3$, —CO—NR$_2$—C$_{3-10}$heterocyclic ring, —CO—C$_{3-10}$heterocyclic ring, —O—C$_{1-6}$alkylene-CO—OR$_2$, —O—C$_{1-6}$alkylene-CO—NR$_2$R$_3$, —O—C$_{1-6}$alkylene-NR$_2$R$_3$, —O—C$_{3-10}$heterocyclic ring, —O—C$_{3-10}$carbocyclic ring, —NR$_2$—C$_{1-6}$alkylene-NR$_2$R$_3$, —NR$_2$—C$_{1-6}$alkylene-C$_{3-10}$ heterocyclic ring, —NR$_2$—C$_{1-6}$alkylene-C$_{5-10}$heteroaryl, —NR$_2$—CO—C$_{5-10}$heteroaryl, —CO—OR$_2$, —CONH$_2$, —CO—NR$_2$OR$_2$, —CO—NR$_2$R$_3$, —NR$_2$R$_3$, —N(R$_2$)(C=O)$_q$R$_2$, —N(R$_2$)(C=O)$_q$NR$_2$R$_3$, —N(R$_2$)(C=O)$_q$OR$_2$, —SO$_2$NR$_2$R$_3$, NR$_2$SO$_2$R$_2$, COR$_2$, SO$_2$R$_2$, C$_{6-10}$aryl, C$_{5-10}$heteroaryl, C$_{3-10}$heterocyclic ring, or C$_{3-10}$carbocyclic ring; and each of which is independently optionally substituted with R$_a$; and each R$_a$ is independently deuterium, halogen, —CN, —OH, —NH$_2$, —NO$_2$, oxo, —CONH$_2$, —SO$_2$NH$_2$, —NH(C$_{1-6}$alkyl), —N(C$_{1-6}$alkyl)$_2$, —C$_{1-6}$alkyl, —C$_{1-6}$alkoxy, —S—C$_{1-6}$alkyl, —SO$_2$C$_{1-6}$alkyl, —NHSO$_2$C$_{1-6}$alkyl, —COC$_{1-6}$alkyl, —CO—C$_{1-6}$alkoxy, —NHCO—C$_{1-6}$alkoxy, —O—OC$_{1-6}$alkyl, or carboxyl; and each p and q is independently 0, 1, 2 or 3; or X$_1$ combines with X$_2$, to form C$_{3-10}$carbocyclic ring, or a C$_{3-10}$heterocyclic ring which contains at least one atom selected from N, O or S, wherein the ring systems is optionally substituted with deuterium, halogen, —NH$_2$, —CN, —OH, —NO$_2$, carbonyl, =O, oxo, carboxyl, C$_{1-6}$alkoxy, or C$_{1-6}$alkyl; or Two X$_1$ can be joined together to form a C$_{3-10}$carbocyclic ring, or a C$_{3-10}$heterocyclic ring which contains at least one atom selected from N, O or S, and each of which is independently optionally substituted with deuterium, halogen, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-8}$carbocyclic;

Each of R$_2$ and R$_3$ is independently —H, deuterium, halogen, —NH$_2$, —CN, —OH, —N$_3$, —NO$_2$, C$_{1-6}$alkyl, C$_{1-6}$alkoxy, C$_{2-6}$alkenyl, —NH(C$_{1-6}$alkyl), —N(C$_{1-6}$alkyl)$_2$, —NH—O—C$_{1-6}$alkyl, —NH—C$_{1-6}$alkylene-O—C$_{1-6}$alkylene, C$_{5-10}$heterocyclic ring or C$_{5-10}$carbocyclic ring, and each of the heterocyclic ring contains at least one heteroatoms selected from N, O or S; and each of which is independently optionally substituted with deuterium, halogen, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-8}$carbocyclic.

p is 0, 1, 2, 3 or 4;

Y is O, S, SO, —(CH$_2$)$_m$CO—(CH$_2$)$_m$—, —(CH$_2$)$_m$SO$_2$—(CH$_2$)$_m$—, or —(CH$_2$)$_m$CR$_4$R$_5$—(CH$_2$)$_m$—, and m is independently 0, 1, 2 or 3;

R$_4$ and R$_5$ is independently selected from —H; deuterium; halogen; —CN; carbonyl; =O; oxo; carboxyl; C$_{1-6}$alkoxy; C$_{1-6}$alkyl; or C$_{1-6}$alkyl or C$_{1-6}$alkoxy independently substituted with deuterium, halogen, —NH$_2$, —CN, —OH, —NO$_2$, carboxyl, oxo, =O, —CONH$_2$, —C$_{1-6}$alkoxy, —C$_{1-6}$alkyl, —C$_{1-6}$alkylene-O—C$_{1-6}$alkyl, —C$_{1-6}$alkylene-COOH, —C$_{1-6}$alkylene-NHCONH$_2$, —CO—N(C$_{1-6}$alky)$_2$, —C$_{1-6}$alkylene-NHCO—C$_{1-6}$alkyl, —CO—CO—N(C$_{1-6}$alkyl)$_2$, —CO—C$_{1-6}$alkyl, —SONH$_2$, —SO$_2$NH$_2$, —SOC$_{1-6}$alky, —SO$_2$C$_{1-6}$alky, —C$_{3-10}$heterocyclic or —C$_{5-10}$heteroaryl; or R$_4$ combines with R$_5$, to form C=O, a C$_{3-10}$carbocyclic ring, or a C$_{3-10}$heterocyclic ring which contains at least one atom selected from N, O or S, and each of which is independently optionally substituted deuterium, halogen, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-8}$carbocyclic;

Ar$_2$ is C$_{6-10}$aryl, C$_{3-10}$carbocyclic ring, C$_{3-10}$heterocyclic ring, or C$_{5-10}$heteroaryl, and each of the heterocyclic ring and heteroaryl contains at least one atom selected from N, O or S; and each of which is independently optionally substituted with one or more of deuterium; halogen; —CN; —OH; —NH$_2$; —NO$_2$; carbonyl; =O; oxo; C$_{1-6}$alkyl; C$_{1-6}$alkoxy; or C$_{1-6}$alkyl or C$_{1-6}$alkoxy independently substituted with deuterium, halogen, —NH$_2$, —CN, —OH, —NO$_2$, carboxyl, oxo, =O, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-8}$carbocyclic;

Ar$_1$ is C$_{6-10}$aryl, C$_{3-10}$carbocyclic ring, C$_{3-10}$heterocyclic ring, or C$_{5-10}$heteroaryl, and each of the heterocyclic ring and heteroaryl contains at least one atom selected from N, O or S; and each of which is independently optionally substituted with one or more of deuterium; halogen; —CN; —OH; —NH$_2$; —NO$_2$; carbonyl; =O; oxo; C$_{1-6}$alkyl; C$_{1-6}$alkoxy; or C$_{1-6}$alkyl or C$_{1-6}$alkoxy independently substituted with deuterium, halogen, —NH$_2$, —CN, —OH, —NO$_2$, carboxyl, oxo, =O, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-8}$carbocyclic.

In some embodiments of Formula I, Z is —H, deuterium, —F, —Cl, —Br, —I, —NH$_2$, —CN, —OH, —N$_3$, —NO$_2$, carboxyl, C$_{1-6}$alkyl, C$_{1-6}$alkoxy, C$_{2-6}$alkenyl, C$_{2-6}$alkynyl, 6-membered aryl, 7-membered aryl, 8-membered aryl, 5-membered heteroaryl, 6-membered heteroaryl, 7-membered heteroaryl, 8-membered heteroaryl, 5-membered heterocyclic ring, 6-membered heterocyclic ring, 7-membered heterocyclic ring, 8-membered heterocyclic ring, 5-membered carbocyclic ring, 6-membered carbocyclic ring, 7-membered carbocyclic ring, or 8-membered carbocyclic ring, and each of the heteroaryl and heterocyclic ring contains 1, 2 or 3 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, C$_{1-6}$alkoxy, or C$_{1-6}$alkyl.

In some embodiments of Formula I, Z is —H, deuterium, —F, —Cl, —Br, —I, —NH$_2$, —CN, —OH, —N$_3$, —NO$_2$, carboxyl, C$_{1-3}$alkyl, C$_{1-3}$alkoxy, C$_{2-4}$alkenyl, C$_{2-4}$alkynyl, 6-membered aryl, 5-membered heteroaryl, 6-membered heteroaryl, 5-membered heterocyclic ring, 6-membered heterocyclic ring, 5-membered carbocyclic ring, or 6-membered carbocyclic ring, and each of the heteroaryl and heterocyclic ring contains 1 or 2 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, C$_{1-3}$alkoxy, or C$_{1-3}$alkyl.

In some embodiments of Formula I, Z is —H, deuterium, —F, —Cl, —Br, —I, —NH$_2$, —CN, —OH, —N$_3$, —NO$_2$, carboxyl, methyl, ethyl, propyl, isopropyl, methoxy, ethoxy, propoxy, isopropoxy, ethylene, 6-membered aryl, 5-membered heteroaryl, 6-membered heteroaryl, 5-membered heterocyclic ring, 6-membered heterocyclic ring, 5-membered carbocyclic ring, or 6-membered carbocyclic ring, and each of the heteroaryl and heterocyclic ring contains 1 or 2 heteroatoms selected from N or O; and each of which is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy or isopropoxy.

In some embodiments of Formula I, Z is —H, deuterium, —F, —Cl, —Br, —I, —NH$_2$, —CN, —OH, —N$_3$, —NO$_2$, carboxyl, methyl, ethyl, propyl, isopropyl, methoxy, ethoxy, propoxy, isopropoxy, and each of which is independently optionally substituted with deuterium, —F, —Cl, —NH$_2$, —CN, —OH, carbonyl, =O, oxo, carboxyl, methyl, ethyl, propyl, isopropyl, methoxy, ethoxy, propoxy or isopropoxy.

In some embodiments of Formula I, Z is —H, deuterium, methyl, —CHD$_2$, —CH$_2$D, —CD$_3$, ethyl, —CHF$_2$, —CH$_2$F, —CF$_3$ or carboxyl.

In some embodiments of Formula I, L$_1$ and L$_2$ is independently CR$_{2a}$R$_{2b}$ or NR$_{2a}$.

In some embodiments of Formula I, each of R$_{2a}$ and R$_{2b}$ is independently —H, deuterium, —NH$_2$, —CN, —OH, carbonyl, =O, oxo, carboxyl, —CO—C$_{1-6}$alkyl, —COO C$_{1-6}$alkyl, —C$_{1-6}$alkylene-CO—C$_{1-6}$alkyl, —C$_{1-6}$alkoxy, —C$_{1-6}$alkyl, —C$_{2-6}$alkenyl; or —C$_{2-6}$alkynyl, and each of which is independently optionally substituted with deuterium, —F, —Cl, —Br, —I, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, or —SO$_2$C$_{1-6}$alkyl.

In some embodiments of Formula I, each of R$_{2a}$ and R$_{2b}$ is independently —H, deuterium, —NH$_2$, —CN, —OH, carbonyl, =O, oxo, carboxyl, —CO—C$_{1-3}$alkyl, —COO C$_{1-3}$alkyl, —C$_{1-3}$alkylene-CO—C$_{1-3}$alkyl, —C$_{1-3}$alkoxy, or —C$_{1-3}$alkyl, and each of which is independently optionally substituted with deuterium, —F, —Cl, —Br, —I, —NH$_2$, —CN, —OH, —NO$_2$, carbonyl, =O, oxo, carboxyl, C$_{1-3}$alkoxy, C$_{1-3}$alkyl, —NH(C$_{1-3}$alkyl), —N(C$_{1-3}$alkyl)$_2$, —S—C$_{1-3}$alkyl, or —SO$_2$C$_{1-3}$alkyl.

In some embodiments of Formula I, each of R$_{2a}$ and R$_{2b}$ is independently —H, deuterium, —OH, carbonyl, =O, oxo, carboxyl, methyl, ethyl, propyl, isopropyl, methoxy, ethoxy, propoxy or isopropoxy, and each of which is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy or isopropoxy.

In some embodiments of Formula I, each of R$_{2a}$ and R$_{2b}$ is independently —H, deuterium, methyl, —CHD$_2$, —CH$_2$D, —CD$_3$, ethyl, —CHF$_2$, —CH$_2$F, —CF$_3$, or carboxyl.

In some embodiments of Formula I, each of R$_{2a}$ and R$_{2b}$ is independently —H or deuterium.

In some embodiments of Formula I, L$_1$ is —CH$_2$—, —CH(COOH)—, or —NH—, and L$_2$ is —NH— or —CH$_2$—.

In some embodiments of Formula I, L$_1$ is —CH$_2$—, and L$_2$ is —NH—.

In some embodiments of Formula I, R$_{y1}$, R$_{y2}$ and R$_{y3}$ is independently deuterium, —F, —Cl, —Br, —I, —CN, —OH, —NH$_2$, —NO$_2$, —NH(C$_{1-6}$alkyl), —N(C$_{1-6}$alkyl)$_2$, —COOH, —CONH$_2$, —CO—C$_{1-6}$alkyl, —S—C$_{1-6}$alkyl, —SO—C$_{1-6}$alkyl, —SO$_2$, —SO$_2$C$_{1-6}$alkyl, C$_{1-6}$alkyl, C$_{1-6}$alkoxy, —CO—C$_{3-8}$heterocyclic ring, C$_{3-8}$carbocyclic ring, C$_{5-6}$aryl, C$_{3-8}$heterocyclic ring, or C$_{5-6}$heteroaryl, and each of the heterocyclic ring and heteroaryl contains 1, 2 or 3 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, or —SO$_2$C$_{1-6}$alkyl.

In some embodiments of Formula I, R$_{y1}$, R$_{y2}$ and R$_{y3}$ is independently deuterium, —F, —Cl, —Br, —I, —CN, —OH, —NH$_2$, —NO$_2$, —NH(C$_{1-3}$alkyl), —N(C$_{1-3}$alkyl)$_2$, —COOH, —CONH$_2$, —CO—C$_{1-3}$alkyl, —S—C$_{1-3}$alkyl, —SO—C$_{1-3}$alkyl, —SO$_2$, —SO$_2$C$_{1-3}$alkyl, C$_{1-3}$alkyl, C$_{1-3}$alkoxy, —CO—C$_{3-8}$heterocyclic ring, 3-membered carbocyclic ring, 4-membered carbocyclic ring, 5-membered carbocyclic ring, 6-membered carbocyclic ring, 7-membered carbocyclic ring, 8-membered carbocyclic ring, 5-membered aryl, 6-membered aryl, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl or 6-membered heteroaryl, and each of the heterocyclic ring and heteroaryl contains 1, 2 or 3 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, C$_{1-3}$alkoxy, C$_{1-3}$alkyl, —NH(C$_{1-3}$alkyl), —N(C$_{1-3}$alkyl)$_2$, —S—C$_{1-3}$alkyl, or —SO$_2$C$_{1-3}$alkyl.

In some embodiments of Formula I, R$_{y1}$, R$_{y2}$ and R$_{y3}$ is independently deuterium, —F, —Cl, —Br, —I, —CN, —OH, —NH$_2$, —NO$_2$, —NH(C$_{1-3}$alkyl), —N(C$_{1-3}$alkyl)$_2$, —COOH, —CONH$_2$, —CO—C$_{1-3}$alkyl, —S—C$_{1-3}$alkyl, —SO—C$_{1-3}$alkyl, —SO$_2$, —SO$_2$C$_{1-3}$alkyl, C$_{1-3}$alkyl, C$_{1-3}$alkoxy, —CO-4-membered heterocyclic ring, —CO-5-membered heterocyclic ring, —CO-6-membered heterocyclic ring, 3-membered carbocyclic ring, 4-membered carbocyclic ring, 5-membered carbocyclic ring, 6-membered carbocyclic ring, 6-membered aryl, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl or 6-membered heteroaryl, and each of the heterocyclic ring and heteroaryl contains 1 or 2 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, or —SO$_2$CH$_3$.

In some embodiments of Formula I, R$_{y1}$, R$_{y2}$ and R$_{y3}$ is independently deuterium, —F, —Cl, —Br, —I, —CN, —OH, —NH$_2$, —NO$_2$, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —COOH, —CONH$_2$, —COCH$_3$, —COCH$_2$CH$_3$, —CO—C(CH$_3$)$_2$, —SCH$_3$, —SOCH$_3$, —SO$_2$, —SO$_2$CH$_3$, —CO-4-membered heterocyclic ring, —CO-5-membered heterocyclic ring, —CO-6-membered heterocyclic ring, 3-membered carbocyclic ring, 4-membered carbocyclic ring, 5-membered carbocyclic ring, 6-membered aryl, 3-membered heterocyclic ring, 4-membered heterocyclic ring, 5-membered heterocyclic ring, 6-membered heterocyclic ring, 5-membered heteroaryl or 6-membered heteroaryl, and each of the heterocyclic ring and heteroaryl contains 1 or 2 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, isopropoxy.

In some embodiments of Formula I, R$_{y1}$, R$_{y2}$ and R$_{y3}$ is independently deuterium, —F, —Cl, —Br, —I, —CN, —OH, —NH$_2$, —NO$_2$, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —COOH, —CONH$_2$, —COCH$_3$, —COCH$_2$CH$_3$, —CO—C(CH$_3$)$_2$, —SCH$_3$, —SOCH$_3$, —SO$_2$, —SO$_2$CH$_3$,

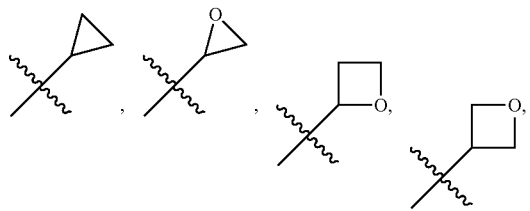

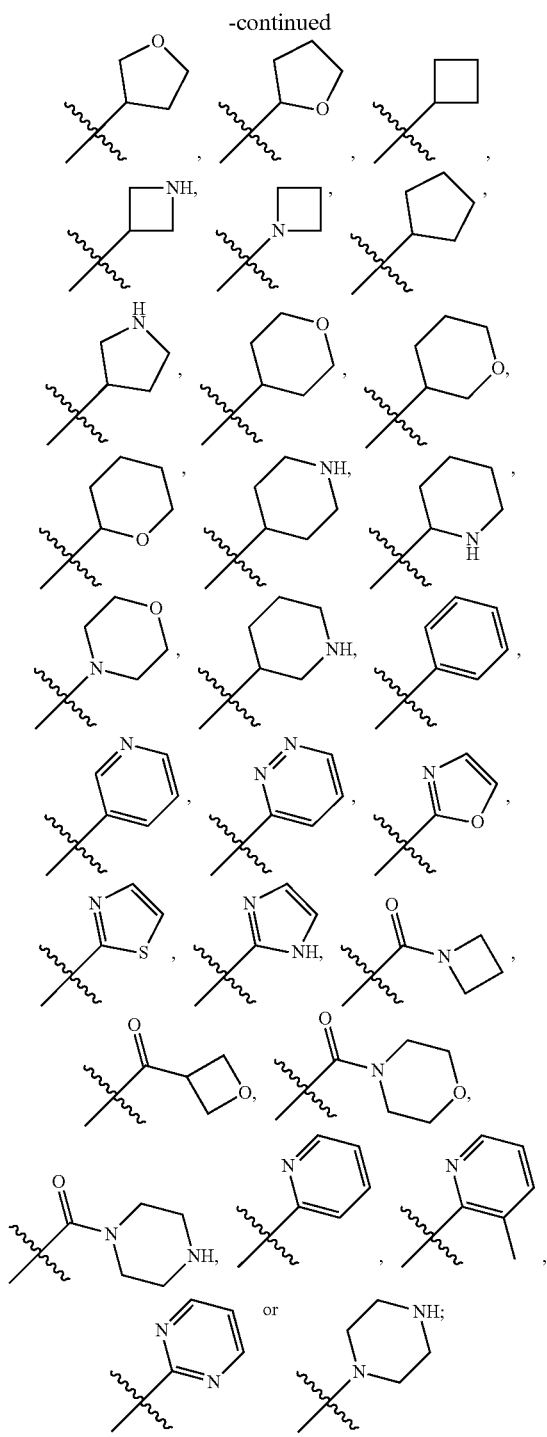

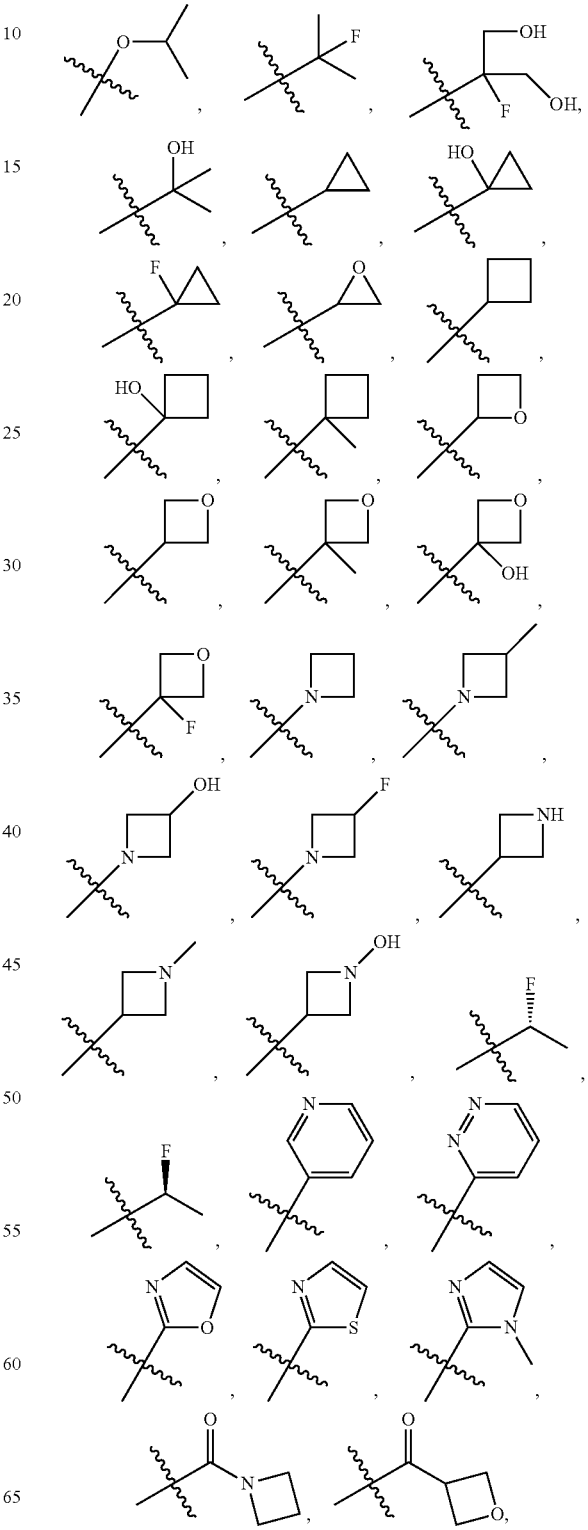

and each of which is independently optionally substituted with deuterium, —F, —Cl, —NH$_2$, —CN, —OH, carbonyl, =O, oxo, carboxyl, methyl, ethyl, propyl, isopropyl, methoxy, ethoxy, propoxy, isopropoxy.

In some embodiments of Formula I, R$_{y1}$, R$_{y2}$ and R$_{y3}$ is independently deuterium, —F, —Cl, —CN, —OH, methyl, ethyl, isopropyl, —NHmethyl, —COOH, —CON(CH$_3$)$_2$, —COCH$_3$, —COCH$_2$CH$_3$, —CO—CH(CH$_3$)$_2$, —CO—C(CH$_3$)$_3$, —COCF$_3$, —CO—C(CH$_3$)$_2$, —SOCH$_3$, —SO$_2$, —SO$_2$CH$_3$, —CHF$_2$, —CF$_3$, —CH(F) CH$_3$, —C(F)$_2$CH$_3$, —OCH$_3$, —OCF$_3$, —CH$_2$OH, —CH$_2$CH$_2$OH, —CHOHCH$_3$, —CH$_2$F, —CH$_2$D, CHD$_2$, —CD$_3$, —CH$_2$CH$_2$F, —CH$_2$CHF$_2$, —CH$_2$CD$_3$, —CH$_2$CF$_3$, —CH$_2$CH$_2$NH$_2$, —CH$_2$CH$_2$NHCH$_3$, —CH$_2$CH$_2$N(CH$_3$)$_2$, —CH$_2$CH$_2$CH$_2$F, —CH$_2$CH$_2$CD$_3$, —CH$_2$CH$_2$CF$_3$, —CH$_2$N(CH$_3$)$_2$, —CH(CH$_3$)(CD$_3$), —CH(CF$_3$)$_2$, —CH(CD$_3$)$_2$, —CH$_2$NHmethyl, —CH$_2$NHethyl, —CH$_2$NHpropyl, —CH$_2$NHisopropyl,

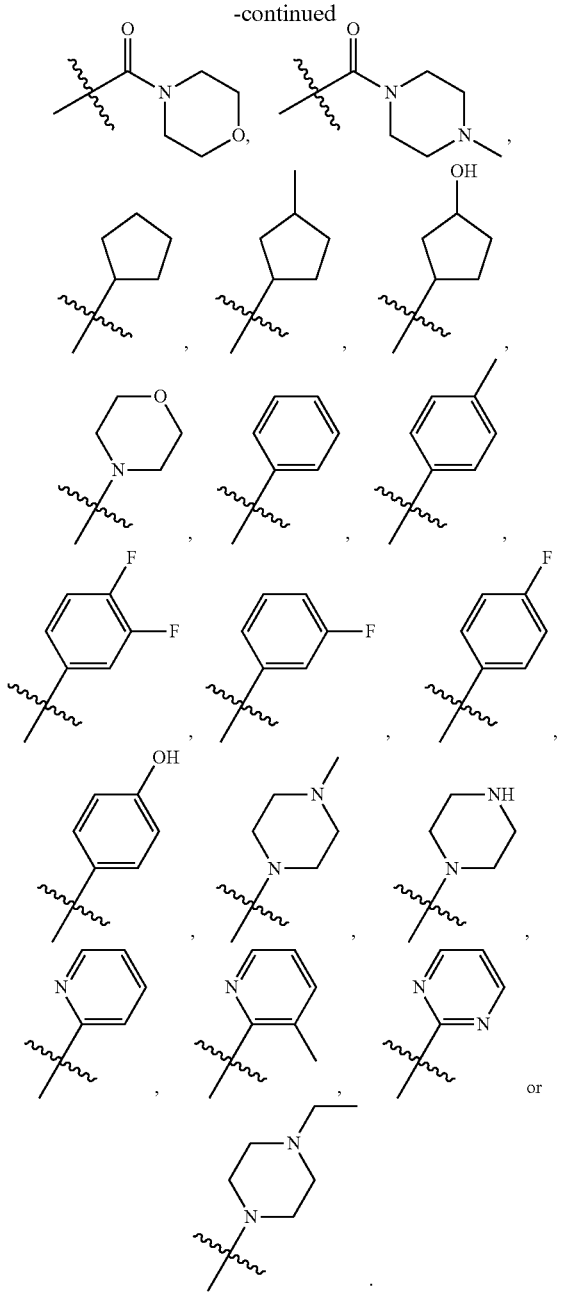

In some embodiments of Formula I, $W_1$ is $CR_w$, and $W_2$ is $CR_w$.

In some embodiments of Formula I, $R_w$ is independently —H; —F; —Cl; —Br; —I; —NH$_2$; —CN; —OH; —NO$_2$; carboxyl; —C$_{1-3}$alkyl; —C$_{1-3}$alkoxy; —C$_{1-6}$alkyl or —C$_{1-6}$alkoxy substituted with deuterium, —F, —Cl, —Br, —I, —NH$_2$, —CN, —OH, —NO$_2$, carboxyl, —C$_{1-3}$alkyl or —C$_{1-3}$alkoxy.

In some embodiments of Formula I, $R_w$ is independently —H; —F; —Cl; —Br; —NH$_2$; —CN; —OH; —NO$_2$; carboxyl; methyl; ethyl; propyl; isopropyl; methoxy; ethoxy; propoxy; isopropoxy; —C$_{1-3}$alkyl or —C$_{1-3}$alkoxy substituted with deuterium, —F, —Cl, —Br, —NH$_2$, —CN, —OH, —NO$_2$, carboxyl, methyl, ethyl, propyl, isopropyl, methoxy, ethoxy, propoxy or isopropoxy.

In some embodiments of Formula I, $R_w$ is independently —H, deuterium, —F, —CN or methyl.

In some embodiments of Formula I, $R_w$ is —H, —F or —CN.

In some embodiments of Formula I, $W_1$ is CH or N, and $W_2$ is CH, CF or N.

In some embodiments of Formula I, $W_1$ is N, and $W_2$ is N.

In some embodiments of Formula I, each $X_1$ and $X_2$ is independently —H, deuterium, —CN, —OH, —NH$_2$, carboxyl, C$_{1-6}$alkyl, C$_{1-6}$alkoxy, —C$_{1-6}$alkylene-NR$_2$R$_3$, —C$_{1-6}$alkylene-O—C$_{1-6}$alkyl, —C$_{1-6}$alkylene-CO—OR$_2$, —C$_{1-6}$alkylene-CO—NR$_2$R$_3$, —C$_{1-6}$alkylene-NR$_2$CO—NR$_2$R$_3$, —C$_{1-6}$alkylene-NR$_2$—COC$_{1-6}$alkyl, —C$_{1-6}$alkylene-C$_{3-10}$heterocyclic ring, —C$_{1-6}$alkylene-C$_{5-10}$heteroaryl, —CO—C$_{1-6}$alkylene-NR$_2$R$_3$, —CO—C$_{3-10}$heterocyclic ring, —O—C$_{1-6}$alkylene-CO—OR$_2$, —O—C$_{1-6}$alkylene-CO—NR$_2$R$_3$, —O—C$_{1-6}$alkylene-NR$_2$R$_3$, —O—C$_{3-10}$heterocyclic ring, —O—C$_{3-10}$carbocyclic ring, —NR$_2$—C$_{1-6}$alkylene-NR$_2$R$_3$, —NR$_2$—C$_{1-6}$alkylene-C$_{3-10}$heterocyclic ring, —NR$_2$—C$_{1-6}$alkylene-C$_{5-10}$heteroaryl, —NR$_2$—CO—C$_{5-10}$heteroaryl, —CO—OR$_2$, —CONH$_2$, —CO—NR$_2$OR$_2$, —CO—NR$_2$R$_3$, —NR$_2$R$_3$, —N(R$_2$)(C=O)$_q$R$_2$, —N(R$_2$)(C=O)$_q$NR$_2$R$_3$, —N(R$_2$)(C=O)$_q$OR$_2$, —SO$_2$NR$_2$R$_3$, NR$_2$SO$_2$R$_2$, COR$_2$, SO$_2$R$_2$, C$_{6-10}$aryl, or C$_{5-10}$heteroaryl; and each of which is independently optionally substituted with R$_a$; and each R$_a$ is independently deuterium, —F, —Cl, —Br, —I, —CN, —OH, —NH$_2$, —NO$_2$, oxo, —CONH$_2$, —SO$_2$NH$_2$, —NH(C$_{1-6}$alkyl), —N(C$_{1-6}$alkyl)$_2$, —C$_{1-6}$alkyl, —C$_{1-6}$alkoxy, —S—C$_{1-6}$alkyl, —SO$_2$C$_{1-6}$alkyl, —NHSO$_2$C$_{1-6}$alkyl, —COC$_{1-6}$alkyl, —CO—C$_{1-6}$alkoxy, —NHCO—C$_{1-6}$alkoxy, —O—OC$_{1-6}$alkyl, or carboxyl.

In some embodiments of Formula I, each $X_1$ and $X_2$ is independently —H, deuterium, —CN, —OH, —NH$_2$, carboxyl, C$_{1-6}$alkyl, C$_{1-6}$alkoxy, —C$_{1-6}$alkylene-NR$_2$R$_3$, —C$_{1-6}$alkylene-O—C$_{1-6}$alkyl, —C$_{1-6}$alkylene-CO—OR$_2$, —C$_{1-6}$alkylene-CO—NR$_2$R$_3$, —C$_{1-6}$alkylene-NR$_2$CO—NR$_2$R$_3$, —C$_{1-6}$alkylene-C$_{3-8}$heterocyclic ring, —C$_{1-6}$alkylene-C$_{5-10}$heteroaryl, —CO—C$_{3-8}$heterocyclic ring, —O—C$_{3-10}$heterocyclic ring, —O—C$_{3-8}$carbocyclic ring, —NR$_2$—C$_{1-6}$alkylene-NR$_2$R$_3$, —NR$_2$—C$_{1-6}$alkylene-C$_{3-8}$heterocyclic ring, —NR$_2$—C$_{1-6}$alkylene-C$_{5-10}$heteroaryl, —NR$_2$—CO—C$_{5-10}$heteroaryl, —CO—OR$_2$, —CO—NR$_2$OR$_2$, —CO—NR$_2$R$_3$, —NR$_2$R$_3$, —N(R$_2$)(C=O)$_q$R$_2$, —N(R$_2$)(C=O)$_q$NR$_2$R$_3$, —N(R$_2$)(C=O)$_q$OR$_2$, —SO$_2$NR$_2$R$_3$, —NR$_2$SO$_2$R$_2$, —COR$_2$, or —SO$_2$R$_2$; and each of which is independently optionally substituted with R$_a$; and each R$_a$ is independently deuterium, —F, —Cl, —Br, —I, —CN, —OH, —NH$_2$, —NO$_2$, oxo, —CONH$_2$, —SO$_2$NH$_2$, —NH(C$_{1-3}$alkyl), —N(C$_{1-3}$alkyl)$_2$, —C$_{1-3}$alkyl, —C$_{1-3}$alkoxy, —S—C$_{1-3}$alkyl, —SO$_2$C$_{1-3}$alkyl, —NHSO$_2$C$_{1-3}$alkyl, —COC$_{1-3}$alkyl, —CO—C$_{1-3}$alkoxy, —NHCO—C$_{1-3}$alkoxy, —O—OC$_{1-3}$alkyl, or carboxyl.

In some embodiments of Formula I, each $X_1$ and $X_2$ is independently —H, deuterium, —CN, —OH, —NH$_2$, carboxyl, C$_{1-3}$alkyl, C$_{1-3}$alkoxy, —C$_{1-3}$alkylene-NR$_2$R$_3$, —C$_{1-3}$alkylene-O—C$_{1-3}$alkyl, —C$_{1-3}$alkylene-CO—OR$_2$, —C$_{1-3}$alkylene-CO—NR$_2$R$_3$, —C$_{1-3}$alkylene-NR$_2$CO—NR$_2$R$_3$, —C$_{1-3}$alkylene-C$_{3-6}$heterocyclic ring, —C$_{1-3}$alkylene-C$_{5-6}$heteroaryl, —CO—C$_{3-6}$heterocyclic ring, —O—C$_{3-6}$carbocyclic ring, —NR$_2$—C$_{1-3}$alkylene-NR$_2$R$_3$, —NR$_2$—C$_{1-3}$alkylene-C$_{3-6}$heterocyclic ring, —CO—OR$_2$, —CO—NR$_2$OR$_2$, —CO—NR$_2$R$_3$, —N(R$_2$)(C=O)$_q$R$_2$, —N(R$_2$)(C=O)$_q$NR$_2$R$_3$, —N(R$_2$)(C=O)$_q$OR$_2$, —SO$_2$NR$_2$R$_3$, —NR$_2$SO$_2$R$_2$, —COR$_2$, or —SO$_2$R$_2$; and each of which is independently optionally substituted with R$_a$; and each R$_a$ is independently deuterium, —F, —Cl, —Br, —I, —CN, —OH, —NH$_2$, —NO$_2$, oxo, —CONH$_2$, —SO$_2$NH$_2$, —NHmethyl, —NHethyl, —NHpropyl, —NHisopropyl, methyl, ethyl, propyl, isopropyl, methoxy, ethoxy, propoxy, isopropoxy or carboxyl.

In some embodiments of Formula I, each X$_1$ and X$_2$ is independently —H, deuterium, —CN, —OH, —NH$_2$, C$_{1-3}$alkyl, or C$_{1-3}$alkoxy; and each of which is independently optionally substituted with one or more substituent R$_a$; and each of R$_a$ is independently deuterium, —F, —Cl, —Br, —CN, —OH, —NH$_2$, oxo, methyl, ethyl, propyl, isopropyl, methoxy, ethoxy, propoxy, isopropoxy or carboxyl.

In some embodiments of Formula I, each X$_1$ and X$_2$ is independently —H, deuterium, —CN, —OH, —NH$_2$, methyl, ethyl, propyl, isopropyl, methoxy, ethoxy, propoxy, or isopropoxy; and each of which is independently optionally substituted with R$_a$; and each R$_a$ is independently deuterium, —F, —Cl, —CN, —OH, —NH$_2$, methyl, ethyl, propyl, isopropyl, methoxy, ethoxy, propoxy, isopropoxy or carboxyl.

In some embodiments of Formula I, each X$_1$ and X$_2$ is independently —H, deuterium, methyl, —CHD$_2$, —CH$_2$D, —CD$_3$, ethyl, or methyl substituted with one or more F.

In some embodiments of Formula I, each X$_1$ and X$_2$ is independently —H, methyl, ethyl, or —CF$_3$.

In some embodiments of Formula I, X$_1$ and X$_2$ are both —H.

In some embodiments of Formula I, X$_1$ combines with X$_2$, to form a C$_{3-8}$carbocyclic ring, or a C$_{3-8}$heterocyclic ring which contains 1, 2 or 3 selected from N, O or S, wherein the ring systems is optionally substituted with deuterium, —F, —Cl, —Br, —I, —NH$_2$, —CN, —OH, —NO$_2$, carbonyl, =O, oxo, carboxyl, C$_{1-6}$alkoxy, or C$_{1-6}$alkyl.

In some embodiments of Formula I, X$_1$ combines with X$_2$, to form a 3-membered carbocyclic ring, 4-membered carbocyclic ring, 5-membered carbocyclic ring, 6-membered carbocyclic ring, 7-membered carbocyclic ring, 8-membered carbocyclic ring, 3-membered heterocyclic ring, 4-membered heterocyclic ring, 5-membered heterocyclic ring, 6-membered heterocyclic ring, 7-membered heterocyclic ring, or 8-membered heterocyclic ring, and each of the heterocyclic ring contains 1 or 2 selected from N, O or S; wherein the ring systems is optionally substituted with deuterium, —F, —Cl, —Br, —I, —NH$_2$, —CN, —OH, —NO$_2$, carbonyl, =O, oxo, carboxyl, C$_{1-3}$alkoxy, or C$_{1-3}$alkyl.

In some embodiments of Formula I, X$_1$ combines with X$_2$, to form a 3-membered carbocyclic ring, 4-membered carbocyclic ring, 5-membered carbocyclic ring, 6-membered carbocyclic ring, 3-membered heterocyclic ring, 4-membered heterocyclic ring, 5-membered heterocyclic ring, or 6-membered heterocyclic ring, and each of the heterocyclic ring contains 1 or 2 selected from N or O; wherein the ring systems is optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, or isopropoxy.

In some embodiments of Formula I, X$_1$ combines with X$_2$, to form a 3-membered carbocyclic ring, 4-membered carbocyclic ring, or 5-membered carbocyclic ring, wherein the ring systems is optionally substituted with deuterium, —F, —Cl, methyl or ethyl.

In some embodiments of Formula I, X$_1$ combines with X$_2$, to form a 5-membered bridge ring.

In some embodiments of Formula I, two X$_1$ can be joined together to form a C$_{3-10}$carbocyclic ring or a C$_{3-10}$heterocyclic ring which contains 1, 2 or 3 heteroatoms selected from N, O or S, and each of which is independently optionally substituted with deuterium, —F, —Cl, —Br, —I, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-6}$carbocyclic ring.

In some embodiments of Formula I, two X$_1$ can be joined together to form a 3-membered carbocyclic ring, 4-membered carbocyclic ring, 5-membered carbocyclic ring, 6-membered carbocyclic ring, 7-membered carbocyclic ring, 8-membered carbocyclic ring, 3-membered heterocyclic ring, 4-membered heterocyclic ring, 5-membered heterocyclic ring, 6-membered heterocyclic ring, 7-membered heterocyclic ring or 8-membered heterocyclic ring, and each of the heterocyclic ring contains 1 or 2 heteroatoms selected from N, O or S, and wherein the ring systems is independently optionally substituted with deuterium, —F, —Cl, —Br, —I, —NH$_2$, —CN, —OH, —NO$_2$, carbonyl, =O, oxo, carboxyl, C$_{1-3}$alkoxy, C$_{1-3}$alkyl, —NH(C$_{1-3}$alkyl), —N(C$_{1-3}$alkyl)$_2$, —SO$_2$C$_{1-3}$alkyl, 3-membered carbocyclic ring, 4-membered carbocyclic ring, 5-membered carbocyclic ring, or 6-membered carbocyclic ring.

In some embodiments of Formula I, two X$_1$ can be joined together to form a 3-membered carbocyclic ring, 4-membered carbocyclic ring, 5-membered carbocyclic ring, 6-membered carbocyclic ring, 3-membered heterocyclic ring, 4-membered heterocyclic ring, 5-membered heterocyclic ring, or 6-membered heterocyclic ring, and each of the heterocyclic ring contains 1 or 2 heteroatom selected from N or O; and wherein the ring systems is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, or isopropoxy, —NHmethyl, —NHethyl, —NHpropyl, —NHisopropyl, or 3-membered carbocyclic ring.

In some embodiments of Formula I, two X$_1$ can be joined together to form a 3-membered carbocyclic ring, 4-membered carbocyclic ring, 5-membered carbocyclic ring, 3-membered heterocyclic ring, 4-membered heterocyclic ring, 5-membered heterocyclic ring, and each of which is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, or isopropoxy.

In some embodiments of Formula I, two X$_1$ can be joined together to form a cyclopropyl, cyclobutyl, or cyclopentyl, and each of which is independently optionally substituted with deuterium, —F, —Cl, —NH$_2$, —CN, —OH, oxo, carboxyl, methyl, ethyl, propyl, isopropyl, methoxy, ethoxy, propoxy, or isopropoxy.

In some embodiments of Formula I, two X$_1$ can be joined together to form a cyclopropyl or cyclobutyl.

In some embodiments of Formula I, each of R$_2$ and R$_3$ is independently —H, deuterium, —F, —Cl, —Br, —I, —CN, —OH, —N$_3$, —NO$_2$, C$_{1-6}$alkyl, C$_{1-6}$alkoxy, C$_{2-6}$alkenyl, —NH(C$_{1-6}$alkyl), —N(C$_{1-6}$alkyl)$_2$, —NH—O—C$_{1-6}$alkyl, —NH—C$_{1-6}$alkylene-O—C$_{1-6}$alkylene, C$_{5-10}$heterocyclic ring or C$_{5-10}$carbocyclic ring, and each of the heterocyclic ring contains 1, 2 or 3 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, C$_{1-3}$alkoxy, C$_{1-3}$alkyl, —NH(C$_{1-3}$alkyl), —N(C$_{1-3}$alkyl)$_2$, —S—C$_{1-3}$alkyl, —SO$_2$C$_{1-3}$alkyl, or —C$_{3-6}$carbocyclic ring.

In some embodiments of Formula I, each of R$_2$ and R$_3$ is independently —H, deuterium, —F, —Cl, —Br, —I, —CN, —OH, —N$_3$, —NO$_2$, C$_{1-3}$alkyl, C$_{1-3}$alkoxy, C$_{2-4}$alkenyl, —NH(C$_{1-3}$alkyl), —N(C$_{1-3}$alkyl)$_2$, —NH—O—C$_{1-3}$alkyl, —NH—C$_{1-3}$alkylene-O—C$_{1-3}$alkylene, 5-membered heterocyclic ring, 6-membered heterocyclic ring, 7-membered heterocyclic ring, 8-membered heterocyclic ring, 9-membered heterocyclic ring, 5-membered carbocyclic ring, 6-membered carbocyclic ring, 7-membered carbocyclic ring, 8-membered carbocyclic ring, or 9-membered carbocyclic ring, and each of the heterocyclic ring contains 1 or 2 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, or 3-membered carbocyclic ring.

In some embodiments of Formula I, each of $R_2$ and $R_3$ is independently —H, deuterium, —F, —Cl, —Br, —I, —CN, —OH, —N$_3$, —NO$_2$, methyl, ethyl, propyl, isopropyl, methoxy, ethoxy, propoxy, isopropoxy, —NHmethyl, —NHethyl, —NHpropyl, —NHisopropyl, —NHOCH$_3$, —NHOCH$_2$CH$_3$, —NHCH$_2$OCH$_3$, —NHOCH$_2$CH$_2$CH$_3$, —NHCH$_2$OCH$_2$CH$_3$, —NHCH$_2$CH$_2$OCH$_3$, —NHOCH(CH$_3$)$_2$, 5-membered heterocyclic ring, 6-membered heterocyclic ring, 5-membered carbocyclic ring, or 6-membered carbocyclic ring, and each of the heterocyclic ring contains 1 or 2 heteroatoms selected from N or O; and each of which is independently optionally substituted with deuterium, —F, —Cl, —NH$_2$, —CN, —OH, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, or 3-membered carbocyclic ring.

In some embodiments of Formula I, each of $R_2$ and $R_3$ is independently —H, deuterium, —F, —Cl, —CN, —OH, methyl, ethyl, propyl, isopropyl, methoxy, ethoxy, propoxy, isopropoxy, —NHmethyl, —NHethyl, —NHpropyl, —NHisopropyl, and each of which is independently optionally substituted with deuterium, —F, —Cl, —NH$_2$, —CN, —OH, carbonyl, =O, oxo, carboxyl, methyl, ethyl, propyl, isopropyl, methoxy, ethoxy, propoxy or isopropoxy.

In some embodiments of Formula I, each of $R_2$ and $R_3$ is independently —H, deuterium, —F, —Cl, —CN, —OH, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, —CH$_2$F, —CHF$_2$, —CF$_3$, —CH$_2$D, CHD$_2$, —CD$_3$, —CH$_2$CH$_2$F, —CH$_2$CHF$_2$, —CH$_2$CD$_3$, —CH$_2$CF$_3$, —CH$_2$CH$_2$NH$_2$, —CH$_2$CH$_2$NHCH$_3$, —CH$_2$CH$_2$N(CH$_3$)$_2$, —CH$_2$CH$_2$CH$_2$F, —CH$_2$CH$_2$CD$_3$, —CH$_2$CH$_2$CF$_3$, —CH$_2$N(CH$_3$)$_2$, —CH(CH$_3$)(CD$_3$), —CH(CF$_3$)$_2$, —CH(CD$_3$)$_2$, —CH$_2$NHmethyl, —CH$_2$NHethyl, —CH$_2$NHpropyl, or —CH$_2$NHisopropyl.

In some embodiments of Formula I, q is 0, 1 or 2.
In some embodiments of Formula I, p is 0, 1, 2 or 3.
In some embodiments of Formula I, Y is O, S, SO, —(CH$_2$)$_m$CO—(CH$_2$)$_m$—, —(CH$_2$)$_m$SO$_2$—(CH$_2$)$_m$—, or —(CH$_2$)$_m$CR$_4$R$_5$—(CH$_2$)$_m$—.

In some embodiments of Formula I, Y is O, —(CH$_2$)$_m$CO—(CH$_2$)$_m$—, —(CH$_2$)$_m$SO$_2$—(CH$_2$)$_m$—, or —(CH$_2$)$_m$CR$_4$R$_5$—(CH$_2$)$_m$—.

In some embodiments of Formula I, m is 0, 1 or 2.
In some embodiments of Formula I, $R_4$ and $R_5$ is independently selected from —H; deuterium; —F; —Cl; —Br; —I; —CN; carbonyl; =O; oxo; carboxyl; C$_{1-6}$alkoxy; C$_{1-6}$alkyl; or C$_{1-6}$alkyl or C$_{1-6}$alkoxy independently substituted with deuterium, —F, —Cl, —Br, —I, —NH$_2$, —CN, —OH, —NO$_2$, carboxyl, oxo, =O, —CONH$_2$, —C$_{1-6}$alkoxy, —C$_{1-6}$alkyl, —C$_{1-6}$alkylene-O—C$_{1-6}$alkyl, —C$_{1-6}$alkylene-COOH, —C$_{1-6}$alkylene-NHCONH$_2$, —CO—N(C$_{1-6}$alky)$_2$, —C$_{1-6}$alkylene-NHCO—C$_{1-6}$alkyl, —CO—CO—N(C$_{1-6}$alkyl)$_2$, —CO—C$_{1-6}$alkyl, —SONH$_2$, —SO$_2$NH$_2$, —SOC$_{1-6}$alky, —SO$_2$C$_{1-6}$alky, —C$_{3-8}$heterocyclic or —C$_{5-10}$heteroaryl; or $R_4$ combines with $R_5$, to form C=O, a C$_{3-8}$carbocyclic ring, or a C$_{3-8}$heterocyclic ring which contains at least one atom selected from N, O or S, and each of which is independently optionally substituted deuterium, —F, —Cl, —Br, —I, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-6}$carbocyclic.

In some embodiments of Formula I, $R_4$ and $R_5$ is independently selected from —H; deuterium; —F; —Cl; —Br; —I; —CN; carbonyl; =O; oxo; carboxyl; C$_{1-3}$alkoxy; C$_{1-3}$alkyl; or C$_{1-6}$alkyl or C$_{1-6}$alkoxy independently substituted with deuterium, —F, —Cl, —Br, —I, —NH$_2$, —CN, —OH, —NO$_2$, carboxyl, oxo, =O, —CONH$_2$, —C$_{1-3}$alkoxy, —C$_{1-3}$alkyl, —C$_{1-3}$alkylene-O—C$_{1-3}$alkyl, —C$_{1-3}$alkylene-COOH, —C$_{1-3}$alkylene-NHCONH$_2$, —CO—N(C$_{1-3}$alky)$_2$, —C$_{1-3}$alkylene-NHCO—C$_{1-3}$alkyl, —CO—CO—N(C$_{1-3}$alkyl)$_2$, —CO—C$_{1-3}$alkyl, —SONH$_2$, —SO$_2$NH$_2$, —SOC$_{1-3}$alky, —SO$_2$C$_{1-3}$alky, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl, 6-membered heteroaryl, 7-membered heteroaryl, or 8-membered heteroaryl; and each of the heterocyclic ring and heteroaryl contains 1, 2 or 3 heteroatoms selected from N, O or S; or $R_4$ combines with $R_5$, to form a 3-membered carbocyclic ring, 4-membered carbocyclic ring, 5-membered carbocyclic ring, 6-membered carbocyclic ring, 7-membered carbocyclic ring, 8-membered carbocyclic ring, 3-member heterocyclic ring, 4-member heterocyclic ring, 5-member heterocyclic ring, 6-member heterocyclic ring, 7-member heterocyclic ring, or 8-member heterocyclic ring, and each of the heterocyclic ring contains 1, 2 or 3 heteroatoms selected from N, O or S; and each of which is independently optionally substituted deuterium, —F, —Cl, —Br, —I, —NH$_2$, —CN, —OH, —NO$_2$, carbonyl, =O, oxo, carboxyl, C$_{1-3}$alkoxy, C$_{1-3}$alkyl, —NH(C$_{1-3}$alkyl), —N(C$_{1-3}$alkyl)$_2$, —S—C$_{1-3}$alkyl, —SO$_2$C$_{1-3}$alkyl, 3-membered carbocyclic ring, 4-membered carbocyclic ring, 5-membered carbocyclic ring, or 6-membered carbocyclic ring.

In some embodiments of Formula I, $R_4$ and $R_5$ is independently selected from —H; deuterium; —F; —Cl; —Br; —I; —CN; carbonyl; =O; oxo; carboxyl; methyl; ethyl; propyl; isopropyl; methoxy; ethoxy; propoxy; isopropoxy; or C$_{1-3}$alkyl or C$_{1-3}$alkoxy independently substituted with deuterium, —F, —Cl, —Br, —I, —NH$_2$, —CN, —OH, —NO$_2$, carboxyl, oxo, =O, —CONH$_2$, —C$_{1-3}$alkoxy, —C$_{1-3}$alkyl, —C$_{1-3}$alkylene-O—C$_{1-3}$alkyl, —C$_{1-3}$alkylene-COOH, —C$_{1-3}$alkylene-NHCONH$_2$, —CO—N(C$_{1-3}$alky)$_2$, —C$_{1-3}$alkylene-NHCO—C$_{1-3}$alkyl, —CO—CO—N(C$_{1-3}$alkyl)$_2$, —CO—C$_{1-3}$alkyl, —SONH$_2$, —SO$_2$NH$_2$, —SOC$_{1-3}$alky, —SO$_2$C$_{1-3}$alky, 3-membered heterocyclic ring, 4-membered heterocyclic ring, 5-membered heterocyclic ring, 6-membered heterocyclic ring, or 6-membered heteroaryl; and each of the heteroaryl contains 1, 2 or 3 heteroatoms selected from N or O; each of the heterocyclic ring contains 1 or 2 heteroatoms selected from N or O; or $R_4$ combines with $R_5$, to form a 3-membered carbocyclic ring, 4-membered carbocyclic ring, 5-membered carbocyclic ring, 6-membered carbocyclic ring, 3-member heterocyclic ring, 4-member heterocyclic ring, 5-member heterocyclic ring, or 6-member heterocyclic ring, and each of the heterocyclic ring contains 1, or 2 heteroatoms selected from N or O; and each of which is independently optionally substituted deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —SCH$_3$, —SO$_2$CH$_3$, or 3-membered carbocyclic ring.

In some embodiments of Formula I, R$_4$ and R$_5$ is independently selected from —H; deuterium; —F; —Cl; —Br; —I; —CN; carbonyl; =O; oxo; carboxyl; methyl; ethyl; propyl; isopropyl; methoxy; ethoxy; propoxy; isopropoxy; or C$_{1-3}$alkyl or C$_{1-3}$alkoxy independently substituted with deuterium, —F, —Cl, —Br, —I, —NH$_2$, —CN, —OH, —NO$_2$, carboxyl, oxo, =O, —CONH$_2$, methyl, ethyl, propyl, isopropyl, methoxy, ethoxy, propoxy, isopropoxy, —NHmethyl, —NHethyl, —NHpropyl, —NHisopropyl, —CH$_2$OCH$_3$, —CH$_2$OCH$_2$CH$_3$, —CH$_2$OCH(CH$_3$)$_2$, —NHOCH$_2$CH$_3$, —CH$_2$—NHCONH$_2$, —CO—N(CH$_3$)$_2$, —CH$_2$—NHCO—C$_{1-3}$alkyl, —CO—CH$_3$, —SONH$_2$, —SO$_2$NH$_2$, —SOCH$_3$, —SO$_2$CH$_3$, 3-membered heterocyclic ring which contains 1 heteroatoms selected from N or O; or R$_4$ combines with R$_5$, to form a 3-membered carbocyclic ring, 4-membered carbocyclic ring, 5-membered carbocyclic ring, 4-member heterocyclic ring, or 5-member heterocyclic ring, and each of the heterocyclic ring contains 1 heteroatoms selected from N or O; and each of which is independently optionally substituted deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —SCH$_3$, —SO$_2$CH$_3$, or 3-membered carbocyclic ring.

In some embodiments of Formula I, R$_4$ and R$_5$ is independently selected from —H; deuterium; —F; —Cl; —Br; —I; —CN; carbonyl; =O; oxo; carboxyl; methyl; ethyl; propyl; isopropyl; methoxy; ethoxy; propoxy; isopropoxy; or methyl, ethyl, propyl, isopropyl, methoxy, ethoxy, propoxy or isopropoxy independently substituted with deuterium, —F, —Cl, —Br, —NH$_2$, —CN, —OH, —NO$_2$, carboxyl, oxo, =O, —CONH$_2$, methyl, ethyl, propyl, isopropyl, methoxy, ethoxy, propoxy, isopropoxy, —NHmethyl, —NHethyl, —NHpropyl, or —NHisopropyl; or R$_4$ combines with R$_5$, to form a cyclopropyl, cyclobutyl, cyclopentyl, 4-membered heterocyclic ring, 5-membered heterocyclic ring, and each of the heterocyclic ring contains 1 heteroatoms selected from O; and each of which is independently optionally substituted deuterium, —F, —Cl, —Br, —NH$_2$, —CN, —OH, carbonyl, =O, oxo, carboxyl, methyl, ethyl, propyl, isopropyl, methoxy, ethoxy, propoxy, isopropoxy, —NHmethyl, —NHethyl, —NHpropyl, or —NHisopropyl.

In some embodiments of Formula I, R$_4$ and R$_5$ is independently selected from —H; deuterium; —F; —Cl; methyl; ethyl; propyl; isopropyl; methoxy; ethoxy; propoxy; isopropoxy; or methyl, ethyl, propyl independently substituted with deuterium, —F, —Cl, —Br, —NH$_2$, —CN, —OH, —NO$_2$, carboxyl, oxo, =O, methyl, ethyl, propyl, isopropyl, methoxy, ethoxy, propoxy, or isopropoxy; or R$_4$ combines with R$_5$, to form a cyclopropyl, cyclobutyl, or 4-membered heterocyclic ring which contains 1 heteroatoms selected from O; and each of which is independently optionally substituted deuterium, —F, —Cl, —NH$_2$, —CN, —OH, —NO$_2$, carbonyl, =O, oxo, carboxyl, methyl, ethyl.

In some embodiments of Formula I, R$_4$ and R$_5$ is independently selected from —H, deuterium, —F, methyl, —CH$_2$D, —CHF$_2$, —CH$_2$F, —CD$_2$H, —CD$_3$, —CF$_3$, or R$_4$ combines with R$_5$, to form cyclopropyl, cyclobutyl, or

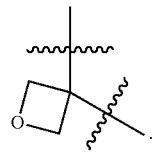 [SMILES: *C1(*)COC1]

In some embodiments of Formula I, Y is independently selected from O, —CH$_2$—, —CH$_2$—CH$_2$—, —CH$_2$CF$_2$—, —CF$_2$—, —CF$_2$CH$_2$—, —CH(CH$_3$)—, —C(CH$_3$)$_2$—, —CH(CF$_3$)—, —CO—, —SO$_2$—, —CH$_2$—CO—, —CH$_2$—SO$_2$—, —CO—CH$_2$—, —SO$_2$—CH$_2$—,

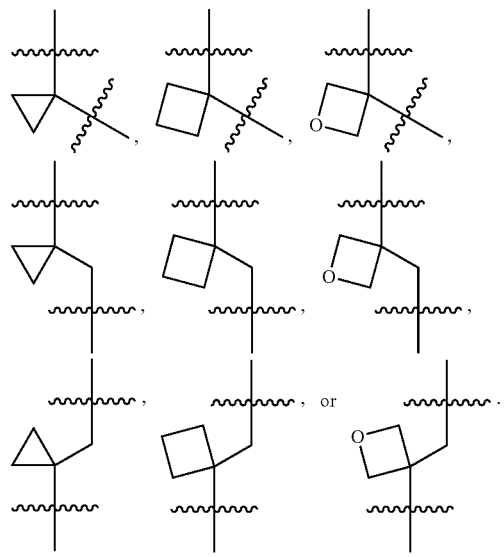

In some embodiments of Formula I, Ar$_2$ is C$_{6-10}$aryl, C$_{3-8}$carbocyclic ring, C$_{3-8}$heterocyclic ring, or C$_{5-10}$heteroaryl, and each of the heterocyclic ring and heteroaryl contains at least one atom selected from N, O or S; and each of which is independently optionally substituted with one or more of deuterium; —F, —Cl, —Br, —I, —CN; —OH; —NH$_2$; —NO$_2$; carbonyl; =O; oxo; C$_{1-6}$alkyl; C$_{1-6}$alkoxy; or C$_{1-6}$alkyl or C$_{1-6}$alkoxy independently substituted with deuterium, —F, —Cl, —Br, —I, —NH$_2$, —CN, —OH, —NO$_2$, carboxyl, oxo, =O, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-6}$carbocyclic.

In some embodiments of Formula I, Ar$_2$ is a 6-membered aryl, 7-membered aryl, 8-membered aryl, 9-membered aryl, 3-membered carbocyclic ring, 4-membered carbocyclic ring, 5-membered carbocyclic ring, 6-membered carbocyclic ring, 7-membered carbocyclic ring, 8-membered carbocyclic ring, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl, 6-membered heteroaryl, 7-membered heteroaryl, 8-membered heteroaryl, or 9-membered heteroaryl; each of the heterocyclic ring and heteroaryl contains 1, 2, 3 heteroatoms selected from N, O or S; and each of which is independently optionally substituted with one or more of deuterium; —F, —Cl, —Br, —I, —CN; —OH; —NH$_2$; —NO$_2$; carbonyl;

=O; oxo; $C_{1-3}$alkyl; $C_{1-3}$alkoxy; or $C_{1-3}$alkyl or $C_{1-3}$alkoxy independently substituted with deuterium, —F, —Cl, —Br, —I, —NH$_2$, —CN, —OH, —NO$_2$, carboxyl, oxo, =O, $C_{1-3}$alkoxy, $C_{1-3}$alkyl, —NH($C_{1-3}$alkyl), —N($C_{1-3}$alkyl)$_2$, —S—$C_{1-3}$alkyl, —SO$_2$$C_{1-3}$alkyl, 3-membered carbocyclic ring, 4-membered carbocyclic ring, 5-membered carbocyclic ring, or 6-membered carbocyclic ring.

In some embodiments of Formula I, Ar$_2$ is a 6-membered aryl, 7-membered aryl, 8-membered aryl, 5-membered carbocyclic ring, 6-membered carbocyclic ring, 7-membered carbocyclic ring, 8-membered carbocyclic ring, 5-membered heterocyclic ring, 6-membered heterocyclic ring, 7-membered heterocyclic ring, 8-membered heterocyclic ring, 5-membered heteroaryl, 6-membered heteroaryl, 7-membered heteroaryl, 8-membered heteroaryl, 9-membered heteroaryl; each of the heterocyclic ring and heteroaryl contains 1, 2 heteroatoms selected from N, O or S; and each of which is independently optionally substituted with one or more of deuterium; —F; —Cl; —Br; —I; —CN; —OH; —NH$_2$; —NO$_2$; carbonyl; =O; oxo; methyl; ethyl; propyl; isopropyl; methoxy; ethoxy; propoxy; isopropoxy; —CH$_2$F; —CHF$_2$; —CF$_3$; —CH$_2$D; CHD$_2$; —CD$_3$; or $C_{1-3}$alkyl or $C_{1-3}$alkoxy independently substituted with deuterium, —F, —Cl, —Br, —I, —NH$_2$, —CN, —OH, —NO$_2$, carboxyl, oxo, =O, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, or 3-membered carbocyclic ring.

In some embodiments of Formula I, Ar$_2$ is a 6-membered aryl, 5-membered heteroaryl, or 9-membered heteroaryl, and each of the heteroaryl contains 1 or 2 heteroatoms selected from N, O or S; and each of which is independently optionally substituted with one or more of deuterium, —F, —Cl, —Br, —CN, —OH, —NH$_2$, carbonyl, =O, oxo, methyl, ethyl, propyl, isopropyl, methoxy, ethoxy, propoxy, isopropoxy, —CH$_2$F, —CHF$_2$, —CF$_3$, —CH$_2$D, CHD$_2$, —CD$_3$.

In some embodiments of Formula I, Ar$_2$ is a phenyl,

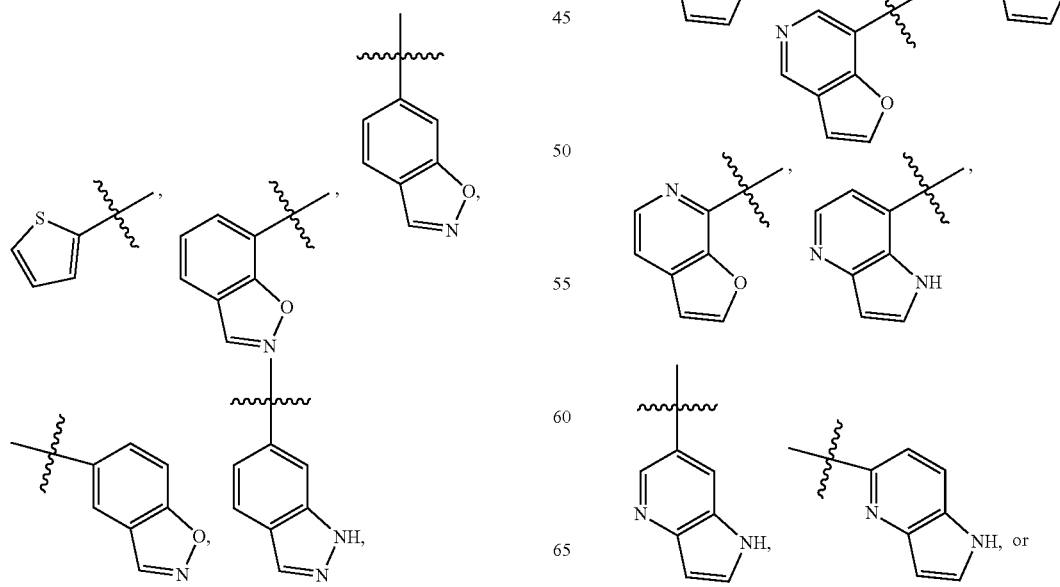

-continued

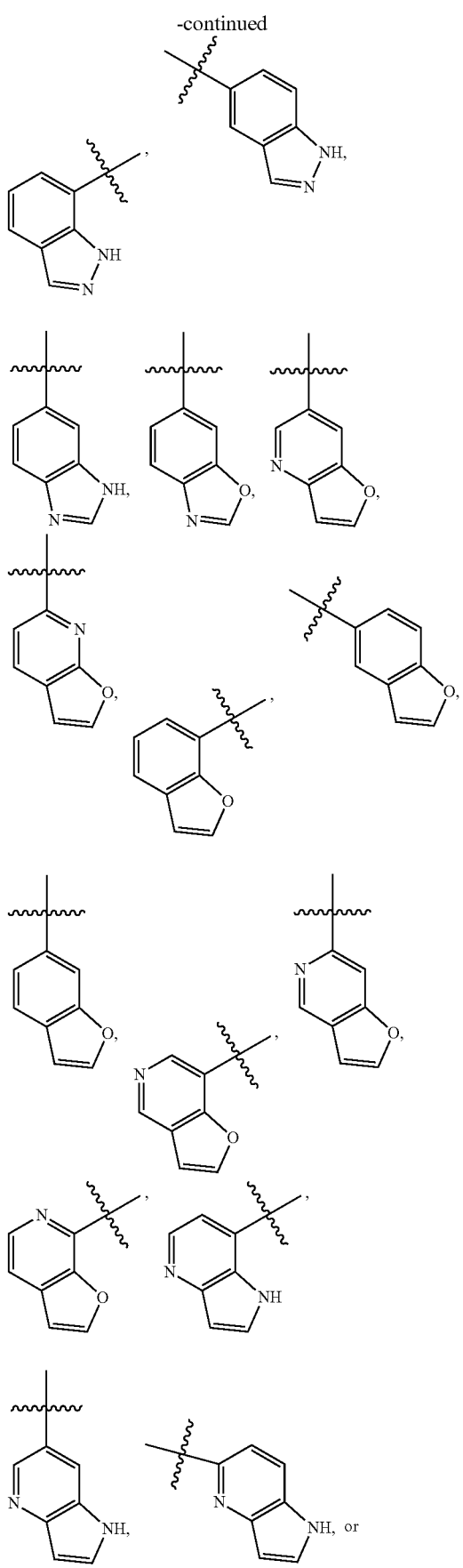

-continued
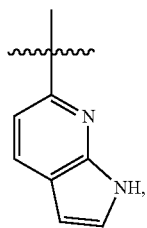
and each of which is independently optionally substituted with one or more of deuterium, —F, —Cl, —Br, —CN, —OH, —NH$_2$, carbonyl, =O, oxo, methyl, ethyl, propyl, isopropyl, methoxy, ethoxy, propoxy, isopropoxy, —CH$_2$F, —CHF$_2$, —CF$_3$, —CH$_2$D, CHD$_2$, —CD$_3$.
In some embodiments of Formula I, Ar$_2$ is
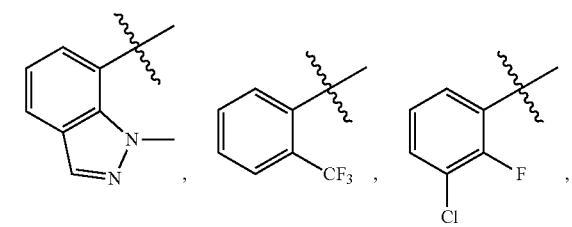
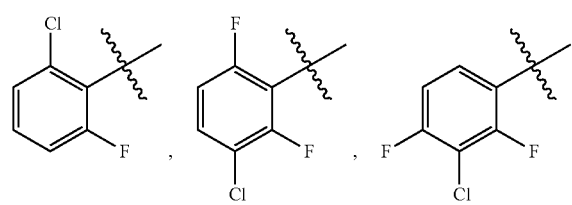
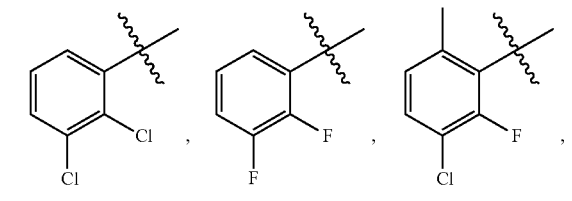
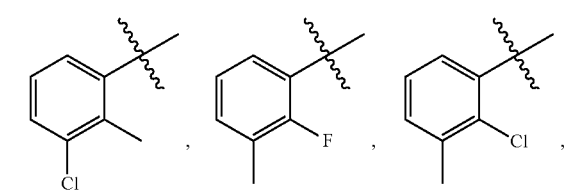
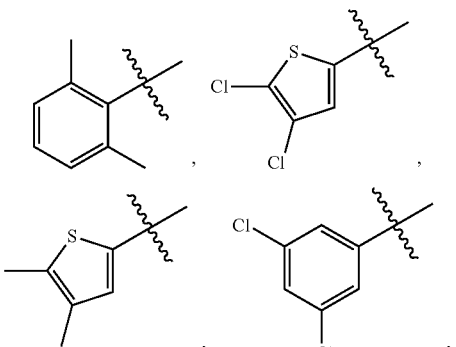
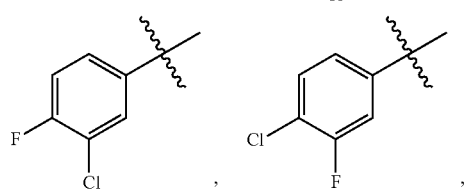
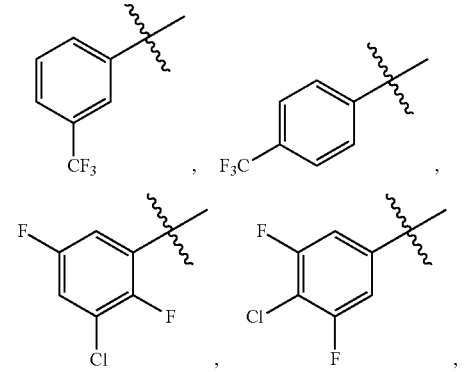
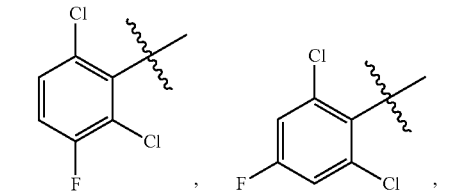
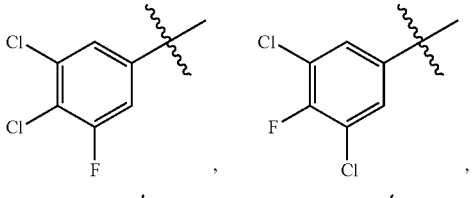
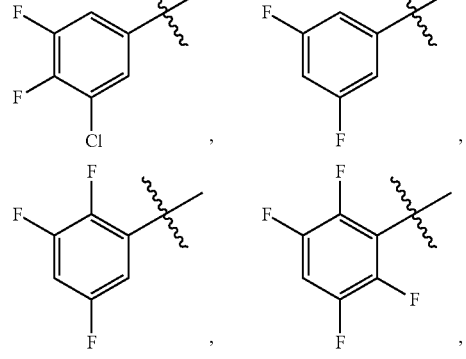

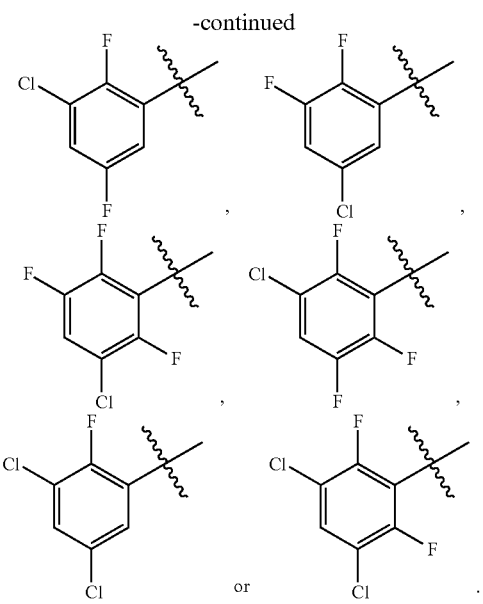

In some embodiments of Formula I, $Ar_1$ is $C_{6-10}$aryl, $C_{3-8}$carbocyclic ring, $C_{3-8}$heterocyclic ring, or $C_{5-10}$heteroaryl, and each of the heterocyclic ring and heteroaryl contains 1, 2 or 3 heteroatoms selected from N, O or S; and each of which is independently optionally substituted with one or more of deuterium; —F; —Cl; —Br; —I; —CN; —OH; —NH$_2$; —NO$_2$; carbonyl; =O; oxo; $C_{1-6}$alkyl; $C_{1-6}$alkoxy; or $C_{1-6}$alkyl or $C_{1-6}$alkoxy independently substituted with deuterium, —F, —Cl, —Br, —I, —NH$_2$, —CN, —OH, —NO$_2$, carboxyl, oxo, =O, $C_{1-3}$alkoxy, $C_{1-3}$alkyl, —NH($C_{1-3}$alkyl), —N($C_{1-3}$alkyl)$_2$, —S—$C_{1-3}$alkyl, —SO$_2C_{1-3}$alkyl, or —$C_{3-6}$carbocyclic.

In some embodiments of Formula I, $Ar_1$ is 6-membered aryl, 7-membered aryl, 8-membered aryl, 9-membered aryl, 3-membered carbocyclic ring, 4-membered carbocyclic ring, 5-membered carbocyclic ring, 6-membered carbocyclic ring, 7-membered carbocyclic ring, 8-membered carbocyclic ring, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl 6-membered heteroaryl, 7-membered heteroaryl, or 8-membered heteroaryl; each of the heterocyclic ring and heteroaryl contains 1, 2 or 3 heteroatoms selected from N, O or S; and each of which is independently optionally substituted with one or more of deuterium; —F; —Cl; —Br; —I; —CN; —OH; —NH$_2$; —NO$_2$; carbonyl; =O; oxo; $C_{1-3}$alkyl; $C_{1-3}$alkoxy; or $C_{1-3}$alkyl or $C_{1-3}$alkoxy independently substituted with deuterium, —F, —Cl, —Br, —I, —NH$_2$, —CN, —OH, —NO$_2$, carboxyl, oxo, =O, $C_{1-3}$alkoxy, $C_{1-3}$alkyl, —NH($C_{1-3}$alkyl), —N($C_{1-3}$alkyl)$_2$, —S—$C_{1-3}$alkyl, —SO$_2C_{1-3}$alkyl, 3-membered carbocyclic ring, 4-membered carbocyclic ring, 5-membered carbocyclic ring, or 6-membered carbocyclic ring.

In some embodiments of Formula I, $Ar_1$ is 5-membered heteroaryl or 6-membered heteroaryl; each of the heteroaryl contains 1, 2 or 3 heteroatoms selected from N or S; and each of which is independently optionally substituted with one or more of deuterium; —F; —Cl; —Br; —I; —CN; —OH; —NH$_2$; —NO$_2$; carbonyl; =O; oxo; methyl; ethyl; propyl; isopropyl; methoxy; ethoxy; propoxy; isopropoxy; or methyl, ethyl, propyl, isopropyl independently substituted with deuterium, —F, —Cl, —Br, —I, —NH$_2$, —CN, —OH, —NO$_2$, carboxyl, oxo, =O, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$.

In some embodiments of Formula I, $Ar_1$ is 5-membered heteroaryl which contains 1, 2 or 3 heteroatoms selected from N or S, and which is independently optionally substituted with one or more of deuterium; —F; —Cl; —Br; —I; —CN; —OH; —NH$_2$; carbonyl; =O; oxo; methyl; ethyl; propyl; isopropyl; methoxy; ethoxy; propoxy; isopropoxy; —CH$_2$F, —CHF$_2$, —CF$_3$, —CH$_2$D, CHD$_2$, —CD$_3$, —CH$_2$NHmethyl, —CH$_2$NHethyl, —CH$_2$NHpropyl, —CH$_2$NHisopropyl, —CH$_2$N(CH$_3$)$_2$.

In some embodiments of Formula I, $Ar_1$ is

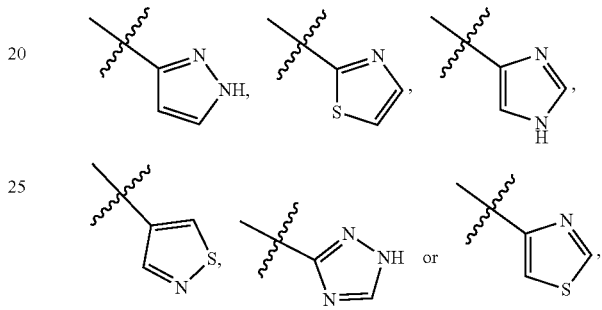

and which is independently optionally substituted with one or more of deuterium, —F, —Cl, —Br, —I, —CN, —OH, —NH$_2$, carbonyl, =O, oxo, methyl, ethyl, propyl, isopropyl, methoxy, ethoxy, propoxy, or isopropoxy.

In some embodiments of Formula I, $Ar_1$ is

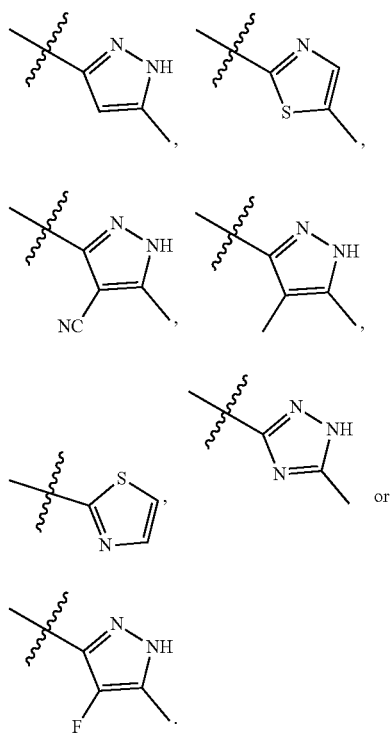

In some embodiments of Formula I, the compound is of Formula II:

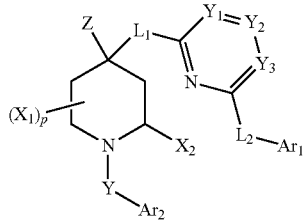
II wherein Z, L₁, L₂, Y₁, Y₂, Y₃, X₁, X₂, Y, Ar₁, Ar₂, and p are as defined herein.

In some embodiments of Formula I or II, the compound is of Formula III, IV or V:

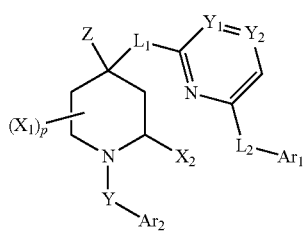
III

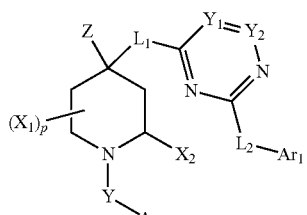
IV

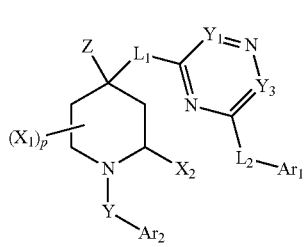
V

Wherein Z, L₁, L₂, Y₁, Y₂, X₁, X₂, Y, Ar₁, Ar₂, and p are as defined herein.

In some embodiments of Formula I or II, the compound is of Formula VI:

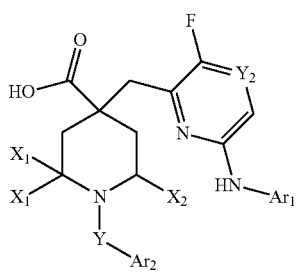
VI wherein, $Y_2$ is independently CH, $CR_{Y2}$ or N;

$R_{Y2}$ is deuterium, halogen, —CN, —OH, —NH₂, —NO₂, —NH($C_{1-6}$alkyl), —N($C_{1-6}$alkyl)₂, —CO—$C_{1-6}$alkyl, —S—$C_{1-6}$alkyl, —SO—$C_{1-6}$alkyl, —SO₂, —SO₂$C_{1-6}$alkyl, $C_{1-6}$alkyl, $C_{1-6}$alkoxy, $C_{3-10}$carbocyclic ring, $C_{6-10}$aryl, $C_{3-10}$heterocyclic ring or $C_{5-10}$heteroaryl, and each of the heterocyclic ring and heteroaryl contains 1, 2 or 3 heteroatoms selected from N, O or S; and each of which is independently optionally substituted with deuterium, halogen, —NH₂, —CN, —OH, —NO₂, carbonyl, =O, oxo, carboxyl, $C_{1-6}$alkoxy, $C_{1-6}$alkyl, —NH($C_{1-6}$alkyl), —N($C_{1-6}$alkyl)₂, —S—$C_{1-6}$alkyl, or —SO₂$C_{1-6}$alkyl;

each X and X₂ is independently —H, deuterium, halogen, —CN, —OH, —NH₂, —NO₂, carboxyl, $C_{1-6}$alkyl, $C_{1-6}$alkoxy, —$C_{1-6}$alkylene-NR₂R₃, —$C_{1-6}$alkylene-O—$C_{1-6}$alkyl, —$C_{1-6}$alkylene-CO—OR₂, —$C_{1-6}$alkylene-CO—NR₂R₃, —$C_{1-6}$alkylene-NR₂CO—NR₂R₃, —$C_{1-6}$alkylene-NR₂—COC$_{1-6}$alkyl, —$C_{1-6}$alkylene-$C_{3-10}$heterocyclic ring, —$C_{1-6}$alkylene-$C_{5-10}$heteroaryl, —CO—$C_{1-6}$alkylene-NR₂R₃, —CO—NR₂—$C_{3-10}$heterocyclic ring, —CO—$C_{3-10}$heterocyclic ring, —O—$C_{1-6}$alkylene-CO—OR₂, —O—$C_{1-6}$alkylene-CO—NR₂R₃, —O—$C_{1-6}$alkylene-NR₂R₃, —O—$C_{3-10}$carbocyclic ring, —NR₂—$C_{1-6}$alkylene-NR₂R₃, —NR₂—$C_{1-6}$alkylene-$C_{3-10}$heterocyclic ring, —NR₂—$C_{1-6}$alkylene-$C_{5-10}$heteroaryl, —NR₂—CO—$C_{5-10}$heteroaryl, —CO—OR₂, —CONH₂, —CO—NR₂OR₂, —CO—NR₂R₃, —NR₂R₃, —N(R₂)(C=O)$_q$R₂, —N(R₂)(C=O)$_q$NR₂R₃, —N(R₂)(C=O)$_q$OR₂, —SO₂NR₂R₃, NR₂SO₂R₂, COR₂, SO₂R₂, $C_{6-10}$aryl, $C_{5-10}$heteroaryl, $C_{3-10}$heterocyclic ring, or $C_{3-10}$carbocyclic ring; and each of which is independently optionally substituted with $R_a$; and each $R_a$ is independently deuterium, halogen, —CN, —OH, —NH₂, —NO₂, oxo, —CONH₂, —SO₂NH₂, —NH($C_{1-6}$alkyl), —N($C_{1-6}$alkyl)₂, —$C_{1-6}$alkyl, —$C_{1-6}$alkoxy, —S—$C_{1-6}$alkyl, —SO₂$C_{1-6}$alkyl, —NHSO₂$C_{1-6}$alkyl, —COC$_{1-6}$alkyl, —CO—$C_{1-6}$alkoxy, —NHCO—$C_{1-6}$alkoxy, —O—OC$_{1-6}$alkyl, or carboxyl; and each q is independently 0, 1, 2 or 3; or X₁ combines with X₂, to form a $C_{3-10}$carbocyclic ring or a $C_{3-10}$heterocyclic ring which contains 1, 2 or 3 heteroatoms selected from N, O or S, wherein the ring systems is optionally substituted with deuterium, halogen, —CN, —OH, $C_{1-6}$alkoxy, or $C_{1-6}$alkyl; or Two X₁ can be joined together to form a $C_{3-10}$carbocyclic ring or a $C_{3-10}$heterocyclic ring which contains 1, 2 or 3 heteroatoms selected from N, O or S, and each of which is independently optionally substituted with deuterium, halogen, —NH₂, —CN, —OH, —NO₂, carbonyl, =O, oxo, carboxyl, $C_{1-6}$alkoxy, $C_{1-6}$alkyl, —NH($C_{1-6}$alkyl), —N($C_{1-6}$alkyl)₂, —S—$C_{1-6}$alkyl, —SO₂$C_{1-6}$alkyl, or —$C_{3-8}$carbocyclic;

Each of R₂ and R₃ is independently —H, deuterium, halogen, —NH₂, —CN, —OH, —N₃, —NO₂, $C_{1-6}$alkyl, $C_{1-6}$alkoxy, $C_{2-6}$alkenyl, —NH($C_{1-6}$alkyl), —N($C_{1-6}$alkyl)₂, —NH—O—$C_{1-6}$alkyl, —NH—$C_{1-6}$alkylene-O—$C_{1-6}$alkylene, $C_{5-10}$heterocyclic ring or $C_{5-10}$carbocyclic ring, and each of the heterocyclic ring contains 1, 2 or 3 heteroatoms selected from N, O or S; and each of which is independently optionally substituted with deuterium, halogen, —NH₂, —CN, —OH, —NO₂, carbonyl, =O, oxo, carboxyl, $C_{1-6}$alkoxy, $C_{1-6}$alkyl, —NH($C_{1-6}$alkyl), —N($C_{1-6}$alkyl)₂, —S—$C_{1-6}$alkyl, —SO₂$C_{1-6}$alkyl, or —$C_{3-8}$carbocyclic;

Y is O, S, SO, —(CH₂)$_m$CO—(CH₂)$_m$—, —(CH₂)$_m$SO₂—(CH₂)$_m$—, or —(CH₂)$_m$CR₄R₅—(CH₂)$_m$—, and m is independently 0, 1, 2 or 3;

R₄ and R₅ is independently selected from —H; deuterium; halogen; —CN; carbonyl; =O; oxo; carboxyl; $C_{1-6}$alkyl; $C_{1-6}$alkyl; or $C_{1-6}$alkyl or $C_{1-6}$alkoxy independently substituted with deuterium, halogen, —NH₂, —CN, —OH, —NO₂, carboxyl, oxo, =O, —CONH₂, —$C_{1-6}$alkoxy, —$C_{1-6}$alkyl, —$C_{1-6}$alkylene-O—$C_{1-6}$alkyl, —$C_{1-6}$alkylene-COOH, —$C_{1-6}$alkylene-NHCONH₂, —CO—N($C_{1-6}$alky)₂, —$C_{1-6}$alkylene-NHCO—$C_{1-6}$alkyl, —CO—CO—N($C_{1-6}$alkyl)₂, —CO—$C_{1-6}$alkyl, —SONH₂, —SO₂NH₂, —SO$C_{1-6}$alky, —SO₂$C_{1-6}$alky, —$C_{3-10}$heterocyclic or —$C_{5-10}$heteroaryl; or R₄ combines with R₅, to form C=O, a $C_{3-10}$carbocyclic ring or a $C_{3-10}$heterocyclic ring which contains 1, 2 or 3 heteroatoms selected from N, O or S, and each of which is independently optionally substituted deuterium, halogen, —NH₂, —CN, —OH, —NO₂, carbonyl, =O, oxo, carboxyl, $C_{1-6}$alkoxy, $C_{1-6}$alkyl, —NH($C_{1-6}$alkyl), —N($C_{1-6}$alkyl)₂, —S—$C_{1-6}$alkyl, —SO₂$C_{1-6}$alkyl, or —$C_{3-8}$carbocyclic;

Ar₂ is $C_{6-10}$aryl, $C_{3-8}$carbocyclic or $C_{5-10}$heteroaryl which contains at 1, 2 or 3 heteroatoms selected from N, O or S; and each of which is independently optionally substituted with one or more of deuterium; halogen; —CN; —OH; —NH₂; —NO₂; carbonyl; =O; oxo; $C_{1-6}$alkyl; $C_{1-6}$alkoxy; or $C_{1-6}$alkyl or $C_{1-6}$alkoxy independently substituted with deuterium, halogen, —NH₂, —CN, —OH, —NO₂, carboxyl, oxo, =O, $C_{1-6}$alkoxy, $C_{1-6}$alkyl, —NH($C_{1-6}$alkyl), —N($C_{1-6}$alkyl)₂, —S—$C_{1-6}$alkyl, or —SO₂$C_{1-6}$alkyl;

Ar₁ is $C_{6-10}$aryl, $C_{3-8}$carbocyclic or $C_{5-10}$heteroaryl which contains at 1, 2 or 3 heteroatoms selected from N, O or S; and each of which is independently optionally substituted with one or more of deuterium; halogen; —CN; —OH; —NH₂; —NO₂; carbonyl; =O; oxo; $C_{1-6}$alkyl; $C_{1-6}$alkoxy; or $C_{1-6}$alkyl or $C_{1-6}$alkoxy independently substituted with deuterium, halogen, —NH₂, —CN, —OH, —NO₂, carboxyl, oxo, =O, $C_{1-6}$alkoxy, $C_{1-6}$alkyl, —NH($C_{1-6}$alkyl), —N($C_{1-6}$alkyl)₂, —S—$C_{1-6}$alkyl, —SO₂$C_{1-6}$alkyl, or —$C_{3-8}$carbocyclic.

In some embodiments of Formula VI, $R_{y2}$ is independently deuterium, —F, —Cl, —Br, —I, —CN, —OH, —NH₂, —NO₂, —NH($C_{1-3}$alkyl), —N($C_{1-3}$alkyl)₂, —CO—$C_{1-3}$alkyl, —S—$C_{1-3}$alkyl, —SO—$C_{1-3}$alkyl, —SO₂, —SO₂$C_{1-3}$alkyl, $C_{1-3}$alkyl, $C_{1-3}$alkoxy, 3-membered carbocyclic ring, 4-membered carbocyclic ring, 5-membered carbocyclic ring, 6-membered carbocyclic ring, 7-membered carbocyclic ring, 8-membered carbocyclic ring, 5-membered aryl, 6-membered aryl, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl or 6-membered heteroaryl, and each of the heterocyclic ring and heteroaryl contains 1, 2 or 3 heteroatoms selected from N, O or S; and each of which is independently optionally substituted with deuterium, —F, —Cl, —Br, —I, —NH₂, —CN, —OH, —NO₂, carbonyl, =O, oxo, carboxyl, $C_{1-3}$alkoxy, $C_{1-3}$alkyl, —NH($C_{1-3}$alkyl), —N($C_{1-3}$alkyl)₂, —S—$C_{1-3}$alkyl, or —SO₂$C_{1-3}$alkyl.

In some embodiments of Formula VI, $R_{y2}$ is independently deuterium, —F, —Cl, —Br, —I, —CN, —OH, —NH₂, —NO₂, methyl, ethyl, propyl, isopropyl, methoxy, ethoxy, propoxy, isopropoxy, —NHmethyl, —NHethyl, —NHpropyl, —NHisopropyl, —N(CH₃)₂, —COCH₃, —COCH₂CH₃, —CO—C(CH₃)₂, —SCH₃, —SOCH₃, —SO₂, —SO₂CH₃, 3-membered carbocyclic ring, 4-membered carbocyclic ring, 5-membered carbocyclic ring, 6-membered aryl, 3-membered heterocyclic ring, 4-membered heterocyclic ring, 5-membered heterocyclic ring, 6-membered heterocyclic ring, or 6-membered heteroaryl, and each of the heterocyclic ring and heteroaryl contains 1 or 2 heteroatoms selected from N or O; and each of which is independently optionally substituted with deuterium, —F, —Cl, —Br, —I, —NH₂, —CN, —OH, —NO₂, carbonyl, =O, oxo, carboxyl, methyl, ethyl, propyl, isopropyl, methoxy, ethoxy, propoxy, isopropoxy.

In some embodiments of Formula VI, $R_{y2}$ is independently deuterium, —F, —Cl, —Br, —I, —CN, —OH, —NH₂, —NO₂, methyl, ethyl, propyl, isopropyl, methoxy, ethoxy, propoxy, isopropoxy, —NHmethyl, —NHethyl, —NHpropyl, —NHisopropyl, —N(CH₃)₂, —COCH₃, —COCH₂CH₃, —CO—C(CH₃)₂, —SCH₃, —SOCH₃, —SO₂, —SO₂CH₃,

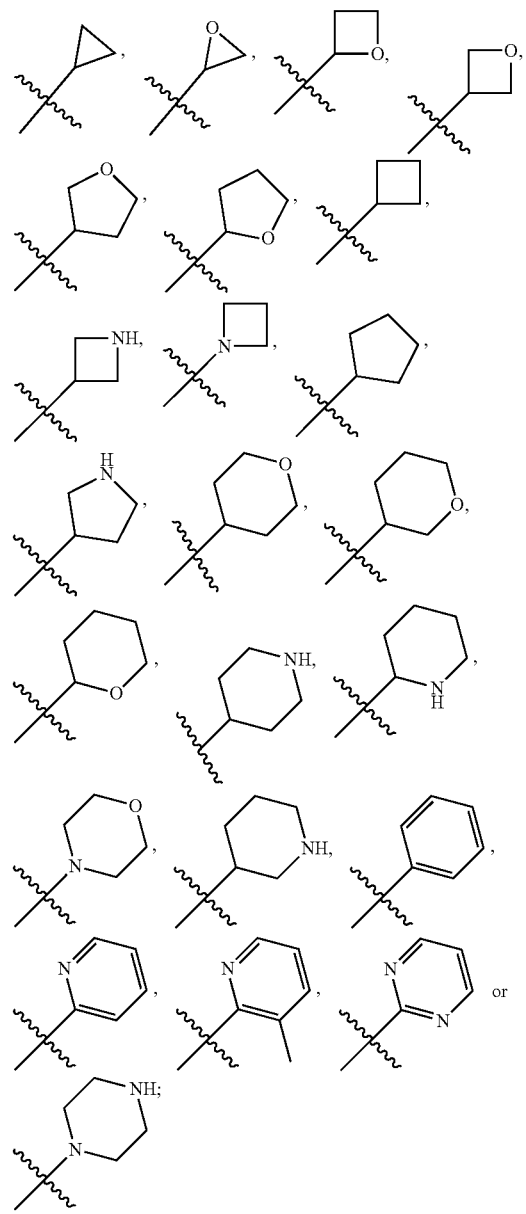

and each of which is independently optionally substituted with deuterium, —F, —Cl, —NH₂, —CN, —OH, carbonyl, =O, oxo, carboxyl, methyl, ethyl, propyl, isopropyl, methoxy, ethoxy, propoxy, isopropoxy.

In some embodiments of Formula VI, $R_{y2}$ is independently deuterium, —F, —Cl, —CN, methyl, ethyl, isopropyl, —NHmethyl, —COCH$_3$, —COCH$_2$CH$_3$, —CO—C(CH$_3$)$_2$, —SOCH$_3$, —SO$_2$, —SO$_2$CH$_3$, —CHF$_2$, —CF$_3$, —CH(F)CH$_3$, —C(F)$_2$CH$_3$, —OCH$_3$, —OCF$_3$, —CH$_2$OH, —CH$_2$CH$_2$OH, —CHOHCH$_3$, —CH$_2$F, —CH$_2$D, CHD$_2$, —CD$_3$, —CH$_2$CH$_2$F, —CH$_2$CHF$_2$, —CH$_2$CD$_3$, —CH$_2$CF$_3$, —CH$_2$CH$_2$NH$_2$, —CH$_2$CH$_2$NHCH$_3$, —CH$_2$CH$_2$N(CH$_3$)$_2$, —CH$_2$CH$_2$CH$_2$F, —CH$_2$CH$_2$CD$_3$, —CH$_2$CH$_2$CF$_3$, —CH$_2$N(CH$_3$)$_2$, —CH(CH$_3$)(CD$_3$), —CH(CF$_3$)$_2$, —CH(CD$_3$)$_2$, —CH$_2$NHmethyl, —CH$_2$NHethyl, —CH$_2$NHpropyl, —CH$_2$NHisopropyl,

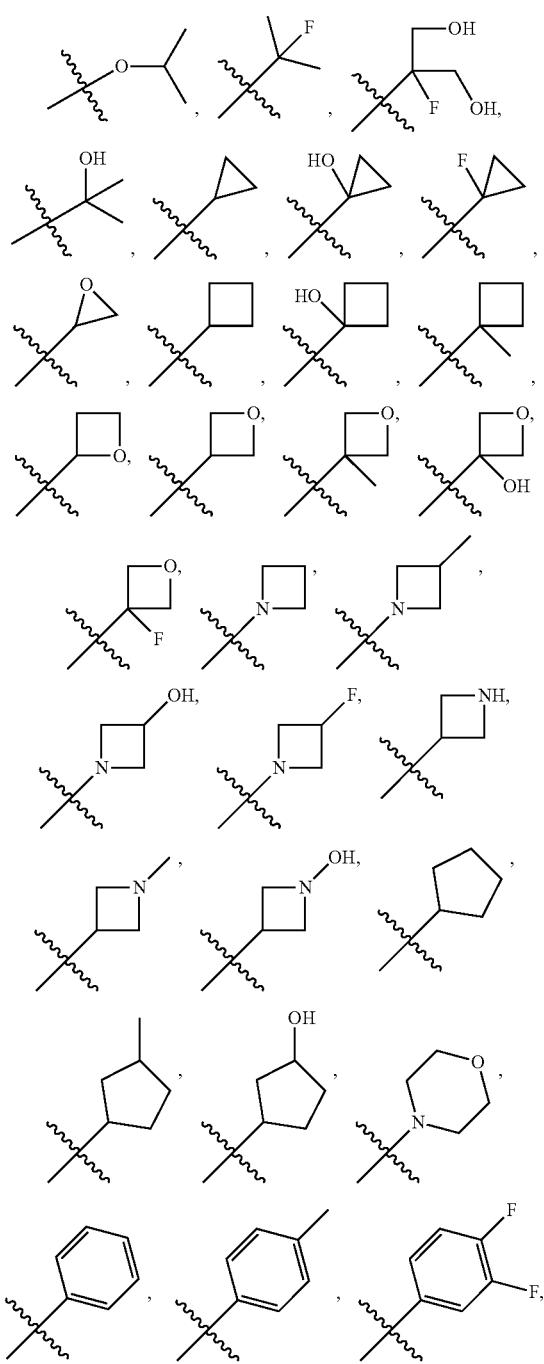

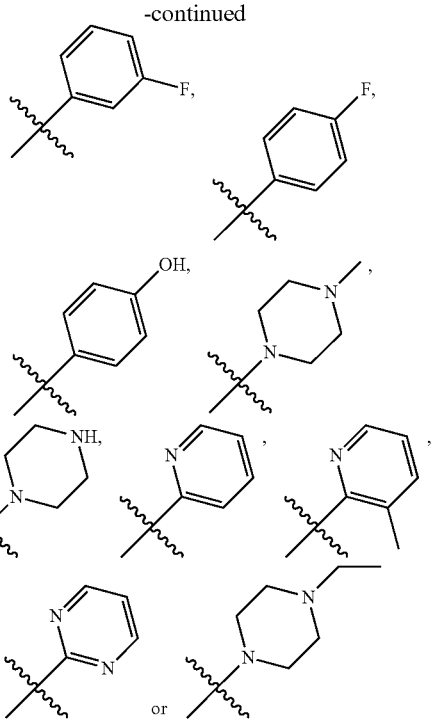

or

In some embodiments of Formula VI, each $X_1$ and $X_2$ is independently —H, deuterium, —F, —Cl, —Br, —I, —CN, —OH, —NH$_2$, —NO$_2$, carboxyl, $C_{1-3}$alkyl, $C_{1-3}$alkoxy, —$C_{1-3}$alkylene-NR$_2$R$_3$, —$C_{1-3}$alkylene-O—$C_{1-3}$alkyl, —$C_{1-3}$alkylene-CO—OR$_2$, —$C_{1-3}$alkylene-CO—NR$_2$R$_3$, —$C_{1-3}$alkylene-NR$_2$CO—NR$_2$R$_3$, —$C_{1-3}$alkylene-$C_{3-6}$heterocyclic ring, —$C_{1-3}$alkylene-$C_{5-6}$heteroaryl, —CO—$C_{3-6}$heterocyclic ring, —O—$C_{3-6}$carbocyclic ring, —NR$_2$—$C_{1-3}$alkylene-NR$_2$R$_3$, —NR$_2$—$C_{1-3}$alkylene-$C_{3-6}$heterocyclic ring, —CO—OR$_2$, —CO—NR$_2$OR$_2$, —CO—NR$_2$R$_3$, —N(R$_2$)(C=O)$_q$R$_2$, —N(R$_2$)(C=O)$_q$NR$_2$R$_3$, —N(R$_2$)(C=O)$_q$OR$_2$, —SO$_2$NR$_2$R$_3$, —NR$_2$SO$_2$R$_2$, —COR$_2$, or —SO$_2$R$_2$; and each of which is independently optionally substituted with $R_a$; and each $R_a$ is independently deuterium, —F, —Cl, —Br, —I, —CN, —OH, —NH$_2$, —NO$_2$, oxo, —CONH$_2$, —SO$_2$NH$_2$, —NH(C$_{1-3}$alkyl), —N(C$_{1-3}$alkyl)$_2$, —C$_{1-3}$alkyl, —C$_{1-3}$alkoxy, —S—C$_{1-3}$alkyl, —SO$_2$C$_{1-3}$alkyl, —NHSO$_2$C$_{1-3}$alkyl, —COC$_{1-3}$alkyl, —CO—C$_{1-3}$alkoxy, —NHCO—C$_{1-3}$alkoxy, —O—OC$_{1-3}$alkyl, or carboxyl.

In some embodiments of Formula VI, each $X_1$ and $X_2$ is independently —H, deuterium, —F, —Cl, —CN, —OH, —NH$_2$, methyl, ethyl, propyl, isopropyl, methoxy, ethoxy, propoxy, or isopropoxy; and each of which is independently optionally substituted with $R_a$; and $R_a$ is independently deuterium, —F, —Cl, —Br, —I, —CN, —OH, —NH$_2$, —NO$_2$, oxo, —CONH$_2$, —SO$_2$NH$_2$, —NHmethyl, —NHethyl, —NHpropyl, —NHisopropyl, methyl, ethyl, propyl, isopropyl, methoxy, ethoxy, propoxy, isopropoxy or carboxyl.

In some embodiments of Formula VI, each $X_1$ and $X_2$ is independently —H, methyl, ethyl, or —CF$_3$.

In some embodiments of Formula VI, $X_1$ and $X_2$ are both —H.

In some embodiments of Formula VI, $X_1$ combines with $X_2$, to form a 3-membered carbocyclic ring, 4-membered carbocyclic ring, 5-membered carbocyclic ring, 6-membered carbocyclic ring, 7-membered carbocyclic ring, 8-membered carbocyclic ring, 3-membered heterocyclic ring, 4-membered heterocyclic ring, 5-membered heterocyclic ring, 6-membered heterocyclic ring, 7-membered heterocyclic ring, or 8-membered heterocyclic ring, and each of the heterocyclic ring contains 1 or 2 selected from N, O or S; wherein the ring systems is optionally substituted with deuterium, —F, —Cl, —Br, —I, —$NH_2$, —CN, —OH, —$NO_2$, carbonyl, =O, oxo, carboxyl, $C_{1-3}$alkoxy, or $C_{1-3}$alkyl.

In some embodiments of Formula VI, $X_1$ combines with $X_2$, to form a 3-membered carbocyclic ring, 4-membered carbocyclic ring, 5-membered carbocyclic ring, 6-membered carbocyclic ring, 3-membered heterocyclic ring, 4-membered heterocyclic ring, 5-membered heterocyclic ring, or 6-membered heterocyclic ring, and each of the heterocyclic ring contains 1 or 2 selected from N or O; wherein the ring systems is optionally substituted with deuterium, —F, —Cl, —Br, —I, —$NH_2$, —CN, —OH, —$NO_2$, carbonyl, =O, oxo, carboxyl, methyl, ethyl, propyl, isopropyl, methoxy, ethoxy, propoxy, or isopropoxy.

In some embodiments of Formula VI, $X_1$ combines with $X_2$, to form a 3-membered carbocyclic ring, 4-membered carbocyclic ring, or 5-membered carbocyclic ring, wherein the ring systems is optionally substituted with deuterium, —F, —Cl, methyl or ethyl.

In some embodiments of Formula VI, $X_1$ combines with $X_2$, to form a 5-membered bridge ring.

In some embodiments of Formula VI, two $X_1$ can be joined together to form a 3-membered carbocyclic ring, 4-membered carbocyclic ring, 5-membered carbocyclic ring, 6-membered carbocyclic ring, 7-membered carbocyclic ring, 8-membered carbocyclic ring, 3-membered heterocyclic ring, 4-membered heterocyclic ring, 5-membered heterocyclic ring, 6-membered heterocyclic ring, 7-membered heterocyclic ring or 8-membered heterocyclic ring, and each of the heterocyclic ring contains 1, 2 or 3 heteroatoms selected from N, O or S, and wherein the ring systems is independently optionally substituted with deuterium, —F, —Cl, —Br, —I, —$NH_2$, —CN, —OH, —$NO_2$, carbonyl, =O, oxo, carboxyl, $C_{1-3}$alkoxy, $C_{1-3}$alkyl, —NH($C_{1-3}$alkyl), —N($C_{1-3}$alkyl)$_2$, —$SO_2C_{1-3}$alkyl, 3-membered carbocyclic ring, 4-membered carbocyclic ring, 5-membered carbocyclic ring, or 6-membered carbocyclic ring.

In some embodiments of Formula VI, two $X_1$ can be joined together to form a 3-membered carbocyclic ring, 4-membered carbocyclic ring, 5-membered carbocyclic ring, 6-membered carbocyclic ring, 3-membered heterocyclic ring, 4-membered heterocyclic ring, 5-membered heterocyclic ring, or 6-membered heterocyclic ring, and each of the heterocyclic ring contains 1 or 2 heteroatom selected from N or O; and wherein the ring systems is independently optionally substituted with deuterium, —F, —Cl, —Br, —I, —$NH_2$, —CN, —OH, —$NO_2$, carbonyl, =O, oxo, carboxyl, methyl, ethyl, propyl, isopropyl, methoxy, ethoxy, propoxy, or isopropoxy, —NHmethyl, —NHethyl, —NHpropyl, or —NHisopropyl.

In some embodiments of Formula VI, two $X_1$ can be joined together to form a cyclopropyl, cyclobutyl, or cyclopentyl, and each of which is independently optionally substituted with deuterium, —F, —Cl, —$NH_2$, —CN, —OH, oxo, carboxyl, methyl, ethyl, propyl, isopropyl, methoxy, ethoxy, propoxy, or isopropoxy.

In some embodiments of Formula VI, two $X_1$ can be joined together to form a cyclopropyl or cyclobutyl.

In some embodiments of Formula VI, each of $R_2$ and $R_3$ is independently —H, deuterium, —F, —Cl, —Br, —I, —CN, —OH, —$N_3$, —$NO_2$, $C_{1-3}$alkyl, $C_{1-3}$alkoxy, $C_{2-4}$alkenyl, —NH($C_{1-3}$alkyl), —N($C_{1-3}$alkyl)$_2$, —NH—O—$C_{1-3}$alkyl, —NH—$C_{1-3}$alkylene-O—$C_{1-3}$alkylene, 5-membered heterocyclic ring, 6-membered heterocyclic ring, 7-membered heterocyclic ring, 8-membered heterocyclic ring, 9-membered heterocyclic ring, 5-membered carbocyclic ring, 6-membered carbocyclic ring, 7-membered carbocyclic ring, 8-membered carbocyclic ring, or 9-membered carbocyclic ring, and each of the heterocyclic ring contains 1 or 2 heteroatoms selected from N, O or S; and each of which is independently optionally substituted with deuterium, —F, —Cl, —Br, —I, —$NH_2$, —CN, —OH, —$NO_2$, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —N($CH_3$)$_2$, —$SCH_3$, —$SO_2CH_3$, or 3-membered carbocyclic ring.

In some embodiments of Formula VI, each of $R_2$ and $R_3$ is independently —H, deuterium, —F, —Cl, —Br, —I, —CN, —OH, —$N_3$, —$NO_2$, methyl, ethyl, propyl, isopropyl, methoxy, ethoxy, propoxy, isopropoxy, —NHmethyl, —NHethyl, —NHpropyl, —NHisopropyl, —$NHOCH_3$, —$NHOCH_2CH_3$, —$NHCH_2OCH_3$, —$NHOCH_2CH_2CH_3$, —$NHCH_2OCH_2CH_3$, —$NHCH_2CH_2OCH_3$, —NHOCH($CH_3$)$_2$, 5-membered heterocyclic ring, 6-membered heterocyclic ring, 5-membered carbocyclic ring, or 6-membered carbocyclic ring, and each of the heterocyclic ring contains 1 or 2 heteroatoms selected from N or O; and each of which is independently optionally substituted with deuterium, —F, —Cl, —$NH_2$, —CN, —OH, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —N($CH_3$)$_2$, —$SCH_3$, —$SO_2CH_3$, or 3-membered carbocyclic ring.

In some embodiments of Formula VI, each of $R_2$ and $R_3$ is independently —H, deuterium, —F, —Cl, —CN, —OH, methyl, ethyl, propyl, isopropyl, methoxy, ethoxy, propoxy, isopropoxy, —NHmethyl, —NHethyl, —NHpropyl, —NHisopropyl, —N($CH_3$)$_2$, —$SCH_3$, —$SO_2CH_3$, —$CH_2F$, —$CHF_2$, —$CF_3$, —$CH_2D$, $CHD_2$, —$CD_3$, —$CH_2CH_2F$, —$CH_2CHF_2$, —$CH_2CD_3$, —$CH_2CF_3$, —$CH_2CH_2NH_2$, —$CH_2CH_2NHCH_3$, —$CH_2CH_2N(CH_3)_2$, —$CH_2CH_2CH_2F$, —$CH_2CH_2CD_3$, —$CH_2CH_2CF_3$, —$CH_2N(CH_3)_2$, —CH($CH_3$)($CD_3$), —CH($CF_3$)$_2$, —CH($CD_3$)$_2$, —$CH_2$NHmethyl, —$CH_2$NHethyl, —$CH_2$NHpropyl, or —$CH_2$NHisopropyl.

In some embodiments of Formula VI, q is 0 or 1.

In some embodiments of Formula VI, Y is O, —$(CH_2)_m$CO—$(CH_2)_m$—, —$(CH_2)_mSO_2$—$(CH_2)_m$—, or —$(CH_2)_mCR_4R_5$—$(CH_2)_m$—.

In some embodiments of Formula VI, m is 0 or 1.

In some embodiments of Formula VI, $R_4$ and $R_5$ is independently selected from —H; deuterium; —F, —Cl, —Br, —I, —CN; carbonyl; =O; oxo; carboxyl; $C_{1-3}$alkoxy; $C_{1-3}$alkyl; or $C_{1-3}$alkyl or $C_{1-3}$alkoxy independently substituted with deuterium, —F, —Cl, —Br, —I, —$NH_2$, —CN, —OH, —$NO_2$, carboxyl, oxo, =O, —$CONH_2$, —$C_{1-3}$alkoxy, —$C_{1-3}$alkyl, —$C_{1-3}$alkylene-O—$C_{1-3}$alkyl, —$C_{1-3}$alkylene-COOH, —$C_{1-3}$alkylene-$NHCONH_2$, —CO—N($C_{1-3}$alky)$_2$, —$C_{1-3}$alkylene-NHCO—$C_{1-3}$alkyl, —CO—CO—N($C_{1-3}$alkyl)$_2$, —CO—$C_{1-3}$alkyl, —$SONH_2$, —$SO_2NH_2$, —$SOC_{1-3}$alky, —$SO_2C_{1-3}$alky, 3-membered heterocyclic ring, 4-membered heterocyclic ring, 5-membered heterocyclic ring, 6-membered heterocyclic ring, 5-membered heteroaryl, or 6-membered heteroaryl; and each of the heteroaryl contains 1, 2 or 3 heteroatoms selected from N or O; each of the heterocyclic ring contains 1 or 2 heteroatoms selected from N or O; or $R_4$ combines with $R_5$, to form a 3-membered carbocyclic ring, 4-membered carbocyclic ring, 5-membered carbocyclic ring, 6-membered carbocyclic ring, 7-membered carbocyclic ring, 8-membered carbocyclic ring, 3-member heterocyclic ring, 4-member heterocyclic ring, 5-member heterocyclic ring, 6-member heterocyclic ring, 7-member heterocyclic ring, or 8-member heterocyclic ring, and each of the heterocyclic ring contains 1, 2 or 3 heteroatoms selected from N, O or S; and each of which is independently optionally substituted deuterium, —F, —Cl, —Br, —I, —NH$_2$, —CN, —OH, —NO$_2$, carbonyl, =O, oxo, carboxyl, C$_{1-3}$alkoxy, C$_{1-3}$alkyl, —NH(C$_{1-3}$alkyl), —N(C$_{1-3}$alkyl)$_2$, —S—C$_{1-3}$alkyl, —SO$_2$C$_{1-3}$alkyl, 3-membered carbocyclic ring, 4-membered carbocyclic ring, 5-membered carbocyclic ring, or 6-membered carbocyclic ring.

In some embodiments of Formula VI, R$_4$ and R$_5$ is independently selected from —H; deuterium; —F, —Cl, —Br, —I, —CN; carbonyl; =O; oxo; carboxyl; methyl; ethyl; propyl; isopropyl; methoxy; ethoxy; propoxy; isopropoxy; or C$_{1-3}$alkyl or C$_{1-3}$alkoxy independently substituted with deuterium, —F, —Cl, —Br, —I, —NH$_2$, —CN, —OH, —NO$_2$, carboxyl, oxo, =O, —CONH$_2$, methyl, ethyl, propyl, isopropyl, methoxy, ethoxy, propoxy, isopropoxy, —NHmethyl, —NHethyl, —NHpropyl, —NHisopropyl, —CH$_2$OCH$_3$, —CH$_2$OCH$_2$CH$_3$, —CH$_2$OCH(CH$_3$)$_2$, —NHOCH$_2$CH$_3$, —CH$_2$—NHCONH$_2$, —CO—N(CH$_3$)$_2$, —CH$_2$—NHCO—C$_{1-3}$alkyl, —CO—CH$_3$, —SONH$_2$, —SO$_2$NH$_2$, —SOCH$_3$, —SO$_2$CH$_3$, 3-membered heterocyclic ring which contains 1 heteroatoms selected from N or O; or R$_4$ combines with R$_5$, to form a 3-membered carbocyclic ring, 4-membered carbocyclic ring, 5-membered carbocyclic ring, 4-member heterocyclic ring, or 5-member heterocyclic ring, and each of the heterocyclic ring contains 1 heteroatoms selected from N or O; and each of which is independently optionally substituted deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —SCH$_3$, —SO$_2$CH$_3$, or 3-membered carbocyclic ring.

In some embodiments of Formula VI, R$_4$ and R$_5$ is independently selected from —H; deuterium; —F, —Cl, —Br, —I, —CN; carbonyl; =O; oxo; carboxyl; methyl; ethyl; propyl; isopropyl; methoxy; ethoxy; propoxy; isopropoxy; or methyl, ethyl, propyl, isopropyl, methoxy, ethoxy, propoxy or isopropoxy independently substituted with deuterium, —F, —Cl, —Br, —NH$_2$, —CN, —OH, —NO$_2$, carboxyl, oxo, =O, —CONH$_2$, methyl, ethyl, propyl, isopropyl, methoxy, ethoxy, propoxy, isopropoxy, —NHmethyl, —NHethyl, —NHpropyl, or —NHisopropyl; or R$_4$ combines with R$_5$, to form a cyclopropyl, cyclobutyl, cyclopentyl, 4-membered heterocyclic ring, 5-membered heterocyclic ring, and each of the heterocyclic ring contains 1 heteroatoms selected from O; and each of which is independently optionally substituted deuterium, —F, —Cl, —Br, —NH$_2$, —CN, —OH, carbonyl, =O, oxo, carboxyl, methyl, ethyl, propyl, isopropyl, methoxy, ethoxy, propoxy, isopropoxy, —NHmethyl, —NHethyl, —NHpropyl, or —NHisopropyl.

In some embodiments of Formula VI, R$_4$ and R$_5$ is independently selected from —H, deuterium, —F, methyl, —CH$_2$D, —CHF$_2$, —CH$_2$F, —CD$_2$H, —CD$_3$, —CF$_3$, or R$_4$ combines with R$_5$, to form cyclopropyl, cyclobutyl, or

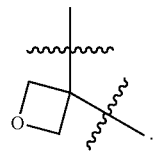

In some embodiments of Formula VI, Y is independently selected from O, —CH$_2$—, —CH$_2$—CH$_2$—, —CH$_2$CF$_2$—, —CF$_2$—, —CF$_2$CH$_2$—, —CH(CH$_3$)—, —C(CH$_3$)$_2$—, —CH(CF$_3$)—, —CO—, —SO$_2$—, —CH$_2$—CO—, —CH$_2$—SO$_2$—, —CO—CH$_2$—, —SO$_2$—CH$_2$—,

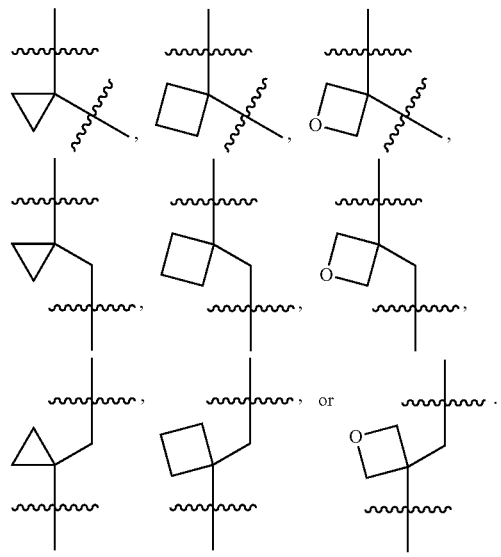

In some embodiments of Formula VI, Ar$_2$ is a 6-membered aryl, 7-membered aryl, 8-membered aryl, 9-membered aryl, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl, 6-membered heteroaryl, 7-membered heteroaryl, 8-membered heteroaryl, or 9-membered heteroaryl; each of the heteroaryl contains 1, 2, 3 heteroatoms selected from N, O or S; and each of which is independently optionally substituted with one or more of deuterium; —F; —Cl; —Br; —I; —CN; —OH; —NH$_2$; —NO$_2$; carbonyl; =O; oxo; methyl; ethyl; propyl; isopropyl; methoxy; ethoxy; propoxy; isopropoxy; or C$_{1-3}$alkyl or C$_{1-3}$alkoxy independently substituted with deuterium, —F, —Cl, —Br, —I, —NH$_2$, —CN, —OH, —NO$_2$, carboxyl, oxo, =O, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, or 3-membered carbocyclic ring.

In some embodiments of Formula VI, Ar$_2$ is a 6-membered aryl, 5-membered heteroaryl or 9-membered heteroaryl, and each of the heteroaryl contains 1 or 2 heteroatoms selected from N, O or S; and each of which is independently optionally substituted with one or more of deuterium, —F, —Cl, —Br, —CN, —OH, —NH$_2$, carbonyl, =O, oxo, methyl, ethyl, propyl, isopropyl, methoxy, ethoxy, propoxy, isopropoxy, —CH$_2$F, —CHF$_2$, —CF$_3$, —CH$_2$D, CHD$_2$, —CD$_3$.

In some embodiments of Formula VI, Ar₂ is a phenyl,
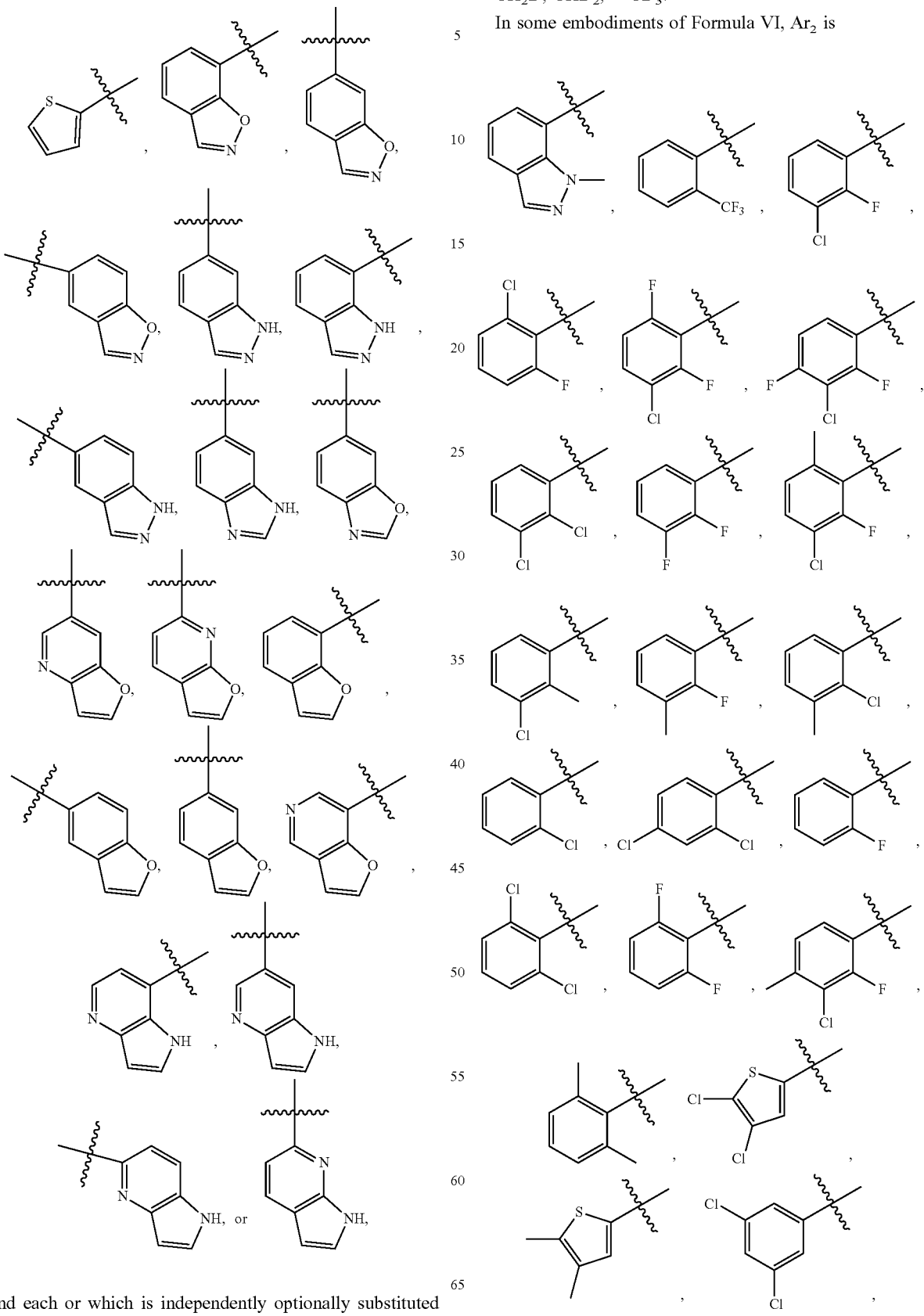
and each or which is independently optionally substituted with one or more of deuterium, —F, —Cl, —Br, —CN, —OH, —NH₂, methyl, ethyl, propyl, isopropyl, methoxy, ethoxy, propoxy, isopropoxy, —CH₂F, —CHF₂, —CF₃, —CH₂D, CHD₂, —CD₃.
In some embodiments of Formula VI, Ar₂ is

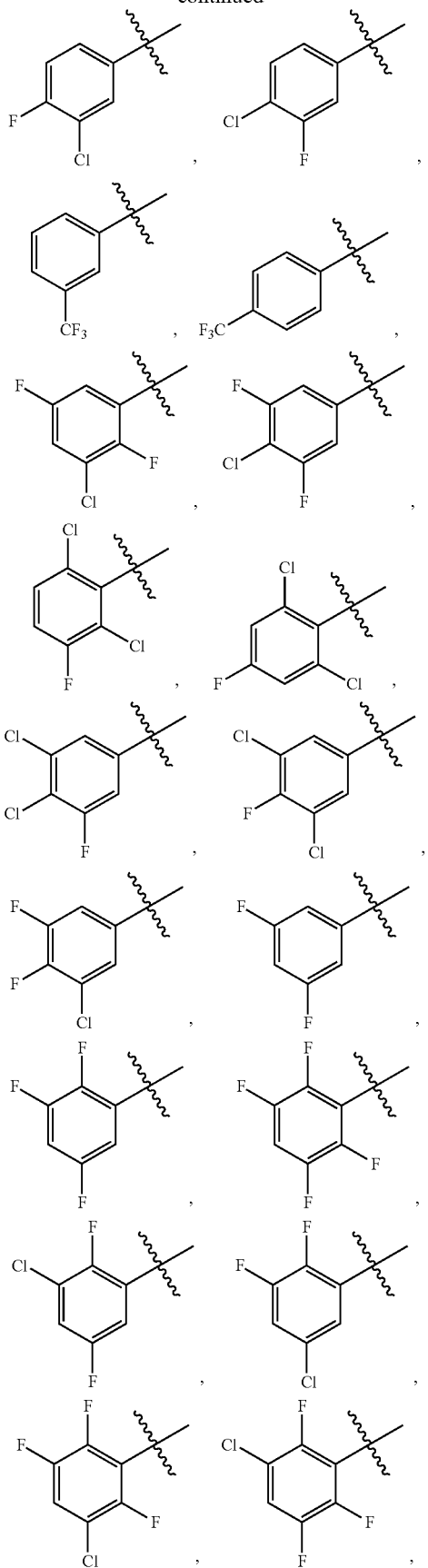

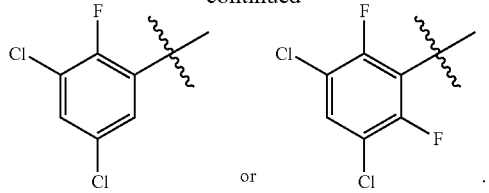

In some embodiments of Formula VI, $Ar_1$ is 5-membered heteroaryl, 6-membered heteroaryl, 7-membered heteroaryl, or 8-membered heteroaryl; each of the heteroaryl contains 1 or 2 heteroatoms selected from N, O or S; and each of which is independently optionally substituted with one or more of deuterium; —F; —Cl; —Br; —I; —CN; —OH; —NH₂; —NO₂; carbonyl; =O; oxo; $C_{1-3}$alkyl; $C_{1-3}$alkoxy; or $C_{1-3}$alkyl or $C_{1-3}$alkoxy independently substituted with deuterium, —F, —Cl, —Br, —I, —NH₂, —CN, —OH, —NO₂, carboxyl, oxo, =O, $C_{1-3}$alkoxy, $C_{1-3}$alkyl, —NH($C_{1-3}$alkyl), —N($C_{1-3}$alkyl)₂, —S—$C_{1-3}$alkyl, —SO₂$C_{1-3}$alkyl, 3-membered carbocyclic ring, 4-membered carbocyclic ring, 5-membered carbocyclic ring, or 6-membered carbocyclic ring.

In some embodiments of Formula VI, $Ar_1$ is 5-membered heteroaryl which contains 1 or 2 heteroatoms selected from N or S, and which is independently optionally substituted with one or more of deuterium; —F; —Cl; —Br; —I; —CN; —OH; —NH₂; carbonyl; =O; oxo; methyl; ethyl; propyl; isopropyl; methoxy; ethoxy; propoxy; isopropoxy; —CH₂F, —CHF₂, —CF₃, —CH₂D, CHD₂, —CD₃, —CH₂NHmethyl, —CH₂NHethyl, —CH₂NHpropyl, —CH₂NHisopropyl, —CH₂N(CH₃)₂.

In some embodiments of Formula VI, $Ar_1$ is

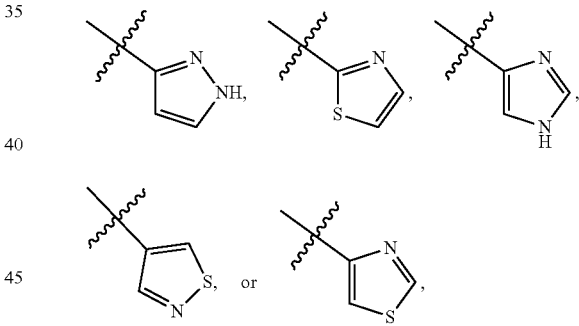

and which is independently optionally substituted with one or more of deuterium, —F, —Cl, —Br, —I, —CN, —OH, —NH₂, carbonyl, =O, oxo, methyl, ethyl, propyl, isopropyl, methoxy, ethoxy, propoxy, or isopropoxy.

In some embodiments of Formula VI, $Ar_1$ is

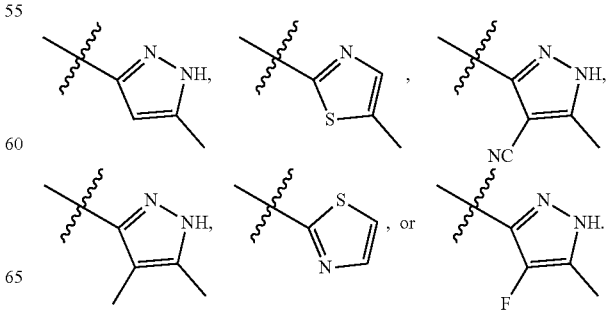

In some embodiments of Formula I or II, the compound is of Formula VII:

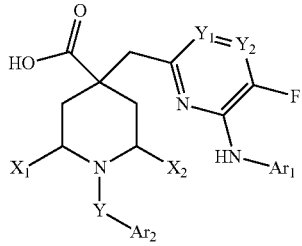

VII wherein, $Y_1$ is independently CH or $CR_{Y1}$;

$Y_2$ is independently CH or $CR_{Y2}$;

$R_{Y2}$ and $R_{Y2}$ is independently selected from deuterium, halogen, —CN, —OH, —NH$_2$, —NO$_2$, —NH(C$_{1-6}$alkyl), —N(C$_{1-6}$alkyl)$_2$, —CO—C$_{1-6}$alkyl, —S—C$_{1-6}$alkyl, —SO—C$_{1-6}$alkyl, —SO$_2$, —SO$_2$C$_{1-6}$alkyl, C$_{1-6}$alkyl, C$_{1-6}$alkoxy, C$_{3-10}$carbocyclic ring, C$_{6-10}$aryl, C$_{3-10}$heterocyclic ring or C$_{5-10}$heteroaryl, and each of the heterocyclic ring and heteroaryl contains 1, 2 or 3 heteroatoms selected from N, O or S; and each of which is independently optionally substituted with deuterium, halogen, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, or —SO$_2$C$_{1-6}$alkyl;

each $X_1$ and $X_2$ is independently selected from —H, deuterium, halogen, —CN, —OH, —NH$_2$, —NO$_2$, carboxyl, C$_{1-6}$alkyl, C$_{1-6}$alkoxy, —C$_{1-6}$alkylene-NR$_2$R$_3$, —C$_{1-6}$alkylene-O—C$_{1-6}$alkyl, —C$_{1-6}$alkylene-CO—OR$_2$, —C$_{1-6}$alkylene-CO—NR$_2$R$_3$, —C$_{1-6}$alkylene-NR$_2$CO—NR$_2$R$_3$, —C$_{1-6}$alkylene-NR$_2$—COC$_{1-6}$alkyl, —C$_{1-6}$alkylene-C$_{3-10}$heterocyclic ring, —C$_{1-6}$alkylene-C$_{5-10}$heteroaryl, —CO—C$_{1-6}$alkylene-NR$_2$R$_3$, —CO—NR$_2$—C$_{3-10}$heterocyclic ring, —CO—C$_{3-10}$heterocyclic ring, —O—C$_{1-6}$alkylene-CO—OR$_2$, —O—C$_{1-6}$alkylene-CO—NR$_2$R$_3$, —O—C$_{1-6}$alkylene-NR$_2$R$_3$, —O—C$_{3-10}$heterocyclic ring, —O—C$_{3-10}$carbocyclic ring, —NR$_2$—C$_{1-6}$alkylene-NR$_2$R$_3$, —NR$_2$—C$_{1-6}$alkylene-C$_{3-10}$heterocyclic ring, —NR$_2$—C$_{1-6}$alkylene-C$_{5-10}$heteroaryl, —NR$_2$—CO—C$_{5-10}$heteroaryl, —CO—OR$_2$, —CONH$_2$, —CO—NR$_2$OR$_2$, —CO—NR$_2$R$_3$, —NR$_2$R$_3$, —N(R$_2$)(C=O)$_q$R$_2$, —N(R$_2$)(C=O)$_q$NR$_2$R$_3$, —N(R$_2$)(C=O)$_q$OR$_2$, —SO$_2$NR$_2$R$_3$, NR$_2$SO$_2$R$_2$, COR$_2$, SO$_2$R$_2$, C$_{6-10}$aryl, C$_{5-10}$heteroaryl, C$_{3-10}$heterocyclic ring, or C$_{3-10}$carbocyclic ring; and each of which is independently optionally substituted with R$_a$; and each R$_a$ is independently deuterium, halogen, —CN, —OH, —NH$_2$, —NO$_2$, oxo, —CONH$_2$, —SO$_2$NH$_2$, —NH(C$_{1-6}$alkyl), —N(C$_{1-6}$alkyl)$_2$, —C$_{1-6}$alkyl, —C$_{1-6}$alkoxy, —S—C$_{1-6}$alkyl, —SO$_2$C$_{1-6}$alkyl, —NHSO$_2$C$_{1-6}$alkyl, —COC$_{1-6}$alkyl, —CO—C$_{1-6}$alkoxy, —NHCO—C$_{1-6}$alkoxy, —O—OC$_{1-6}$alkyl, or carboxyl; and each q is independently 0, 1, 2 or 3; or $X_1$ combines with $X_2$, to form a C$_{3-10}$carbocyclic ring or a C$_{3-10}$heterocyclic ring which contains 1, 2 or 3 heteroatoms selected from N, O or S, wherein each of the ring systems is independently optionally substituted with deuterium, halogen, —CN, —OH, C$_{1-6}$alkoxy, or C$_{1-6}$alkyl; or Each of $R_2$ and $R_3$ is independently selected from —H, deuterium, halogen, —NH$_2$, —CN, —OH, —N$_3$, —NO$_2$, C$_{1-6}$alkyl, C$_{1-6}$alkoxy, C$_{2-6}$alkenyl, —NH(C$_{1-6}$alkyl), —N(C$_{1-6}$alkyl)$_2$, —NH—O—C$_{1-6}$alkyl, —NH—C$_{1-6}$alkylene-O—C$_{1-6}$alkylene, C$_{5-10}$heterocyclic ring or C$_{5-10}$carbocyclic ring, and each of the heterocyclic ring contains 1, 2 or 3 heteroatoms selected from N, O or S; and each of which is independently optionally substituted with deuterium, halogen, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-8}$carbocyclic.

Y is selected from O, S, SO, —(CH$_2$)$_m$CO—(CH$_2$)$_m$—, —(CH$_2$)$_m$SO$_2$—(CH$_2$)$_m$—, or —(CH$_2$)$_m$—CR$_4$R$_5$—(CH$_2$)$_m$—, and m is independently 0, 1, 2 or 3;

$R_4$ and $R_5$ is independently selected from —H; deuterium; halogen; —CN; carbonyl; =O; oxo; carboxyl; C$_{1-6}$alkoxy; C$_{1-6}$alkyl; or C$_{1-6}$alkyl or C$_{1-6}$alkoxy independently substituted with deuterium, halogen, —NH$_2$, —CN, —OH, —NO$_2$, carboxyl, oxo, =O, —CONH$_2$, —C$_{1-6}$alkoxy, —C$_{1-6}$alkyl, —C$_{1-6}$alkylene-O—C$_{1-6}$alkyl, —C$_{1-6}$alkylene-COOH, —C$_{1-6}$alkylene-NHCONH$_2$, —CO—N(C$_{1-6}$alky)$_2$, —C$_{1-6}$alkylene-NHCO—C$_{1-6}$alkyl, —CO—CO—N(C$_{1-6}$alkyl)$_2$, —CO—C$_{1-6}$alkyl, —SONH$_2$, —SO$_2$NH$_2$, —SO C$_{1-6}$alky, —SO$_2$C$_{1-6}$alky, —C$_{3-10}$heterocyclic or —C$_{5-10}$heteroaryl; or $R_4$ combines with $R_5$, to form C=O, a C$_{3-10}$carbocyclic ring, or a C$_{3-10}$heterocyclic ring which contains 1, 2 or 3 heteroatoms selected from N, O or S, and each of which is independently optionally substituted deuterium, halogen, —NH$_2$, —CN, —OH, —NO$_2$, carbonyl, =O, oxo, carboxyl, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-8}$carbocyclic;

$Ar_2$ is selected from C$_{6-10}$aryl, C$_{3-8}$carbocyclic or C$_{5-10}$heteroaryl which contains at 1, 2 or 3 heteroatoms selected from N, O or S; and each of which is independently optionally substituted with deuterium; halogen; —CN; —OH; —NH$_2$; —NO$_2$; carbonyl; =O; oxo; C$_{1-6}$alkyl; C$_{1-6}$alkoxy; or C$_{1-6}$alkyl or C$_{1-6}$alkoxy independently substituted with one or more of deuterium, halogen, —NH$_2$, —CN, —OH, —NO$_2$, carboxyl, oxo, =O, C$_{1-6}$alkoxy, C$_{1-6}$alkyl, —NH(C$_{1-6}$alkyl), —N(C$_{1-6}$alkyl)$_2$, —S—C$_{1-6}$alkyl, or —SO$_2$C$_{1-6}$alkyl;

$Ar_1$ is selected from C$_{6-10}$aryl, C$_{3-8}$carbocyclic or C$_{5-10}$heteroaryl which contains at 1, 2 or 3 heteroatoms selected from N, O or S; and each of which is independently optionally substituted with deuterium; halogen; —CN; —OH; —NH$_2$; —NO$_2$; carbonyl; =O; oxo; C$_{1-6}$alkyl; C$_{1-6}$alkoxy; or C$_{1-6}$alkyl or C$_{1-6}$alkoxy independently substituted with one or more of deuterium, halogen, —NH$_2$, —CN, —OH, —NO$_2$, carboxyl, oxo, =O, C$_{1-6}$alkoxy, C$_{1-6}$alkyl, —NH(C$_{1-6}$alkyl), —N(C$_{1-6}$alkyl)$_2$, —S—C$_{1-6}$alkyl, —SO$_2$C$_{1-6}$alkyl, or —C$_{3-8}$carbocyclic.

In some embodiments of Formula VII, $R_{Y1}$ and $R_{Y2}$ is independently selected from deuterium, —F, —Cl, —Br, —I, —CN, —OH, —NH$_2$, —NO$_2$, —NH(C$_{1-3}$alkyl), —N(C$_{1-3}$alkyl)$_2$, —CO—C$_{1-3}$alkyl, —S—C$_{1-3}$alkyl, —SO—C$_{1-3}$alkyl, —SO$_2$, —SO$_2$C$_{1-3}$alkyl, C$_{1-3}$alkyl, C$_{1-3}$alkoxy, 3-membered carbocyclic ring, 4-membered carbocyclic ring, 5-membered carbocyclic ring, 6-membered carbocyclic ring, 7-membered carbocyclic ring, 8-membered carbocyclic ring, 5-membered aryl, 6-membered aryl, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl or 6-membered heteroaryl, and each of the heterocyclic ring and heteroaryl contains 1, 2 or 3 heteroatoms selected from N, O or S; and each of which is independently optionally substituted with deuterium, —F, —Cl, —Br, —I, —NH$_2$, —CN, —OH, —NO₂, carbonyl, =O, oxo, carboxyl, C₁₋₃alkoxy, C₁₋₃alkyl, —NH(C₁₋₃alkyl), —N(C₁₋₃alkyl)₂, —S—C₁₋₃alkyl, or —SO₂C₁₋₃alkyl.

In some embodiments of Formula VII, R$_{Y1}$ and R$_{Y2}$ is independently selected from deuterium, —F, —Cl, —Br, —I, —CN, —OH, —NH₂, —NO₂, methyl, ethyl, propyl, isopropyl, methoxy, ethoxy, propoxy, isopropoxy, —NHmethyl, —NHethyl, —NHpropyl, —NHisopropyl, —N(CH₃)₂, —COCH₃, —COCH₂CH₃, —CO—C(CH₃)₂, —SCH₃, —SOCH₃, —SO₂, —SO₂CH₃, 3-membered carbocyclic ring, 4-membered carbocyclic ring, 5-membered carbocyclic ring, 6-membered aryl, 3-membered heterocyclic ring, 4-membered heterocyclic ring, 5-membered heterocyclic ring, 6-membered heterocyclic ring, or 6-membered heteroaryl; and each of the heterocyclic ring and heteroaryl contains 1 or 2 heteroatoms selected from N or O; and each of which is independently optionally substituted with deuterium, —F, —Cl, —Br, —I, —NH₂, —CN, —OH, —NO₂, carbonyl, =O, oxo, carboxyl, methyl, ethyl, propyl, isopropyl, methoxy, ethoxy, propoxy, isopropoxy.

In some embodiments of Formula VII, R$_{Y1}$ and R$_{Y2}$ is independently selected from deuterium, —F, —Cl, —Br, —I, —CN, —OH, —NH₂, —NO₂, methyl, ethyl, propyl, isopropyl, methoxy, ethoxy, propoxy, isopropoxy, —NHmethyl, —NHethyl, —NHpropyl, —NHisopropyl, —N(CH₃)₂, —COCH₃, —COCH₂CH₃, —CO—C(CH₃)₂, —SCH₃, —SOCH₃, —SO₂, —SO₂CH₃,

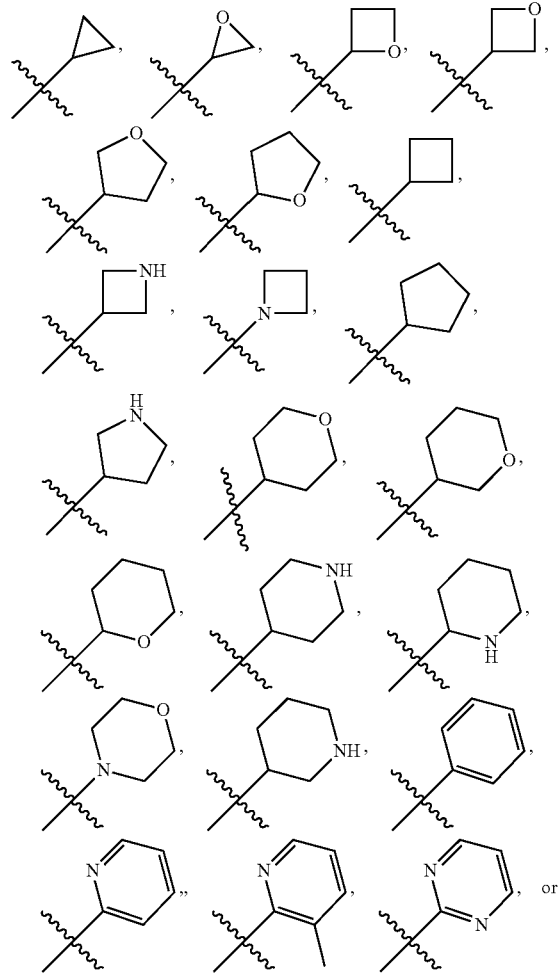

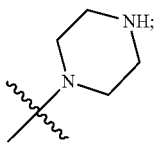

and each of which is independently optionally substituted with deuterium, —F, —Cl, —NH₂, —CN, —OH, carbonyl, =O, oxo, carboxyl, methyl, ethyl, propyl, isopropyl, methoxy, ethoxy, propoxy, isopropoxy.

In some embodiments of Formula VII, R$_{Y1}$ and R$_{Y2}$ is independently selected from deuterium, —F, —Cl, —CN, methyl, ethyl, isopropyl, —NHmethyl, —COCH₃, —SOCH₃, —SO₂, —SO₂CH₃, —CHF₂, —CF₃, —COCH₃, —COCH₂CH₃, —CO—C(CH₃)₂, —CH(F) CH₃, —C(F)₂CH₃, —OCH₃, —OCF₃, —CH₂OH, —CH₂CH₂OH, —CHOHCH₃; —CH₂F, —CH₂D, CHD₂, —CD₃, —CH₂CH₂F, —CH₂CHF₂, —CH₂CD₃, —CH₂CF₃, —CH₂CH₂NH₂, —CH₂CH₂NHCH₃, —CH₂CH₂N(CH₃)₂, —CH₂CH₂CH₂F, —CH₂CH₂CD₃, —CH₂CH₂CF₃, —CH₂N(CH₃)₂, —CH(CH₃)(CD₃), —CH(CF₃)₂, —CH(CD₃)₂, —CH₂NHmethyl, —CH₂NHethyl, —CH₂NHpropyl, —CH₂NHisopropyl,

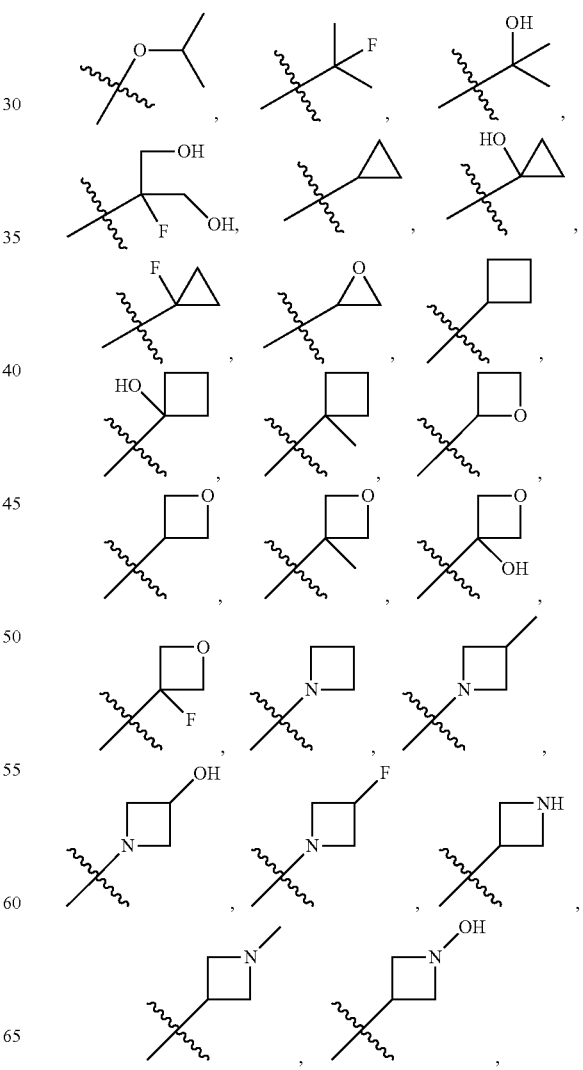

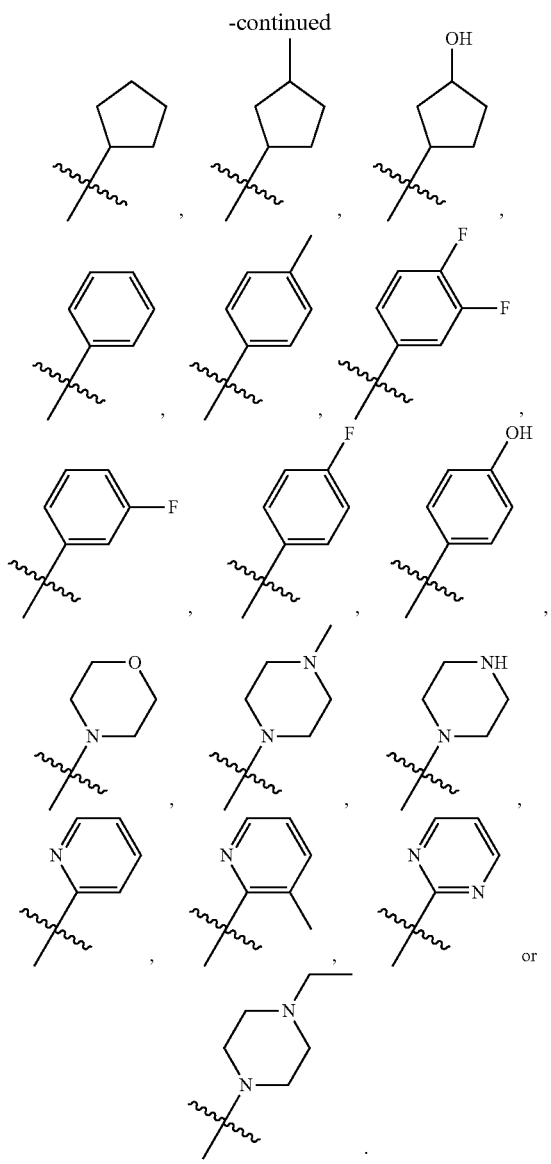

In some embodiments of Formula VII, each $X_1$ and $X_2$ is independently selected from —H, deuterium, —F, —Cl, —Br, —I, —CN, —OH, —NH$_2$, —NO$_2$, carboxyl, $C_{1-3}$alkyl, $C_{1-3}$alkoxy, —$C_{1-3}$alkylene-NR$_2$R$_3$, —$C_{1-3}$alkylene-O—$C_{1-3}$alkyl, —$C_{1-3}$alkylene-CO—OR$_2$, —$C_{1-3}$alkylene-CO—NR$_2$R$_3$, —$C_{1-3}$alkylene-NR$_2$CO—NR$_2$R$_3$, —$C_{1-3}$alkylene-$C_{3-6}$heterocyclic ring, —$C_{1-3}$alkylene-$C_{5-6}$heteroaryl, —CO—$C_{3-6}$heterocyclic ring, —O—$C_{3-6}$carbocyclic ring, —NR$_2$—$C_{1-3}$alkylene-NR$_2$R$_3$, —NR$_2$—$C_{1-3}$alkylene-$C_{3-6}$heterocyclic ring, —CO—OR$_2$, —CO—NR$_2$OR$_2$, —CO—NR$_2$R$_3$, —N(R$_2$)(C=O)$_q$R$_2$, —N(R$_2$)(C=O)$_q$NR$_2$R$_3$, —N(R$_2$)(C=O)$_q$OR$_2$, —SO$_2$NR$_2$R$_3$, —NR$_2$SO$_2$R$_2$, —COR$_2$, or —SO$_2$R$_2$; and each of which is independently optionally substituted with R$_a$; and each R$_a$ is independently deuterium, —F, —Cl, —Br, —I, —CN, —OH, —NH$_2$, —NO$_2$, oxo, —CONH$_2$, —SO$_2$NH$_2$, —NH(C$_{1-3}$alkyl), —N(C$_{1-3}$alkyl)$_2$, —C$_{1-3}$alkyl, —C$_{1-3}$alkoxy, —S—C$_{1-3}$alkyl, —SO$_2$C$_{1-3}$alkyl, —NHSO$_2$C$_{1-3}$alkyl, —COC$_{1-3}$alkyl, —CO—C$_{1-3}$alkoxy, —NHCO—C$_{1-3}$alkoxy, —O—OC$_{1-3}$alkyl, or carboxyl.

In some embodiments of Formula VII, each $X_1$ and $X_2$ is independently selected from —H, deuterium, —F, —Cl, —CN, —OH, —NH$_2$, methyl, ethyl, propyl, isopropyl, methoxy, ethoxy, propoxy, or isopropoxy; and each of which is independently optionally substituted with R$_a$; and R$_a$ is independently deuterium, —F, —Cl, —Br, —I, —CN, —OH, —NH$_2$, —NO$_2$, oxo, —CONH$_2$, —SO$_2$NH$_2$, —NHmethyl, —NHethyl, —NHpropyl, —NHisopropyl, methyl, ethyl, propyl, isopropyl, methoxy, ethoxy, propoxy, isopropoxy or carboxyl.

In some embodiments of Formula VII, $X_1$ and $X_2$ is independently selected from —H, methyl, ethyl, or —CF$_3$.

In some embodiments of Formula VII, $X_1$ and $X_2$ are both —H.

In some embodiments of Formula VII, $X_1$ combines with $X_2$, to form a 3-membered carbocyclic ring, 4-membered carbocyclic ring, 5-membered carbocyclic ring, 6-membered carbocyclic ring, 7-membered carbocyclic ring, 8-membered carbocyclic ring, 3-membered heterocyclic ring, 4-membered heterocyclic ring, 5-membered heterocyclic ring, 6-membered heterocyclic ring, 7-membered heterocyclic ring, or 8-membered heterocyclic ring, and each of the heterocyclic ring contains 1 or 2 selected from N, O or S; wherein each of the ring systems is independently optionally substituted with deuterium, —F, —Cl, —Br, —I, —NH$_2$, —CN, —OH, —NO$_2$, carbonyl, =O, oxo, carboxyl, $C_{1-3}$alkoxy, or $C_{1-3}$alkyl.

In some embodiments of Formula VII, $X_1$ combines with $X_2$, to form an a 3-membered carbocyclic ring, 4-membered carbocyclic ring, 5-membered carbocyclic ring, 6-membered carbocyclic ring, 3-membered heterocyclic ring, 4-membered heterocyclic ring, 5-membered heterocyclic ring, or 6-membered heterocyclic ring, and each of the heterocyclic ring contains 1 or 2 selected from N or O; wherein each of the ring systems is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, or isopropoxy.

In some embodiments of Formula VII, $X_1$ combines with $X_2$, to form a 3-membered carbocyclic ring, 4-membered carbocyclic ring, or 5-membered carbocyclic ring, wherein each of the ring systems is independently optionally substituted with deuterium, —F, —Cl, methyl or ethyl.

In some embodiments of Formula VII, $X_1$ combines with $X_2$, to form a 5-membered bridge ring. In some embodiments of Formula VII, each of $R_2$ and $R_3$ is independently selected from —H, deuterium, —F, —Cl, —Br, —I, —CN, —OH, —N$_3$, —NO$_2$, $C_{1-3}$alkyl, $C_{1-3}$alkoxy, $C_{2-4}$alkenyl, —NH(C$_{1-3}$alkyl), —N(C$_{1-3}$alkyl)$_2$, —NH—O—C$_{1-3}$alkyl, —NH—C$_{1-3}$alkylene-O—C$_{1-3}$alkylene, 5-membered heterocyclic ring, 6-membered heterocyclic ring, 7-membered heterocyclic ring, 8-membered heterocyclic ring, 9-membered heterocyclic ring, 5-membered carbocyclic ring, 6-membered carbocyclic ring, 7-membered carbocyclic ring, 8-membered carbocyclic ring, or 9-membered carbocyclic ring, and each of the heterocyclic ring contains 1 or 2 heteroatoms selected from N, O or S; and each of which is independently optionally substituted with deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, or 3-membered carbocyclic ring.

In some embodiments of Formula VII, each of $R_2$ and $R_3$ is independently selected from —H, deuterium, —F, —Cl, —Br, —I, —CN, —OH, —N$_3$, —NO$_2$, methyl, ethyl, propyl, isopropyl, methoxy, ethoxy, propoxy, isopropoxy, —NHmethyl, —NHethyl, —NHpropyl, —NHisopropyl, —NHOCH$_3$, —NHOCH$_2$CH$_3$, —NHCH$_2$OCH$_3$, —NHOCH$_2$CH$_2$CH$_3$, —NHCH$_2$OCH$_2$CH$_3$, —NHCH$_2$CH$_2$OCH$_3$, —NHOCH(CH$_3$)$_2$, 5-membered heterocyclic ring, 6-membered heterocyclic ring, 5-membered carbocyclic ring, or 6-membered carbocyclic ring, and each of the heterocyclic ring contains 1 or 2 heteroatoms selected from N or O; and each of which is independently optionally substituted with deuterium, —F, —Cl, —NH$_2$, —CN, —OH, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, or 3-membered carbocyclic ring.

In some embodiments of Formula VII, each of R$_2$ and R$_3$ is independently selected from —H, deuterium, —F, —Cl, —CN, —OH, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, —CH$_2$F, —CHF$_2$, —CF$_3$, —CH$_2$D, CHD$_2$, —CD$_3$, —CH$_2$CH$_2$F, —CH$_2$CHF$_2$, —CH$_2$CD$_3$, —CH$_2$CF$_3$, —CH$_2$CH$_2$NH$_2$, —CH$_2$CH$_2$NHCH$_3$, —CH$_2$CH$_2$N(CH$_3$)$_2$, —CH$_2$CH$_2$CH$_2$F, —CH$_2$CH$_2$CD$_3$, —CH$_2$CH$_2$CF$_3$, —CH$_2$N(CH$_3$)$_2$, —CH(CH$_3$)(CD$_3$), —CH(CF$_3$)$_2$, —CH(CD$_3$)$_2$, —CH$_2$NHmethyl, —CH$_2$NHethyl, —CH$_2$NHpropyl, or —CH$_2$NHisopropyl.

In some embodiments of Formula VII, q is 0 or 1.

In some embodiments of Formula VII, Y is selected from O, —(CH$_2$)$_m$CO—(CH$_2$)$_m$—, —(CH$_2$)$_m$SO$_2$—(CH$_2$)$_m$—, or —(CH$_2$)$_m$—CR$_4$R$_5$—(CH$_2$)$_m$—.

In some embodiments of Formula VII, m is 0 or 1.

In some embodiments of Formula VII, R$_4$ and R$_5$ is independently selected from —H; deuterium; —F, —Cl, —Br, —I, —CN; carbonyl; =O; oxo; carboxyl; C$_{1-3}$alkoxy; C$_{1-3}$alkyl; or C$_{1-3}$alkyl or C$_{1-3}$alkoxy independently substituted with deuterium, —F, —Cl, —Br, —I, —NH$_2$, —CN, —OH, —NO$_2$, carboxyl, oxo, =O, —CONH$_2$, —C$_{1-3}$ alkoxy, —C$_{1-3}$alkyl, —C$_{1-3}$alkylene-O—C$_{1-3}$alkyl, —C$_{1-3}$ alkylene-COOH, —C$_{1-3}$alkylene-NHCONH$_2$, —CO—N (C$_{1-3}$alky)$_2$, —C$_{1-3}$alkylene-NHCO—C$_{1-3}$alkyl, —CO—CO—N(C$_{1-3}$alkyl)$_2$, —CO—C$_{1-3}$alkyl, —SONH$_2$, —SO$_2$NH$_2$, —SOC$_{1-3}$alky, —SO$_2$C$_{1-3}$alky, 3-membered heterocyclic ring, 4-membered heterocyclic ring, 5-membered heterocyclic ring, 6-membered heterocyclic ring, 5-membered heteroaryl, or 6-membered heteroaryl; and each of the heteroaryl contains 1, 2 or 3 heteroatoms selected from N or O; each of the heterocyclic ring contains 1 or 2 heteroatoms selected from N or O; or R$_4$ combines with R$_5$, to form a 3-membered carbocyclic ring, 4-membered carbocyclic ring, 5-membered carbocyclic ring, 6-membered carbocyclic ring, 7-membered carbocyclic ring, 8-membered carbocyclic ring, 3-member heterocyclic ring, 4-member heterocyclic ring, 5-member heterocyclic ring, 6-member heterocyclic ring, 7-member heterocyclic ring, or 8-member heterocyclic ring, and each of the heterocyclic ring contains 1, 2 or 3 heteroatoms selected from N, O or S; and each of which is independently optionally substituted deuterium, —F, —Cl, —Br, —I, —NH$_2$, —CN, —OH, —NO$_2$, carbonyl, =O, oxo, carboxyl, C$_{1-3}$alkoxy, C$_{1-3}$alkyl, —NH(C$_{1-3}$alkyl), —N(C$_{1-3}$alkyl)$_2$, —S—C$_{1-3}$alkyl, —SO$_2$C$_{1-3}$alkyl, 3-membered carbocyclic ring, 4-membered carbocyclic ring, 5-membered carbocyclic ring, or 6-membered carbocyclic ring.

In some embodiments of Formula VII, R$_4$ and R$_5$ is independently selected from —H; deuterium; —F, —Cl, —Br, —I, —CN; carbonyl; =O; oxo; carboxyl; methyl; ethyl; propyl; isopropyl; methoxy; ethoxy; propoxy; isopropoxy; or C$_{1-3}$alkyl or C$_{1-3}$alkoxy independently substituted with deuterium, —F, —Cl, —Br, —I, —NH$_2$, —CN, —OH, —NO$_2$, carboxyl, oxo, =O, —CONH$_2$, methyl, ethyl, propyl, isopropyl, methoxy, ethoxy, propoxy, isopropoxy, —NHmethyl, —NHethyl, —NHpropyl, —NHisopropyl, —CH$_2$OCH$_3$, —CH$_2$OCH$_2$CH$_3$, —CH$_2$OCH(CH$_3$)$_2$, —NHOCH$_2$CH$_3$, —CH$_2$—NHCONH$_2$, —CO—N(CH$_3$)$_2$, —CH$_2$—NHCO—C$_{1-3}$alkyl, —CO—CH$_3$, —SONH$_2$, —SO$_2$NH$_2$, —SOCH$_3$, —SO$_2$CH$_3$, 3-membered heterocyclic ring which contains 1 heteroatoms selected from N or O; or R$_4$ combines with R$_5$, to form a 3-membered carbocyclic ring, 4-membered carbocyclic ring, 5-membered carbocyclic ring, 4-member heterocyclic ring, or 5-member heterocyclic ring, and each of the heterocyclic ring contains 1 heteroatoms selected from N or O; and each of which is independently optionally substituted deuterium, —F, —Cl, —Br, —I, —NH$_2$, —CN, —OH, —NO$_2$, carbonyl, =O, oxo, carboxyl, methyl, ethyl, propyl, isopropyl, methoxy, ethoxy, propoxy, isopropoxy, —NHmethyl, —NHethyl, —NHpropyl, —NHisopropyl, —SCH$_3$, —SO$_2$CH$_3$, or 3-membered carbocyclic ring.

In some embodiments of Formula VII, R$_4$ and R$_5$ is independently selected from —H; deuterium; —F, —Cl, —Br, —I, —CN; carbonyl; =O; oxo; carboxyl; methyl; ethyl; propyl; isopropyl; methoxy; ethoxy; propoxy; isopropoxy; or methyl, ethyl, propyl, isopropyl, methoxy, ethoxy, propoxy or isopropoxy independently substituted with deuterium, —F, —Cl, —Br, —NH$_2$, —CN, —OH, —NO$_2$, carboxyl, oxo, =O, —CONH$_2$, methyl, ethyl, propyl, isopropyl, methoxy, ethoxy, propoxy, isopropoxy, —NHmethyl, —NHethyl, —NHpropyl, or —NHisopropyl; or R$_4$ combines with R$_5$, to form a cyclopropyl, cyclobutyl, cyclopentyl, 4-membered heterocyclic ring, 5-membered heterocyclic ring, and each of the heterocyclic ring contains 1 heteroatoms selected from O; and each of which is independently optionally substituted deuterium, —F, —Cl, —Br, —NH$_2$, —CN, —OH, carbonyl, =O, oxo, carboxyl, methyl, ethyl, propyl, isopropyl, methoxy, ethoxy, propoxy, isopropoxy, —NHmethyl, —NHethyl, —NHpropyl, or —NHisopropyl.

In some embodiments of Formula VII, R$_4$ and R$_5$ is independently selected from —H, deuterium, —F, methyl, —CH$_2$D, —CHF$_2$, —CH$_2$F, —CD$_2$H, —CD$_3$, —CF$_3$, or R$_4$ combines with R$_5$, to form cyclopropyl, cyclobutyl, or

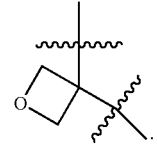 [SMILES: *C1(*)COC1]

In some embodiments of Formula VII, Y is selected from O, —CH$_2$—, —CH$_2$—CH$_2$—, —CH$_2$CF$_2$—, —CF$_2$—, —CF$_2$CH$_2$—, —CH(CH$_3$)—, —C(CH$_3$)$_2$—, —CH(CF$_3$)—, —CO—, —SO$_2$—, —CH$_2$—CO—, —CH$_2$—SO$_2$—, —CO—CH$_2$—, —SO$_2$—CH$_2$—,

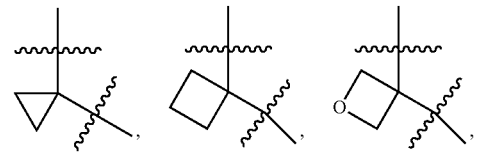

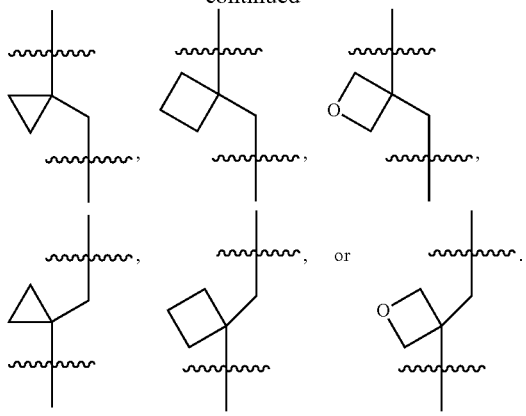

In some embodiments of Formula VII, Ar$_2$ is a 6-membered aryl, 7-membered aryl, 8-membered aryl, 9-membered aryl, 3-membered heterocyclic ring, 4-membered heterocyclic ring, 5-membered heterocyclic ring, 6-membered heterocyclic ring, 7-membered heterocyclic ring, 8-membered heterocyclic ring, 5-membered heteroaryl, 6-membered heteroaryl, 7-membered heteroaryl, 8-membered heteroaryl, or 9-membered heteroaryl; each of the heteroaryl contains 1, 2, 3 heteroatoms selected from N, O or S; and each of which is independently optionally substituted with one or more of deuterium; —F; —Cl; —Br; —I; —CN; —OH; —NH$_2$; —NO$_2$; carbonyl; =O; oxo; methyl; ethyl; propyl; isopropyl; methoxy; ethoxy; propoxy; isopropoxy; or C$_{1-3}$alkyl or C$_{1-3}$alkoxy independently substituted with deuterium, —F, —Cl, —Br, —I, —NH$_2$, —CN, —OH, —NO$_2$, carboxyl, oxo, =O, methyl, ethyl, propyl, isopropyl, methoxy, ethoxy, propoxy, isopropoxy, —NHmethyl, —NHethyl, —NHpropyl, —NHisopropyl, —N(CH$_3$)$_2$, —SCH$_3$, —SO$_2$CH$_3$, or 3-membered carbocyclic ring.

In some embodiments of Formula VII, Ar$_2$ is a 6-membered aryl, 5-membered heteroaryl or 9-membered heteroaryl, and each of the heteroaryl contains 1 or 2 heteroatoms selected from N, O or S; and each of which is independently optionally substituted with one or more of deuterium, —F, —Cl, —Br, —CN, —OH, —NH$_2$, carbonyl, =O, oxo, methyl, ethyl, propyl, isopropyl, methoxy, ethoxy, propoxy, isopropoxy, —CH$_2$F, —CHF$_2$, —CF$_3$, —CH$_2$D, CHD$_2$, —CD$_3$.

In some embodiments of Formula VII, Ar$_2$ is a phenyl

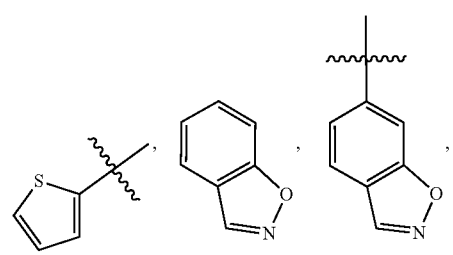

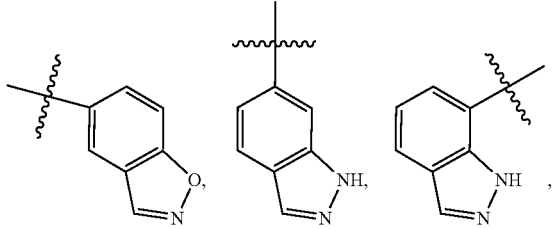

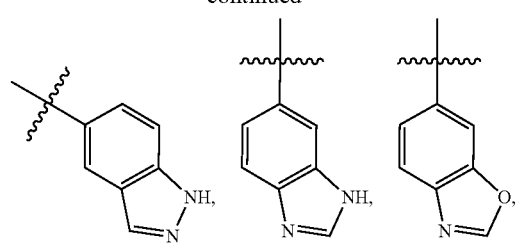

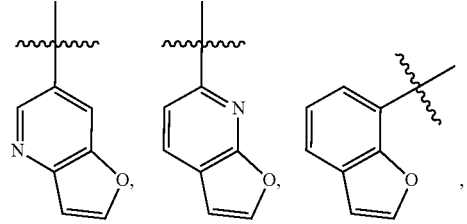

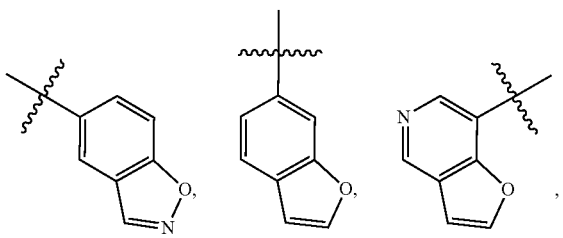

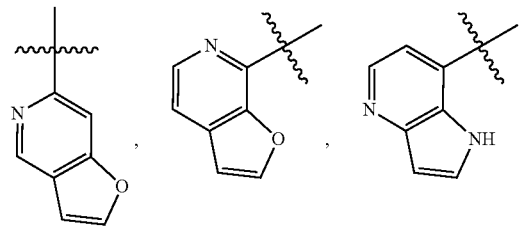

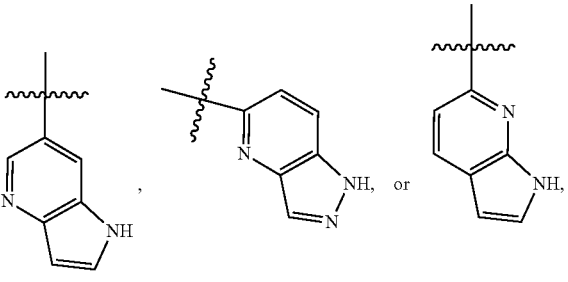

and each of which is independently optionally substituted with one or more of deuterium, —F, —Cl, —Br, —CN, —OH, —NH$_2$, methyl, ethyl, propyl, isopropyl, methoxy, ethoxy, propoxy, isopropoxy, —CH$_2$F, —CHF$_2$, —CF$_3$, —CH$_2$D, CHD$_2$, —CD$_3$.

In some embodiments of Formula VII, Ar$_2$ is

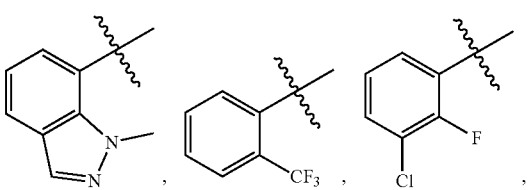

-continued

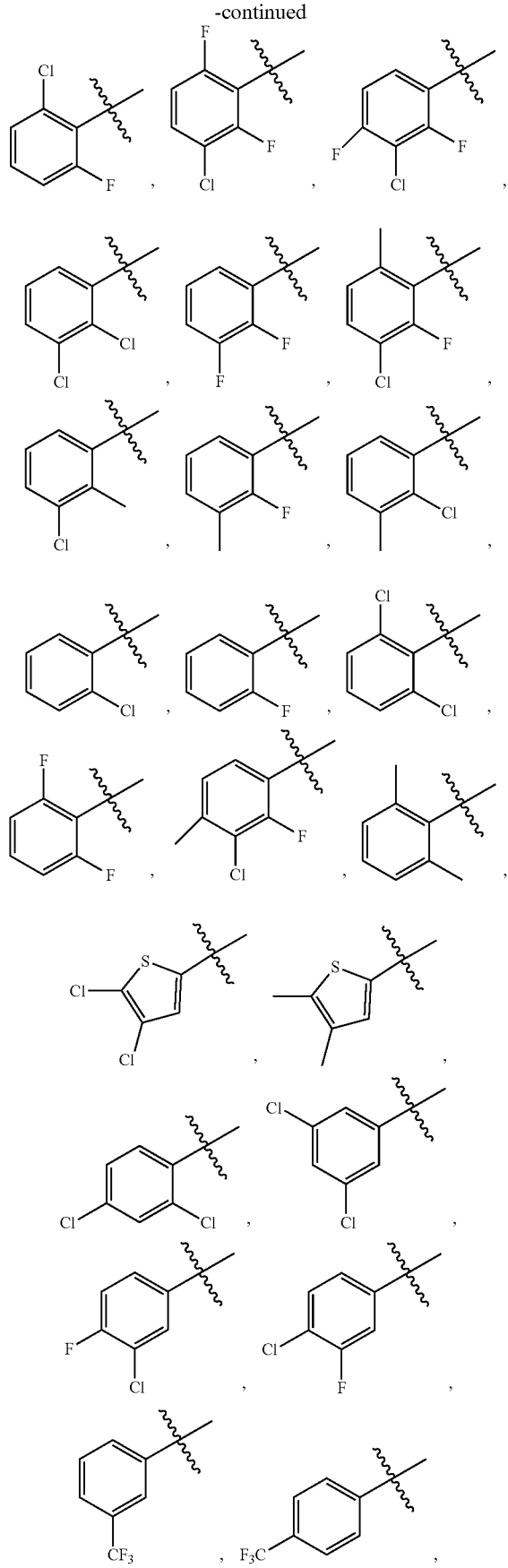

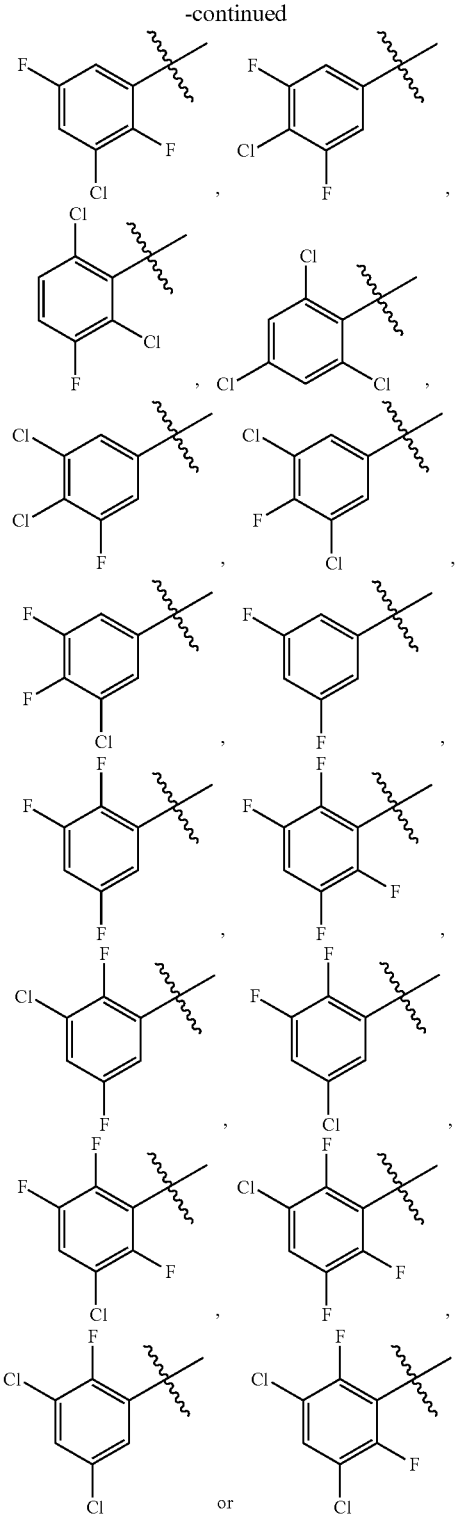

In some embodiments of Formula VII, $Ar_1$ is 5-membered heteroaryl 6-membered heteroaryl, 7-membered heteroaryl, or 8-membered heteroaryl; each of the heteroaryl contains 1 or 2 heteroatoms selected from N, O or S; and each of which is independently optionally substituted with one or more of deuterium; —F; —Cl; —Br; —I; —CN; —OH; —NH$_2$; —NO$_2$; carbonyl; =O; oxo; $C_{1-3}$alkyl; $C_{1-3}$alkoxy; or $C_{1-3}$alkyl or $C_{1-3}$alkoxy independently substituted with one or more of deuterium, —F, —Cl, —Br, —I, —NH$_2$, —CN, —OH, —NO$_2$, carboxyl, oxo, =O, $C_{1-3}$alkoxy, $C_{1-3}$alkyl, —NH(C$_{1-3}$alkyl), —N(C$_{1-3}$alkyl)$_2$, —S—C$_{1-3}$alkyl, —SO$_2$C$_{1-3}$alkyl, 3-membered carbocyclic ring, 4-membered carbocyclic ring, 5-membered carbocyclic ring, or 6-membered carbocyclic ring.

In some embodiments of Formula VII, Ar$_1$ is 5-membered heteroaryl which contains 1 or 2 heteroatoms selected from N or S, and which is independently optionally substituted with one or more of deuterium; —F; —Cl; —Br; —I; —CN; —OH; —NH$_2$; carbonyl; =O; oxo; methyl; ethyl; propyl; isopropyl; methoxy; ethoxy; propoxy; isopropoxy; —CH$_2$F, —CHF$_2$, —CF$_3$, —CH$_2$D, CHD$_2$, —CD$_3$, —CH$_2$NHmethyl, —CH$_2$NHethyl, —CH$_2$NHpropyl, —CH$_2$NHisopropyl, —CH$_2$N(CH$_3$)$_2$.

In some embodiments of Formula VII, Ar$_1$ is

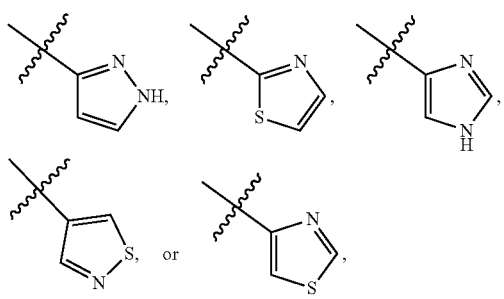

and which is independently optionally substituted with one or more of deuterium, —F, —Cl, —Br, —I, —CN, —OH, —NH$_2$, carbonyl, =O, oxo, methyl, ethyl, propyl, isopropyl, methoxy, ethoxy, propoxy, or isopropoxy.

In some embodiments of Formula VII, Ar$_1$ is

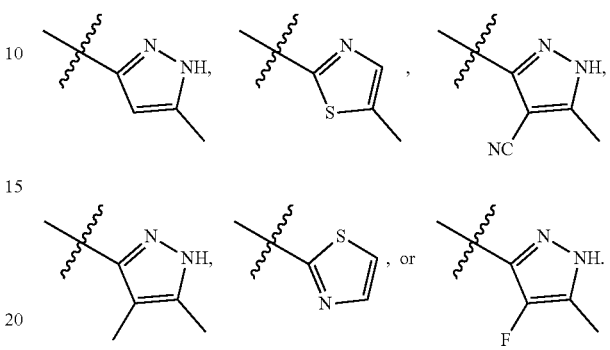

The present invention further provides some preferred technical solution with regard to a compound of Formula I, II, III, IV, V, VI or VII, or pharmaceutically acceptable salt thereof, and the compound includes the group consisting of:

1. 1-(3-chloro-2-fluorobenzyl)-4-((3-fluoro-6-((5-methyl-1H-pyrazol-3-yl)amino)pyridin-2-yl)methyl)piperidine-4-carboxylic acid
2. 1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid
3. 1-(3-chloro-2-fluorobenzyl)-4-((3-fluoro-6-((5-methyl-1H-pyrazol-3-yl)amino)pyridin-2-yl)methyl)-2,6-dimethylpiperidine-4-carboxylic acid
4. 1-(3-chloro-2-fluorobenzyl)-4-((3-fluoro-6-(thiazol-2-ylamino)pyridin-2-yl)methyl)-2-methylpiperidine-4-carboxylic acid
5. (2R,4R)-1-(3-chloro-2-fluorobenzyl)-4-((5-fluoro-6-((5-methyl-1H-pyrazol-3-yl)amino)pyridin-2-yl)methyl)-2-methylpiperidine-4-carboxylic acid
6. (2R,4R)-1-(3-chloro-2,6-difluorobenzyl)-4-((3-fluoro-6-((5-methyl-1H-pyrazol-3-yl)amino)pyridin-2-yl)methyl)-2-methylpiperidine-4-carboxylic acid
7. 4-((3-fluoro-6-((5-methyl-1H-pyrazol-3-yl)amino)pyridin-2-yl)methyl)-2-methyl-1-((1-methyl-1H-indazol-7-yl)methyl)piperidine-4-carboxylic acid
8. (2R,4R)-1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid
9. (2R,4R)-1-(3-chloro-2-fluorobenzyl)-4-((4-cyclopropyl-3-fluoro-6-((5-methyl-1H-pyrazol-3-yl)amino)pyridin-2-yl)methyl)-2-methylpiperidine-4-carboxylic acid
10. (2R,4R)-1-(3-chloro-2-fluorobenzyl)-2-methyl-4-((3-methyl-6-((5-methyl-1H-pyrazol-3-yl)amino)pyridin-2-yl)methyl)piperidine-4-carboxylic acid
11. (2R,4R)-1-(3-chloro-2-fluorobenzyl)-4-((3-chloro-6-((5-methyl-1H-pyrazol-3-yl)amino)pyridin-2-yl)methyl)-2-methylpiperidine-4-carboxylic acid
12. (2R,4R)-1-(2,6-difluorobenzyl)-4-((3-fluoro-6-((5-methyl-1H-pyrazol-3-yl)amino)pyridin-2-yl)methyl)-2-methylpiperidine-4-carboxylic acid
13. (2R,4R)-1-(2,6-dimethylbenzyl)-4-((3-fluoro-6-((5-methyl-1H-pyrazol-3-yl)amino)pyridin-2-yl)methyl)-2-methylpiperidine-4-carboxylic acid
14. (2R,4R)-1-(2,3-dichlorobenzyl)-4-((3-fluoro-6-((5-methyl-1H-pyrazol-3-yl)amino)pyridin-2-yl)methyl)-2-methylpiperidine-4-carboxylic acid
15. (2R,4R)-1-(2,3-difluorobenzyl)-4-((3-fluoro-6-((5-methyl-1H-pyrazol-3-yl)amino)pyridin-2-yl)methyl)-2-methylpiperidine-4-carboxylic acid
16. (2R,4R)-1-(2-fluoro-3-methylbenzyl)-4-((3-fluoro-6-((5-methyl-1H-pyrazol-3-yl)amino)pyridin-2-yl)methyl)-2-methylpiperidine-4-carboxylic acid
17. (2R,4R)-1-(2,6-dichlorobenzyl)-4-((3-fluoro-6-((5-methyl-1H-pyrazol-3-yl)amino)pyridin-2-yl)methyl)-2-methylpiperidine-4-carboxylic acid
18. (2R,4R)-1-(3-chloro-4-fluorobenzyl)-4-((3-fluoro-6-((5-methyl-1H-pyrazol-3-yl)amino)pyridin-2-yl)methyl)-2-methylpiperidine-4-carboxylic acid
19. (2R,4R)-1-(4-chloro-3-fluorobenzyl)-4-((3-fluoro-6-((5-methyl-1H-pyrazol-3-yl)amino)pyridin-2-yl)methyl)-2-methylpiperidine-4-carboxylic acid
20. (2R,4R)-1-(3,5-dichlorobenzyl)-4-((3-fluoro-6-((5-methyl-1H-pyrazol-3-yl)amino)pyridin-2-yl)methyl)-2-methylpiperidine-4-carboxylic acid
21. (2R,4R)-4-((3-fluoro-6-((5-methyl-1H-pyrazol-3-yl)amino)pyridin-2-yl)methyl)-2-methyl-1-(3-(trifluoromethyl)benzyl)piperidine-4-carboxylic acid
22. (2R,4R)-1-(3,4-dichloro-5-fluorobenzyl)-4-((3-fluoro-6-((5-methyl-1H-pyrazol-3-yl)amino)pyridin-2-yl)methyl)-2-methylpiperidine-4-carboxylic acid
23. (2R,4R)-1-(3,5-dichloro-4-fluorobenzyl)-4-((3-fluoro-6-((5-methyl-1H-pyrazol-3-yl)amino)pyridin-2-yl)methyl)-2-methylpiperidine-4-carboxylic acid -continued 24. (2R,4R)-1-(3,5-difluorobenzyl)-4-((3-fluoro-6-((5-methyl-1H-pyrazol-3-yl)amino)pyridin-2-yl)methyl)-2-methylpiperidine-4-carboxylic acid
25. (2R,4R)-1-(3-chloro-2-fluorobenzyl)-2-methyl-4-((3-methyl-6-((5-methyl-1H-pyrazol-3-yl)amino)pyrazin-2-yl)methyl)piperidine-4-carboxylic acid
26. (2R,4R)-1-(3-chloro-2-fluorobenzyl)-4-((5-fluoro-2-((5-methyl-1H-pyrazol-3-yl)amino)pyrimidin-4-yl)methyl)-2-methylpiperidine-4-carboxylic acid
27. (2R,4R)-1-(3-chloro-2,4-difluorobenzyl)-4-((3-fluoro-6-((5-methyl-1H-pyrazol-3-yl)amino)pyridin-2-yl)methyl)-2-methylpiperidine-4-carboxylic acid
28. (2S,4S)-1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid
29. (2R,4R)-1-(3-chloro-2-fluorobenzyl)-2-methyl-4-((6-((5-methyl-1H-pyrazol-3-yl)amino)pyridin-2-yl)methyl)piperidine-4-carboxylic acid
30. (2R,4R)-1-(3-chloro-2-fluorobenzyl)-4-((4-fluoro-6-((5-methyl-1H-pyrazol-3-yl)amino)pyridin-2-yl)methyl)-2-methylpiperidine-4-carboxylic acid
31. (2R,4R)-1-(3-chloro-2-fluorobenzyl)-2-methyl-4-((4-methyl-6-((5-methyl-1H-pyrazol-3-yl)amino)pyrimidin-2-yl)methyl)piperidine-4-carboxylic acid
32. (2R,4R)-1-(3-chloro-2-fluorobenzyl)-4-((3,5-dimethyl-6-((5-methyl-1H-pyrazol-3-yl)amino)pyrazin-2-yl)methyl)-2-methylpiperidine-4-carboxylic acid
33. (2R,4R)-1-(3-chloro-2-fluorobenzyl)-2-methyl-4-((5-methyl-6-((5-methyl-1H-pyrazol-3-yl)amino)pyrazin-2-yl)methyl)piperidine-4-carboxylic acid
34. (2R,4R)-4-((3-fluoro-6-((5-methyl-1H-pyrazol-3-yl)amino)pyridin-2-yl)methyl)-2-methyl-1-(2-(trifluoromethyl)benzyl)piperidine-4-carboxylic acid
35. (2R,4R)-1-(3-chloro-2-fluorobenzyl)-4-((3-fluoro-5-methyl-6-((3-methyl-1H-pyrazol-5-yl)amino)pyridin-2-yl)methyl)-2-methylpiperidine-4-carboxylic acid
36. (2R,4R)-1-(3-chloro-2-fluorobenzyl)-4-(2,6-difluoro-3-((5-methyl-1H-pyrazol-3-yl)amino)benzyl)-2-methylpiperidine-4-carboxylic acid
37. (2R,4R)-4-((3-fluoro-6-((5-methyl-1H-pyrazol-3-yl)amino)pyridin-2-yl)methyl)-2-methyl-1-(2-(trifluoromethyl)benzoyl)piperidine-4-carboxylic acid
38. (2R,4R)-1-(2-(3-chloro-2-fluorophenyl)acetyl)-4-((3-fluoro-6-((5-methyl-1H-pyrazol-3-yl)amino)pyridin-2-yl)methyl)-2-methylpiperidine-4-carboxylic acid
39. (2R,4R)-4-((3-fluoro-6-((5-methyl-1H-pyrazol-3-yl)amino)pyridin-2-yl)methyl)-2-methyl-1-42-(trifluoromethyl)phenyl)sulfonyl)piperidine-4-carboxylic acid
40. (2R,4R)-1-((R)-1-(3-chloro-2-fluorophenyl)ethyl)-4-((3-fluoro-6-((5-methyl-1H-pyrazol-3-yl)amino)pyridin-2-yl)methyl)-2-methylpiperidine-4-carboxylic acid
41. (2R,4R)-1-((S)-1-(3-chloro-2-fluorophenyl)ethyl)-4-((3-fluoro-6-((5-methyl-1H-pyrazol-3-yl)amino)pyridin-2-yl)methyl)-2-methylpiperidine-4-carboxylic acid
42. (2R,4R)-1-(3-chloro-2-fluorophenethyl)-4-((3-fluoro-6-((5-methyl-1H-pyrazol-3-yl)amino)pyridin-2-yl)methyl)-2-methylpiperidine-4-carboxylic acid
43. (2R,4R)-1-(2,6-dichlorophenethyl)-4-((3-fluoro-6-((5-methyl-1H-pyrazol-3-yl)amino)pyridin-2-yl)methyl)-2-methylpiperidine-4-carboxylic acid
44. (2R,4R)-1-(2-(3-chloro-2-fluorophenyl)-2-oxoethyl)-4-((3-fluoro-6-((5-methyl-1H-pyrazol-3-yl)amino)pyridin-2-yl)methyl)-2-methylpiperidine-4-carboxylic acid
45. (2R,4R)-1-(3-chloro-2-fluorobenzyl)-2-methyl-4-((6-((5-methyl-1H-pyrazol-3-yl)amino)pyrazin-2-yl)methyl)piperidine-4-carboxylic acid
46. 1-(3-chloro-2-fluorobenzyl)-4-((3-fluoro-6-((5-methyl-1H-pyrazol-3-yl)amino)-4-(oxetan-3-yl)pyridin-2-yl)methyl)piperidine-4-carboxylic acid
47. (2R,4R)-1-(3-chloro-2-fluorobenzyl)-4-((3-fluoro-4-(3-hydroxyoxetan-3-yl)-6-((5-methyl-1H-pyrazol-3-yl)amino)pyridin-2-yl)methyl)-2-methylpiperidine-4-carboxylic acid
48. (2R,4R)-1-(3-chloro-2-fluorobenzyl)-4-((3-fluoro-4-(3-fluorooxetan-3-yl)-6-((5-methyl-1H-pyrazol-3-yl)amino)pyridin-2-yl)methyl)-2-methylpiperidine-4-carboxylic acid
49. (2R,4R)-1-(3-chloro-2-fluorobenzyl)-4-((3-fluoro-4-methyl-6-((5-methyl-1H-pyrazol-3-yl)amino)pyridin-2-yl)methyl)-2-methylpiperidine-4-carboxylic acid
50. (2R,4R)-1-(3-chloro-2,6-difluorobenzyl)-4-((3-fluoro-4-methyl-6-((5-methyl-1H-pyrazol-3-yl)amino)pyridin-2-yl)methyl)-2-methylpiperidine-4-carboxylic acid
51. 1-(3-chloro-2-fluorobenzyl)-4-((3-fluoro-4-methyl-6-((5-methyl-1H-pyrazol-3-yl)amino)pyridin-2-yl)methyl)piperidine-4-carboxylic acid
52. 1-(2,3-difluorobenzyl)-4-((3-fluoro-4-methyl-6-((5-methyl-1H-pyrazol-3-yl)amino)pyridin-2-yl)methyl)piperidine-4-carboxylic acid
53. (2R,4R)-1-(2,3-dichlorobenzyl)-4-((3-fluoro-4-methyl-6-((5-methyl-1H-pyrazol-3-yl)amino)pyridin-2-yl)methyl)-2-methylpiperidine-4-carboxylic acid
54. 1-(2,3-dichlorobenzyl)-4-((3-fluoro-4-methyl-6-((5-methyl-1H-pyrazol-3-yl)amino)pyridin-2-yl)methyl)piperidine-4-carboxylic acid
55. 1-(3-chloro-2,6-difluorobenzyl)-4-((3-fluoro-4-methyl-6-((5-methyl-1H-pyrazol-3-yl)amino)pyridin-2-yl)methyl)piperidine-4-carboxylic acid
56. 1-(2,3-difluorophenethyl)-4-((3-fluoro-4-methyl-6-((5-methyl-1H-pyrazol-3-yl)amino)pyridin-2-yl)methyl)piperidine-4-carboxylic acid
57. 1-(2,3-dichlorophenethyl)-4-((3-fluoro-4-methyl-6-((5-methyl-1H-pyrazol-3-yl)amino)pyridin-2-yl)methyl)piperidine-4-carboxylic acid
58. 1-(3-chloro-2,6-difluorophenethyl)-4-((3-fluoro-4-methyl-6-((5-methyl-1H-pyrazol-3-yl)amino)pyridin-2-yl)methyl)piperidine-4-carboxylic acid
59. 1-(2,6-dichlorophenethyl)-4-((3-fluoro-4-methyl-6-((5-methyl-1H-pyrazol-3-yl)amino)pyridin-2-yl)methyl)piperidine-4-carboxylic acid
60. 1-(2,4-dichlorophenethyl)-4-((3-fluoro-4-methyl-6-((5-methyl-1H-pyrazol-3-yl)amino)pyridin-2-yl)methyl)piperidine-4-carboxylic acid
61. (2R,4R)-1-(2,3-difluorobenzyl)-4-((3-fluoro-4-methyl-6-((5-methyl-1H-pyrazol-3-yl)amino)pyridin-2-yl)methyl)-2-methylpiperidine-4-carboxylic acid
62. (2R,4R)-1-(3-chloro-2-fluorobenzyl)-4-((3-fluoro-4-(2-hydroxypropan-2-yl)-6-((5-methyl-1H-pyrazol-3-yl)amino)pyridin-2-yl)methyl)-2-methylpiperidine-4-carboxylic acid -continued 63. (2R,4R)-1-(3-chloro-2-fluorobenzyl)-4-((3-fluoro-4-isopropyl-6-((5-methyl-1H-pyrazol-3-yl)amino)pyridin-2-yl)methyl)-2-methylpiperidine-4-carboxylic acid
64. (2R,4R)-1-(3-chloro-2-fluorobenzyl)-4-((4-(difluoromethyl)-3-fluoro-6-((5-methyl-1H-pyrazol-3-yl)amino)pyridin-2-yl)methyl)-2-methylpiperidine-4-carboxylic acid
65. (2R,4R)-1-(3-chloro-2-fluorobenzyl)-4-((4-ethyl-3-fluoro-6-((5-methyl-1H-pyrazol-3-yl)amino)pyridin-2-yl)methyl)-2-methylpiperidine-4-carboxylic acid
66. 1-(3-chloro-2-fluorobenzyl)-4-((4-ethyl-3-fluoro-6-((5-methyl-1H-pyrazol-3-yl)amino)pyridin-2-yl)methyl)piperidine-4-carboxylic acid
67. (2R,4R)-1-(3-chloro-2-fluorobenzyl)-4-((4-cyano-3-fluoro-6-((5-methyl-1H-pyrazol-3-yl)amino)pyridin-2-yl)methyl)-2-methylpiperidine-4-carboxylic acid
68. (2R,4R)-4-((4-acetyl-3-fluoro-6-((5-methyl-1H-pyrazol-3-yl)amino)pyridin-2-yl)methyl)-1-(3-chloro-2-fluorobenzyl)-2-methylpiperidine-4-carboxylic acid
69. 4-((4-acetyl-3-fluoro-6-((5-methyl-1H-pyrazol-3-yl)amino)pyridin-2-yl)methyl)-1-(3-chloro-2-fluorobenzyl)piperidine-4-carboxylic acid
70. (2R,4R)-4-((4-acetyl-5-fluoro-6-((5-methyl-1H-pyrazol-3-yl)amino)pyridin-2-yl)methyl)-1-(3-chloro-2-fluorobenzyl)-2-methylpiperidine-4-carboxylic acid
71. (2R,4R)-1-(3-chloro-2-fluorobenzyl)-4-((4-(1,1-difluoroethyl)-3-fluoro-6-((5-methyl-1H-pyrazol-3-yl)amino)pyridin-2-yl)methyl)-2-methylpiperidine-4-carboxylic acid
72. (2R,4R)-1-(3-chloro-2-fluorobenzyl)-4-((4-chloro-3-fluoro-6-((5-methyl-1H-pyrazol-3-yl)amino)pyridin-2-yl)methyl)-2-methylpiperidine-4-carboxylic acid
73. (2R,4R)-1-(3-chloro-2-fluorobenzyl)-4-((4-chloro-5-fluoro-6-((5-methyl-1H-pyrazol-3-yl)amino)pyridin-2-yl)methyl)-2-methylpiperidine-4-carboxylic acid
74. (2R,4R)-1-(3-chloro-2-fluorobenzyl)-4-((4-chloro-3,5-difluoro-6-((5-methyl-1H-pyrazol-3-yl)amino)pyridin-2-yl)methyl)-2-methylpiperidine-4-carboxylic acid
75. (2R,4R)-4-((4-(azetidin-1-yl)-3-fluoro-6-((5-methyl-1H-pyrazol-3-yl)amino)pyridin-2-yl)methyl)-1-(3-chloro-2-fluorobenzyl)-2-methylpiperidine-4-carboxylic acid
76. (2R,4R)-1-(3-chloro-2-fluorobenzyl)-4-((3-fluoro-4-(1-hydroxyethyl)-6-((5-methyl-1H-pyrazol-3-yl)amino)pyridin-2-yl)methyl)-2-methylpiperidine-4-carboxylic acid
77. (2R,4R)-1-(3-chloro-2-fluorobenzyl)-4-((3-fluoro-4-(1-fluoroethyl)-6-((5-methyl-1H-pyrazol-3-yl)amino)pyridin-2-yl)methyl)-2-methylpiperidine-4-carboxylic acid
78. (2R,4R)-1-(3-chloro-2-fluorobenzyl)-4-((5-fluoro-4-methyl-6-((5-methyl-1H-pyrazol-3-yl)amino)pyridin-2-yl)methyl)-2-methylpiperidine-4-carboxylic acid
79. 1-(3-chloro-2-fluorobenzyl)-4-((5-fluoro-4-methyl-6-((5-methyl-1H-pyrazol-3-yl)amino)pyridin-2-yl)methyl)piperidine-4-carboxylic acid
80. (2R,4R)-1-(3-chloro-2-fluorobenzyl)-4-((3-fluoro-6-((5-methyl-1H-pyrazol-3-yl)amino)-4-propionylpyridin-2-yl)methyl)-2-methylpiperidine-4-carboxylic acid
81. (2R,4R)-1-(3-chloro-2-fluorobenzyl)-4-((3-fluoro-6-((5-methyl-1H-pyrazol-3-yl)amino)-4-(methylsulfonyl)pyridin-2-yl)methyl)-2-methylpiperidine-4-carboxylic acid
82. (2R,4R)-1-(3-chloro-2-fluorobenzyl)-4-((5-fluoro-3,4-dimethyl-6-((5-methyl-1H-pyrazol-3-yl)amino)pyridin-2-yl)methyl)-2-methylpiperidine-4-carboxylic acid
83. (2R,4R)-1-(3-chloro-2-fluorobenzyl)-4-((3'-fluoro-6'-((5-methyl-1H-pyrazol-3-yl)amino)-[2,4'-bipyridin]-2'-yl)methyl)-2-methylpiperidine-4-carboxylic acid
84. (2R,4R)-1-(3-chloro-2-fluorobenzyl)-4-((4,5-dichloro-3-fluoro-6-((5-methyl-1H-pyrazol-3-yl)amino)pyridin-2-yl)methyl)-2-methylpiperidine-4-carboxylic acid
85. (2R,4R)-1-(3-chloro-2-fluorobenzyl)-4-((3-fluoro-4-isobutyryl-6-((5-methyl-1H-pyrazol-3-yl)amino)pyridin-2-yl)methyl)-2-methylpiperidine-4-carboxylic acid
86. 2-(((2R,4R)-4-carboxy-1-(3-chloro-2-fluorobenzyl)-2-methylpiperidin-4-yl)methyl)-3-fluoro-6-((5-methyl-1H-pyrazol-3-yl)amino)isonicotinic acid
87. (2R,4R)-1-(3-chloro-2-fluorobenzyl)-4-((4-(dimethylcarbamoyl)-3-fluoro-6-((5-methyl-1H-pyrazol-3-yl)amino)pyridin-2-yl)methyl)-2-methylpiperidine-4-carboxylic acid
88. (2R,4R)-1-(3-chloro-2-fluorobenzyl)-4-((3-fluoro-6-((5-methyl-1H-pyrazol-3-yl)amino)-4-(morpholine-4-carbonyl)pyridin-2-yl)methyl)-2-methylpiperidine-4-carboxylic acid
89. (2R,4R)-1-(3-chloro-2-fluorobenzyl)-4-((3-fluoro-6-((5-methyl-1H-pyrazol-3-yl)amino)-4-(4-methylpiperazine-1-carbonyl)pyridin-2-yl)methyl)-2-methylpiperidine-4-carboxylic acid
90. (2R,4R)-1-(3-chloro-2-fluorobenzyl)-4-((4-cyano-5-fluoro-6-((5-methyl-1H-pyrazol-3-yl)amino)pyridin-2-yl)methyl)-2-methylpiperidine-4-carboxylic acid
91. (2R,4R)-1-(3-chloro-2-fluorobenzyl)-4-((3,5-difluoro-6-((5-methyl-1H-pyrazol-3-yl)amino)pyridin-2-yl)methyl)-2-methylpiperidine-4-carboxylic acid
92. 1-(3-chloro-2-fluorobenzyl)-4-((3,5-difluoro-6-((5-methyl-1H-pyrazol-3-yl)amino)pyridin-2-yl)methyl)piperidine-4-carboxylic acid
93. (2R,4R)-1-(3-chloro-2-fluorobenzyl)-4-((3,5-difluoro-4-methyl-6-((5-methyl-1H-pyrazol-3-yl)amino)pyridin-2-yl)methyl)-2-methylpiperidine-4-carboxylic acid
94. (2R,4R)-4-((6-((1H-pyrazol-3-yl)amino)-3-fluoro-4-(2-fluoropropan-2-yl)pyridin-2-yl)methyl)-1-(3-chloro-2-fluorobenzyl)-2-methylpiperidine-4-carboxylic acid
95. (1R,5 S)-8-(3-chloro-2-fluorobenzyl)-3-((3-fluoro-6-((5-methyl-1H-pyrazol-3-yl)amino)pyridin-2-yl)methyl)-8-azabicyclo[3.2.1]octane-3-carboxylic acid
96. (2R,4R)-1-(3-chloro-2-fluorobenzyl)-4-((3-fluoro-6-((4-fluoro-5-methyl-1H-pyrazol-3-yl)amino)pyridin-2-yl)methyl)-2-methylpiperidine-4-carboxylic acid
97. 1-(3-chloro-2-fluorobenzyl)-4-((3-fluoro-6-((5-methyl-1H-pyrazol-3-yl)amino)pyridin-2-yl)methyl)-2-(trifluoromethyl)piperidine-4-carboxylic acid
98. 4-(3-chloro-2-fluorobenzyl)-7-((3-fluoro-6-((5-methyl-1H-pyrazol-3-yl)amino)pyridin-2-yl)methyl)-4-azaspiro[2.5]octane-7-carboxylic acid
99. (2R,4S)-1-(3-chloro-2-fluorobenzyl)-4-((3-fluoro-6-((5-methyl-1H-pyrazol-3-yl)amino)pyridin-2-yl)oxy)-2-methylpiperidine-4-carboxylic acid
100. (2R,4R)-1-(2-chloro-6-fluorobenzyl)-4-((3-fluoro-6-((5-methyl-1H-pyrazol-3-yl)amino)pyridin-2-yl)methyl)-2-methylpiperidine-4-carboxylic acid
101. (2R,4R)-1-(3-chloro-2-fluorobenzyl)-4-((3-cyano-6-((5-methyl-1H-pyrazol-3-yl)amino)pyridin-2-yl)methyl)-2-methylpiperidine-4-carboxylic acid -continued 102. 1-(3-chloro-2-fluorobenzyl)-4-((6-((4,5-dimethyl-1H-pyrazol-3-yl)amino)-3-fluoropyridin-2-yl)methyl)-2-methylpiperidine-4-carboxylic acid
103. 1-(3-chloro-2-fluorobenzyl)-4-((6-((4-cyano-5-methyl-1H-pyrazol-3-yl)amino)-3-fluoropyridin-2-yl)methyl)-2-methylpiperidine-4-carboxylic acid
104. (2R,4R)-1-(3-chloro-2-fluorobenzyl)-4-((4-cyano-6-((5-methyl-1H-pyrazol-3-yl)amino)pyridin-2-yl)methyl)-2-methylpiperidine-4-carboxylic acid
105. 1-(3-chloro-2-fluorobenzyl)-4-((3-fluoro-6-((5-methyl-1H-pyrazol-3-yl)amino)-4-(3-methyloxetan-3-yl)pyridin-2-yl)methyl)piperidine-4-carboxylic acid
106. 1-(3-chloro-2-fluorobenzyl)-4-((3-fluoro-4-(3-hydroxyoxetan-3-yl)-6-((5-methyl-1H-pyrazol-3-yl)amino)pyridin-2-yl)methyl)piperidine-4-carboxylic acid
107. 1-(3-chloro-2-fluorobenzyl)-4-((3-fluoro-4-(3-hydroxyazetidin-1-yl)-6-((5-methylthiazol-2-yl)amino)pyridin-2-yl)methyl)piperidine-4-carboxylic acid
108. 1-(3-chloro-2-fluorobenzyl)-4-((3-fluoro-6-((5-methyl-1H-pyrazol-3-yl)amino)-4-(4-methylpiperazin-1-yl)pyridin-2-yl)methyl)piperidine-4-carboxylic acid
109. (2R,4R)-4-((3-fluoro-6-((5-methyl-1H-pyrazol-3-yl)amino)pyridin-2-yl)methyl)-2-methyl-1-((S)-1-(2-(trifluoromethyl)phenyl)ethyl)piperidine-4-carboxylic acid
110. (2R,4R)-4-((3-fluoro-6-((5-methyl-1H-pyrazol-3-yl)amino)pyridin-2-yl)methyl)-2-methyl-1-((R)-1-(2-(trifluoromethyl)phenyl)ethyl)piperidine-4-carboxylic acid
111. (S)-4-((3-fluoro-6-((5-methyl-1H-pyrazol-3-yl)amino)pyridin-2-yl)methyl)-1-(1-(2-(trifluoromethyl)phenyl)ethyl)piperidine-4-carboxylic acid
112. (S)-1-(1-(3-chloro-2-fluorophenyl)ethyl)-4-((3-fluoro-6-((5-methyl-1H-pyrazol-3-yl)amino)pyridin-2-yl)methyl)piperidine-4-carboxylic acid
113. (R)-1-(1-(3-chloro-2-fluorophenyl)ethyl)-4-((3-fluoro-6-((5-methyl-1H-pyrazol-3-yl)amino)pyridin-2-yl)methyl)piperidine-4-carboxylic acid
114. (R)-4-((3-fluoro-6-((5-methyl-1H-pyrazol-3-yl)amino)pyridin-2-yl)methyl)-1-(1-(2-(trifluoromethyl)phenyl)ethyl)piperidine-4-carboxylic acid
115. 4-((3-fluoro-6-((5-methyl-1H-pyrazol-3-yl)amino)pyridin-2-yl)methyl)-1-(2-(2-(trifluoromethyl)phenyl)propan-2-yl)piperidine-4-carboxylic acid
116. 4-((3-fluoro-6-((5-methyl-1H-pyrazol-3-yl)amino)pyridin-2-yl)methyl)-1-(1-(2-(trifluoromethyl)phenyl)cyclopropyl)piperidine-4-carboxylic acid
117. 4-((3-fluoro-6-((5-methyl-1H-pyrazol-3-yl)amino)pyridin-2-yl)methyl)-1-(3-(2-(trifluoromethyl)phenyl)oxetan-3-yl)piperidine-4-carboxylic acid
118. 1-((3-chloro-2-fluorophenyl)difluoromethyl)-4-((3-fluoro-6-((5-methyl-1H-pyrazol-3-yl)amino)pyridin-2-yl)methyl)piperidine-4-carboxylic acid
119. (R)-1-(1-(3-chloro-2-fluorophenyl)-2,2,2-trifluoroethyl)-4-((3-fluoro-6-((5-methyl-1H-pyrazol-3-yl)amino)pyridin-2-yl)methyl)piperidine-4-carboxylic acid
120. (S)-1-(1-(3-chloro-2-fluorophenyl)-2,2,2-trifluoroethyl)-4-((3-fluoro-6-((5-methyl-1H-pyrazol-3-yl)amino)pyridin-2-yl)methyl)piperidine-4-carboxylic acid
121. (2R,4R)-1-(3-chloro-2-fluorobenzoyl)-2-ethyl-4-((3-fluoro-6-((5-methyl-1H-pyrazol-3-yl)amino)pyridin-2-yl)methyl)piperidine-4-carboxylic acid
122. (2R,4R)-2-ethyl-4-((3-fluoro-6-((5-methyl-1H-pyrazol-3-yl)amino)pyridin-2-yl)methyl)-1-(2-(trifluoromethyl)benzyl)piperidine-4-carboxylic acid
123. (2R,4R)-2-ethyl-4-((3-fluoro-6-((5-methyl-1H-pyrazol-3-yl)amino)pyridin-2-yl)methyl)-1-(2-(trifluoromethyl)benzoyl)piperidine-4-carboxylic acid
124. (2R,4R)-2-ethyl-4-((3-fluoro-6-((5-methyl-1H-pyrazol-3-yl)amino)pyridin-2-yl)methyl)-1-((2-(trifluoromethyl)phenyl)sulfonyl)piperidine-4-carboxylic acid
125. (2R,4R)-2-ethyl-4-((3-fluoro-6-((5-methyl-1H-pyrazol-3-yl)amino)pyridin-2-yl)methyl)-1-((S)-1-(2-(trifluoromethyl)phenyl)ethyl)piperidine-4-carboxylic acid
126. (2R,4R)-2-ethyl-4-((3-fluoro-6-((5-methyl-1H-pyrazol-3-yl)amino)pyridin-2-yl)methyl)-1-((R)-1-(2-(trifluoromethyl)phenyl)ethyl)piperidine-4-carboxylic acid
127. (2R,4R)-1-((3-chloro-2-fluorophenyl)sulfonyl)-2-ethyl-4-((3-fluoro-6-((5-methyl-1H-pyrazol-3-yl)amino)pyridin-2-yl)methyl)piperidine-4-carboxylic acid
128. (2R,4R)-1-(1-(3-chloro-2-fluorophenyl)cyclopropyl)-2-ethyl-4-((3-fluoro-6-((5-methyl-1H-pyrazol-3-yl)amino)pyridin-2-yl)methyl)piperidine-4-carboxylic acid
129. (2R,4R)-1-((3-chloro-2-fluorophenyl)difluoromethyl)-2-ethyl-4-((3-fluoro-6-((5-methyl-1H-pyrazol-3-yl)amino)pyridin-2-yl)methyl)piperidine-4-carboxylic acid
130. (2R,6R)-1-(3-chloro-2-fluorobenzyl)-4-((3-fluoro-6-((5-methyl-1H-pyrazol-3-yl)amino)pyridin-2-yl)methyl)-2,6-dimethylpiperidine-4-carboxylic acid
131. (3R)-1-(3-chloro-2-fluorobenzyl)-4-((3-fluoro-6-((5-methyl-1H-pyrazol-3-yl)amino)pyridin-2-yl)methyl)-3-methylpiperidine-4-carboxylic acid
132. (2R)-1-(3-chloro-2-fluorobenzyl)-4-((3-fluoro-6-((5-methyl-1H-pyrazol-3-yl)amino)pyridin-2-yl)methyl)-2-methylpiperidine-4-carboxylic acid
133. (2R)-1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid
134. 1-(3-chloro-2,6-difluorobenzyl)-4-((3-fluoro-6-((5-methyl-1H-pyrazol-3-yl)amino)pyridin-2-yl)methyl)piperidine-4-carboxylic acid
135. (2R)-1-(3-chloro-2,6-difluorobenzyl)-4-((3-fluoro-6-((5-methyl-1H-pyrazol-3-yl)amino)pyridin-2-yl)methyl)-2-methylpiperidine-4-carboxylic acid
136. (2R)-1-(3-chloro-2,6-difluorobenzyl)-2-ethyl-4-((3-fluoro-6-((5-methyl-1H-pyrazol-3-yl)amino)pyridin-2-yl)methyl)piperidine-4-carboxylic acid
137. 1-(3-chloro-2,4-difluorobenzyl)-4-((3-fluoro-6-((5-methyl-1H-pyrazol-3-yl)amino)pyridin-2-yl)methyl)piperidine-4-carboxylic acid
138. (2R)-1-(3-chloro-2,4-difluorobenzyl)-4-((3-fluoro-6-((5-methyl-1H-pyrazol-3-yl)amino)pyridin-2-yl)methyl)-2-methylpiperidine-4-carboxylic acid
139. (2R)-1-(3-chloro-2,4-difluorobenzyl)-2-ethyl-4-((3-fluoro-6-((5-methyl-1H-pyrazol-3-yl)amino)pyridin-2-yl)methyl)piperidine-4-carboxylic acid
140. 1-(2,3-dichlorobenzyl)-4-((3-fluoro-6-((5-methyl-1H-pyrazol-3-yl)amino)pyridin-2-yl)methyl)piperidine-4-carboxylic acid 141. (2R)-1-(2,3-dichlorobenzyl)-4-((3-fluoro-6-((5-methyl-1H-pyrazol-3-yl)amino)pyridin-2-yl)methyl)-2-methylpiperidine-4-carboxylic acid
142. (2R)-1-(2,3-dichlorobenzyl)-2-ethyl-4-((3-fluoro-6-((5-methyl-1H-pyrazol-3-yl)amino)pyridin-2-yl)methyl)piperidine-4-carboxylic acid
143. 1-(2,3-difluorobenzyl)-4-((3-fluoro-6-((5-methyl-1H-pyrazol-3-yl)amino)pyridin-2-yl)methyl)piperidine-4-carboxylic acid
144. (2R)-1-(2,3-difluorobenzyl)-4-((3-fluoro-6-((5-methyl-1H-pyrazol-3-yl)amino)pyridin-2-yl)methyl)-2-methylpiperidine-4-carboxylic acid
145. (2R)-1-(2,3-difluorobenzyl)-2-ethyl-4-((3-fluoro-6-((5-methyl-1H-pyrazol-3-yl)amino)pyridin-2-yl)methyl)piperidine-4-carboxylic acid
146. 1-(3-chloro-2-fluoro-6-methylbenzyl)-4-((3-fluoro-6-((5-methyl-1H-pyrazol-3-yl)amino)pyridin-2-yl)methyl)piperidine-4-carboxylic acid
147. (2R)-1-(3-chloro-2-fluoro-6-methylbenzyl)-4-((3-fluoro-6-((5-methyl-1H-pyrazol-3-yl)amino)pyridin-2-yl)methyl)-2-methylpiperidine-4-carboxylic acid
148. (2R)-1-(3-chloro-2-fluoro-6-methylbenzyl)-2-ethyl-4-((3-fluoro-6-((5-methyl-1H-pyrazol-3-yl)amino)pyridin-2-yl)methyl)piperidine-4-carboxylic acid
149. 1-(3-chloro-2-methylbenzyl)-4-((3-fluoro-6-((5-methyl-1H-pyrazol-3-yl)amino)pyridin-2-yl)methyl)piperidine-4-carboxylic acid
150. (2R)-1-(3-chloro-2-methylbenzyl)-4-((3-fluoro-6-((5-methyl-1H-pyrazol-3-yl)amino)pyridin-2-yl)methyl)-2-methylpiperidine-4-carboxylic acid
151. (2R)-1-(3-chloro-2-methylbenzyl)-2-ethyl-4-((3-fluoro-6-((5-methyl-1H-pyrazol-3-yl)amino)pyridin-2-yl)methyl)piperidine-4-carboxylic acid
152. 4-((6-((1H-pyrazol-3-yl)amino)-3-fluoropyridin-2-yl)methyl)-1-(2-fluoro-3-methylbenzyl)piperidine-4-carboxylic acid
153. (2R)-4-((6-((1H-pyrazol-3-yl)amino)-3-fluoropyridin-2-yl)methyl)-1-(2-fluoro-3-methylbenzyl)-2-methylpiperidine-4-carboxylic acid
154. (2R)-4-((6-((1H-pyrazol-3-yl)amino)-3-fluoropyridin-2-yl)methyl)-2-ethyl-1-(2-fluoro-3-methylbenzyl)piperidine-4-carboxylic acid
155. 4-((3-fluoro-6-((5-methyl-1H-pyrazol-3-yl)amino)pyridin-2-yl)methyl)-1-(2-fluorobenzyl)piperidine-4-carboxylic acid
156. (2R)-4-((3-fluoro-6-((5-methyl-1H-pyrazol-3-yl)amino)pyridin-2-yl)methyl)-1-(2-fluorobenzyl)-2-methylpiperidine-4-carboxylic acid
157. (2R)-2-ethyl-4-((3-fluoro-6-((5-methyl-1H-pyrazol-3-yl)amino)pyridin-2-yl)methyl)-1-(2-fluorobenzyl)piperidine-4-carboxylic acid
158. 1-(2,6-dichlorobenzyl)-4-((3-fluoro-6-((5-methyl-1H-pyrazol-3-yl)amino)pyridin-2-yl)methyl)piperidine-4-carboxylic acid
159. (2R)-1-(2,6-dichlorobenzyl)-4-((3-fluoro-6-((5-methyl-1H-pyrazol-3-yl)amino)pyridin-2-yl)methyl)-2-methylpiperidine-4-carboxylic acid
160. (2R)-1-(2,6-dichlorobenzyl)-2-ethyl-4-((3-fluoro-6-((5-methyl-1H-pyrazol-3-yl)amino)pyridin-2-yl)methyl)piperidine-4-carboxylic acid
161. 1-(2,6-difluorobenzyl)-4-((3-fluoro-6-((5-methyl-1H-pyrazol-3-yl)amino)pyridin-2-yl)methyl)piperidine-4-carboxylic acid
162. (2R)-1-(2,6-difluorobenzyl)-4-((3-fluoro-6-((5-methyl-1H-pyrazol-3-yl)amino)pyridin-2-yl)methyl)-2-methylpiperidine-4-carboxylic acid
163. (2R)-1-(2,6-difluorobenzyl)-2-ethyl-4-((3-fluoro-6-((5-methyl-1H-pyrazol-3-yl)amino)pyridin-2-yl)methyl)piperidine-4-carboxylic acid
164. 1-(3-chloro-2-fluoro-4-methylbenzyl)-4-((3-fluoro-6-((5-methyl-1H-pyrazol-3-yl)amino)pyridin-2-yl)methyl)piperidine-4-carboxylic acid
165. (2R)-1-(3-chloro-2-fluoro-4-methylbenzyl)-4-((3-fluoro-6-((5-methyl-1H-pyrazol-3-yl)amino)pyridin-2-yl)methyl)-2-methylpiperidine-4-carboxylic acid
166. (2R)-1-(3-chloro-2-fluoro-4-methylbenzyl)-2-ethyl-4-((3-fluoro-6-((5-methyl-1H-pyrazol-3-yl)amino)pyridin-2-yl)methyl)piperidine-4-carboxylic acid
167. 1-(2-(3-chloro-2-fluorophenyl)propan-2-yl)-4-((3-fluoro-6-((5-methyl-1H-pyrazol-3-yl)amino)pyridin-2-yl)methyl)piperidine-4-carboxylic acid
168. (2R,4R)-1-(2-(3-chloro-2-fluorophenyl)propan-2-yl)-4-((3-fluoro-6-((5-methyl-1H-pyrazol-3-yl)amino)pyridin-2-yl)methyl)-2-methylpiperidine-4-carboxylic acid
169. (2R,4R)-1-(2-(3-chloro-2-fluorophenyl)propan-2-yl)-2-ethyl-4-((3-fluoro-6-((5-methyl-1H-pyrazol-3-yl)amino)pyridin-2-yl)methyl)piperidine-4-carboxylic acid
170. 1-(1-(3-chloro-2-fluorophenyl)cyclopropyl)-4-((3-fluoro-6-((5-methyl-1H-pyrazol-3-yl)amino)pyridin-2-yl)methyl)piperidine-4-carboxylic acid
171. (2R,4R)-1-(1-(3-chloro-2-fluorophenyl)cyclopropyl)-4-((3-fluoro-6-((5-methyl-1H-pyrazol-3-yl)amino)pyridin-2-yl)methyl)-2-methylpiperidine-4-carboxylic acid
172. 1-(3-(3-chloro-2-fluorophenyl)oxetan-3-yl)-4-((3-fluoro-6-((5-methyl-1H-pyrazol-3-yl)amino)pyridin-2-yl)methyl)piperidine-4-carboxylic acid
173. (2R,4R)-1-(3-(3-chloro-2-fluorophenyl)oxetan-3-yl)-4-((3-fluoro-6-((5-methyl-1H-pyrazol-3-yl)amino)pyridin-2-yl)methyl)-2-methylpiperidine-4-carboxylic acid
174. (2R,4R)-1-(3-(3-chloro-2-fluorophenyl)oxetan-3-yl)-2-ethyl-4-((3-fluoro-6-((5-methyl-1H-pyrazol-3-yl)amino)pyridin-2-yl)methyl)piperidine-4-carboxylic acid
175. 1-(1-(3-chloro-2-fluorophenyl)cyclobutyl)-4-((3-fluoro-6-((5-methyl-1H-pyrazol-3-yl)amino)pyridin-2-yl)methyl)piperidine-4-carboxylic acid
176. (2R,4R)-1-(1-(3-chloro-2-fluorophenyl)cyclobutyl)-4-((3-fluoro-6-((5-methyl-1H-pyrazol-3-yl)amino)pyridin-2-yl)methyl)-2-methylpiperidine-4-carboxylic acid
177. (2R,4R)-1-(1-(3-chloro-2-fluorophenyl)cyclobutyl)-2-ethyl-4-((3-fluoro-6-((5-methyl-1H-pyrazol-3-yl)amino)pyridin-2-yl)methyl)piperidine-4-carboxylic acid
178. (2R,4R)-1-(3-chloro-2-fluorobenzyl)-4-((3-fluoro-6-((5-methyl-1H-pyrazol-3-yl)amino)pyridin-2-yl)methyl)-2-methylpiperidine-4-carboxylic acid
179. (2R,4R)-1-(3-chloro-2-fluorobenzyl)-2-ethyl-4-((3-fluoro-4-(3-hydroxyoxetan-3-yl)-6-((5-methyl-1H-pyrazol-3-yl)amino)pyridin-2-yl)methyl)piperidine-4-carboxylic acid -continued 180. (2R,4R)-1-(3-chloro-2-fluorobenzyl)-4-((3-fluoro-6-((5-methyl-1H-pyrazol-3-yl)amino)-4-(oxetan-3-yl)pyridin-2-yl)methyl)-2-methylpiperidine-4-carboxylic acid
181. (2R,4R)-1-(3-chloro-2-fluorobenzyl)-2-ethyl-4-((3-fluoro-6-((5-methyl-1H-pyrazol-3-yl)amino)-4-(oxetan-3-yl)pyridin-2-yl)methyl)piperidine-4-carboxylic acid
182. 1-(3-chloro-2-fluorobenzyl)-4-((3-fluoro-4-(3-hydroxyazetidin-1-yl)-6-((5-methyl-1H-pyrazol-3-yl)amino)pyridin-2-yl)methyl)piperidine-4-carboxylic acid
183. (2R,4R)-1-(3-chloro-2-fluorobenzyl)-2-ethyl-4-((3-fluoro-4-(3-hydroxyazetidin-1-yl)-6-((5-methyl-1H-pyrazol-3-yl)amino)pyridin-2-yl)methyl)piperidine-4-carboxylic acid
184. (2R,4R)-1-(3-chloro-2-fluorobenzyl)-4-((3-fluoro-4-(3-hydroxyazetidin-1-yl)-6-((5-methyl-1H-pyrazol-3-yl)amino)pyridin-2-yl)methyl)-2-methylpiperidine-4-carboxylic acid
185. (2R,4R)-1-(3-chloro-2-fluorobenzyl)-4-((3-fluoro-6-((5-methyl-1H-pyrazol-3-yl)amino)-4-(4-methylpiperazin-1-yl)pyridin-2-yl)methyl)-2-methylpiperidine-4-carboxylic acid
186. (2R,4R)-1-(3-chloro-2-fluorobenzyl)-2-ethyl-4-((3-fluoro-6-((5-methyl-1H-pyrazol-3-yl)amino)-4-(4-methylpiperazin-1-yl)pyridin-2-yl)methyl)piperidine-4-carboxylic acid
187. (2R,4R)-4-((4-(azetidin-3-yl)-3-fluoro-6-((5-methyl-1H-pyrazol-3-yl)amino)pyridin-2-yl)methyl)-1-(3-chloro-2-fluorobenzyl)-2-methylpiperidine-4-carboxylic acid
188. 4-((4-(azetidin-3-yl)-3-fluoro-6-((5-methyl-1H-pyrazol-3-yl)amino)pyridin-2-yl)methyl)-1-(3-chloro-2-fluorobenzyl)piperidine-4-carboxylic acid
189. (2R,4R)-4-((4-(azetidin-3-yl)-3-fluoro-6-((5-methyl-1H-pyrazol-3-yl)amino)pyridin-2-yl)methyl)-1-(3-chloro-2-fluorobenzyl)-2-ethylpiperidine-4-carboxylic acid
190. (2R,4R)-1-(3-chloro-2-fluorobenzyl)-4-((3-fluoro-6-((5-methyl-1H-pyrazol-3-yl)amino)-4-(1-methylazetidin-3-yl)pyridin-2-yl)methyl)-2-methylpiperidine-4-carboxylic acid
191. 1-(3-chloro-2-fluorobenzyl)-4-((3-fluoro-6-((5-methyl-1H-pyrazol-3-yl)amino)-4-(1-methylazetidin-3-yl)pyridin-2-yl)methyl)piperidine-4-carboxylic acid
192. (2R,4R)-1-(3-chloro-2-fluorobenzyl)-2-ethyl-4-((3-fluoro-6-((5-methyl-1H-pyrazol-3-yl)amino)-4-(1-methylazetidin-3-yl)pyridin-2-yl)methyl)piperidine-4-carboxylic acid
193. (2R,4R)-1-(3-chloro-2-fluorobenzyl)-2-ethyl-4-((3-fluoro-4-methyl-6-((5-methyl-1H-pyrazol-3-yl)amino)pyridin-2-yl)methyl)piperidine-4-carboxylic acid
194. (2R,4R)-1-(3-chloro-2-fluorobenzyl)-2-ethyl-4-((4-ethyl-3-fluoro-6-((5-methyl-1H-pyrazol-3-yl)amino)pyridin-2-yl)methyl)piperidine-4-carboxylic acid
195. 1-(3-chloro-2-fluorobenzyl)-4-((3-fluoro-4-isopropyl-6-((5-methyl-1H-pyrazol-3-yl)amino)pyridin-2-yl)methyl)piperidine-4-carboxylic acid
196. (2R,4R)-1-(3-chloro-2-fluorobenzyl)-2-ethyl-4-((3-fluoro-4-isopropyl-6-((5-methyl-1H-pyrazol-3-yl)amino)pyridin-2-yl)methyl)piperidine-4-carboxylic acid
197. 1-(3-chloro-2-fluorobenzyl)-4-((4-cyclopropyl-3-fluoro-6-((5-methyl-1H-pyrazol-3-yl)amino)pyridin-2-yl)methyl)piperidine-4-carboxylic acid
198. (2R,4R)-1-(3-chloro-2-fluorobenzyl)-4-((4-cyclopropyl-3-fluoro-6-((5-methyl-1H-pyrazol-3-yl)amino)pyridin-2-yl)methyl)-2-ethylpiperidine-4-carboxylic acid
199. 1-(3-chloro-2-fluorobenzyl)-4-((3-fluoro-4-(2-hydroxypropan-2-yl)-6-((5-methyl-1H-pyrazol-3-yl)amino)pyridin-2-yl)methyl)piperidine-4-carboxylic acid
200. (2R,4R)-1-(3-chloro-2-fluorobenzyl)-2-ethyl-4-((3-fluoro-4-(2-hydroxypropan-2-yl)-6-((5-methyl-1H-pyrazol-3-yl)amino)pyridin-2-yl)methyl)piperidine-4-carboxylic acid
201. 1-(3-chloro-2-fluorobenzyl)-4-((3-fluoro-6-((5-methyl-1H-pyrazol-3-yl)amino)-4-phenylpyridin-2-yl)methyl)piperidine-4-carboxylic acid
202. (2R,4R)-1-(3-chloro-2-fluorobenzyl)-4-((3-fluoro-6-((5-methyl-1H-pyrazol-3-yl)amino)-4-phenylpyridin-2-yl)methyl)-2-methylpiperidine-4-carboxylic acid
203. (2R,4R)-1-(3-chloro-2-fluorobenzyl)-2-ethyl-4-((3-fluoro-6-((5-methyl-1H-pyrazol-3-yl)amino)-4-phenylpyridin-2-yl)methyl)piperidine-4-carboxylic acid
204. 1-(3-chloro-2-fluorobenzyl)-4-((3-fluoro-4-(1-hydroxycyclopropyl)-6-((5-methyl-1H-pyrazol-3-yl)amino)pyridin-2-yl)methyl)piperidine-4-carboxylic acid
205. (2R,4R)-1-(3-chloro-2-fluorobenzyl)-4-((3-fluoro-4-(1-hydroxycyclopropyl)-6-((5-methyl-1H-pyrazol-3-yl)amino)pyridin-2-yl)methyl)-2-methylpiperidine-4-carboxylic acid
206. (2R,4R)-1-(3-chloro-2-fluorobenzyl)-2-ethyl-4-((3-fluoro-4-(1-hydroxycyclopropyl)-6-((5-methyl-1H-pyrazol-3-yl)amino)pyridin-2-yl)methyl)piperidine-4-carboxylic acid
207. (2R,4R)-4-((4-(azetidin-1-yl)-3-fluoro-6-((5-methyl-1H-pyrazol-3-yl)amino)pyridin-2-yl)methyl)-1-(3-chloro-2-fluorobenzyl)-2-ethylpiperidine-4-carboxylic acid
208. 4-((4-(azetidin-1-yl)-3-fluoro-6-((5-methyl-1H-pyrazol-3-yl)amino)pyridin-2-yl)methyl)-1-(3-chloro-2-fluorobenzyl)piperidine-4-carboxylic acid
209. (2R,4R)-1-(3-chloro-2-fluorobenzyl)-4-((4-(difluoromethyl)-3-fluoro-6-((5-methyl-1H-pyrazol-3-yl)amino)pyridin-2-yl)methyl)-2-ethylpiperidine-4-carboxylic acid
210. 1-(3-chloro-2-fluorobenzyl)-4-((4-(difluoromethyl)-3-fluoro-6-((5-methyl-1H-pyrazol-3-yl)amino)pyridin-2-yl)methyl)piperidine-4-carboxylic acid
211. (2R,4R)-1-(3-chloro-2-fluorobenzyl)-2-ethyl-4-((3-fluoro-6-((5-methyl-1H-pyrazol-3-yl)amino)-4-(trifluoromethyl)pyridin-2-yl)methyl)piperidine-4-carboxylic acid
212. 1-(3-chloro-2-fluorobenzyl)-4-((3-fluoro-6-((5-methyl-1H-pyrazol-3-yl)amino)-4-(trifluoromethyl)pyridin-2-yl)methyl)piperidine-4-carboxylic acid
213. (2R,4R)-1-(3-chloro-2-fluorobenzyl)-4-((3-fluoro-6-((5-methyl-1H-pyrazol-3-yl)amino)-4-(trifluoromethyl)pyridin-2-yl)methyl)-2-methylpiperidine-4-carboxylic acid
214. (2R,4R)-1-(3-chloro-2-fluorobenzyl)-2-ethyl-4-((3-fluoro-4-(1-hydroxycyclobutyl)-6-((5-methyl-1H-pyrazol-3-yl)amino)pyridin-2-yl)methyl)piperidine-4-carboxylic acid
215. 1-(3-chloro-2-fluorobenzyl)-4-((3-fluoro-4-(1-hydroxycyclobutyl)-6-((5-methyl-1H-pyrazol-3-yl)amino)pyridin-2-yl)methyl)piperidine-4-carboxylic acid
216. (2R,4R)-1-(3-chloro-2-fluorobenzyl)-4-((3-fluoro-4-(1-hydroxycyclobutyl)-6-((5-methyl-1H-pyrazol-3-yl)amino)pyridin-2-yl)methyl)-2-methylpiperidine-4-carboxylic acid
217. (2R,4R)-1-(3-chloro-2-fluorobenzyl)-4-((4-cyclobutyl-3-fluoro-6-((5-methyl-1H-pyrazol-3-yl)amino)pyridin-2-yl)methyl)-2-ethylpiperidine-4-carboxylic acid
218. 1-(3-chloro-2-fluorobenzyl)-4-((4-cyclobutyl-3-fluoro-6-((5-methyl-1H-pyrazol-3-yl)amino)pyridin-2-yl)methyl)piperidine-4-carboxylic acid 219. (2R,4R)-1-(3-chloro-2-fluorobenzyl)-4-((4-cyclobutyl-3-fluoro-6-((5-methyl-1H-pyrazol-3-yl)amino)pyridin-2-yl)methyl)-2-methylpiperidine-4-carboxylic acid
220. (2R,4R)-1-(3-chloro-2-fluorobenzyl)-4-((4-cyano-3-fluoro-6-((5-methyl-1H-pyrazol-3-yl)amino)pyridin-2-yl)methyl)-2-ethylpiperidine-4-carboxylic acid
221. 1-(3-chloro-2-fluorobenzyl)-4-((4-cyano-3-fluoro-6-((5-methyl-1H-pyrazol-3-yl)amino)pyridin-2-yl)methyl)piperidine-4-carboxylic acid
222. (2R,4R)-1-(3-chloro-2-fluorobenzyl)-2-ethyl-4-((3-methyl-6-((5-methyl-1H-pyrazol-3-yl)amino)pyridin-2-yl)methyl)piperidine-4-carboxylic acid
223. (2R,4R)-1-(3-chloro-2-fluorobenzyl)-4-((3-cyano-6-((5-methyl-1H-pyrazol-3-yl)amino)pyridin-2-yl)methyl)-2-ethylpiperidine-4-carboxylic acid
224. (2R,4R)-1-(3-chloro-2-fluorobenzyl)-4-((3-chloro-6-((5-methyl-1H-pyrazol-3-yl)amino)pyridin-2-yl)methyl)-2-ethylpiperidine-4-carboxylic acid
225. 1-(3-chloro-2-fluorobenzyl)-4-((3-methyl-6-((5-methyl-1H-pyrazol-3-yl)amino)pyridin-2-yl)methyl)piperidine-4-carboxylic acid
226. 1-(3-chloro-2-fluorobenzyl)-4-((3-cyano-6-((5-methyl-1H-pyrazol-3-yl)amino)pyridin-2-yl)methyl)piperidine-4-carboxylic acid
227. 1-(3-chloro-2-fluorobenzyl)-4-((3-chloro-6-((5-methyl-1H-pyrazol-3-yl)amino)pyridin-2-yl)methyl)piperidine-4-carboxylic acid
228. (2S)-1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid
229. 1-(1-(3-chloro-2-fluorophenyl)ethyl)-4-((3-fluoro-6-((5-methyl-1H-pyrazol-3-yl)amino)pyridin-2-yl)methyl)piperidine-4-carboxylic acid
230. 1-(difluoro(2-(trifluoromethyl)phenyl)methyl)-4-((3-fluoro-6-((5-methyl-1H-pyrazol-3-yl)amino)pyridin-2-yl)methyl)piperidine-4-carboxylic acid
231. (2R,4R)-1-(3-chloro-2-fluoro-6-methylbenzyl)-4-((3-fluoro-6-((5-methyl-1H-pyrazol-3-yl)amino)pyridin-2-yl)methyl)-2-methylpiperidine-4-carboxylic acid
232. (2R,4R)-1-(3-chloro-2-fluoro-4-methylbenzyl)-4-((3-fluoro-6-((5-methyl-1H-pyrazol-3-yl)amino)pyridin-2-yl)methyl)-2-methylpiperidine-4-carboxylic acid
233. (2R,4R)-1-(3-chloro-2-fluorobenzyl)-4-((3-fluoro-4-(3-hydroxyazetidin-1-yl)-6-((5-methylthiazol-2-yl)amino)pyridin-2-yl)methyl)-2-methylpiperidine-4-carboxylic acid
234. (2R,4R)-1-((4,5-dichlorothiophen-2-yl)methyl)-4-((3-fluoro-6-((5-methyl-1H-pyrazol-3-yl)amino)pyridin-2-yl)methyl)-2-methylpiperidine-4-carboxylic acid
235. (2R,4R)-1-((4,5-dimethylthiophen-2-yl)methyl)-4-((3-fluoro-6-((5-methyl-1H-pyrazol-3-yl)amino)pyridin-2-yl)methyl)-2-methylpiperidine-4-carboxylic acid
236. (3R,4S)-1-(3-chloro-2-fluorobenzyl)-4-((3-fluoro-6-((5-methyl-1H-pyrazol-3-yl)amino)pyridin-2-yl)methyl)-3-methylpiperidine-4-carboxylic acid
237. (2R,4R)-1-((3-chloro-2-fluorophenyl)difluoromethyl)-4-((3-fluoro-6-((5-methyl-1H-pyrazol-3-yl)amino)pyridin-2-yl)methyl)-2-methylpiperidine-4-carboxylic acid
238. 1-(3-chloro-2-fluorobenzyl)-4-((3-fluoro-6-((5-methyl-1H-pyrazol-3-yl)amino)pyridin-2-yl)methyl)-3-methylpiperidine-4-carboxylic acid
239. (3 S,4R)-1-(3-chloro-2-fluorobenzyl)-4-((3-fluoro-6-((5-methyl-1H-pyrazol-3-yl)amino)pyridin-2-yl)methyl)-3-methylpiperidine-4-carboxylic acid
240. 1-(3-chloro-2-fluorobenzyl)-4-((3-fluoro-4-(1-fluorocyclopropyl)-6-((5-methyl-1H-pyrazol-3-yl)amino)pyridin-2-yl)methyl)piperidine-4-carboxylic acid
241. 1-(3-chloro-2-fluorobenzyl)-4-((3-fluoro-6-((5-methyl-1H-pyrazol-3-yl)amino)-4-(methylamino)pyridin-2-yl)methyl)piperidine-4-carboxylic acid
242. 1-(3-chloro-2-fluorobenzyl)-4-((3-fluoro-4-isopropoxy-6-((5-methyl-1H-pyrazol-3-yl)amino)pyridin-2-yl)methyl)piperidine-4-carboxylic acid
243. (2R,4R)-1-(((3-chloro-2-fluorophenyl)sulfonyl)methyl)-4-((3-fluoro-6-((5-methyl-1H-pyrazol-3-yl)amino)pyridin-2-yl)methyl)-2-methylpiperidine-4-carboxylic acid
244. 1-(1-(3,5-dichlorophenyl)cyclopropyl)-4-((3-fluoro-6-((5-methyl-1H-pyrazol-3-yl)amino)pyridin-2-yl)methyl)piperidine-4-carboxylic acid
245. 1-(3-(3,5-dichlorophenyl)oxetan-3-yl)-4-((3-fluoro-6-((5-methyl-1H-pyrazol-3-yl)amino)pyridin-2-yl)methyl)piperidine-4-carboxylic acid
246. (2R,4R)-1-(3-chloro-4,5-difluorobenzyl)-4-((3-fluoro-6-((5-methyl-1H-pyrazol-3-yl)amino)pyridin-2-yl)methyl)-2-methylpiperidine-4-carboxylic acid
247. (2R,4R)-1-(2,3-difluorobenzyl)-4-((3-fluoro-4-(1-hydroxycyclopropyl)-6-((5-methyl-1H-pyrazol-3-yl)amino)pyridin-2-yl)methyl)-2-methylpiperidine-4-carboxylic acid
248. (2R,4R)-1-(2,3-difluorobenzyl)-4-((3-fluoro-4-(2-hydroxypropan-2-yl)-6-((5-methyl-1H-pyrazol-3-yl)amino)pyridin-2-yl)methyl)-2-methylpiperidine-4-carboxylic acid
249. 1-(2,3-difluorobenzyl)-4-((3-fluoro-4-(1-hydroxycyclopropyl)-6-((5-methyl-1H-pyrazol-3-yl)amino)pyridin-2-yl)methyl)piperidine-4-carboxylic acid
250. 1-(2,3-difluorobenzyl)-4-((3-fluoro-4-(2-hydroxypropan-2-yl)-6-((5-methyl-1H-pyrazol-3-yl)amino)pyridin-2-yl)methyl)piperidine-4-carboxylic acid
251. (2R,4R)-1-(2,3-difluorobenzyl)-2-ethyl-4-((3-fluoro-4-(1-hydroxycyclopropyl)-6-((5-methyl-1H-pyrazol-3-yl)amino)pyridin-2-yl)methyl)piperidine-4-carboxylic acid
252. (2R,4R)-1-(2,3-difluorobenzyl)-2-ethyl-4-((3-fluoro-4-methyl-6-((5-methyl-1H-pyrazol-3-yl)amino)pyridin-2-yl)methyl)piperidine-4-carboxylic acid
253. (2R,4R)-1-(2,3-difluorobenzyl)-2-ethyl-4-((3-fluoro-4-(2-hydroxypropan-2-yl)-6-((5-methyl-1H-pyrazol-3-yl)amino)pyridin-2-yl)methyl)piperidine-4-carboxylic acid
254. (2R,4R)-1-(2,3-dichlorobenzyl)-2-ethyl-4-((3-fluoro-4-methyl-6-((5-methyl-1H-pyrazol-3-yl)amino)pyridin-2-yl)methyl)piperidine-4-carboxylic acid
255. (2R,4R)-1-(3-chloro-2,6-difluorobenzyl)-2-ethyl-4-((3-fluoro-4-(1-hydroxycyclopropyl)-6-((5-methyl-1H-pyrazol-3-yl)amino)pyridin-2-yl)methyl)piperidine-4-carboxylic acid
256. (2R,4R)-1-(3-chloro-2,6-difluorobenzyl)-2-ethyl-4-((3-fluoro-4-methyl-6-((5-methyl-1H-pyrazol-3-yl)amino)pyridin-2-yl)methyl)piperidine-4-carboxylic acid
257. (2R,4R)-1-(3-chloro-2,6-difluorobenzyl)-2-ethyl-4-((3-fluoro-4-(2-hydroxypropan-2-yl)-6-((5-methyl-1H-pyrazol-3-yl)amino)pyridin-2-yl)methyl)piperidine-4-carboxylic acid

| | |
|---|---|
| 258. | 1-(3-chloro-2,6-difluorobenzyl)-4-((3-fluoro-4-(1-hydroxycyclopropyl)-6-((5-methyl-1H-pyrazol-3-yl)amino)pyridin-2-yl)methyl)piperidine-4-carboxylic acid |
| 259. | 1-(3-chloro-2,6-difluorobenzyl)-4-((3-fluoro-4-(2-hydroxypropan-2-yl)-6-((5-methyl-1H-pyrazol-3-yl)amino)pyridin-2-yl)methyl)piperidine-4-carboxylic acid |
| 260. | (2R,4R)-1-(3-chloro-2,6-difluorobenzyl)-4-((3-fluoro-4-(1-hydroxycyclopropyl)-6-((5-methyl-1H-pyrazol-3-yl)amino)pyridin-2-yl)methyl)-2-methylpiperidine-4-carboxylic acid |
| 261. | (2R,4R)-1-(3-chloro-2,6-difluorobenzyl)-4-((3-fluoro-4-(2-hydroxypropan-2-yl)-6-((5-methyl-1H-pyrazol-3-yl)amino)pyridin-2-yl)methyl)-2-methylpiperidine-4-carboxylic acid |
| 262. | 1-(3-chloro-2-fluorobenzyl)-4-((6-ethyl-5-fluoro-2-((5-methyl-1H-pyrazol-3-yl)amino)pyrimidin-4-yl)methyl)piperidine-4-carboxylic acid |
| 263. | (2R,4R)-1-(3-chloro-2-fluorobenzyl)-4-((6-ethyl-5-fluoro-2-((5-methyl-1H-pyrazol-3-yl)amino)pyrimidin-4-yl)methyl)-2-methylpiperidine-4-carboxylic acid |
| 264. | (2R,4R)-1-(3-chloro-2-fluorobenzyl)-2-ethyl-4-((6-ethyl-5-fluoro-2-((5-methyl-1H-pyrazol-3-yl)amino)pyrimidin-4-yl)methyl)piperidine-4-carboxylic acid |
| 265. | 1-(3-chloro-2-fluorobenzyl)-4-((5-fluoro-6-methyl-2-((5-methyl-1H-pyrazol-3-yl)amino)pyrimidin-4-yl)methyl)piperidine-4-carboxylic acid |
| 266. | (2R,4R)-1-(3-chloro-2-fluorobenzyl)-4-((5-fluoro-6-methyl-2-((5-methyl-1H-pyrazol-3-yl)amino)pyrimidin-4-yl)methyl)-2-methylpiperidine-4-carboxylic acid |
| 267. | (2R,4R)-1-(3-chloro-2-fluorobenzyl)-2-ethyl-4-((5-fluoro-6-methyl-2-((5-methyl-1H-pyrazol-3-yl)amino)pyrimidin-4-yl)methyl)piperidine-4-carboxylic acid |
| 268. | 1-(3-chloro-2-fluorobenzyl)-4-((5-fluoro-6-isopropyl-2-((5-methyl-1H-pyrazol-3-yl)amino)pyrimidin-4-yl)methyl)piperidine-4-carboxylic acid |
| 269. | (2R,4R)-1-(3-chloro-2-fluorobenzyl)-4-((5-fluoro-6-isopropyl-2-((5-methyl-1H-pyrazol-3-yl)amino)pyrimidin-4-yl)methyl)-2-methylpiperidine-4-carboxylic acid |
| 270. | (2R,4R)-1-(3-chloro-2-fluorobenzyl)-2-ethyl-4-((5-fluoro-6-isopropyl-2-((5-methyl-1H-pyrazol-3-yl)amino)pyrimidin-4-yl)methyl)piperidine-4-carboxylic acid |
| 271. | 1-(3-chloro-2-fluorobenzyl)-4-((6-cyclopropyl-5-fluoro-2-((5-methyl-1H-pyrazol-3-yl)amino)pyrimidin-4-yl)methyl)piperidine-4-carboxylic acid |
| 272. | (2R,4R)-1-(3-chloro-2-fluorobenzyl)-4-((6-cyclopropyl-5-fluoro-2-((5-methyl-1H-pyrazol-3-yl)amino)pyrimidin-4-yl)methyl)-2-methylpiperidine-4-carboxylic acid |
| 273. | (2R,4R)-1-(3-chloro-2-fluorobenzyl)-4-((6-cyclopropyl-5-fluoro-2-((5-methyl-1H-pyrazol-3-yl)amino)pyrimidin-4-yl)methyl)-2-ethylpiperidine-4-carboxylic acid |
| 274. | 1-(3-chloro-2-fluorobenzyl)-4-((5-fluoro-6-(2-hydroxypropan-2-yl)-2-((5-methyl-1H-pyrazol-3-yl)amino)pyrimidin-4-yl)methyl)piperidine-4-carboxylic acid |
| 275. | (2R,4R)-1-(3-chloro-2-fluorobenzyl)-4-((5-fluoro-6-(2-hydroxypropan-2-yl)-2-((5-methyl-1H-pyrazol-3-yl)amino)pyrimidin-4-yl)methyl)-2-methylpiperidine-4-carboxylic acid |
| 276. | (2R,4R)-1-(3-chloro-2-fluorobenzyl)-2-ethyl-4-((5-fluoro-6-(2-hydroxypropan-2-yl)-2-((5-methyl-1H-pyrazol-3-yl)amino)pyrimidin-4-yl)methyl)piperidine-4-carboxylic acid |
| 277. | 1-(3-chloro-2-fluorobenzyl)-4-((5-fluoro-2-((5-methyl-1H-pyrazol-3-yl)amino)-6-phenylpyrimidin-4-yl)methyl)piperidine-4-carboxylic acid |
| 278. | (2R,4R)-1-(3-chloro-2-fluorobenzyl)-4-((5-fluoro-2-((5-methyl-1H-pyrazol-3-yl)amino)-6-phenylpyrimidin-4-yl)methyl)-2-methylpiperidine-4-carboxylic acid |
| 279. | (2R,4R)-1-(3-chloro-2-fluorobenzyl)-2-ethyl-4-((5-fluoro-2-((5-methyl-1H-pyrazol-3-yl)amino)-6-phenylpyrimidin-4-yl)methyl)piperidine-4-carboxylic acid |
| 280. | 1-(3-chloro-2-fluorobenzyl)-4-((5-fluoro-6-(1-hydroxycyclopropyl)-2-((5-methyl-1H-pyrazol-3-yl)amino)pyrimidin-4-yl)methyl)piperidine-4-carboxylic acid |
| 281. | (2R,4R)-1-(3-chloro-2-fluorobenzyl)-4-((5-fluoro-6-(1-hydroxycyclopropyl)-2-((5-methyl-1H-pyrazol-3-yl)amino)pyrimidin-4-yl)methyl)-2-methylpiperidine-4-carboxylic acid |
| 282. | (2R,4R)-1-(3-chloro-2-fluorobenzyl)-2-ethyl-4-((5-fluoro-6-(1-hydroxycyclopropyl)-2-((5-methyl-1H-pyrazol-3-yl)amino)pyrimidin-4-yl)methyl)piperidine-4-carboxylic acid |
| 283. | (2R,4R)-4-((6-(azetidin-1-yl)-5-fluoro-2-((5-methyl-1H-pyrazol-3-yl)amino)pyrimidin-4-yl)methyl)-1-(3-chloro-2-fluorobenzyl)-2-ethylpiperidine-4-carboxylic acid |
| 284. | 4-((6-(azetidin-1-yl)-5-fluoro-2-((5-methyl-1H-pyrazol-3-yl)amino)pyrimidin-4-yl)methyl)-1-(3-chloro-2-fluorobenzyl)piperidine-4-carboxylic acid |
| 285. | (2R,4R)-4-((6-(azetidin-1-yl)-5-fluoro-2-((5-methyl-1H-pyrazol-3-yl)amino)pyrimidin-4-yl)methyl)-1-(3-chloro-2-fluorobenzyl)-2-methylpiperidine-4-carboxylic acid |
| 286. | (2R,4R)-1-(3-chloro-2-fluorobenzyl)-4-((6-(difluoromethyl)-5-fluoro-2-((5-methyl-1H-pyrazol-3-yl)amino)pyrimidin-4-yl)methyl)-2-ethylpiperidine-4-carboxylic acid |
| 287. | 1-(3-chloro-2-fluorobenzyl)-4-((6-(difluoromethyl)-5-fluoro-2-((5-methyl-1H-pyrazol-3-yl)amino)pyrimidin-4-yl)methyl)piperidine-4-carboxylic acid |
| 288. | (2R,4R)-1-(3-chloro-2-fluorobenzyl)-4-((6-(difluoromethyl)-5-fluoro-2-((5-methyl-1H-pyrazol-3-yl)amino)pyrimidin-4-yl)methyl)-2-methylpiperidine-4-carboxylic acid |
| 289. | (2R,4R)-1-(3-chloro-2-fluorobenzyl)-2-ethyl-4-((5-fluoro-2-((5-methyl-1H-pyrazol-3-yl)amino)-6-(trifluoromethyl)pyrimidin-4-yl)methyl)piperidine-4-carboxylic acid |
| 290. | 1-(3-chloro-2-fluorobenzyl)-4-((5-fluoro-2-((5-methyl-1H-pyrazol-3-yl)amino)-6-(trifluoromethyl)pyrimidin-4-yl)methyl)piperidine-4-carboxylic acid |
| 291. | (2R,4R)-1-(3-chloro-2-fluorobenzyl)-4-((5-fluoro-2-((5-methyl-1H-pyrazol-3-yl)amino)-6-(trifluoromethyl)pyrimidin-4-yl)methyl)-2-methylpiperidine-4-carboxylic acid |
| 292. | (2R,4R)-1-(3-chloro-2-fluorobenzyl)-2-ethyl-4-((5-fluoro-6-(1-hydroxycyclobutyl)-2-((5-methyl-1H-pyrazol-3-yl)amino)pyrimidin-4-yl)methyl)piperidine-4-carboxylic acid |
| 293. | 1-(3-chloro-2-fluorobenzyl)-4-((5-fluoro-6-(1-hydroxycyclobutyl)-2-((5-methyl-1H-pyrazol-3-yl)amino)pyrimidin-4-yl)methyl)piperidine-4-carboxylic acid |
| 294. | (2R,4R)-1-(3-chloro-2-fluorobenzyl)-4-((5-fluoro-6-(1-hydroxycyclobutyl)-2-((5-methyl-1H-pyrazol-3-yl)amino)pyrimidin-4-yl)methyl)-2-methylpiperidine-4-carboxylic acid |
| 295. | (2R,4R)-1-(3-chloro-2-fluorobenzyl)-4-((6-cyclobutyl-5-fluoro-2-((5-methyl-1H-pyrazol-3-yl)amino)pyrimidin-4-yl)methyl)-2-ethylpiperidine-4-carboxylic acid |
| 296. | 1-(3-chloro-2-fluorobenzyl)-4-((6-cyclobutyl-5-fluoro-2-((5-methyl-1H-pyrazol-3-yl)amino)pyrimidin-4-yl)methyl)piperidine-4-carboxylic acid |

| | |
|---|---|
| 297. | (2R,4R)-1-(3-chloro-2-fluorobenzyl)-4-((6-cyclobutyl-5-fluoro-2-((5-methyl-1H-pyrazol-3-yl)amino)pyrimidin-4-yl)methyl)-2-methylpiperidine-4-carboxylic acid |
| 298. | (2R,4R)-1-(3-chloro-2-fluorobenzyl)-4-((6-cyano-5-fluoro-2-((5-methyl-1H-pyrazol-3-yl)amino)pyrimidin-4-yl)methyl)-2-ethylpiperidine-4-carboxylic acid |
| 299. | 1-(3-chloro-2-fluorobenzyl)-4-((6-cyano-5-fluoro-2-((5-methyl-1H-pyrazol-3-yl)amino)pyrimidin-4-yl)methyl)piperidine-4-carboxylic acid |
| 300. | (2R,4R)-1-(3-chloro-2-fluorobenzyl)-4-((6-cyano-5-fluoro-2-((5-methyl-1H-pyrazol-3-yl)amino)pyrimidin-4-yl)methyl)-2-methylpiperidine-4-carboxylic acid |
| 301. | (2R,4R)-1-(3-chloro-2-fluorobenzyl)-4-((5-fluoro-6-(3-hydroxyoxetan-3-yl)-2-((5-methyl-1H-pyrazol-3-yl)amino)pyrimidin-4-yl)methyl)-2-methylpiperidine-4-carboxylic acid |
| 302. | 1-(3-chloro-2-fluorobenzyl)-4-((5-fluoro-6-(3-hydroxyoxetan-3-yl)-2-((5-methyl-1H-pyrazol-3-yl)amino)pyrimidin-4-yl)methyl)piperidine-4-carboxylic acid |
| 303. | (2R,4R)-1-(3-chloro-2-fluorobenzyl)-2-ethyl-4-((5-fluoro-6-(3-hydroxyoxetan-3-yl)-2-((5-methyl-1H-pyrazol-3-yl)amino)pyrimidin-4-yl)methyl)piperidine-4-carboxylic acid |
| 304. | (2R,4R)-1-(3-chloro-2-fluorobenzyl)-4-((5-fluoro-2-((5-methyl-1H-pyrazol-3-yl)amino)-6-(oxetan-3-yl)pyrimidin-4-yl)methyl)-2-methylpiperidine-4-carboxylic acid |
| 305. | 1-(3-chloro-2-fluorobenzyl)-4-((5-fluoro-2-((5-methyl-1H-pyrazol-3-yl)amino)-6-(oxetan-3-yl)pyrimidin-4-yl)methyl)piperidine-4-carboxylic acid |
| 306. | (2R,4R)-1-(3-chloro-2-fluorobenzyl)-2-ethyl-4-((5-fluoro-2-((5-methyl-1H-pyrazol-3-yl)amino)-6-(oxetan-3-yl)pyrimidin-4-yl)methyl)piperidine-4-carboxylic acid |
| 307. | (2R,4R)-1-(3-chloro-2-fluorobenzyl)-4-((3-fluoro-6-((5-methyl-1H-pyrazol-3-yl)amino)pyrazin-2-yl)methyl)-2-methylpiperidine-4-carboxylic acid |
| 308. | (2R,4R)-1-(3-chloro-2-fluorobenzyl)-2-methyl-4-((5-methyl-2-((5-methyl-1H-pyrazol-3-yl)amino)pyrimidin-4-yl)methyl)piperidine-4-carboxylic acid |
| 309. | (2R,4R)-1-(3-chloro-2-fluorobenzyl)-4-((6-fluoro-3-((5-methyl-1H-pyrazol-3-yl)amino)-1,2,4-triazin-5-yl)methyl)-2-methylpiperidine-4-carboxylic acid |
| 310. | (2R,4R)-1-(3-chloro-2-fluorobenzyl)-2-ethyl-4-((3-fluoro-6-((5-methyl-1H-pyrazol-3-yl)amino)pyrazin-2-yl)methyl)piperidine-4-carboxylic acid |
| 311. | (2R,4R)-1-(3-chloro-2-fluorobenzyl)-2-ethyl-4-((5-fluoro-2-((5-methyl-1H-pyrazol-3-yl)amino)pyrimidin-4-yl)methyl)piperidine-4-carboxylic acid |
| 312. | (2R,4R)-1-(3-chloro-2-fluorobenzyl)-2-ethyl-4-((6-fluoro-3-((5-methyl-1H-pyrazol-3-yl)amino)-1,2,4-triazin-5-yl)methyl)piperidine-4-carboxylic acid |
| 313. | 1-(3-chloro-2-fluorobenzyl)-4-((3-fluoro-6-((5-methyl-1H-pyrazol-3-yl)amino)pyrazin-2-yl)methyl)piperidine-4-carboxylic acid |
| 314. | 1-(3-chloro-2-fluorobenzyl)-4-((5-fluoro-2-((5-methyl-1H-pyrazol-3-yl)amino)pyrimidin-4-yl)methyl)piperidine-4-carboxylic acid |
| 315. | 1-(3-chloro-2-fluorobenzyl)-4-((6-fluoro-3-((5-methyl-1H-pyrazol-3-yl)amino)-1,2,4-triazin-5-yl)methyl)piperidine-4-carboxylic acid |
| 316. | (2R)-1-(((3-chloro-2-fluorophenyl)sulfonyl)methyl)-4-((3-fluoro-6-((5-methyl-1H-pyrazol-3-yl)amino)pyridin-2-yl)methyl)-2-methylpiperidine-4-carboxylic acid |
| 317. | (2R)-1-((1-(3-chloro-2-fluorophenyl)cyclopropyl)methyl)-4-((3-fluoro-6-((5-methyl-1H-pyrazol-3-yl)amino)pyridin-2-yl)methyl)-2-methylpiperidine-4-carboxylic acid |
| 318. | (2R)-1-((1-(3-chloro-2-fluorophenyl)cyclobutyl)methyl)-4-((3-fluoro-6-((5-methyl-1H-pyrazol-3-yl)amino)pyridin-2-yl)methyl)-2-methylpiperidine-4-carboxylic acid |
| 319. | (2R)-1-43-(3-chloro-2-fluorophenyl)oxetan-3-yl)methyl)-4-((3-fluoro-6-((5-methyl-1H-pyrazol-3-yl)amino)pyridin-2-yl)methyl)-2-methylpiperidine-4-carboxylic acid |
| 320. | (2R)-1-(1-(3-chloro-2-fluorobenzyl)cyclopropyl)-4-((3-fluoro-6-((5-methyl-1H-pyrazol-3-yl)amino)pyridin-2-yl)methyl)-2-methylpiperidine-4-carboxylic acid |
| 321. | (2R)-1-(1-(3-chloro-2-fluorobenzyl)cyclobutyl)-4-((3-fluoro-6-((5-methyl-1H-pyrazol-3-yl)amino)pyridin-2-yl)methyl)-2-methylpiperidine-4-carboxylic acid |
| 322. | (2R)-1-(3-(3-chloro-2-fluorobenzyl)oxetan-3-yl)-4-((3-fluoro-6-((5-methyl-1H-pyrazol-3-yl)amino)pyridin-2-yl)methyl)-2-methylpiperidine-4-carboxylic acid |
| 323. | (2R)-1-(2-(3-chloro-2-fluorophenyl)-2,2-difluoroethyl)-4-((3-fluoro-6-((5-methyl-1H-pyrazol-3-yl)amino)pyridin-2-yl)methyl)-2-methylpiperidine-4-carboxylic acid |
| 324. | (2R,4R)-1-(3-chloro-2-fluorobenzyl)-4-((3-fluoro-6-((5-methyl-1H-pyrazol-3-yl)amino)-4-(methylamino)pyridin-2-yl)methyl)-2-methylpiperidine-4-carboxylic acid |
| 325. | (2R,4R)-1-(3-chloro-2-fluorobenzyl)-4-((3-fluoro-4-isopropoxy-6-((5-methyl-1H-pyrazol-3-yl)amino)pyridin-2-yl)methyl)-2-methylpiperidine-4-carboxylic acid |
| 326. | (2R,4R)-1-(3-chloro-2-fluorobenzyl)-4-((3-fluoro-4-(1-fluorocyclopropyl)-6-((5-methyl-1H-pyrazol-3-yl)amino)pyridin-2-yl)methyl)-2-methylpiperidine-4-carboxylic acid |
| 327. | (2R,4R)-1-(3-chloro-2-fluorobenzyl)-4-((3-fluoro-4-(2-hydroxyethyl)-6-((5-methyl-1H-pyrazol-3-yl)amino)pyridin-2-yl)methyl)-2-methylpiperidine-4-carboxylic acid |
| 328. | (2R,4R)-1-(3-chloro-2-fluorobenzyl)-4-((3-fluoro-4,5-dimethyl-6-((5-methyl-1H-pyrazol-3-yl)amino)pyridin-2-yl)methyl)-2-methylpiperidine-4-carboxylic acid |
| 329. | (2R,4R)-1-(2,3-difluorophenethyl)-4-((3-fluoro-6-((5-methyl-1H-pyrazol-3-yl)amino)pyridin-2-yl)methyl)-2-methylpiperidine-4-carboxylic acid |
| 330. | (2R,4R)-1-(2,3-dichlorophenethyl)-4-((3-fluoro-6-((5-methyl-1H-pyrazol-3-yl)amino)pyridin-2-yl)methyl)-2-methylpiperidine-4-carboxylic acid |
| 331. | (2R,4R)-1-(3-chloro-2,6-difluorophenethyl)-4-((3-fluoro-6-((5-methyl-1H-pyrazol-3-yl)amino)pyridin-2-yl)methyl)-2-methylpiperidine-4-carboxylic acid |
| 332. | (2R,4R)-1-(2,4-dichlorophenethyl)-4-((3-fluoro-6-((5-methyl-1H-pyrazol-3-yl)amino)pyridin-2-yl)methyl)-2-methylpiperidine-4-carboxylic acid |
| 333. | (2R,4R)-1-(2-(3-chloro-2-fluorophenyl)-2,2-difluoroethyl)-4-((3-fluoro-6-((5-methyl-1H-pyrazol-3-yl)amino)pyridin-2-yl)methyl)-2-methylpiperidine-4-carboxylic acid |
| 334. | (2R,4R)-1-((1-(3-chloro-2-fluorophenyl)cyclopropyl)methyl)-4-((3-fluoro-6-((5-methyl-1H-pyrazol-3-yl)amino)pyridin-2-yl)methyl)-2-methylpiperidine-4-carboxylic acid |
| 335. | (2R,4R)-1-((1-(3-chloro-2-fluorophenyl)cyclobutyl)methyl)-4-((3-fluoro-6-((5-methyl-1H-pyrazol-3-yl)amino)pyridin-2-yl)methyl)-2-methylpiperidine-4-carboxylic acid |

336. (2R,4R)-1-(3-chloro-2-fluorobenzyl)-4-((3-fluoro-4-(2-fluoro-1,3-dihydroxypropan-2-yl)-6-((5-methyl-1H-pyrazol-3-yl)amino)pyridin-2-yl)methyl)-2-methylpiperidine-4-carboxylic acid
337. (2R,4R)-1-(3-chloro-2-fluorobenzyl)-2-methyl-4-((6-((5-methyl-1H-pyrazol-3-yl)amino)-3-(trifluoromethyl)pyridin-2-yl)methyl)piperidine-4-carboxylic acid
338. (2R,4R)-1-(3-chloro-2-fluorobenzyl)-4-((3-fluoro-6-((5-methyl-1H-pyrazol-3-yl)amino)-4-morpholinopyridin-2-yl)methyl)-2-methylpiperidine-4-carboxylic acid
339. (2R,4R)-4-((3-fluoro-6-((5-methyl-1H-pyrazol-3-yl)amino)-4-(4-methylpiperazin-1-yl)pyridin-2-yl)methyl)-2-methyl-1-((2-(trifluoromethyl)phenyl)sulfonyl)piperidine-4-carboxylic acid
340. (2R,4R)-4-((3-fluoro-6-((5-methyl-1H-pyrazol-3-yl)amino)-4-(1-methylazetidin-3-yl)pyridin-2-yl)methyl)-2-methyl-1-((2-(trifluoromethyl)phenyl)sulfonyl)piperidine-4-carboxylic acid
341. (2R,4R)-4-((4-(azetidin-1-yl)-3-fluoro-6-((5-methyl-1H-pyrazol-3-yl)amino)pyridin-2-yl)methyl)-2-methyl-1-((2-(trifluoromethyl)phenyl)sulfonyl)piperidine-4-carboxylic acid
342. (2R,4R)-1-(3-chloro-2-fluorobenzyl)-4-((3-fluoro-6-((5-methyl-1H-pyrazol-3-yl)amino)-4-(3-methyloxetan-3-yl)pyridin-2-yl)methyl)-2-methylpiperidine-4-carboxylic acid
343. (2R,4R)-1-(3-chloro-2-fluorobenzyl)-4-((3-fluoro-5-methyl-6-((5-methyl-1H-pyrazol-3-yl)amino)pyridin-2-yl)methyl)-2-methylpiperidine-4-carboxylic acid
344. (2R,4R)-1-(3-chloro-2-fluorobenzyl)-2-methyl-4-((4-((5-methyl-1H-pyrazol-3-yl)amino)pyrimidin-2-yl)methyl)piperidine-4-carboxylic acid
345. (2R,4R)-1-(3-chloro-2-fluorobenzyl)-2-methyl-4-((6-((5-methyl-1H-pyrazol-3-yl)amino)-4-(trifluoromethoxy)pyridin-2-yl)methyl)piperidine-4-carboxylic acid
346. (2R,4R)-1-(3-chloro-2-fluorobenzyl)-4-((3-fluoro-6-((5-methyl-1H-pyrazol-3-yl)amino)-4-(trifluoromethoxy)pyridin-2-yl)methyl)-2-methylpiperidine-4-carboxylic acid
347. (2R,4R)-1-(3-chloro-2-fluorobenzyl)-2-methyl-4-((6-((5-methyl-1H-pyrazol-3-yl)amino)-3-(trifluoromethyl)pyrazin-2-yl)methyl)piperidine-4-carboxylic acid
348. 1-(3-chloro-2,6-difluorobenzyl)-4-((4-ethyl-3-fluoro-6-((5-methyl-1H-pyrazol-3-yl)amino)pyridin-2-yl)methyl)piperidine-4-carboxylic acid
349. 4-((4-acetyl-3-fluoro-6-((5-methyl-1H-pyrazol-3-yl)amino)pyridin-2-yl)methyl)-1-(3-chloro-2,6-difluorobenzyl)piperidine-4-carboxylic acid
350. (2R,4R)-4-((4-acetyl-3-methyl-6-((5-methyl-1H-pyrazol-3-yl)amino)pyridin-2-yl)methyl)-1-(3-chloro-2-fluorobenzyl)-2-methylpiperidine-4-carboxylic acid
351. (2R,4R)-4-((4-acetyl-6-((5-methyl-1H-pyrazol-3-yl)amino)pyridin-2-yl)methyl)-1-(3-chloro-2-fluorobenzyl)-2-methylpiperidine-4-carboxylic acid
352. (2R,4R)-1-(3-chloro-2-fluorobenzyl)-4-((3'-fluoro-3-methyl-6'-((5-methyl-1H-pyrazol-3-yl)amino)-[2,4'-bipyridin]-2'-yl)methyl)-2-methylpiperidine-4-carboxylic acid
353. (2R,4R)-1-(3-chloro-2-fluorobenzyl)-4-((3-fluoro-6-((5-methyl-1H-pyrazol-3-yl)amino)-4-(pyrimidin-2-yl)pyridin-2-yl)methyl)-2-methylpiperidine-4-carboxylic acid
354. (2R,4R)-4-((4-acetyl-3-chloro-6-((5-methyl-1H-pyrazol-3-yl)amino)pyridin-2-yl)methyl)-1-(3-chloro-2-fluorobenzyl)-2-methylpiperidine-4-carboxylic acid
355. (2R,4R)-1-(3-chloro-2-fluorobenzyl)-2-methyl-4-((6'-((5-methyl-1H-pyrazol-3-yl)amino)-[2,4'-bipyridin]-2'-yl)methyl)piperidine-4-carboxylic acid
356. (2R,4R)-1-(3-chloro-2-fluorobenzyl)-2-methyl-4-((3-methyl-6'-((5-methyl-1H-pyrazol-3-yl)amino)-[2,4'-bipyridin]-2'-yl)methyl)piperidine-4-carboxylic acid
357. (2R,4R)-1-(3-chloro-2-fluorobenzyl)-2-methyl-4-((6-((5-methyl-1H-pyrazol-3-yl)amino)-4-(pyrimidin-2-yl)pyridin-2-yl)methyl)piperidine-4-carboxylic acid
358. (2R,4R)-1-(3-chloro-2-fluorobenzyl)-2-methyl-4-((3'-methyl-6'-((5-methyl-1H-pyrazol-3-yl)amino)-[2,4'-bipyridin]-2'-yl)methyl)piperidine-4-carboxylic acid
359. (2R,4R)-1-(3-chloro-2-fluorobenzyl)-4-((3,3'-dimethyl-6'-((5-methyl-1H-pyrazol-3-yl)amino)-[2,4'-bipyridin]-2'-yl)methyl)-2-methylpiperidine-4-carboxylic acid
360. (2R,4R)-1-(3-chloro-2-fluorobenzyl)-2-methyl-4-((3-methyl-6-((5-methyl-1H-pyrazol-3-yl)amino)-4-(pyrimidin-2-yl)pyridin-2-yl)methyl)piperidine-4-carboxylic acid
361. (2R,4R)-1-(3-chloro-2-fluorobenzyl)-4-((3'-chloro-6'-((5-methyl-1H-pyrazol-3-yl)amino)-[2,4'-bipyridin]-2'-yl)methyl)-2-methylpiperidine-4-carboxylic acid
362. (2R,4R)-1-(3-chloro-2-fluorobenzyl)-4-((3'-chloro-3-methyl-6'-((5-methyl-1H-pyrazol-3-yl)amino)-[2,4'-bipyridin]-2'-yl)methyl)-2-methylpiperidine-4-carboxylic acid
363. (2R,4R)-1-(3-chloro-2-fluorobenzyl)-4-((3-chloro-6-((5-methyl-1H-pyrazol-3-yl)amino)-4-(pyrimidin-2-yl)pyridin-2-yl)methyl)-2-methylpiperidine-4-carboxylic acid
364. 1-(3-chloro-2-fluorobenzyl)-4-(2,6-difluoro-3-((5-methyl-1H-pyrazol-3-yl)amino)benzyl)piperidine-4-carboxylic acid
365. (2R,4R)-4-((4-acetyl-3,5-difluoro-6-((5-methyl-1H-pyrazol-3-yl)amino)pyridin-2-yl)methyl)-1-(3-chloro-2-fluorobenzyl)-2-methylpiperidine-4-carboxylic acid
366. (2R,4R)-4-((4-acetyl-3-fluoro-5-methyl-6-((5-methyl-1H-pyrazol-3-yl)amino)pyridin-2-yl)methyl)-1-(3-chloro-2-fluorobenzyl)-2-methylpiperidine-4-carboxylic acid
367. (2R,4R)-1-(3-chloro-2-fluorobenzyl)-4-((4-(1,1-difluoroethyl)-3,5-difluoro-6-((5-methyl-1H-pyrazol-3-yl)amino)pyridin-2-yl)methyl)-2-methylpiperidine-4-carboxylic acid
368. (2R,4R)-1-(3-chloro-2-fluorobenzyl)-4-((3,5-difluoro-6-((5-methyl-1H-pyrazol-3-yl)amino)-4-(3-methyloxetan-3-yl)pyridin-2-yl)methyl)-2-methylpiperidine-4-carboxylic acid
369. (2R,4R)-1-(3-chloro-2-fluorobenzyl)-4-((3,5-difluoro-4-(1-fluoroethyl)-6-((5-methyl-1H-pyrazol-3-yl)amino)pyridin-2-yl)methyl)-2-methylpiperidine-4-carboxylic acid
370. (2R,4R)-1-(3-chloro-2-fluorobenzyl)-4-((3,5-difluoro-6-((5-methyl-1H-pyrazol-3-yl)amino)-4-(methylsulfonyl)pyridin-2-yl)methyl)-2-methylpiperidine-4-carboxylic acid
371. (2R,4R)-1-(3-chloro-2-fluorobenzyl)-4-((4-(1,1-difluoroethyl)-3-fluoro-5-methyl-6-((5-methyl-1H-pyrazol-3-yl)amino)pyridin-2-yl)methyl)-2-methylpiperidine-4-carboxylic acid
372. (2R,4R)-1-(3-chloro-2-fluorobenzyl)-4-((3-fluoro-5-methyl-6-((5-methyl-1H-pyrazol-3-yl)amino)-4-(3-methyloxetan-3-yl)pyridin-2-yl)methyl)-2-methylpiperidine-4-carboxylic acid
373. (2R,4R)-1-(3-chloro-2-fluorobenzyl)-4-((5-fluoro-3-methyl-6-((5-methyl-1H-pyrazol-3-yl)amino)pyridin-2-yl)methyl)-2-methylpiperidine-4-carboxylic acid -continued 374. (2R,4R)-1-(3-chloro-2-fluorobenzyl)-4-((4-ethyl-5-fluoro-3-methyl-6-((5-methyl-1H-pyrazol-3-yl)amino)pyridin-2-yl)methyl)-2-methylpiperidine-4-carboxylic acid
375. (2R,4R)-1-(3-chloro-2-fluorobenzyl)-4-((4-chloro-3-methyl-5-fluoro-6-((5-methyl-1H-pyrazol-3-yl)amino)pyridin-2-yl)methyl)-2-methylpiperidine-4-carboxylic acid
376. (2R,4R)-1-(3-chloro-2-fluorobenzyl)-4-((5-fluoro-3-methyl-6-((5-methyl-1H-pyrazol-3-yl)amino)-4-propionylpyridin-2-yl)methyl)-2-methylpiperidine-4-carboxylic acid
377. (2R,4R)-4-((4-acetyl-3-methyl-5-fluoro-6-((5-methyl-1H-pyrazol-3-yl)amino)pyridin-2-yl)methyl)-1-(3-chloro-2-fluorobenzyl)-2-methylpiperidine-4-carboxylic acid
378. (2R,4R)-1-(3-chloro-2-fluorobenzyl)-4-((4-ethyl-5-fluoro-6-((5-methyl-1H-pyrazol-3-yl)amino)pyridin-2-yl)methyl)-2-methylpiperidine-4-carboxylic acid
379. (2R,4R)-1-(3-chloro-2-fluorobenzyl)-4-((5-fluoro-6-((5-methyl-1H-pyrazol-3-yl)amino)-4-propionylpyridin-2-yl)methyl)-2-methylpiperidine-4-carboxylic acid
380. (2R,4R)-1-(3-chloro-2-fluorobenzyl)-4-((4-ethyl-3,5-difluoro-6-((5-methyl-1H-pyrazol-3-yl)amino)pyridin-2-yl)methyl)-2-methylpiperidine-4-carboxylic acid
381. (2R,4R)-1-(3-chloro-2-fluorobenzyl)-4-((3,5-difluoro-6-((5-methyl-1H-pyrazol-3-yl)amino)-4-propionylpyridin-2-yl)methyl)-2-methylpiperidine-4-carboxylic acid
382. 1-(3-chloro-2-fluorobenzyl)-4-((3-methyl-5-fluoro-6-((5-methyl-1H-pyrazol-3-yl)amino)pyridin-2-yl)methyl)piperidine-4-carboxylic acid
383. 1-(3-chloro-2-fluorobenzyl)-4-((3-methyl-5-fluoro-4-methyl-6-((5-methyl-1H-pyrazol-3-yl)amino)pyridin-2-yl)methyl)piperidine-4-carboxylic acid
384. 1-(3-chloro-2-fluorobenzyl)-4-((4-ethyl-5-fluoro-3-methyl-6-((5-methyl-1H-pyrazol-3-yl)amino)pyridin-2-yl)methyl)piperidine-4-carboxylic acid
385. 1-(3-chloro-2-fluorobenzyl)-4-((4-chloro-3-methyl-5-fluoro-6-((5-methyl-1H-pyrazol-3-yl)amino)pyridin-2-yl)methyl)piperidine-4-carboxylic acid
386. 1-(3-chloro-2-fluorobenzyl)-4-((3-methyl-5-fluoro-6-((5-methyl-1H-pyrazol-3-yl)amino)-4-propionylpyridin-2-yl)methyl)piperidine-4-carboxylic acid
387. 4-((4-acetyl-3-methyl-5-fluoro-6-((5-methyl-1H-pyrazol-3-yl)amino)pyridin-2-yl)methyl)-1-(3-chloro-2-fluorobenzyl)piperidine-4-carboxylic acid
388. 1-(3-chloro-2-fluorobenzyl)-4-((5-fluoro-6-((5-methyl-1H-pyrazol-3-yl)amino)pyridin-2-yl)methyl)piperidine-4-carboxylic acid
389. 1-(3-chloro-2-fluorobenzyl)-4-((4-ethyl-5-fluoro-6-((5-methyl-1H-pyrazol-3-yl)amino)pyridin-2-yl)methyl)piperidine-4-carboxylic acid
390. 1-(3-chloro-2-fluorobenzyl)-4-((4-chloro-5-fluoro-6-((5-methyl-1H-pyrazol-3-yl)amino)pyridin-2-yl)methyl)piperidine-4-carboxylic acid
391. 1-(3-chloro-2-fluorobenzyl)-4-((5-fluoro-6-((5-methyl-1H-pyrazol-3-yl)amino)-4-propionylpyridin-2-yl)methyl)piperidine-4-carboxylic acid
392. 4-((4-acetyl-5-fluoro-6-((5-methyl-1H-pyrazol-3-yl)amino)pyridin-2-yl)methyl)-1-(3-chloro-2-fluorobenzyl)piperidine-4-carboxylic acid
393. 1-(3-chloro-2-fluorobenzyl)-4-((3,5-difluoro-4-methyl-6-((5-methyl-1H-pyrazol-3-yl)amino)pyridin-2-yl)methyl)piperidine-4-carboxylic acid
394. 1-(3-chloro-2-fluorobenzyl)-4-((4-ethyl-3,5-difluoro-6-((5-methyl-1H-pyrazol-3-yl)amino)pyridin-2-yl)methyl)piperidine-4-carboxylic acid
395. 1-(3-chloro-2-fluorobenzyl)-4-((4-chloro-3,5-difluoro-6-((5-methyl-1H-pyrazol-3-yl)amino)pyridin-2-yl)methyl)piperidine-4-carboxylic acid
396. 1-(3-chloro-2-fluorobenzyl)-4-((3,5-difluoro-6-((5-methyl-1H-pyrazol-3-yl)amino)-4-propionylpyridin-2-yl)methyl)piperidine-4-carboxylic acid
397. 4-((4-acetyl-3,5-difluoro-6-((5-methyl-1H-pyrazol-3-yl)amino)pyridin-2-yl)methyl)-1-(3-chloro-2-fluorobenzyl)piperidine-4-carboxylic acid
398. 1-(3-chloro-2-fluorobenzyl)-4-((3-fluoro-4,5-dimethyl-6-((5-methyl-1H-pyrazol-3-yl)amino)pyridin-2-yl)methyl)piperidine-4-carboxylic acid
399. 4-((4-acetyl-3-fluoro-5-methyl-6-((5-methyl-1H-pyrazol-3-yl)amino)pyridin-2-yl)methyl)-1-(3-chloro-2-fluorobenzyl)piperidine-4-carboxylic acid
400. 1-(3-chloro-2-fluorobenzyl)-4-((4-(1,1-difluoroethyl)-3,5-difluoro-6-((5-methyl-1H-pyrazol-3-yl)amino)pyridin-2-yl)methyl)piperidine-4-carboxylic acid
401. 1-(3-chloro-2-fluorobenzyl)-4-((3,5-difluoro-6-((5-methyl-1H-pyrazol-3-yl)amino)-4-(3-methyloxetan-3-yl)pyridin-2-yl)methyl)piperidine-4-carboxylic acid
402. 1-(3-chloro-2-fluorobenzyl)-4-((3,5-difluoro-4-(1-fluoroethyl)-6-((5-methyl-1H-pyrazol-3-yl)amino)pyridin-2-yl)methyl)piperidine-4-carboxylic acid
403. 1-(3-chloro-2-fluorobenzyl)-4-((3,5-difluoro-6-((5-methyl-1H-pyrazol-3-yl)amino)-4-(methylsulfonyl)pyridin-2-yl)methyl)piperidine-4-carboxylic acid
404. 1-(3-chloro-2-fluorobenzyl)-4-((4-(1,1-difluoroethyl)-3-fluoro-5-methyl-6-((5-methyl-1H-pyrazol-3-yl)amino)pyridin-2-yl)methyl)piperidine-4-carboxylic acid
405. 1-(3-chloro-2-fluorobenzyl)-4-((3-fluoro-5-methyl-6-((5-methyl-1H-pyrazol-3-yl)amino)-4-(3-methyloxetan-3-yl)pyridin-2-yl)methyl)piperidine-4-carboxylic acid
406. 1-(3-chloro-2-fluorobenzyl)-4-((3,5-dimethyl-6-((5-methyl-1H-pyrazol-3-yl)amino)pyridin-2-yl)methyl)piperidine-4-carboxylic acid
407. 1-(3-chloro-2-fluorobenzyl)-4-((3,4,5-trimethyl-6-((5-methyl-1H-pyrazol-3-yl)amino)pyridin-2-yl)methyl)piperidine-4-carboxylic acid
408. 1-(3-chloro-2-fluorobenzyl)-4-((4-ethyl-3,5-dimethyl-6-((5-methyl-1H-pyrazol-3-yl)amino)pyridin-2-yl)methyl)piperidine-4-carboxylic acid
409. 1-(3-chloro-2-fluorobenzyl)-4-((4-chloro-3,5-dimethyl-6-((5-methyl-1H-pyrazol-3-yl)amino)pyridin-2-yl)methyl)piperidine-4-carboxylic acid
410. 1-(3-chloro-2-fluorobenzyl)-4-((3,5-dimethyl-6-((5-methyl-1H-pyrazol-3-yl)amino)-4-propionylpyridin-2-yl)methyl)piperidine-4-carboxylic acid
411. 4-((4-acetyl-3,5-dimethyl-6-((5-methyl-1H-pyrazol-3-yl)amino)pyridin-2-yl)methyl)-1-(3-chloro-2-fluorobenzyl)piperidine-4-carboxylic acid
412. 1-(3-chloro-2-fluorobenzyl)-4-((5-methyl-6-((5-methyl-1H-pyrazol-3-yl)amino)pyridin-2-yl)methyl)piperidine-4-carboxylic acid 413. 1-(3-chloro-2-fluorobenzyl)-4-((4,5-dimethyl-6-((5-methyl-1H-pyrazol-3-yl)amino)pyridin-2-yl)methyl)piperidine-4-carboxylic acid
414. 1-(3-chloro-2-fluorobenzyl)-4-((4-ethyl-5-methyl-6-((5-methyl-1H-pyrazol-3-yl)amino)pyridin-2-yl)methyl)piperidine-4-carboxylic acid
415. 1-(3-chloro-2-fluorobenzyl)-4-((4-chloro-5-methyl-6-((5-methyl-1H-pyrazol-3-yl)amino)pyridin-2-yl)methyl)piperidine-4-carboxylic acid
416. 1-(3-chloro-2-fluorobenzyl)-4-((5-methyl-6-((5-methyl-1H-pyrazol-3-yl)amino)-4-propionylpyridin-2-yl)methyl)piperidine-4-carboxylic acid
417. 4-((4-acetyl-5-methyl-6-((5-methyl-1H-pyrazol-3-yl)amino)pyridin-2-yl)methyl)-1-(3-chloro-2-fluorobenzyl)piperidine-4-carboxylic acid
418. 1-(3-chloro-2-fluorobenzyl)-4-((3-fluoro-5-methyl-6-((5-methyl-1H-pyrazol-3-yl)amino)pyridin-2-yl)methyl)piperidine-4-carboxylic acid
419. 1-(3-chloro-2-fluorobenzyl)-4-((4-ethyl-3-fluoro-5-methyl-6-((5-methyl-1H-pyrazol-3-yl)amino)pyridin-2-yl)methyl)piperidine-4-carboxylic acid
420. 1-(3-chloro-2-fluorobenzyl)-4-((4-chloro-3-fluoro-5-methyl-6-((5-methyl-1H-pyrazol-3-yl)amino)pyridin-2-yl)methyl)piperidine-4-carboxylic acid
421. 1-(3-chloro-2-fluorobenzyl)-4-((3-fluoro-5-methyl-6-((5-methyl-1H-pyrazol-3-yl)amino)-4-propionylpyridin-2-yl)methyl)piperidine-4-carboxylic acid
422. (2R,4R)-1-(3-chloro-2-fluorobenzyl)-4-((3,5-dimethyl-6-((5-methyl-1H-pyrazol-3-yl)amino)pyridin-2-yl)methyl)-2-methylpiperidine-4-carboxylic acid
423. (2R,4R)-1-(3-chloro-2-fluorobenzyl)-2-methyl-4-((3,4,5-trimethyl-6-((5-methyl-1H-pyrazol-3-yl)amino)pyridin-2-yl)methyl)piperidine-4-carboxylic acid
424. (2R,4R)-1-(3-chloro-2-fluorobenzyl)-4-((4-ethyl-3,5-dimethyl-6-((5-methyl-1H-pyrazol-3-yl)amino)pyridin-2-yl)methyl)-2-methylpiperidine-4-carboxylic acid
425. (2R,4R)-1-(3-chloro-2-fluorobenzyl)-4-((4-chloro-3,5-dimethyl-6-((5-methyl-1H-pyrazol-3-yl)amino)pyridin-2-yl)methyl)-2-methylpiperidine-4-carboxylic acid
426. (2R,4R)-1-(3-chloro-2-fluorobenzyl)-4-((3,5-dimethyl-6-((5-methyl-1H-pyrazol-3-yl)amino)-4-propionylpyridin-2-yl)methyl)-2-methylpiperidine-4-carboxylic acid
427. (2R,4R)-4-((4-acetyl-3,5-dimethyl-6-((5-methyl-1H-pyrazol-3-yl)amino)pyridin-2-yl)methyl)-1-(3-chloro-2-fluorobenzyl)-2-methylpiperidine-4-carboxylic acid
428. (2R,4R)-1-(3-chloro-2-fluorobenzyl)-2-methyl-4-((5-methyl-6-((5-methyl-1H-pyrazol-3-yl)amino)pyridin-2-yl)methyl)piperidine-4-carboxylic acid
429. (2R,4R)-1-(3-chloro-2-fluorobenzyl)-4-((4,5-dimethyl-6-((5-methyl-1H-pyrazol-3-yl)amino)pyridin-2-yl)methyl)-2-methylpiperidine-4-carboxylic acid
430. (2R,4R)-1-(3-chloro-2-fluorobenzyl)-4-((4-ethyl-5-methyl-6-((5-methyl-1H-pyrazol-3-yl)amino)pyridin-2-yl)methyl)-2-methylpiperidine-4-carboxylic acid
431. (2R,4R)-1-(3-chloro-2-fluorobenzyl)-4-((4-chloro-5-methyl-6-((5-methyl-1H-pyrazol-3-yl)amino)pyridin-2-yl)methyl)-2-methylpiperidine-4-carboxylic acid
432. (2R,4R)-1-(3-chloro-2-fluorobenzyl)-2-methyl-4-((5-methyl-6-((5-methyl-1H-pyrazol-3-yl)amino)-4-propionylpyridin-2-yl)methyl)piperidine-4-carboxylic acid
433. (2R,4R)-4-((4-acetyl-5-methyl-6-((5-methyl-1H-pyrazol-3-yl)amino)pyridin-2-yl)methyl)-1-(3-chloro-2-fluorobenzyl)-2-methylpiperidine-4-carboxylic acid
434. (2R,4R)-1-(3-chloro-2-fluorobenzyl)-4-((4-ethyl-3-fluoro-5-methyl-6-((5-methyl-1H-pyrazol-3-yl)amino)pyridin-2-yl)methyl)-2-methylpiperidine-4-carboxylic acid
435. (2R,4R)-1-(3-chloro-2-fluorobenzyl)-4-((4-chloro-3-fluoro-5-methyl-6-((5-methyl-1H-pyrazol-3-yl)amino)pyridin-2-yl)methyl)-2-methylpiperidine-4-carboxylic acid
436. (2R,4R)-1-(3-chloro-2-fluorobenzyl)-4-((3-fluoro-5-methyl-6-((5-methyl-1H-pyrazol-3-yl)amino)-4-propionylpyridin-2-yl)methyl)-2-methylpiperidine-4-carboxylic acid
437. (2R,4R)-1-(3-chloro-2-fluorobenzyl)-4-((5-fluoro-4-((R)-1-fluoroethyl)-6-((5-methyl-1H-pyrazol-3-yl)amino)pyridin-2-yl)methyl)-2-methylpiperidine-4-carboxylic acid
438. (2R,4R)-1-(3-chloro-2-fluorobenzyl)-4-((5-fluoro-4-((S)-1-fluoroethyl)-6-((5-methyl-1H-pyrazol-3-yl)amino)pyridin-2-yl)methyl)-2-methylpiperidine-4-carboxylic acid
439. (2R,4R)-1-(3-chloro-2-fluorobenzyl)-4-((4-(1,1-difluoroethyl)-5-fluoro-6-((5-methyl-1H-pyrazol-3-yl)amino)pyridin-2-yl)methyl)-2-methylpiperidine-4-carboxylic acid
440. (2R,4R)-1-(3-chloro-2-fluorobenzyl)-4-((5-fluoro-6-((5-methyl-1H-pyrazol-3-yl)amino)-4-(3-methyloxetan-3-yl)pyridin-2-yl)methyl)-2-methylpiperidine-4-carboxylic acid
441. (2R,4R)-1-(3-chloro-2-fluorobenzyl)-4-((5'-fluoro-6'-((5-methyl-1H-pyrazol-3-yl)amino)-[2,4'-bipyridin]-2'-yl)methyl)-2-methylpiperidine-4-carboxylic acid
442. (2R,4R)-1-(3-chloro-2-fluorobenzyl)-4-((5-fluoro-6-((5-methyl-1H-pyrazol-3-yl)amino)-4-(pyrimidin-2-yl)pyridin-2-yl)methyl)-2-methylpiperidine-4-carboxylic acid
443. (2R,4R)-1-(3-chloro-2-fluorobenzyl)-4-((5'-fluoro-3-methyl-6'-((5-methyl-1H-pyrazol-3-yl)amino)-[2,4'-bipyridin]-2'-yl)methyl)-2-methylpiperidine-4-carboxylic acid
444. (2R,4R)-1-(3-chloro-2-fluorobenzyl)-4-((5'-fluoro-6'-((5-methyl-1H-pyrazol-3-yl)amino)-[3,4'-bipyridin]-2'-yl)methyl)-2-methylpiperidine-4-carboxylic acid
445. (2R,4R)-1-(3-chloro-2-fluorobenzyl)-4-((5-fluoro-6-((5-methyl-1H-pyrazol-3-yl)amino)-4-(pyridazin-3-yl)pyridin-2-yl)methyl)-2-methylpiperidine-4-carboxylic acid
446. (2R,4R)-1-(3-chloro-2-fluorobenzyl)-4-((5-fluoro-6-((5-methyl-1H-pyrazol-3-yl)amino)-4-(oxazol-2-yl)pyridin-2-yl)methyl)-2-methylpiperidine-4-carboxylic acid
447. (2R,4R)-1-(3-chloro-2-fluorobenzyl)-4-((5-fluoro-6-((5-methyl-1H-pyrazol-3-yl)amino)-4-(thiazol-2-yl)pyridin-2-yl)methyl)-2-methylpiperidine-4-carboxylic acid
448. (2R,4R)-1-(3-chloro-2-fluorobenzyl)-4-((5-fluoro-4-(1-methyl-1H-imidazol-2-yl)-6-((5-methyl-1H-pyrazol-3-yl)amino)pyridin-2-yl)methyl)-2-methylpiperidine-4-carboxylic acid
449. 6-(((2R,4R)-4-carboxy-1-(3-chloro-2-fluorobenzyl)-2-methylpiperidin-4-yl)methyl)-3-fluoro-2-((5-methyl-1H-pyrazol-3-yl)amino)isonicotinic acid
450. (2R,4R)-1-(3-chloro-2-fluorobenzyl)-4-((4-(dimethylcarbamoyl)-5-fluoro-6-((5-methyl-1H-pyrazol-3-yl)amino)pyridin-2-yl)methyl)-2-methylpiperidine-4-carboxylic acid
451. (2R,4R)-4-((4-(azetidine-1-carbonyl)-5-fluoro-6-((5-methyl-1H-pyrazol-3-yl)amino)pyridin-2-yl)methyl)-1-(3-chloro-2-fluorobenzyl)-2-methylpiperidine-4-carboxylic acid 452. (2R,4R)-1-(3-chloro-2-fluorobenzyl)-4-((5-fluoro-6-((5-methyl-1H-pyrazol-3-yl)amino)-4-(morpholine-4-carbonyl)pyridin-2-yl)methyl)-2-methylpiperidine-4-carboxylic acid
453. (2R,4R)-1-(3-chloro-2-fluorobenzyl)-4-((5-fluoro-6-((5-methyl-1H-pyrazol-3-yl)amino)-4-(4-methylpiperazine-1-carbonyl)pyridin-2-yl)methyl)-2-methylpiperidine-4-carboxylic acid
454. (2R,4R)-1-(3-chloro-2-fluorobenzyl)-4-((4-chloro-5-fluoro-3-methyl-6-((5-methyl-1H-pyrazol-3-yl)amino)pyridin-2-yl)methyl)-2-methylpiperidine-4-carboxylic acid
455. (2R,4R)-4-((4-acetyl-5-fluoro-3-methyl-6-((5-methyl-1H-pyrazol-3-yl)amino)pyridin-2-yl)methyl)-1-(3-chloro-2-fluorobenzyl)-2-methylpiperidine-4-carboxylic acid
456. (2R,4R)-1-(3-chloro-2-fluorobenzyl)-4-((5-fluoro-4-isobutyryl-6-((5-methyl-1H-pyrazol-3-yl)amino)pyridin-2-yl)methyl)-2-methylpiperidine-4-carboxylic acid
457. (2R,4R)-1-(3-chloro-2-fluorobenzyl)-4-((5-fluoro-6-((5-methyl-1H-pyrazol-3-yl)amino)-4-pivaloylpyridin-2-yl)methyl)-2-methylpiperidine-4-carboxylic acid
458. (2R,4R)-1-(3-chloro-2-fluorobenzyl)-4-((3'-fluoro-5'-methyl-6'-((5-methyl-1H-pyrazol-3-yl)amino)-[2,4'-bipyridin]-2'-yl)methyl)-2-methylpiperidine-4-carboxylic acid
459. (2R,4R)-1-(3-chloro-2-fluorobenzyl)-4-((3-fluoro-5-methyl-6-((5-methyl-1H-pyrazol-3-yl)amino)-4-(pyrimidin-2-yl)pyridin-2-yl)methyl)-2-methylpiperidine-4-carboxylic acid
460. (2R,4R)-1-(3-chloro-2-fluorobenzyl)-4-((3-fluoro-5-methyl-6-((5-methyl-1H-pyrazol-3-yl)amino)-4-(oxazol-2-yl)pyridin-2-yl)methyl)-2-methylpiperidine-4-carboxylic acid
461. (2R,4R)-1-(3-chloro-2-fluorobenzyl)-4-((5-fluoro-4-isobutyryl-3-methyl-6-((5-methyl-1H-pyrazol-3-yl)amino)pyridin-2-yl)methyl)-2-methylpiperidine-4-carboxylic acid
462. (2R,4R)-1-(3-chloro-2-fluorobenzyl)-4-((5-fluoro-3-methyl-6-((5-methyl-1H-pyrazol-3-yl)amino)-4-pivaloylpyridin-2-yl)methyl)-2-methylpiperidine-4-carboxylic acid
463. (2R,4R)-1-(3-chloro-2-fluorobenzyl)-4-((3-fluoro-4-isobutyryl-5-methyl-6-((5-methyl-1H-pyrazol-3-yl)amino)pyridin-2-yl)methyl)-2-methylpiperidine-4-carboxylic acid
464. (2R,4R)-1-(3-chloro-2-fluorobenzyl)-4-((3-fluoro-5-methyl-6-((5-methyl-1H-pyrazol-3-yl)amino)-4-pivaloylpyridin-2-yl)methyl)-2-methylpiperidine-4-carboxylic acid
465. (2R,4R)-1-(3-chloro-2-fluorobenzyl)-4-((3,5-difluoro-4-((R)-1-fluoroethyl)-6-((5-methyl-1H-pyrazol-3-yl)amino)pyridin-2-yl)methyl)-2-methylpiperidine-4-carboxylic acid
466. (2R,4R)-1-(3-chloro-2-fluorobenzyl)-4-((3,5-difluoro-4-((S)-1-fluoroethyl)-6-((5-methyl-1H-pyrazol-3-yl)amino)pyridin-2-yl)methyl)-2-methylpiperidine-4-carboxylic acid
467. (2R,4R)-1-(3-chloro-2-fluorobenzyl)-4-((3',5'-difluoro-6'-((5-methyl-1H-pyrazol-3-yl)amino)-[2,4'-bipyridin]-2'-yl)methyl)-2-methylpiperidine-4-carboxylic acid
468. (2R,4R)-1-(3-chloro-2-fluorobenzyl)-4-((3,5-difluoro-6-((5-methyl-1H-pyrazol-3-yl)amino)-4-(pyrimidin-2-yl)pyridin-2-yl)methyl)-2-methylpiperidine-4-carboxylic acid
469. (2R,4R)-1-(3-chloro-2-fluorobenzyl)-4-((3',5'-difluoro-3-methyl-6'-((5-methyl-1H-pyrazol-3-yl)amino)-[2,4'-bipyridin]-2'-yl)methyl)-2-methylpiperidine-4-carboxylic acid
470. (2R,4R)-1-(3-chloro-2-fluorobenzyl)-4-((3',5'-difluoro-6'-((5-methyl-1H-pyrazol-3-yl)amino)-[3,4'-bipyridin]-2'-yl)methyl)-2-methylpiperidine-4-carboxylic acid
471. (2R,4R)-1-(3-chloro-2-fluorobenzyl)-4-((3,5-difluoro-6-((5-methyl-1H-pyrazol-3-yl)amino)-4-(pyridazin-3-yl)pyridin-2-yl)methyl)-2-methylpiperidine-4-carboxylic acid
472. (2R,4R)-1-(3-chloro-2-fluorobenzyl)-4-((3,5-difluoro-6-((5-methyl-1H-pyrazol-3-yl)amino)-4-(oxazol-2-yl)pyridin-2-yl)methyl)-2-methylpiperidine-4-carboxylic acid
473. (2R,4R)-1-(3-chloro-2-fluorobenzyl)-4-((3,5-difluoro-6-((5-methyl-1H-pyrazol-3-yl)amino)-4-(thiazol-2-yl)pyridin-2-yl)methyl)-2-methylpiperidine-4-carboxylic acid
474. (2R,4R)-1-(3-chloro-2-fluorobenzyl)-4-((3,5-difluoro-4-(1-methyl-1H-imidazol-2-yl)-6-((5-methyl-1H-pyrazol-3-yl)amino)pyridin-2-yl)methyl)-2-methylpiperidine-4-carboxylic acid
475. 2-(((2R,4R)-4-carboxy-1-(3-chloro-2-fluorobenzyl)-2-methylpiperidin-4-yl)methyl)-3,5-difluoro-6-((5-methyl-1H-pyrazol-3-yl)amino)isonicotinic acid
476. (2R,4R)-1-(3-chloro-2-fluorobenzyl)-4-((4-(dimethylcarbamoyl)-3,5-difluoro-6-((5-methyl-1H-pyrazol-3-yl)amino)pyridin-2-yl)methyl)-2-methylpiperidine-4-carboxylic acid
477. (2R,4R)-4-((4-(azetidine-1-carbonyl)-3,5-difluoro-6-((5-methyl-1H-pyrazol-3-yl)amino)pyridin-2-yl)methyl)-1-(3-chloro-2-fluorobenzyl)-2-methylpiperidine-4-carboxylic acid
478. (2R,4R)-1-(3-chloro-2-fluorobenzyl)-4-((3,5-difluoro-6-((5-methyl-1H-pyrazol-3-yl)amino)-4-(morpholine-4-carbonyl)pyridin-2-yl)methyl)-2-methylpiperidine-4-carboxylic acid
479. (2R,4R)-1-(3-chloro-2-fluorobenzyl)-4-((3,5-difluoro-6-((5-methyl-1H-pyrazol-3-yl)amino)-4-(4-methylpiperazine-1-carbonyl)pyridin-2-yl)methyl)-2-methylpiperidine-4-carboxylic acid
480. (2R,4R)-1-(3-chloro-2-fluorobenzyl)-4-((3,5-difluoro-4-isobutyryl-6-((5-methyl-1H-pyrazol-3-yl)amino)pyridin-2-yl)methyl)-2-methylpiperidine-4-carboxylic acid
481. (2R,4R)-1-(3-chloro-2-fluorobenzyl)-4-((3,5-difluoro-6-((5-methyl-1H-pyrazol-3-yl)amino)-4-pivaloylpyridin-2-yl)methyl)-2-methylpiperidine-4-carboxylic acid
482. (2R,4R)-1-(3-chloro-2-fluorobenzyl)-4-((3-fluoro-4-((R)-1-fluoroethyl)-6-((5-methyl-1H-pyrazol-3-yl)amino)pyridin-2-yl)methyl)-2-methylpiperidine-4-carboxylic acid
483. (2R,4R)-1-(3-chloro-2-fluorobenzyl)-4-((3-fluoro-4-((S)-1-fluoroethyl)-6-((5-methyl-1H-pyrazol-3-yl)amino)pyridin-2-yl)methyl)-2-methylpiperidine-4-carboxylic acid
484. (2R,4R)-1-(3-chloro-2-fluorobenzyl)-4-((3'-fluoro-6'-((5-methyl-1H-pyrazol-3-yl)amino)-[3,4'-bipyridin]-2'-yl)methyl)-2-methylpiperidine-4-carboxylic acid
485. (2R,4R)-1-(3-chloro-2-fluorobenzyl)-4-((3-fluoro-6-((5-methyl-1H-pyrazol-3-yl)amino)-4-(pyridazin-3-yl)pyridin-2-yl)methyl)-2-methylpiperidine-4-carboxylic acid
486. (2R,4R)-1-(3-chloro-2-fluorobenzyl)-4-((3-fluoro-6-((5-methyl-1H-pyrazol-3-yl)amino)-4-(oxazol-2-yl)pyridin-2-yl)methyl)-2-methylpiperidine-4-carboxylic acid
487. (2R,4R)-1-(3-chloro-2-fluorobenzyl)-4-((3-fluoro-6-((5-methyl-1H-pyrazol-3-yl)amino)-4-(thiazol-2-yl)pyridin-2-yl)methyl)-2-methylpiperidine-4-carboxylic acid
488. (2R,4R)-1-(3-chloro-2-fluorobenzyl)-4-((3-fluoro-4-(1-methyl-1H-imidazol-2-yl)-6-((5-methyl-1H-pyrazol-3-yl)amino)pyridin-2-yl)methyl)-2-methylpiperidine-4-carboxylic acid
489. (2R,4R)-4-((4-(azetidine-1-carbonyl)-3-fluoro-6-((5-methyl-1H-pyrazol-3-yl)amino)pyridin-2-yl)methyl)-1-(3-chloro-2-fluorobenzyl)-2-methylpiperidine-4-carboxylic acid
490. (2R,4R)-1-(3-chloro-2-fluorobenzyl)-4-((3-fluoro-6-((5-methyl-1H-pyrazol-3-yl)amino)-4-pivaloylpyridin-2-yl)methyl)-2-methylpiperidine-4-carboxylic acid

| | |
|---|---|
| 491. | 1-(3-chloro-2-fluorobenzyl)-4-((4-(1,1-difluoroethyl)-3-fluoro-6-((5-methyl-1H-pyrazol-3-yl)amino)pyridin-2-yl)methyl)piperidine-4-carboxylic acid |
| 492. | (2R,4R)-1-(3-chloro-2-fluorobenzyl)-4-((3,4-difluoro-6-((5-methyl-1H-pyrazol-3-yl)amino)pyridin-2-yl)methyl)-2-methylpiperidine-4-carboxylic acid |
| 493. | (2R,4R)-1-(3-chloro-2-fluorobenzyl)-4-((4-hydroxy-6-((3-methyl-1H-pyrazol-5-yl)amino)pyridin-2-yl)methyl)-2-methylpiperidine-4-carboxylic acid |
| 494. | (2R,4R)-1-(3-chloro-2-fluorobenzyl)-4-((3-fluoro-6-((5-methyl-1H-pyrazol-3-yl)amino)-4-(2,2,2-trifluoroacetyl)pyridin-2-yl)methyl)-2-methylpiperidine-4-carboxylic acid |
| 495. | (2R,4R)-1-(3-chloro-2-fluorobenzyl)-4-((3-fluoro-6-((5-methyl-1H-pyrazol-3-yl)amino)-4-(oxetane-3-carbonyl)pyridin-2-yl)methyl)-2-methylpiperidine-4-carboxylic acid |
| 496. | (2R,4R)-1-(3-chloro-2-fluorobenzyl)-4-(2-fluoro-5-((5-methyl-1H-1,2,4-triazol-3-yl)amino)benzyl)-2-methylpiperidine-4-carboxylic acid |

Methods of Preparation

The compounds of the present invention can be prepared in a number ways well known to one skilled in the art of organic synthesis using the methods described below or variations thereon as appreciated by those skilled in the art. The references cited herein are hereby incorporated by reference in their entirety.

The methods of synthesis described herein after are intended as an illustration of the invention, without restricting its subject matter and the scope of the compounds claimed to these examples. Where the preparation of starting compounds is not described, they are commercially obtainable or may be prepared analogously to known compounds or methods described herein. Compounds of any of the formulae described herein may be synthesized by reference to methods illustrated in the following schemes. As shown herein, the end compound is a product having the same structural formula depicted as any of the formulaes. It will be understood that any compound of the formulaes may be prepared by the suitable selection of reagents with appropriate substitution. Solvents, temperature, pressures, and other reaction conditions may be readily selected by one of ordinary skill in the art. Protecting groups are manipulated according to standard methods of organic synthesis (T. W. Green and P. G. M. Wuts (1999) Protective Groups in Organic Synthesis, 3$^{th}$ edition, John Wiley & Sons). These groups are removed at certain stage of the compound synthesis using the methods that are apparent to those skilled in the art.

For illustrative purposes, Schemes 1, 2 and 3 show a general synthetic method for preparing the compounds described herein. For a more detailed description of the individual reaction steps, see the Examples section below. Those skilled in the art will appreciate that other synthetic routes may be used to synthesize the compounds. In addition, many of the compounds prepared by the methods described below can be further modified in light of this disclosure using conventional chemistry well known those skilled in the art.

Scheme 1

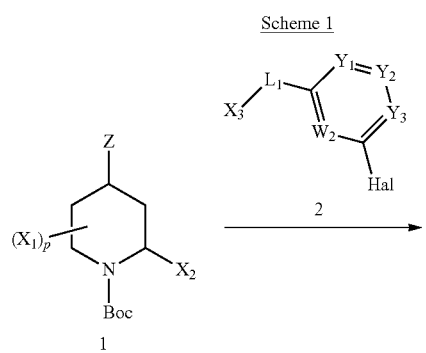

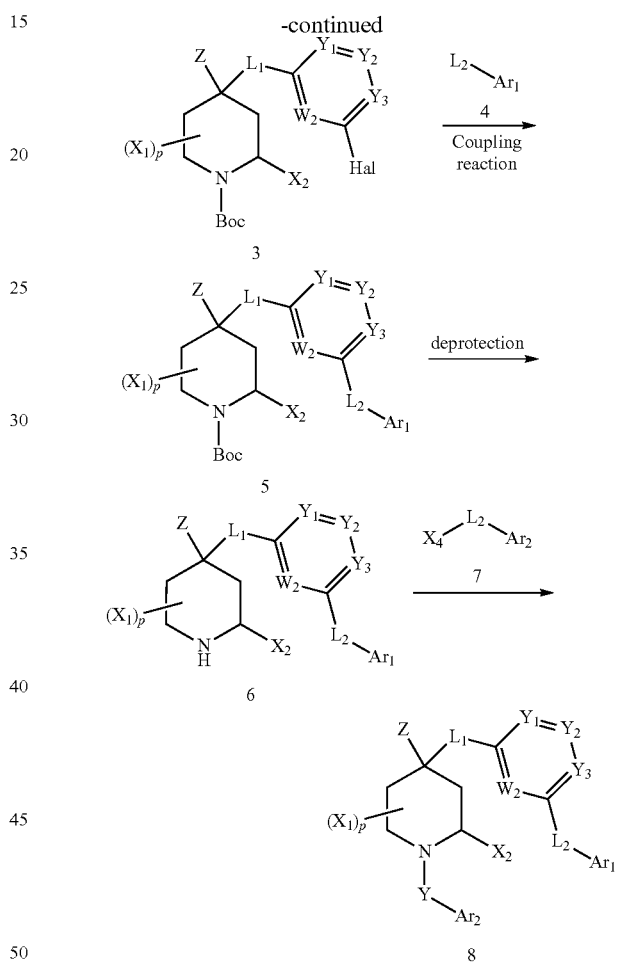

General routes to compounds illustrated in the invention is described in Scheme 1, where the $L_1$, $L_2$, Y, $Y_1$, $Y_2$, $Y_3$, p, $X_1$, $X_2$, $Ar_1$, $Ar_2$, and Z etc. substituents are defined previously in the text or a functional group that can be converted to the desired final substituent. The substituent Hal is a halide, and $X_3$ and $X_4$ is a leaving group such as a halide or OH that can easily converted to a leaving group such as triflate or tosylate.

As depicted in Scheme 1, nucleophilic substitution reaction of 1 with the aromatic heterocyclic benzyl halides 2 to give 3. Palladium catalysed cross coupling reaction of 3 and 4 can provide 5. The deprotection reaction of 5 gives 6. Nucleophilic substitution or condensation reaction of 6 with 7 can be required to obtain the final product 8.

Scheme 2

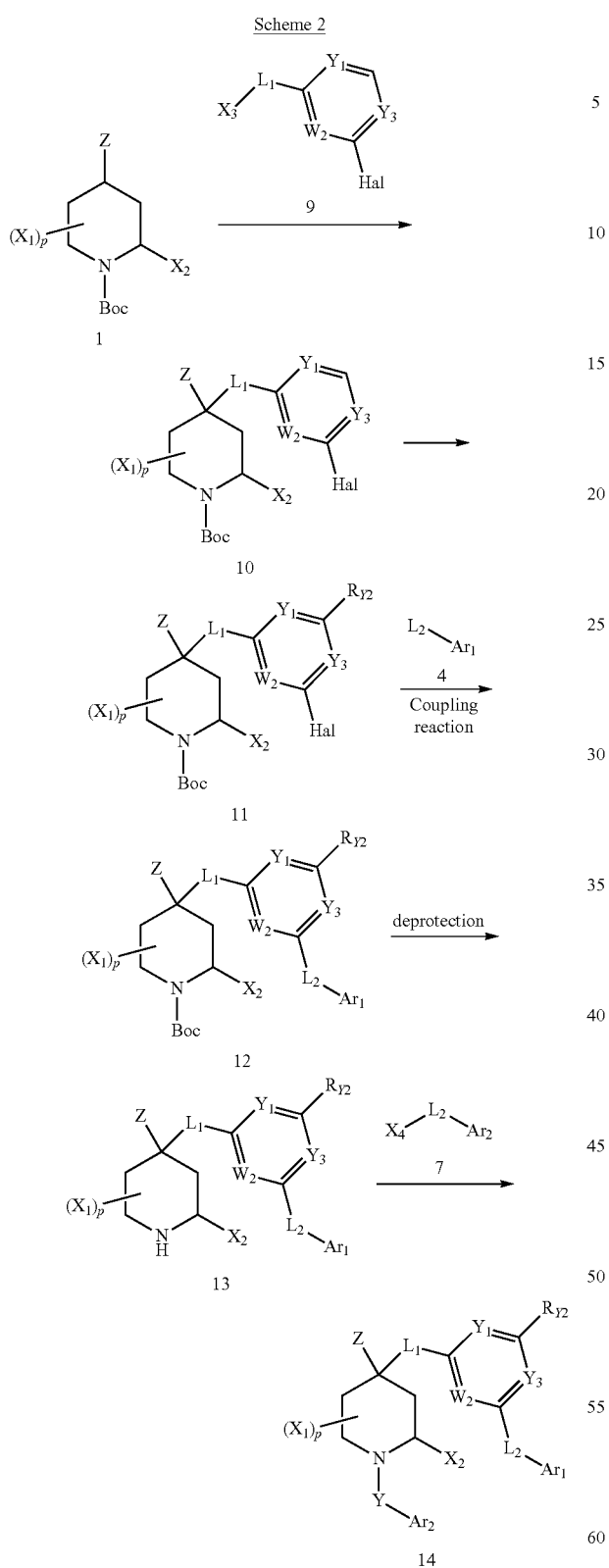

Scheme 3

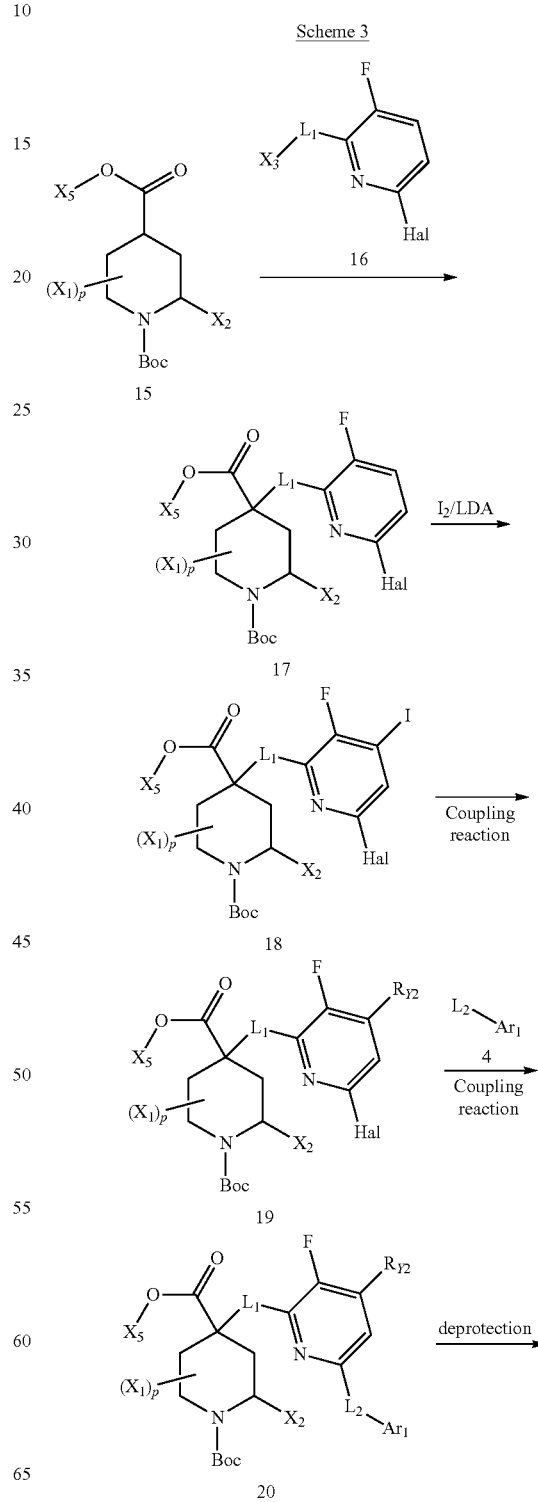

Hal is a halide, and $X_3$ and $X_4$ is a leaving group such as a halide or OH that can easily converted to a leaving group such as triflate or tosylate.

As depicted in Scheme 2, 10 reacts with nucleophilic reagents to give 11 under alkaline conditions, using alkaline such as lithium diisopropylamide (LDA), Lithium bis(trimethylsilyl)amide (HMDSLi) etc. The synthesis method of other steps is shown in scheme 1.

General routes to compounds illustrated in the invention is described in Scheme 2, where the $L_1$, $L_2$, Y, $Y_1$, $Y_2$, $Y_3$, p, $X_1$, $X_2$, $Ar_1$, $Ar_2$, $R_{Y2}$ and Z etc. substituents are defined previously in the text or a functional group that can be converted to the desired final substituent. The substituent

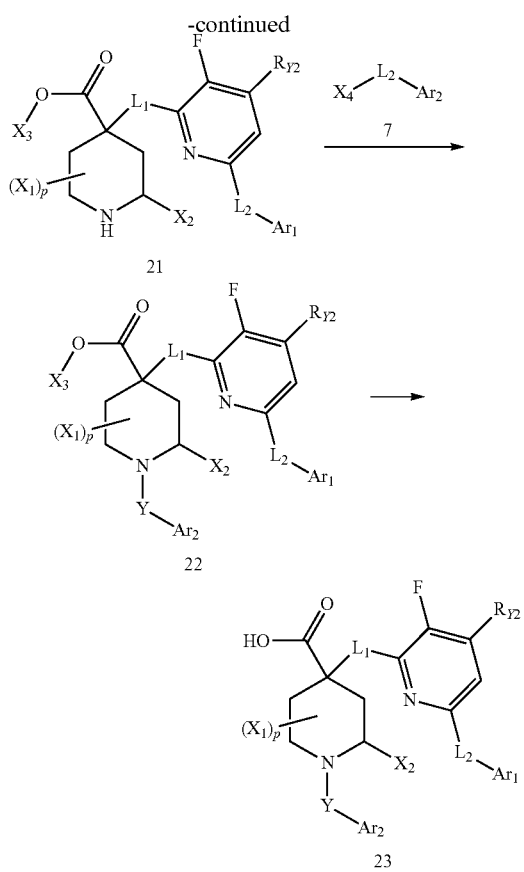

General routes to compounds illustrated in the invention is described in Scheme 2, where the $L_1$, $L_2$, Y, $Y_1$, $Y_2$, $Y_3$, p, $X_1$, $X_2$, Ari, $Ar_2$, $R_{y2}$ and Z etc. substituents are defined previously in the text or a functional group that can be converted to the desired final substituent. The substituent Hal is a halide, and $X_3$ and $X_4$ is a leaving group such as a halide or OH that can easily converted to a leaving group such as triflate or tosylate. $X_5$ is a protecting group, $C_1$-$C_4$ lower alkyl, PMB etc.

It will be appreciated that other synthetic routes may be available for practice of the present invention.

The invention is further illustrated by the following examples, which may be synthesized and isolated as free bases or as salts.

The present invention also provides a pharmaceutical composition comprising a therapeutically effective amount of at least one compound or pharmaceutically acceptable salt thereof of Formula I, II, III, IV, V, VI or VII, and at least one pharmaceutically acceptable excipient. In composition, the said compound or pharmaceutically acceptable salt thereof of Formula I, II, III, IV, V, VI or VII, in a weight ratio to the said excipient within the range from about 0.0001 to about 10.

The present invention additionally provides a use of at least one compound or pharmaceutically acceptable salt thereof of Formula I, II, III, IV, V, VI or VII, and/or a pharmaceutical composition described herein for the manufacture of a medicament.

In some embodiments, a medicament thus prepared can be used for the treatment or prevention of cancer or cancer metastasis.

In some embodiments, a medicament thus prepared can be used as an Aurora A selective inhibitor.

In some embodiments, the cancer is selected from the group consisting of small cell lung cancer, colorectal cancer, gastric cancer, prostate cancer, breast cancer, triple-negative breast cancer, cervical cancer, head and neck cancer, esophageal cancer, ovarian cancer, non-small cell lung cancer, non-Hodgkin lymphoma, or any of combination thereof.

In some preferred embodiments, the cancer is selected from small cell lung cancer, prostate cancer, triple-negative breast cancer, cervical cancer, or head and neck cancer.

At least one compound or pharmaceutically acceptable salt thereof of Formula I, II, III, IV, V, VI or VII, and/or a pharmaceutical composition described herein, which is for use in the treatment of cancer or the prevention of cancer metastasis.

In some embodiments, the cancer is selected from the group consisting of small cell lung cancer, colorectal cancer, gastric cancer, prostate cancer, breast cancer, triple-negative breast cancer, cervical cancer, head and neck cancer, esophageal cancer, ovarian cancer, non-small cell lung cancer, non-Hodgkin lymphoma, or any of combination thereof.

In some embodiments, the cancer is selected from small cell lung cancer, prostate cancer, triple-negative breast cancer, cervical cancer, or head and neck cancer.

At least one compound or pharmaceutically acceptable salt thereof of Formula I, II, III, IV, V, VI or VII, and/or a pharmaceutical composition described herein, which is used as an Aurora A selective inhibitor.

At least one compound or pharmaceutically acceptable salt thereof of Formula I, II, III, IV, V, VI or VII, and/or a pharmaceutical composition described herein, which is used as a medicament.

The present invention additionally provides a method of treating a patient having a condition which is mediated by the activity of Aurora A, said method comprising administering to the patient a therapeutically effective amount of at least one compound or pharmaceutically acceptable salt thereof of Formula I, II, III, IV, V, VI or VII, and/or a pharmaceutical composition described above.

In some embodiments, the condition mediated by the activity of Aurora A is cancer.

In some embodiments, the condition mediated by the activity of Aurora A is small cell lung cancer, colorectal cancer, gastric cancer, prostate cancer, breast cancer, triple-negative breast cancer, cervical cancer, head and neck cancer, esophageal cancer, ovarian cancer, non-small cell lung cancer, non-Hodgkin lymphoma, or any of combination thereof.

In some embodiments, the cancer is selected from small cell lung cancer, prostate cancer, triple-negative breast cancer, cervical cancer, or head and neck cancer.

The present invention additionally provides a method of treating cancer selected from the group consisting of small cell lung cancer, colorectal cancer, gastric cancer, prostate cancer, breast cancer, triple-negative breast cancer, cervical cancer, head and neck cancer, esophageal cancer, ovarian cancer, non-small cell lung cancer, or non-Hodgkin lymphoma in a mammal comprising administering to a mammal in need of such treatment an effective amount of at least one compound or pharmaceutically acceptable salt of Formula I, II, III, IV, V, VI or VII, and/or a pharmaceutical composition of described above.

The term "halogen", as used herein, unless otherwise indicated, means fluoro, chloro, bromo or iodo. The preferred halogen groups include F, Cl and Br. The terms "halo$C_{1-6}$alkyl", "halo$C_{2-6}$alkenyl", "halo$C_{2-6}$alkynyl" and "halo$C_{1-6}$alkoxy" mean a $C_{1-6}$alkyl, $C_{2-6}$alkenyl, $C_{2-6}$alkynyl or $C_{1-6}$alkoxy in which one or more (in particular, 1 to 3) hydrogen atoms have been replaced by halogen atoms, especially fluorine or chlorine atoms. In some embodiment, preferred are fluoroC$_{1-6}$alkyl, fluoroC$_{2-6}$alkenyl, fluoroC$_{2-6}$alkynyl and fluoroC$_{1-6}$alkoxy groups, in particular fluoro-C$_{1-3}$alkyl, for example, CF$_3$, CHF$_2$, CH$_2$F, CH$_2$CH$_2$F, CH$_2$CHF$_2$, CH$_2$CF$_3$ and fluoroC$_{1-3}$alkoxy groups, for example, OCF$_3$, OCHF$_2$, OCH$_2$F, OCH$_2$CH$_2$F, OCH$_2$CHF$_2$ or OCH$_2$CF$_3$, and most especially CF$_3$, OCF$_3$ and OCHF$_2$.

As used herein, unless otherwise indicated, alkyl includes saturated monovalent hydrocarbon radicals having straight, branched or cyclic moieties. For example, alkyl radicals include methyl, ethyl, propyl, isopropyl, cyclopropyl, n-butyl, isobutyl, sec-butyl, t-butyl, cyclobutyl, n-pentyl, 3-(2-methyl) butyl, 2-pentyl, 2-methylbutyl, neopentyl, cyclopentyl, n-hexyl, 2-hexyl, 2-methylpentyl and cyclohexyl. Similarly, C$_{1-8}$, as in C$_{1-8}$alkyl is defined to identify the group as having 1, 2, 3, 4, 5, 6, 7 or 8 carbon atoms in a linear or branched arrangement.

Alkylene means a difunctional group obtained by removal of a hydrogen atom from an alkyl group that is defined above. For example, methylene (i.e., —CH$_2$—), ethylene (i.e., —CH$_2$—CH$_2$— or —CH(CH$_3$)—) and propylene (i.e., —CH$_2$—CH$_2$—CH$_2$—, —CH(—CH$_2$—CH$_3$)— or —CH$_2$—CH(CH$_3$)—).

Alkenyl and alkynyl groups include straight, branched chain or cyclic alkenes and alkynes. Likewise, "C$_{2-8}$alkenyl" and "C$_{2-8}$alkynyl" means an alkenyl or alkynyl radicals having 2, 3, 4, 5, 6, 7 or 8 carbon atoms in a linear or branched arrangement.

Alkoxy radicals are oxygen ethers formed from the previously described straight, branched chain or cyclic alkyl groups.

The term "aryl", as used herein, unless otherwise indicated, refers to an unsubstituted or substituted mono- or polycyclic ring system containing carbon ring atoms. The preferred aryls are mono cyclic or bicyclic 6-10 membered aromatic ring systems. Phenyl and naphthyl are preferred aryls. The most preferred aryl is phenyl.

The term "heterocyclic ring" or "heterocyclyl", as used herein, unless otherwise indicated, refers to unsubstituted and substituted mono- or polycyclic non-aromatic ring system containing one or more heteroatoms. Preferred heteroatoms include N, O, and S, including N-oxides, sulfur oxides, and dioxides. Preferably the ring is three to eight membered and is either fully saturated or has one or more degrees of unsaturation. Multiple degrees of substitution, preferably one, two or three, are included within the present definition.

Examples of such heterocyclic groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junction, for example, bicyclic heteroaryl is a polycyclic heteroaryl. Bicyclic heteroaryl rings may contain from 8 to 12 member atoms. Monocyclic heteroaryl rings may contain from 5 to 8 member atoms (cabons and heteroatoms). Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "cycloalkyl" refers to a substituted or unsubstituted monocyclic, bicyclic or polycyclic non-aromatic saturated ring, which optionally includes an alkylene linker through which the cycloalkyl may be attached. Exemplary "cycloalkyl" groups includes but not limited to, cyclopropyl, cyclobutyl, cyclopentyl, cyclohexyl and so on.

The term "carbonyl", "=O", "—C=O", "C=O", "—CO", "—C(O)" and ""CO refers to the group

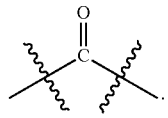 [SMILES: *C(*)=O]

The term "oxo" refers to the radical =O.

Whenever the term "alkyl" or "aryl" or either of their prefix roots appear in a name of a substituent (e.g., aralky or dialkylamino) it shall be interpreted as including those limitations given above for "alkyl" and "aryl". Designated numbers of carbon atoms (e.g., C$_{4-6}$) shall refer independently to the number of carbon atoms in an alkyl moiety or to the alkyl portion of a larger substituent in which alkyl appears as its prefix root.

wherein the term "substituted" refers to a group mentioned above in which one or more (preferably 1-6, more preferably 1-3) hydrogen atoms are each independently replaced with the same or different substituent(s). Typical substituents include, but are not limited to, X, C$_{1-6}$alkyl, C$_{1-6}$alkoxy, C$_{3-20}$ cycloalkyl, —OR$_{13}$, SR$_{13}$, =O, =S, —C(O)R$_{13}$, —C(S)R$_{13}$, =NR$_{13}$, —C(O)OR$_{13}$, —C(S)OR$_{13}$, —NR$_{13}$R$_{14}$, —C(O)NR$_{13}$R$_{14}$, cyano, nitro, —S(O)$_2$R$_{13}$, —OS(O$_2$)OR$_{13}$, —OS(O)$_2$R$_{13}$, or —OP(O)(OR$_{13}$)(OR$_{14}$); wherein each X is independently a halogen (F, Cl, Br or I), and R$_{13}$ and R$_{14}$ is independently selected from —H, C$_{1-6}$ alkyl and C$_{1-6}$ haloalkyl. In some embodiments, the substituent(s) is independently selected from the group consisting of —F, —Cl, —Br, —I, —OH, trifluromethoxy, ethoxy, propyloxy, iso-propyloxy, n-butyloxy, isobutyloxy, t-butyloxy, —SCH$_3$, —SC$_2$H$_5$, formaldehyde group, —C(OCH$_3$), cyano, nitro, CF$_3$, —OCF$_3$, amino, dimethylamino, methyl thio, sulfonyl and acetyl. Particularly preferred substituent(s) is —F, —Cl or —Br.

Compounds described herein, such as certain compounds of Formula I, II, III, IV, V, VI or VII may contain asymmetrically substituted carbon atoms (or chiral centers) in the R or S configuration. The present invention includes racemic mixtures, relative and absolute stereoisomers, and mixtures of relative and absolute stereoisomers.

The compounds described herein, when specifically designated as the R- or S-isomer, either in a chemical name or in a drawing, should be understood as an enriched R-isomer or S-isomer, respectively. For example, in any of the embodiments described herein, such enriched R- or S-designated isomer can be substantially free (e.g., with less than 5%, less than 1%, or non-detectable, as determined by chiral HPLC) of the other isomer for the respective chiral center. The enriched R- or S-isomers can be prepared by methods exemplified in this application, such as by using a chiral auxiliary such as R- or S-tert-butylsulfinamide in the synthetic process. Other methods for preparing the enriched R- or S-isomers herein include, but are not limited to, chiral HPLC purifications of a stereoisomeric mixture, such as a racemic mixture. General methods for separating stereoisomers (such as enantiomers and/or diastereomers) using HPLC are known in the art.

Compounds described herein can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to 2H, 3H, 13C, 14C, 15N, 18O, 32P, 35S, 18F, 36Cl, and 125I. Compounds that contain other isotopes of these and/or other atoms are within the scope of this invention. In some embodiments, one or more hydrogen atoms of any of the compounds described herein can be substituted with deuterium to provide the corresponding deuterium-labeled or -enriched compounds.

The term "subject" (alternatively referred to herein as "patient") as used herein refers to an animal, preferably a mammal, most preferably a human, who has been the object of treatment, observation or experiment.

Compounds of Formula I, II, III, IV, V, VI or VII may have different isomeric forms. For example, any asymmetric carbon atom may be present in the (R)-, (S)- or (R,S)-configuration, preferably in the (R)- or (S)-configuration. Substituents at a double bond or especially a ring may be present m cis-(=Z—) or trans (=E-) form. The compounds may thus be present as mixtures of isomers or preferably as pure isomers, preferably as pure diastereomers or pure enantiomers.

Where the plural form (e.g. compounds, salts) is used, this includes the singular (e.g. a single compound, a single salt). "A compound" does not exclude that (e.g. in a pharmaceutical formulation) more than one compound of the Formula I, II, III, IV, V, VI or VII (or a salt thereof) is present, the "a" merely representing the indefinite article. "A" can thus preferably be read as "one or more", less preferably alternatively as "one".

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salts. For use in medicine, the salts of the compounds of this invention refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The above Formula I, II, III, IV, V, VI or VII are shown without a definitive stereochemistry at certain positions. The present invention includes all stereoisomers of Formula I, II, III, IV, V, VI or VII and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula I, II, III, IV, V, VI or VII exists, the present invention includes any possible tautomers and pharmaceutically acceptable salts thereof, and mixtures thereof, except where specifically stated otherwise.

When the compound of Formula I, II, III, IV, V, VI or VII and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. When the compound of the present invention is basic, its corresponding salt can be conveniently prepared from pharmaceutically acceptable non-toxic acids, including inorganic and organic acids. Since the compounds of Formula I, II, III, IV, V, VI or VII are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound represented by Formula I, II, III, IV, V, VI or VII (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, II, III, IV, V, VI or VII, or a prodrug, or a metabolite, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, II, III, IV, V, VI or VII, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound, or a pharmaceutically acceptable salt, of Formula I, II, III, IV, V, VI or VII. The compounds of Formula I, II, III, IV, V, VI or VII, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I, II, III, IV, V, VI or VII of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, II, III, IV, V, VI or VII, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

EXAMPLES

The following Examples are provided to better illustrate the present invention. All parts and percentages are by weight and all temperatures are degrees Celsius, unless explicitly stated otherwise.

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Examples are provided herein to facilitate a more complete understanding of the disclosure. The following examples serve to illustrate the exemplary modes of making and practicing the subject matter of the disclosure. However, the scope of the disclosure is not to be construed as limited to specific embodiments disclosed in these examples, which are illustrative only.

Meanings of Abbreviations are as Follows.

| | |
|---|---|
| CCl$_4$ | Carbontetrachloride |
| EtOAc | Ethyl acetate |
| ACN | Acetonitrile |
| MeOH | Methanol |
| DCM | Dichloromethane |
| DIBAH | Diisobutylalumium hydride |
| EtOH | Ethanol |
| NaBH$_4$ | Sodium borohydride |
| NH$_4$Cl | Ammonium chloride |
| THF | Tetrahydrofuran |
| K$_3$PO+6HD 4 | Potassium phosphate |
| H$_2$ | Hydrogen |
| DIEA | N,N-Diisopropylethylamine |
| Pd/C | Palladium-carbon |
| LDA | Lithium diisopropylamide |
| CsF | Cesium fluoride |
| K$_2$CO$_3$ | Potassium carbonate |
| XPhos | 2-(2,4,6-Triisopropylphenethyl)phenyl) dicyclohexylphosphine |
| XPhos.Pd.G2 | (SP-4-4)-[2'-Amino[1,1'-biphenyl]-2-yl] chloro[dicyclohexyl[2',4',6'-tris(1-methylethyl) [1,1'-biphenyl]-2-yl] phosphine]palladium |
| Cs$_2$CO$_3$ | Cesium carbonate |
| HCl | Hydrochloric acid |
| HATU | Azabenzotriazolyl tetramethyluronium hexafluorophosphate |
| DAST | (N,N-diethylamino)sulfurtrifluoride |
| SOCl$_2$ | Dichlorosulfoxide |
| HOBT | 1-Hydroxybenzotrizole |
| Pd$_2$(dba)$_3$ | Tris(dibenzylideneacetone)dipalladium(0) |
| Pd(dppf)Cl$_2$ | [1,1'-Bis(diphenylphosphino)ferrocene] dichloropalladium(II) |
| ETCI | 1-Ethyl[3-(dimethylamino)propyl]carbodiimide |
| NCS | N-Chlorosuccinimide |
| AIBN | Azodiisobutyronitrile |
| NBS | N-Bromosuccinimide |
| TFA | 2,2,2-Trifluoroacetic acid |
| RT | Room temperature |
| min | minute(s) |
| h | hour(s) |
| INT | Intermediate |
| TLC | Thin layer chromatography |
| Prep - TLC | Preparative thin layer chromatography |
| Prep - HPLC | Preparation high performance liquid chromatography |

Syntheses of Intermediates:

INT A1: 6-bromo-2-(bromomethyl)-3-fluoropyridine

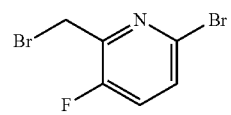

A solution of 6-bromo-3-fluoro-2-methylpyridine (20.17 g, 106.15 mmol) in CCl$_4$ (300 mL), NBS (28.49 g, 160.07 mmol) and benzoyl peroxide (5.17 g, 21.34 mmol) was stirred at reflux for overnight under nitrogen. The reaction was cooled to room temperature. The resulting mixture was added saturated sodium bicarbonate aqueous solution and extracted with ethyl acetate. The organic layer was washed with brine, dried over anhydrous sodium sulfate, filtered and concentrated under reduced pressure. The obtained residue was purified by C18 reversed phase column chromatography eluting with H$_2$O/ACN to afford 6-bromo-2-(bromomethyl)-3-fluoropyridine (13.78 g, Y=48%) as a white solid. LCMS (ESI, m/z): 270 [M+H]$^+$.

INT A2: 2-(bromomethyl)-6-chloro-3-fluoropyridine

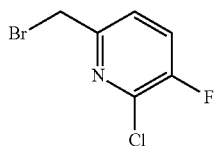

A solution of 2-chloro-3-fluoro-6-methylpyridine (23.55 g, 161.787 mmol) in ACN (400 mL), NBS (43.06 g, 241.932 mmol) and AIBN (14.10 g, 85.867 mmol) was stirred at 80° C. for overnight under nitrogen. The reaction was cooled to room temperature. The mixture was added saturated sodium bicarbonate aqueous solution and extracted with ethyl acetate. The organic layer was washed with brine, dried over anhydrous sodium sulfate, filtered and concentrated under reduced pressure. The resulting residue was purified by $C_{1-8}$ reversed phase column chromatography eluting with $H_2O$/ACN to afford 2-(bromomethyl)-6-chloro-3-fluoropyridine (18.72 g, Y=52%) as a yellow oil. LCMS (ESI, m/z): 224, 226 [M+H]$^+$.

INT A3: 2-(bromomethyl)-6-chloro-3,5-dimethylpyrazine

Step 1: (6-chloro-3,5-dimethylpyrazin-2-yl)methanol

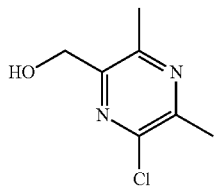

Ethyl 6-chloro-3,5-dimethylpyrazine-2-carboxylate (0.846 g, 3.941 mmol) was dissolved in anhydrous THF under nitrogen. A solution of DIBAH (3.9 mL, 3.900 mmol) 1M in THF was added slowly at −30° C.~−50° C. under nitrogen. The resulting mixture was allowed to warm to room temperature. After completion, the reaction was quenched with saturated ammonium chloride aqueous solution (20 mL) at 0~10° C. The resulting solution was diluted with brine and extracted with 50 mL of EtOAc washed with. The organic layer was washed with brine, dried over anhydrous sodium sulfate, filtered and concentrated under reduced pressure. The resulting residue was purified by silica gel column chromatography eluting with EtOAc/hexane (0~30%) to afford 702 mg of the title compound as a white solid. LCMS (ESI, m/z): 173 [M+H]$^+$.

Step 2: 2-(bromomethyl)-6-chloro-3,5-dimethylpyrazine

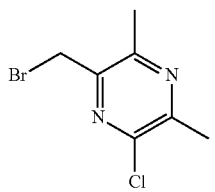

A solution of (6-chloro-3,5-dimethylpyrazin-2-yl)methanol (0.642 g, 3.719 mmol), triphenylphosphine (2.986 g, 11.385 mmol) in THF (40 mL) was cooled to 0° C.~−10° C. under nitrogen. NBS (2.085 g, 11.715 mmol) in THF (20 mL) was added to the above solution. The reaction mixture was allowed to warm to room temperature and stirred for 2 h. The resulting solution was diluted with brine and extracted with 50 mL of EtOAc. The organic layer was washed with brine, dried over anhydrous sodium sulfate, filtered and concentrated under reduced pressure. The resulting residue was purified by silica gel column chromatography eluting with EtOAc/hexane (0~10%) to afford 559 mg of the title compound as a white solid. LCMS (ESI, m/z): 235,237 [M+H]$^+$.

INT A4: 2-(bromomethyl)-6-chloro-3-methylpyridine

Step 1: (6-chloro-3-methylpyridin-2-yl) methanol

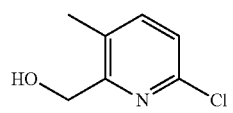

To a solution of methyl-6-chloro-3-methylpicolinate (2.046 g, 11.023 mmol) in methanol (30 mL) was added NaBH$_4$ (570 mg, 15.066 mmol) at 0° C. The reaction mixture was stirred for 3 h at room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with $H_2O$/ACN to afford (6-chloro-3-methylpyridin-2-yl)methanol (1.23 g Y=71%) as a yellow oil. LCMS (ESI, m/z): 158 [M+H]$^+$.

Step 2: 2-(bromomethyl)-6-chloro-3-methylpyridine

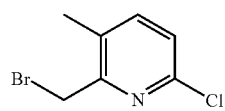

To a solution of (2-chloro-5-fluoropyrimidin-4-yl)methanol (804 mg, 4.946 mmol) in DCM (10 mL) was added tribromophosphine (2.880 g, 10.640 mmol) at 0° C. The resulting mixture was stirred for 3 h at room temperature. The reaction solution was quenched with saturated NH$_4$Cl aqueous solution. The resulting mixture was extracted with ethyl acetate, dried over anhydrous sodium sulfate, filtered and concentrated under reduced pressure. The resulting residue was purified by C18 reversed phase column chromatography eluting with $H_2O$/ACN to afford 2-(bromomethyl)-6-chloro-3-methylpyridine (326 mg, Y=29%) as a yellow oil. LCMS (ESI, m/z): 220 [M+H]$^+$.

INT A5:
2-bromo-4-(bromomethyl)-5-methylthiazole

Step 1: (2-bromo-5-methylthiazol-4-yl)methanol

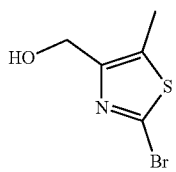

To a solution of methyl 2-bromo-5-methylthiazole-4-carboxylate (5.179 g, 21.937 mmol) in methanol (100 mL) and water (10 mL) was added NaBH$_4$ (4.474 g, 118.258 mmol) at 0° C. The reaction mixture was stirred for 3 h at room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with H$_2$O/ACN to afford (2-bromo-5-methylthiazol-4-yl)methanol (1996 mg, Y=44%) as a yellow oil. LCMS (ESI, m/z): 208 [M+H]$^+$.

Step 2: 2-bromo-4-(bromomethyl)-5-methylthiazole

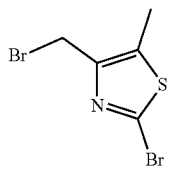

To a solution of (2-bromo-5-methylthiazol-4-yl) methanol (1.70 g, 8.170 mmol) in THF (20 mL) was added triphenylphosphine (2.37 g, 9.036 mmol) and carbon tetrabromide (3.00 g, 9.046 mmol) at 0° C. The reaction mixture was stirred for 3 h at room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with H$_2$O/ACN to afford 2-bromo-4-(bromomethyl)-5-methylthiazole (890 mg, Y=40%) as a yellow oil. LCMS (ESI, m/z): 270 [M+H]$^+$.

The following compounds were synthesized using the above procedure or modifications to the above procedure with the corresponding starting materials.

| | |
|---|---|
| INT A6 | 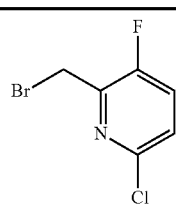 |
| INT A7 | 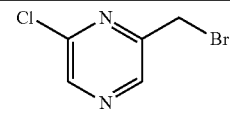 |
| INT A8 | 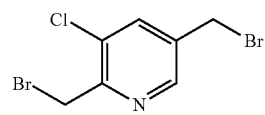 [SMILES: Clc1cc(CBr)cnc1CBr] |
| INT A9 | 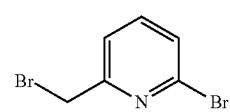 |
| INT A10 | 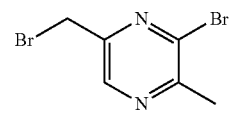 |
| INT A11 | 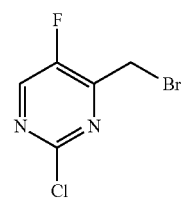 |
| INT A12: |  |
| INT A13 | 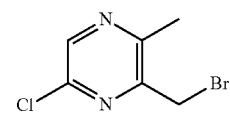 |

INT A14:
4-chloro-2-(chloromethyl)-6-methylpyrimidine

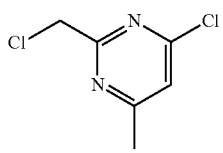

A mixture of 2-(chloromethyl)-6-methylpyrimidin-4-ol (1.87 g, 11.792 mmol) and phosphorus oxychloride (15 mL) was stirred at 80° C. for 1 h. The mixture was added saturated sodium bicarbonate aqueous solution to adjust pH to 7~8. The resulting mixture was extracted with DCM (50 mL). The organic layer was washed with brine (100 mL), dried over anhydrous sodium sulfate, filtered and concentrated under reduced pressure. The resulting residue was purified by C18 reversed phase column chromatography eluting with H$_2$O/ACN to afford 4-chloro-2-(chloromethyl)-6-methylpyrimidine (1.74 g, Y=83%) as a yellow oil. LCMS (ESI, m/z): 177 [M+H]$^+$.

INT A15: 2-bromo-6-(bromomethyl)-4-fluoropyridine

Step 1: 2-bromo-4-fluoro-6-methylpyridine

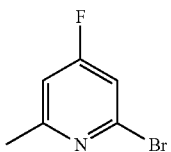

To a solution of 2-bromo-6-methylpyridin-4-amine (2.08 g, 11.121 mmol) in pyridinium fluoride (30 mL) was added sodium nitrite (1.42 g, 20.581 mmol). The reaction mixture was heated to 55° C. and stirred for 3 h. The reaction solution was cooled to room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with H₂O/ACN to afford 2-bromo-4-fluoro-6-methylpyridine (669 mg, Y=32%) as a yellow oil. LCMS (ESI, m/z): 190, 192 [M+H]⁺.

Step 2: 2-bromo-6-(bromomethyl)-4-fluoropyridine

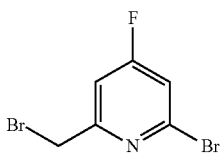

Following the procedure analogous to that described in the synthesis of INT A1, 2-bromo-4-fluoro-6-methylpyridine (341 mg, 1.795 mmol) was converted to the title compound (483 g, Y=100%) as a red oil. LCMS (ESI, m/z): 270 [M+H]⁺.

INT A16: 2-(bromomethyl)-6-chloro-4-cyclopropyl-3-fluoropyridine

Step 1: 6-chloro-3-fluoro-4-iodo-2-methylpyridine

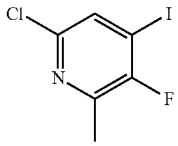

A solution of diisopropylamine (13.54 g, 133.809 mmol) in THF (30 mL) was added n-butyl lithium (2.5M) in hexane (47 mL, 117.500 mmol) dropwise at −78° C. under nitrogen. The reaction was stirred at 0° C. for 1 h. A solution of 6-chloro-3-fluoro-2-methylpyridine (10.37 g, 71.241 mmol) in THF (20 ml) was added above solution at −78° C. The resulting solution was stirred at −40° C. for 1 h.

A solution of iodine (24.71 g, 97.357 mmol) in THF (20 ml) was added at −78° C. The solution was stirred at −60° C. for 1 h. The reaction solution was quenched with saturated NH₄Cl aqueous solution. The resulting mixture was extracted with ethyl acetate. The organic layer was dried over anhydrous sodium sulfate, filtered and concentrated under reduced pressure. The resulting residue was purified by C18 reversed phase column chromatography eluting with H₂O/ACN to afford 6-chloro-3-fluoro-4-iodo-2-methylpyridine (13.46 g, Y=70%) as white solid. LCMS (ESI, m/z): 272 [M+H]⁺.

Step 2: 6-chloro-4-cyclopropyl-3-fluoro-2-methylpyridine

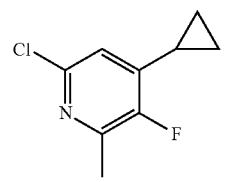

To a solution of 6-chloro-3-fluoro-4-iodo-2-methylpyridine (2083 mg, 7.673 mmol) in toluene (30 mL) and water (5 mL) was added cyclopropylboronic acid (1207 mg, 14.052 mmol), palladium(II) acetate (353 mg, 1.572 mmol), tricyclohexylphosphonium tetrafluoroborate (1135 mg, 3.082 mmol) and K₃PO₄ (6319 mg, 29.769 mmol) under nitrogen. The reaction mixture was heated to 110° C. and stirred for 12 h. The reaction was cooled to room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with H₂O/ACN to afford 6-chloro-4-cyclopropyl-3-fluoro-2-methylpyridine (1.30 g, Y=91%) as white solid. LCMS (ESI, m/z): 186 [M+H]⁺.

Step 3: 2-(bromomethyl)-6-chloro-4-cyclopropyl-3-fluoropyridine

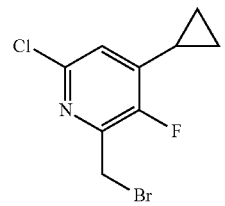

Following the procedure analogous to that described in the synthesis of INT A2, 6-chloro-4-cyclopropyl-3-fluoro-2-methylpyridine (1.30 g, 7.003 mmol) was converted to the title compound (302 mg, Y=16%) as a yellow oil. LCMS (ESI, m/z): 264 [M+H]⁺.

INT A17: 2-(bromomethyl)-6-chloro-3-fluoro-5-methylpyridine

Step 1: methyl 3-amino-5-methylpicolinate

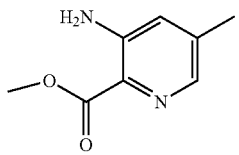

A solution of 3-amino-5-methylpicolinonitrile (4.75 g, 35.674 mmol) in 12M hydrochloric acid aqueous solution (50 mL) was stirred at refluxed for 24 h. After the reaction completion, the solvent was evaporated. The resulting residue was added methanol (100 mL) and 98% sulphuric acid (10 mL). The reaction mixture was refluxed for 24 h. The resulting solution was adjusted pH to 7~8 with saturated sodium bicarbonate aqueous solution. The resulting mixture was extracted with DCM. The organic layer was washed with brine, dried over anhydrous sodium sulfate, filtered and concentrated under reduced pressure to afford methyl 3-amino-5-methylpicolinate (4.70 g, Y=72%) as a yellow solid. LCMS (ESI, m/z): 167 [M+H]$^+$.

Step 2: methyl 3-amino-6-chloro-5-methylpicolinate

To a solution of methyl 3-amino-5-methylpicolinate (8.5 g, 51.150 mmol) in ACN (100 mL) was added NCS (9.20 g, 68.897 mmol) under nitrogen. The reaction mixture was heated to 70° C. and stirred for 12 h. The reaction was cooled to room temperature. The resulting solution was diluted with water and extracted with ethyl acetate. The organic layer was washed with saturated sodium bicarbonate aqueous solution, dried over anhydrous sodium sulfate, filtered and concentrated under reduced pressure. The resulting residue was purified by C18 reversed phase column chromatography eluting with H$_2$O/ACN to afford methyl 3-amino-6-chloro-5-methylpicolinate (6.17 g Y=60%) as a yellow solid. LCMS (ESI, m/z): 201 [M+H]$^+$.

Step 3: methyl 6-chloro-3-fluoro-5-methylpicolinate

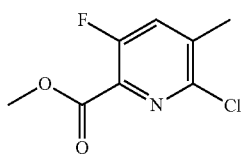

Following the procedure analogous to that described in Step 1 for the synthesis of INT A15, methyl 3-amino-6-chloro-5-methylpicolinate (5.96 g, 29.708 mmol) was converted to the title compound (3.67 g, Y=65%) as a yellow oil. LCMS (ESI, m/z): 204 [M+H]$^+$.

Step 4: (6-chloro-3-fluoro-5-methylpyridin-2-yl)methanol

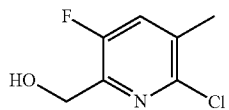

Following the procedure analogous to that described in Step 4 for the synthesis of INT A5, methyl 6-chloro-3-fluoro-5-methylpicolinate (3.57 g, 18.832 mmol) was converted to the title compound (1.60 g, Y=48%) as a white solid. LCMS (ESI, m/z): 176 [M+H]$^+$.

Step 5: 2-(bromomethyl)-6-chloro-3-fluoro-5-methylpyridine

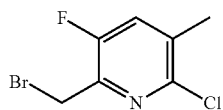

Following the procedure analogous to that described in Step 1 for the synthesis of INT A5, (6-chloro-3-fluoro-5-methylpyridin-2-yl)methanol (1.50 g, 8.543 mmol) was converted to the title compound (1.93 g, Y=95%) as a yellow oil. LCMS (ESI, m/z): 238 [M+H]$^+$.

INT A18: 2-(bromomethyl)-3,5-difluoropyridine

Step 1: 3-amino-5-fluoropicolinonitrile

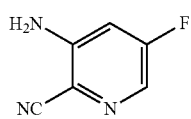

A solution of 5-fluoro-3-nitropicolinonitrile (20.01 g, 119.751 mmol) in methanol (250 mL) was purged with nitrogen and pressurized with H$_2$. The solution was added Pd/C (9.23 g, 86.732 mmol) and stirred for 16 h. After completion, the mixture was filtrated and washed the filter cake with methanol (200 mL×3). The filtrate was removed under reduced pressure to afford 3-amino-5-fluoropicolinonitrile (15.42 g, 94%) as a yellow solid. LCMS (ESI, m/z): 138 [M+H]$^+$.

Step 2: methyl 3-amino-5-fluoropicolinate

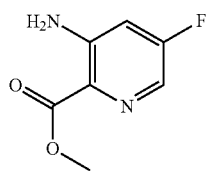

A solution of 3-amino-5-fluoropicolinonitrile (17.49 g, 127.558 mmol) in 12M hydrochloric acid aqueous solution (250 mL) was refluxed for 24 h. After completion, the solvent was evaporated. The resulting residue was added methanol (300 mL) and 98% sulphuric acid (60 mL). The reaction mixture was refluxed for 24 h before it was cooled to room temperature. The resulting solution was added saturated sodium bicarbonate aqueous solution to adjust pH to 7~8. The resulting mixture was extracted with DCM. The organic layer was washed with brine, dried over anhydrous sodium sulfate, filtered and concentrated under reduced pressure to afford methyl 3-amino-5-fluoropicolinate (16.60 g, Y=76%) as a yellow solid. LCMS (ESI, m/z): 171 [M+H]$^+$.

Step 3: methyl-3,5-difluoropicolinate

To a solution of methyl 3-amino-5-fluoropicolinate (16.60 g, 97.566 mmol) in pyridinium fluoride (220 mL) was added sodium nitrite (13.87 g, 201.028 mmol). The mixture was heated to 55° C. and stirred for 3 h. The reaction mixture was cooled to room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with H$_2$O/ACN to afford methyl-3,5-difluoropicolinate (10.86 g, Y=64%) as a yellow oil. LCMS (ESI, m/z): 174 [M+H]$^+$.

Step 4: (3,5-difluoropyridin-2-yl)methanol

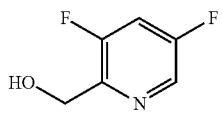

To a solution of methyl-3,5-difluoropicolinate (10.86 g, 62.732 mmol) in methanol (100 mL) and water (20 mL) was added NaBH$_4$ (7.39 g, 195.335 mmol) at 0° C. The mixture was stirred for 3 h at room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with H$_2$O/ACN to afford (3,5-difluoropyridin-2-yl)methanol (8.19 g Y=90%) as a yellow oil. LCMS (ESI, m/z): 146 [M+H]$^+$.

Step 5: 2-(bromomethyl)-3,5-difluoropyridine

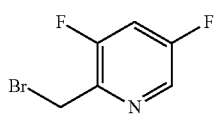

Following the procedure analogous to that described in Step 2 for the synthesis of INT A5, (3,5-difluoropyridin-2-yl)methanol (8.19 g, 56.441 mmol) was converted to the title compound (9.16 g, Y=78%) as a yellow oil. LCMS (ESI, m/z): 208, 210 [M+H]$^+$.

INT B1: di-tert-butyl-piperidine-1,4-dicarboxylate

Step 1:
1-(tert-butoxycarbonyl)piperidine-4-carboxylic acid

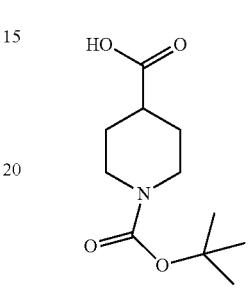

To a solution of 1-(tert-butyl) 4-methyl piperidine-1,4-dicarboxylate (4.95 g, 20.35 mmol), THF (90 mL), methanol (90 mL) and water (30 mL) was added lithium hydroxide (2.39 g, 99.715 mmol). The solution was stirred at room temperature for overnight. The resulting mixture was adjusted pH to 5 with 1N HCl aqueous solution, extracted with ethyl acetate (500 mL) and washed with brine. The organic layer was dried over anhydrous sodium sulfate, filtered and concentrated under reduced pressure to give 1-(tert-butoxycarbonyl) piperidine-4-carboxylic acid (4.55 g, crude) as a white solid.

The crude product is directly used in the next step without purification. LCMS (ESI, m/z): 230 [M+H]$^+$.

Step 2: di-tert-butylpiperidine-1,4-dicarboxylate

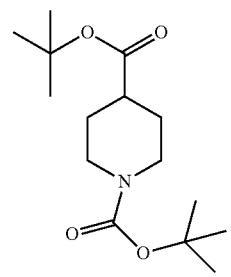 [SMILES: CC(C)(C)OC(=O)C1CCN(C(=O)OC(C)(C)C)CC1]

A solution of 1-(tert-butoxycarbonyl)piperidine-4-carboxylic acid (4.55 g, crude), 4-dimethylaminopyridine (0.64 g, 5.24 mmol) and di-tert-butyl dicarbonate (9.02 g, 41.33 mol) in tert-butanol (50 mL) was stirred at room temperature for overnight. The reaction solution was heated to 30° C. and stirred for overnight. The solvent was evaporated to remove. The resulting residue was purified by silica gel column chromatography eluting with EtOAc/hexane (0~10%) to afford di-tert-butyl piperidine-1,4-dicarboxylate (5.23 g, Y=92%) as a white solid. LCMS (ESI, m/z): 286 [M+H]$^+$.

INT B2: di-tert-butyl (2R,4R)-2-methylpiperidine-1,4-dicarboxylate

Step 1: methyl 2-methylpiperidine-4-carboxylate hydrochloride

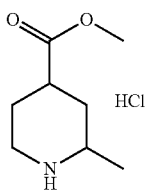

A solution of methyl 2-chloro-6-methylpyridine-4-carboxylate (99.10 g, 533.924 mmol), platinum dioxide (10.46 g, 46.064 mmol) and acetic acid (1.0 L) was purged with nitrogen and pressurized with $H_2$. The reaction mixture was heated at 65° C. for 24 h. After completion, the reaction solution was filtered and the filtrate was removed under reduced pressure. The resulting residue was added methyl tert-butyl ether (1 L) and stirred at room temperature. The resulting solids was rinsed with methyl tert-butyl ether (2×500 mL), collected and dried under vacuum to provide the title compound as a white solid (101.70 g). LCMS (ESI, m/z): 158 [M+H]$^+$.

Step 2: methyl-1-(4-methoxybenzyl)-2-methylpiperidine-4-carboxylate

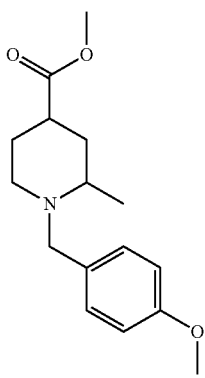

A solution of methyl 2-methylpiperidine-4-carboxylate (99.62 g, 514.379 mmol), potassium carbonate (284.360 g, 2.058 mol) in ACN (1.2 L) was refluxed for 2 h. The reaction was cooled to room temperature. The resulting solution was added 4-methoxybenzyl chloride (80.556 g, 514.379 mmol) dropwise and stirred for overnight. After completion, the mixture was filtered and the filtrate was removed under reduced pressure. The residue was dissolved in EtOAc and added 4N HCl aqueous solution to adjust pH to 1. The organic layer was separated, washed with saturated sodium bicarbonate aqueous solution and brine, dried over anhydrous sodium sulfate, filtered and concentrated under reduced pressure. The resulting residue was purified by C18 reversed phase column chromatography eluting with $H_2O$/ACN to afford methyl 1-[(4-methoxyphenyl)methyl]-2-methyl-piperidine-4-carboxylate (113.09 g) as a yellow oil. LCMS (ESI, m/z): 278 [M+H]$^+$.

Step 3: methyl (2R,4R)-1-(4-methoxybenzyl)-2-methylpiperidine-4-carboxylate

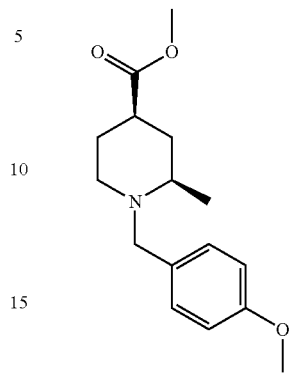

Two enantiomers of methyl 1-(4-methoxybenzyl)-2-methylpiperidine-4-carboxylate (36.67 g) was separated using chiral chromatography. Stationary phase: CHIRALPAK IA, Column size: 0.46 cm I.D.×15 cm L, mobile phase: n-hexane/EtOH 0.1% DIEA=75/25 (V/V), flow rate: 1.0 mL/min, wave length: UV 210 nm, temperature: 25° C. The first eluted enantiomer was collected as the title compound (20.01 g, 54.67% yield; Rr=2.615 min; LCMS (ESI, m/z): 278 [M+H]$^+$), the second eluted enantiomer was collected to give 15.88 g, Rr=4.449 min; LCMS (ESI, m/z): 278 [M+H]$^+$.

Step 4: methyl-(2R,4R)-2-methylpiperidine-4-carboxylate-hydrochloride

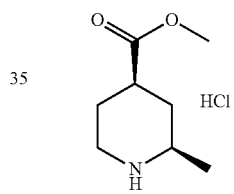

A solution of methyl (2R,4R)-1-(4-m ethoxy benzyl)-2-methylpiperidine-4-carboxylate (50.75 g, 182.977 mmol) in methanol (500 mL) was added Pd/C (10.44 g, 98.102 mmol), purged with nitrogen and pressurized with $H_2$. The mixture was heated to 45° C. and stirred for 16 h. After completion, the resulting mixture was filtered and the filter cake was washed with methanol (200 mL×3). The filtrate was collected and removed under reduced pressure. The resulting residue was added 4M HCl/ethyl acetate and stirred 2 h at room temperature. The solid was collected. The filter cake was rinsed with ethyl acetate and dried under vacuum to afford methyl (2R,4R)-2-methyl piperidine-4-carboxylate hydrochloride (32.97 g, Y=93%) as a white solid. LCMS (ESI, m/z): 158 [M+H]$^+$.

Step 5: 1-(tert-butyl)-4-methyl (2R,4R)-2-methylpiperidine-1,4-dicarboxylate

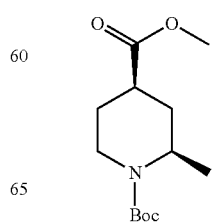

A solution of (2R,4R)-2-methylpiperidine-4-carboxylate hydrochloride (32.87 g, 169.721 mmol), N,N-diisopropylethylamine (102.58 g, 793.702 mmol), N-(4-pyridyl) dimethylamine (3.14 g, 25.703 mmol) and di-tert-butyl dicarbonate (56.31 g, 258.011 mmol) in DCM (500 mL) was stirred at room temperature for 2 h. The resulting solution was diluted with water and extracted with DCM. The organic layer was dried over anhydrous sodium sulfate, filtered and concentrated under reduced pressure. The resulting residue was purified by a silica gel column chromatography (eluent: 0~100% hexane/DCM) to afford 1-(tert-butyl) 4-methyl (2R,4R)-2-methylpiperidine-1,4-dicarboxylate (37.11 g, Y=84.97%) as a yellow oil. LCMS (ESI, m/z): 258 [M+H]⁺.

Step 6: (2R,4R)-1-(tert-butoxycarbonyl)-2-methylpiperidine-4-carboxylic acid

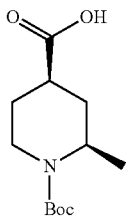 [SMILES: C[C@@H]1C[C@H](C(=O)O)CCN1C(=O)OC(C)(C)C]

A mixture of 1-(tert-butyl) 4-methyl (2R,4R)-2-methylpiperidine-1,4-dicarboxylate (37.11 g, 144.214 mmol) in THF (260 mL) and water (130 mL) was added lithium hydroxide (16.95 g, 707.775 mmol). The reaction mixture was stirred at room temperature for overnight. The resulting solution was added 1N HCl aqueous solution to adjust pH to 3~4 and extracted with ethyl acetate. The organic layer was washed with brine, dried over anhydrous sodium sulfate, and concentrated under reduced pressure to give (2R,4R)-1-(tert-butoxycarbonyl)-2-methyl piperidine-4-carboxylic acid (39.5 g, crude) as a yellow oil. LCMS (ESI, m/z): 244 [M+H]⁺.

Step 7: di-tert-butyl-(2R,4R)-2-methyl piperidine-1,4-dicarboxy late

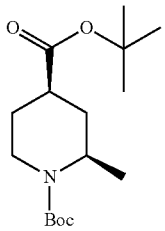 [SMILES: C[C@@H]1C[C@H](C(=O)OC(C)(C)C)CCN1C(=O)OC(C)(C)C]

A solution of (2R, 4R)-1-(tert-butoxycarbonyl)-2-methylpiperidine-4-carboxylic acid (39.5 g, crude), N-(4-pyridyl)-dimethylamine (4.84 g, 39.618 mmol) and di-tert-butyl-di-carbonate (63.94 g, 292.972 mmol) in tert-Butanol (400 mL) was stirred at room temperature for overnight under nitrogen. After completion, the resulting solution was diluted with water and extracted with ethyl acetate. The organic layer was washed with brine, dried over anhydrous sodium sulfate, and concentrated under reduced pressure. The resulting residue by a silica gel column chromatography (eluent: 0~10% ethyl acetate/hexane) to afford di-tert-butyl (2R,4R)-2-methylpiperidine-1,4-di-carboxylate (35.7 g, Y=73%) as a white solid. LCMS (ESI, m/z): 300 [M+H]⁺.

The following compounds were synthesized using the above procedure with the corresponding starting materials.

| INT B3 | 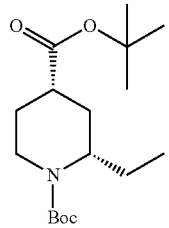 [SMILES: CC[C@H]1C[C@@H](C(=O)OC(C)(C)C)CCN1C(=O)OC(C)(C)C] |
|---|---|
| INT B4 | 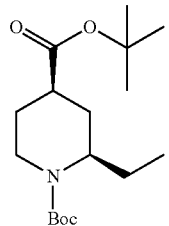 [SMILES: CC[C@@H]1C[C@H](C(=O)OC(C)(C)C)CCN1C(=O)OC(C)(C)C] |

INT B5: methyl 1-(3-chloro-2-fluorobenzyl)-2-ethylpiperidine-4-carboxylate

Step 1: methyl 2-vinylisonicotinate

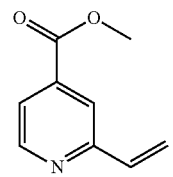

To a solution of methyl 2-bromoisonicotinate (3.05 g, 14.12 mmol) in 1,4-dioxane (60 mL) was added tributyl (vinyl)stannane (7.44 g, 23.46 mmol), tetrakis(triphenylphosphine)palladium (1.72 g, 1.49 mmol) and cesium fluoride (4.37 g, 28.77 mmol) under nitrogen. The reaction mixture was stirred at 80° C. for 4 h. After cooling to room temperature, the resulting mixture was diluted with ethyl acetate (50 mL) and filtered. The filtrate was concentrated under reduced pressure. The resulting residue was purified with column chromatography on silica gel eluting with ethyl acetate/hexane (10%~30% to afford methyl 2-vinylisonicotinate (1.65 g) as light yellow oil. LCMS (ESI, m/z): 164 [M+H]⁺.

Step 2: methyl 2-ethylpiperidine-4-carboxylate

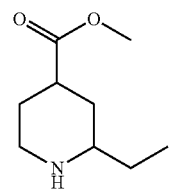

To a solution of methyl 2-vinylisonicotinate (1.65 g, 10.11 mmol) in HOAc (30 mL) was added PtO₂ (0.48 g, 2.11 mmol). The mixture was purged with nitrogen and pressurized with H₂. The reaction mixture was stirred at 65° C. for 16 h. The resulting mixture was cooled to room temperature and filtered. The filter cake was washed with HOAc (3×50 mL) and the filtrate was concentrated under vacuum afford crude methyl 2-ethylpiperidine-4-carboxylate (1.83 g) as light yellow oil. LCMS (ESI, m/z): 172 [M+H]⁺.

Step 3: methyl 1-(3-chloro-2-fluorobenzyl)-2-ethylpiperidine-4-carboxylate

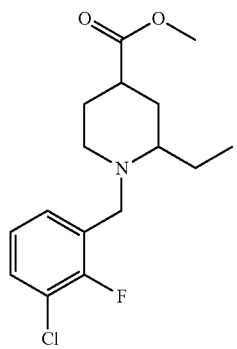 [SMILES: CCC1CC(C(=O)OC)CCN1Cc1cccc(Cl)c1F]

To a solution of methyl 2-ethylpiperidine-4-carboxylate (1.83 g, 10.50 mmol) in ACN (30 mL) was added K₂CO₃ (4.65 g, 33.65 mmol) and 1-(bromomethyl)-3-chloro-2-fluorobenzene (3.05 g, 13.06 mmol). The reaction mixture was stirred at room temperature for 16 h. The resulting mixture was diluted with ethyl acetate (50 mL) and filtered. The filter cake was washed with ethyl acetate (3×50 mL) and the filtrate was concentrated under vacuum. The resulting residue was purified by column chromatography on silica gel eluting with ethyl acetate/hexane (0%~30%) to afford methyl 1-(3-chloro-2-fluorobenzyl)-2-ethylpiperidine-4-carboxylate (2.36 g) as colorless oil. LCMS (ESI, m/z): 314 [M+H]⁺.

INT B6: methyl 1-(3-chloro-2-fluorobenzyl)-2,6-dimethylpiperidine-4-carboxylate

Step 1: methyl 2,6-dimethylpiperidine-4-carboxylate

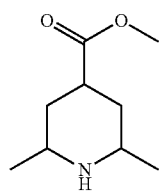

A solution of methyl 2,6-dimethylisonicotinate (1.92 g, 11.623 mmol), platinum dioxide (236 mg, 1.039 mmol) in acetic acid (20 mL) was purged with nitrogen and pressurized with H₂. The reaction mixture was heated at 65° C. for 24 h. After completion, the resulting mixture was filtered and the filtrate was removed under reduced pressure. The resulting residue was added methyl tert-butyl ether (20 mL) and stirred at room temperature for 1 h. The solids was collected and dried in vacuum to provide methyl-2,6-dimethyl-piperidine-4-carboxylate (1.72 g Y=94%) as a white solid. LCMS (ESI, m/z): 172 [M+H]⁺.

Step 2: methyl 1-(3-chloro-2-fluorobenzyl)-2,6-dimethylpiperidine-4-carboxylate

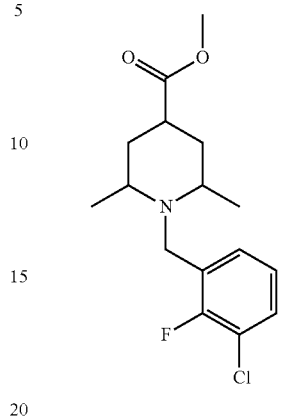

To a solution of methyl 2-methylpiperidine-4-carboxylate (520 mg, 3.037 mmol) in acetonitrile (30 ml) was added 1-(bromomethyl)-3-chloro-2-fluorobenzene (830 mg, 3.714 mmol) and K₂CO₃ (1.26 g, 9.117 mmol) at room temperature. The resulting mixture was stirred for 3 h at room temperature before it was filtrated. The filtrate was removed under reduced pressure. The resulting residue was purified by C18 reversed phase column chromatography eluting with H₂O/ACN to afford methyl-1-(3-chloro-2-fluorobenzyl)-2,6-dimethyl-piperidine-4-carboxylate (500 mg Y=52%) as a yellow oil. LCMS (ESI, m/z): 314 [M+H]⁺.

The following compounds were synthesized using the above procedure with the corresponding starting materials.

| INT B7 | 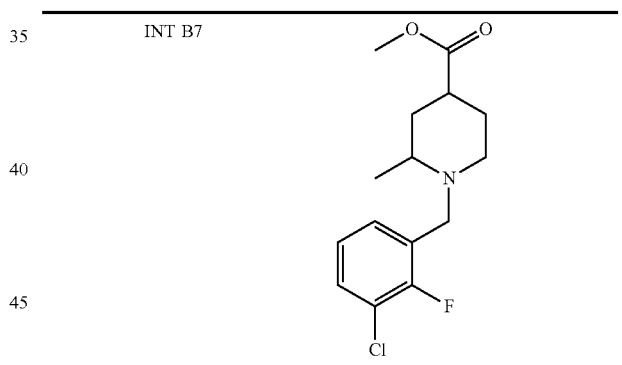 |
| --- | --- |

INT C1: di-tert-butyl (2R,4R)-4-((6-chloro-5-fluoropyridin-2-yl)methyl)-2 methylpiperidine-1,4-dicarboxylate

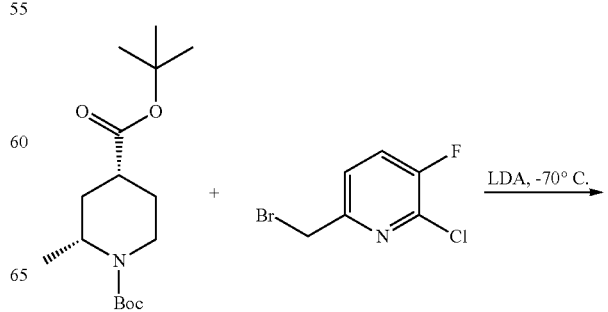

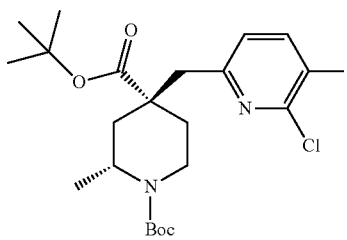

A solution of diisopropylamine (928 mg, 9.171 mmol) in THF (2 ml) was cooled to −70~80° C. under nitrogen. n-Butyl lithium 2.5 M in THF (4.0 ml, 10 mmol) was added and the resulting solution was stirred at 0° C. for 30 min. Then a solution of INT B2 (1.28 g, 4.275 mmol) in THF (4 ml) was added slowly and the reaction was stirred at −50° C.~−70° C. for 1 h.

A solution of INT A2 (1094 mg, 4.874 mmol) was added to above solution and the reaction solution was stirred at −70° C. to ~80° C. for 2 h. After completion, the resulting solution was quenched with saturated ammonium chloride aqueous solution (50 mL) and extracted with EtOAc (100 ml×3). The organic layer was concentrated under reduced pressure. The resulting residue was purified by $C_{1-8}$ reverse phase chromatography eluting with $H_2O$/ACN to afford 879 mg of the title compound. LCMS (ESI, m/z): 443 [M+H]$^+$.

The following compounds were synthesized using the above procedure with the corresponding starting materials.

INT C2

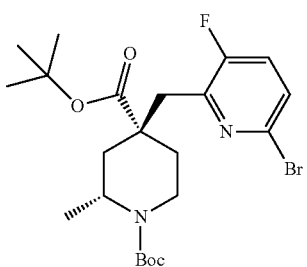 [SMILES: C[C@@H]1C[C@](Cc2nc(Br)ccc2F)(C(=O)OC(C)(C)C)CCN1C(=O)OC(C)(C)C]

INT C3

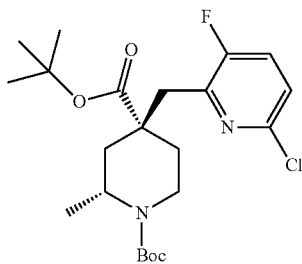 [SMILES: C[C@@H]1C[C@](Cc2nc(Cl)ccc2F)(C(=O)OC(C)(C)C)CCN1C(=O)OC(C)(C)C]

INT C4

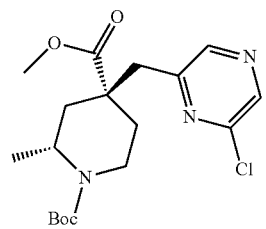 [SMILES: COC(=O)[C@]1(Cc2cncc(Cl)n2)CCN(C(=O)OC(C)(C)C)[C@H](C)C1]

INT C5

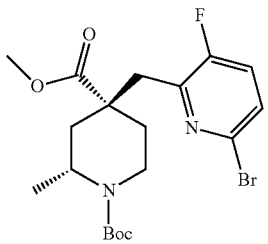 [SMILES: COC(=O)[C@]1(Cc2nc(Br)ccc2F)CCN(C(=O)OC(C)(C)C)[C@H](C)C1]

INT C6: di-tert-butyl (2R,4R)-4-((6-chloro-3,5-difluoropyridin-2-yl)methyl)-2-methylpiperidine-1,4-dicarboxylate Step 1: di-tert-butyl-(2R,4R)-4-((3,5-difluoropyridin-2-yl)methyl)-2-methyl-piperidine-1,4-dicarboxylate

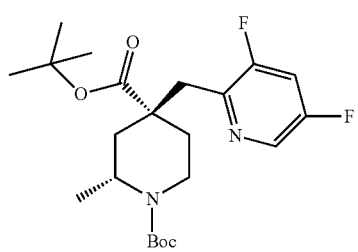 [SMILES: C[C@@H]1C[C@](Cc2ncc(F)cc2F)(C(=O)OC(C)(C)C)CCN1C(=O)OC(C)(C)C]

Following the procedure analogous to that described in the synthesis of INT C1, INT A18 (5.62 g, 27.019 mmol) and INT B2 (5.98 g, 19.973 mmol) was converted to the title compound (7.47 g, Y=88%) as a yellow oil. MS: 427 [M+H]$^+$.

Step 2: 2-(((2R,4R)-1,4-bis(tert-butoxycarbonyl)-2-methylpiperidin-4-yl)methyl)-3,5-difluoropyridine-1-oxide To a solution of di-tert-butyl (2R,4R)-4-((3,5-difluoropyridin-2-yl)methyl)-2-methyl-piperidine-1,4-dicarboxylate (7.47 g, 17.515 mmol) in DCM (60 mL) was added m-chloroperoxybenzoic (6.12 g, 35.465 mmol) at 0° C. The reaction mixture was stirred for 4 h at room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with $H_2O$/ACN to afford 2-(((2R,4R)-1,4-bis(tert-butoxycarbonyl)-2-methylpiperidin-4-yl)methyl)-3,5-difluoropyridine-1-oxide (2.06 g Y=27%) as a yellow oil. MS: 443 [M+1]⁺.

Step 3: di-tert-butyl-(2R,4R)-4-((6-chloro-3,5-difluoropyridin-2-yl)methyl)-2-methylpiperidine-1,4-dicarboxylate

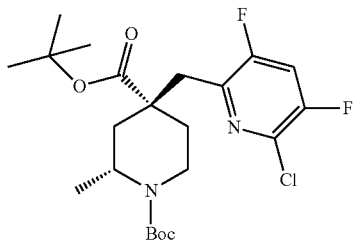 [SMILES: C[C@@H]1C[C@](Cc2nc(Cl)c(F)cc2F)(C(=O)OC(C)(C)C)CCN1C(=O)OC(C)(C)C]

To a solution of 2-(((2R,4R)-1,4-bis(tert-butoxycarbonyl)-2-methylpiperidin-4-yl)methyl)-3,5-difluoropyridine 1-oxide (2.06 g, 4.656 mmol) in DMF (10 mL) was added phosphorus oxychloride (6.41 g, 41.805 mmol) at 0° C. The reaction mixture was stirred for 4 h at room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with H₂O/ACN to afford di-tert-butyl-(2R,4R)-4-((6-chloro-3,5-difluoropyridin-2-yl)methyl)-2-methylpiperidine-1,4-dicarboxylate (1.23 g Y=57%) as a yellow oil. MS: 461 [M+1]⁺.

Example 1

1-(3-chloro-2-fluorobenzyl)-4-((3-fluoro-6-((5-methyl-1H-pyrazol-3-yl)amino)pyridin-2-yl)methyl)piperidine-4-carboxylic acid Step 1: methyl 1-(3-chloro-2-fluorobenzyl)piperidine-4-carboxylate

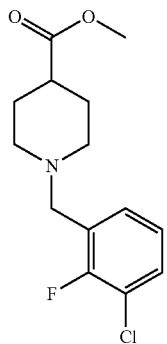 [SMILES: COC(=O)C1CCN(Cc2cccc(Cl)c2F)CC1]

To a solution of methyl piperidine-4-carboxylate (1.04 g, 7.26 mmol) in ACN (10 mL) was added K₂CO₃ (3.15 g, 22.79 mmol) and 1-(bromomethyl)-3-chloro-2-fluorobenzene (1.91 g, 8.55 mmol). The reaction mixture was stirred at room temperature for 16 h. The mixture was diluted with ethyl acetate (50 mL) and filtered. The filter cake was washed with ethyl acetate (3×50 mL) and the filtrate was combined and concentrated under reduced pressure. The resulting residue was purified by column chromatography on silica gel with (ethyl acetate/hexane, 0%-30%) to afford methyl 1-(3-chloro-2-fluorobenzyl) piperidine-4-carboxylate (1.69 g) as colorless oil. LCMS (ESI, m/z): 286 [M+H]⁺.

Step 2: methyl 4-((6-bromo-3-fluoropyridin-2-yl)methyl)-1-(3-chloro-2-fluoro-benzyl) piperidine-4-carboxylate

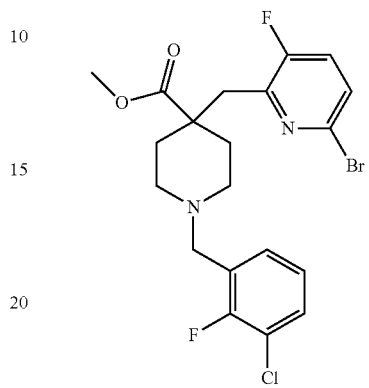

A solution of methyl 1-(3-chloro-2-fluorobenzyl)piperidine-4-carboxylate (1.18 g, 4.13 mmol) in THF (15 mL) was cooled to −70° C. under nitrogen before LDA in hexane (2M, 5 mL) was added dropwise. The reaction mixture was stirred at −70° C. for 30 min. A solution of INT A1 (1.43 g, 5.32 mmol) in THF (5 mL) was added. The mixture was stirred at −70° C. for 90 min before it is quenched with saturated ammonium chloride aqueous solution (20 mL) and extracted with ethyl acetate (3×50 mL).

The combined organic layer was dried over anhydrous sodium sulfate, filtered and concentrated under reduced pressure. The resulting residue was purified by column chromatography on silica gel with ethyl acetate/hexane (0%~30) to afford methyl 4-((6-bromo-3-fluoropyridin-2-yl)methyl)-1-(3-chloro-2-fluorobenzyl)-piperidine-4-carboxylate (480 mg) as a light yellow oil. LCMS (ESI, m/z): 473 [M+H]⁺.

Step 3: methyl 4-((6-((1-(tert-butoxycarbonyl)-5-methyl-1H-pyrazol-3-yl)amino)-3-fluoropyridin-2-yl)methyl)-1-(3-chloro-2-fluorobenzyl)piperidine-4-carboxylate

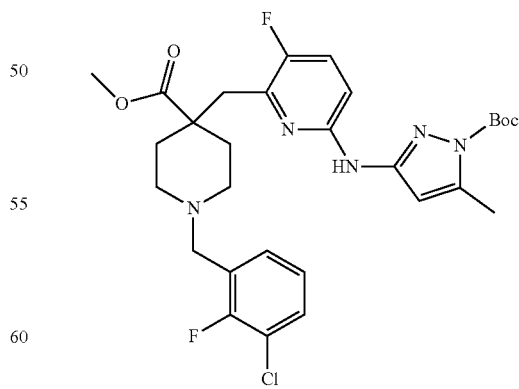

To a solution of methyl 4-((6-bromo-3-fluoropyridin-2-yl)methyl)-1-(3-chloro-2-fluorobenzyl)piperidine-4-carboxylate (201 mg, 0.42 mmol) in 1,4-dioxane (10 mL), was added tert-butyl 3-amino-5-methyl-1H-pyrazole-1-carboxylate (95 mg, 0.48 mmol), Xphos.Pd.G2 (39 mg, 0.05 mmol), Xphos (25 mg, 0.057 mmol) and Cs$_2$CO$_3$ (282 mg, 0.87 mmol) under nitrogen. The reaction mixture was stirred at 110° C. for 2 h. The mixture was cooled to room temperature and poured into water (50 mL). The resulting mixture was extracted with ethyl acetate (3×50 mL). The combined organic layer was concentrated under reduced pressure and the resulting residue was purified with column chromatography on silica gel with (ethyl acetate/hexane=10%~50%) to afford methyl 4-((6-((1-(tert-butoxycarbonyl)-5-methyl-1H-pyrazol-3-yl)amino)-3-fluoropyridin-2-yl)methyl)-1-(3-chloro-2-fluorobenzyl)piperidine-4-carboxylate (79 mg) as an off-white solid. LCMS (ESI, m/z): 590 [M+H]$^+$.

Step 4: methyl 1-(3-chloro-2-fluorobenzyl)-4-((3-fluoro-6-((5-methyl-1H-pyrazol-3-yl)amino)pyridin-2-yl)methyl)piperidine-4-carboxylate

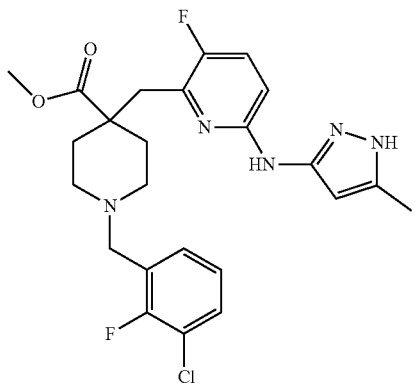

To a solution of methyl 4-((6-((1-(tert-butoxycarbonyl)-5-methyl-1H-pyrazol-3-yl)amino)-3-fluoropyridin-2-yl)methyl)-1-(3-chloro-2-fluorobenzyl)piperidine-4-carboxylate (79 mg, 0.13 mmol) in DCM (5 mL) was added TFA (5 mL). The reaction mixture was stirred at room temperature for 2 h before it is quenched with sat.NaHCO$_3$ aqueous solution (20 mL). The mixture was extracted with DCM (20 mL). The organic layer was dried over anhydrous sodium sulfate, filtered and the filtrate was concentrated under the vacuum to afford methyl 1-(3-chloro-2-fluorobenzyl)-4-((3-fluoro-6-((5-methyl-1H-pyrazol-3-yl)amino)pyridin-2-yl)methyl)piperidine-4-carboxylate (68 mg) as a light yellow solid. LCMS (ESI, m/z): 490 [M+H]$^+$.

Step 5: 1-(3-chloro-2-fluorobenzyl)-4-((3-fluoro-6-((5-methyl-1H-pyrazol-3-yl) amino)pyridin-2-yl)methyl)piperidine-4-carboxylic acid

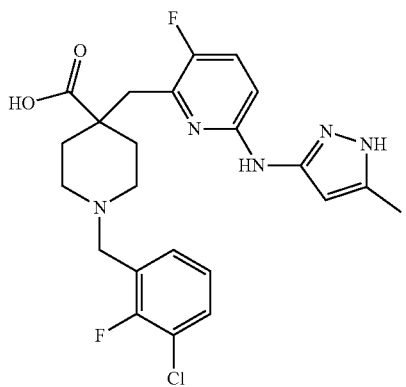 [SMILES: Cc1cc(Nc2ccc(F)c(CC3(C(=O)O)CCN(Cc4cccc(Cl)c4F)CC3)n2)n[nH]1]

To a solution of methyl 1-(3-chloro-2-fluorobenzyl)-4-((3-fluoro-6-((5-methyl-1H-pyrazol-3-yl)amino)pyridin-2-yl)methyl)piperidine-4-carboxylate (68 mg, 0.13 mmol) in MeOH (3 mL) and water (1 mL) was added sodium hydroxide (46 mg, 1.15 mmol). The reaction mixture was stirred at 70° C. overnight. The mixture was concentrated under reduced pressure. The resulting residue was added hydrochloric acid aqueous solution to adjust pH=6~7. The mixture was extracted with ethyl acetate (3×20 mL). The combined organic layers were concentrated under reduced pressure. The resulting residue was purified by prep-HPLC to afford 1-(3-chloro-2-fluorobenzyl)-4-((3-fluoro-6-((5-methyl-1H-pyrazol-3-yl)amino)pyridin-2-yl) methyl)piperidine-4-carboxylic acid (38 mg) as an off-white solid. LCMS (ESI, m/z): 476 [M+H]$^+$. $^1$H NMR (400 MHz, MeOD) δ 7.72 (t, J=7.2 Hz, 1H), 7.53 (t, J=6.4 Hz, 1H), 7.46 (t, J=9.2 Hz, 1H), 7.32 (t, J=7.6 Hz, 1H), 7.11 (d, J=6.4, 1H), 6.08 (s, 1H), 4.40 (s, 2H), 3.41 (d, J=11.6 Hz, 2H), 2.97-2.89 (m, 2H), 2.89 (s, 2H), 2.30-2.11 (m, 5H), 1.79 (t, J=12.5, 2H).

Example 2

1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid Step 1: methyl 4-((6-bromo-3-fluoropyridin-2-yl)methyl)-1-(3-chloro-2-fluoro-benzyl)-2-ethyl piperidine-4-carboxylate

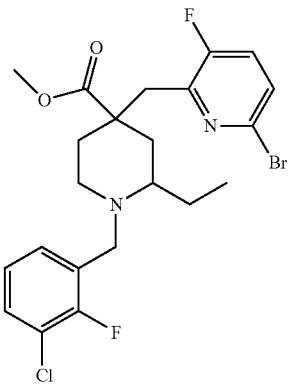 [SMILES: CCC1CC(Cc2nc(Br)ccc2F)(C(=O)OC)CCN1Cc1cccc(Cl)c1F]

Following the procedure analogous to that described in Step 2 for the synthesis of Example 1, INT B5 (1.10 g, 3.51 mmol) and INT A1 (1.19 g, 4.43 mmol) were converted to the title compound (1.07 g) as a light yellow oil. LCMS (ESI, m/z): 501 [M+H]$^+$.

Step 2: methyl 4-((6-((1-(tert-butoxycarbonyl)-5-methyl-1H-pyrazol-3-yl)amino)-3-fluoropyridin-2-yl)methyl)-1-(3-chloro-2-fluorobenzyl)-2-ethylpiperidine-4-carboxylate

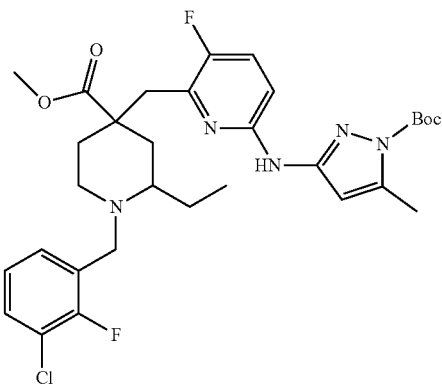 [SMILES: CCC1CC(Cc2nc(Nc3cc(C)n(C(=O)OC(C)(C)C)n3)ccc2F)(C(=O)OC)CCN1Cc1cccc(Cl)c1F]

Following the procedure analogous to that described in Step 3 for the synthesis of Example 1, methyl 4-((6-bromo-3-fluoropyridin-2-yl)methyl)-1-(3-chloro-2-fluorobenzyl)-2-ethylpiperidine-4-carboxylate (208 mg, 0.41 mmol) was converted to the title compound (201 mg) as colorless oil. LCMS (ESI, m/z): 618 [M+H]⁺.

Step 3: methyl 1-(3-chloro-2-fluorobenzyl)-2-ethyl-4-((3-fluoro-6-((5-methyl-1H-pyrazol-3-yl) amino) pyridin-2-yl)methyl)piperidine-4-carboxylate

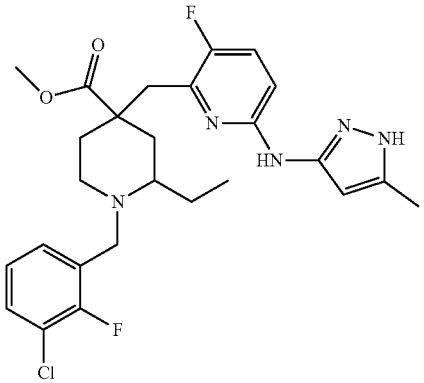 [SMILES: CCC1CC(Cc2nc(Nc3cc(C)[nH]n3)ccc2F)(C(=O)OC)CCN1Cc1cccc(Cl)c1F]

Following the procedure analogous to that described in Step 4 for the synthesis of Example 1, methyl 4-((6-((1-(tert-butoxycarbonyl)-5-methyl-1H-pyrazol-3-yl)amino)-3-fluoropyridin-2-yl) methyl)-1-(3-chloro-2-fluorobenzyl)-2-ethylpiperidine-4-carboxylate (201 mg, 0.33 mmol) was converted to the title compound (170 mg) as a light yellow solid. LCMS (ESI, m/z): 518 [M+H]⁺.

Step 4: 1-(3-chloro-2-fluorobenzyl)-2-ethyl-4-((3-fluoro-6-((5-methyl-1H-pyrazol-3-yl)amino) pyridin-2-yl)methyl)piperidine-4-carboxylic acid

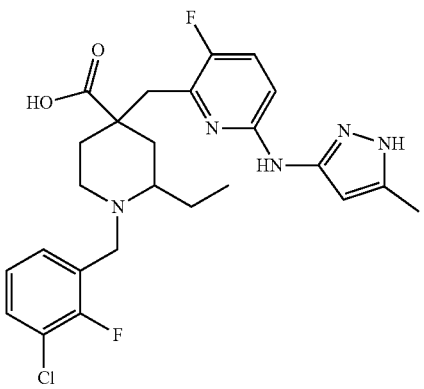 [SMILES: CCC1CC(Cc2nc(Nc3cc(C)[nH]n3)ccc2F)(C(=O)O)CCN1Cc1cccc(Cl)c1F]

Following the procedure analogous to that described in Step 5 for the synthesis of Example 1, methyl 1-(3-chloro-2-fluorobenzyl)-2-ethyl-4-((3-fluoro-6-((5-methyl-1H-pyrazol-3-yl)amino) pyridin-2-yl)methyl)piperidine-4-carboxylate (170 mg, 0.33 mmol) was converted to the title compound (23 mg) as an off-white solid. LCMS (ESI, m/z): 504 [M+H]⁺. ¹H NMR (400 MHz, MeOD) δ 7.73-7.67 (m, 1H), 7.64-7.47 (m, 2H), 7.38-7.31 (m, 1H), 6.92-6.88 (m, 1H), 6.02 (s, 1H), 4.40 (s, 2H), 3.75-3.67 (m, 1H), 3.53-3.36 (m, 3H), 3.27-3.04 (m, 2H), 2.39 (s, 3H), 2.31-2.05 (m, 3H), 1.91-1.77 (m, 2H), 1.09 (t, J=7.2 Hz, 3H).

Example 3

1-(3-chloro-2-fluorobenzyl)-4-((3-fluoro-6-((5-methyl-1H-pyrazol-3-yl)amino)pyridin-2-yl) methyl)-2,6-dimethylpiperidine-4-carboxylic acid Step 1: methyl-4-((6-bromo-3-fluoropyridin-2-yl) methyl)-1-(3-chloro-2-fluorobenzyl)-2,6-dimethylpiperidine-4-carboxylate

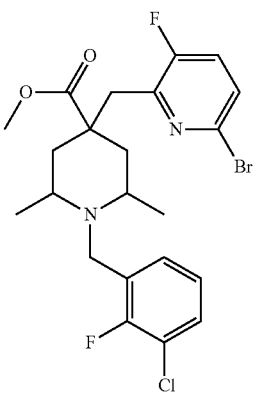 [SMILES: COC(=O)C1(Cc2nc(Br)ccc2F)CC(C)N(Cc2cccc(Cl)c2F)C(C)C1]

Following the procedure analogous to that described in Step 2 for the synthesis of Example 1, INT B6 (604 mg, 1.929 mmol) was converted to the title compound (443 mg, Y=46%) as a yellow oil.
LCMS (ESI, m/z): 503 [M+H]⁺.

Step 2: Methyl 1-(3-chloro-2-fluorobenzyl)-4-((3-fluoro-6-((5-methyl-1-((2-(trimethylsilyl)-ethoxy) methyl)-1H-pyrazol-3-yl)amino)pyridin-2-yl) methyl)-2,6-dimethylpiperidine-4-carboxylate

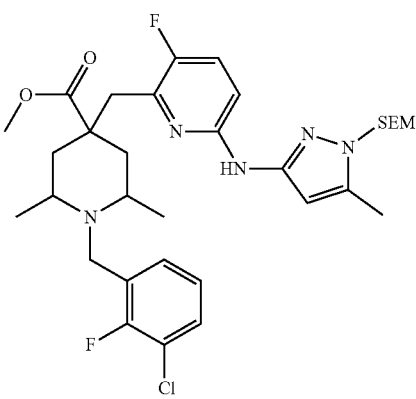 [SMILES: COC(=O)C1(Cc2nc(Nc3cc(C)n(COCC[Si](C)(C)C)n3)ccc2F)CC(C)N(Cc2cccc(Cl)c2F)C(C)C1]

To a solution of methyl-4-((6-bromo-3-fluoropyridin-2-yl)methyl)-1-(3-chloro-2-fluorobenzyl)-2,6-dimethylpiperidine-4-carboxylate (391 mg, 0.779 mmol) in 1,4-dioxane (20 ml) was added 5-methyl-1-((2-(trimethylsilyl)ethoxy) methyl)-1H-pyrazol-3-amine (328 mg, 1.443 mmol), XPhos.Pd.G2 (98 mg, 0.125 mmol), Xphos (121 mg, 0.254 mmol) and Cs₂CO₃ (570 mg, 1.749 mmol) under nitrogen. The mixture was heated to 110° C. and stirred for 5 h. The reaction was cooled to room temperature. The resulting solution was diluted with water and extracted with ethyl acetate. The organic layer was dried over anhydrous sodium sulfate, filtered and concentrated under reduced pressure. The resulting residue was purified by C18 reversed phase column chromatography eluting with H₂O/ACN to afford methyl 1-(3-chloro-2-fluorobenzyl)-4-((3-fluoro-6-((5-methyl-1-((2-(trimethylsilyl)ethoxy)methyl)-1H-pyrazol-3-yl)amino)pyridin-2-yl)methyl)-2,6-dimethylpiperidine-4-carboxylate (295 mg, Y=58%) as a yellow oil. LCMS (ESI, m/z): 648 [M+H]⁺.

Step 3: methyl-1-(3-chloro-2-fluorobenzyl)-4-((3-fluoro-6-((5-methyl-1H-pyrazol-3-yl)amino) pyridin-2-yl)methyl)-2,6-dimethylpiperidine-4-carboxylate

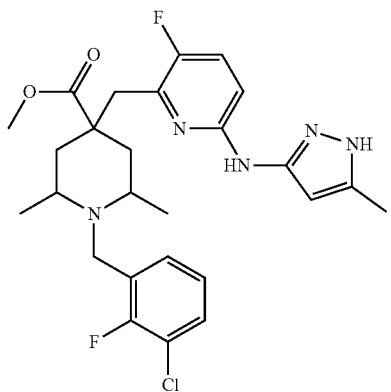

To a solution of methyl 1-(3-chloro-2-fluorobenzyl)-4-((3-fluoro-6-((5-methyl-1-((2-(trimethylsilyl)ethoxy)methyl)-1H-pyrazol-3-yl)amino)pyridin-2-yl)methyl)-2,6-dimethylpiperidine-4-carboxylate (295 mg, 0.455 mmol) in DCM (1 mL) was added TFA (10 mL). The reaction mixture was stirred at room temperature for 2 h before it is quenched with saturated sodium bicarbonate solution (50 mL). Then the resulting mixture was extracted with DCM (50 mL). The organic layer was washed with brine (100 mL), dried over anhydrous sodium sulfate, filtered and concentrated under reduced pressure. The resulting residue was purified by C18 reversed phase column chromatography eluting with H₂O/ACN to afford methyl-1-(3-chloro-2-fluorobenzyl)-4-((3-fluoro-6-((5-methyl-1H-pyrazol-3-yl)amino)pyridin-2-yl)methyl)-2,6-dimethylpiperidine-4-carboxylate (171 mg, Y=73%) as a yellow oil. LCMS (ESI, m/z): 518 [M+H]⁺.

Step 4: 1-(3-chloro-2-fluorobenzyl)-4-((3-fluoro-6-((5-methyl-1H-pyrazol-3-yl)amino)pyridin-2-yl)methyl)-2,6-dimethylpiperidine-4-carboxylic acid

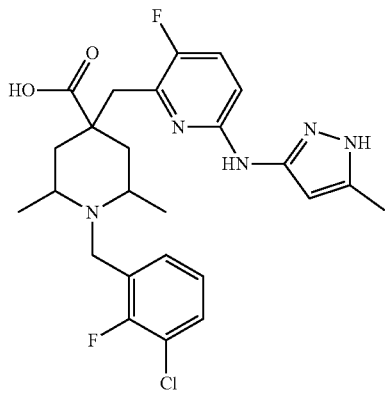

Following the procedure analogous to that described in Step 5 for the synthesis of Example 1, Methyl-1-(3-chloro-2-fluorobenzyl)-4-((3-fluoro-6-((5-methyl-1H-pyrazol-3-yl) amino) pyridin-2-yl)methyl)-2,6-dimethylpiperidine-4-carboxylate (97 mg, 0.187 mmol) was converted to the tile compound (15 mg) as a white solid. LCMS (ESI, m/z): 504 [M+H]⁺. ¹H NMR (400 MHz, DMSO) δ 9.07 (s, 1H), 7.59 (s, 1H), 7.39 (m, 2H), 7.16 (s, 1H), 7.03 (m, 1H), 6.17 (s, 1H), 4.03 (s, 2H), 3.66 (s, 2H), 2.78 (s, 1H), 2.67 (s, 1H), 2.43 (s, 1H), 2.33 (s, 1H), 2.16 (s, 3H), 2.05 (d, J=12.7 Hz, 2H), 1.24 (s, 3H), 0.86 (d, J=5.7 Hz, 3H).

Example 4

1-(3-chloro-2-fluorobenzyl)-4-((3-fluoro-6-(thiazol-2-ylamino)pyridin-2-yl)methyl)-2-methylpiperidine-4-carboxylic acid Step 1: methyl 4-((6-bromo-3-fluoropyridin-2-yl)methyl)-1-(3-chloro-2-fluorobenzyl)-2-methylpiperidine-4-carboxylate

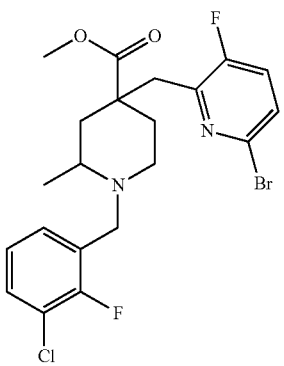 [SMILES: COC(=O)C1(Cc2nc(Br)ccc2F)CCN(Cc2cccc(Cl)c2F)C(C)C1]

Following the procedure analogous to that described in Step 2 for the synthesis of Example 1, INT B7 (2.12 g, 4.963 mmol) and INT A1 (1.52 g, 6.802 mmol) were converted to the title compound (904 mg) as a yellow oil. LCMS (ESI, m/z): 467, 469 [M+H]⁺.

Step 2: methyl 1-(3-chloro-2-fluorobenzyl)-4-((3-fluoro-6-(thiazol-2-ylamino) pyridin-2-yl) methyl)-2-methylpiperidine-4-carboxylate

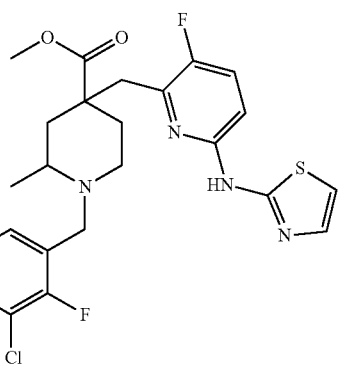

To a solution of methyl 4-((6-bromo-3-fluoropyridin-2-yl)methyl)-1-(3-chloro-2-fluorobenzyl)-2-methylpiperidine-4-carboxylate (151 mg, 0.31 mmol) in 1,4-dioxane (5 mL) was added thiazol-2-amine (53 mg, 0.53 mmol), tris (dibenzylideneacetone)dipalladium (157 mg, 0.17 mmol), brettphos (99 mg, 0.18 mmol) and Cs₂CO₃ (346 mg, 1.06 mmol) under nitrogen. The reaction mixture was stirred at 110° C. for 4 h. The mixture was cooled to room temperature and poured into water (50 mL). The mixture was extracted with ethyl acetate (3×50 mL). The combined organic layers were concentrated under reduced pressure. The resulting residue was purified with column chromatography on silica gel with (ethyl acetate/hexane=20%~100%) to afford methyl 1-(3-chloro-2-fluorobenzyl)-4-((3-fluoro-6-(thiazol-2-ylamino)pyridin-2-yl)methyl)-2-methylpiperidine-4-carboxylate (130 mg) as a light yellow solid. LCMS (ESI, m/z): 507 [M+H]⁺.

Step 3: 1-(3-chloro-2-fluorobenzyl)-4-((3-fluoro-6-(thiazol-2-ylamino)pyridin-2-yl)methyl)-2-methylpiperidine-4-carboxylic acid

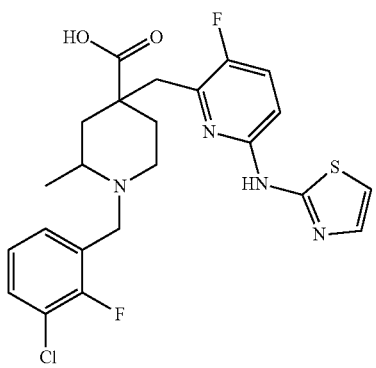 [SMILES: CC1CC(Cc2nc(Nc3nccs3)ccc2F)(C(=O)O)CCN1Cc1cccc(Cl)c1F]

Following the procedure analogous to that described in Step 5 for the synthesis of Example 1, methyl 1-(3-chloro-2-fluorobenzyl)-4-((3-fluoro-6-(thiazol-2-ylamino)pyridin-2-yl)methyl)-2-methylpiperidine-4-carboxylate (130 mg, 0.26 mmol) was converted to the title compound (14 mg) as a light yellow solid. LCMS (ESI, m/z): 493 [M+H]⁺. ¹H NMR (400 MHz, MeOD) δ 7.75-7.67 (m, 1H), 7.63-7.53 (m, 2H), 7.46 (d, J=4.0 Hz, 1H), 7.41-7.30 (m, 1H), 7.11-7.01 (m, 2H), 4.40 (d, J=12.4 Hz, 2H), 4.04-3.90 (m, 1H), 3.66-3.36 (m, 4H), 2.43-2.19 (m, 2H), 2.11-19.2 (m, 2H), 1.63 (s, 3H).

Example 5

(2R,4R)-1-(3-chloro-2-fluorobenzyl)-4-((5-fluoro-6-((3-methyl-1H-pyrazol-5-yl)amino) pyridin-2-yl)methyl)-2-methylpiperidine-4-carboxylic acid Step 1: di-tert-butyl-(2R, 4R)-4-((6-chloro-5-fluoro-pyridin-2-yl)methyl)-2-methylpiperidine-1,4-dicarboxylate

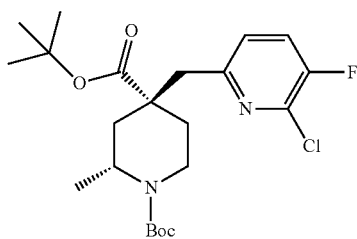 [SMILES: C[C@@H]1C[C@](Cc2ccc(F)c(Cl)n2)(C(=O)OC(C)(C)C)CCN1C(=O)OC(C)(C)C]

A solution of diisopropylamine (928 mg, 9.171 mmol) in THF (2 ml) was cooled to −70~−80° C. under nitrogen. n-Butyl lithium 2.5 M in THF (4.0 ml, 10 mmol) was added dropwise. The resulting solution was stirred for 30 min at 0° C. Then a solution of INT B2 (1.28 g, 4.275 mmol) in THF (4 ml) was added slowly and the reaction was stirred at −50° C.~−70° C. for 1 h.

A solution of INT A2 (1094 mg, 4.874 mmol) in THF (4 mL) was added and the reaction solution was stirred at −70° C. to −80° C. for 2 h. After completion, the reaction was quenched with saturated ammonium chloride solution (50 mL). The resulting solution was diluted with EtOAc (100 ml×3). The organic layers were concentrated under reduced pressure and the resulting residue was purified by C18 reversed phase column chromatography eluting with H₂O/ACN to afford 879 mg of the title compound. LCMS (ESI, m/z): 443 [M+H]⁺.

Step 2: di-tert-butyl-(2R,4R)-4-((6-((1-(tert-butyl)-3-methyl-1H-pyrazol-5-yl)amino)-5-fluoropyridin-2-yl)methyl)-2-methylpiperidine-1,4-dicarboxylate

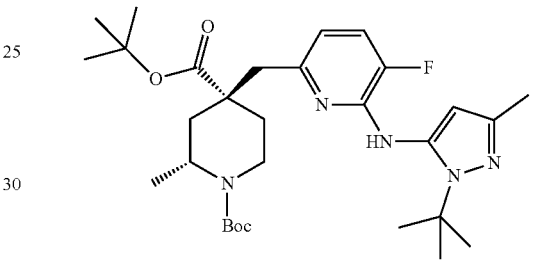

A mixture of di-tert-butyl-(2R,4R)-4-((6-chloro-5-fluoro-pyridin-2-yl)methyl)-2-methyl piperidine-1,4-dicarboxylate (1071 mg, 2.418 mmol), tris(dibenzylideneacetone)dipalladium (553 mg, 603.899 μmol), dimethylbisdiphenylphosphinoxant-hene (413 mg, 713.771 μmol), 1-tert-butyl-3-methyl-1H-pyrazol-5-amine (398 mg, 2.598 mmol) and K₃PO₄ (1442 mg, 6.793 mmol) in 1,4-dioxane (30 ml) was stirred at 110° C. for 5 h under nitrogen. The resulting solution was cooled to room temperature, diluted with brine and extracted with ethyl acetate. The organic layer was dried over anhydrous sodium sulfate, filtered and concentrated under reduced pressure. The resulting residue was purified by C18 reverse phase chromatography eluting with H₂O/ACN to afford 0.83 g of the title compound as a yellow solid. LCMS (ESI, m/z): 560 [M+H]⁺.

Step 3: tert-butyl-(2R,4R)-4-((6-((1-(tert-butyl)-3-methyl-1H-pyrazol-5-yl)amino)-5-fluoropyridin-2-yl)methyl)-2-methylpiperidine-4-carboxylate

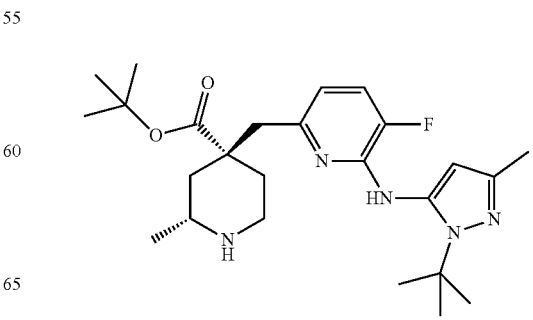

A solution of di-tert-butyl-(2R,4R)-4-((6-((1-(tert-butyl)-3-methyl-1H-pyrazol-5-yl)amino)-5-fluoropyridin-2-yl)methyl)-2-methylpiperidine-1,4-dicarboxylate (1.98 g, 3.538 mmol) in dichloromethane (24 ml) was added trifluoroacetic acid (4 ml) and stirred at room temperature for 4 h. After completion, the reaction was quenched with saturated sodium bicarbonate aqueous solution (100 ml) and extracted with DCM. The organic layer was dried over anhydrous sodium sulfate, filtered and concentrated under reduced pressure. The crude product was purified by C18 reverse phase chromatography eluting with H₂O/ACN/0.03 formic acid to afford 1.24 g of the title compound as a yellow solid. LCMS (ESI, m/z): 460 [M+H]⁺.

Step 4: tert-butyl-(2R,4R)-4-((6-((1-(tert-butyl)-3-methyl-1H-pyrazol-5-yl)amino)-5-fluoropyridin-2-yl)methyl)-1-(3-chloro-2-fluorobenzyl)-2-methylpiperidine-4-carboxylate

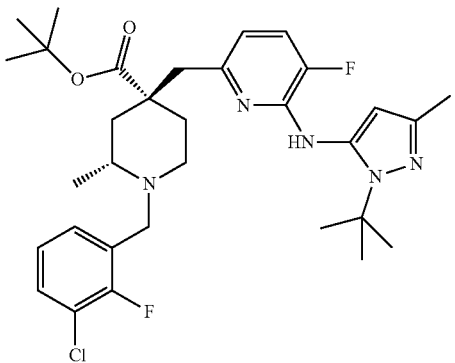 [SMILES: Cc1cc(Nc2nc(C[C@@]3(C(=O)OC(C)(C)C)CCN(Cc4cccc(Cl)c4F)[C@H](C)C3)ccc2F)n(C(C)(C)C)n1]

A mixture of tert-butyl (2R,4R)-4-((6-((1-(tert-butyl)-3-methyl-1H-pyrazol-5-yl) amino)-5-fluoropyridin-2-yl)methyl)-2-methylpiperidine-4-carboxylate (1.19 g, 2.589 mmol), potassium carbonate (1.65 g, 11.939 mmol) and 6-chloropyridine-3-carbonitrile (1.38 g, 9.96 mmol) in ACN (30 mL) was stirred for 6 h at room temperature. After completion, the resulting mixture was filtered and concentrated under reduced pressure. The crude product was purified by silica gel column chromatography eluting with EtOAc/hexane (0~30%) to afford 1.309 g of the title compound as a yellow solid. LCMS (ESI, m/z): 602 [M+H]⁺.

Step 5: (2R,4R)-1-(3-chloro-2-fluorobenzyl)-4-((5-fluoro-6-((3-methyl-1H-pyrazol-5-yl)amino) pyridin-2-yl)methyl)-2-methylpiperidine-4-carboxylic acid

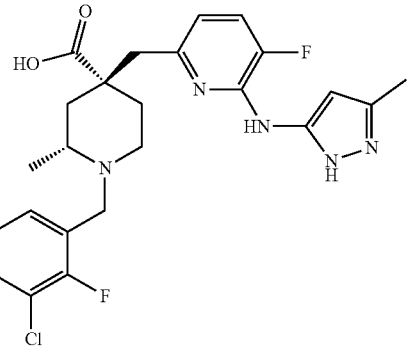

A solution of tert-butyl (2R,4R)-4-((6-((1-(tert-butyl)-3-methyl-1H-pyrazol-5-yl)amino)-5-fluoropyridin-2-yl)methyl)-1-(3-chloro-2-fluorobenzyl)-2-methylpiperidine-4-carboxylate (1.28 g, 2.126 mmol) in formic acid (20 mL) was stirred at reflux for 4 h. After completion, the resulting solution was concentrated. The resulting residue was dissolved in water (40 mL) at 0° C. and adjusted PH=6~7 with sodium hydroxide aqueous solution (5 M). The resulting mixture was extracted with DCM (3×100 mL). The organic layer was dried over anhydrous sodium sulfate, filtered and concentrated under reduced pressure. The crude product was purified by C18 reverse phase chromatography eluting with MeOH/water to afford 658 mg of the title compound as a white solid. LCMS (ESI, m/z): 490 [M+H]⁺. ¹H NMR (400 MHz, MeOD) δ 7.56-7.42 (m, 2H), 7.29 (dd, J=11.1, 8.0 Hz, 1H), 7.23 (t, 1H), 6.68 (dd, J=8.0, 3.1 Hz, 1H), 6.08 (s, 1H), 4.41 (d, J=13.4 Hz, 1H), 3.78 (d, J=13.6 Hz, 1H), 3.28-3.16 (m, 2H), 3.12 (d, J=13.4 Hz, 1H), 2.97 (d, J=12.2 Hz, 1H), 2.86 (t, 1H), 2.27 (s, 3H), 1.92 (t, 2H), 1.84 (dd, J=14.2, 10.6 Hz, 2H), 1.32 (d, J=6.2 Hz, 3H).

The following example in Table 1 was synthesized using the above procedure with the corresponding starting materials and intermediates.

TABLE 1

| Example No. | Structure | Chemical Name | ¹HNMR & MS: (M + H)⁺ |
|---|---|---|---|
| 6. | 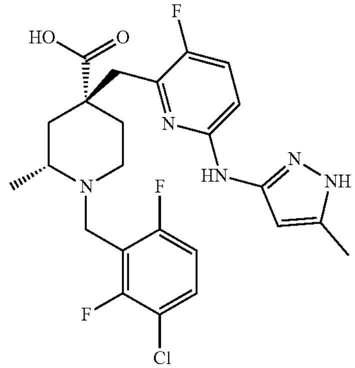 | (2R,4R)-1-(3-chloro-2,6-difluorobenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.57 (d, J = 5.6 Hz, 1H), 7.36 (s, 1H), 7.10 (t, J = 8.7 Hz, 1H), 6.75 (d, J = 8.6 Hz, 1H), 5.78 (s, 1H), 4.39 (d, J = 13.1 Hz, 1H), 3.84 (d, J = 12.8 Hz, 1H), 3.16 (d, J = 66.6 Hz, 3H), 3.00 (s, 1H), 2.87 (d, J = 11.9 Hz, 1H), 2.22 (s, 3H), 2.07-1.66 (m, 4H), 1.34 (t, J = 18.2 Hz, 3H). MS: 508(M + H)⁺ |

TABLE 1-continued

| Example No. | Structure | Chemical Name | ¹HNMR & MS: (M + H)⁺ |
|---|---|---|---|
| 7. | 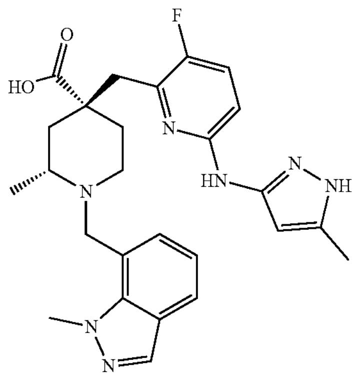 | 4-((3-fluoro-6-((5-methyl-1H-pyrazol-3-yl)amino)pyridin-2-yl)methyl)-2-methyl-1-((1-methyl-1H-indazol-7-yl)methyl)piperidine-4-carboxylic acid | ¹H NMR (400 MHz, DMSO) δ 8.16 (s, 1H), 7.92 (d, J = 8.1 Hz, 1H), 7.58 (d, J = 6.9 Hz, 1H), 7.47 (t, J = 9.0 Hz, 1H), 7.25 (dd, J = 10.2, 4.9 Hz, 2H), 6.95 (dd, J = 8.8, 2.8 Hz, 1H), 4.36 (s, 3H), 4.29 (s, 2H), 3.52 (d, J = 9.5 Hz, 2H), 3.28 (d, J = 13.5 Hz, 3H), 3.13 (d, J = 12.0 Hz, 1H), 2.19 (s, 3H), 2.07-1.85 (m, 2H), 1.57 (dd, J = 14.3, 6.1 Hz, 4H). MS: 492(M + H)⁺ |
| 8. | 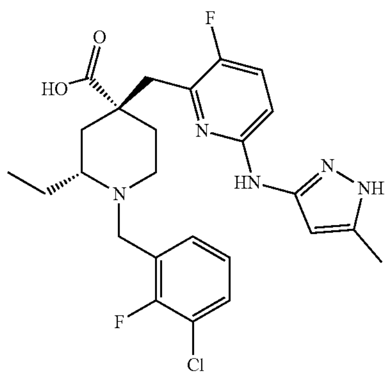 [SMILES: CC[C@@H]1C[C@](Cc2nc(Nc3cc(C)[nH]n3)ccc2F)(C(=O)O)CCN1Cc1cccc(Cl)c1F] | (2R,4R)-1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid | 1H NMR (400 MHz, MeOD) δ 7.43 (t, J = 7.4 Hz, 1H), 7.37 (t, J = 6.8 Hz, 1H), 7.26 (s, 1H), 7.13 (t, J = 7.8 Hz, 1H), 6.66 (d, J = 7.5 Hz, 1H), 5.68 (s, 1H), 4.34 (d, J = 13.5 Hz, 1H), 3.82 (d, J = 13.1 Hz, 1H), 3.18-3.08 (m, 2H), 3.03 (s, 2H), 2.87 (d, J = 10.7 Hz, 1H), 2.12 (s, 3H), 1.89 (dd, J = 37.2, 15.9 Hz, 6H), 0.85 (dd, J = 18.8, 11.9 Hz, 3H). MS: 504 (M + H)⁺ |
| 9. | 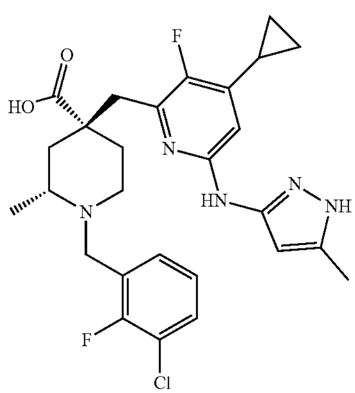 | (2R,4R)-1-(3-chloro-2-fluorobenzyl)-4-((4-cyclopropyl-3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.68 (s, 1H), 7.54 (s, 1H), 7.33 (s, 1H), 6.33 (d, J = 4.2 Hz, 2H), 3.88 (s, 2H), 3.39 (s, 2H), 2.30 (s, 3H), 2.24 (s, 1H), 2.21 (s, 1H), 2.10 (s, 4H), 1.57 (d, J = 5.8 Hz, 3H), 1.14 (d, J = 7.5 Hz, 2H), 0.83 (s, 2H). MS: 530 (M + H)⁺ |
| 10. | 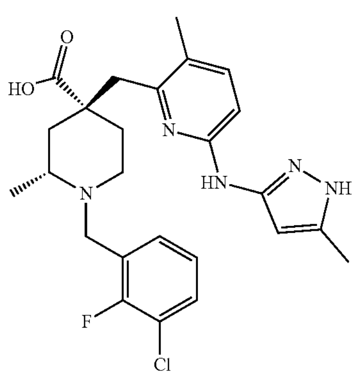 | (2R,4R)-1-(3-chloro-2-fluorobenzyl)-2-methyl-4-((3-methyl-6-((5-methyl-1H-pyrazol-3-yl)amino)pyridin-2-yl)methyl)piperidine-4-carboxylic acid | ¹H NMR (400 MHz, MeOD) δ 7.85 (d, J = 8.8 Hz, 1H), 7.67 (t, J = 7.2 Hz, 1H), 7.58 (dd, J = 10.4, 4.0 Hz, 1H), 7.32 (t, J = 8.0 Hz, 1H), 7.03 (d, J = 8.8 Hz, 1H), 5.91 (s, 1H), 4.41 (d, J = 13.4 Hz, 1H), 3.96 (d, J = 5.2 Hz, 1H), 3.54-3.35 (m, 3H), 3.31-3.30 (m, 2H), 2.44-2.07 (m, 10H), 1.57 (s, 3H). MS: 486 (M + H)⁺ |

TABLE 1-continued

| Example No. | Structure | Chemical Name | ¹HNMR & MS: (M + H)⁺ |
|---|---|---|---|
| 11. | 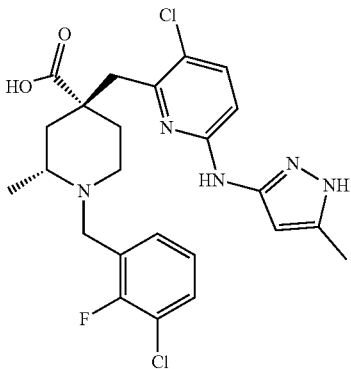 | (2R,4R)-1-(3-chloro-2-fluorobenzyl)-4-((3-chloro-6-((5-methyl-1H-pyrazol-3-yl)amino)pyridin-2-yl)methyl)-2-methylpiperidine-4-carboxylic acid | ¹H NMR (400 MHz, MeOD) δ = 7.76 (d, J = 8.8 Hz, 1H), 7.70 (t, J = 7.2 Hz, 1H), 7.57 (t, J = 7.2 Hz, 1H), 7.35 (t, J = 8.0 Hz, 1H), 6.88 (d, J = 8.8 Hz, 1H), 6.02 (s, 1H), 4.39 (d, J = 13.2 Hz, 1H), 3.90 (s, 1H), 3.59-3.37 (m, 4H), 2.40 (s, 3H), 2.35-2.04 (m, 4H), 1.60 (d, J = 6.0, 3H), 1.43-1.35 (m, 1H). MS: 506 (M + H)⁺ |
| 12. | 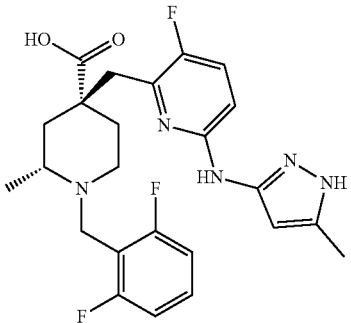 | (2R,4R)-1-(2,6-difluorobenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.57-7.35 (m, 1H), 7.25 (t, J = 8.4 Hz, 1H), 7.01 (t, J = 8.1 Hz, 2H), 6.66 (d, J = 8.5 Hz, 1H), 5.69 (s, 1H), 4.40 (d, J = 13.5 Hz, 1H), 3.91 (d, J = 13.3 Hz, 1H), 3.28 (d, J = 30.3 Hz, 1H), 3.20-2.86 (m, 4H) 2.12 (s, 3H), 1.86 (dd, J = 31.0, 1 9.9 Hz, 4H), 1.30 (t, J = 19.4 Hz, 3H). MS: 474 (M + H)⁺ |
| 13. | 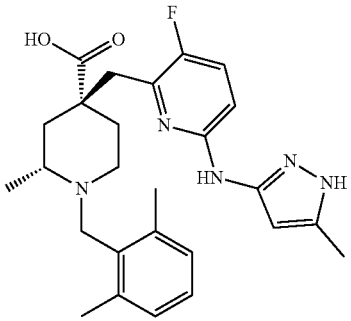 | (2R,4R)-1-(2,6-dimethylbenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.49 (t, J = 8.9 Hz, 1H), 7.41-7.28 (m, 1H), 7.22 (d, J = 7.5 Hz, 2H), 6.85 (d, J = 8.9 Hz, 1H), 5.91 (s, 1H), 4.42 (d, J = 13.7 Hz, 1H), 4.02 (s, 1H), 3.45 (s, 2H), 3.30 (s, 3H), 2.52 (s, 6H), 2.32 (s, 3H), 2.29-1.99 (m, 4H), 1.65 (d, J = 5.8 Hz, 3H). MS: 466 (M + H)⁺ |
| 14. | 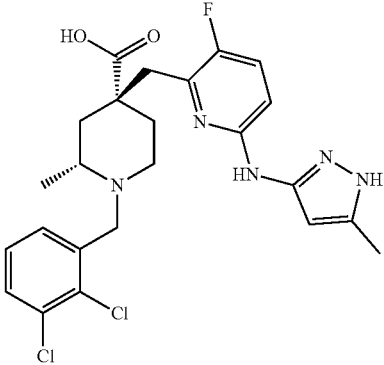 [SMILES: Cc1cc(Nc2ccc(F)c(C[C@@]3(C(=O)O)CCN(Cc4cccc(Cl)c4Cl)[C@H](C)C3)n2)n[nH]1] | (2R,4R)-1-(2,3-dichlorobenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.61 (s, 2H), 7.40 (d, J = 6.9 Hz, 2H), 6.80 (s, 1H), 5.80 (s, 1H), 4.59 (d J = 12.5 Hz, 1H), 4.05 (s, 1H), 3.66-3.38 (m, 2H), 3.08 (d, J = 45.2 Hz, 3H), 2.18 (d, J = 32.8 Hz, 3H), 1.99 (d, J = 58.4 Hz, 4H), 1.37 (d, J = 35.4 Hz, 3H). MS: 506 (M + H)⁺ |

TABLE 1-continued

| Example No. | Structure | Chemical Name | ¹HNMR & MS: (M + H)⁺ |
|---|---|---|---|
| 15. | 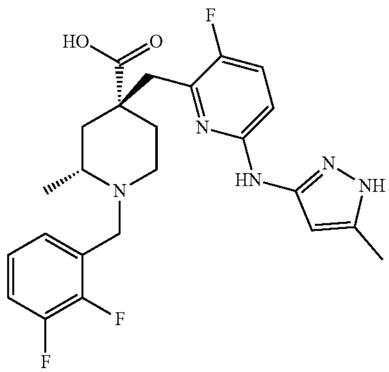 [SMILES: Cc1cc(Nc2ccc(F)c(C[C@@]3(C(=O)O)CCN(Cc4cccc(F)c4F)[C@H](C)C3)n2)n[nH]1] | (2R,4R)-1-(2,3-difluorobenzyl)-4-((3-fluoro-6-((5-methyl-1H-pyrazol-3-yl)amino)pyridin-2-yl)methyl)-2-methylpiperidine-4-carboxylic acid | $^1$H NMR (400 MHz, MeOD) δ 7.35-7.17 (m, 3H), 7.14 (s, 1H), 6.65 (d, J = 9.0 Hz, 1H), 5.69 (s, 1H), 4.36 (d, J = 13.5 Hz, 1H), 3.82 (d, J = 13.2 Hz, 1H), 3.22 (s, 1H), 3.18-3.06 (m, 2H), 2.97 (s, 1H), 2.83 (t, J = 11.2 Hz, 1H), 2.12 (s, 3H), 1.89 (dd, J = 35.3, 16.3 Hz, 4H), 1.29 (d, J = 5.5 Hz, 3H). MS: 474 (M + H)⁺ |
| 16. | 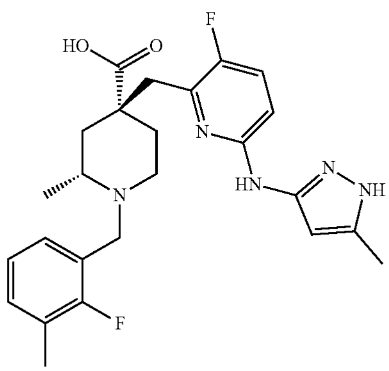 [SMILES: Cc1cc(Nc2ccc(F)c(C[C@@]3(C(=O)O)CCN(Cc4cccc(C)c4F)[C@H](C)C3)n2)n[nH]1] | (2R,4R)-1-(2-fluoro-3-methylbenzyl)-4-((3-fluoro-6-((5-methyl-1H-pyrazol-3-yl)amino)pyridin-2-yl)methyl)-2-methylpiperidine-4-carboxylic acid | 1H NMR (400 MHz, MeOD) δ 7.37 (d, J = 6.8 Hz, 3H), 7.17 (t, J = 7.2 Hz, 1H), 6.79 (d, J = 7.7 Hz, 1H), 5.82 (s, 1H), 4.58 (d, J = 12.8 Hz, 1H), 4.09 (d, J = 13.5 Hz, 1H), 3.60 (s, 1H), 3.30 - 3.10 (m, 4H), 2.34 (s, 3H), 2.24 (s, 3H), 2.09 (dd, J = 39.6, 20.0 Hz, 4H), 1.49 (d, J = 5.7 Hz, 3H). MS: 470 (M + H)⁺ |
| 17. | 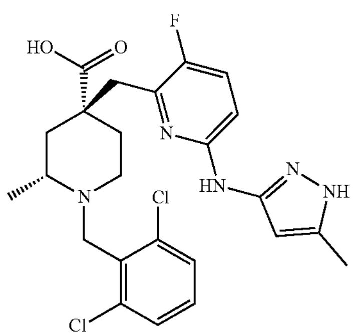 | (2R,4R)-1-(2,6-dichlorobenzyl)-4-((3-fluoro-6-((5-methyl-1H-pyrazol-3-yl)amino)pyridin-2-yl)methyl)-2-methylpiperidine-4-carboxylic acid | $^1$H NMR (400 MHz, MeOD) δ 7.51 (d, J = 8.0 Hz, 2H), 7.42 (dd, J = 17.7, 9.9 Hz, 2H), 6.78 (d, J = 7.3 Hz, 1H), 5.85 (d, J = 34.4 Hz, 1H), 4.63 (d, J = 13.1 Hz, 1H), 4.19 (d, J = 13.0 Hz, 1H), 3.47 (s, 1H), 3.29 (s, 2H), 3.07 (s, 2H), 2.23 (s, 3H), 2.05 (s, 3H), 1.87 (d, J = 13.8 Hz, 1H), 1.49 (t, J = 12.1 Hz, 3H). MS: 506 (M + H)⁺ |
| 18. | 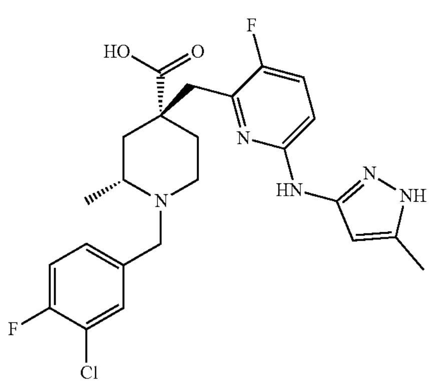 [SMILES: Cc1cc(Nc2ccc(F)c(C[C@@]3(C(=O)O)CCN(Cc4ccc(F)c(Cl)c4)[C@H](C)C3)n2)n[nH]1] | (2R,4R)-1-(3-chloro-4-fluorobenzyl)-4-((3-fluoro-6-((5-methyl-1H-pyrazol-3-yl)amino)pyridin-2-yl)methyl)-2-methylpiperidine-4-carboxylic acid | $^1$H NMR (400 MHz, MeOD) δ 7.64 (d, J = 6.3 Hz, 1H), 7.44 (s, 1H), 7.32 (dd, J = 17.4, 8.6 Hz, 2H), 6.78 (d, J = 8.1 Hz, 1H), 5.80 (s, 1H), 4.48 (d, J = 13.3 Hz, 1H), 3.85 (d, J = 12.2 Hz, 1H), 3.46-3.35 (m, 1H), 3.24 (t, J = 13.1 Hz, 2H), 3.07 (s, 1H), 2.96 (s, 1H), 2.23 (s, 3H), 2.01 (d, J = 46.3 Hz, 4H), 1.41 (d, J = 5.1 Hz, 3H). MS: 490 (M + H)⁺ |

TABLE 1-continued

| Example No. | Structure | Chemical Name | ¹HNMR & MS: (M + H)⁺ |
|---|---|---|---|
| 19. | 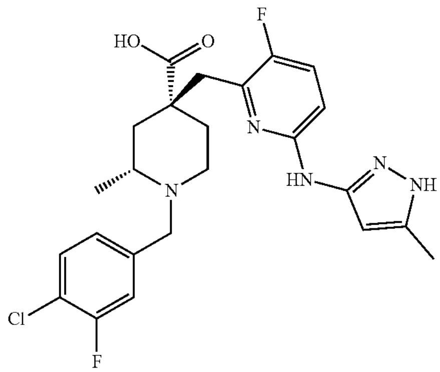 [SMILES: Cc1cc(Nc2ccc(F)c(C[C@@]3(C(=O)O)CCN(Cc4ccc(Cl)c(F)c4)[C@H](C)C3)n2)n[nH]1] | (2R,4R)-1-(4-chloro-3-fluorobenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.83 (s, 1H), 7.75 (t, J = 7.1 Hz, 2H), 7.65 (t, J = 7.4 Hz, 1H), 7.36 (s, 1H), 6.77 (d, J = 8.1 Hz, 1H), 5.80 (s, 1H), 4.59 (d, J = 13.1 Hz, 1H), 3.95 (d, J = 12.7 Hz, 1H), 3.39 (d, J = 22.0 Hz, 1H), 3.25 (t, J = 14.0 Hz, 2H), 3.01 (d, J = 27.8 Hz, 2H), 2.22 (s, 3H), 2.00 (d, J = 53.4 Hz, 4H), 1.51-1.35 (m, 3H). MS: 490 (M + H)⁺ |
| 20. | 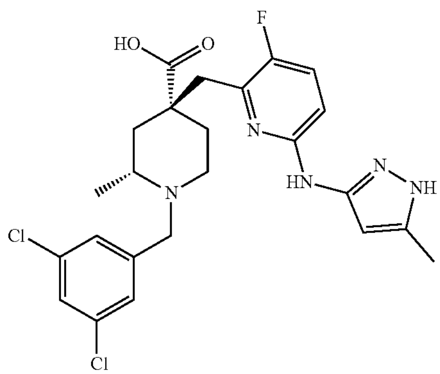 [SMILES: Cc1cc(Nc2ccc(F)c(C[C@@]3(C(=O)O)CCN(Cc4cc(Cl)cc(Cl)c4)[C@H](C)C3)n2)n[nH]1] | (2R,4R)-1-(3,5-dichlorobenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.47 (d, J = 5.6 Hz, 3H), 7.42-7.22 (m, 1H), 6.83-6.70 (m, 1H), 5.80 (s, 1H), 4.40 (d, J = 13.5 Hz, 1H), 3.69 (d, J = 13.3 Hz, 1H), 3.30-3.14 (m, 3H), 2.96 (s, 1H), 2.85 (t, J = 11.0 Hz, 1H), 2.24 (s, 3H), 1.95 (dd, J = 39.8, 15.4 Hz, 4H), 1.33 (t, J = 8.2 Hz, 3H). MS: 506 (M + H)⁺ |
| 21. | 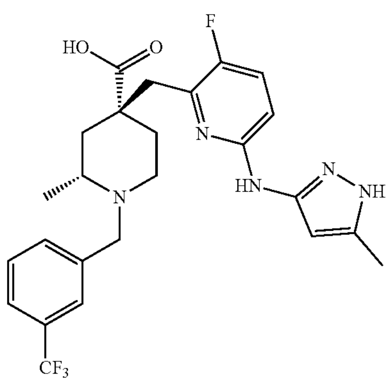 [SMILES: Cc1cc(Nc2ccc(F)c(C[C@@]3(C(=O)O)CCN(Cc4cccc(C(F)(F)F)c4)[C@H](C)C3)n2)n[nH]1] | (2R,4R)-4-((3-fluoro-6-((5-methyl-1H-pyrazol-3-yl)amino)pyridin-2-yl)methyl)-2-methyl-1-(3-(trifluoromethyl)benzyl)piperidine-4-carboxylic acid | ¹H NMR (400 MHz, MeOD) δ 7.83 (s, 1H), 7.75 (t, J = 7.1 Hz, 2H), 7.65 (t, J = 7.4 Hz, 1H), 7.36 (s, 1H), 6.77 (d, J = 8.1 Hz, 1H), 5.80 (s, 1H), 4.59 (d, J = 13.1 Hz, 1H), 3.95 (d, J = 12.7 Hz, 1H), 3.39 (d, J = 22.0 Hz, 1H), 3.25 (t, J = 14.0 Hz, 2H), 3.01 (d, J = 27.8 Hz, 2H), 2.22 (s, 3H), 2.00 (d, J = 53.4 Hz, 4H), 1.51-1.35 (m, 3H). MS: 506 (M + H)⁺ |
| 22. | 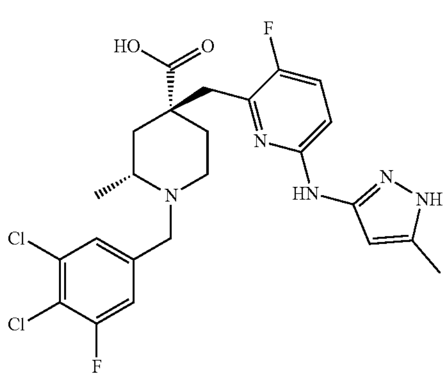 [SMILES: Cc1cc(Nc2ccc(F)c(C[C@@]3(C(=O)O)CCN(Cc4cc(F)c(Cl)c(Cl)c4)[C@H](C)C3)n2)n[nH]1] | (2R,4R)-1-(3,4-dichloro-5-fluorobenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.53 (s, 1H), 7.39 (s, 2H), 6.78 (s, 1H), 5.79 (s, 1H), 4.37 (s, 1H), 3.69 (s, 1H), 3.21 (d, J = 51.7 Hz, 3H), 2.84 (s, 2H), 2.23 (s, 3H), 2.02 (s, 4H), 1.33 (s, 3H). MS: 524 (M + H)⁺ |

TABLE 1-continued

| Example No. | Structure | Chemical Name | ¹HNMR & MS: (M + H)⁺ |
| --- | --- | --- | --- |
| 23. | 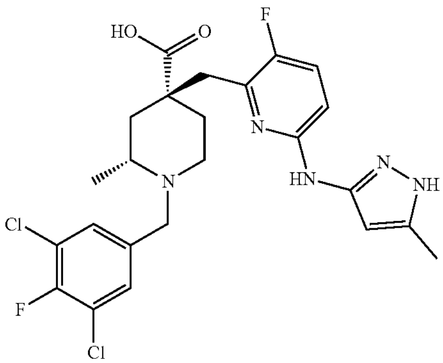 [SMILES: Cc1cc(Nc2ccc(F)c(C[C@@]3(C(=O)O)CCN(Cc4cc(Cl)c(F)c(Cl)c4)[C@H](C)C3)n2)n[nH]1] | (2R,4R)-1-(3,5-dichloro-4-fluorobenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.58 (s, 2H), 7.40 (s, 1H), 6.77 (s, 1H), 5.79 (s, 1H), 4.39 (s, 1H), 3.81-3.62 (m, 1H), 3.15 (s, 3H), 2.86 (s, 2H), 2.23 (s, 3H), 2.04 (s, 4H), 1.31 (s, 3H). MS: 524 (M + H)⁺ |
| 24. | 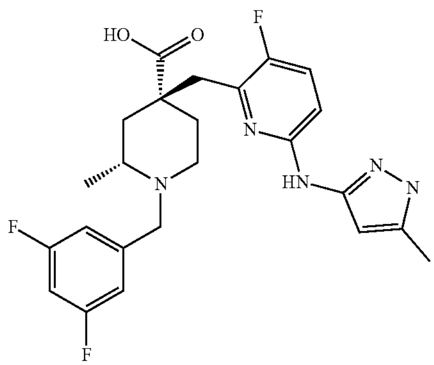 [SMILES: Cc1cc(Nc2ccc(F)c(C[C@@]3(C(=O)O)CCN(Cc4cc(F)cc(F)c4)[C@H](C)C3)n2)n[nH]1] | (2R,4R)-1-(3,5-difluorobenzyl)-4-((3-fluoro-6-((5-methyl-1H-pyrazol-3-yl)amino)pyridin-2-yl)methyl)-2-methylpiperidine-4-carboxylic acid | ¹H-NMR (400 MHz, MeOD) δ 7.36 (s, 1H), 7.12 (d, J = 5.7 Hz, 2H), 7.00 (s, 1H), 6.77 (d, J = 7.7 Hz, 1H), 5.79 (s, 1H), 4.44 (d, J = 13.3 Hz, 1H), 3.78 (d, J = 13.3 Hz, 1H), 3.35 (d, J = 11.6 Hz, 1H), 3.23 (d, J = 11.2 Hz, 2H), 3.01 (s, 1H), 2.89 (s, 1H), 2.23 (s, 3H), 1.98 (d, J = 43.1 Hz, 4H), 1.36 (d, J = 4.4 Hz, 3H). MS: 474 (M + H)⁺ |
| 25. | 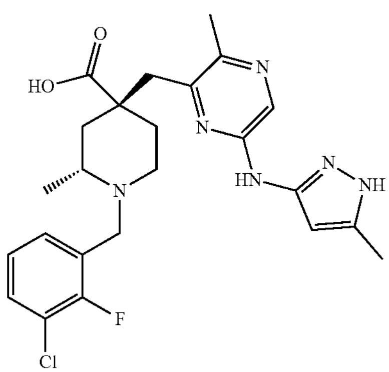 [SMILES: Cc1cc(Nc2cnc(C)c(C[C@@]3(C(=O)O)CCN(Cc4cccc(Cl)c4F)[C@H](C)C3)n2)n[nH]1] | (2R,4R)-1-(3-chloro-2-fluorobenzyl)-2-methyl-4-((3-methyl-6-((5-methyl-1H-pyrazol-3-yl)amino)pyrazin-2-yl)methyl)piperidine-4-carboxylic acid | ¹H-NMR (400 MHz, MeOD) δ 8.05 (s, 1H), 7.48 (dt, J = 14.3, 6.7 Hz, 2H), 7.22 (t, J = 7.8 Hz, 1H), 5.92 (s, 1H), 3.15 (m, 4H), 2.82 (s, 2H), 2.42 (s, 3H), 2.24 (s, 3H), 2.14 (d, J = 15.1 Hz, 1H), 2.03 (d, J = 14.8 Hz, 2H), 1.91 (m, 2H), 1.34 (d, J = 6.2 Hz, 3H). MS: 487 (M + H)⁺ |
| 26. | 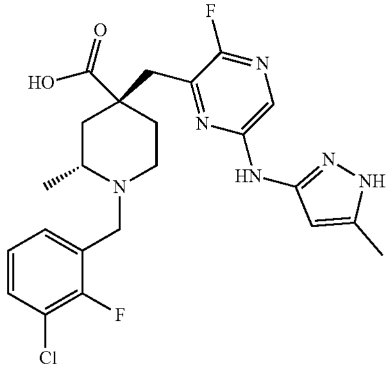 [SMILES: Cc1cc(Nc2cnc(F)c(C[C@@]3(C(=O)O)CCN(Cc4cccc(Cl)c4F)[C@H](C)C3)n2)n[nH]1] | (2R,4R)-1-(3-chloro-2-fluorobenzyl)-4-((5-fluoro-2-((5-methyl-1H-pyrazol-3-yl)amino)pyrimidin-4-yl)methyl)-2-methylpiperidine-4-carboxylic acid | MS: 491 (M + H)⁺ |

TABLE 1-continued

| Example No. | Structure | Chemical Name | ¹HNMR & MS: (M + H)⁺ |
|---|---|---|---|
| 27. | 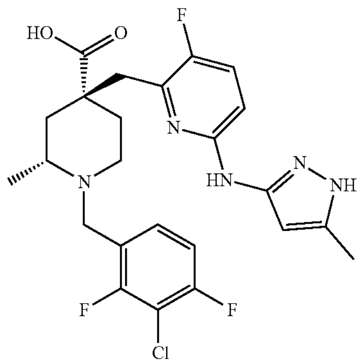 | (2R,4R)-1-(3-chloro-2,4-difluorobenzyl)-4-((3-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.50 (dd, J = 14.5, 7.9 Hz, 1H), 7.35 (s, 1H), 7.18 (t, J = 8.5 Hz, 1H), 6.75 (d, J = 7.6 Hz, 1H), 5.77 (s, 1H), 4.38 (d, J = 13.8 Hz, 1H), 3.81 (d, J = 13.6 Hz, 1H), 3.23 (s, 3H), 3.01 (s, 1H), 2.84 (t, J = 11.3 Hz, 1H), 2.21 (s, 3H), 2.10-1.77 (m, 4H), 1.35 (d, J = 5.8 Hz, 3H). MS: 508 (M + H)⁺ |
| 28. | 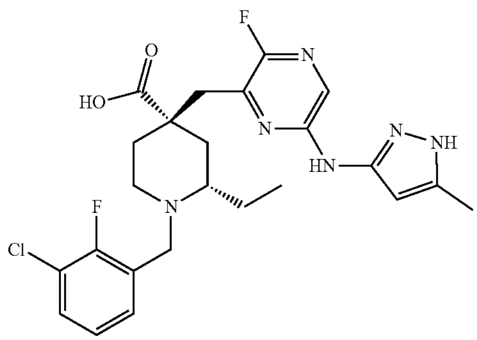 [SMILES: CC[C@H]1C[C@@](Cc2nc(Nc3cc(C)[nH]n3)cnc2F)(C(=O)O)CCN1Cc1cccc(Cl)c1F] | (2S,4S)-1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid | ¹H NMR (400 MHz, MeOD) δ 7.38 (ddt, J = 60.4, 51.4, 7.7 Hz, 4H), 6.75 (d, J = 6.5 Hz, 1H), 5.77 (s, 1H), 4.37 (d, J = 13.8 Hz, 1H), 3.84 (d, J = 13.7 Hz, 1H), 3.26-3.14 (m, 2H), 3.04 (s, 2H), 2.88 (t, J = 11.5 Hz, 1H), 2.21 (s, 3H), 2.11-1.78 (m, 5H), 1.72-1.48 (m, 1H), 1.04-0.81 (m, 3H). MS: 504 (M + H)⁺ |
| 29. | 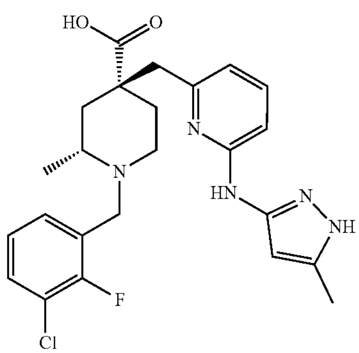 [SMILES: Cc1cc(Nc2cccc(C[C@@]3(C(=O)O)CCN(Cc4cccc(Cl)c4F)[C@H](C)C3)n2)n[nH]1] | (2R,4R)-1-(3-chloro-2-fluorobenzyl)-2-methyl-4-((6-((5-methyl-1H-pyrazol-3-yl)amino)pyridin-2-yl)methyl)piperidine-4-carboxylic acid | ¹H NMR (400 MHz, MeOD) δ 7.86 (t, J = 7.6 Hz, 1H), 7.68-7.53 (m, 2H), 7.24 (t, J = 7.2 Hz, 1H), 7.02 (d, J = 8.8 Hz, 1H), 6.96 (d, J = 5.6 Hz, 1H), 5.85 (s, 1H), 4.90-4.78 (m, 2H), 4.38 (d, J = 12.8 Hz, 1H), 3.99-3.87 (m, 1H), 3.51-3.40 (m, 2H), 3.29 (d, J = 11.6 Hz, 1H), 2.27 (s, 3H), 2.18-1.99 (m, 3H), 1.56 (s, 3H), 1.25-1.16 (m, 1H). MS: 472 (M + H)⁺ |
| 30. | 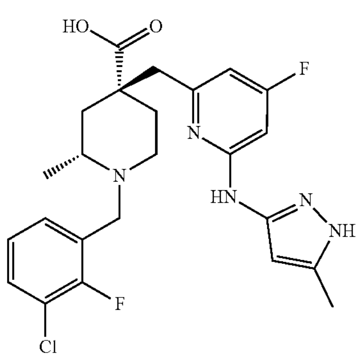 | (2R,4R)-1-(3-chloro-2-fluorobenzyl)-4-((4-fluoro-6-((5-methyl-1H-pyrazol-3-yl)amino)pyridin-2-yl)methyl)-2-methylpiperidine-4-carboxylic acid | ¹H-NMR (400 MHz, MeOD) δ 7.74-7.65 (m, 2H), 7.35 (t, J = 7.6 Hz, 1H), 6.90 (d, J = 9.6 Hz, 1H), 6.72 (d, J = 9.2 Hz, 1H), 6.03 (s, 1H), 4.46 (d, J = 12.4 Hz, 1H), 4.08-3.96 (m, 1H), 3.61-3.46 (m, 3H), 3.42-3.36 (m, 1H), 2.41 (s, 3H), 2.28-1.99 (m, 4H), 1.61 (s, 3H), 1.35-1.26 (m, 1H). MS: 409 (M + H)⁺ |

TABLE 1-continued

| Example No. | Structure | Chemical Name | ¹HNMR & MS: (M + H)⁺ |
|---|---|---|---|
| 31. | 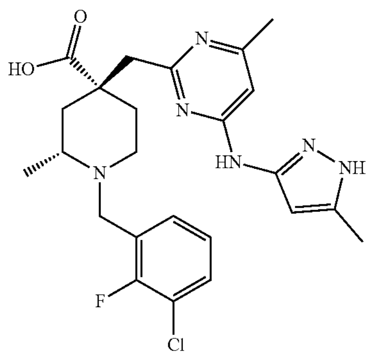 | (2R,4R)-1-(3-chloro-2-fluorobenzyl)-2-methyl-4-((4-methyl-6-((5-methyl-1H-pyrazol-3-yl)amino)pyrimidin-2-yl)methyl)piperidine-4-carboxylic acid | MS: 409 (M + H)⁺ |
| 32. | 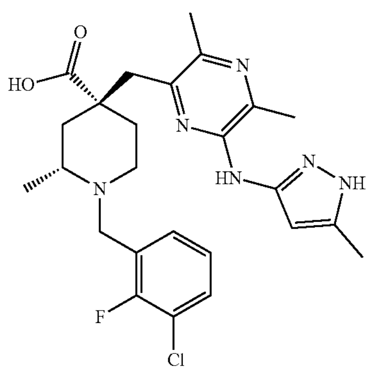 | (2R,4R)-1-(3-chloro-2-fluorobenzyl)-4-((3,5-dimethyl-6-((5-methyl-1H-pyrazol-3-yl)amino)pyrazin-2-yl)methyl)-2-methylpiperidine-4-carboxylic acid | ¹H-NMR (400 MHz, MeOD) δ 7.75-7.64 (m, 2H), 7.35 (t, 1H), 6.48 (s, 1H), 4.52 (d, J = 13.3 Hz, 1H), 4.13 (s, 1H), 3.79 (d, J = 16.2 Hz, 1H), 3.72-3.48 (m, 2H), 3.41 (m, 2H), 2.79 (s, 3H), 2.73 (s, 3H), 2.50 (s, 3H), 2.40-2.17 (m, 4H), 1.57 (d, J = 5.6 Hz, 3H). MS: 501(M + H)⁺ |
| 33. | 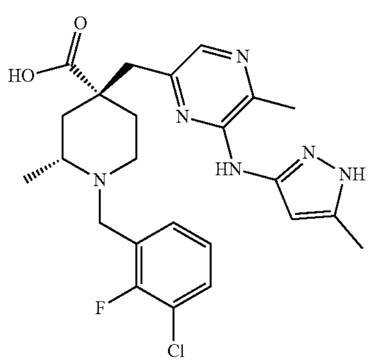 | (2R,4R)-1-(3-chloro-2-fluorobenzyl)-2-methyl-4-((5-methyl-6-((5-methyl-1H-pyrazol-3-yl)amino)pyrazin-2-yl)methyl)piperidine-4-carboxylic acid | 1H NMR (400 MHz, DMSO) δ 7.76 (t, J = 7.4 Hz, 1H), 7.64-7.57 (m, 2H), 7.37 (t, J = 7.8 Hz, 1H), , 6.33 (s, 1H), 4.85 (d, J = 12.6 Hz, 1H), 4.33 (d, J = 13.5 Hz, 2H), 3.89 (s, 1H), 3.44-3.40 (s, 1H), 3.08-3.10 (dd, J = 31.8, 13.6 Hz, 2H), 2.42 (s, 3H), 2.23 (s, 3H), 2.09-2.08 (d, J = 14.8 Hz, 1H), 1.99 (t, J = 7.3 Hz, 1H), 1.87-1.85 (t, J = 13.2 Hz, 2H), 1.42 (d, J = 6.0 Hz, 3H), 1.27 (d, J = 22.2 Hz, 1H). MS: 487(M + H)⁺ |
| 34. | 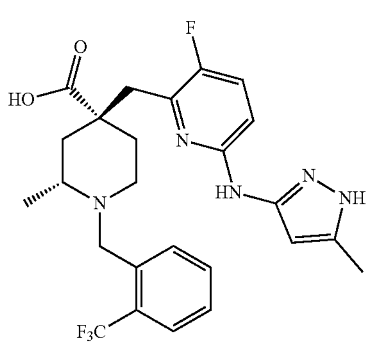 | (2R,4R)-4-((3-fluoro-6-((5-methyl-1H-pyrazol-3-yl)amino)pyridin-2-yl)methyl)-2-methyl-1-(2-(trifluoromethyl)benzyl)piperidine-4-carboxylic acid | ¹H NMR (400 MHz, DMSO) δ 9.15 (s, 1H), 8.97 (s, 1H), 7.79 (d, J = 64.3 Hz, 4H), 7.43 (t, J = 9.0 Hz, 1H), 6.96 (s, 1H), 6.11 (s, 1H), 4.06 (s, 2H), 3.38-3.33 (m, 1H), 3.22 (s, 2H), 3.04-3.15 (m, 2H), 2.34-2.20 (m, 2H), 2.14 (s, 3H), 1.96 (d, J = 14.0 Hz, 2H), 1.44 (s, 3H). MS: 506(M + H)⁺ |

TABLE 1-continued

| Example No. | Structure | Chemical Name | ¹HNMR & MS: (M + H)⁺ |
|---|---|---|---|
| 35. | 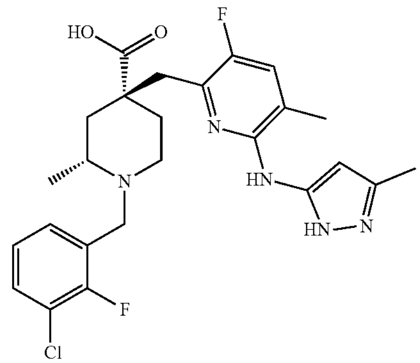 [SMILES: Cc1cc(Nc2nc(C[C@@]3(C(=O)O)CCN(Cc4cccc(Cl)c4F)[C@H](C)C3)c(F)cc2C)[nH]n1] | (2R,4R)-1-(3-chloro-2-fluorobenzyl)-4-((3-fluoro-5-methyl-6-((3-methyl-1H-pyrazol-5-yl)amino)pyridin-2-yl)methyl)-2-methylpiperidine-4-carboxylic acid | ¹H NMR (400 MHz, MeOD) δ 7.71-7.65 (m, 2H), 7.58 (d, J = 9.6 Hz, 1H), 7.36 (t, J = 7.8 Hz, 1H), 6.20 (s, 1H), 4.45 (d, J = 13.2 Hz, 1H), 4.02-3.93 (m, 1H), 3.58-3.35 (m, 4H), 3.32-3.25 (m, 2H), 2.44 (s, 3H), 2.38 (s, 3H), 2.26-2.11 (m, 2H), 2.11-2.01 (m, 1H), 1.63 (s, 3H). MS: 504(M + H)⁺ |
| 36. | 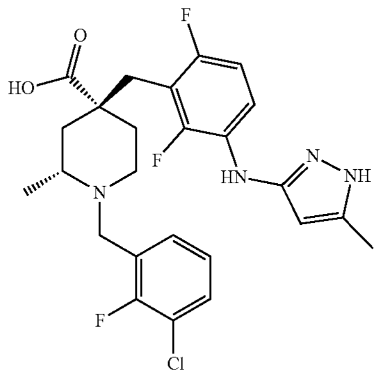 | (2R,4R)-1-(3-chloro-2-fluorobenzyl)-4-(2,6-difluoro-3-((5-methyl-1H-pyrazol-3-yl)amino)benzyl)-2-methylpiperidine-4-carboxylic acid | 1H NMR (400 MHz, DMSO) δ 7.94 (d, J = 8.6 Hz, 2H), 7.76 (dd, J = 15.3, 7.6 Hz, 1H), 7.59 (t, J = 7.0 Hz, 1H), 7.44-7.25 (m, 1H), 6.90 (t, J = 9.3 Hz, 1H), 4.82 (d, J = 13.2 Hz, 1H), 4.38 (dd, J = 23.0, 12.8 Hz, 2H), 3.85 (s, 1H), 3.41 (s, 1H), 3.21 (d, J = 12.3 Hz, 1H), 3.15 (s, 1H), 2.92 (d, J = 20.5 Hz, 1H), 2.17 (s, 3H), 2.10-2.07(m, 1H)1.92-1.82 (m, 2H), 1.51 (d, J = 6.0 Hz, 3H), 1.33 (d, J = 6.4 Hz, 1H). MS: 507(M + H)⁺ |

Example 37

(2R,4R)-4-((3-fluoro-6-((5-methyl-1H-pyrazol-3-yl)amino)pyridin-2-yl)methyl)-2-methyl-1-(2-(trifluoromethyl)benzoyl)piperidine-4-carboxylic acid Step 1: methyl (2R,4R)-4-((6-bromo-3-fluoropyridin-2-yl)methyl)-2-methylpiperidine-4-carboxylate trifluoroacetate

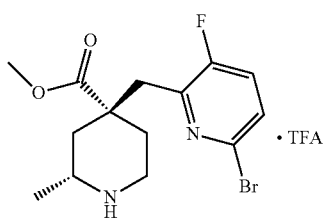 [SMILES: COC(=O)[C@]1(Cc2nc(Br)ccc2F)CCN[C@H](C)C1]

To a solution of INT C5 (310 mg, 0.898 mmol) in DCM (4 ml) was added trifluoroacetic acid (2 mL). The resulting solution was stirred for 1 h at room temperature. The resulting solution was removed under reduced pressure to afford methyl-(2R,4R)-4-((6-bromo-3-fluoropyridin-2-yl)methyl)-2-methyl-1-(2-(trifluoromethyl)benzoyl)piperidine-4-carboxylate hydrochloride (310 mg) as a yellow oil. LCMS (ESI, m/z): 517 [M+H]⁺.

Step 2: methyl-(2R,4R)-4-((6-bromo-3-fluoropyridin-2-yl)methyl)-2-methyl-1-(2-(trifluoromethyl)benzoyl)piperidine-4-carboxylate

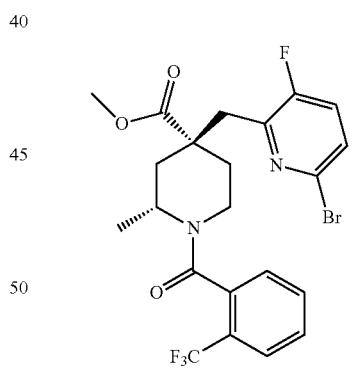

To a solution of methyl (2R,4R)-4-((6-bromo-3-fluoropyridin-2-yl)methyl)-2-methyl piperidine-4-carboxylate trifluoroacetat (310 mg, 0.898 mmol) in DMF (10 ml) was added 2-(trifluoromethyl)benzoic acid (255 mg, 1.341 mmol), DIEA (698 mg, 6.911 mmol) and HATU (689 mg, 1.812 mmol). The resulting solution was stirred for 3 h at room temperature. The resulting mixture was filtrated. The filtrate was removed under reduced pressure. The resulting residue was purified by C18 reversed phase column chromatography eluting with H₂O/ACN to afford methyl-(2R,4R)-4-((6-bromo-3-fluoropyridin-2-yl)methyl)-2-methyl-1-(2-(trifluoromethyl) benzoyl)piperidine-4-carboxylate (451 mg, Y=97%) as a yellow oil. LCMS (ESI, m/z): 517 [M+H]⁺.

Step 3: methyl-(2R,4R)-4-((6-((1-(tert-butoxycarbonyl)-5-methyl-1H-pyrazol-3-yl)amino)-3-fluoropyridin-2-yl)methyl)-2-methyl-1-(2-(trifluoromethyl)benzoyl)piperidine-4-carboxylate

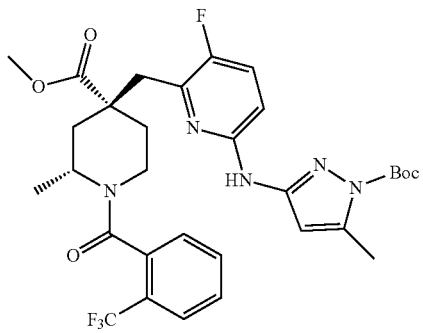 [SMILES: COC(=O)[C@]1(Cc2nc(Nc3cc(C)n(C(=O)OC(C)(C)C)n3)ccc2F)CCN(C(=O)c2ccccc2C(F)(F)F)[C@H](C)C1]

Following the procedure analogous to that described in Step 3 for the synthesis of Example 1, methyl 1-(2R,4R)-4-((6-bromo-3-fluoropyridin-2-yl)methyl)-2-methyl-1-(2-(trifluoromethyl) benzoyl)piperidine-4-carboxylate (451 mg, 0.872 mmol) was converted to the title compound (450 mg) as a yellow oil. LCMS (ESI, m/z): 634 [M+H]+.

Step 4: methyl-(2R,4R)-4-((3-fluoro-6-((5-methyl-1H-pyrazol-3-yl)amino)pyridin-2-yl) methyl)-2-methyl-1-(2-(trifluoromethyl)benzoyl)piperidine-4-carboxylate

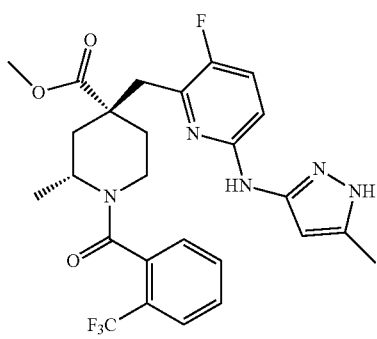

Following the procedure analogous to that described in Step 4 for the synthesis of Example 1, methyl-(2R,4R)-4-((6-((1-(tert-butoxycarbonyl)-5-methyl-1H-pyrazol-3-yl)amino)-3-fluoropyridin-2-yl)methyl)-2-methyl-1-(2-(trifluoromethyl)-benzoyl)piperidine-4-carboxylate (450 mg, 0.699 mmol) was converted to the title compound (391 mg) as a yellow oil. LCMS (ESI, m/z): 534 [M+H]+.

Step 5: (2R,4R)-4-((3-fluoro-6-((5-methyl-1H-pyrazol-3-yl)amino)pyridin-2-yl)methyl)-2-methyl-1-(2-(trifluoromethyl)benzoyl)piperidine-4-carboxylic acid

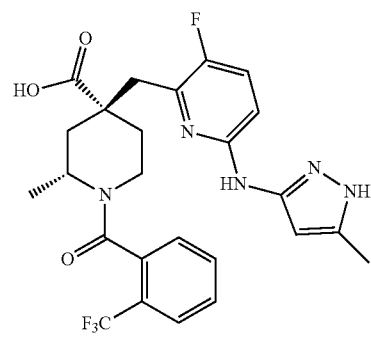

Following the procedure analogous to that described in Step 5 for the synthesis of Example 1, methyl-(2R,4R)-4-((3-fluoro-6-((5-methyl-1H-pyrazol-3-yl)amino)-pyridin-2-yl)methyl)-2-methyl-1-(2-(trifluoromethyl)benzoyl)piperidine-4-carboxylate (191 mg, 0.367 mmol) was converted to the title compound 11 mg as a white solid. LCMS (ESI, m/z): 520 [M+H]+. 1H NMR (400 MHz, MeOD) δ 7.89-7.26 (m, 5H), 6.89 (dd, J=15.6, 6.3 Hz, 1H), 6.07-5.91 (m, 1H), 3.75-3.34 (m, 2H), 3.25-2.94 (m, 3H), 2.57-2.26 (m, 4H), 2.16-1.77 (m, 2H), 1.52 (dd, J=27.1, 13.7 Hz, 1H), 1.24 (ddd, J=31.3, 22.2, 7.1 Hz, 3H).

The following examples in Table 2 were synthesized using the above procedure with the corresponding starting materials and intermediates.

TABLE 2

| Example No. | Structure | Chemical Name | 1HNMR & MS: (M + H)+ |
|---|---|---|---|
| 38 | 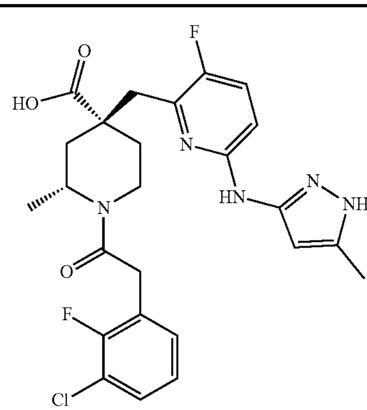 | (2R,4R)-1-(2-(3-chloro-2-fluorophenyl)acetyl)-4-((3-fluoro-6-((5-methyl-1H-pyrazol-3-yl)amino)pyridin-2-yl)methyl)-2-methyl-piperidine-4-carboxylic acid | 1H NMR (400 MHz, MeOD) δ 7.25 (t, J = 7.6 Hz, 2H), 7.07 (s, 1H), 6.99 (t, J = 7.7 Hz, 1H), 6.67 (s, 1H), 5.65 (s, 1H), 4.25 (s, 1H), 3.66 (dd, J = 34.5. 19.0 Hz, 4H), 2.86 (dd, J = 25.6, 8.9 Hz, 2H), 2.71 (s, 3H), 2.06 (dd, J = 34.9, 27.2 Hz, 4H), 1.19 (s, 3H). MS: 518 (M + H)+ |

Example 39

(2R,4R)-4-((3-fluoro-6-((5-methyl-1H-pyrazol-3-yl)amino)pyridin-2-yl)methyl)-2-methyl-1-(2-(trifluoromethyl)benzoyl)piperidine-4-carboxylic acid

Step 1: methyl (2R,4R)-4-((6-bromo-3-fluoropyridin-2-yl)methyl)-2-methylpiperidine-4-carboxylate trifluoroacetate

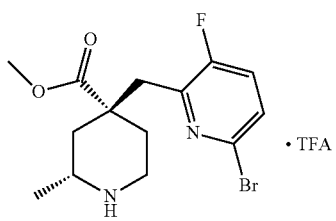 [SMILES: COC(=O)[C@]1(Cc2nc(Br)ccc2F)CCN[C@H](C)C1]

Following the procedure analogous to that described in Step 1 for the synthesis of Example 37, INT C5 (1.54 g, 3.458 mmol) was converted to the title compound (1.33 g) as a yellow oil. LCMS (ESI, m/z): 345, 347 [M+H]$^+$.

Step 2: methyl (2R,4R)-4-((6-bromo-3-fluoropyridin-2-yl)methyl)-2-methyl-1-((2-(trifluoromethyl)phenyl)sulfonyl)piperidine-4-carboxylate

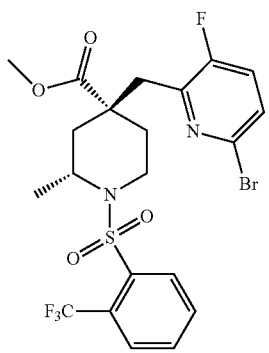 [SMILES: COC(=O)[C@]1(Cc2nc(Br)ccc2F)CCN(S(=O)(=O)c2ccccc2C(F)(F)F)[C@H](C)C1]

To a solution of methyl (2R,4R)-4-((6-bromo-3-fluoropyridin-2-yl)methyl)-2-methyl piperidine-4-carboxylate trifluoroacetate (1.33 g, 3.853 mmol) and K$_2$CO$_3$ (1.62 g, 11.721 mmol) in THF (15 ml) was added 2-(trifluoromethyl)benzenesulfonyl chloride (1.42 g, 5.805 mmol). The resulting solution was stirred for 3 h at 60° C. The resulting mixture was filtrated and the filtrate was removed under reduced pressure. The resulting residue was purified by C18 reversed phase column chromatography eluting with H$_2$O/ACN to afford methyl (2R,4R)-4-((6-bromo-3-fluoropyridin-2-yl)methyl)-2-methyl-1-((2-(trifluoro-methyl)phenyl)sulfonyl)piperidine-4-carboxylate (1.07 g) as a yellow oil. LCMS (ESI, m/z): 553,555 [M+H]$^+$.

Step 3: methyl (2R,4R)-4-((6-((1-(tert-butoxycarbonyl)-5-methyl-1H-pyrazol-3-yl)amino)-3-fluoropyridin-2-yl)methyl)-2-methyl-1-((2-(trifluoromethyl)phenyl)sulfonyl)piperidine-4-carboxylate

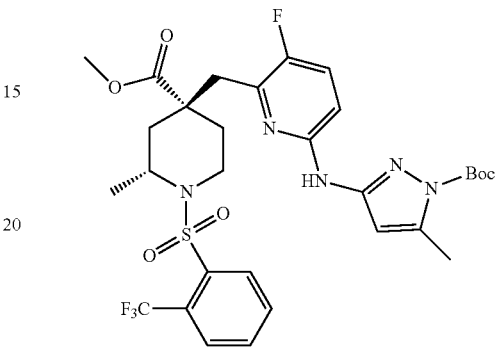

Following the procedure analogous to that described in Step 3 for the synthesis of Example 1, methyl (2R,4R)-4-((6-bromo-3-fluoropyridin-2-yl)methyl)-2-methyl-1-((2-(trifluoromethyl) phenyl)sulfonyl)piperidine-4-carboxylate (1.07 g, 1.927 mmol) was converted to the title compound (2.56 g) as a yellow oil. LCMS (ESI, m/z): 670 [M+H]$^+$.

Step 4: methyl (2R,4R)-4-((3-fluoro-6-((5-methyl-1H-pyrazol-3-yl)amino)pyridin-2-yl)methyl)-2-methyl-1-((2-(trifluoromethyl)phenyl)sulfonyl)piperidine-4-carboxylate

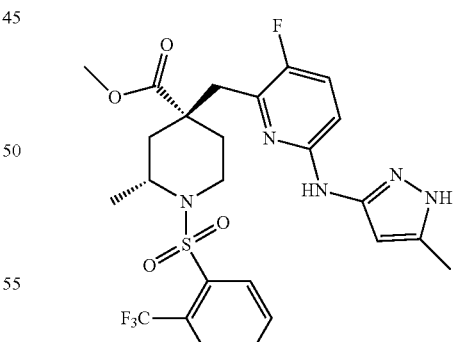

Following the procedure analogous to that described in Step 4 for the synthesis of Example 1, methyl(2R,4R)-4-((6-((1-(tert-butoxycarbonyl)-5-methyl-1H-pyrazol-3-yl)amino)-3-fluoropyridin-2-yl)methyl)-2-methyl-1-((2-(trifluoromethyl)phenyl)sulfonyl)piperidine-4-carboxylate (2.51 g, 3.746 mmol) was converted to the title compound (812 mg) as a yellow oil. LCMS (ESI, m/z): 570 [M+H]$^+$.

Step 5: (2R,4R)-4-((3-fluoro-6-((5-methyl-1H-pyrazol-3-yl)amino)pyridin-2-yl) methyl)-2-methyl-1-((2-(trifluoromethyl)phenyl)sulfonyl)piperidine-4-carboxylic acid

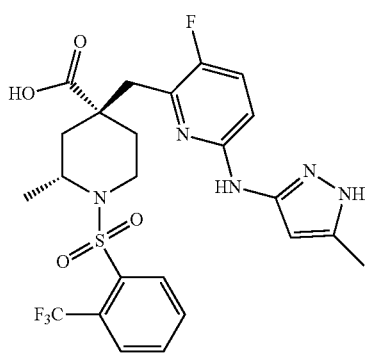

Following the procedure analogous to that described in Step 5 for the synthesis of Example 1, methyl (2R,4R)-4-((3-fluoro-6-((5-methyl-1H-pyrazol-3-yl)amino)-pyridin-2-yl)methyl)-2-methyl-1-((2-(trifluoromethyl)phenyl)sulfonyl)piperidine-4-carboxylate (812 mg, 1.425 mmol) was converted to the title compound 215 mg as a white solid. LCMS (ESI, m/z): 556 [M+H]+. $^1$H NMR (400 MHz, MeOD) δ 8.22 (dd, J=5.6, 3.6 Hz, 1H), 7.95 (dd, J=5.6, 3.6 Hz, 1H), 7.85-7.77 (m, 2H), 7.59 (t, J=8.9 Hz, 1H), 6.88 (dd, J=9.0, 3.1 Hz, 1H), 6.01 (d, J=0.4 Hz, 1H), 4.35-4.20 (m, 1H), 3.69-3.58 (m, 1H), 3.47-3.35 (m, 1H), 3.15 (dd, J=13.7, 2.8 Hz, 1H), 2.99 (dd, J=13.7, 2.4 Hz, 1H), 2.41 (s, 3H), 2.37 (s, 1H), 2.21-2.10 (m, 1H), 1.90 (dd, J=13.9, 5.7 Hz, 1H), 1.54-1.41 (m, 1H), 1.14 (d, J=7.2 Hz, 3H).

Example 40 & Example 41

(2R,4R)-1-((S)-1-(3-chloro-2-fluorophenyl)ethyl)-4-((3-fluoro-6-((5-methyl-1H-pyrazol-3-yl)amino)pyridin-2-yl)methyl)-2-methylpiperidine-4-carboxylic acid Example 40

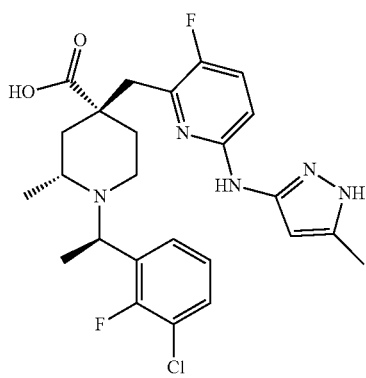

Example 41

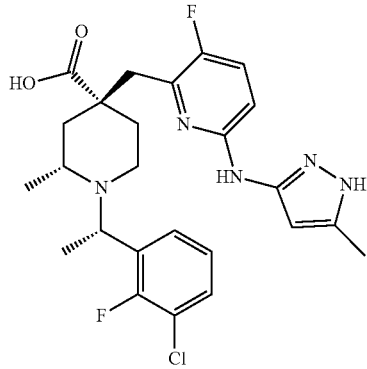

Step 1: 1-(3-chloro-2-fluorophenyl)ethan-1-ol

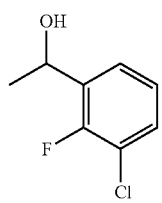

To a solution of 1-(3-chloro-2-fluorophenyl)ethan-1-one (2.69 g, 15.587 mmol) in methanol (20 mL) was added sodium borohydride (1.24 g, 32.778 mmol) at 0° C. The resulting solution was stirred at 0° C. for 1 h before it is quenched with 1 N HCl aqueous solution (50 mL). The resulting solution was diluted with water and extracted with ethyl acetate. The organic layer was dried over anhydrous sodium sulfate and concentrated under reduced pressure. The resulting residue was applied onto a silica gel column eluting with EtOAc/hexane (0~20%) to afford 2.57 g of the title compound as a yellow oil.

Step 2: 1-(1-bromoethyl)-3-chloro-2-fluorobenzene

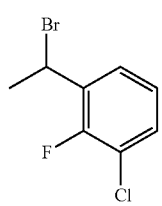

A solution of 1-(3-chloro-2-fluorophenyl)ethan-1-ol (2.57 g, 14.719 mmol), phosphorus tribromide (4.03 g, 14.888 mmol) and 4-dimethylaminopyridine (120 mg, 0.982 mmol) in DCM (20 mL) was stirred for 1 h at room temperature. The resulting solution was concentrated under reduced pressure. The resulting residue was applied onto a silica gel column eluting with EtOAc/hexane (0~10%) to afford 2.12 g of the title compound as colorless oil.

Step 3: methyl (2R,4R)-4-((6-bromo-3-fluoropyridin-2-yl)methyl)-2-methylpiperidine-4-carboxylate hydrochloride

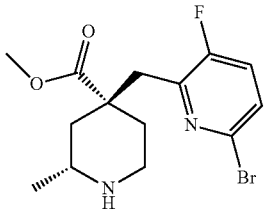 [SMILES: COC(=O)[C@]1(Cc2nc(Br)ccc2F)CCN[C@H](C)C1]

Following the procedure analogous to that described in Step 1 for the synthesis of Example 37, INT C5 (2.10 g, 4.719 mmol) was converted to the title compound (1.75 g) as a yellow oil. LCMS (ESI, m/z): 345, 347 [M+H]+.

Step 4: methyl-(2R,4R)-4-((6-bromo-3-fluoropyridin-2-yl)methyl)-1-(−1-(3-chloro-2-fluo-rophenyl)ethyl)-2-methylpiperidine-4-carboxylate

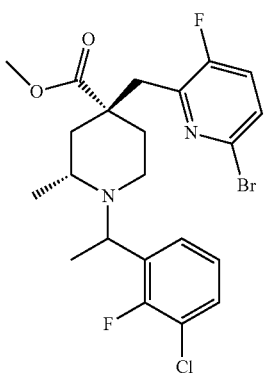 [SMILES: COC(=O)[C@]1(Cc2nc(Br)ccc2F)CCN(C(C)c2cccc(Cl)c2F)[C@H](C)C1]

Following the procedure analogous to that described in Step 1 for the synthesis of Example 1, methyl (2R,4R)-4-((6-bromo-3-fluoropyridin-2-yl)methyl)-2-methylpiperidine-4-carboxylate (1.03 g, 2.984 mmol) was converted to the title compound (756 mg, Y=51%) as a yellow oil. LCMS (ESI, m/z): 501, 503 [M+1]+.

Step 5: methyl-(2R,4R)-4-((6-((1-(tert-butoxycarbonyl)-5-methyl-1H-pyrazol-3-yl)amino)-3-fluoropyridin-2-yl)methyl)-1-(−1-(3-chloro-2-fluorophenyl)ethyl)-2-methylpiperidine-4-carboxylate

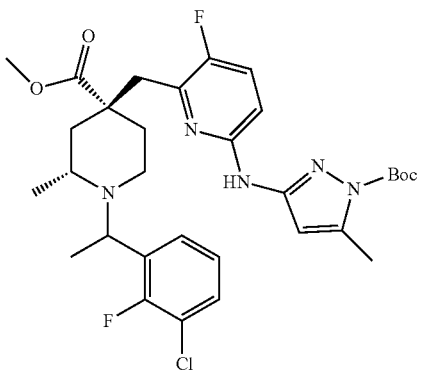 [SMILES: COC(=O)[C@]1(Cc2nc(Nc3cc(C)n(C(=O)OC(C)(C)C)n3)ccc2F)CCN(C(C)c2cccc(Cl)c2F)[C@H](C)C1]

Following the procedure analogous to that described in Step 3 for the synthesis of Example 1, methyl-(2R,4R)-4-((6-bromo-3-fluoropyridin-2-yl)methyl)-1-(−1-(3-chloro-2-fluorophenyl)ethyl)-2-methylpiperidine-4-carboxylate (756 mg, 1.509 mmol) was converted to the title compound (953 mg) as a yellow oil. LCMS (ESI, m/z): 618 [M+H]+.

Step 6: methyl-(2R,4R)-1-(1-(3-chloro-2-fluorophenyl)ethyl)-4-((3-fluoro-6-((5-methyl-1H-pyrazol-3-yl)amino)pyridin-2-yl)methyl)-2-methylpiperidine-4-carboxylate

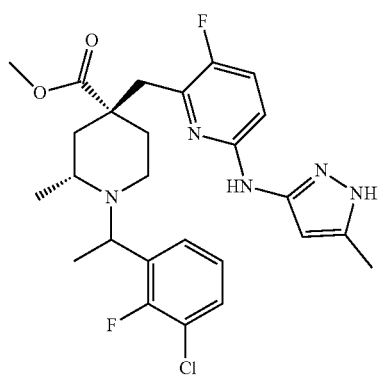

Following the procedure analogous to that described in Step 4 for the synthesis of Example 1, methyl-(2R,4R)-4-((6-((1-(tert-butoxycarbonyl)-5-methyl-1H-pyrazol-3-yl)amino)-3-fluoropyridin-2-yl)methyl)-1-(1-(3-chloro-2-fluorophenyl)ethyl)-2-methylpiperidine-4-carboxylate (953 mg, 1.542 mmol) was converted to the title compound (421 mg) as a yellow solid. LCMS (ESI, m/z): 518 [M+H]+.

Step 7: (2R,4R)-1-(1-(3-chloro-2-fluorophenyl)ethyl)-4-((3-fluoro-6-((5-methyl-1H-pyrazol-3-yl)amino)pyridin-2-yl)methyl)-2-methylpiperidine-4-carboxylic acid

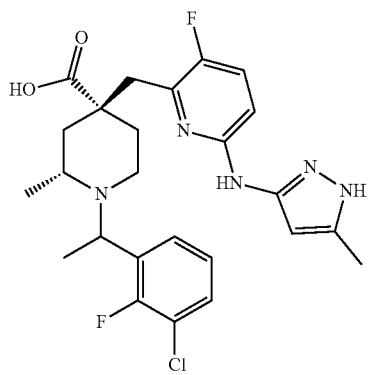

Following the procedure analogous to that described in Step 5 for the synthesis of Example 1, methyl-(2R,4R)-1-(−1-(3-chloro-2-fluorophenyl)ethyl)-4-((3-fluoro-6-((5-methyl-1H-pyrazol-3-yl)amino)pyridin-2-yl)methyl)-2-methylpiperidine-4-carboxylate (421 mg, 0.813 mmol) was converted to the title compound 224 mg as a white solid. LCMS (ESI, m/z): 504 [M+H]+.

(2R,4R)-1-(1-(3-chloro-2-fluorophenyl)ethyl)-4-((3-fluoro-6-((5-methyl-1H-pyrazol-3-yl) amino)pyridin-2-yl)methyl)-2-methylpiperidine-4-carboxylic acid was further purified by Prep-HPLC, yielding Example 40 (121 mg) and Example 41 (87 mg) as white solids.

Example 40

LCMS (ESI, m/z): 504 [M+H]⁺.
¹H NMR (400 MHz, MeOD) δ 7.85-7.53 (m, 3H), 7.37 (t, J=8.0 Hz, 1H), 6.91 (dd, J=8.9, 2.8 Hz, 1H), 6.03 (s, 1H), 3.92 (s, 1H), 3.64-3.42 (m, 2H), 3.40-3.33 (m, 3H), 2.40 (s, 3H), 2.19 (d, J=37.9 Hz, 4H), 1.80 (d, J=5.3 Hz, 3H), 1.59 (s, 3H).

Example 41

LCMS (ESI, m/z): 504 [M+H]⁺.
¹H NMR (400 MHz, MeOD) δ 7.70 (t, J=7.0 Hz, 2H), 7.57 (t, 1=8.8 Hz, 1H), 7.39 (t, J=7.9 Hz, 1H), 6.88 (dd, J=8.9, 2.6 Hz, 1H), 6.01 (s, 1H), 5.46 (s, 1H), 3.67 (d, J=35.9 Hz, 1H), 3.50 (s, 1H), 3.14 (dd, J=20.5, 12.4 Hz, 2H), 2.90 (s, 1H), 2.40 (s, 3H), 2.26 (d, J=14.5 Hz, 2H), 2.11 (d, J=25.2 Hz, 1H), 1.81 (s, 3H), 1.61 (s, 1H), 1.45-1.11 (m, 3H).

Example 42

(2R,4R)-1-(3-chloro-2-fluorophenethyl)-4-((3-fluoro-6-((5-methyl-1H-pyrazol-3-yl)amino)pyridin-2-yl)methyl)-2-methylpiperidine-4-carboxylic acid Step 1: 2-(3-chloro-2-fluorophenyl)ethan-1-ol

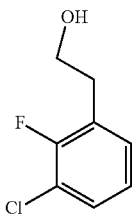 [SMILES: OCCc1cccc(Cl)c1F]

To a solution of 2-(3-chloro-2-fluorophenyl)acetic acid (510 mg, 2.704 mmol) in THF (5 mL) was added borane-tetrahydrofuran complex (5.4 ml). The resulting solution was stirred at reflux for 3 h. Then the mixture was evaporated to remove solvent. The resulting residue was purified by silica gel chromatography eluting with EtOAc/hexane (0~30%) to afford 2-(3-chloro-2-fluorophenyl)ethan-1-ol (466 mg) as an oil.

Step 2: 3-chloro-2-fluorophenethyl methanesulfonate

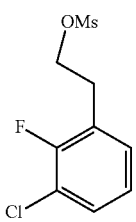 [SMILES: CS(=O)(=O)OCCc1cccc(Cl)c1F]

To a solution of 2-(3-chloro-2-fluorophenyl)ethan-1-ol (107 mg, 0.613 mmol) and triethylamine (183 mg, 1.808 mmol) in dichloromethane (4 ml) was added dropwise methanesulfonyl chloride (129 mg, 1.126 mmol) at 0~5° C. The mixture was stirred for 2 h before it is quenched with water (10 mL). The resulting solution was extracted with DCM (3×30 mL). The organic layer was combined, dried over anhydrous sodium sulfate and concentrated under vacuum to give 3-chloro-2-fluorophenethyl methanesulfonate (164 mg, 0.649 mmol) as a yellow oil. The crude product was used in the next step without purification.

Step 3: tert-butyl (2R,4R)-4-((6-((1-(tert-butyl)-5-methyl-1H-pyrazol-3-yl)amino)-3-fluoropyridin-2-yl)methyl)-1-(3-chloro-2-fluorophenethyl)-2-methylpiperidine-4-carboxylate

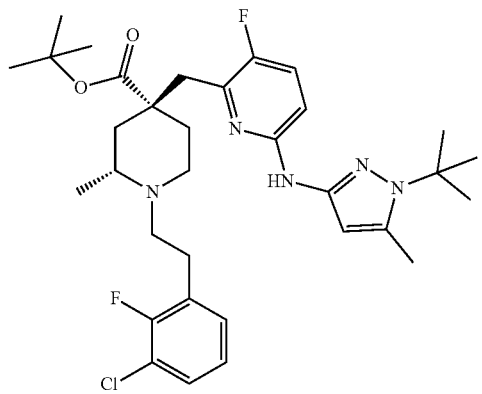 [SMILES: Cc1cc(Nc2ccc(F)c(C[C@@]3(C(=O)OC(C)(C)C)CCN(CCc4cccc(Cl)c4F)[C@H](C)C3)n2)nn1C(C)(C)C]

To a mixture of tert-butyl (2R,4R)-4-((6-((1-(tert-butyl)-5-methyl-1H-pyrazol-3-yl)amino)-3-fluoropyridin-2-yl) methyl)-2-methylpiperidine-4-carboxylate (97 mg, 0.211 mmol), potassium carbonate (138 mg, 0.999 mmol) in ACN (4 ml) was added 3-chloro-2-fluorophenethyl methanesulfonate (164 mg, 0.649 mmol). The reaction mixture was stirred at 80° C. for 15 h, then the solids were filtered out and the resulting solution was concentrated under vacuum. The resulting residue was applied onto a silica gel column eluting with EtOAc/hexane (0~70%) to afford the title compound (17 mg, 0.130 mmol) as a yellow oil. LCMS (ESI, m/z): 616 [M+1]⁺.

Step 4: (2R,4R)-1-(3-chloro-2-fluorophenethyl)-4-((3-fluoro-6-((5-methyl-1H-pyrazol-3-yl) amino) pyridin-2-yl)methyl)-2-methylpiperidine-4-carboxylic acid

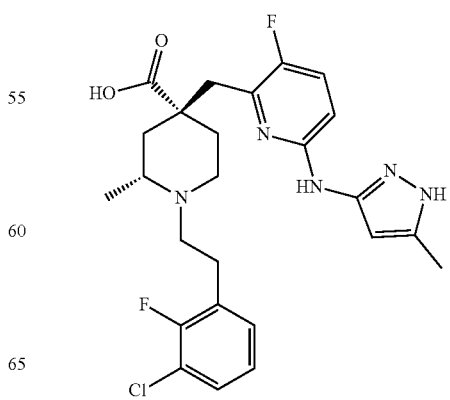

Following the procedure analogous to that described in step 5 of Example 5, tert-butyl (2R,4R)-4-((6-((1-(tert-butyl)-5-methyl-1H-pyrazol-3-yl)amino)-3-fluoropyridin-2-yl)methyl)-1-(3-chloro-2-fluorophenethyl)-2-methylpiperidine-4-carboxylate (17 mg, 0.130 mmol) was converted to the title compound (12 mg) as a white solid. LCMS (ESI, m/z): 504 [M+H]⁺. ¹H NMR (400 MHz, MeOD) δ 7.57 (t, J=9.0 Hz, 1H), 7.45 (t, J=7.5 Hz, 1H), 7.35 (s, 1H), 7.19 (t, J=7.8 Hz, 1H), 6.88 (dd, J=9.0, 3.1 Hz, 1H), 6.00 (d, J=9.7 Hz, 1H), 3.77 (s, 2H), 3.68-3.33 (m, 5H), 3.20-3.08 (m, 2H), 2.36 (s, 3H), 2.21 (d, J=11.9 Hz, 2H), 2.05 (s, 2H), 1.44 (s, 3H).

The following example in Table 3 was synthesized using the above procedure with the corresponding starting materials and intermediates.

TABLE 3

| Example No. | Structure | Chemical Name | ¹HNMR & MS: (M + H)⁺ |
|---|---|---|---|
| 43 | 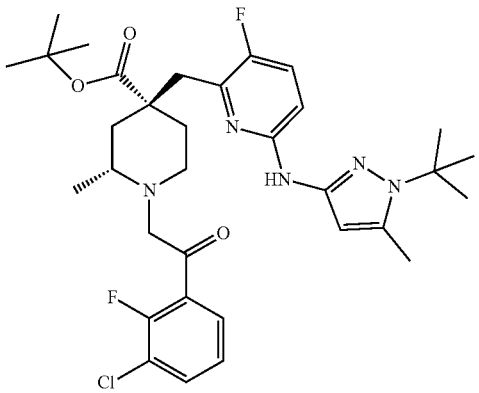 | (2R,4R)-1-(2,6-dichlorophenethyl)-4-((3-fluoro-6-((5-methyl-1H-pyrazol-3-yl)amino)-pyridin-2-yl)methyl)-2-methyl piperidine-4-carboxylic acid | ¹H NMR (400 MHz, MeOD) δ 7.61 (t, J = 9.0 Hz, 1H), 7.53-7.43 (m, 2H), 7.32 (t, J = 8.0 Hz, 1H), 6.90 (dd, J = 9.0, 3.0 Hz, 1H), 6.02 (s, 1H), 3.84 (s, 1H), 3.68-3.35 (m, 6H), 2.38 (d, J = 3.8 Hz, 3H), 2.19 (t, J = 30.8 Hz, 4H), 1.50 (d, J = 13.7 Hz, 3H), −0.00 (s, 2H). MS: 520 (M + H)⁺ |

Example 44

(2R,4R)-1-(2-(3-chloro-2-fluorophenyl)-2-oxoethyl)-4-((3-fluoro-6-((5-methyl-1H-pyrazol-3-yl)amino) pyridin-2-yl)methyl)-2-methylpiperidine-4-carboxylic acid

Step 1: 2-bromo-1-(3-chloro-2-fluorophenyl)ethan-1-one

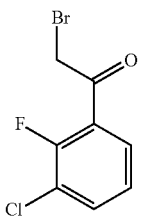 [SMILES: O=C(CBr)c1cccc(Cl)c1F]

The mixture of 1-(3-chloro-2-fluorophenyl)ethan-1-one (1.004 g, 5.817 mmol), NBS (1.393 g, 7.827 mmol), potassium dihydrogen phosphate (0.282 g, 2.072 mmol) and ethanol (12 mL) was refluxed for 3 h. The reaction mixture was evaporated to remove solvent. The resulting residue was purified by C18 reversed phase column chromatography eluting with H₂O/ACN to afford 2-bromo-1-(3-chloro-2-fluoro phenyl)ethan-1-one (297 mg, 1.181 mmol) as an brown oil. LCMS (ESI, m/z): 251,253 [M+1]⁺.

Step 2: tert-butyl (2R,4R)-4-((6-((1-(tert-butyl)-5-methyl-1H-pyrazol-3-yl)amino)-3-fluoropyridin-2-yl)methyl)-1-(2-(3-chloro-2-fluorophenyl)-2-oxoethyl)-2-methylpiperidine-4-carboxylate To a solution of tert-butyl (2R,4R)-4-((6-((1-(tert-butyl)-5-methyl-1H-pyrazol-3-yl)amino)-3-fluoropyridin-2-yl) methyl)-2-methylpiperidine-4-carboxylate (156 mg, 0.339 mmol), 2-bromo-1-(3-chloro-2-fluorophenyl)ethan-1-one (109 mg, 0.433 mmol) in THF (8 ml) was added trimethylamine (362 mg, 3.577 mmol) at 0° C. The resulting solution was stirred at room temperature for overnight. The mixture was evaporated to remove solvent. The resulting residue was purified by silica gel column chromatography eluting with EtOAc/hexane (0~30%) to give tert-butyl (2R,4R)-4-((6-((1-(tert-butyl)-5-methyl-1H-pyrazol-3-yl)amino)-3-fluoropyridin-2-yl)methyl)-1-(2-(3-chloro-2-fluorophenyl)-2-oxoethyl)-2-methylpiperidine-4-carboxylate (68 mg, 0.107 mmol) as a yellow oil. LCMS (ESI, m/z): 630 [M+1]⁺.

Step 3: (2R,4R)-1-(2-(3-chloro-2-fluorophenyl)-2-oxoethyl)-4-((3-fluoro-6-((5-methyl-1H-pyrazol-3-yl)amino)pyridin-2-yl)methyl)-2-methylpiperidine-4-carboxylic acid

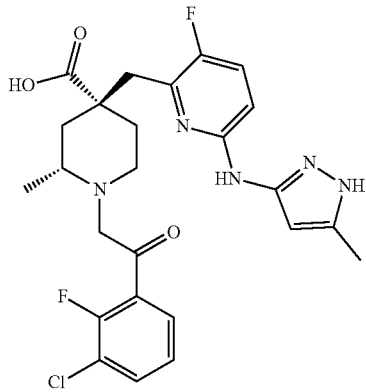

Following the procedure analogous to that described in step 5 of Example 5, tert-butyl (2R,4R)-4-((6-((1-(tert-butyl)-5-methyl-1H-pyrazol-3-yl)amino)-3-fluoropyridin-2-yl)methyl)-1-(2-(3-chloro-2-fluorophenyl)-2-oxoethyl)-2-methylpiperidine-4-carboxylate (68 mg, 0.107 mmol) was converted to the title compound (34 mg) as a white solid. LCMS (ESI, m/z): 518 [M+1]⁺. ¹H NMR (400 MHz, MeOD) δ 8.00 (ddd, J=8.0, 6.4, 1.6 Hz, 1H), 7.92-7.83 (m, 1H), 7.62 (t, J=9.0 Hz, 1H), 7.40 (t, J=8.0 Hz, 1H), 6.90 (dd, J=9.0, 3.1 Hz, 1H), 4.86 (d, J=18.0 Hz, 1H), 4.05-3.87 (m, 1H), 3.71 (s, 2H), 3.56 (t, J=11.1 Hz, 2H), 3.46 (s, 2H), 2.40 (s, 3H), 2.24 (s, 2H), 2.10 (d, J=14.1 Hz, 2H), 1.42 (d, J=6.3 Hz, 3H).

Example 45

(2R,4R)-1-(3-chloro-2-fluorobenzyl)-2-methyl-4-((6-((5-methyl-1H-pyrazol-3-yl)amino)pyrazin-2-yl)methyl)piperidine-4-carboxylic acid Step 1: methyl (2R,4R)-4-((6-chloropyrazin-2-yl)methyl)-2-methylpiperidine-4-carboxylate

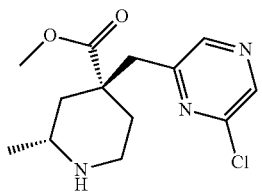 [SMILES: COC(=O)[C@]1(Cc2cncc(Cl)n2)CCN[C@H](C)C1]

Following the procedure analogous to that described in Step 1 for the synthesis of Example 37, INT C4 (298 mg, 0.776 mmol) was converted to the title compound (210 mg) as a yellow oil. LCMS (ESI, m/z): 284 [M+H]⁺.

Step 2: methyl-(2R,4R)-1-(3-chloro-2-fluorobenzyl)-4-((6-chloropyrazin-2-yl)methyl)-2-methylpiperidine-4-carboxylate

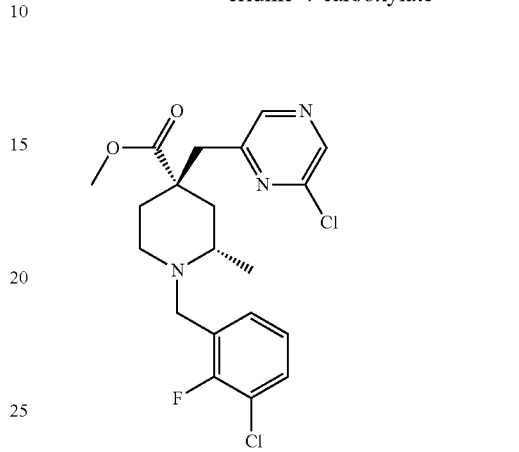

Following the procedure analogous to that described in Step 1 for the synthesis of Example 1, methyl (2R,4R)-4-((6-chloropyrazin-2-yl)methyl)-2-methylpiperidine-4-carboxylate (210 mg, 0.0.64 mmol) was converted to the title compound (216 mg, crude) as a yellow oil. LCMS (ESI, m/z): 426 [M+H]⁺.

Step 3: methyl-(2R,4R)-4-((6-((1-(tert-butoxycarbonyl)-5-methyl-1H-pyrazol-3-yl)amino)pyrazin-2-yl)methyl)-1-(3-chloro-2-fluorobenzyl)-2-methylpiperidine-4-carboxylate

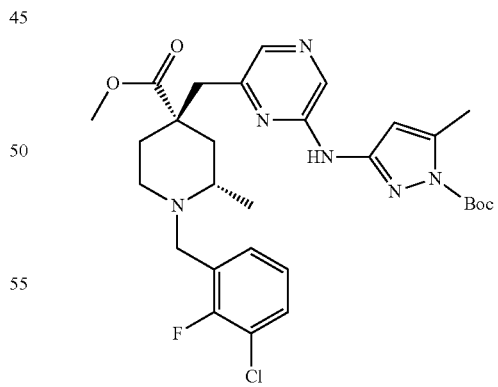

Following the procedure analogous to that described in Step 3 for the synthesis of Example 1, methyl-(2R,4R)-1-(3-chloro-2-fluorobenzyl)-4-((6-chloropyrazin-2-yl)methyl)-2-methyl piperidine-4-carboxylate (216 mg, crude) was converted to the title compound (923 mg) as a yellow oil. LCMS (ESI, m/z): 587 [M+H]⁺.

Step 4: methyl-(2R,4R)-1-(3-chloro-2-fluorobenzyl)-2-methyl-4-((6-((5-methyl-1H-pyrazol-3-yl)amino)pyrazin-2-yl)methyl)piperidine-4-carboxylate

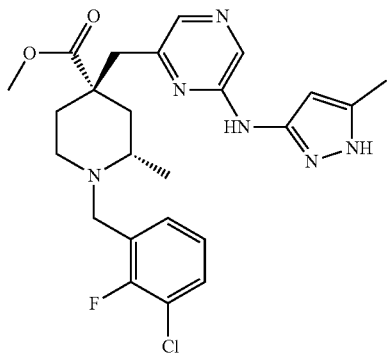

Following the procedure analogous to that described in Step 4 for the synthesis of Example 1, methyl-(2R,4R)-4-((6-((1-(tert-butoxycarbonyl)-5-methyl-1H-pyrazol-3-yl)amino) pyrazin-2-yl)methyl)-1-(3-chloro-2-fluorobenzyl)-2-methylpiperidine-4-carboxylate (923 mg) was converted to the title compound (325 mg, crude) as a yellow oil. LCMS (ESI, m/z): 487 [M+H]⁺.

Step 5: (2R,4R)-1-(3-chloro-2-fluorobenzyl)-2-methyl-4-((6-((5-methyl-1H-pyrazol-3-yl)amino)pyrazin-2-yl)methyl)piperidine-4-carboxylic acid

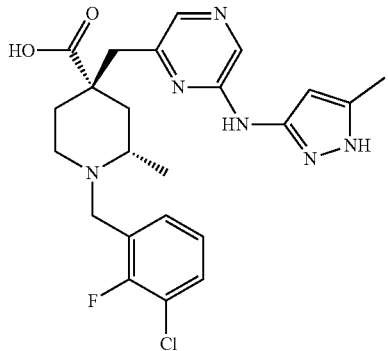 [SMILES: Cc1cc(Nc2cncc(C[C@]3(C(=O)O)CCN(Cc4cccc(Cl)c4F)[C@@H](C)C3)n2)n[nH]1]

Following the procedure analogous to that described in Step 5 for the synthesis of Example 1, methyl-(2R,4R)-1-(3-chloro-2-fluorobenzyl)-2-methyl-4-((6-((5-methyl-1H-pyrazol-3-yl)amino)pyrazin-2-yl)methyl)piperidine-4-carboxylate (325 mg) was converted to the title compound 9 mg as a yellow solid. LCMS (ESI, m/z): 487 [M+H]⁺. ¹H NMR (400 MHz, DLCMS (ESI, m/z)O) 89.61 (s, 1H), 8.19 (s, 1H), 7.77 (t, J=7.9 Hz, 1H), 7.68 (s, 1H), 7.68 (s, 2H), 7.59 (d, J=6.4 Hz, 2H), 7.38 (t, J=7.9 Hz, 2H), 6.28 (s, 1H), 3.54 (s, 50H), 3.14 (d, J=9.9 Hz, 4H), 2.50 (m, 109H), 2.33 (s, 1H), 2.23 (s, 4H), 2.23 (s, 6H), 2.02 (d, J=13.4 Hz, 3H), 1.88 (m, 4H), 1.48 (d, J=6.1 Hz, 5H).

Example 46

1-(3-chloro-2-fluorobenzyl)-4-((3-fluoro-4-(3-hydroxyoxetan-3-yl)-6-((5-methyl-1H-pyrazol-3-yl)amino)pyridin-2-yl)methyl)piperidine-4-carboxylic acid

Step 1: 1-(tert-butyl)-4-methyl-4-((6-bromo-3-fluoropyridin-2-yl)methyl)piperidine-1,4-dicarboxylate

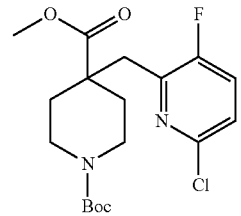 [SMILES: COC(=O)C1(Cc2nc(Cl)ccc2F)CCN(C(=O)OC(C)(C)C)CC1]

Following the procedure analogous to that described in Step 1 for the synthesis of Example 5, 1-(tert-butyl) 4-methyl piperidine-1,4-dicarboxylate (2.47 g, 10.152 mmol), INT A6 (2.95 g, 13.142 mmol) was converted to the title compound (1808 mg, Y=46%) as a yellow oil. LCMS (ESI, m/z): 387 [M+H]⁺.

Step 2: 1-(tert-butyl)-4-methyl-4-((6-chloro-3-fluoro-4-(3-hydroxyoxetan-3-yl)pyridin-2-yl)methyl)piperidine-1,4-dicarboxylate

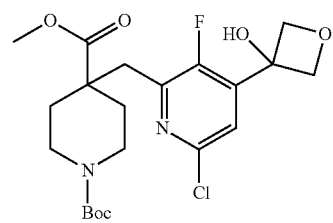 [SMILES: COC(=O)C1(Cc2nc(Cl)cc(C3(O)COC3)c2F)CCN(C(=O)OC(C)(C)C)CC1]

To a solution of diisopropylamine (374 mg, 3.696 mmol) in THF (5 mL) was cooled to −78° C. under nitrogen. n-Butyl lithium (2.5M) in hexane (1.3 mL, 3.250 mmol) was added dropwise over 10 min maintaining the internal temperature below −40° C. The resulting solution was stirred at 0° C. for 30 min before a solution of 1-(tert-butyl)-4-methyl-4-((6-bromo-3-fluoropyridin-2-yl)methyl) piperidine-1,4-dicarboxylate (777 mg, 2.013 mmol) in THF (5 ml) was added dropwise at −78° C. The mixture was stirred at −40° C. for 1 h.

A solution of oxetan-3-one (295 mg, 4.094 mmol) in THF (5 ml) was added. The resulting solution was stirred at −60° C. for 1 h before it was quenched with saturated aqueous NH₄Cl aqueous solution. The resulting mixture was extracted with ethyl acetate. The organic layer was dried over anhydrous sodium sulfate, filtered and concentrated under reduced pressure. The resulting residue was purified by C18 reversed phase column chromatography eluting with H₂O/ACN to afford 1-(tert-butyl)-4-methyl-4-((6-chloro-3-fluoro-4-(3-hydroxyoxetan-3-yl)pyridin-2-yl)methyl) piperidine-1,4-dicarboxylate (476 mg, Y=52%) as yellow oil. LCMS (ESI, m/z): 459 [M+H]⁺.

Step 3: methyl-1-(3-chloro-2-fluorobenzyl)-4-((6-chloro-3-fluoro-4-(3-hydroxyoxetan-3-yl) p-yridin-2-yl)methyl)piperidine-4-carboxylate

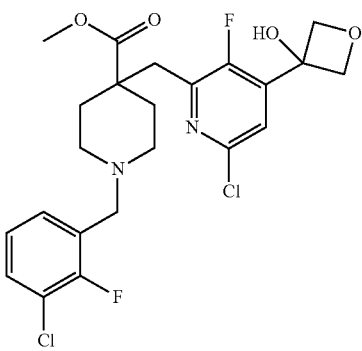 [SMILES: COC(=O)C1(Cc2nc(Cl)cc(C3(O)COC3)c2F)CCN(Cc2cccc(Cl)c2F)CC1]

Following the procedure analogous to that described in Step 3&4 for the synthesis of Example 5, 1-(tert-butyl)-4-methyl-4-((6-chloro-3-fluoro-4-(3-hydroxyoxetan-3-yl) pyridin-2-yl) methyl)piperidine-1,4-dicarboxylate (476 mg, 1.037 mmol) was converted to the title compound (168 mg, Y=32%) as a yellow oil. LCMS (ESI, m/z): 501 [M+H]+.

Step 4: methyl-4-((6-((1-(tert-butoxycarbonyl)-5-methyl-1H-pyrazol-3-yl)amino)-3-fluoro-4-(3-hydroxyoxetan-3-yl)pyridin-2-yl)methyl)-1-(3-chloro-2-fluorobenzyl)piperidine-4-carboxylate

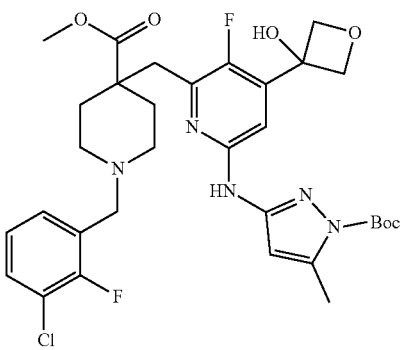 [SMILES: COC(=O)C1(Cc2nc(Nc3cc(C)n(C(=O)OC(C)(C)C)n3)cc(C3(O)COC3)c2F)CCN(Cc2cccc(Cl)c2F)CC1]

Following the procedure analogous to that described in step 3 for the synthesis of Example 1, methyl-1-(3-chloro-2-fluorobenzyl)-4-((6-chloro-3-fluoro-4-(3-hydroxyoxetan-3-yl) p-yridin-2-yl)methyl)piperidine-4-carboxylate (168 mg, 0.335 mmol) was converted to the title compound (255 mg, crude) as a yellow oil. LCMS (ESI, m/z): 662 [M+H]+.

Step 5: methyl-1-(3-chloro-2-fluorobenzyl)-4-((3-fluoro-4-(3-hydroxyoxetan-3-yl)-6-((5-methyl-1H-pyrazol-3-yl)amino)pyridin-2-yl)methyl)piperidine-4-carboxylate

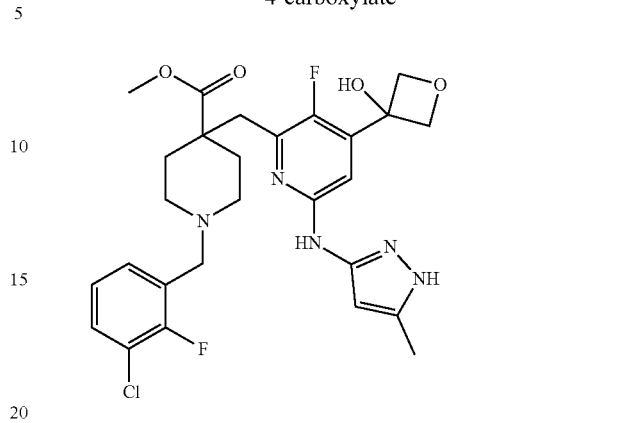

Following the procedure analogous to that described in step 4 for the synthesis of Example 1, methyl-4-((6-((1-(tert-butoxycarbonyl)-5-methyl-1H-pyrazol-3-yl)amino)-3-fluoro-4-(3-hydroxyoxetan-3-yl)pyridin-2-yl)methyl)-1-(3-chloro-2-fluorobenzyl)piperidine-4-c-arboxylate (255 mg, crude) was converted to the title compound (65 mg, crude) as a yellow oil. LCMS (ESI, m/z): 562 [M+H]+.

Step 6: 1-(3-chloro-2-fluorobenzyl)-4-((3-fluoro-4-(3-hydroxyoxetan-3-yl)~6-((5-methyl-1H-pyrazol-3-yl)amino)pyridin-2-yl)methyl)piperidine-4-carboxylic acid

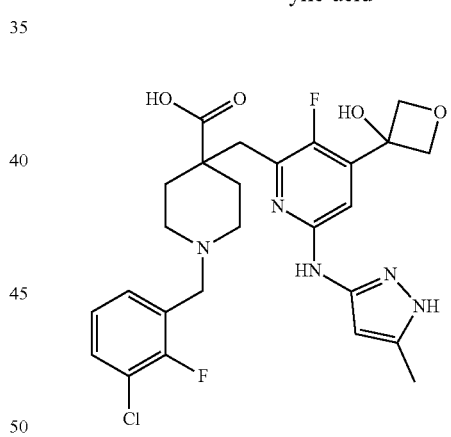

Following the procedure analogous to that described in step 5 for the synthesis of Example 1, methyl-1-(3-chloro-2-fluorobenzyl)-4-((3-fluoro-4-(3-hydroxyoxetan-3-yl)-6-((5-met-hyl-1H-pyrazol-3-yl)amino)pyridin-2-yl)methyl) piperidine-4-carboxylate (65 mg) was converted to the title compound 10 mg as a yellow solid. LCMS (ESI, m/z): 548 [M+H]+. 1H NMR (400 MHz, MeOD) δ 7.69 (t, J=7.4 Hz, 1H), 7.52 (s, 1H), 7.33 (t, J=8.0 Hz, 1H), 6.96 (d, J=4.7 Hz, 1H), 5.99 (s, 1H), 5.08 (d, J=7.1 Hz, 2H), 4.80 (d, J=7.1 Hz, 1H), 4.46 (s, 2H), 3.53 (m, 3H), 3.17 (d, J=13.1 Hz, 3H), 2.46 (s, 2H), 2.35 (s, 3H), 1.93 (s, 2H), 1.31 (s, 2H).

The following example in Table 4 was synthesized using the above procedure with the corresponding starting materials and intermediates.

TABLE 4

| Example No. | Structure | Chemical Name | ¹HNMR & MS: (M + H)⁺ |
|---|---|---|---|
| 47 | 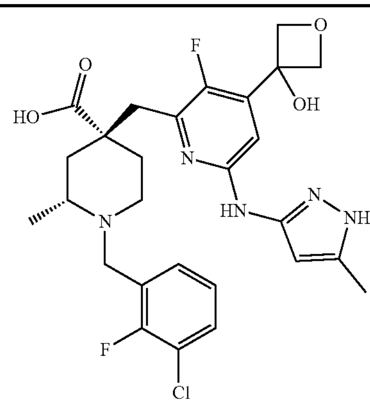 | (2R,4R)-1-(3-chloro-2-fluorobenzyl)-4-((3-fluoro-4-(3-hydroxyoxetan-3-yl)-6-((5-methyl-1H-pyrazol-3-yl)amino)-pyridin-2-yl)methyl)-2-methyl piperidine-4-carboxylic acid | ¹H NMR (400 MHz, MeOD) δ 7.68 (t, J = 7.6 Hz, 1H), 7.55 (t, J = 6.4 Hz, 1H), 7.34 (t, J = 7.9 Hz, 1H), 6.93 (d, J = 4.7 Hz, 1H), 5.95 (s, 1H), 5.07 (d, J = 7.0 Hz, 2H), 4.79 (d, J = 7.0 Hz, 2H), 4.33 (d, J = 12.6 Hz, 1H), 3.91 (s, 2H), 3.44 (d, J = 29.1 Hz, 4H), 2.33 (s, 3H), 2.15 (dd, J = 73.5, 26.6 Hz, 5H), 1.57 (d, J = 6.0 Hz, 3H), MS: 562 (M + H)⁺ |

Example 48

(2R,4R)-1-(3-chloro-2-fluorobenzyl)-4-((3-fluoro-4-(3-fluorooxetan-3-yl)-6-((5-methyl-1H-pyrazol-3-yl)amino)pyridin-2-yl)methyl)-2-methylpiperidine-4-carboxylic acid Step 1: di-tert-butyl-(2R,4R)-4-((6-bromo-3-fluoro-4-(3-hydroxyoxetan-3-yl)pyridin-2-yl) methyl)-2-methylpipendine-1,4-dicarboxylate

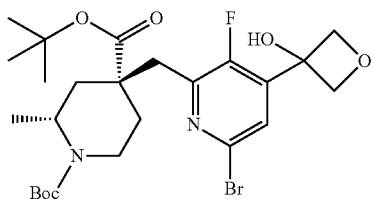 [SMILES: C[C@@H]1C[C@](Cc2nc(Br)cc(C3(O)COC3)c2F)(C(=O)OC(C)(C)C)CCN1C(=O)OC(C)(C)C]

Following the procedure analogous to that described in Step 2 for the synthesis of Example 43, INT C2 (881 mg, 1.808 mmol) was converted to the title compound (826 mg, Y=83%) as a yellow oil. LCMS (ESI, m/z): 559 [M+H]⁺.

Step 2: tert-butyl-(2R,4R)-4-((6-bromo-3-fluoro-4-(3-hydroxyoxetan-3-yl)pyridin-2-yl)methyl)-2-methylpiperidine-4-carboxylate

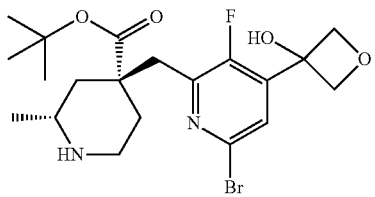 [SMILES: C[C@@H]1C[C@](Cc2nc(Br)cc(C3(O)COC3)c2F)(C(=O)OC(C)(C)C)CCN1]

Following the procedure analogous to that described in step 3 for the synthesis of Example 5, di-tert-butyl-(2R,4R)-4-((6-bromo-3-fluoro-4-(3-hydroxyoxetan-3-yl)pyridin-2-yl)methyl)-2-methylpiperidine-1,4-dicarboxylate (826 mg, 1.476 mmol) was converted to the title compound (669 mg, Y=98%) as a yellow oil. LCMS (ESI, m/z): 459 [M+H]⁺.

Step 3: tert-butyl-(2R,4R)-4-((6-bromo-3-fluoro-4-(3-hydroxyoxetan-3-yl)pyridin-2-yl)methyl)-1-(3-chloro-2-fluorobenzyl)-2-methylpiperidine-4-carboxylate

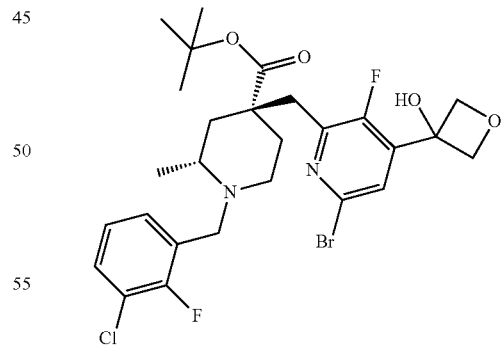

Following the procedure analogous to that described in Step 4 for the synthesis of Example 5, tert-butyl-(2R,4R)-4-((6-bromo-3-fluoro-4-(3-hydroxyoxetan-3-yl)pyridin-2-yl) methyl)-2-methylpiperidine-4-carboxylate (669 mg, 1.456 mmol) was converted to the title compound (577 mg, Y=66%) as a yellow oil. LCMS (ESI, m/z): 601 [M+H]⁺.

Step 4: tert-butyl-(2R,4R)-4-((6-((1-(tert-butyl)-5-methyl-1H-pyrazol-3-yl)amino)-3-fluoro-4-(3-hydroxyoxetan-3-yl)pyridin-2-yl)methyl)-1-(3-chloro-2-fluorobenzyl)-2-methylpiperidine-4-carboxylate

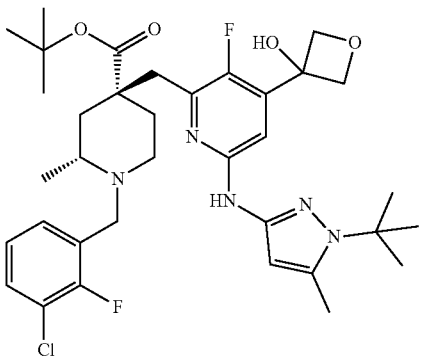 [SMILES: Cc1cc(Nc2cc(C3(O)COC3)c(F)c(C[C@@]3(C(=O)OC(C)(C)C)CCN(Cc4cccc(Cl)c4F)[C@H](C)C3)n2)nn1C(C)(C)C]

Following the procedure analogous to that described in step 2 for the synthesis of Example 5, tert-butyl-(2R,4R)-4-((6-bromo-3-fluoro-4-(3-hydroxyoxetan-3-yl)pyridin-2-yl)methyl)-1-(3-chloro-2-fluorobenzyl)-2-methylpiperidine-4-carboxylate (577 mg, 958.62 umol) was converted to the title compound (445 mg, Y=69%) as a yellow oil. LCMS (ESI, m/z): 674 [M+H]$^+$.

Step 5: tert-butyl-(2R,4R)-4-((6-((1-(tert-butyl)-5-methyl-1H-pyrazol-3-yl)amino)-3-fluoro-4-(3-fluorooxetan-3-yl)pyridin-2-yl)methyl)-1-(3-chloro-2-fluorobenzyl)-2-methylpiperidine-4-carboxylate

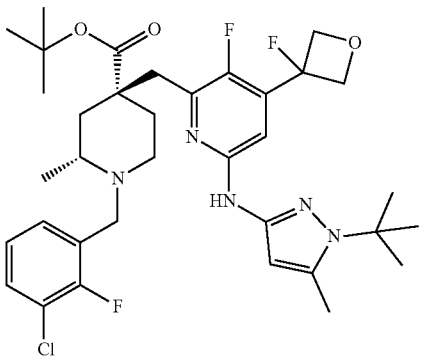 [SMILES: Cc1cc(Nc2cc(C3(F)COC3)c(F)c(C[C@@]3(C(=O)OC(C)(C)C)CCN(Cc4cccc(Cl)c4F)[C@H](C)C3)n2)nn1C(C)(C)C]

To a solution of tert-butyl-(2R,4R)-4-((6-((1-(tert-butyl)-5-methyl-1H-pyrazol-3-yl)amino)-3-fluoro-4-(3-hydroxyoxetan-3-yl)pyridin-2-yl)methyl)-1-(3-chloro-2-fluorobenzyl)-2-methylpiperidine-4-carboxylate (194 mg, 0.288 mmol) in DCM (10 ml) was added DAST (0.5 mL). The solution was stirred at room temperature for 2 h. The resulting solution was quenched with saturated sodium bicarbonate aqueous solution. The resulting solution was diluted with water and extracted with ethyl acetate. The organic layer was dried over anhydrous sodium sulfate, filtered and concentrated under reduced pressure. The resulting residue was applied onto a silica gel column eluting with EtOAc/hexane (0~30%) to afford the title compound (146 mg, Y=75%) as a yellow oil. LCMS (ESI, m/z): 676 [M+H]$^+$.

Step 6; (2R,4R)-1-(3-chloro-2-fluorobenzyl)-4-((3-fluoro-4-(3-fluorooxetan-3-yl)-6-((5-methyl-1H-pyrazol-3-yl)amino)pyridin-2-yl)methyl)-2-methylpiperidine-4-carboxylic acid

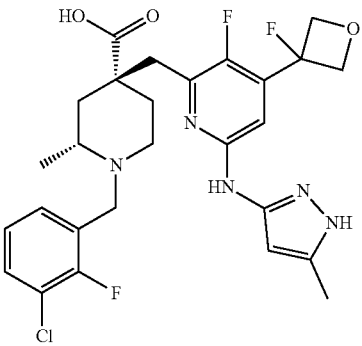 [SMILES: Cc1cc(Nc2cc(C3(F)COC3)c(F)c(C[C@@]3(C(=O)O)CCN(Cc4cccc(Cl)c4F)[C@H](C)C3)n2)n[nH]1]

Following the procedure analogous to that described in step 5 for the synthesis of Example 5, tert-butyl-(2R,4R)-4-((6-((1-(tert-butyl)-5-methyl-1H-pyrazol-3-yl)amino)-3-fluoro-4-(3-fluorooxetan-3-yl)pyridin-2-yl)methyl)-1-(3-chloro-2-fluorobenzyl)-2-methylpiperidine-4-carboxylate (146 mg, 215.909 umol) was converted to the title compound 21 mg as a white solid. LCMS (ESI, m/z): 564 [M+H]$^+$. $^1$H NMR (400 MHz, MeOD) δ 7.71 (t, J=7.6 Hz, 1H), 7.56 (t, J=6.4 Hz, 1H), 7.36 (t, J=7.9 Hz, 1H), 6.95 (d, J=4.4 Hz, 1H), 6.03 (s, 1H), 5.07 (m, 4H), 3.97 (d, J=23.5 Hz, 2H), 3.47 (dd, J=24.6, 3.3 Hz, 4H), 2.37 (s, 3H), 2.10 (m, 5H), 1.60 (m, 3H).

Example 49

(2R,4R)-1-(3-chloro-2-fluorobenzyl)-4-((3-fluoro-4-methyl-6-((5-methyl-1H-pyraz-ol-3-yl)amino)pyridin-2-yl)methyl)-2-methylpiperidine-4-carboxylic acid Step 1: di-tert-butyl-(2R,4R)-4-((6-chloro-3-fluoro-4-methylpyridin-2-yl)methyl)-2-methylpiperidine-1,4-dicarboxylate

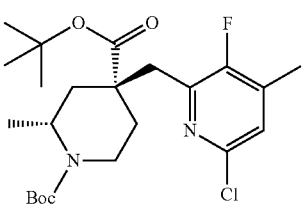 [SMILES: Cc1cc(Cl)nc(C[C@@]2(C(=O)OC(C)(C)C)CCN(C(=O)OC(C)(C)C)[C@H](C)C2)c1F]

A solution of diisopropylamine (2.13 g, 21.050 mmol) in THF (10 mL) was cooled to −78° C. under nitrogen. n-Butyl lithium (2.5M) in n-hexane (7.2 mL, 18.286 mmol) was added. The solution was stirred at 0° C. for 30 min before it was added a solution of INT C2 (4.05 g, 9.143 mmol) in THF (5 ml) dropwise over 10 min maintaining the internal temperature below −40° C. The resulting solution was stirred at −40° C. for 1 h.

A solution of iodomethane (2.22 mg, 15.641 mmol) in THF (5 ml) was added dropwise below −70° C. and stirred 1 h. The reaction was quenched with saturated NH$_4$Cl aqueous solution and extracted with ethyl acetate. The organic layer was dried over anhydrous sodium sulfate, filtered and concentrated under reduced pressure. The residue was purified by C18 reversed phase column chromatography eluting with H₂O/ACN to afford di-tert-butyl (2R, 4R)-4-((6-chloro-3-fluoro-4-methylpyridin-2-yl)methyl)-2-methylpiperidine-1,4-dicarboxylate (3.55 g, Y=85%) as yellow oil. LCMS (ESI, m/z): 457 [M+H]⁺.

Step 2: di-tert-butyl(2R,4R)-4-((6-((1-(tert-butyl)-5-methyl-1H-pyrazol-3-yl) amino)-3-fluoro-4-methylpyridin-2-yl)methyl)-2-methylpiperidine-1,4-dicarboxylate

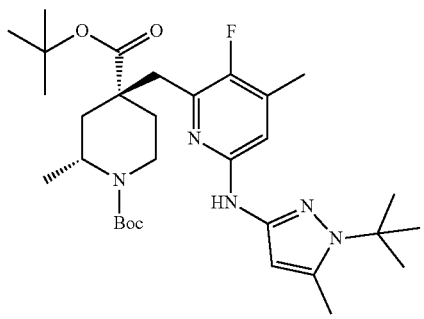 [SMILES: Cc1cc(Nc2cc(C)n(C(C)(C)C)n2)nc(C[C@@]2(C(=O)OC(C)(C)C)CCN(C(=O)OC(C)(C)C)[C@H](C)C2)c1F]

A mixture of di-tert-butyl-(2R,4R)-4-((6-chloro-3-fluoro-4-methylpyridin-2-yl)methyl)-2-methylpiperidine-1,4-dicarboxylate (3.54 g, 7.747 mmol), tris(dibenzylideneacetone)dipalladium (2.01 g, 2.195 mmol), dimethylbisdiphenylphosphinoxanthene (1.43 g, 2.471 mmol), 1-tert-butyl-3-methyl-1H-pyrazol-5-amine (1.56 mg, 10.181 mmol) and K₃PO₄ (5.30 g, 24.969 mmol) in 1,4-dioxane (50 ml) was stirred at 110° C. for 5 h under nitrogen. The resulting solution was cooled to room temperature and diluted with brine and extracted with ethyl acetate. The organic layer was dried over anhydrous sodium sulfate, filtered and concentrated under reduced pressure. The residue was purified by C18 reverse phase chromatography eluting with H₂O/ACN to afford (4.03 g, 7.024 mmol, Y=91%) of the title compound as a yellow solid. LCMS (ESI, m/z): 574 [M+H]⁺.

Step 3: tert-butyl-(2R,4R)-4-((6-((1-(tert-butyl)-5-methyl-1H-pyrazol-3-yl)amino)-3-fluoro-4-methylpyridin-2-yl)methyl)-2-methylpiperidine-4-carboxylate

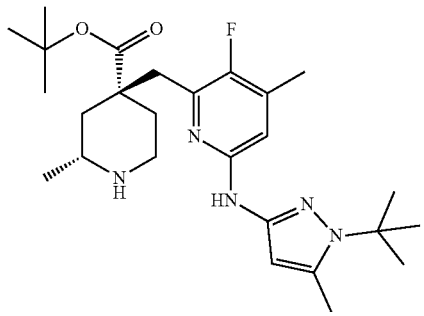 [SMILES: Cc1cc(Nc2cc(C)n(C(C)(C)C)n2)nc(C[C@@]2(C(=O)OC(C)(C)C)CCN[C@H](C)C2)c1F]

A solution of di-tert-butyl(2R,4R)-4-((6-((1-(tert-butyl)-5-methyl-1H-pyrazol-3-yl)amino)-3-fluoro-4-methylpyridin-2-yl)methyl)-2-methylpiperidine-1,4-dicarboxylate (3.95 g, 6.885 mmol) in dichloromethane (60 ml) was added trifluoroacetic acid (6 ml) and stirred at room temperature for 4 h. After completion, the reaction was quenched with saturated sodium bicarbonate aqueous solution (100 ml) and extracted with dichloromethane. The organic layer was dried over anhydrous sodium sulfate, filtered and concentrated under reduced pressure. The crude product was purified by C18 reverse phase chromatography eluting with H₂O/ACN to afford (3.47 g, 7.326 mmol, Y=106%) of the title compound as a yellow solid. LCMS (ESI, m/z): 474 [M+H]⁺.

Step 4: tert-butyl(2R,4R)-4-((6-((1-(tert-butyl)-5-methyl-1H-pyrazol-3-yl)amino)-3-fluoro-4-methylpyridin-2-yl)methyl)-1-(3-chloro-2-fluorobenzyl)-2-methylpiperidine-4-carboxylate

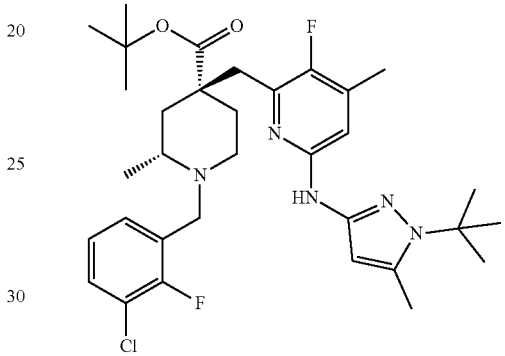

A mixture of tert-butyl-(2R,4R)-4-((6-((1-(tert-butyl)-5-methyl-1H-pyrazol-3-yl)amino)-3-fluoro-4-methylpyridin-2-yl)methyl)-2-methylpiperidine-4-carboxylate (3.39 g, 7.158 mmol), potassium carbonate (3.49 g, 25.252 mmol) and 1-(bromomethyl)-3-chloro-2-fluorobenzene (1.48 g, 6.623 mmol) in ACN (10 mL) was stirred for 6 h at room temperature. After completion, the resulting mixture was filtered and concentrated under vacuum. The crude product was purified by silica gel column chromatography eluting with EtOAc/hexane (0~30%) to afford (3.02 g, 4.410 mmol, Y=68%) of the title compound as a yellow solid. LCMS (ESI, m/z): 616 [M+H]⁺.

Step 5: (2R,4R)~ 1-(3-chloro-2-fluorobenzyl)-4-((3-fluoro-4-methyl-6-((5-methyl-1H-pyrazol-3-yl) amino)pyridin-2-yl)methyl)-2-methylpiperidine-4-carboxylic acid

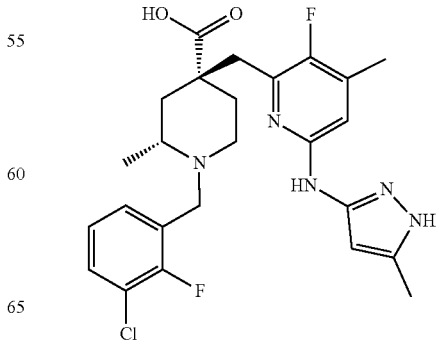

A solution of tert-butyl(2R,4R)-4-((6-((1-(tert-butyl)-5-methyl-1H-pyrazol-3-yl)amino)-3-fluoro-4-methylpyridin-2-yl)methyl)-1-(3-chloro-2-fluorobenzyl)-2-methylpiperidine-4-carboxylate (1.81 g, 2.937 mmol) in formic acid (10 mL) was stirred at reflux for 4 h. After completion, the resulting solution was concentrated under reduced pressure. The residue was dissolved in water (60 mL) at 0° C. and adjusted PH=6~7 with sodium hydroxide aqueous solution (5 M). The resulting mixture was extracted with DCM (3×100 mL). The organic layer was dried over anhydrous sodium sulfate, filtered and concentrated under reduced pressure. The crude product was purified by C18 reverse phase chromatography eluting with MeOH/water to afford (1.25 g, 2.480 mmol, Y=84%) of the title compound as a white solid. LCMS (ESI, m/z): 504 [M+H]+. 1H NMR (400 MHz, MeOD) δ 7.71 (t, J=7.7 Hz, 1H), 7.56 (t, J=6.7 Hz, 1H), 7.36 (t, J=8.0 Hz, 1H), 6.75 (d, J=4.6 Hz, 1H), 5.94 (s, 1H), 4.36 (d, J=14.0 Hz, 1H), 3.89 (s, 1H), 3.44 (t, J=19.8 Hz, 8H), 2.40-2.04 (m, 7H), 1.60 (d, J=6.0 Hz, 2H), 1.31 (s, 1H).

The following examples in Table 5 were synthesized using the above procedure with the corresponding starting materials and intermediates.

TABLE 5

| Example No. | Structure | Chemical Name | 1HNMR & MS: (M + H)+ |
|---|---|---|---|
| 50 | 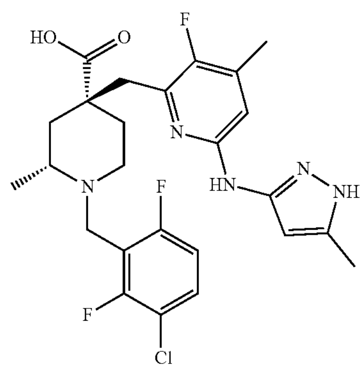 | (2R,4R)-1-(3-chloro-2,6-difluorobenzyl)-4-((3-fluoro-4-methyl-6-((5-methyl-1H-pyrazol-3-yl)amino)pyridin-2-yl)methyl)-2-methylpiperidine-4-carboxylic acid | 1H NMR (400 MHz, MeOD) δ 7.60 (dd, J = 14.3, 8.6 Hz, 1H), 7.13 (t, J = 8.8 Hz, 1H), 6.64 (s, 1H), 5.77 (d, J = 17.9 Hz, 1H), 4.41 (d, J = 13.4 Hz, 1H), 3.87 (d, J = 11.7 Hz, 1H), 3.20 (d, J = 38.9 Hz, 3H), 3.03 (s, 1H), 2.88 (d, J = 12.7 Hz, 1H), 2.24 (d, J = 16.1 Hz, 6H), 1.95 (dd, J = 38.0, 18.5 Hz, 4H), 1.43-1.37 (m, 3H). MS: 522 (M + H)+ |
| 51 | 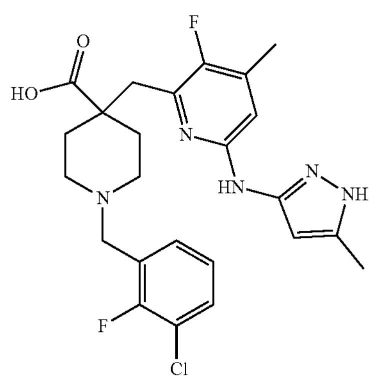 [SMILES: Cc1cc(Nc2cc(C)c(F)c(CC3(C(=O)O)CCN(Cc4cccc(Cl)c4F)CC3)n2)n[nH]1] | 1-(3-chloro-2-fluorobenzyl)-4-((3-fluoro-4-methyl-6-((5-methyl-1H-pyrazol-3-yl)amino)pyridin-2-yl)methyl)piperidine-4-carboxylic acid | 1H NMR (400 MHz, MeOD) δ 8.22 (s, 2H), 7.62 (s, 1H), 7.50 (s, 1H), 7.28 (t, J = 7.7 Hz, 1H), 6.68 (s, 1H), 5.81 (s, 1H), 4.27 (s, 2H), 3.37 (s, 5H), 3.12 (d, J = 22.1 Hz, 3H), 2.37 (s, 2H), 2.27 (s, 4H), 1.86 (s, 2H), MS: 490 (M + H)+ |
| 52 | 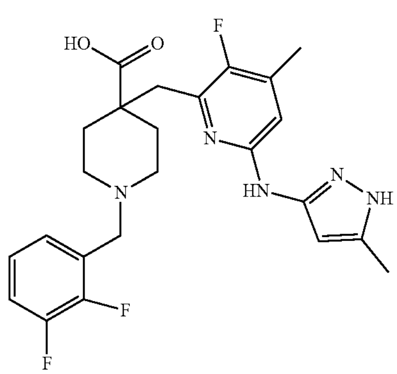 [SMILES: Cc1cc(Nc2cc(C)c(F)c(CC3(C(=O)O)CCN(Cc4cccc(F)c4F)CC3)n2)n[nH]1] | 1-(2,3-difluorobenzyl)-4-((3-fluoro-4-methyl-6-((5-methyl-1H-pyrazol-3-yl)amino)pyridyl-2-yl)methyl)piperidine-4)-carboxylic acid | 1H NMR (400 MHz, MeOD) δ 8.27 (s, 1H), 7.47-7.16 (m, 2H), 6.67 (s, 1H), 5.81 (s, 1H), 4.20 (s, 2H), 3.40-3.34 (m, 3H), 3.08 (dd, J = 73.2, 39.5 Hz, 5H), 2.30 (d, J = 35.5 Hz, 6H), 1.82 (s, 2H). MS: 474 (M + H)+ |

TABLE 5-continued

| Example No. | Structure | Chemical Name | ¹HNMR & MS: (M + H)⁺ |
|---|---|---|---|
| 53 | 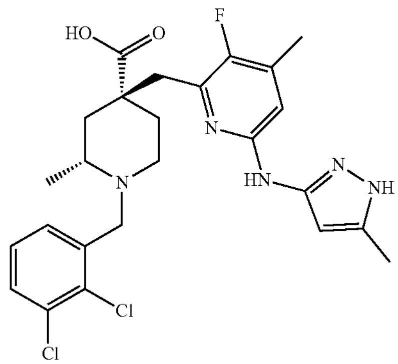 [SMILES: Cc1cc(Nc2cc(C)c(F)c(C[C@@]3(C(=O)O)CCN(Cc4cccc(Cl)c4Cl)[C@H](C)C3)n2)n[nH]1] | (2R,4R)-1-(2,3-dichloro-benzyl)-4-((3-fluoro-4-methyl-6-((5-methyl-1H-pyrazol-3-yl)-amino)pyridin-2-yl)methyl)-2-methylpiperidine-4-carboxylic acid | ¹H NMR (400 MHz, MeOD) δ 7.47 (d, J = 7.7 Hz, 2H), 7.25 (t, J = 7.8 Hz, 1H), 6.52 (s, 1H), 5.66 (d, J = 17.9 Hz, 1H), 4.39 (d, J = 13.6 Hz, 1H), 3.82 (s, 1H), 3.31 (dd, J = 58.4, 5.0 Hz, 1H), 3.15 (s, 2H), 2.90 (s, 1H), 2.79 (s, 1H), 2.13 (d, J = 14.0 Hz, 6H), 1.83 (d, J = 55.0 Hz, 4H), 1.25 (d, J = 7.2 Hz, 3H). MS: 520 (M + H)⁺ |
| 54 | 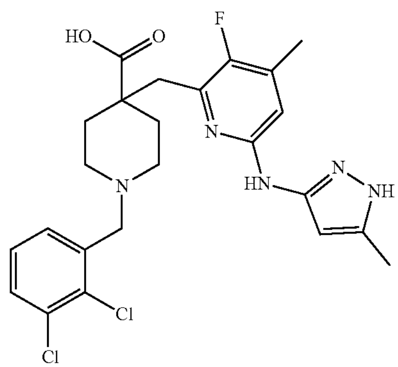 [SMILES: Cc1cc(Nc2cc(C)c(F)c(CC3(C(=O)O)CCN(Cc4cccc(Cl)c4Cl)CC3)n2)n[nH]1] | 1-(2,3-dichlorobenzyl)-4-((3-fluoro-4-methyl-6-((5-methyl-1H-pyrazol-3-yl)amino)pyridin-2-yl)methyl)piperidine-4-carboxylic acid | ¹H NMR (400 MHz, MeOD) δ 8.27 (s, 1H), 7.60 (d, J = 5.8 Hz, 1H), 7.11 (t, J = 8.6 Hz, 1H), 6.66 (s, 1H), 5.78 (s, 1H), 4.10 (dd, J = 16.5, 9.4 Hz, 2H), 3.23-2.66 (m, 6H), 2.27 (s, 4H), 2.19 (s, 2H), 1.78 (t, J = 11.1 Hz, 2H), 1.44-1.16 (m, 2H). MS: 506 (M + H)⁺ |
| 55 | 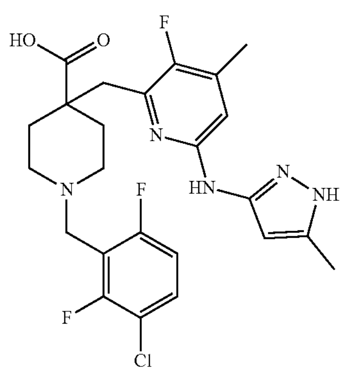 [SMILES: Cc1cc(Nc2cc(C)c(F)c(CC3(C(=O)O)CCN(Cc4c(F)ccc(Cl)c4F)CC3)n2)n[nH]1] | 1-(3-chloro-2,6-difluoro-benzyl)-4-((3-fluoro-4-methyl-6-((5-methyl-1H-pyrazol-3-yl)-amino)pyridin-2-yl)methyl) piperidine-4-carboxylic acid | ¹H NMR (400 MHz, MeOD) δ 8.27 (s, 1H), 7.60 (d, J = 5.8 Hz, 1H), 7.11 (t, J = 8.6 Hz, 1H), 6.66 (s, 1H), 5.78 (s, 1H), 4.10 (dd, J = 16.5, 9.4 Hz, 2H), 3.23-2.66 (m, 6H), 2.27 (s, 4H), 2.19 (s, 2H), 1.78 (t, J = 11.1 Hz, 2H), 1.49-0.73 (m, 4H). MS: 508 (M + H)⁺ |
| 56 | 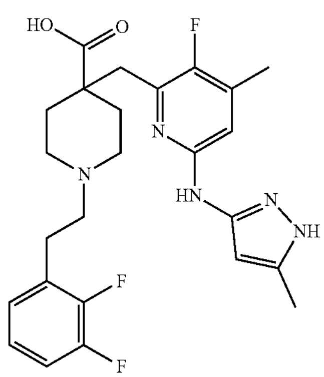 [SMILES: Cc1cc(Nc2cc(C)c(F)c(CC3(C(=O)O)CCN(CCc4cccc(F)c4F)CC3)n2)n[nH]1] | 1-(2,3-difluorophenethyl)-4-((3-fluoro-4-methyl-6-((5-methyl-1H-pyrazol-3-yl)amino)-pyridin-2-yl)methyl)piperidine-4-carboxylic acid | ¹H NMR (400 MHz, MeOD) δ 7.18 (dd, J = 20.6, 10.0 Hz, 3H), 6.75 (d, J = 4.6 Hz, 1H), 5.94 (s, 1H), 3.67 (d, J = 11.9 Hz, 2H), 3.34 (s, 2H), 3.23-2.99 (m, 6H), 2.48 (d, J = 14.7 Hz, 2H), 2.33 (d, J = 15.3 Hz, 6H), 1.95 (s, 2H). MS: 488 (M + H)⁺ |

TABLE 5-continued

| Example No. | Structure | Chemical Name | ¹HNMR & MS: (M + H)⁺ |
|---|---|---|---|
| 57 | 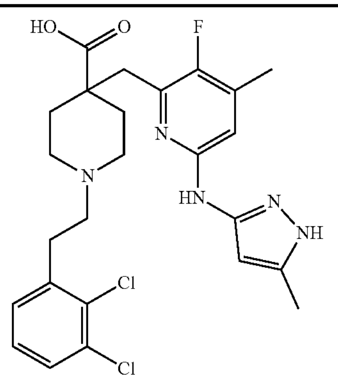 | 1-(2,3-dichlorophenethyl)-4-((3-fluoro-4-methyl-6-((5-methyl-1H-pyrazol-3-yl)amino)-pyridin-2-yl)methyl)piperidine-4-carboxylic acid | ¹H NMR (400 MHz, MeOD) δ 7.49 (d, J = 7.5 Hz, 1H), 7.40-7.20 (m, 2H), 6.78 (d, J = 4.6 Hz, 1H), 5.99 (s, 1H), 3.70 (d, J = 12.8 Hz, 2H), 3.45 (d, J = 19.0 Hz, 2H), 3.21 (s, 2H), 3.09 (t, J = 12.9 Hz, 2H), 2.50 (t, J = 16.2 Hz, 2H), 2.36 (d, J = 20.6 Hz, 6H), 2.00 (t, J = 13.8 Hz, 2H), 0.00 (d, J = 3.1 Hz, 2H). MS: 520 (M + H)⁺ |
| 58 | 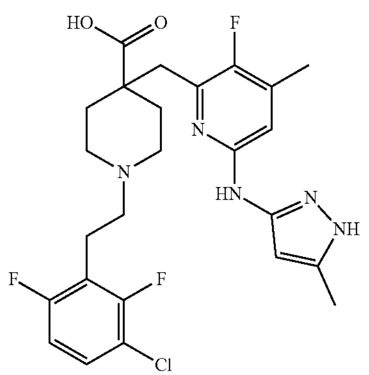 [SMILES: Cc1cc(Nc2cc(C)c(F)c(CC3(C(=O)O)CCN(CCc4c(F)ccc(Cl)c4F)CC3)n2)n[nH]1] | 1-(3-chloro-2,6-difluorophenethyl)-4-((3-fluoro-4-methyl-6-((5-methyl-1H-pyrazol-3-yl)amino)pyridin-2-yl)methyl)-piperidine-4-carboxylic acid | ¹H NMR (400 MHz, MeOD) δ 7.48 (dd, J = 14.4, 8.6 Hz, 1H), 7.06 (t, J = 8.8 Hz, 1H), 6.76 (d, J = 4.7 Hz, 1H), 5.96 (s, 1H), 3.69 (d, J = 10.1 Hz, 2H), 3.15 (d, J = 21.2 Hz, 4H), 2.49 (d, J = 13.7 Hz, 2H), 2.34 (d, J = 17.2 Hz, 6H), 1.95 (s, 2H), 0.01--0.01 (m, 4H). MS: 522 (M + H)⁺ |
| 59 | 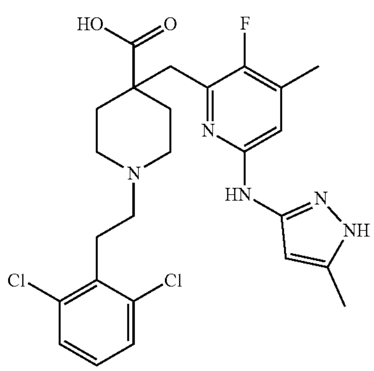 [SMILES: Cc1cc(Nc2cc(C)c(F)c(CC3(C(=O)O)CCN(CCc4c(Cl)cccc4Cl)CC3)n2)n[nH]1] | 1-(2,6-dichlorophenethyl)-4-((3-fluoro-4-methyl-6-((5-methyl-1H-pyrazol-3-yl)amino)-pyridin-2-yl)methyl)piperidine-4-carboxylic acid | ¹H NMR (400 MHz, MeOD) δ 7.43 (d, J = 8.0 Hz, 2H), 7.29 (t, J = 8.0 Hz, 1H), 6.77 (d, J = 4.7 Hz, 1H), 5.97 (s, 1H), 3.75 (d, J = 12.0 Hz, 2H), 3.39 (t, J = 19.5 Hz, 3H), 3.28-3.04 (m, 5H), 2.50 (d, J = 13.3 Hz, 2H), 2.35 (d, J = 18.0 Hz, 6H), 2.01 (d, J = 13.7 Hz, 2H). MS: 520 (M + H)⁺ |
| 60 | 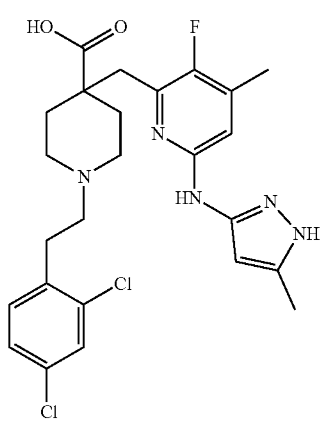 [SMILES: Cc1cc(Nc2cc(C)c(F)c(CC3(C(=O)O)CCN(CCc4ccc(Cl)cc4Cl)CC3)n2)n[nH]1] | 1-(2,4-dichlorophenethyl)-4-((3-fluoro-4-methyl-6-((5-methyl-1H-pyrazol-3-yl)amino)-pyridin-2-yl)methyl)piperidine-4-carboxylic acid | ¹H NMR (400 MHz, MeOD) δ 7.51 (s, 1H), 7.35 (dd, J = 15.7, 8.1 Hz, 2H), 6.77 (d, J = 4.7 Hz, 1H), 5.97 (s, 1H), 3.69 (d, J = 12.3 Hz, 2H), 3.19 (s, 4H), 3.09 (t, J = 13.3 Hz, 2H), 2.48 (d, J = 14.3 Hz, 2H), 2.35 (d, J = 18.3 Hz, 6H), 1.97 (t, J = 12.9 Hz, 2H), −0.00 (s, 2H). MS: 520 (M + H)⁺ |

TABLE 5-continued

| Example No. | Structure | Chemical Name | ¹HNMR & MS: (M + H)⁺ |
|---|---|---|---|
| 61 | 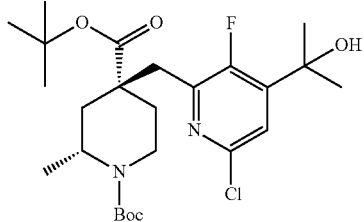 | (2R,4R)-1-(2,3-difluoro-benzyl)-4-((3-fluoro-4-methyl-6-((5-methyl-1H-pyrazol-3-yl)-amino)pyridin-2-yl)methyl)-2-methylpiperidine-4-carboxylic acid | $^1$H NMR (400 MHz, MeOD) δ 7.60 (dd ,J = 14.3, 8.6 Hz, 1H), 7.13 (t, J = 8.8 Hz, 1H), 6.64 (s, 1H), 5.77 (d, J = 17.9 Hz, 1H), 4.41 (d, J = 13.4 Hz, 1H), 3.87 (d, J = 11.7 Hz, 1H), 3.20 (d, J = 38.9 Hz, 3H), 3.03 (s, 1H), 2.88 (d, J = 12.7 Hz, 1H), 2.24 (d, J = 16.1 Hz, 6H), 1.95 (dd, J = 38.0, 18.5 Hz, 4H), 1.43-1.37 (m, 3H). MS: 488 (M + H)⁺ |

Example 62

(2R,4R)-1-(3-chloro-2-fluorobenzyl)-4-((3-fluoro-4-(2-hydroxypropan-2-yl)-6-((5-methyl-1H-pyrazol-3-yl)amino)pyridin-2-yl)methyl)-2-methylpiperidine-4-carboxylic acid Step 1: di-tert-butyl-(2R,4R)-4-((6-chloro-3-fluoro-4-(2-hydroxypropan-2-yl)pyridin-2-yl)methyl)-2-methylpiperidine-1,4-dicarboxylate

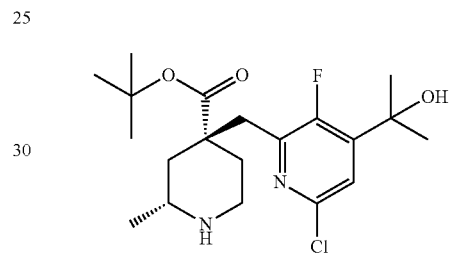

A solution of diisopropylamine (365 mg, 3.607 mmol) in THF (5 mL) was added n-butyl lithium (2.5M) in hexane (1.2 mL, 3.000 mmol) at −78° C. under nitrogen. The solution was stirred at 0° C. for 30 min before it was added a solution of INT C3 (616 mg, 1.391 mmol) in THF (5 ml) dropwise at −70° C. The resulting solution was stirred at −40° C. for 1 h. The resulting solution was added a solution of acetone (1.17 g, 0.202 mol) in THF (5 ml) dropwise over 10 min maintaining the internal temperature below −70° C. and stirred for 1 h. The reaction was quenched with saturated aqueous NH₄Cl solution. The resulting mixture was extracted with ethyl acetate. The organic layer was dried over anhydrous sodium sulfate, filtered and concentrated under reduced pressure. The resulting residue was purified by C18 reversed phase column chromatography eluting with H₂O/ACN to afford di-tert-butyl-(2R,4R)-4-((6-chloro-3-fluoro-4-(2-hydroxypropan-2-yl)pyridin-2-yl)methyl)-2-methylpiperidine-1,4-dicarboxylate (519 mg, Y=74%) as yellow oil. LCMS (ESI, m/z): 501 [M+H]⁺.

Step 2: tert-butyl-(2R,4R)-4-((6-chloro-3-fluoro-4-(2-hydroxypropan-2-yl)pyridin-2-yl)methyl)-2-methylpiperidine-4-carboxylate

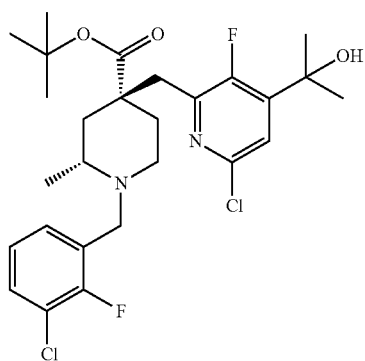 [SMILES: C[C@@H]1C[C@](Cc2nc(Cl)cc(C(C)(C)O)c2F)(C(=O)OC(C)(C)C)CCN1Cc1cccc(Cl)c1F]

Following the procedure analogous to that described in Step 3 for the synthesis of Example 5, di-tert-butyl-(2R,4R)-4-((6-chloro-3-fluoro-4-(2-hydroxypropan-2-yl)pyridin-2-yl)methyl)-2-methylpiperidine-1,4-dicarboxylate (519 mg, 1.036 mmol) was converted to the title compound (326 mg, Y=79%) as a yellow oil. LCMS (ESI, m/z): 401 [M+H]⁺.

Step 3: tert-butyl-(2R,4R)-1-(3-chloro-2-fluorobenzyl)-4-((6-chloro-3-fluoro-4-(2-hydroxypropan-2-yl)pyridin-2-yl)methyl)-2-methylpiperidine-4-carboxylate Following the procedure analogous to that described in Step 4 for the synthesis of Example 5, tert-butyl-(2R,4R)-4-((6-chloro-3-fluoro-4-(2-hydroxypropan-2-yl)-pyridin-2-yl)methyl)-2-methylpiperidine-4-carboxylate (326 mg, 0.813 mmol) was converted to the title compound (377 mg, Y=85%) as a yellow oil. LCMS (ESI, m/z): 543 [M+H]⁺.

Step 4: tert-butyl-(2R,4R)-4-((6-((1-(tert-butyl)-5-methyl-1H-pyrazol-3-yl)amino)-3-fluoro-4-(2-hydroxypropan-2-yl)pyridin-2-yl)methyl)-1-(3-chloro-2-fluorobenzyl)-2-methylpiperidine-4-carboxylate

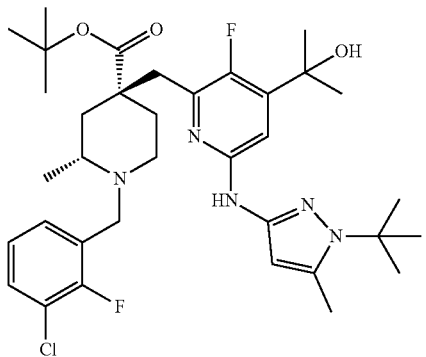 [SMILES: Cc1cc(Nc2cc(C(C)(C)O)c(F)c(C[C@@]3(C(=O)OC(C)(C)C)CCN(Cc4cccc(Cl)c4F)[C@H](C)C3)n2)nn1C(C)(C)C]

Following the procedure analogous to that described in Step 2 for the synthesis of Example 5, tert-butyl-(2R,4R)-1-(3-chloro-2-fluorobenzyl)-4-((6-chloro-3-fluoro-4-(2-hydroxypropan-2-yl) pyridin-2-yl)methyl)-2-methylpiperidine-4-carboxylate (243 mg, 0.447 mmol) was converted to the title compound (168 mg, Y=57%) as a yellow oil. LCMS (ESI, m/z): 660 [M+H]⁺.

Step 5: (2R,4R)-1-(3-chloro-2-fluorobenzyl)-4-((3-fluoro-4-(2-hydroxypropan-2-yl)-6-((5-methyl-1H-pyrazol-3-yl)amino)pyridin-2-yl)methyl)-2-methylpiperidine-4-carboxylic acid

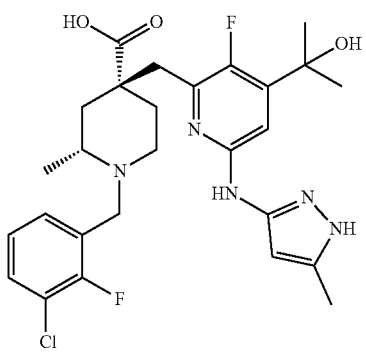 [SMILES: Cc1cc(Nc2cc(C(C)(C)O)c(F)c(C[C@@]3(C(=O)O)CCN(Cc4cccc(Cl)c4F)[C@H](C)C3)n2)n[nH]1]

Following the procedure analogous to that described in Step 5 for the synthesis of Example 5, tert-butyl-(2R,4R)-4-((6-((1-(tert-butyl)-5-methyl-1H-pyrazol-3-yl)-amino)-3-fluoro-4-(2-hydroxypropan-2-yl)pyridin-2-yl)methyl)-1-(3-chloro-2-fluorobenzyl)-2-methylpiperidine-4-carboxylate (168 mg, 0.254 mmol) was converted to the title compound (34 mg) as a white solid. LCMS (ESI, m/z): 548 [M+H]⁺. NMR (400 MHz, MeOD) δ 7.34 (m, 2H), 7.08 (t, J=7.7 Hz, 1H), 6.84 (s, 1H), 5.56 (s, 1H), 4.13 (s, 1H), 3.52 (d, J=17.6 Hz, 2H), 3.12 (d, J=6.6 Hz, 2H), 2.74 (s, 2H), 2.11 (s, 3H), 1.76 (s, 2H), 1.69 (s, 2H), 1.45 (s, 6H), 1.19 (s, 3H).

Example 63

(2R,4R)-1-(3-chloro-2-fluorobenzyl)-4-((3-fluoro-4-isopropyl-6-((5-methyl-1H-pyrazol-3-yl)amino)pyridin-2-yl)methyl)-2-methylpiperidine-4-carboxylic acid Step 1: tert-butyl-(2R,4R)-1-(3-chloro-2-fluorobenzyl)-4-((6-chloro-3-fluoro-4-(prop-1-en-2-yl)pyridin-2-yl)methyl)-2-methylpiperidine-4-carboxylate

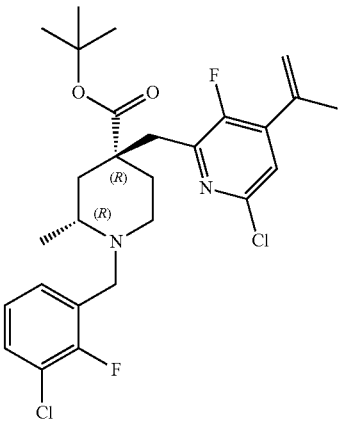

To a solution of tert-butyl-(2R,4R)-1-(3-chloro-2-fluorobenzyl)-4-((6-chloro-3-fluoro-4-(2-hydroxypropan-2-yl) pyridin-2-yl)methyl)-2-methylpiperidine-4-carboxylate (185 mg, 0.340 μmol) in THF (5 mL) was added thionyl chloride (2.5 ml) and pyridine (1 mL). The reaction mixture was stirred at room temperature for 2 h. The resulting mixture was quenched with saturated sodium bicarbonate aqueous solution and extracted with DCM (50 mL). The organic layer was washed with brine (50 mL), dried over anhydrous sodium sulfate, filtered and concentrated under reduced pressure. The resulting residue was purified by C18 reversed phase column chromatography eluting with H₂O/ACN to afford tert-butyl (2R,4R)-1-(3-chloro-2-fluorobenzyl)-4-((6-chloro-3-fluoro-4-(prop-1-en-2-yl)pyridin-2-yl) methyl)-2-methylpiperidine-4-carboxylate (118 mg Y=66%) as a yellow oil. LCMS (ESI, m/z): 525 [M+H]⁺.

Step 2: tert-butyl-(2R,4R)-4-((6-((1-(tert-butyl)-5-methyl-1H-pyrazol-3-yl)amino)-3-fluoro-4-(prop-1-en-2-yl)pyridin-2-yl)methyl)-1-(3-chloro-2-fluorobenzyl)-2-methylpiperidine-4-carboxylate

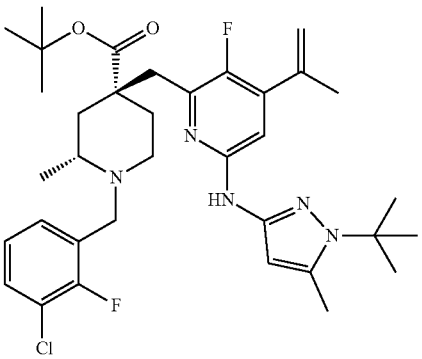 [SMILES: C=C(C)c1cc(Nc2cc(C)n(C(C)(C)C)n2)nc(C[C@@]2(C(=O)OC(C)(C)C)CCN(Cc3cccc(Cl)c3F)[C@H](C)C2)c1F]

Following the procedure analogous to that described in Step 2 for the synthesis of Example 5, tert-butyl-(2R,4R)-1-(3-chloro-2-fluorobenzyl)-4-(((6-chloro-3-fluoro-4-(prop-1-en-2-yl) pyridin-2-yl)methyl)-2-methylpiperidine-4-carboxylate (118 mg, 0.225 mmol) was converted to the title compound (111 mg, Y=77%) as a yellow oil. LCMS (ESI, m/z): 642 [M+H]⁺.

Step 3: tert-butyl-(2R,4R)-4-((6-((1-(tert-butyl)-5-methyl-1H-pyrazol-3-yl)amino)-3-fluoro-4-isopropylpyridin-2-yl)methyl)-1-(3-chloro-2-fluorobenzyl)-2-methylpiperidine-4-carboxylate

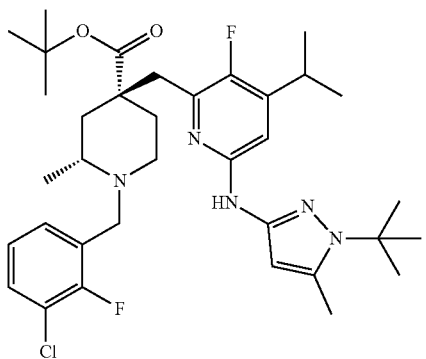

A solution of tert-butyl-(2R,4R)-4-((6-((1-(tert-butyl)-5-methyl-1H-pyrazol-3-yl)amino)-3-fluoro-4-(prop-1-en-2-yl)pyridin-2-yl)methyl)-1-(3-chloro-2-fluorobenzyl)-2-methylpiperidine-4-carboxylate (111 mg, 0.173 mmol) and Pd/C (32 mg) in ethyl acetate (20 mL) was purged it with H₂ and pressurized with H₂. The reaction mixture was stirred at room temperature for 4 h. After completion, the resulting mixture was filtrated. The filtrate was removed under reduced pressure. The resulting residue was purified by C18 reversed phase column chromatography eluting with H₂O/ACN to afford tert-butyl (2R,4R)-4-((6-((1-(tert-butyl)-5-methyl-1H-pyrazol-3-yl)amino)-3-fluoro-4-isopropylpyridin-2-yl)methyl)-1-(3-chloro-2-fluorobenzyl)-2-methylpiperidine-4-carboxylate (95 mg, Y=85%) as yellow oil. LCMS (ESI, m/z): 644 [M+H]~.

Step 4: (2R,4R)-1-(3-chloro-2-fluorobenzyl)-4-((3-fluoro-4-isopropyl-6-((5-methyl-1H-pyrazol-3-yl)amino)pyridin-2-yl)methyl)-2-methylpiperidine-4-carboxylic acid

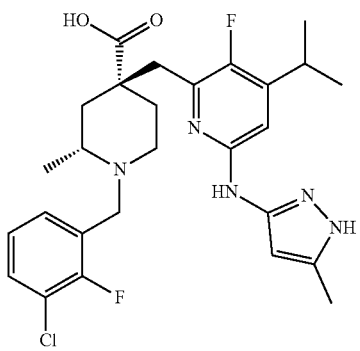 [SMILES: Cc1cc(Nc2cc(C(C)C)c(F)c(C[C@@]3(C(=O)O)CCN(Cc4cccc(Cl)c4F)[C@H](C)C3)n2)n[nH]1]

Following the procedure analogous to that described in Step 5 for the synthesis of Example 5, tert-butyl-(2R,4R)-4-((6-((1-(tert-butyl)-5-methyl-1H-pyrazol-3-yl)-amino)-3-fluoro-4-isopropylpyridin-2-yl)methyl)-1-(3-chloro-2-fluorobenzyl)-2-methylpiperidine-4-carboxylate (95 mg, 0.147 mmol) was converted to the title compound (35 mg) as a white solid. LCMS (ESI, m/z): 532 [M+H]⁺. ¹H NMR (400 MHz, MeOD) δ 7.68 (t, J=7.6 Hz, 1H), 7.56 (dd, J=16.2, 8.7 Hz, 1H), 7.33 (t, J=7.9 Hz, 1H), 6.78 (d, J=4.6 Hz, 1H), 5.97 (s, 1H), 3.41 (d, J=5.5 Hz, 4H), 3.20 (m, 2H), 2.38 (s, 3H), 2.13 (m, 6H), 1.59 (d, J=6.0 Hz, 3H), 1.29 (d, J=6.9 Hz, 6H).

Example 64

(2R,4R)-1-(3-chloro-2-fluorobenzyl)-4-((4-(difluoromethyl)-3-fluoro-6-((5-methyl-1H-pyrazol-3-yl)amino)pyridin-2-yl)methyl)-2-methylpiperidine-4-carboxylic acid Step 1: di-tert-butyl-(2R,4R)-4-((6-chloro-3-fluoro-4-formylpyridin-2-yl)methyl)-2-methylpiperidine-1,4-dicarboxylate

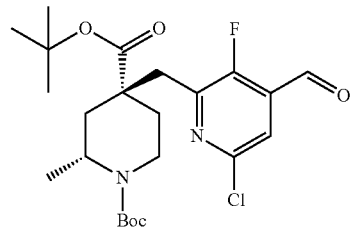 [SMILES: C[C@@H]1C[C@](Cc2nc(Cl)cc(C=O)c2F)(C(=O)OC(C)(C)C)CCN1C(=O)OC(C)(C)C]

A solution of diisopropylamine (1.68 g, 16.603 mmol) in THF (10 mL) was added n-butyl lithium (2.5M) in hexane (4 mL, 10.00 mmol) at −78° C. under nitrogen. The solution was stirred at 0° C. for 30 min. The resulting solution was added a solution of INT C3 (2.16 g, 4.876 mmol) in THF (15 ml) dropwise over 10 min maintaining the internal temperature below −78° C. and stirred at −40° C. for 1 h.

A solution of DMF (2.19 g, 29.962 mmol) in THF (5 ml) was added to the above solution at −78° C. The resulting solution was stirred at −78° C. for 1 h. The reaction was quenched with saturated NH₄Cl aqueous solution. The resulting mixture was extracted with ethyl acetate. The organic layer was dried over anhydrous sodium sulfate, filtered and concentrated under reduced pressure. The resulting residue was purified by C18 reversed phase column chromatography eluting with H₂O/ACN to afford di-tert-butyl-(2R,4R)-4-((6-chloro-3-fluoro-4-formylpyridin-2-yl)methyl)-2-methylpiperidine-1,4-dicarboxylate (1316 mg, Y=57%) as yellow oil. LCMS (ESI, m/z): 471 [M+H]⁺.

Step 2: di-tert-butyl-(2R,4R)-4-((6-chloro-4-(difluoromethyl)-3-fluoropyridin-2-yl)methyl)-2-methylpiperidine-1,4-dicarboxylate

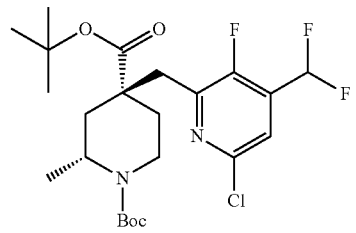 [SMILES: C[C@@H]1C[C@](Cc2nc(Cl)cc(C(F)F)c2F)(C(=O)OC(C)(C)C)CCN1C(=O)OC(C)(C)C]

To a solution of di-tert-butyl-(2R,4R)-4-((6-chloro-3-fluoro-4-formylpyridin-2-yl)methyl)-2-methylpiperidine-1,4-dicarboxylate (0.189 g, 401.307 μmol) in DCM (50 ml) was added DAST (0.5 ml). The reaction was stirred at room temperature for 2 h. The reaction was quenched with saturated sodium bicarbonate aqueous solution. The resulting mixture was extracted with DCM. The organic layer was washed with brine, dried over anhydrous sodium sulfate, filtered and concentrated under reduced pressure. The resulting residue was purified by C18 reversed phase column chromatography eluting with $H_2O$/ACN to afford di-tert-butyl-(2R,4R)-4-((6-chloro-4-(difluoromethyl)-3-fluoropyridin-2-yl)methyl)-2-methylpiperidine-1,4-dicarboxylate (151 mg Y=76%) as a yellow oil. LCMS (ESI, m/z): 493 [M+H]$^+$.

Step 3: di-tert-butyl-(2R,4R)-4-((6-((1-(tert-butyl)-5-methyl-1H-pyrazol-3-yl)amino)-4-(difluoromethyl)-3-fluoropyridin-2-yl)methyl)-2-methylpiperidine-1,4-dicarboxylate

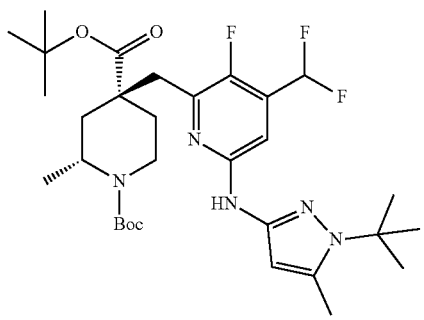 [SMILES: Cc1cc(Nc2cc(C(F)F)c(F)c(C[C@@]3(C(=O)OC(C)(C)C)CCN(C(=O)OC(C)(C)C)[C@H](C)C3)n2)nn1C(C)(C)C]

Following the procedure analogous to that described in Step 2 for the synthesis of Example 5, di-tert-butyl-(2R,4R)-4-((6-chloro-4-(difluoromethyl)-3-fluoropyridin-2-yl)methyl)-2-methylpiperidine-1,4-dicarboxylate (0.151 g, 306.314 μmol) was converted to the title compound (107 mg, Y=57%) as a yellow oil. LCMS (ESI, m/z): 610 [M+H]$^+$.

Step 4: tert-butyl-(2R,4R)-4-((6-((1-(tert-butyl)-5-methyl-1H-pyrazol-3-yl)amino)-4-(difluoromethyl)-3-fluoropyridin-2-yl)methyl)-2-methylpiperidine-4-carboxylate

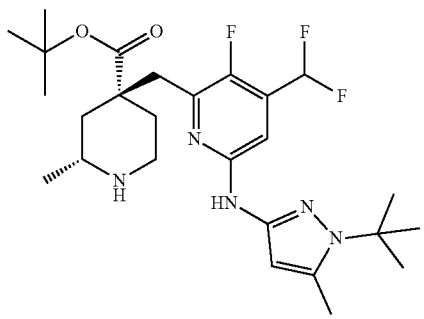 [SMILES: Cc1cc(Nc2cc(C(F)F)c(F)c(C[C@@]3(C(=O)OC(C)(C)C)CCN[C@H](C)C3)n2)nn1C(C)(C)C]

Following the procedure analogous to that described in Step 3 for the synthesis of Example 5, di-tert-butyl-(2R,4R)-4-((6-((1-(tert-butyl)-5-methyl-1H-pyrazol-3-yl)amino)-4-(difluoromethyl)-3-fluoropyridin-2-yl)methyl)-2-methylpiperidine-1,4-dicarboxylate (0.107 g, 175.490 μmol) was converted to the title compound (72 mg, Y=80%) as a yellow oil. LCMS (ESI, m/z): 510 [M+H]$^+$.

Step 5: tert-butyl-(2R,4R)-4-((6-((1-(tert-butyl)-5-methyl-1H-pyrazol-3-yl)amino)-4-(difluoromethyl)-3-fluoropyridin-2-yl)methyl)-1-(3-chloro-2-fluorobenzyl)-2-methylpiperidine-4-carboxylate

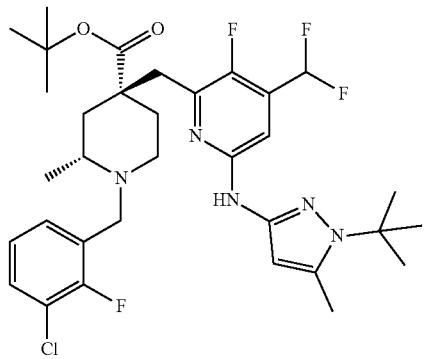 [SMILES: Cc1cc(Nc2cc(C(F)F)c(F)c(C[C@@]3(C(=O)OC(C)(C)C)CCN(Cc4cccc(Cl)c4F)[C@H](C)C3)n2)nn1C(C)(C)C]

Following the procedure analogous to that described in Step 4 for the synthesis of Example 5, tert-butyl-(2R,4R)-4-((6-((1-(tert-butyl)-5-methyl-1H-pyrazol-3-yl)amino)-4-(difluoromethyl)-3-fluoropyridin-2-yl)methyl)-2-methylpiperidine-4-carboxylate (72 mg, 141.176 μmol) was converted to the title compound (68 mg, Y=74%) as a yellow oil. LCMS (ESI, m/z): 652 [M+H]$^+$.

Step 6: (2R,4R)-1-(3-chloro-2-fluorobenzyl)-4-((4-(difluoromethyl)-3-fluoro-6-((5-methyl-1H-pyrazol-3-yl)amino)pyridin-2-yl)methyl)-2-methylpiperidine-4-carboxylic acid

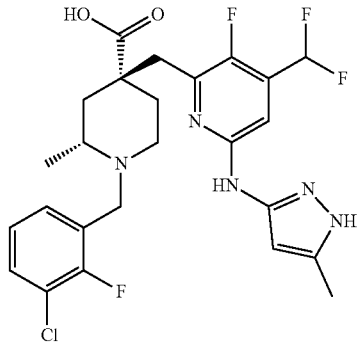 [SMILES: Cc1cc(Nc2cc(C(F)F)c(F)c(C[C@@]3(C(=O)O)CCN(Cc4cccc(Cl)c4F)[C@H](C)C3)n2)n[nH]1]

Following the procedure analogous to that described in Step 5 for the synthesis of Example 5, tert-butyl-(2R,4R)-4-((6-((1-(tert-butyl)-5-methyl-1H-pyrazol-3-yl)-amino)-4-(difluoromethyl)-3-fluoropyridin-2-yl)methyl)-1-(3-chloro-2-fluorobenzyl)-2-methylpiperidine-4-carboxylate (68 mg, 104.294 μmol) was converted to the title compound (11 mg) as a white solid. LCMS (ESI, m/z): 540 [M+H]$^+$. NMR (400 MHz, DMSO) δ 7.77 (t, J=7.1 Hz, 1H), 7.60 (t, J=6.5 Hz, 1H), 7.39 (t, J=7.9 Hz, 1H), 7.30-7.01 (m, 2H), 6.12 (s, 1H), 4.85 (d, J=13.4 Hz, 1H), 4.36-4.23 (m, 1H), 3.89 (s, 2H), 3.28-3.12 (m, 3H), 2.71-2.64 (m, 1H), 2.32 (dd, J=11.0, 9.2 Hz, 1H), 2.28-2.13 (m, 3H), 1.97-1.81 (m, 2H), 1.42 (t, J=27.9 Hz, 3H).

Example 65

(2R,4R)-1-(3-chloro-2-fluorobenzyl)-4-((4-ethyl-3-fluoro-6-((5-methyl-1H-pyrazol-3-yl)amino)pyridin-2-yl)methyl)-2-methylpiperidine-4-carboxylic acid

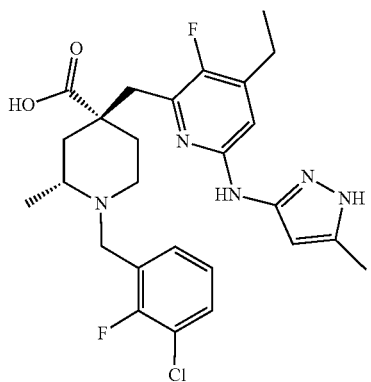

Step 1: di-tert-butyl-(2R,4R)-4-((6-chloro-3-fluoro-4-iodopyridin-2-yl)methyl)-2-methylpiperidine-1,4-dicarboxylate

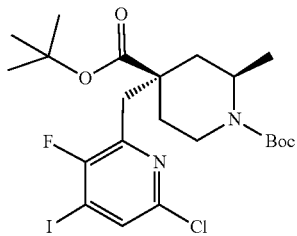 [SMILES: C[C@@H]1C[C@](Cc2nc(Cl)cc(I)c2F)(C(=O)OC(C)(C)C)CCN1C(=O)OC(C)(C)C]

To a solution of diisopropylamine (1.380 g, 13.636 mmol) in THF (15 mL) was added n-butyl lithium (2.5M) in hexane (2.4 mL, 6.00 mmol) dropwise at −78° C. under nitrogen. The resulting solution was stirred at 0° C. for 30 min. A solution of INT C3 (3.02 g, 6.818 mmol) in THF (10 ml) was added below −78° C. The mixture was stirred at −78° C. for 1 h.

The resulting mixture was added a solution of iodine (2.06 g, 8.116 mmol) in THF (5 ml) dropwise at −70° C. The reaction solution was stirred at −60° C. for 1 h before it was quenched with saturated NH$_4$Cl aqueous solution. The resulting mixture was extracted with ethyl acetate. The organic layer was dried over anhydrous sodium sulfate, filtered and concentrated under reduced pressure. The resulting residue was purified by C18 reversed phase column chromatography eluting with H$_2$O/ACN to afford di-tert-butyl-(2R,4R)-4-((6-chloro-3-fluoro-4-iodopyridin-2-yl)methyl)-2-methylpiperidine-1,4-dicarboxylate (2.8 g, Y=72%) as a yellow solid. LCMS (ESI, m/z): 569 [M+H]$^+$ Step 2: di-tert-butyl (2R,4R)-4-((6-chloro-3-fluoro-4-vinylpyridin-2-yl)methyl)-2-methylpiperidine-1,4-dicarboxylate

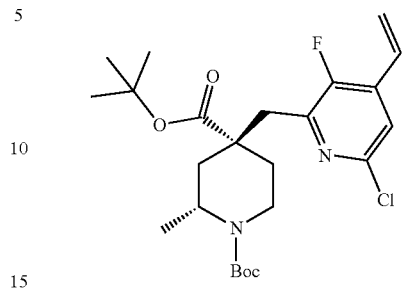

A solution of di-tert-butyl (2R,4R)-4-((6-chloro-3-fluoro-4-iodopyridin-2-yl)methyl)-2-methylpiperidine-1,4-dicarboxylate (504 mg, 886.003 µmol), tributyl(vinyl)tin (310 mg, 977.619 µmol), C$_s$F (180 mg, 1.185 mmol) and tetrakis(triphenylphosphine)palladium (112 mg, 737.311 µmol) in 1,4-Dioxane (15 mL) was stirred at 95° C. for 4 h under nitrogen. The mixture was cooled to room temperature. The resulting solution was diluting with EtOAc (130 mL) and washed with brine. The organic layer was dried over anhydrous sodium sulfate, filtered and concentrated under reduced pressure. The resulting residue was purified by silica gel column chromatography eluting with EtOAc/hexane (0~10%) to afford the title compound (394 mg, Y=95%) as a white oil. LCMS (ESI, m/z): 469 [M+H]$^+$.

Step 3: di-tert-butyl-(2R,4R)-4-((6-((1-(tert-butyl)-5-methyl-1H-pyrazol-3-yl)amino)-3-fluoro-4-vinylpyridin-2-yl)methyl)-2-methylpiperidine-1,4-dicarboxylate

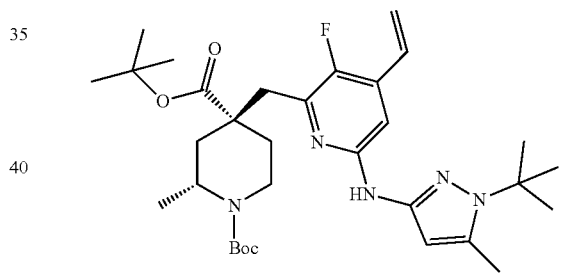

Following the procedure analogous to that described in Step 2 for the synthesis of Example 5, di-tert-butyl(2R,4R)-4-((6-chloro-3-fluoro-4-vinylpyridin-2-yl)methyl)-2-methylpiperidine-1,4-dicarboxylate (394 mg, 840.107 µmol) was converted to the title compound (110 mg, Y=22%) as a white oil. LCMS (ESI, m/z): 586 [M+H]$^+$.

Step 4; di-tert-butyl (2R,4R)-4-((6-((1-(tert-butyl)-5-methyl-1H-pyrazol-3-yl)-amino)-4-ethyl-3-fluoropyridin-2-yl)methyl)-2-methylpiperidine-1,4-dicarboxylate

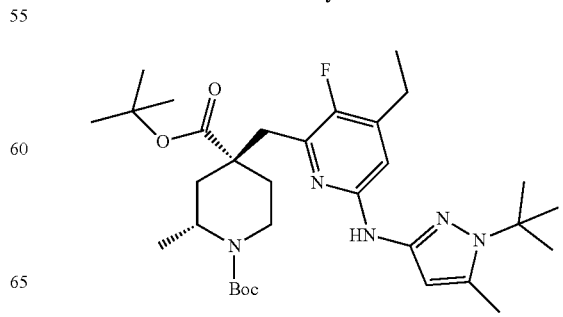

A solution of di-tert-butyl (2R,4R)-4-((6-((1-(tert-butyl)-5-methyl-1H-pyrazol-3-yl)amino)-3-fluoro-4-vinylpyridin-2-yl)methyl)-2-methylpiperidine-1,4-dicarboxylate (110 mg, 187.793 µmol) and Pd/C (175 mg) in MeOH (10 mL) was purged with H₂ and pressurized with H₂. The resulting mixture was stirred at room temperature for 4 h. After completion, the mixture was filtered and the filter cake was washed with MeOH. The filtrate was concentrated under reduced pressure to afford the title compound (110 mg) as a yellow oil. LCMS (ESI, m/z): 588 [M+H]⁺.

Step 5: tert-butyl (2R,4R)-4-((6-((1-(tert-butyl)-5-methyl-1H-pyrazol-3-yl)amino)-4-ethyl-3-fluoro-pyridin-2-yl)methyl)-2-methylpiperidine-4-carboxylate

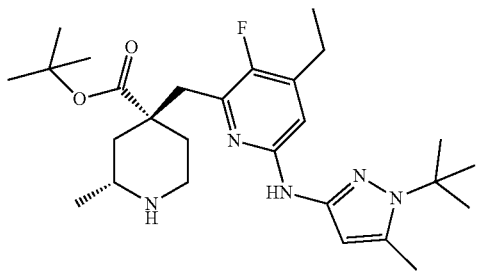 [SMILES: CCc1cc(Nc2cc(C)n(C(C)(C)C)n2)nc(C[C@@]2(C(=O)OC(C)(C)C)CCN[C@H](C)C2)c1F]

Following the procedure analogous to that described in Step 3 for the synthesis of Example 5, di-tert-butyl (2R,4R)-4-((6-((1-(tert-butyl)-5-methyl-1H-pyrazol-3-yl)amino)-4-ethyl-3-fluoropyridin-2-yl)methyl)-2-methylpiperidine-1,4-dicarboxylate (110 mg, 187.15 µmol) was converted to the title compound (107 mg) as a crude yellow oil. LCMS (ESI, m/z): 488 [M+H]⁺.

Step 6: tert-butyl (2R,4R)-4-((6-((1-(tert-butyl)-5-methyl-1H-pyrazol-3-yl)amino)-4-ethyl-3-fluoro-pyridin-2-yl)methyl)-1-(3-chloro-2-fluorobenzyl)-2-methylpiperidine-4-carboxylate

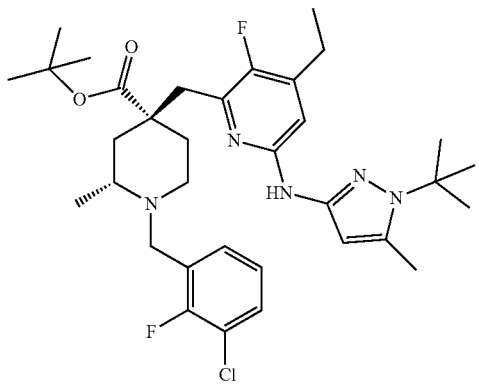 [SMILES: CCc1cc(Nc2cc(C)n(C(C)(C)C)n2)nc(C[C@@]2(C(=O)OC(C)(C)C)CCN(Cc3cccc(Cl)c3F)[C@H](C)C2)c1F]

Following the procedure analogous to that described in Step 4 for the synthesis of Example 5, tert-butyl (2R,4R)-4-((6-((1-(tert-butyl)-5-methyl-1H-pyrazol-3-yl)amino)-4-ethyl-3-fluoropyridin-2-yl)methyl)-2-methylpiperidine-4-carboxylate (107 mg) was converted to the title compound (70 mg, Y=50%) as a yellow oil. LCMS (ESI, m/z): 616 [M+H]⁺.

Step 7: (2R,4R)-1-(3-chloro-2-fluorobenzyl)-4-((4-ethyl-3-fluoro-6-((5-methyl-1H-pyrazol-3-yl)amino)pyridin-2-yl)methyl)-2-methylpiperidine-4-carboxylic acid

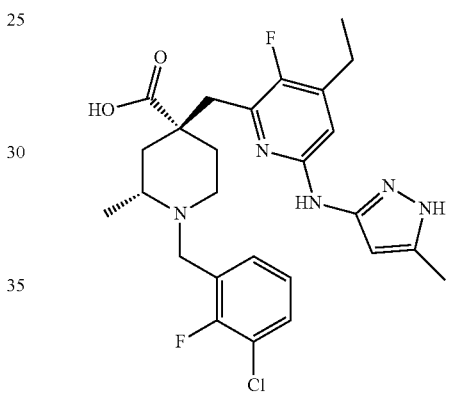

Following the procedure analogous to that described in Step 5 for the synthesis of Example 5, tert-butyl (2R,4R)-4-((6-((1-(tert-butyl)-5-methyl-1H-pyrazol-3-yl)amino)-4-ethyl-3-fluoropyridin-2-yl)methyl)-1-(3-chloro-2-fluorophenyl)-2-methylpiperidine-4-carboxylate (70 mg, 110.074 µmol) was converted to the title compound (38 mg, Y=71%) as a white solid. LCMS (ESI, m/z): 518 [M+H]⁺. ¹H NMR (400 MHz, MeOD) δ 7.69-7.66 (t, J=7.4 Hz, 1H), 7.56-7.54 (t, J=6.7 Hz, 1H), 7.34-7.32 (t, J=7.8 Hz, 1H), 6.77 (d, J=4.3 Hz, 1H), 5.98 (s, 1H), 4.36 (s, 1H), 3.90 (s, 1H), 3.41 (s, 4H), 2.73 (q, J=7.5 Hz, 3H), 2.38 (s, 3H), 2.20 (s, 2H), 2.08-2.06 (m, 2H), 1.60-1.57 (s, 3H), 1.29-1.24 (t, J=7.4 Hz, 3H).

The following example in Table 6 was synthesized using the above procedure with the corresponding starting materials and intermediates.

TABLE 6

| Example No. | Structure | Chemical Name | $^1$HNMR & MS: $(M + H)^+$ |
|---|---|---|---|
| 66 | 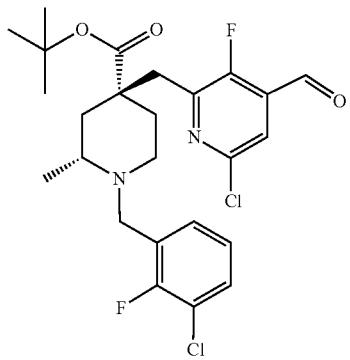 | 1-(3-chloro-2-fluorobenzyl)-4-((4-ethyl-3-fluoro-6-((5-methyl-1H-pyrazol-3-yl)amino)-pyridin-2-yl)methyl)piperidine-4-carboxylic acid | NMR (400 MHz, MeOD) δ 7.66 (t, J = 7.3 Hz, 2H), 7.32 (t, J = 7.6 Hz, 1H), 6.85 (d, J = 4.4 Hz, 1H), 6.03 (s, 1H), 4.46 (s, 2H), 3.61-3.50 (m, 2H), 3.25 (s, 2H), 3.13 (t, J = 12.3 Hz, 2H), 2.73 (q, J = 7.5 Hz, 2H), 2.44 (d, J = 14.4 Hz, 5H), 2.12 (t, J = 13.0 Hz, 2H), 1.25 (dt, J = 26.2, 12.3 Hz, 3H). MS: 504 (M + H)$^+$ |

Example 67

(2R,4R)-1-(3-chloro-2-fluorobenzyl)-4-((4-cyano-3-fluoro-6-((3-methyl-1H-pyrazol-5-yl)amino)pyridin-2-yl)methyl)-2-methylpiperidine-4-carboxylic acid Step 1: tert-butyl (2R,4R)-1-(3-chloro-2-fluorobenzyl)-4-((6-chloro-3-fluoro-4-formylpyridin-2-yl)methyl)-2-methylpiperidine-4-carboxylate A solution of tert-butyl-(2R,4R)-1-(3-chloro-2-fluorobenzyl)-4-((6-chloro-3-fluoropyridin-2-yl)methyl)-2-methylpiperidine-4-carboxylate (0.258 g, 531.528 μmol) in THF (10 mL) was added lithium diisopropylamide (2.0M) in hexane (2.0 mL, 4.000 mmol) at −78° C. under nitrogen. The resulting solution was stirred at −40° C. for 1 h.

A solution of DMF (0.5 mL) in THF (10 ml) was added dropwise to the above solution at −78° C. The resulting solution was stirred at −78° C. for 1 h. The reaction was quenched with saturated aqueous NH$_4$Cl aqueous solution. The resulting mixture was extracted with ethyl acetate. The organic layer was dried over anhydrous sodium sulfate, filtered and concentrated under reduced pressure. The resulting residue was purified by C18 reversed phase column chromatography eluting with H$_2$O/ACN to afford tert-butyl-(2R,4R)-1-(3-chloro-2-fluorobenzyl)-4-((6-chloro-3-fluoro-4-formylpyridin-2-yl)methyl)-2-methylpiperidine-4-carboxylate (78 mg, Y=29%) as a yellow oil. LCMS (ESI, m/z): 513 [M+H]$^+$.

Step 2: tert-butyl (2R,4R)-4-((6-((1-(tert-butyl)-3-methyl-1H-pyrazol-5-yl)amino)-3-fluoro-4-formylpyridin-2-yl)methyl)-1-(3-chloro-2-fluorobenzyl)-2-methylpiperidine-4-carboxylate

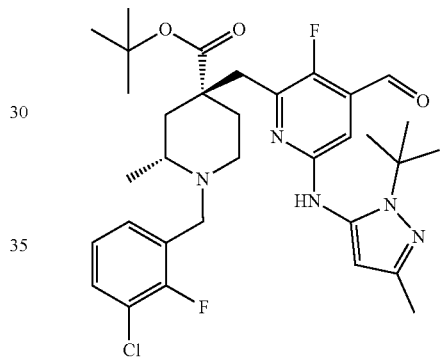

Following the procedure analogous to that described in Step 2 for the synthesis of Example 5, tert-butyl (2R,4R)-1-(3-chloro-2-fluorobenzyl)-4-((6-chloro-3-fluoro-4-formylpyridin-2-yl) methyl)-2-methylpiperidine-4-carboxylate (78 mg, 151.927 μmol) was converted to the title compound (95 mg, Y=100%) as a yellow oil. LCMS (ESI, m/z): 630 [M+H]$^+$.

Step 3: tert-butyl (2R,4R)-4-((6-((1-(tert-butyl)-3-methyl-1H-pyrazol-5-yl)amino)-3-fluoro-4-((E)-(hydroxyimino)methyl)pyridin-2-yl)methyl)-1-(3-chloro-2-fluorobenzyl)-2-methylpiperidine-4-carboxylate

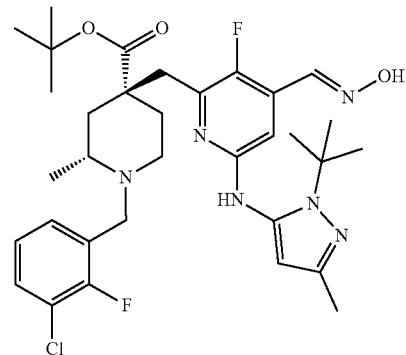 [SMILES: Cc1cc(Nc2cc(/C=N/O)c(F)c(C[C@@]3(C(=O)OC(C)(C)C)CCN(Cc4cccc(Cl)c4F)[C@H](C)C3)n2)n(C(C)(C)C)n1]

A solution of tert-butyl (2R,4R)-4-((6-((1-(tert-butyl)-3-methyl-1H-pyrazol-5-yl)amino)-3-fluoro-4-formylpyridin-2-yl)methyl)-1-(3-chloro-2-fluorobenzyl)-2-methylpiperidine-4-carboxylate (96 mg, 152.341 µmol), hydroxylammoniumchlorid (27 mg, 388.541 µmol) and potassium carbonate (75 mg, 542.670 µmol) in methanol (3 mL) was stirred for 3 h at room temperature. The resulting solution added water and extracted with ethyl acetate. The organic layer was dried over anhydrous sodium sulfate, filtered and concentrated under reduced pressure. The resulting residue was purified by C18 reversed phase column chromatography eluting with H₂O/ACN to afford (6-chloro-3-methylpyridin-2-yl)methanol (98 mg Y=100%) as a yellow oil. LCMS (ESI, m/z): 645 [M+H]⁺.

Step 4: (2R,4R)-1-(3-chloro-2-fluorobenzyl)-4-((4-cyano-3-fluoro-6-((3-methyl-1H-pyrazol-5-yl)amino)pyridin-2-yl)methyl)-2-methylpiperidine-4-carboxylic acid

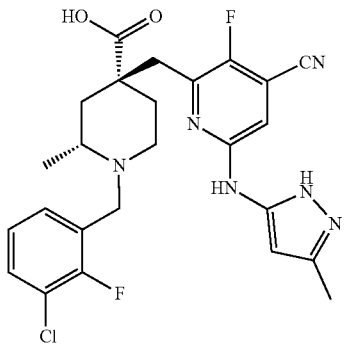 [SMILES: Cc1cc(Nc2cc(C#N)c(F)c(C[C@@]3(C(=O)O)CCN(Cc4cccc(Cl)c4F)[C@H](C)C3)n2)[nH]n1]

Following the procedure analogous to that described in Step 5 for the synthesis of Example 5, tert-butyl-(2R,4R)-4-((6-((1-(tert-butyl)-3-methyl-1H-pyrazol-5-yl)amino)-3-fluoro-4-((E)-(hydroxyimino)methyl)pyridin-2-yl)methyl)-1-(3-chloro-2-fluorobenzyl)-2-methylpiperidine-4-carboxylate (98 mg, 151.895 µmol) was converted to the title compound (7 mg) as a white solid. LCMS (ESI, m/z): 515 [M+H]⁺.

Example 68

(2R,4R)-4-((4-acetyl-3-fluoro-6-((5-methyl-1H-pyrazol-3-yl)amino)pyridin-2-yl)methyl)-1-(3-chloro-2-fluorobenzyl)-2-methylpiperidine-4-carboxylic acid Step 1: di-tert-butyl-(2R,4R)-4-((6-chloro-3-fluoro-4-iodopyridin-2-yl)methyl)-2-methylpiperidine-1,4-dicarboxylate

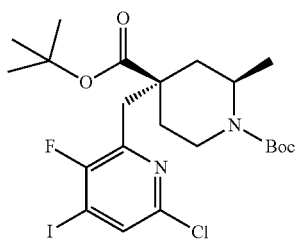 [SMILES: C[C@@H]1C[C@](Cc2nc(Cl)cc(I)c2F)(C(=O)OC(C)(C)C)CCN1C(=O)OC(C)(C)C]

Following the procedure analogous to that described in step 1 of Example 65, INT C3 (3.02 g, 6.818 mmol) was converted to the title compound (2.8 g, Y=72%) as a yellow solid. LCMS (ESI, m/z): 569 [M+H]⁺.

Step 2: di-tert-butyl (2R,4R)-4-((6-chloro-4-(1-ethoxyvinyl)-3-fluoropyridin-2-yl)methyl)-2-methylpiperidine-1,4-dicarboxylate

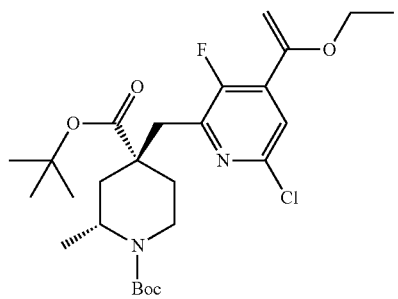 [SMILES: C=C(OCC)c1cc(Cl)nc(C[C@@]2(C(=O)OC(C)(C)C)CCN(C(=O)OC(C)(C)C)[C@H](C)C2)c1F]

To a solution of di-tert-butyl (2R,4R)-4-((6-chloro-3-fluoro-4-iodopyridin-2-yl)methyl)-2-methylpiperidine-1,4-dicarboxylate (1.54 g, 2.707 mmol) in 1,4-dioxane (20 mL) was added tributyl(1-ethoxyvinyl)-stannane (1.11 g, 3.074 mmol) bis(triphenylphosphine)palladium(II) chloride (0.39 g, 552.465 µmol) and cesium fluoride (0.84 g, 5.530 mmol) under nitrogen. The mixture was refluxed at 90° C. for 3 h. The resulting mixture was cooled to room temperature and filtrated. The filtrate was diluted with ethyl acetate and washed with brine. The organic layer was dried over anhydrous sodium sulfate, filtered and concentrated under reduced pressure. The resulting residue was purified by C18 reversed phase column chromatography eluting with H₂O/ACN to afford di-tert-butyl (2R,4R)-4-((6-amino-4-(1-ethoxyvinyl)-3-fluoropyridin-2-yl) methyl)-2-methylpiperidine-1,4-dicarboxylate (960 mg, Y=72%) as a yellow oil. LCMS (ESI, m/z): 494 [M+H]⁺.

Step 3: di-tert-butyl(2R,4R)-4-((6-((1-(tert-butyl)-5-methyl-1H-pyrazol-3-yl)amino)-4-(1-ethoxyvinyl)-3-fluoropyridin-2-yl)methyl)-2-methylpiperidine-1,4-dicarboxylate

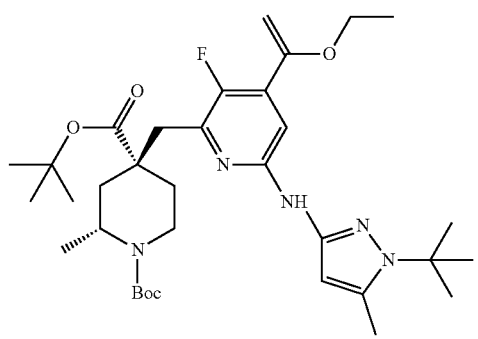 [SMILES: C=C(OCC)c1cc(Nc2cc(C)n(C(C)(C)C)n2)nc(C[C@@]2(C(=O)OC(C)(C)C)CCN(C(=O)OC(C)(C)C)[C@H](C)C2)c1F]

Following the procedure analogous to that described in step 2 of Example 5, di-tert-butyl-(2R,4R)-4-((6-amino-4-(1-ethoxyvinyl)-3-fluoropyridin-2-yl)methyl)-2-methylpiperidine-1,4-dicarboxylate (960 mg, 1.871 mmol) was converted to the title compound (1.06 g, Y=90%) as a yellow oil. LCMS (ESI, m/z): 630 [M+H]+.

Step 4: tert-butyl(2R,4R)-4-((4-acetyl-6-((1-(tert-butyl)-5-methyl-1H-pyrazol-3-yl)ami-no)-3-fluoro-pyridin-2-yl)methyl)-2-methylpiperidine-4-carboxylate

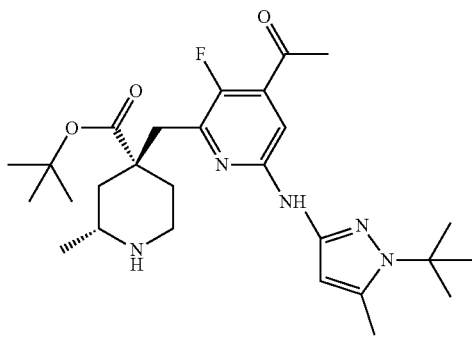 [SMILES: CC(=O)c1cc(Nc2cc(C)n(C(C)(C)C)n2)nc(C[C@@]2(C(=O)OC(C)(C)C)CCN[C@H](C)C2)c1F]

Following the procedure analogous to that described in step 3 of Example 5, di-tert-butyl(2R,4R)-4-((6-((1-(tert-butyl)-5-methyl-1H-pyrazol-3-yl)amino)-4-(1-ethoxyvinyl)-3-fluoropyridin-2-yl)methyl)-2-methylpiperidine-1,4-dicarboxylate (806 mg, 1.280 mmol) was converted to the title compound (766 mg) as a yellow oil. LCMS (ESI, m/z): 502 [M+H]+.

Step 5: tert-butyl(2R,4R)-4-((4-acetyl-6-((1-(tert-butyl)-5-methyl-1H-pyrazol-3-yl)a-mino)-3-fluoro-pyridin-2-yl)methyl)-1-(3-chloro-2-fluorobenzyl)-2-methylpiperidine-4-carboxylate

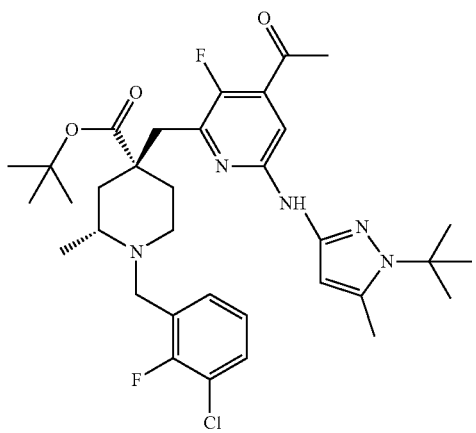 [SMILES: CC(=O)c1cc(Nc2cc(C)n(C(C)(C)C)n2)nc(C[C@@]2(C(=O)OC(C)(C)C)CCN(Cc3cccc(Cl)c3F)[C@H](C)C2)c1F]

Following the procedure analogous to that described in step 4 of Example 5, tert-butyl(2R,4R)-4-((4-acetyl-6-((1-(tert-butyl)-5-methyl-1H-pyrazol-3-yl)amino)-3-fluoropyridin-2-yl)methyl)-2-methylpiperidine-4-carboxylate (766 mg, 1.527 mmol) was converted to the title compound (420 mg) as a white solid. LCMS (ESI, m/z): 644 [M+H]+.

Step 6: (2R,4R)-4-((4-acetyl-3-fluoro-6-((5-methyl-1H-pyrazol-3-yl) amino)-pyridin-2-yl)met-hyl)-1-(3-chloro-2-fluorobenzyl)-2-methylpiperidine-4-carboxylic acid

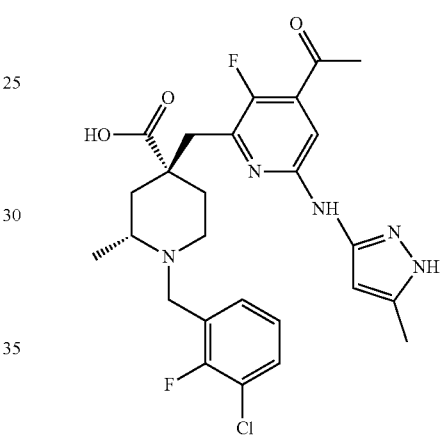

Following the procedure analogous to that described in step 5 of Example 5, tert-butyl(2R,4R)-4-((4-acetyl-6-((1-(tert-butyl)-5-methyl-1H-pyrazol-3-yl)amino)-3-fluoropyridin-2-yl)methyl)-1-(3-chloro-2-fluorobenzyl)-2-methylpiperidine-4-carboxylate (74 mg, 114.872 μmol) was converted to the title compound (21 mg) as a white solid. LCMS (ESI, m/z): 532 [M+H]+. $^1$H NMR (400 MHz, MeOD) δ 8.42 (s, 1H), 7.49 (dt, J=23.1, 7.1 Hz, 2H), 7.23 (t, J=7.9 Hz, 1H), 7.07 (d, J=3.8 Hz, 1H), 5.88 (s, 1H), 4.44 (d, J=13.4 Hz, 1H), 3.86 (d, J=13.5 Hz, 1H), 3.30-3.29 (m, 2H), 3.25 (s, 1H), 3.05 (d, J=13.1 Hz, 1H), 2.90 (t, J=10.6 Hz, 1H), 2.58 (d, J=3.5 Hz, 3H), 2.24 (s, 3H), 2.10-1.81 (m, 4H), 1.37 (d, J=6.1 Hz, 3H).

The following examples in Table 7 were synthesized using the above procedure with the corresponding starting materials and intermediates.

TABLE 7

| Example No. | Structure | Chemical Name | ¹HNMR & MS: (M + H)⁺ |
|---|---|---|---|
| 69 | 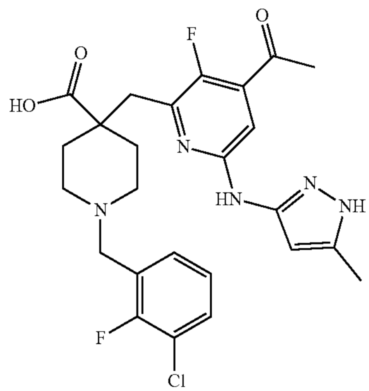 | 4-((4-acetyl-3-fluoro-6-((5-methyl-1H-pyrazol-3-yl)-amino)pyridin-2-yl)methyl)-1-(3-chloro-2-fluorobenzyl)-piperidine-4-carboxylic acid | ¹H NMR (400 MHz, MeOD) δ 7.66 (t, J = 7.7 Hz, 2H), 7.32 (t, J = 7.9 Hz, 1H), 7.16 (d, J = 4.0 Hz, 1H), 6.13 (s, 1H), 4.46 (s, 2H), 3.64-3.49 (m, 4H), 3.12 (t, J = 12.6 Hz, 2H), 2.64 (d, J = 3.6 Hz, 3H), 2.48-2.43 (m, 2H), 2.45 (s, 3H), 2.15 (t, J = 12.4 Hz, 2H). MS: 515 (M + H)⁺ |
| 70 | 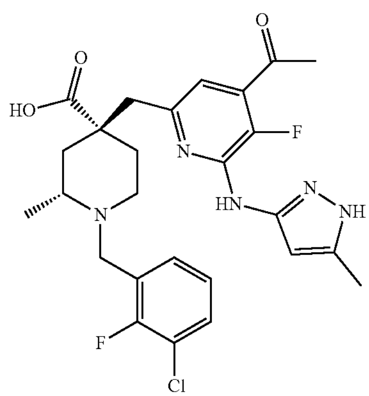 | (2R,4R)-4-((4-acetyl-5-fluoro-6-((5-methyl-1H-pyrazol-3-yl)amino)pyridin-2-yl)methyl)-1-(3-chloro-2-fluorobenzyl)-2-methylpiperidine-4-carboxylic acid | ¹H NMR (400 MHz, MeOD) δ 7.70 (t, J = 7.3 Hz, 1H), 7.62 (t, J = 7.0 Hz, 1H), 7.36 (t, J = 7.8 Hz, 1H), 7.21 (s, 1H), 6.25 (s, 1H), 4.42 (s, 1H), 3.99 (s, 1H), 3.42 (d, J = 59.9 Hz, 5H), 2.68 (d, J = 3.5 Hz, 3H), 2.44 (s, 3H), 2.24-1.94 (m, 4H), 1.59 (s, 3H). MS: 532 (M + H)⁺ |

Example 71

(2R,4R)-1-(3-chloro-2-fluorobenzyl)-4-((4-(1,1-difluoroethyl)-3-fluoro-6-((5-methyl-1H-pyrazol-3-yl)amino)pyridin-2-yl)methyl)-2-methylpiperidine-4-carboxylic acid Step 1: tert-butyl(2R,4R)-4-((4-acetyl-6-chloro-3-fluoropyridin-2-yl)methyl)-2-methylpiperidine-4-carboxylate

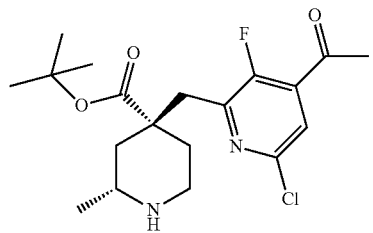 [SMILES: CC(=O)c1cc(Cl)nc(C[C@@]2(C(=O)OC(C)(C)C)CCN[C@H](C)C2)c1F]

To a solution of di-tert-butyl (2R,4R)-4-((6-chloro-4-(1-ethoxyvinyl)-3-fluoropyridin-2-yl)methyl)-2-methylpiperidine-1,4-dicarboxylate (346 mg, 674.411 μmol) in DCM (15 mL) was added trifluoroacetic acid (1.5 mL) at room temperature. The reaction mixture was stirred for 4 h before it was quenched with sodium bicarbonate solution at 0° C. The resulting mixture was extracted with DCM (100 mL). The organic layer was washed with brine, dried over anhydrous sodium sulfate, filtered and concentrated under reduced pressure to afford the title compound (340 mg) as a crude yellow oil. LCMS (ESI, m/z): 385 [M+H]⁺.

Step 2: tert-butyl (2R,4R)-4-((4-acetyl-6-chloro-3-fluoropyridin-2-yl)methyl)-1-(3-chloro-2-fluorobenzyl)-2-methylpiperidine-4-carboxylate

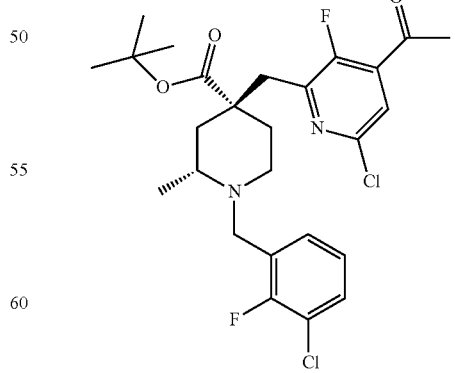

Following the procedure analogous to that described in Step 4 for the synthesis of Example 5, tert-butyl(2R,4R)-4-((4-acetyl-6-chloro-3-fluoropyridin-2-yl)methyl)-2-methylpiperidine-4-carboxylate (340 mg) was converted to the title compound (148 mg, Y=32%) as a yellow oil. LCMS (ESI, m/z): 527 [M+H]⁺.

Step 3: tert-butyl (2R,4R)-1-(3-chloro-2-fluorobenzyl)-4-((6-chloro-4-(1,1-difluoroethyl)-3-fluoropyridin-2-yl)methyl)-2-methylpiperidine-4-carboxylate

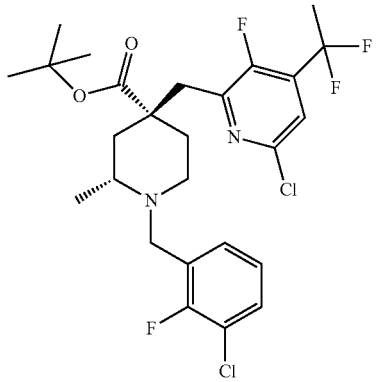 [SMILES: C[C@@H]1C[C@](Cc2nc(Cl)cc(C(C)(F)F)c2F)(C(=O)OC(C)(C)C)CCN1Cc1cccc(Cl)c1F]

To a solution of tert-butyl(2R,4R)-4-((4-acetyl-6-chloro-3-fluoropyridin-2-yl)methyl)-1-(3-chloro-2-fluorobenzyl)-2-methylpiperidine-4-carboxylate (133 mg, 345.570 µmol) in toluene (5 mL) was added bis(2-methoxyethyl)aminosulfur trifluoride (377 mg, 1.704 mmol) under nitrogen. The reaction mixture was stirred at 75° C. for 10 h before it was quenched with sodium bicarbonate solution at 0° C. The resulting mixture was extracted with ethyl acetate (50 mL). The organic layer was washed with brine, dried over anhydrous sodium sulfate, filtered and concentrated under reduced pressure. The resulting residue was purified by TLC to afford the title compound (82 mg, Y=43%) as a white solid. LCMS (ESI, m/z): 549 [M+H]⁺.

Step 4: tert-butyl (2R,4R)-4-((6-((1-(tert-butyl)-5-methyl-1H-pyrazol-3-yl)amino)-4-(1,1-difluoroethyl)-3-fluoropyridin-2-yl)methyl)-1-(3-chloro-2-fluorobenzyl)-2-methylpiperidine-4-carboxylate

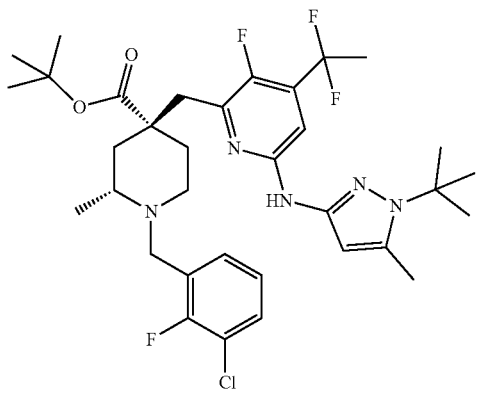 [SMILES: Cc1cc(Nc2cc(C(C)(F)F)c(F)c(C[C@@]3(C(=O)OC(C)(C)C)CCN(Cc4cccc(Cl)c4F)[C@H](C)C3)n2)nn1C(C)(C)C]

Following the procedure analogous to that described in Step 2 for the synthesis of Example 5, tert-butyl (2R,4R)-1-(3-chloro-2-fluorobenzyl)-4-((6-chloro-4-(1,1-difluoroethyl)-3-fluoropyridin-2-yl)methyl)-2-methylpiperidine-4-carboxylate (82 mg, 149.246 µmol) was converted to the title compound (72 mg, 73% yield) as a white solid. LCMS (ESI, m/z): 666 [M+H]⁺.

Step 5: (2R,4R)-1-(3-chloro-2-fluorobenzyl)-4-((4-(1,1-difluoroethyl)-3-fluoro-6-((5-methyl-1H-pyrazol-3-yl)amino)pyridin-2-yl)methyl)-2-methylpiperidine-4-carboxylic acid

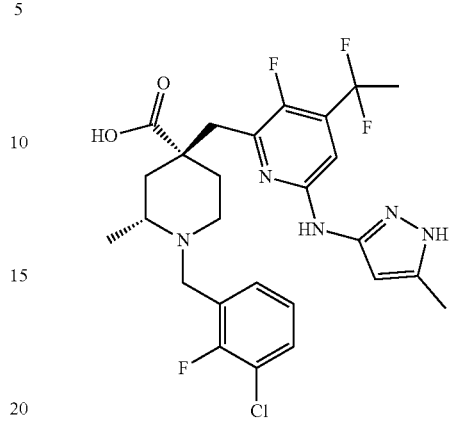

Following the procedure analogous to that described in Step 5 for the synthesis of Example 5, tert-butyl(2R,4R)-4-((6-((1-(tert-butyl)-5-methyl-1H-pyrazol-3-yl)-amino)-4-(1,1-difluoroethyl)-3-fluoropyridin-2-yl)methyl)-1-(3-chloro-2-fluorobenzyl)-2-methylpiperidine-4-carboxylate (72 mg, 108.077 µmol) was converted to the title compound (21 mg, Y=70%) as a white solid. LCMS (ESI, m/z): 554 [M+H]⁺. ¹H NMR (400 MHz, DLCMS (ESI, m/z)O) δ 7.77 (d, J=28.1 Hz, 2H), 7.35 (d, J=7.2 Hz, 1H), 7.15 (s, 1H), 6.18 (s, 1H), 4.80 (d, J=12.7 Hz, 1H), 4.38 (s, 2H), 3.99-4.01 4.38 (s, 1H), 3.39 (d, J=14.4 Hz, 3H), 3.28-3.27 (d, J=13.2 Hz, 1H), 3.13-3.11 (s, 1H), 2.25 (s, 3H), 2.03-2.02 (d, J=11.1 Hz, 2H), 2.01-1.95 (d, J=19.5 Hz, 2H), 1.44 (d, J=5.3 Hz, 3H), 1.36-1.15 (m, 1H).

Example 72

(2R,4R)-1-(3-chloro-2-fluorobenzyl)-4-((4-chloro-3-fluoro-6-((5-methyl-1H-pyrazol-3-yl)amino)pyridin-2-yl)methyl)-2-methylpiperidine-4-carboxylic acid Step 1: di-tert-butyl-(2R,4R)-4-((4,6-dichloro-3-fluoropyridin-2-yl)methyl)-2-methylpiperidine-1,4-dicarboxylate

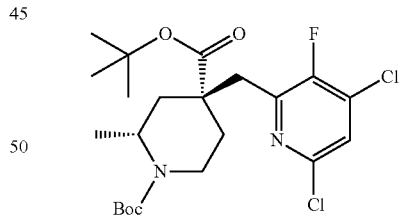

A solution of diisopropylamine (3.37 g, 33.304 mmol) in THF (15 mL) was added n-butyl lithium (2.5M) in hexane (11 mL, 27.5 mmol) dropwise at −78° C. under nitrogen. The resulting solution was stirred at 0° C. for 30 min before it was added a solution of INT C3 (6.30 g, 14.223 mmol) in THF (15 ml) at −78° C. The resulting solution was stirred at −40° C. for 1 h.

A solution of hexachloroethane (2.38 g, 10.053 mmol) in THF (15 ml) was added dropwise to above solution at −78° C. The resulting solution was stirred at −40° C. for 1 h. The reaction was quenched with saturated aqueous NH4Cl aqueous solution. The resulting mixture was extracted with ethyl acetate. The organic layer was dried over anhydrous sodium sulfate, filtered and concentrated under reduced pressure. The residue was purified by C18 reversed phase column chromatography eluting with H2O/ACN to afford di-tert-butyl-(2R,4R)-4-((4,6-dichloro-3-fluoropyridin-2-yl)methyl)-2-methylpiperidine-1,4-dicarboxylate (2.30 g, Y=34%) as yellow oil. LCMS (ESI, m/z): 477 [M+H]+.

Step 2: di-tert-butyl-(2R,4R)-4-((6-((1-(tert-butyl)-5-methyl-1H-pyrazol-3-yl)amino)-4-chloro-3-fluoro-pyridin-2-yl)methyl)-2-methylpiperidine-1,4-dicarboxylate

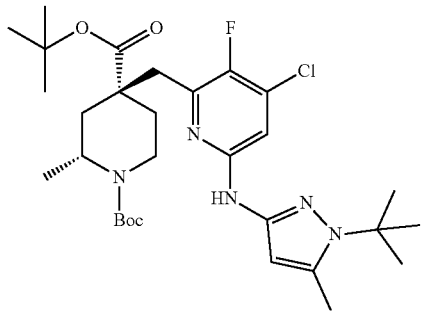 [SMILES: Cc1cc(Nc2cc(Cl)c(F)c(C[C@@]3(C(=O)OC(C)(C)C)CCN(C(=O)OC(C)(C)C)[C@H](C)C3)n2)nn1C(C)(C)C]

A mixture of di-tert-butyl-(2R,4R)-4-((4,6-dichloro-3-fluoropyridin-2-yl)methyl)-2-methylpiperidine-1,4-dicarboxylate (2.3 g, 4.818 mmol), tris(dibenzylideneacetone)dipalladium (437 mg, 477.233 μmol), dimethylbisdiphenylphosphinoxanthene (198 mg, 953.955 μmol), 1-tert-butyl-3-methyl-1H-pyrazol-5-amine (797 mg, 5.202 mmol) and Cs$_2$CO$_3$ (3137 mg, 9.628 mmol) in N,N-dimethylacetamide (180 ml) was stirred at 110° C. for 5 h under nitrogen. The resulting solution was cooled to room temperature, diluted with brine and extracted with ethyl acetate. The organic layer was dried over anhydrous sodium sulfate, filtered and concentrated under reduced pressure. The residue was purified by C18 reverse phase chromatography eluting with H$_2$O/ACN to afford the title compound (1.38 g, Y=48%) as a yellow solid. LCMS (ESI, m/z): 594 [M+H]$^+$.

Step 3: tert-butyl-(2R,4R)-4-((6-((1-(tert-butyl)-5-methyl-1H-pyrazol-3-yl)amino)-4-chloro-3-fluoro-pyridin-2-yl)methyl)-2-methylpiperidine-4-carboxylate

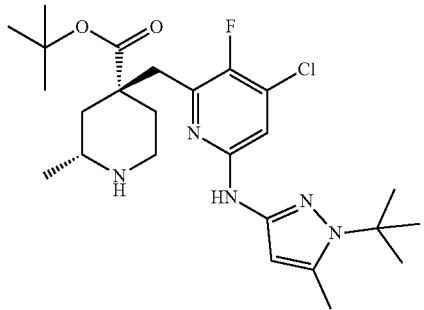 [SMILES: Cc1cc(Nc2cc(Cl)c(F)c(C[C@@]3(C(=O)OC(C)(C)C)CCN[C@H](C)C3)n2)nn1C(C)(C)C]

A solution of di-tert-butyl-(2R,4R)-4-((6-((1-(tert-butyl)-5-methyl-1H-pyrazol-3-yl)amino)-4-chloro-3-fluoropyridin-2-yl)methyl)-2-methylpiperidine-1,4-dicarboxylate (1.38 g, 2.323 mmol) in dichloromethane (20 ml) was added trifluoroacetic acid (2 ml) and stirred at room temperature for 4 h. After completion, the reaction was quenched with saturated sodium bicarbonate aqueous solution (100 ml) and extracted with DCM. The organic layer was dried over anhydrous sodium sulfate, filtered and concentrated under reduced pressure. The crude product was purified by C$_{1-8}$ reverse phase chromatography eluting with H$_2$O/CH$_3$CN/ 0.03 formic acid to afford (1.24 g, Y=69%) of the title compound as a yellow solid. LCMS (ESI, m/z): 494 [M+H]$^+$.

Step 4: tert-butyl-(2R,4R)-4-((6-((1-(tert-butyl)-5-methyl-1H-pyrazol-3-yl)amino)-4-chloro-3-fluoro-pyridin-2-yl)methyl)-1-(3-chloro-2-fluorobenzyl)-2-methylpiperidine-4-carboxylate

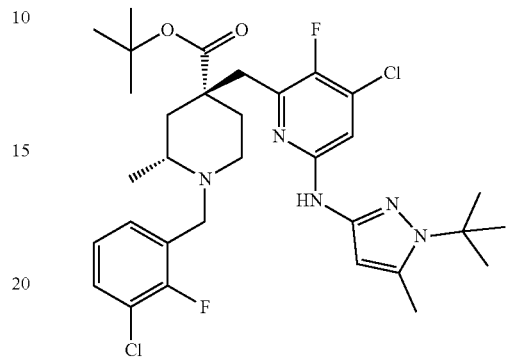

A mixture of tert-butyl-(2R,4R)-4-((6-((1-(tert-butyl)-5-methyl-1H-pyrazol-3-yl)amino)-4-chloro-3-fluoropyridin-2-yl)methyl)-2-methylpiperidine-4-carboxylate (792 mg, 1.603 mmol), potassium carbonate (0.69 g, 4.993 mmol) and 1-(bromomethyl)-3-chloro-2-fluorobenzene (0.4 g, 1.790 mmol) in ACN (20 mL) was stirred for 6 h at room temperature. After completion, the resulting mixture was filtered and concentrated under vacuum. The crude product was purified by silica gel column chromatography eluting with EtOAc/hexane (0~30%) to afford (910 g, Y=89%) of the title compound as a yellow solid. LCMS (ESI, m/z): 636 [M+H]$^+$.

Step 5: (2R,4R)-1-(3-chloro-2-fluorobenzyl)-4-((4-chloro-3-fluoro-6-((5-methyl-1H-pyrazol-3-yl)amino)pyridin-2-yl) methyl)-2-methylpiperidine-4-carboxylic acid

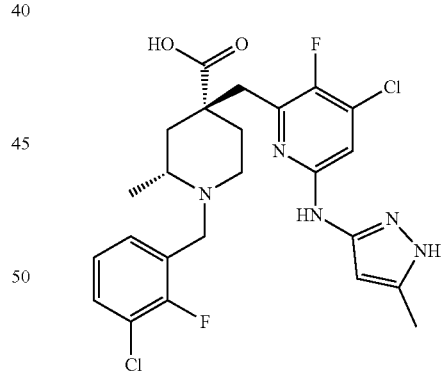

A solution of tert-butyl-(2R,4R)-4-((6-((1-(tert-butyl)-5-methyl-1H-pyrazol-3-yl)amino)-4-chloro-3-fluoropyridin-2-yl)methyl)-1-(3-chloro-2-fluorobenzyl)-2-methylpiperidine-4-carboxylate (910 mg, 1.429 mmol) in formic acid (10 mL) was stirred at reflux for 4 h. After completion, the resulting solution was concentrated. The residue was dissolved in water (40 mL) at 0° C. and adjusted PH=6~7 with sodium hydroxide aqueous solution (5 M). The resulting mixture was extracted with DCM (3×100 mL). The organic layer was dried over anhydrous sodium sulfate, filtered and concentrated under reduced pressure. The crude product was purified by C18 reverse phase chromatography eluting with MeOH/water to afford (612 mg, 1.167 mmol, Y=82%) of the title compound as a white solid. LCMS (ESI, m/z): 524

[M+H]⁺. ¹H NMR (400 MHz, MeOD) δ 7.50 (dt, J=18.9, 7.1 Hz, 2H), 7.23 (t, J=7.9 Hz, 1H), 7.00 (s, 1H), 5.86 (s, 1H), 4.40 (d, J=13.6 Hz, 1H), 3.79 (t, J=18.0 Hz, 1H), 3.23 (s, 2H), 3.23-3.02 (m, 1H), 3.02 (s, 1H), 2.83 (s, 1H), 2.24 (s, 3H), 2.08-1.86 (m, 4H), 1.37 (d, J=6.0 Hz, 3H).

The following examples in Table 8 were synthesized using the above procedure with the corresponding starting materials and intermediates.

TABLE 8

| Example No. | Structure | Chemical Name | ¹HNMR & MS: (M + H)⁺ |
|---|---|---|---|
| 73 | 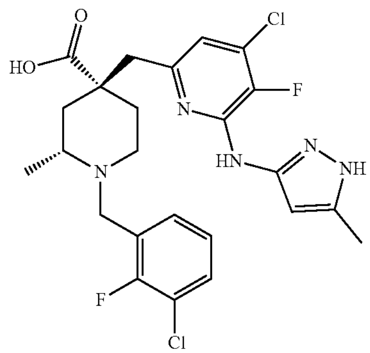 | (2R,4R)-1-(3-chloro-2-fluoro benzyl)-4-((4-chloro-5-fluoro-6-((5-methyl-1H-pyrazol-3-yl)amino)pyridin-2-yl)methyl)-2-methylpiperidine-4-carboxylic acid | ¹H NMR (400 MHz, MeOD) δ 7.67 (t, J = 7.6 Hz, 2H), 7.33 (t, J = 7.8 Hz, 1H), 7.14 (t, J = 18.3 Hz, 1H), 6.23 (s, 1H), 4.94 (d, J = 11.1 Hz, 2H), 4.46 (t, J = 21.8 Hz, 1H), 4.08 (d, J = 6.3 Hz, 1H), 3.69-3.38 (m, 3H), 2.46 (s, 3H), 2.21-1.92 (m, 4H), 1.58 (d, J = 6.0 Hz, 3H). MS: 524 (M + H)⁺ |
| 74 | 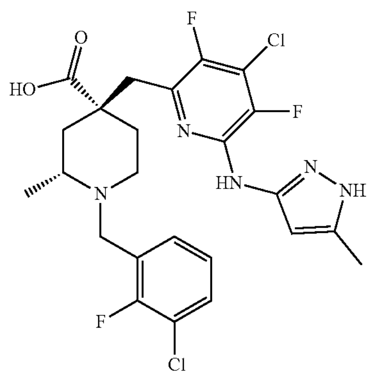 | (2R,4R)-1-(3-chloro-2-fluoro benzyl)-4-((4-chloro-3,5-difluoro-6-((5-methyl-1H-pyrazol-3-yl)amino)pyridin-2-yl)methyl)-2-methylpiperidine-4)-carboxylic acid | ¹H NMR (400 MHz, MeOD) δ 7.67 (dt, J = 19.3, 7.0 Hz, 2H), 7.36 (t, J = 7.9 Hz, 1H), 6.25 (s, 1H), 4.45 (d, J = 13.0 Hz, 1H), 4.00 (s, 1H), 3.51 (dd, J = 53.6, 35.6 Hz, 4H), 2.44 (s, 3H), 2.26 (d, J = 12.9 Hz, 2H), 2.08 (d, J = 25.5 Hz, 3H), 1.59 (s, 3H). MS: 542 (M + H)⁺ |

Example 75

(2R,4R)-4-((4-(azetidin-1-yl)-3-fluoro-6-((5-methyl-1H-pyrazol-3-yl)amino)pyridin-2-yl)methyl)-1-(3-chloro-2-fluorobenzyl)-2-methylpiperidine-4-carboxylic acid

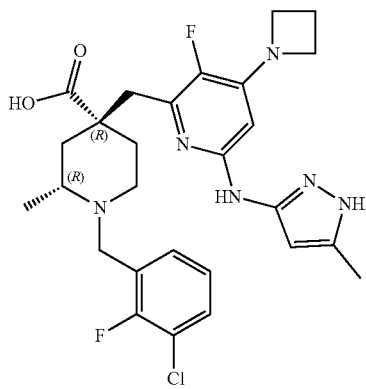

Step 1: di-tert-butyl(2R,4R)-4-((4-(azetidin-1-yl)-6-chloro-3-fluoropyridin-2-yl)methyl)-2-methylpiperidine-1,4-dicarboxylate

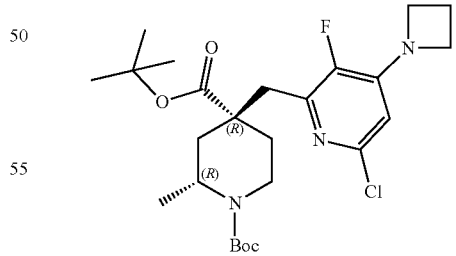

To a solution of di-tert-butyl (2R,4R)-4-((4,6-dichloro-3-fluoropyridin-2-yl)methyl)-2-methylpiperidine-1,4-dicarboxylate (102 mg, 213.659 μmol) in 1-Methylpyrrolidin-3-one (5 mL) was added azetidine (64 mg, 1.121 mmol) and N,N-diisopropylethylamine (123 mg, 951.700 μmol). The resulting mixture was stirred at 110° C. for 2 h before was cooled to room temperature. The mixture was added brine (15 mL) and extracted with EtOAc (60 mL). The organic layer was washed with brine, dried over anhydrous sodium sulfate, filtered and concentrated under reduced pressure. The resulting residue was purified by silica gel column chromatography eluting with EtOAc/hexane (10~20%) to afford the title compound (136 mg, crude) as a white oil. LCMS (ESI, m/z): 498 [M+H]⁺.

Step 2: Di-tert-butyl (2R,4R)-4-((4-(azetidin-1-yl)-6-((1-(tert-butyl)-5-methyl-1H-pyrazol-3-yl)amino)-3-fluoropyridin-2-yl)methyl)-2-methylpiperidine-1,4-dicarboxylate

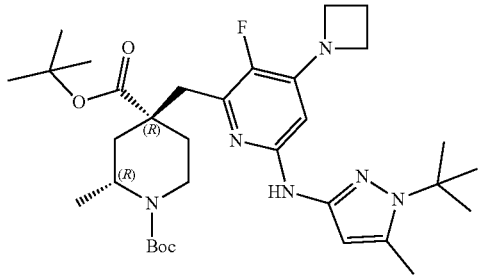

Following the procedure analogous to that described in Step 2 for the synthesis of Example 5, di-tert-butyl (2R,4R)-4-((4-(azetidin-1-yl)-6-chloro-3-fluoro pyridin-2-yl)methyl)-2-methyl piperidine-1,4-dicarboxylate (136 mg, 273.076 μmol) was converted to the title compound (132 mg, Y=78%) as a white oil. LCMS (ESI, m/z): 615 [M+H]⁺.

Step 3: Tert-butyl (2R,4R)-4-((4-(azetidin-1-yl)-6-((1-(tert-butyl)-5-methyl-1H-pyrazol-3-yl)-amino)-3-fluoropyridin-2-yl)methyl)-2-methylpiperidine-4-carboxylate

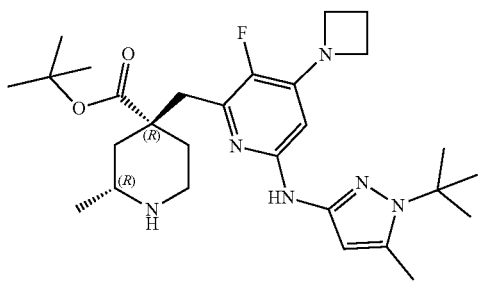

Following the procedure analogous to that described in Step 3 for the synthesis of Example 5, di-tert-butyl (2R,4R)-4-((4-(azetidin-1-yl)-6-((1-(tert-butyl)-5-methyl-1H-pyrazol-3-yl)amino)-3-fluoropyridin-2-yl)methyl)-2-methylpiperidine-1,4-dicarboxylate (132 mg, 214.707 μmol) was converted to the title compound (115 mg) as a crude yellow oil. LCMS (ESI, m/z): 515 [M+H]⁺.

Step 4: tert-butyl (2R,4R)-4-((4-(azetidin-1-yl)-6-((1-(tert-butyl)-5-methyl-1H-pyrazol-3-yl)amino)-3-fluoropyridin-2-yl)methyl)-1-(3-chloro-2-fluorobenzyl)-2-methylpiperidine-4-carboxylate

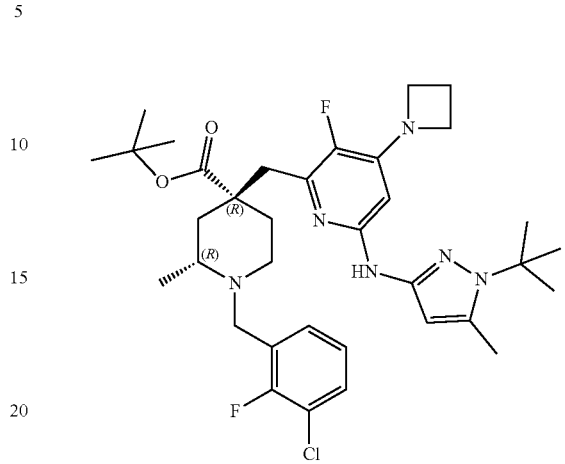

Following the procedure analogous to that described in Step 4 for the synthesis of Example 5, tert-butyl (2R,4R)-4-((4-(azetidin-1-yl)-6-((1-(tert-butyl)-5-methyl-1H-pyrazol-3-yl)amino)-3-fluoropyridin-2-yl)methyl)-2-methylpiperidine-4-carboxylate (115 mg, 223.441 μmol) was converted to the title compound (102 mg, Y=69%) as a yellow oil. LCMS (ESI, m/z): 657 [M+H]⁺.

Step 5: (2R,4R)-4-((4-(azetidin-1-yl)-3-fluoro-6-((5-methyl-1H-pyrazol-3-yl)amino)pyridin-2-yl)methyl)-1-(3-chloro-2-fluorobenzyl)-2-methylpiperidine-4-carboxylic acid

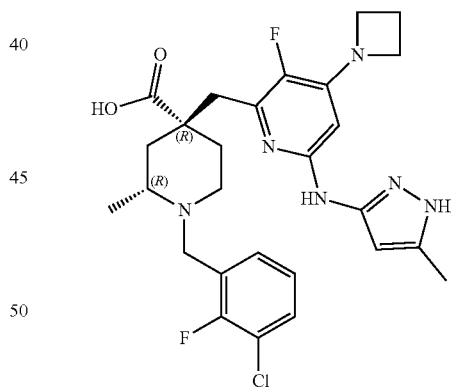

Following the procedure analogous to that described in Step 5 for the synthesis of Example 5, tert-butyl (2R,4R)-4-((4-(azetidin-1-yl)-6-((1-(tert-butyl)-5-methyl-1H-pyrazol-3-yl)amino)-3-fluoropyridin-2-yl)methyl)-1-(3-chloro-2-fluorobenzyl)-2-methylpiperidine-4-carboxylate (102 mg, 155.196 μmol) was converted to the title compound (21 mg, Y=25%) as a white solid. LCMS (ESI, m/z): 545 [M+H]⁺.
¹H NMR (400 MHz, MeOD) δ 7.71-7.67 (t, J=7.4 Hz, 1H), 7.56-7.54 (t, J=6.8 Hz, 1H), 7.35-7.33 (t, J=8.0 Hz, 1H), 5.73 (s, 1H), 5.65-5.63 (d, J=7.3 Hz, 1H), 4.35 (s, 5H), 3.84 (s, 2H), 3.43 (dd, J=29.3, 16.3 Hz, 4H), 2.54 (dd, J=15.3, 7.8 Hz, 3H), 2.29 (s, 3H), 2.21-2.19 (m, 2H), 2.06-2.05 ((m, 1H) 1.60 (s, 3H).

Example 76

(2R,4R)-1-(3-chloro-2-fluorobenzyl)-4-((3-fluoro-4-(1-hydroxyethyl)-6-((5-methyl-1H-pyrazol-3-yl)amino)pyridin-2-yl)methyl)-2-methylpiperidine-4-carboxylic acid

Step 1: tert-butyl (2R,4R)-4-((6-((1-(tert-butyl)-5-methyl-1H-pyrazol-3-yl)amino)-3-fluoro-4-(1-hydroxyethyl)pyridin-2-yl)methyl)-1-(3-chloro-2-fluorobenzyl)-2-methylpiperidine-4-carboxylate

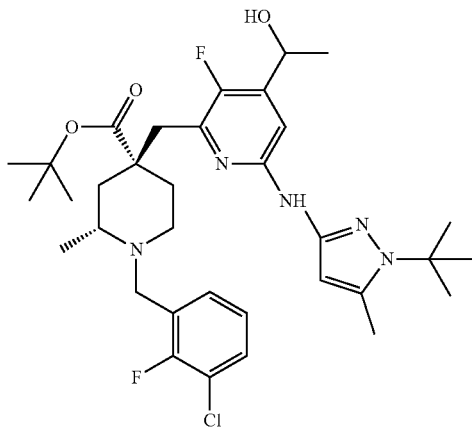 [SMILES: Cc1cc(Nc2cc(C(C)O)c(F)c(C[C@@]3(C(=O)OC(C)(C)C)CCN(Cc4cccc(Cl)c4F)[C@H](C)C3)n2)nn1C(C)(C)C]

NaBH4 (25 mg, 660.809 μmol) was added to a mixture of tert-butyl (2R,4R)-4-((4-acetyl-6-((1-(tert-butyl)-5-methyl-1H-pyrazol-3-yl)amino)-3-fluoropyridin-2-yl)methyl)-1-(3-chloro-2-fluorobenzyl)-2-methylpiperidine-4-carboxylate (180 mg, 279.419 μmol) in methanol (5 mL). The resulting mixture was stirred at room temperature for 1.5 h. After completion, the resulting solution was diluted with brine (10 ml) and extracted with EtOAc (10 ml). The organic layer was washed with brine, dried over anhydrous sodium sulfate and concentrated under reduced pressure to give tert-butyl (2R,4R)-4-((6-((1-(tert-butyl)-5-methyl-1H-pyrazol-3-yl)amino)-3-fluoro-4-(1-hydroxyethyl) pyridin-2-yl)methyl)-1-(3-chloro-2-fluorobenzyl)-2-methylpiperidine-4-carboxylate (222 mg) as a white solid. LCMS (ESI, m/z): 647 [M+H]+.

Step 2: (2R,4R)-1-(3-chloro-2-fluorobenzyl)-4-((3-fluoro-4-(1-hydroxyethyl)-6-((5-methyl-1H-pyrazol-3-yl)amino)pyridin-2-yl)methyl)-2-methylpiperidine-4-carboxylic acid

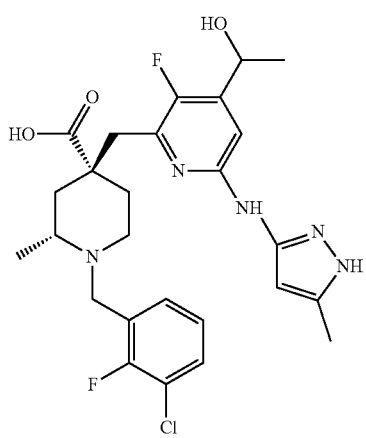 [SMILES: Cc1cc(Nc2cc(C(C)O)c(F)c(C[C@@]3(C(=O)O)CCN(Cc4cccc(Cl)c4F)[C@H](C)C3)n2)n[nH]1]

Following the procedure analogous to that described in step 5 of Example 5, tert-butyl (2R,4R)-4-((6-((1-(tert-butyl)-5-methyl-1H-pyrazol-3-yl)amino)-3-fluoro-4-(1-hydroxyethyl) pyridin-2-yl)methyl)-1-(3-chloro-2-fluorobenzyl)-2-methylpiperidine-4-carboxylate (64 mg, 99.039 μmol) was converted to the title compound (46 mg) as a white solid. LCMS (ESI, m/z): 571 [M+H]+. NMR (400 MHz, MeOD) δ 7.68 (t, J=7.6 Hz, 1H), 7.55 (t, J=7.1 Hz, 1H), 7.33 (t, J=7.8 Hz, 1H), 7.04 (d, J=4.3 Hz, 1H), 5.06 (q, J=6.4 Hz, 1H), 4.93 (s, 1H), 4.34 (d, J=13.1 Hz, 1H), 3.89 (s, 1H), 3.40 (s, 3H), 3.31 (s, 2H), 2.38 (s, 3H), 2.16 (t, J=32.8 Hz, 4H), 1.58 (d, J=5.6 Hz, 3H), 1.44 (d, J=6.5 Hz, 3H).

Example 77

(2R,4R)-1-(3-chloro-2-fluorobenzyl)-4-((3-fluoro-4-(1-fluoroethyl)-6-((5-methyl-1H-pyrazol-3-yl)amino)pyridin-2-yl)methyl)-2-methylpiperidine-4-carboxylic acid

Step 1: tert-butyl (2R,4R)-4-((6-((1-(tert-butyl)-5-methyl-1H-pyrazol-3-yl)amino)-3-fluoro-4-(1-fluoroethyl)pyridin-2-yl)methyl)-1-(3-chloro-2-fluorobenzyl)-2-methylpiperidine-4-carboxylate

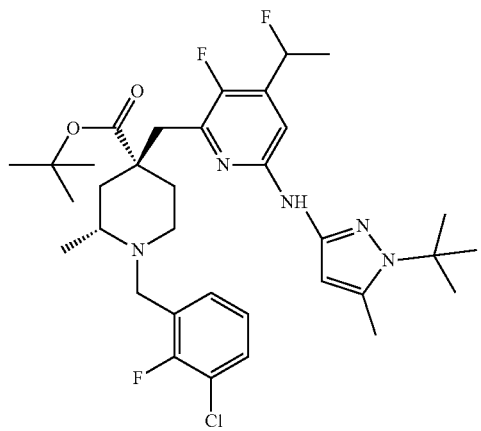 [SMILES: Cc1cc(Nc2cc(C(C)F)c(F)c(C[C@@]3(C(=O)OC(C)(C)C)CCN(Cc4cccc(Cl)c4F)[C@H](C)C3)n2)nn1C(C)(C)C]

DAST (64 mg, 397.050 μmol) was added to a solution of tert-butyl (2R,4R)-4-((6-((1-(tert-butyl)-5-methyl-1H-pyrazol-3-yl)amino)-3-fluoro-4-(1-hydroxyethyl)pyridin-2-yl) methyl)-1-(3-chloro-2-fluorobenzyl)-2-methylpiperidine-4-carboxylate (120 mg, 185.699 μmol) in DCM (3 mL). The resulting solution was stirred at 0° C. for 1 h. The solution was quenched with saturated NaHCO3 aqueous and extract with ethyl acetate. The organic layer was dried over anhydrous sodium sulfate, filtered and concentrated under reduced pressure to give tert-butyl (2R,4R)-4-((6-((1-(tert-butyl)-5-methyl-1H-pyrazol-3-yl)amino)-3-fluoro-4-(1-hydroxyethyl)pyridin-2-yl)methyl)-1-(3-chloro-2-fluorobenzyl)-2-methylpiperidine-4-carboxylate (81 mg) as a yellow oil. LCMS (ESI, m/z): 649 [M+H]+.

Step 2: (2R,4R)-1-(3-chloro-2-fluorobenzyl)-4-((3-fluoro-4-(1-fluoroethyl)-6-((5-methyl-1H-pyrazol-3-yl)amino)pyridin-2-yl)methyl)-2-methylpiperidine-4-carboxylic acid

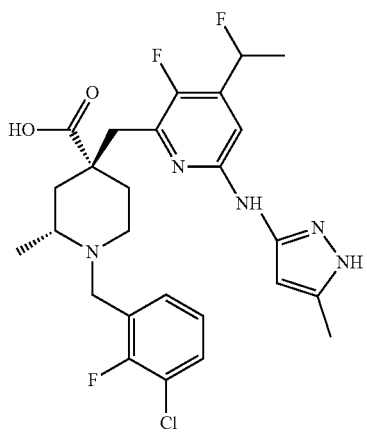 [SMILES: Cc1cc(Nc2cc(C(C)F)c(F)c(C[C@@]3(C(=O)O)CCN(Cc4cccc(Cl)c4F)[C@H](C)C3)n2)n[nH]1]

Following the procedure analogous to that described in step 5 of Example 5, tert-butyl (2R,4R)-4-((6-((1-(tert-butyl)-5-methyl-1H-pyrazol-3-yl)amino)-3-fluoro-4-(1-fluoroethyl) pyridin-2-yl)methyl)-1-(3-chloro-2-fluorobenzyl)-2-methylpiperidine-4-carboxylate (81 mg, 124.961 μmol) was converted to the title compound (56 mg) as a white solid. LCMS (ESI, m/z): 573 [M+H]$^+$. $^1$H NMR (400 MHz, MeOD) δ 7.68 (t, J=7.5 Hz, 1H), 7.54 (t, J=6.9 Hz, 1H), 7.33 (t, J=7.9 Hz, 1H), 6.92 (d, J=3.9 Hz, 1H), 6.01 (s, 1H), 5.88 (dd, J=46.9, 6.5 Hz, 1H), 4.34 (d, J=12.7 Hz, 1H), 3.90 (s, 1H), 3.36 (d, J=36.1 Hz, 5H), 2.38 (s, 3H), 2.33-1.91 (m, 4H), 1.73-1.47 (m, 6H).

Example 78

(2R,4R)-1-(3-chloro-2-fluorobenzyl)-4-((5-fluoro-4-methyl-6-((5-methyl-1H-pyrazol-3-yl)amino)pyridin-2-yl)methyl)-2-methylpiperidine-4-carboxylic acid Step 1: di-tert-butyl (2R,4R)-4-((6-chloro-5-fluoro-4-methylpyridin-2-yl)methyl)-2-methylpiperidine-1,4-dicarboxylate

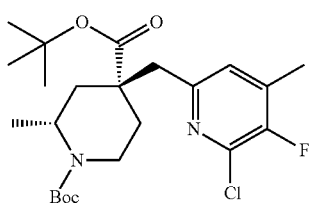 [SMILES: Cc1cc(C[C@@]2(C(=O)OC(C)(C)C)CCN(C(=O)OC(C)(C)C)[C@H](C)C2)nc(Cl)c1F]

A solution of diisopropylamine (2.46 g, 24.311 mmol) in THF (10 ml) was added n-butyl lithium 2.5 M in THF (8.4 ml, 21086 mmol) at −70~−60° C. under nitrogen. The solution was stirred for 1 h at −10° C.~0° C. The resulting solution was slowly added INT C1 (4.67 g, 10.543 mmol) in THF (10 ml). The solution was stirred at −70° C.~−60° C. for 1 h.

A solution of iodomethane (1.82 g, 12.822 mmol) in THF (2 ml) was added to the above solution. The resulting solution was stirred at −70° C.–−60° C. for 2 h. After completion, the reaction was quenched with saturated ammonium chloride aqueous solution and extracted with EtOAc. The organic layer was combined, dried over anhydrous sodium sulfate and concentrated under reduced pressure. The residue was purified by C18 reverse phase chromatography eluting with H$_2$O/ACN to afford 2.84 g of the title compound as a yellow oil. LCMS (ESI, m/z): 457 [M+H]$^+$.

Step 2: di-tert-butyl-(2R,4R)-4-((6-((1-(tert-butyl)-5-methyl-1H-pyrazol-3-yl)amino)-5-fluoro-4-methylpyridin-2-yl)methyl)-2-methylpiperidine-1,4-dicarboxylate

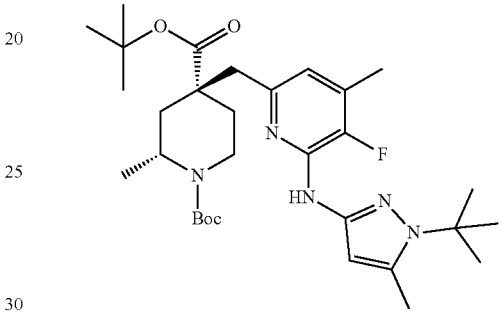

A mixture of di-tert-butyl-(2R,4R)-4-((6-chloro-5-fluoro-4-methylpyridin-2-yl) methyl)-2-methylpiperidine-1,4-dicarboxylate (2.77 g, 6.062 mmol), tris(dibenzylideneacetone)dipalladium (1.63 g, 1.780 mmol), dimethylbisdiphenylphosphinoxanthene (1.06 g, 1.832 mmol), 1-tert-butyl-3-methyl-1H-pyrazol-5-amine (1.22 g, 7.962 mmol) and K$_3$PO$_4$ (5.56 g, 26.194 mmol) in 1,4-dioxane (30 ml) was stirred at 110° C. for 5 h under nitrogen. The resulting solution was cooled to room temperature, diluted with brine and extracted with ethyl acetate. The organic layer was dried over anhydrous sodium sulfate, filtered and concentrated under reduced pressure. The residue was purified by C18 reverse phase chromatography eluting with H$_2$O/ACN to afford (2.92 g, 5.089 mmol, Y=83%) of the title compound as a yellow solid. LCMS (ESI, m/z): 574 [M+H]$^+$.

Step 3: tert-butyl-(2R,4R)-4-((6-((1-(tert-butyl)-5-methyl-1H-pyrazol-3-yl)amino)-5-fluoro-4-methylpyridin-2-yl)methyl)-2-methylpipendine-4-carboxylate

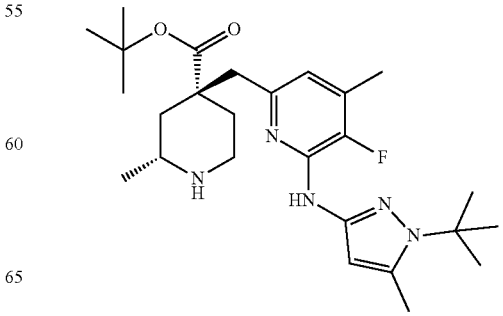

A solution of di-tert-butyl-(2R,4R)-4-((6-((1-(tert-butyl)-5-methyl-1H-pyrazol-3-yl)amino)-5-fluoro-4-methylpyridin-2-yl)methyl)-2-methylpiperidine-1,4-dicarboxylate (2.92 g, 5.089 mmol) in dichloromethane (30 ml) was added trifluoroacetic acid (3 ml) and stirred at room temperature for 4 h. After completion, the reaction was quenched with saturated sodium bicarbonate aqueous solution (100 ml) and extracted with DCM. The organic layer was dried over anhydrous sodium sulfate, filtered and concentrated under reduced pressure. The crude product was purified by C18 reverse phase column chromatography eluting with $H_2O$/CAN/0.03 formic acid to afford (1.71 g, 3.610 mmol, Y=71%) of the title compound as a yellow solid. LCMS (ESI, m/z): 474 [M+H]$^+$.

Step 4: tert-butyl-(2R,4R)-4-((6-((1-(tert-butyl)-5-methyl-1H-pyrazol-3-yl)amino)-5-fluoro-4-methylpyridin-2-yl) methyl)-1-(3-chloro-2-fluorobenzyl)-2-methylpipendine-4-carboxylate

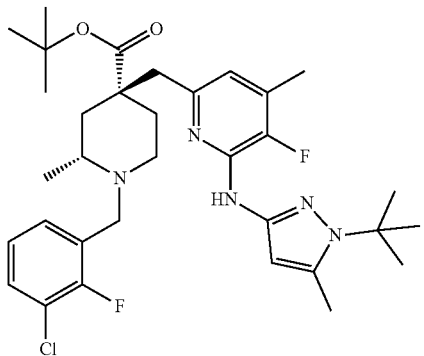 [SMILES: Cc1cc(C[C@@]2(C(=O)OC(C)(C)C)CCN(Cc3cccc(Cl)c3F)[C@H](C)C2)nc(Nc2cc(C)n(C(C)(C)C)n2)c1F]

A mixture of tert-butyl (2R,4R)-4-((6-((1-(tert-butyl)-5-methyl-1H-pyrazol-3-yl)amino)-5-fluoro-4-methylpyridin-2-yl)methyl)-2-methylpiperidine-4-carboxylate (1.70 g, 3.589 mmol) and potassium carbonate (2.54 g, 18.387 mmol), 1-(bromomethyl)-3-chloro-2-fluorobenzene (0.91 g, 4.072 mmol) in ACN (20 mL) was stirred for 6 h at room temperature. After completion, the resulting mixture was filtered and concentrated under reduced pressure. The crude product was purified by silica gel column chromatography eluting with EtOAc/n-hexane (0~30%) to afford (1.96 g, 3.818 mmol, Y=89%) of the title compound as a yellow solid. LCMS (ESI, m/z): 616 [M+H]$^+$.

Step 5: (2R,4R)-1-(3-chloro-2-fluorobenzyl)-4-((5-fluoro-4-methyl-6-((5-methyl-1H-pyrazol-3-yl) amino)pyridin-2-yl) methyl)-2-methylpiperidine-4-carboxylic acid

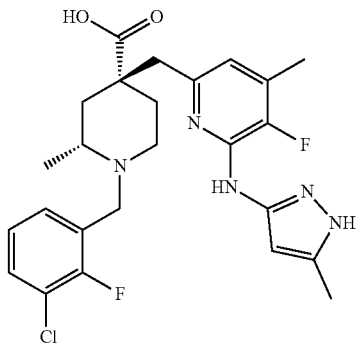 [SMILES: Cc1cc(Nc2nc(C[C@@]3(C(=O)O)CCN(Cc4cccc(Cl)c4F)[C@H](C)C3)cc(C)c2F)n[nH]1]

A solution of tert-butyl (2R,4R)-4-((6-((1-(tert-butyl)-5-methyl-1H-pyrazol-3-yl)amino)-5-fluoro-4-methylpyridin-2-yl)methyl)-1-(3-chloro-2-fluorobenzyl)-2-methylpiperidine-4-carboxylate (1.95 g, 3.165 mmol) in formic acid (15 mL) was stirred at reflux for 1.5 h. After completion, the resulting solution was concentrated. The residue was dissolved in water (40 mL) at 0° C., and adjusted PH=6~7 with sodium hydroxide aqueous solution (5 M). The resulting mixture was extracted with DCM. The organic layer was dried over anhydrous sodium sulfate, filtered and concentrated under reduced pressure. The crude product was purified by $C_{1-8}$ reverse phase column chromatography eluting with MeOH/water to afford (1.595 g, 2.937 mmol, Y=93%) of the title compound as a white solid. LCMS (ESI, m/z): 504 [M+H]$^+$. NMR (400 MHz, MeOD) δ 7.47-7.33 (m, 2H), 7.12 (t, 1H), 6.47 (d, J=4.5 Hz, 1H), 5.93 (s, 1H), 4.29 (d, J=13.6 Hz, 1H), 3.68 (d, J=13.5 Hz, 1H), 3.13 (s, 1H), 3.04 (d, J=13.4 Hz, 1H), 2.96 (d, J=13.5 Hz, 1H), 2.87 (d, J=12.3 Hz, 1H), 2.75 (t, 1H), 2.16 (s, 3H), 2.13 (s, 3H), 1.83 (d, J=11.2 Hz, 2H), 1.75 (t, 2H), 1.22 (d, J=6.0 Hz, 3H).

The following examples in Table 9 were synthesized using the above procedure with the corresponding starting materials and intermediates.

TABLE 9

| Example No. | Structure | Chemical Name | $^1$HNMR & MS: (M + H)$^+$ |
|---|---|---|---|
| 79 | 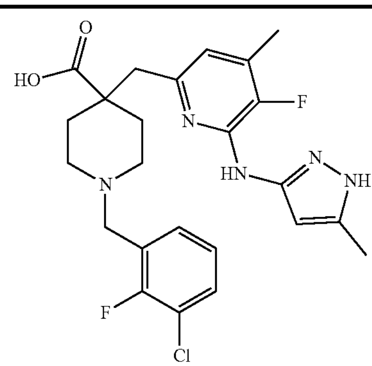 | 1-(3-chloro-2-fluorobenzyl)-4-((5-fluoro-4-methyl-6-((5-methyl-1H-pyrazol-3-yl)amino)-pyridin-2-yl)methyl)piperidine-4-carboxylic acid | $^1$H NMR (400 MHz, MeOD) δ 7.73-7.59 (m, 2H), 7.33 (t, J = 7.9 Hz, 1H), 6.87 (d, J = 4.9 Hz, 1H), 6.13 (s, 1H), 4.45 (s, 2H), 3.56 (d, J = 12.7 Hz, 2H), 3.40-3.50 (m, 1H), 3.14 (s, 2H), 3.18-3.09 (m, 1H), 2.42 (s, 3H), 2.40 (d, J = 19.8 Hz, 2H), 2.37 (s, 3H), 2.07 (t, J = 12.8 Hz, 2H). MS: 490 (M + H)$^+$ |

Example 80

(2R,4R)-1-(3-chloro-2-fluorobenzyl)-4-((3-fluoro-6-((5-methyl-1H-pyrazol-3-yl)amino)-4-propionylpyridin-2-yl)methyl)-2-methylpiperidine-4-carboxylic acid

Step 1: di-tert-butyl-(2R,4R)-4-((6-chloro-3-fluoro-4-(1-hydroxypropyl)pyridin-2-yl)methyl)-2-methylpiperidine-1,4-dicarboxylate

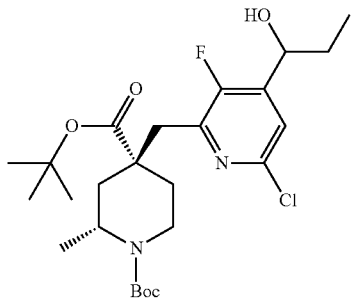 [SMILES: CCC(O)c1cc(Cl)nc(C[C@@]2(C(=O)OC(C)(C)C)CCN(C(=O)OC(C)(C)C)[C@H](C)C2)c1F]

A solution of diisopropylamine (228 mg, 2.253 mmol) in THF (2 ml) was cooled to −78° C. under nitrogen, n-butyl lithium 2.5 M in THF (1.0 ml, 2.500 mmol) was added. The resulting solution was stirred for 1 h at 0° C. and a solution of INT C3 (4.67 g, 10.543 mmol) in THF (2 ml) was slowly added. The resulting solution was stirred at −30° C.~−40° C. for 1 h.

A solution of propionaldehyde (102 mg, 1.756 mmol) in THF (1 ml) was added to above solution at −70° C.~−60° C. The resulting solution was stirred for 2 h. After completion, the reaction was quenched with saturated ammonium chloride aqueous solution and extracted with EtOAc. The organic layer was combined, dried over anhydrous sodium sulfate and concentrated under reduced pressure. The resulting residue was purified by C18 reverse phase chromatography eluting with $H_2O$/ACN to afford the title compound (426 mg, Y=74%) as a white solid. LCMS (ESI, m/z): 501 [M+H]$^+$.

Step 2: di-tert-butyl-(2R,4R)-4-((6-chloro-3-fluoro-4-propionylpyridin-2-yl)methyl)-2-methylpiperidine-1,4-dicarboxylate

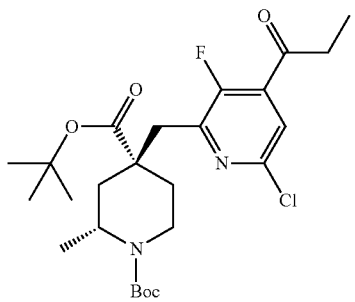 [SMILES: CCC(=O)c1cc(Cl)nc(C[C@@]2(C(=O)OC(C)(C)C)CCN(C(=O)OC(C)(C)C)[C@H](C)C2)c1F]

To a solution of di-tert-butyl-(2R,4R)-4-((6-chloro-3-fluoro-4-(1-hydroxy-propyl)pyridin-2-yl)methyl)-2-methylpiperidine-1,4-dicarboxylate (483 mg, 964.015 μmol) in DCM (10 ml) was added Dess-Martin periodinane (818 mg, 1.929 mmol). The reaction was stirred at room temperature for 2 h. The resulting mixture was added water and extracted with DCM. The organic layer was washed with brine, dried over anhydrous sodium sulfate, filtered and concentrated under reduced pressure. The resulting residue was purified by C18 reversed phase column chromatography eluting with $H_2O$/ACN to afford di-tert-butyl (2R,4R)-4-((6-chloro-3-fluoro-4-propionyl pyridin-2-yl) methyl)-2-methylpiperidine-1,4-dicarboxylate (389 mg, Y=81%) as a yellow oil. LCMS (ESI, m/z): 499 [M+H]$^+$.

Step 3: di-tert-butyl-(2R,4R)-4-((6-((1-(tert-butyl)-5-methyl-1H-pyrazol-3-yl)-amino)-3-fluoro-4-propionylpyridin-2-yl)methyl)-2-methylpiperidine-1,4-dicarboxylate

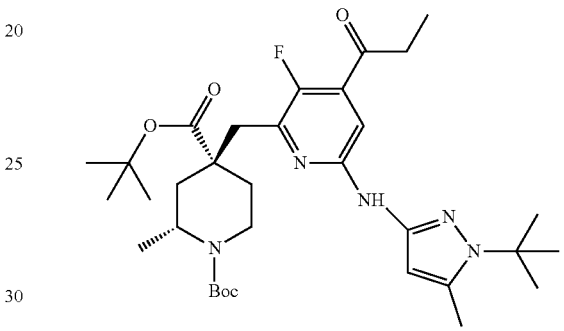

Following the procedure analogous to that described in Step 2 for the synthesis of Example 5, di-tert-butyl-(2R,4R)-4-((6-chloro-3-fluoro-4-propionylpyridin-2-yl)methyl)-2-methylpiperidine-1,4-dicarboxylate (389 mg, 779.538 μmol) was converted to the title compound (122 mg, Y=25%) as a yellow oil. LCMS (ESI, m/z): 616 [M+H]$^+$.

Step 4: tert-butyl-(2R,4R)-4-((6-((1-(tert-butyl)-5-methyl-1H-pyrazol-3-yl)amino)-3-fluoro-4-propionylpyridin-2-yl)methyl)-2-methylpiperidine-4-carboxylate

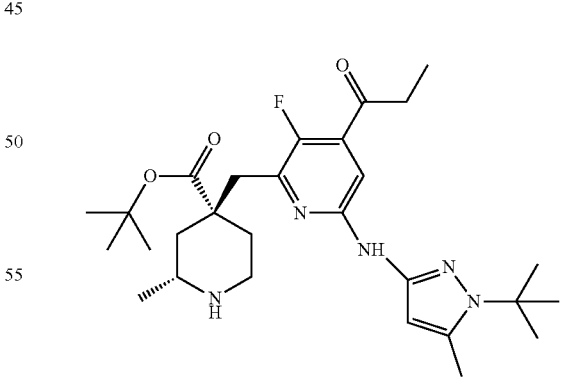

Following the procedure analogous to that described in Step 3 for the synthesis of Example 5, di-tert-butyl-(2R,4R)-4-((6-((1-(tert-butyl)-5-methyl-1H-pyrazol-3-yl)amino)-3-fluoro-4-propionylpyridin-2-yl)methyl)-2-methylpiperidine-1,4-dicarboxylate (177 mg, 287.442 μmol) was converted to the title compound (148 mg) as a yellow oil. LCMS (ESI, m/z): 516 [M+H]$^+$.

Step 5: tert-butyl-(2R,4R)-4-((6-((1-(tert-butyl)-5-methyl-1H-pyrazol-3-yl)amino)-3-fluoro-4-propionylpyridin-2-yl)methyl)-1-(3-chloro-2-fluorobenzyl)-2-methylpiperidine-4-carboxylate

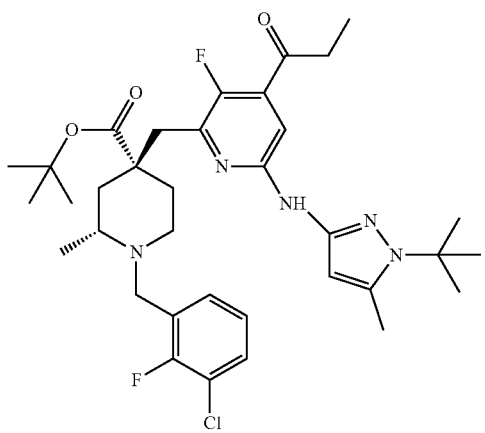 [SMILES: CCC(=O)c1cc(Nc2cc(C)n(C(C)(C)C)n2)nc(C[C@@]2(C(=O)OC(C)(C)C)CCN(Cc3cccc(Cl)c3F)[C@H](C)C2)c1F]

Following the procedure analogous to that described in Step 4 for the synthesis of Example 5, tert-butyl-(2R,4R)-4-((6-((1-(tert-butyl)-5-methyl-1H-pyrazol-3-yl)amino)-3-fluoro-4-propionylpyridin-2-yl)methyl)-2-methylpiperidine-4-carboxylate (148 mg, 287.010 μmol) was converted to the title compound (112 mg, Y=59%) as a yellow oil. LCMS (ESI, m/z): 658 [M+H]$^+$.

Step 6: (2R,4R)-1-(3-chloro-2-fluorobenzyl)-4-((3-fluoro-6-((5-methyl-1H-pyrazol-3-yl)amino)-4-propionylpyridin-2-yl)methyl)-2-methylpiperidine-4-carboxylic acid

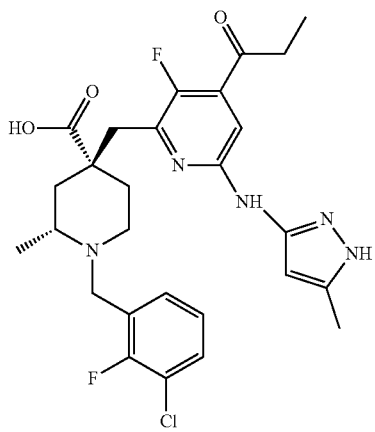 [SMILES: CCC(=O)c1cc(Nc2cc(C)[nH]n2)nc(C[C@@]2(C(=O)O)CCN(Cc3cccc(Cl)c3F)[C@H](C)C2)c1F]

Following the procedure analogous to that described in Step 5 for the synthesis of Example 5, tert-butyl-(2R,4R)-4-((6-((1-(tert-butyl)-5-methyl-1H-pyrazol-3-yl)amino)-3-fluoro-4-propionylpyridin-2-yl)methyl)-1-(3-chloro-2-fluorobenzyl)-2-methylpiperidine-4-carboxylate (112 mg, 170.156 μmol) was converted to the title compound 66 mg as a white solid. LCMS (ESI, m/z): 546 [M+H]$^+$. NMR (400 MHz, MeOD) δ 7.62-7.51 (m, 2H), 7.24 (t, J=7.9 Hz, 1H), 7.04 (t, J=6.7 Hz, 1H), 6.00 (s, 1H), 4.40-4.28 (m, 1H), 3.92 (s, 1H), 3.61-3.23 (m, 5H), 2.93 (d, J=7.0 Hz, 2H), 2.33 (s, 3H), 2.24-1.94 (m, 4H), 1.49 (t, J=21.0 Hz, 3H), 1.09 (t, J=7.1 Hz, 3H).

Example 81

(2R,4R)-1-(3-chloro-2-fluorobenzyl)-4-((3-fluoro-6-((5-methyl-1H-pyrazol-3-yl)amino)-4-(methylsulfonyl)pyridin-2-yl)methyl)-2-methylpiperidine-4-carboxylic acid

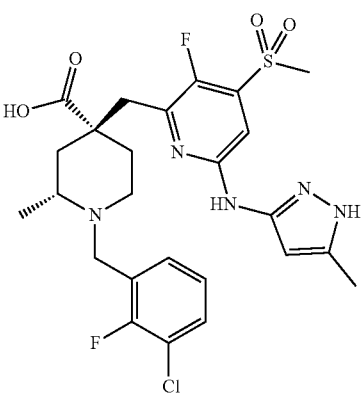

Step 1: di-tert-butyl (2R,4R)-4-((6-chloro-3-fluoro-4-(methylthio)pyridin-2-yl)methyl)-2-methylpiperidine-1,4-dicarboxylate

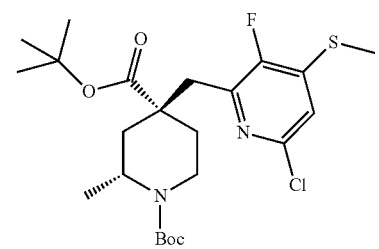 [SMILES: CSc1cc(Cl)nc(C[C@@]2(C(=O)OC(C)(C)C)CCN(C(=O)OC(C)(C)C)[C@H](C)C2)c1F]

To a solution of di-tert-butyl (2R,4R)-4-((6-chloro-3-fluoro-4-iodopyridin-2-yl)methyl)-2-methylpiperidine-1,4-dicarboxylate (457 mg, 803.397 μmol) in 1,4-Dioxane (15 mL) was added tris(dibenzylideneacetonyl)bis-palladium (153 mg, 167.082 μmol), sodium thiomethoxide (168 mg, 2.413 mmol), diisopropylethylamine (450 mg, 3.482 mmol), dimethylbisdiphenylphosphinoxanthene (217 mg, 375.032 μmol) under nitrogen. The mixture was stirred for 3 h at 100° C. The resulting mixture was cooled to room temperature and diluted with water. The resulting solution was extracted with ethyl acetate (150 mL). The organic layer was washed with sodium bicarbonate solution and brine, dried over anhydrous sodium sulfate, filtered and concentrated under reduced pressure. The resulting residue was purified by silica gel column chromatography eluting with EtOAc/hexane (10~20%) to afford the title compound (380 mg, Y=90%) as a white solid. LCMS (ESI, m/z): 489 [M+H]$^+$.

Step 2: di-tert-butyl (2R,4R)-4-((6-chloro-3-fluoro-4-(methylsulfonyl)pyridin-2-yl)methyl)-2-methylpiperidine-1,4-dicarboxylate

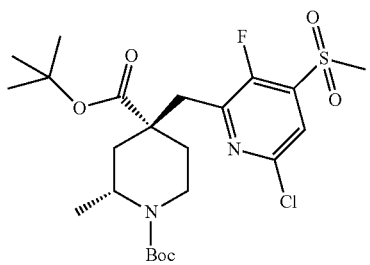 [SMILES: C[C@@H]1C[C@](Cc2nc(Cl)cc(S(C)(=O)=O)c2F)(C(=O)OC(C)(C)C)CCN1C(=O)OC(C)(C)C]

To a solution of di-tert-butyl (2R,4R)-4-((6-chloro-3-fluoro-4-(methylthio)pyridin-2-yl)methyl)-2-methylpiperidine-1,4-dicarboxylate (330 mg, 674.789 μmol) in DCM (20 mL) was added m-chloroperoxybenzoic acid (733 mg, 4.248 mmol) at room temperature. The mixture was stirred for 10 h. The resulting mixture was quenched with sodium bicarbonate solution and extracted with DCM (100 mL). The organic layer was washed with brine, dried over anhydrous sodium sulfate, filtered and concentrated under reduced pressure. The resulting residue was purified by prep-TLC to afford the title compound (207 mg, Y=59%) as a white solid. LCMS (ESI, m/z): 521 [M+H]$^+$.

Step 3: di-tert-butyl (2R,4R)-4-((6-((1-(tert-butyl)-5-methyl-1H-pyrazol-3-yl)amino)-3-fluoro-4-(methylsulfonyl)pyridin-2-yl)methyl)-2-methylpiperidine-1,4-dicarboxylate

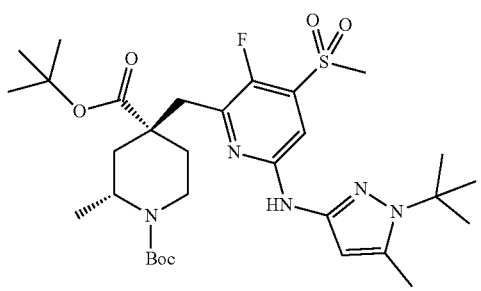 [SMILES: Cc1cc(Nc2cc(S(C)(=O)=O)c(F)c(C[C@@]3(C(=O)OC(C)(C)C)CCN(C(=O)OC(C)(C)C)[C@H](C)C3)n2)nn1C(C)(C)C]

Following the procedure analogous to that described in step 2 for the synthesis of Example 5, di-tert-butyl (2R,4R)-4-((6-chloro-3-fluoro-4-(methylsulfonyl) pyridin-2-yl) methyl)-2-methylpiperidine-1,4-dicarboxylate (207 mg, 397.282 μmol) was converted to the title compound (212 mg, 83% yield) as a white solid. LCMS (ESI, m/z): 638 [M+H]$^+$.

Step 4: tert-butyl (2R,4R)-4-((6-((1-(tert-butyl)-5-methyl-1H-pyrazol-3-yl)amino)-3-fluoro-4-(methylsulfonyl)pyridin-2-yl)methyl)-2-methylpiperidine-4-carboxylate

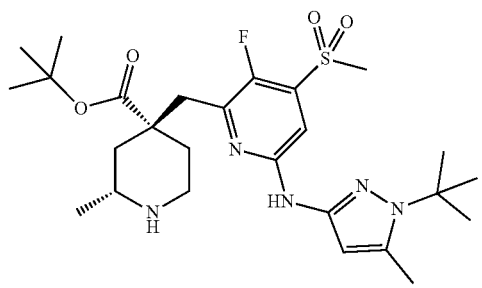 [SMILES: Cc1cc(Nc2cc(S(C)(=O)=O)c(F)c(C[C@@]3(C(=O)OC(C)(C)C)CCN[C@H](C)C3)n2)nn1C(C)(C)C]

Following the procedure analogous to that described in step 3 for the synthesis of Example 5, di-tert-butyl (2R,4R)-4-((6-((1-(tert-butyl)-5-methyl-1H-pyrazol-3-yl)amino)-3-fluoro-4-(methylsulfonyl)pyridin-2-yl)methyl)-2-methylpiperidine-1,4-dicarboxylate (212 mg, 332.391 μmol) was converted to the title compound (225 mg) as a crude white solid. LCMS (ESI, m/z): 538 [M+H]$^+$.

Step 5: tert-butyl (2R,4R)-4-((6-((1-(tert-butyl)-5-methyl-1H-pyrazol-3-yl)amino)-3-fluoro-4-(methylsulfonyl)pyridin-2-yl)methyl)-1-(3-chloro-2-fluorobenzyl)-2-methylpiperidine-4-carboxylate

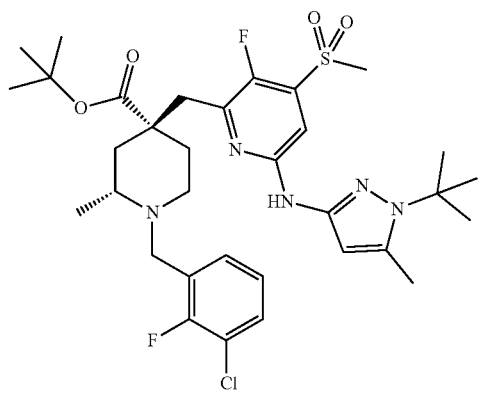 [SMILES: Cc1cc(Nc2cc(S(C)(=O)=O)c(F)c(C[C@@]3(C(=O)OC(C)(C)C)CCN(Cc4cccc(Cl)c4F)[C@H](C)C3)n2)nn1C(C)(C)C]

Following the procedure analogous to that described in step 4 for the synthesis of Example 5, tert-butyl (2R,4R)-4-((6-((1-(tert-butyl)-5-methyl-1H-pyrazol-3-yl)amino)-3-fluoro-4-(methylsulfonyl)pyridin-2-yl)methyl)-2-methylpiperidine-4-carboxylate (225 mg, 418.458 μmol) was converted to the title compound (122 mg) as a white oil. LCMS (ESI, m/z): 680 [M+H]$^+$.

Step 6: (2R,4R)-1-(3-chloro-2-fluorobenzyl)-4-((3-fluoro-6-((5-methyl-1H-pyrazol-3-yl)amino)-4-(methylsulfonyl)pyridin-2-yl)methyl)-2-methylpiperidine-4-carboxylic acid

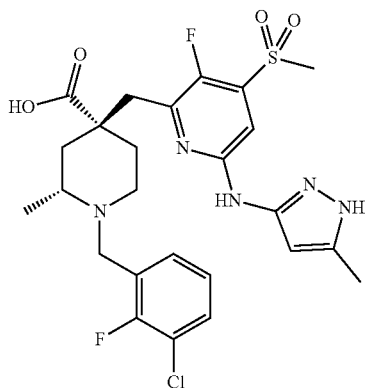

Following the procedure analogous to that described in step 5 for the synthesis of Example 5, tert-butyl (2R,4R)-4-((6-((1-(tert-butyl)-5-methyl-1H-pyrazol-3-yl)amino)-3-fluoro-4-(methylsulfonyl)pyridin-2-yl)methyl)-1-(3-chloro-2-fluorobenzyl)-2-methylpiperidine-4-carboxylate (122 mg, 418.458 μmol) was converted to the title compound (92 mg, Y=90%) as a white solid. LCMS (ESI, m/z): 568 [M+H]$^+$. $^1$H NMR (400 MHz, DLCMS (ESI, m/z)O-d6) δ9.56 (s, 1H), 9.32 (s, 1H), 7.76 (t, J=7.5 Hz, 1H), 7.58 (dd, J=18.3, 11.0 Hz, 2H), 7.38 (t, J=7.8 Hz, 1H), 6.14 (s, 1H), 4.85 (d, J=14.1 Hz, 2H), 4.32 (d, J=14.1 Hz, 2H), 3.46 (s, 2H), 3.34 (s, 3H), 3.28 (d, J=7.5 Hz, 2H), 3.18 (d, J=12.2 Hz, 1H), 2.21 (s, 3H), 1.94-1.84 (m, 2H), 1.45-1.47 (d, J=5.8 Hz, 3H).

Example 82

(2R,4R)-1-(3-chloro-2-fluorobenzyl)-4-((4-ethyl-5-fluoro-6-((5-methyl-1H-pyrazol-3-yl)amino)pyridin-2-yl)methyl)-2-methylpiperidine-4-carboxylic acid Step 1: di-tert-butyl-(2R,4R)-4-((6-chloro-4-ethyl-5-fluoropyridin-2-yl)methyl)-2-methylpiperidine-1,4-dicarboxylate

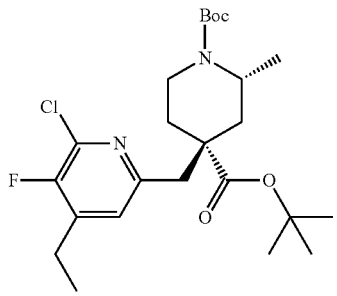 [SMILES: CCc1cc(C[C@@]2(C(=O)OC(C)(C)C)CCN(C(=O)OC(C)(C)C)[C@H](C)C2)nc(Cl)c1F]

A solution of diisopropylamine (625 mg, 6.177 mmol) in THF (2 mL) was added n-butyl lithium (2.5M) in hexane (2.0 mL, 5.00 mmol) dropwise below −40° C. The solution was stirred at 0° C. for 30 min. A solution of INT C3 (831 mg, 1.876 mmol) in THF (5 mL) was added below −70° C. The resulting solution was stirred at −40° C. for 1 h.

A solution of methyl iodide (430 mg, 3.029 mmol) in THF (2 ml) dropwise was added to above solution below −70° C. The resulting solution was stirred at −30° C. for 1 h. The reaction was quenched with saturated aqueous NF$_4$Cl aqueous solution. The resulting mixture was extracted with ethyl acetate. The organic layer was dried over anhydrous sodium sulfate, filtered and concentrated under reduced pressure. The resulting residue was purified by C18 reversed phase column chromatography eluting with H$_2$O/ACN to afford di-tert-butyl-(2R,4R)-4-((6-chloro-4-ethyl-5-fluoropyridin-2-yl)methyl)-2-methylpiperidine-1,4-dicarboxylate (249 mg, Y=28%) as yellow oil. LCMS (ESI, m/z): 471 [M+H]$^+$.

Step 2: di-tert-butyl-(2R,4R)-4-((6-((1-(tert-butyl)-5-methyl-1H-pyrazol-3-yl)amino)-4-ethyl-5-fluoro-pyridin-2-yl)methyl)-2-methylpiperidine-1,4-dicarboxylate

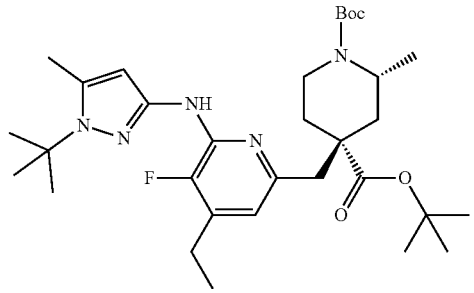 [SMILES: CCc1cc(C[C@@]2(C(=O)OC(C)(C)C)CCN(C(=O)OC(C)(C)C)[C@H](C)C2)nc(Nc2cc(C)n(C(C)(C)C)n2)c1F]

Following the procedure analogous to that described in Step 2 for the synthesis of Example 5, di-tert-butyl-(2R,4R)-4-((6-chloro-4-ethyl-5-fluoropyridin-2-yl)methyl)-2-methylpiperidine-1,4-dicarboxylate (249 mg, 528.658 μmol) was converted to the title compound (153 mg, Y=61%) as a yellow oil. LCMS (ESI, m/z): 588 [M+H]$^+$.

Step 3: tert-butyl-(2R,4R)-4-((6-((1-(tert-butyl)-5-methyl-1H-pyrazol-3-yl)amino)-4-ethyl-5-fluoro-pyridin-2-yl)methyl)-2-methylpiperidine-4-carboxylate

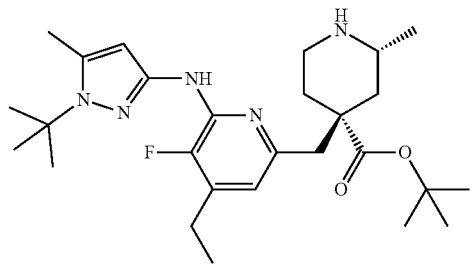 [SMILES: CCc1cc(C[C@@]2(C(=O)OC(C)(C)C)CCN[C@H](C)C2)nc(Nc2cc(C)n(C(C)(C)C)n2)c1F]

Following the procedure analogous to that described in Step 3 for the synthesis of Example 5, di-tert-butyl-(2R,4R)-4-((6-((1-(tert-butyl)-5-methyl-1H-pyrazol-3-yl)amino)-4-ethyl-5-fluoropyridin-2-yl)methyl)-2-methylpiperidine-1,4-dicarboxylate (153 mg, 253.502 μmol) was converted to the title compound (78 mg, Y=63%) as a yellow oil. LCMS (ESI, m/z): 488 [M+H]$^+$.

Step 4; tert-butyl-(2R,4R)-4-((6-((1-(tert-butyl)-5-methyl-1H-pyrazol-3-yl)amino)-4-ethyl-5-fluoropyridin-2-yl)methyl)-1-(3-chloro-2-fluorobenzyl)-2-methylpiperidine-4-carboxylate

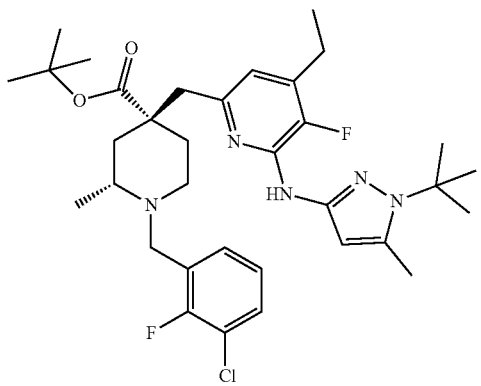 [SMILES: CCc1cc(C[C@@]2(C(=O)OC(C)(C)C)CCN(Cc3cccc(Cl)c3F)[C@H](C)C2)nc(Nc2cc(C)n(C(C)(C)C)n2)c1F]

Following the procedure analogous to that described in Step 4 for the synthesis of Example 5, tert-butyl-(2R,4R)-4-((6-((1-(tert-butyl)-5-methyl-1H-pyrazol-3-yl)amino)-4-ethyl-5-fluoropyridin-2-yl)methyl)-2-methylpiperidine-4-carboxylate (78 mg, 159.836 μmol) was converted to the title compound (61 mg, Y=61%) as a yellow oil. LCMS (ESI, m/z): 630 [M+H]⁺.

Step 5: (2R,4R)-1-(3-chloro-2-fluorobenzyl)-4-((4-ethyl-5-fluoro-6-((5-methyl-1H-pyrazol-3-yl) amino) pyridin-2-yl) methyl)-2-methylpiperidine-4-carboxylic acid

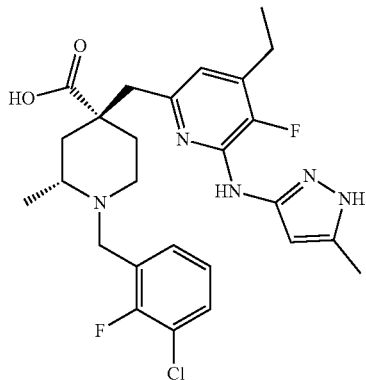

Following the procedure analogous to that described in Step 5 for the synthesis of Example 5, tert-butyl-(2R,4R)-4-((6-((1-(tert-butyl)-5-methyl-1H-pyrazol-3-yl)amino)-4-ethyl-5-fluoropyridin-2-yl)methyl)-1-(3-chloro-2-fluorobenzyl)-2-methylpiperidine-4-carboxylate (61 mg, 96.793 μmol) was converted to the title compound 16 mg as a white solid. LCMS (ESI, m/z): 518 [M+H]⁺. NMR (400 MHz, MeOD) δ 7.70 (s, 2H), 7.36 (t, J=7.9 Hz, 1H), 6.99 (d, J=4.7 Hz, 1H), 6.15 (s, 1H), 3.50 (s, 2H), 3.33 (s, 2H), 3.32 (s, 2H), 2.78 (d, J=7.6 Hz, 2H), 2.44 (s, 3H), 2.08 (d, J=77.6 Hz, 5H), 1.62 (d, J=6.0 Hz, 3H), 1.30 (t, J=7.5 Hz, 3H).

Example 83

(2R,4R)-1-(3-chloro-2-fluorobenzyl)-4-((3'-fluoro-6'-((5-methyl-1H-pyrazol-3-yl)amino)-[2,4'-bipyridin[−2'-yl)methyl)-2-methylpiperidine-4-carboxylic acid

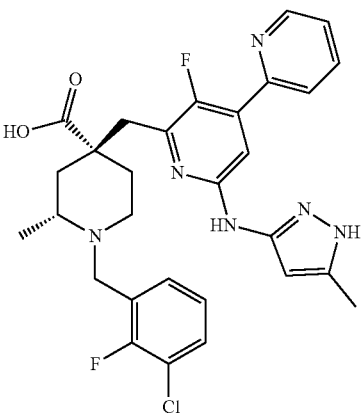

Step 1: di-tert-butyl (2R,4R)-4-((6'-chloro-3'-fluoro-[2,4'-bipyridin]−2'-yl)methyl)-2-methylpipendine-1,4-dicarboxylate

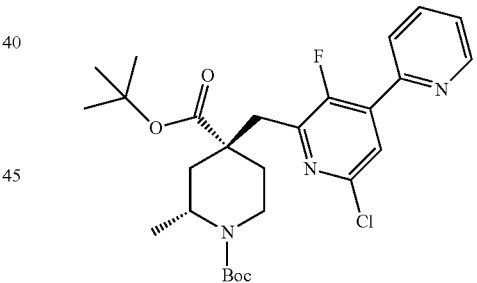

To a solution of di-tert-butyl (2R,4R)-4-((6-chloro-3-fluoro-4-iodopyridin-2-yl)methyl)-2-methylpiperidine-1,4-dicarboxylate (450 mg, 791.074 μmol) in THF (12 mL) and water (4 mL) was added 2-pyridineboronic acid (149 mg, 1.212 mmol), 1,1'-bis(diphenylphosphino)ferrocene palladium dichloride (102 mg, 139.401 μmol), K₃PO₄ (914 mg, 4.306 mmol) under nitrogen. The reaction mixture was stirred for 3 h at 90° C. The reaction was cooled to room temperature. The resulting mixture was diluting with water and extracted with ethyl acetate (100 mL). The organic layer was washed with brine, dried over anhydrous sodium sulfate, filtered and concentrated under reduced pressure. The resulting residue was purified by TLC to afford the title compound (87 mg, 22% yield) as a white oil. LCMS (ESI, m/z): 520 [M+H]⁺.

Step 2; (2R,4R)-1-(3-chloro-2-fluorobenzyl)-4-((3'-fluoro-6'-((5-methyl-1H-pyrazol-3-yl)amino)-[2N'-bipyridin]-2'-yl)methyl)-2-methylpiperidine-4-carboxylic acid

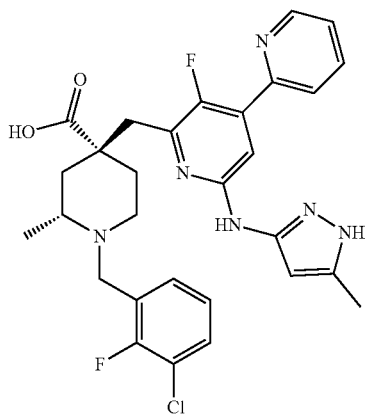

Following the procedure analogous to that described in step2, step3, step4, step5 for the synthesis of example 5, di-tert-butyl(2R,4R)-4-((6'-chloro-3'-fluoro-[2,4'-bipyridin]-2'-yl) methyl)-2-methylpiperidine-1,4-dicarboxylate (87 mg, 167.296 μmol) was converted to the title compound (14 mg) as a white solid. LCMS (ESI, m/z): 567 [M+H]$^+$. $^1$H NMR (400 MHz, DLCMS (ESI, m/z)O) δ7.99-7.96 (t, J=7.3 Hz, 1H), 7.78-7.74 (t, J=7.6 Hz, 2H), 7.63-7.60 (t, J=7.2 Hz, 1H), 7.51-7.48 (dd, J=7.2, 5.4 Hz, 2H), 7.40-7.35 (t, J=7.8 Hz, 1H), 7.29-6.98 (m, 1H), 6.17 (s, 1H), 4.86 (d, J=12.9 Hz, 1H), 4.35 (d, J=7.8 Hz, 2H), 3.94 (s, 1H), 3.45 (d, J=12.6 Hz, 2H), 3.31 (t, J=16.8 Hz, 2H), 3.19 (d, J=11.9 Hz, 1H), 2.30 (m, 3H), 1.99-1.80 (m, 1H), 1.48-1.50 (t, J=10.6 Hz, 3H), 1.39-1.10 (m, 3H).

Example 84

(2R,4R)-1-(3-chloro-2-fluorobenzyl)-4-((4,5-dichloro-3-fluoro-6-((5-methyl-1H-pyrazol-3-yl)amino)pyridin-2-yl)methyl)-2-methylpiperidine-4-carboxylic acid Step 1: di-tert-butyl-(2R,4R)-2-methyl-4-((4,5,6-trichloro-3-fluoropyridin-2-yl)methyl) piperidine-1,4-dicarboxylate

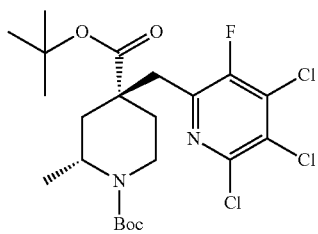 [SMILES: C[C@@H]1C[C@](Cc2nc(Cl)c(Cl)c(Cl)c2F)(C(=O)OC(C)(C)C)CCN1C(=O)OC(C)(C)C]

Following the procedure analogous to that described in Step 1 for the synthesis of Example 72, di-tert-butyl-(2R,4R)-4-((6-chloro-3-fluoropyridin-2-yl)methyl)-2-methylpiperidine-1,4-dicarboxylate (1.50 g, 3.386 mmol) was converted to the title compound (1.38 g, Y=80%) as a yellow oil. LCMS (ESI, m/z): 511 [M+H]$^+$.

Step 2: di-tert-butyl-(2R,4R)-4-((6-((1-(tert-butyl)-5-methyl-1H-pyrazol-3-yl)amino)-4,5-dichloro-3-fluoropyridin-2-yl)methyl)-2-methylpiperidine-1,4-dicarboxylate

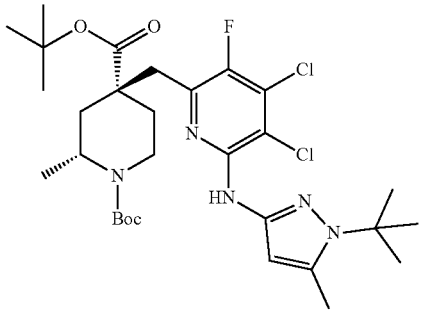 [SMILES: Cc1cc(Nc2nc(C[C@@]3(C(=O)OC(C)(C)C)CCN(C(=O)OC(C)(C)C)[C@H](C)C3)c(F)c(Cl)c2Cl)nn1C(C)(C)C]

Following the procedure analogous to that described in Step 2 for the synthesis of Example 5, di-tert-butyl-(2R,4R)-2-methyl-4-((4,5,6-trichloro-3-fluoropyridin-2-yl)methyl) piperidine-1,4-dicarboxylate (2.10 g, 4.103 mmol) was converted to the title compound (1.21 g, Y=47%) as a yellow oil. LCMS (ESI, m/z): 628 [M+H]$^+$.

Step 3: tert-butyl-(2R,4R)-4-((6-((1-(tert-butyl)-5-methyl-1H-pyrazol-3-yl)amino)-4,5-dichloro-3-fluoropyridin-2-yl)methyl)-2-methylpiperidine-4-carboxylate

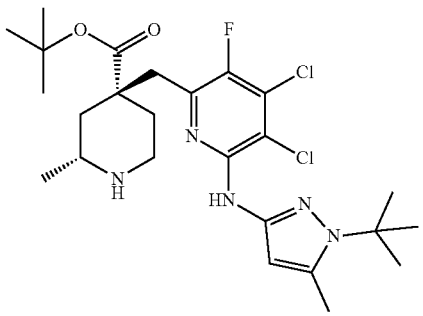 [SMILES: Cc1cc(Nc2nc(C[C@@]3(C(=O)OC(C)(C)C)CCN[C@H](C)C3)c(F)c(Cl)c2Cl)nn1C(C)(C)C]

Following the procedure analogous to that described in Step 3 for the synthesis of Example 5, di-tert-butyl-(2R,4R)-4-((6-((1-(tert-butyl)-5-methyl-1H-pyrazol-3-yl)amino)-4,5-dichloro-3-fluoropyridin-2-yl)methyl)-2-methylpiperidine-1,4-dicarboxylate (1.21 g, 1.925 mmol) was converted to the title compound (0.98 g, Y=96%) as a yellow oil. LCMS (ESI, m/z): 528 [M+H]$^+$.

Step 4: tert-butyl-(2R,4R)-4-((6-((1-(tert-butyl)-5-methyl-1H-pyrazol-3-yl)amino)-4,5-dichloro-3-fluoropyridin-2-yl)methyl)-1-(3-chloro-2-fluorobenzyl)-2-methylpiperidine-4-carboxylate

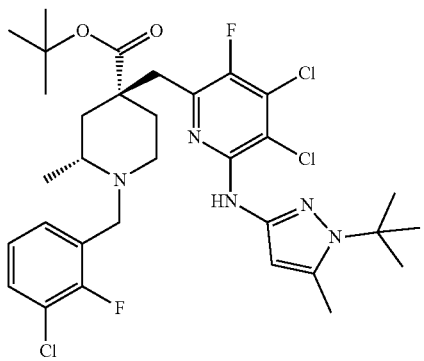 [SMILES: Cc1cc(Nc2nc(C[C@@]3(C(=O)OC(C)(C)C)CCN(Cc4cccc(Cl)c4F)[C@H](C)C3)c(F)c(Cl)c2Cl)nn1C(C)(C)C]

Following the procedure analogous to that described in Step 4 for the synthesis of Example 5, tert-butyl-(2R,4R)-4-((6-((1-(tert-butyl)-5-methyl-1H-pyrazol-3-yl)amino)-4,5-dichloro-3-fluoropyridin-2-yl)methyl)-2-methylpiperidine-4-carboxylate (0.98 g, 1.856 mmol) was converted to the title compound (0.86 g, Y=69%) as a yellow oil. LCMS (ESI, m/z): 671 [M+H]$^+$.

Step 5: (2R,4R)-1-(3-chloro-2-fluorobenzyl)-4-((4,S-dichloro-3-fluoro-6-((5-methyl-1H-pyrazol-3-yl)amino)pyridin-2-yl)methyl)-2-methylpiperidine-4-carboxylic acid

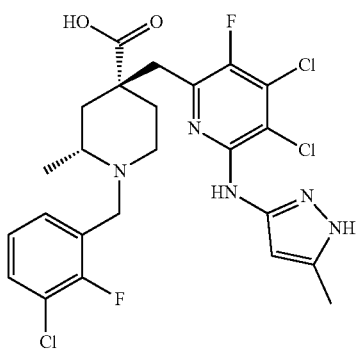 [SMILES: Cc1cc(Nc2nc(C[C@@]3(C(=O)O)CCN(Cc4cccc(Cl)c4F)[C@H](C)C3)c(F)c(Cl)c2Cl)n[nH]1]

Following the procedure analogous to that described in Step 5 for the synthesis of Example 5, tert-butyl-(2R,4R)-4-((6-((1-(tert-butyl)-5-methyl-1H-pyrazol-3-yl)amino)-4,5-dichloro-3-fluoropyridin-2-yl)methyl)-1-(3-chloro-2-fluorobenzyl)-2-methylpiperidine-4-carboxylate (0.86 g, 1.282 mmol) was converted to the title compound 589 mg as a white solid. LCMS (ESI, m/z): 558 [M+H]$^+$. NMR (400 MHz, MeOD) δ 7.70 (dd, J=14.9, 7.0 Hz, 2H), 7.35 (t, J=7.9 Hz, 1H), 6.40 (s, 1H), 4.93 (s, 2H), 4.53 (d, J=13.5 Hz, 1H), 4.18-3.99 (m, 1H), 3.74-3.50 (m, 3H), 2.49 (s, 3H), 2.28-2.06 (m, 4H), 1.61 (d, J=6.2 Hz, 3H).

Example 85

(2R,4R)-1-(3-chloro-2-fluorobenzyl)-4-((3-fluoro-4-isobutyryl-6-((5-methyl-1H-pyrazol-3-yl) amino)pyridin-2-yl)methyl)-2-methylpiperidine-4-carboxylic acid

Step 1: di-tert-butyl (2R,4R)-4-((6-chloro-3-fluoro-4-formylpyridin-2-yl)methyl)-2-methylpiperidine-1,4-dicarboxylate

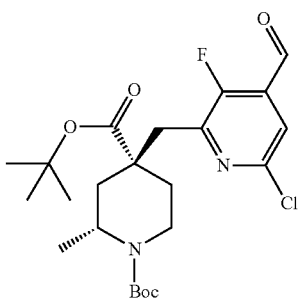 [SMILES: C[C@@H]1C[C@](Cc2nc(Cl)cc(C=O)c2F)(C(=O)OC(C)(C)C)CCN1C(=O)OC(C)(C)C]

Following the procedure analogous to that described in Step 1 for the synthesis of Example 64, INT C3 (1.22 g, 2.754 mmol) was converted to the title compound (1.071 g, 2.274 mmol) as a white solid. LCMS (ESI, m/z): 471 [M+H]$^+$.

Step 2: di-tert-butyl (2R,4R)-4-((6-chloro-3-fluoro-4-(1-hydroxy-2-methylpropyl)~pyridin-2-yl)methyl)-2-methylpiperidine-1,4-dicarboxylate

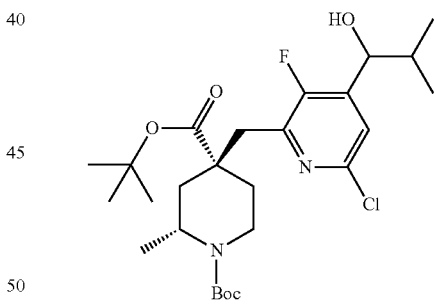

To a solution of (2R,4R)-4-((6-chloro-3-fluoro-4-formylpyridin-2-yl)methyl)-2-methylpiperidine-1,4-dicarboxylate (839 mg, 1.781 mmol) in THF (10 mL) was added isopropylmagnesium bromide (2.8 ml, 1 mol/L) at 0~5° C. under nitrogen. The resulting solution was stirred for 2 h. After completion, the reaction solution was quenched with saturated ammonium chloride aqueous solution and extracted with ethyl acetate. The organic layer was washed with brine, dried anhydrous sodium sulfate and concentrated under reduced pressure. The crude product was purified by prep-TLC using a gradient ethyl acetate/Hex=1/5 solvent to give (2R,4R)-4-((6-chloro-3-fluoro-4-(1-hydroxy-2-methylpropyl)pyridin-2-yl)methyl)-2-methylpiperidine-1,4-dicarboxylate (323 mg, 0.627 mmol) as a white solid. LCMS (ESI, m/z): 515 [M+H]$^+$.

Step 3: di-tert-butyl (2R,4R)-4-((6-chloro-3-fluoro-4-isobutyrylpyridin-2-yl) methyl)-2-methylpiperidine-1,4-dicarboxylate

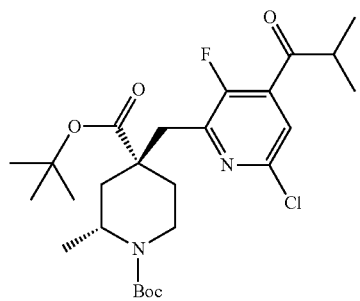 [SMILES: CC(C)C(=O)c1cc(Cl)nc(C[C@@]2(C(=O)OC(C)(C)C)CCN(C(=O)OC(C)(C)C)[C@H](C)C2)c1F]

A solution of (2R,4R)-4-((6-chloro-3-fluoro-4-(1-hydroxy-2-methylpropyl)pyridin-2-yl)methyl)-2-methylpiperidine-1,4-dicarboxylate (323 mg, 627.116 μmol), Dess-Martin periodinane (877.753 mg, 2.069 mmol) in dichloromethane (10 mL) was stirred at room temperature for 5 h. The reaction solution was quenched with saturated sodium thiosulfate solution and extracted with DCM. The organic layer was concentrated under reduced pressure. The crude product was purified by prep-TLC using a gradient ethyl acetate/Hex=1/5 to give di-tert-butyl (2R,4R)-4-((6-chloro-3-fluoro-4-isobutyrylpyridin-2-yl)methyl)-2-methylpiperidine-1,4-dicarboxylate (315 mg) as a yellow oil. LCMS (ESI, m/z): 513 [M+H]$^+$.

Step 4: di-tert-butyl (2R,4R)-4-((6-((1-(tert-butyl)-5-methyl-1H-pyrazol-3-yl)amino)-3-fluoro-4-isobutyrylpyridin-2-yl)methyl)-2-methylpiperidine-1,4-dicarboxylate

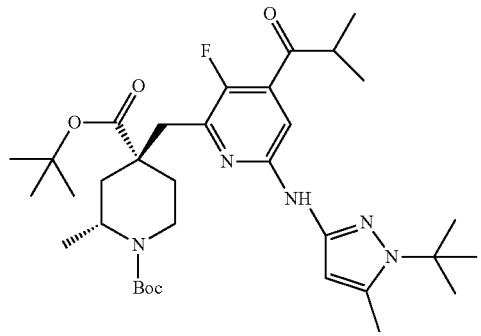 [SMILES: Cc1cc(Nc2cc(C(=O)C(C)C)c(F)c(C[C@@]3(C(=O)OC(C)(C)C)CCN(C(=O)OC(C)(C)C)[C@H](C)C3)n2)nn1C(C)(C)C]

Following the procedure analogous to that described in step 2 of Example 5, di-tert-butyl (2R,4R)-4-((6-chloro-3-fluoro-4-isobutyrylpyridin-2-yl)methyl)-2-methylpiperidine-1,4-dicarboxylate (315 mg, 0.613 mmol) was converted to the title compound (333 mg) as a yellow solid. LCMS (ESI, m/z): 630 [M+H]$^+$.

Step 5: tert-butyl (2R,4R)-4-((6-((1-(tert-butyl)-5-methyl-1H-pyrazol-3-yl)amino)-3-fluoro-4-isobutyrylpyridin-2-yl)methyl)-2-methylpiperidine-4-carboxylate

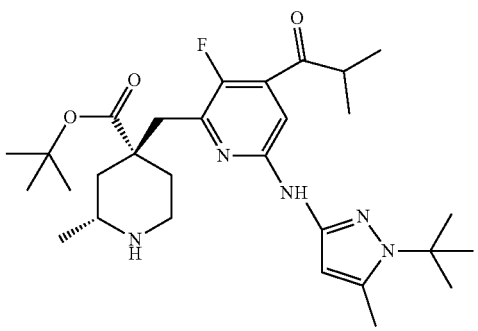 [SMILES: Cc1cc(Nc2cc(C(=O)C(C)C)c(F)c(C[C@@]3(C(=O)OC(C)(C)C)CCN[C@H](C)C3)n2)nn1C(C)(C)C]

Following the procedure analogous to that described in step 3 of Example 5, di-tert-butyl (2R,4R)-4-((6-((1-(tert-butyl)-5-methyl-1H-pyrazol-3-yl)amino)-3-fluoro-4-isobutyrylpyridin-2-yl)methyl)-2-methylpiperidine-1,4-dicarboxylate (333 mg, 0.529 mmol) was converted to the title compound (233 mg) as a yellow solid. LCMS (ESI, m/z): 530 [M+H]$^+$.

Step 6: tert-butyl (2R,4R)-4-((6-((1-(tert-butyl)-5-methyl-1H-pyrazol-3-yl)amino)-3-fluoro-4-isobutyrylpyridin-2-yl)methyl)-1-(3-chloro-2-fluorobenzyl)-2-methylpiperidine-4-carboxylate

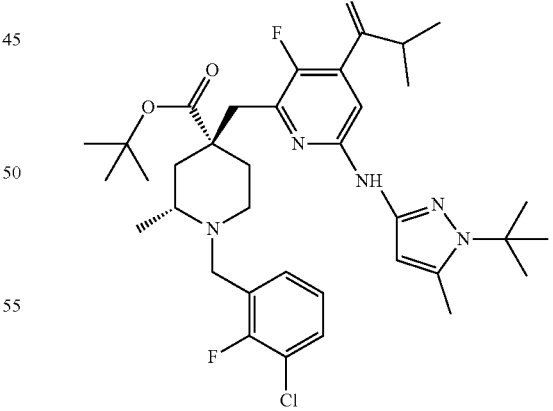

Following the procedure analogous to that described in step 4 of Example 5, tert-butyl (2R,4R)-4-((6-((1-(tert-butyl)-5-methyl-1H-pyrazol-3-yl)amino)-3-fluoro-4-isobutyrylpyridin-2-yl)methyl)-2-methylpiperidine-4-carboxylate (233 mg, 0.440 mmol) was converted to the title compound (375 mg) as a yellow solid. LCMS (ESI, m/z): 672 [M+H]$^+$.

Step 7: (2R,4R)-1-(3-chloro-2-fluorobenzyl)-4-((3-fluoro-4-isobutyryl-6-((5-methyl-1H-pyrazol-3-yl)amino)pyridin-2-yl)methyl)-2-methylpiperidine-4-carboxylic acid

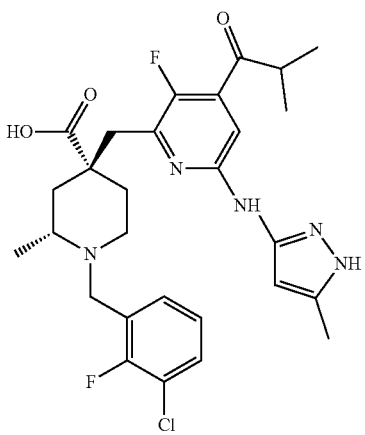 [SMILES: Cc1cc(Nc2cc(C(=O)C(C)C)c(F)c(C[C@@]3(C(=O)O)CCN(Cc4cccc(Cl)c4F)[C@H](C)C3)n2)n[nH]1]

Following the procedure analogous to that described in step 5 of Example 5, tert-butyl (2R,4R)-4-((6-((1-(tert-butyl)-5-methyl-1H-pyrazol-3-yl)amino)-3-fluoro-4-isobutyrylpyridin-2-yl)methyl)-1-(3-chloro-2-fluorobenzyl)-2-methylpiperidine-4-carboxylate (375 mg, 0.558 mmol) was converted to the title compound (94 mg) as a white solid. LCMS (ESI, m/z): 560 [M+H]$^+$. $^1$H NMR (400 MHz, MeOD) δ 8.47 (d, J=8.9 Hz, 1H), 8.40 (d, J=5.0 Hz, 1H), 7.24 (d, J=4.5 Hz, 1H), 6.82 (dd, J=16.7, 10.6 Hz, 1H), 6.30 (dd, J=16.7, 1.9 Hz, 1H), 5.81 (dd, J=10.6, 1.9 Hz, 1H), 4.70 (s, 2H), 4.60-4.37 (m, 2H), 3.83 (t, J=13.6 Hz, 2H), 2.89-2.69 (m, 2H), 2.03 (d, J=10.7 Hz, 3H), 1.51 (d, J=4.1 Hz, 2H), 1.46 (t, J=6.7 Hz, 3H), 1.29 (s, 1H), 1.18 (d, J=6.8 Hz, 3H), 1.00 (dd, J=12.2, 6.8 Hz, 3H).

Example 86

2-(((2R,4R)-4-carboxy-1-(3-chloro-2-fluorobenzyl)-2-methylpiperidin-4-yl)methyl)-3-fluoro-6-((5-methyl-1H-pyrazol-3-yl)amino)isonicotinic acid

Step 1: tert-butyl-(2R,4R)-4-((6-chloro-3-fluoropyridin-2-yl)methyl)-2-methylpiperidine-4-carboxylate

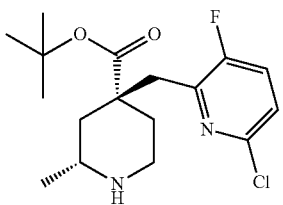 [SMILES: C[C@@H]1C[C@](Cc2nc(Cl)ccc2F)(C(=O)OC(C)(C)C)CCN1]

Following the procedure analogous to that described in Step 3 for the synthesis of Example 5, INT C3 (3.79 g, 8.556 mmol) was converted to the title compound (2.63 g, Y=89%) as a yellow oil. LCMS (ESI, m/z): 343 [M+H]$^+$.

Step 2: tert-butyl-(2R,4R)-1-(3-chloro-2-fluorobenzyl)-4-((6-chloro-3-fluoropyridin-2-yl) methyl)-2-methylpiperidine-4-carboxylate

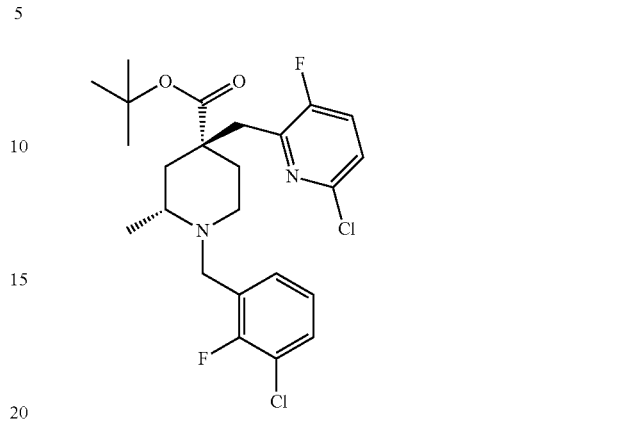

Following the procedure analogous to that described in Step 4 for the synthesis of Example 5, tert-butyl-(2R,4R)-4-((6-chloro-3-fluoropyridin-2-yl)methyl)-2-methylpiperidine-4-carboxylate (2.63 g, 7.671 mmol) was converted to the title compound (2.09 g, Y=56%) as a yellow oil. LCMS (ESI, m/z): 485 [M+H]$^+$.

Step 3: 2-(((2R,4R)-4-(tert-butoxycarbonyl)-1-(3-chloro-2-fluorobenzyl)-2-methylpiperidin-4-yl)methyl)-6-chloro-3-fluoroisonicotinic acid

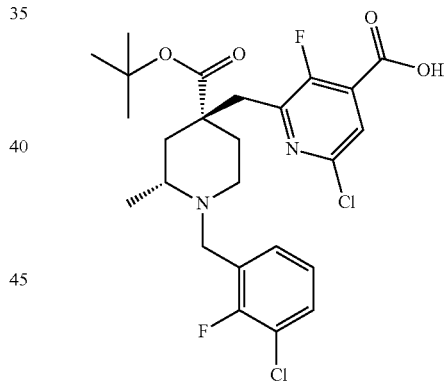

A solution of diisopropylamine (1.18 g, 11.661 mmol) in THF (5 mL) was added n-Butyl lithium (2.5M) in hexane (3.5 mL, 8.75 mmol) at −78° C. under nitrogen. The solution was stirred at 0° C. for 30 min. A solution of tert-butyl-(2R,4R)-1-(3-chloro-2-fluorobenzyl)-4-((6-chloro-3-fluoropyridin-2-yl)methyl)-2-methylpiperidine-4-carboxylate (2.09 g, 4.306 mmol) in THF (5 ml) was added dropwise to above solution. The resulting solution was stirred at −40° C. for 1 h. Carbon dioxide was bubbled into the reaction and the solution was stirred at −60° C. for 1 h. The resulting solution was quenched with saturated aqueous NH$_4$Cl aqueous solution and extracted with ethyl acetate. The organic layer was dried over anhydrous sodium sulfate, filtered and concentrated under reduced pressure. The resulting residue was purified by C18 reversed phase column chromatography eluting with H$_2$O/ACN to afford 2-(((2R,4R)-4-(tert-butoxycarbonyl)-1-(3-chloro-2-fluorobenzyl)-2-methylpiperidin- 4-yl)methyl)-6-chloro-3-fluoroisonicotinic acid (906 mg, Y=40%) as white solid. LCMS (ESI, m/z): 529 [M+H]⁺.

Step 4: Methyl-2-(((2R,4R)-4-(tert-butoxycarbonyl)-1-(3-chloro-2-fluorobenzyl)-2-methylpiperidin-4-yl)methyl)-6-chloro-3-fluoroisonicotinate

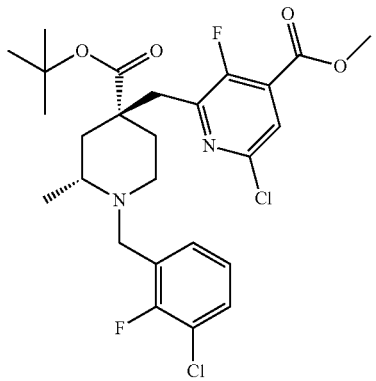 [SMILES: COC(=O)c1cc(Cl)nc(C[C@@]2(C(=O)OC(C)(C)C)CCN(Cc3cccc(Cl)c3F)[C@H](C)C2)c1F]

To a solution of 2-(((2R,4R)-4-(tert-butoxycarbonyl)-1-(3-chloro-2-fluorobenzyl)-2-methylpiperidin-4-yl)methyl)-6-chloro-3-fluoroisonicotinic-acid (906 mg, 1.711 mmol) in DMF (30 ml) was added methyl iodide (408 mg, 2.874 mmol), $K_2CO_3$ (489 mg, 3.538 mmol) at room temperature. The resulting solution was stirred for 3 h at room temperature. The resulting mixture was filtrated. The filtrate was removed under reduced pressure. The resulting residue was purified by C18 reversed phase column chromatography eluting with $H_2O$/ACN to afford methyl-2-(((2R,4R)-4-(tert-butoxycarbonyl)-1-(3-chloro-2-fluorobenzyl)-2-methylpiperidin-4-yl) methyl)-6-chloro-3-fluoroisonicotinate (607 mg Y=65%) as a yellow oil. LCMS (ESI, m/z): 543 [M+H]⁺.

Step 5: methyl-2-(((2R,4R)-4-(tert-butoxycarbonyl)-1-(3-chloro-2-fluoro-benzyl)-2-methylpiperidin-4-yl) methyl)-6-((1-(tert-butyl)-5-methyl-1H-pyrazol-3-yl)amino)-3-fluoroisonicotinate

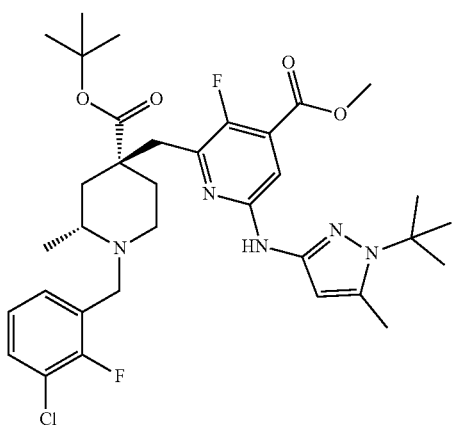 [SMILES: COC(=O)c1cc(Nc2cc(C)n(C(C)(C)C)n2)nc(C[C@@]2(C(=O)OC(C)(C)C)CCN(Cc3cccc(Cl)c3F)[C@H](C)C2)c1F]

Following the procedure analogous to that described in Step 2 for the synthesis of Example 5, methyl-2-(((2R,4R)-4-(tert-butoxycarbonyl)-1-(3-chloro-2-fluorobenzyl)-2-methylpiperidin-4-yl)methyl)-6-chloro-3-fluoroisonicotinate (426 mg, 783.911 μmol) was converted to the title compound (433 mg, Y=84%) as a yellow oil. LCMS (ESI, m/z): 660 [M+H]⁺.

Step 6: 2-(((2R,4R)-4-(tert-butoxycarbonyl)-1-(3-chloro-2-fluorobenzyl)-2-methylpiperidin-4-yl)methyl)-6-((1-(tert-butyl)-5-methyl-1H-pyrazol-3-yl)amino)-3-fluoroisonicotinic acid

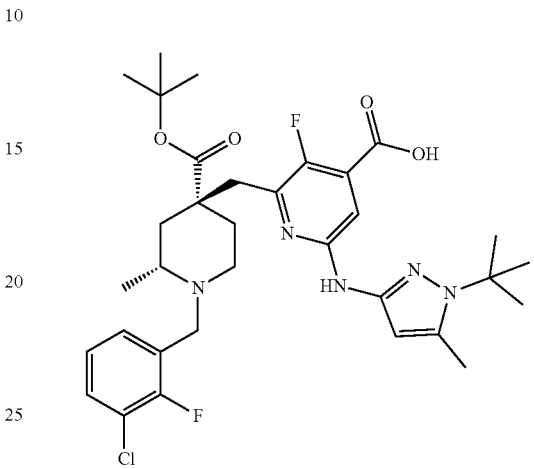

A solution of methyl-2-(((2R,4R)-4-(tert-butoxycarbonyl)-1-(3-chloro-2-fluorobenzyl)-2-methylpiperidin-4-yl)methyl)-6-((1-(tert-butyl)-5-methyl-1H-pyrazol-3-yl)amino)-3-fluoroisonicotinate (433 mg, 655.870 μmol), lithium hydroxide (122 mg, 2.907 mmol) in methanol (10 mL) and water (10 mL) was stirred at room temperature for 3 h. The resulting solution was added 1N HCl aq. to adjust pH to 5 and extracted with ethyl acetate (100 mL). The organic layer was washed with brine, dried over anhydrous sodium sulfate, filtered and concentrated under reduced pressure to give 2-(((2R,4R)-4-(tert-butoxycarbonyl)-1-(3-chloro-2-fluorobenzyl)-2-methylpiperidin-4-yl)methyl)-6-((1-(tert-butyl)-5-methyl-1H-pyrazol-3-yl)amino)-3-fluoroisonicotinic acid (402 mg, crude) as a yellow solid. The crude product was not purified and used for the next step directly. LCMS (ESI, m/z): 646 [M+H]⁺

Step 7: 2-(((2R,4R)-4-carboxy-1-(3-chloro-2-fluorobenzyl)-2-methylpiperidin-4-yl)methyl)-3-fluoro-6-((5-methyl-1H-pyrazol-3-yl)amino)isonicotinic acid

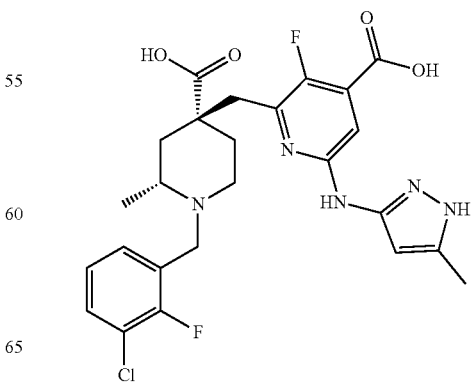

Following the procedure analogous to that described in Step 5 for the synthesis of Example 5, 2-(((2R,4R)-4-(tert-butoxycarbonyl)-1-(3-chloro-2-fluorobenzyl)-2-methylpiperidin-4-yl) methyl)-6-((1-(tert-butyl)-5-methyl-1H-pyrazol-3-yl)amino)-3-fluoroisonicotinic acid (47 mg, 72.737 μmol) was converted to the title compound (24 mg) as a white solid. LCMS (ESI, m/z): 534 [M+H]$^+$. NMR (400 MHz, MeOD) δ 7.68 (t, J=73 Hz, 1H), 7.60 (t, J=7.0 Hz, 1H), 7.32 (m, 2H), 6.09 (s, 1H), 3.56 (s, 2H), 3.41 (t, J=25.3 Hz, 4H), 2.42 (s, 3H), 2.21 (m, 5H), 1.61 (s, 3H).

Example 87

(2R,4R)-1-(3-chloro-2-fluorobenzyl)-4-((4-(dimethylcarbamoyl)-3-fluoro-6-((5-methyl-1H-pyrazol-3-yl)amino)pyridin-2-yl)methyl)-2-methylpiperidine-4-carboxylic acid Step 1: tert-butyl-(2R,4R)-4-((6-((1-(tert-butyl)-5-methyl-1H-pyrazol-3-yl)amino)-4-(dimethylcarbamoyl)-3-fluoropyridin-2-yl)methyl)-1-(3-chloro-2-fluorobenzyl)-2-methylpiperidine-4-carboxylate

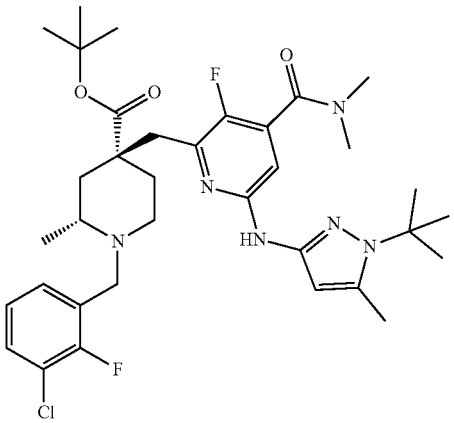 [SMILES: Cc1cc(Nc2cc(C(=O)N(C)C)c(F)c(C[C@@]3(C(=O)OC(C)(C)C)CCN(Cc4cccc(Cl)c4F)[C@H](C)C3)n2)nn1C(C)(C)C]

To a solution of 2-(((2R,4R)-4-(tert-butoxycarbonyl)-1-(3-chloro-2-fluorobenzyl)-2-methylpiperidin-4-yl)methyl)-6-((1-(tert-butyl)-5-methyl-1H-pyrazol-3-yl)amino)-3-fluoroisonicotinic acid (100 mg, 154.759 μmol) in ACN (30 ml) was added dimethylamine (20.931 mg, 464.277 μmol), triethylamine (46.980 mg, 464.277 μmol) and HATU (117.688 mg, 309.518 μmol). The resulting solution was stirred for 3 h at room temperature. The resulting mixture was filtrated. The filtrate was removed under reduced pressure. The resulting residue was purified by C18 reversed phase column chromatography eluting with H$_2$O/ACN to afford tert-butyl-(2R,4R)-4-((6-((1-(tert-butyl)-5-methyl-1H-pyrazol-3-yl)amino)-4-(dimethylcarbamoyl)-3-fluoropyridin-2-yl) methyl)-1-(3-chloro-2-fluorobenzyl)-2-methylpiperidine-4-carboxylate (72 mg Y=69%) as a yellow oil. LCMS (ESI, m/z): 673 [M+H]$^+$.

Step 2: (2R,4R)-1-(3-chloro-2-fluorobenzyl)-4-((4-(dimethylcarbamoyl)-3-fluoro-6-((5-methyl-1H-pyrazol-3-yl)amino)pyridin-2-yl)methyl)-2-methylpiperidine-4-carboxylic acid

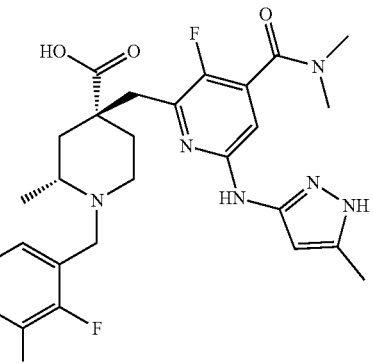

Following the procedure analogous to that described in Step 5 for the synthesis of Example 5, tert-butyl-(2R,4R)-4-((6-((1-(tert-butyl)-5-methyl-1H-pyrazol-3-yl)amino)-4-(dimethylcarbamoyl)-3-fluoropyridin-2-yl)methyl)-1-(3-chloro-2-fluorobenzyl)-2-methylpiperidine-4-carboxylate (72 mg, 106.984 μmol) was converted to the title compound (24 mg) as a white solid. LCMS (ESI, m/z): 561 [M+H]$^+$. $^1$H NMR (400 MHz, MeOD) δ 7.64 (dt, J=13.8, 7.1 Hz, 2H), 7.34 (t, J=7.9 Hz, 1H), 6.84 (d, J=3.6 Hz, 1H), 6.10 (s, 1H), 3.56 (s, 2H), 3.41 (t, J=24.0 Hz, 4H), 3.13 (s, 3H), 2.97 (s, 3H), 2.43 (s, 3H), 2.26 (d, J=14.0 Hz, 1H), 2.05 (dd, J=67.0, 21.9 Hz, 4H), 1.61 (d, J=5.7 Hz, 3H).

The following example in Table 10 was synthesized using the above procedure with the corresponding starting materials and intermediates.

TABLE 10

| Example No. | Structure | Chemical Name | $^1$HNMR & MS: (M + H)$^+$ |
|---|---|---|---|
| 88 | 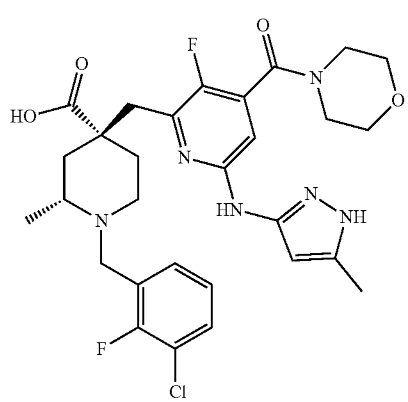 [SMILES: Cc1cc(Nc2cc(C(=O)N3CCOCC3)c(F)c(C[C@@]3(C(=O)O)CCN(Cc4cccc(Cl)c4F)[C@H](C)C3)n2)n[nH]1] | (2R,4R)-1-(3-chloro-2-fluoro benzyl)-4-((3-fluoro-6-((5-methyl-1H-pyrazol-3-yl)amino)-4-(morpholine-4-carbonyl)-pyridin-2-yl)methyl)-2-methyl-piperidine-4-carboxylic acid | $^1$H NMR (400 MHz, MeOD) δ 7.49 (dd, J = 15.1, 7.3 Hz, 2H), 7.22 (t, J = 7.8 Hz, 1H), 6.82 (s, 1H), 5.90 (s, 1H), 3.76 (s, 4H), 3.67 (s, 2H), 3.39 (s, 2H), 3.16 (m, 4H), 2.77 (s, 2H), 2.26 (s, 3H), 2.02 (m, 5H), 1.33 (d, J = 4.2 Hz, 3H). MS: 603 (M + H)$^+$ |

TABLE 10-continued

| Example No. | Structure | Chemical Name | ¹HNMR & MS: (M + H)⁺ |
|---|---|---|---|
| 89 | 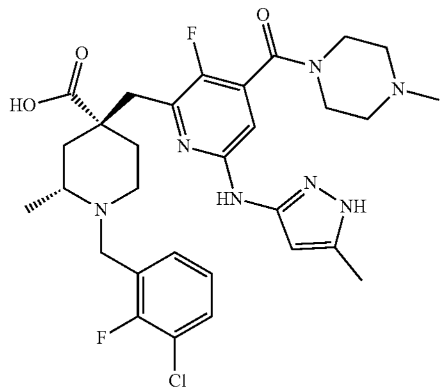 | (2R,4R)-1-(3-chloro-2-fluoro benzyl)-4-((3-fluoro-6-((5-methyl-1H-pyrazol-3-yl)amino)-4-(4-methylpiperazine-1-carbonyl)pyridin-2-yl)methyl)-2-methylpiperidine-4-carboxylic acid | ¹H NMR (400 MHz, MeOD) δ 7.66 (d, J = 7.3 Hz, 3H), 7.33(t, J = 7.6 Hz, 1H), 6.97 (s, 1H), 6.13 (s, 1H), 3.75 (d, J = 26.1 Hz, 2H), 3.56 (d, J = 67.8 Hz, 8H), 3.34 (s, 2H), 3.21 (d, J = 6.7 Hz, 2H), 2.98 (s, 3H), 2.44 (s, 3H), 2.14 (t, ,7 = 47.8 Hz, 5H), 1.59 (s, 3H). MS: 616 (M + H)⁺ |

Example 90

(2R,4R)-1-(3-chloro-2-fluorobenzyl)-4-((4-cyano-5-fluoro-6-((5-methyl-1H-pyrazol-3-yl)amino)pyridin-2-yl)methyl)-2-methylpiperidine-4-carboxylic acid Step 1: tert-butyl (2R,4R)-4-((4-carbamoyl-6-chloro-5-fluoropyridin-2-yl)methyl)-1-(3-chloro-2-fluorobenzyl)-2-methylpiperidine-4-carboxylate

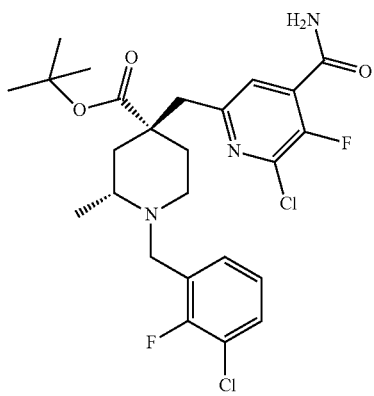 [SMILES: C[C@@H]1C[C@](Cc2cc(C(N)=O)c(F)c(Cl)n2)(C(=O)OC(C)(C)C)CCN1Cc1cccc(Cl)c1F]

A solution of 6-(((2R,4R)-4-(tert-butoxycarbonyl)-1-(3-chloro-2-fluorobenzyl)-2-methylpiperidin-4-yl)methyl)-2-chloro-3-fluoroisonicotinic acid (699 mg, 1.320 mmol) in DMF (8 mL), ammonium chloride (204 mg, 3.814 mmol), 1-hydroxy benzotriazole anhydrous (191 mg, 1.414 mmol), N-(3-(Dimethylamino)propyl) propionimidamidehydrochloride (423 mg, 2.207 mmol), triethylamine (315 mg, 3.113 mmol) was stirred at room temperature for 20 h. After completion, the reaction solution was diluted with brine and extracted with ethyl acetate. The organic layer was washed with brine, dried over anhydrous sodium sulfate, filtered and concentrated under reduced pressure. The resulting residue was purified by C18 reversed phase column chromatography eluting with H₂O/ACN to afford tert-butyl (2R,4R)-4-((4-carbamoyl-6-chloro-5-fluoropyridin-2-yl)methyl)-1-(3-chloro-2-fluorobenzyl)-2-methyl piperidine-4-carboxylate (573 mg) as a white solid. LCMS (ESI, m/z): 530 [M+H]⁺.

Step 2: tert-butyl (2R,4R)-1-(3-chloro-2-fluorobenzyl)-4-((6-chloro-4-cyano-5-fluoropyridin-2-yl) methyl)-2-methylpiperidine-4-carboxylate

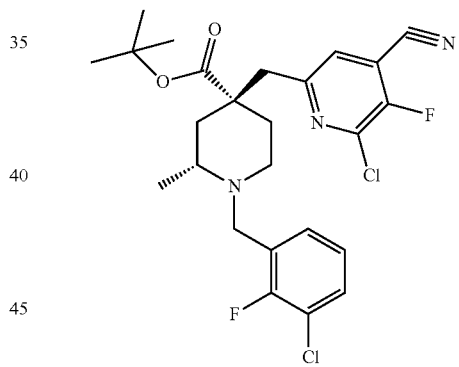

To a solution of tert-butyl (2R,4R)-4-((4-carbamoyl-6-chloro-5-fluoropyridin-2-yl) methyl)-1-(3-chloro-2-fluorobenzyl)-2-methylpiperidine-4-carboxylate (473 mg, 893.459 μmol) and pyridine (298 mg, 3.767 mmol) in THF (6 mL) was added trifluoroacetic anhydride (530 mg, 2.523) at 0~5° C. The resulting solution was stirred at room temperature for 3 h. After completion, the reaction was quenched with saturated sodium bicarbonate solution and extracted with ethyl acetate. The organic layer was dried over anhydrous sodium sulfate, filtered and concentrated under reduced pressure. The resulting residue was purified by C18 reversed phase column chromatography eluting with H₂O/ACN to afford tert-butyl (2R,4R)-1-(3-chloro-2-fluorobenzyl)-4-((6-chloro-4-cyano-5-fluoropyridin-2-yl) methyl)-2-methylpiperidine-4-carboxylate (547 mg). LCMS (ESI, m/z): 510 [M+H]⁺.

Step 3: tert-butyl (2R,4R)-4-((6-(((1-(tert-butyl)-5-methyl-1H-pyrazol-3-yl)amino)-4-cyano-5-fluoropyridin-2-yl)methyl)-1-(3-chloro-2-fluorobenzyl)-2-methylpiperidine-4-carboxylate

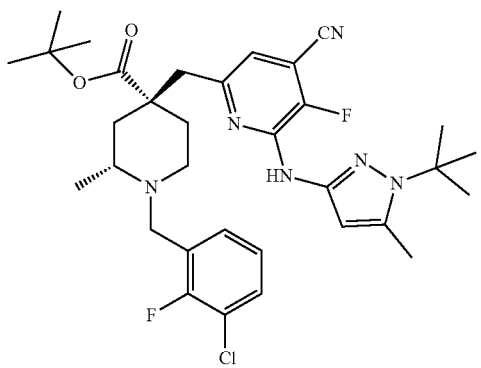 [SMILES: Cc1cc(Nc2nc(C[C@@]3(C(=O)OC(C)(C)C)CCN(Cc4cccc(Cl)c4F)[C@H](C)C3)cc(C#N)c2F)nn1C(C)(C)C]

Following the procedure analogous to that described in step 2 of Example 5, tert-butyl (2R,4R)-1-(3-chloro-2-fluorobenzyl)-4-((6-chloro-4-cyano-5-fluoropyridin-2-yl)methyl)-2-methylpiperidine-4-carboxylate (547 mg, 1.072 mmol) was converted to the title compound (87 mg) as a white solid. LCMS (ESI, m/z): 627 [M+H]+.

Step 4: (2R,4R)-1-(3-chloro-2-fluorobenzyl)-4-((4-cyano-5-fluoro-6-((5-methyl-1H-pyrazol-3-yl)amino)pyridin-2-yl) methyl)-2-methylpiperidine-4-carboxylic acid

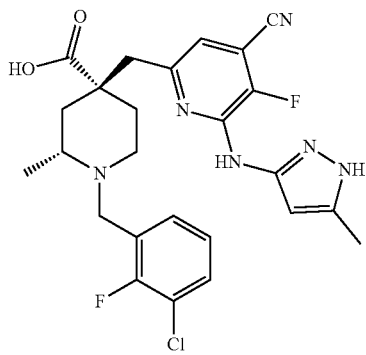

Following the procedure analogous to that described in step 5 of Example 5, tert-butyl (2R,4R)-4-((6-(((1-(tert-butyl)-5-methyl-1H-pyrazol-3-yl)amino)-4-cyano-5-fluoropyridin-2-yl) methyl)-1-(3-chloro-2-fluorobenzyl)-2-methylpiperidine-4-carboxylate (87 mg, 0.139 mmol) was converted to the title compound (47 mg) as a yellow solid. LCMS (ESI, m/z): 515 [M+H]+. 1H NMR (400 MHz, MeOD) δ 7.67 (dt, J=14.1, 7.0 Hz, 2H), 7.35 (t, J=7.9 Hz, 1H), 7.17 (s, 1H), 6.30 (s, 1H), 4.44 (d, J=12.2 Hz, 2H), 4.02 (s, 2H), 3.50 (s, 1H), 3.50 (s, 2H), 2.44 (s, 3H), 2.18 (dd, J=51.9, 37.7 Hz, 4H), 1.56 (s, 3H).

Example 91

(2R,4R)-1-(3-chloro-2-fluorobenzyl)-4-((3,5-difluoro-6-((5-methyl-1H-pyrazol-3-yl)amino)pyridin-2-yl)methyl)-2-methylpiperidine-4-carboxylic acid Step 1: di-tert-butyl-(2R,4R)-4-((6-(((1-(tert-butyl)-5-methyl-1H-pyrazol-3-yl)amino)-3,5-difluoropyridin-2-yl) methyl)-2-methylpiperidine-1,4-dicarboxylate

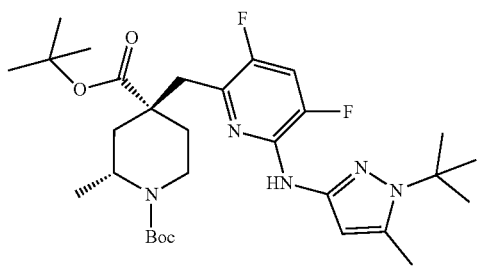 [SMILES: Cc1cc(Nc2nc(C[C@@]3(C(=O)OC(C)(C)C)CCN(C(=O)OC(C)(C)C)[C@H](C)C3)c(F)cc2F)nn1C(C)(C)C]

Following the procedure analogous to that described in Step 2 for the synthesis of Example 5, INT C6 (275 mg, 596.606 μmol) was converted to the title compound (178 mg, Y=52%) as a yellow oil. LCMS (ESI, m/z): 578 [M+H]+.

Step 2: (2R,4R)-4-((6-(((1-(tert-butyl)-5-methyl-1H-pyrazol-3-yl)amino)-3,5-difluoropyridin-2-yl) methyl)-2-methylpiperidine-4-carboxylate

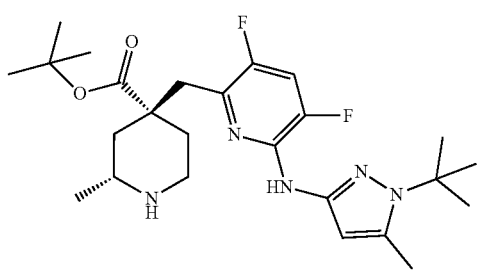 [SMILES: Cc1cc(Nc2nc(C[C@@]3(C(=O)OC(C)(C)C)CCN[C@H](C)C3)c(F)cc2F)nn1C(C)(C)C]

Following the procedure analogous to that described in Step 3 for the synthesis of Example 5, di-tert-butyl-(2R,4R)-4-((6-((1-(tert-butyl)-5-methyl-1H-pyrazol-3-yl)amino)-3,5-difluoropyridin-2-yl)methyl)-2-methylpiperidine-1,4-dicarboxylate (178 mg, 308.116 μmol) was converted to the title compound (131 mg, Y=89%) as a yellow oil. LCMS (ESI, m/z): 478 [M+H]⁺.

Step 3: tert-butyl-(2R,4R)-4-((6-((1-(tert-butyl)-5-methyl-1H-pyrazol-3-yl)amino)-3,5-difluoropyridin-2-yl)methyl)-1-(3-chloro-2-fluorobenzyl)-2-methylpiperidine-4-carboxylate

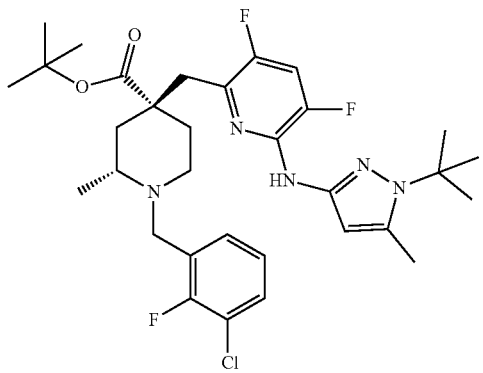 [SMILES: Cc1cc(Nc2nc(C[C@@]3(C(=O)OC(C)(C)C)CCN(Cc4cccc(Cl)c4F)[C@H](C)C3)c(F)cc2F)nn1C(C)(C)C]

Following the procedure analogous to that described in Step 4 for the synthesis of Example 5, (2R,4R)-4-((6-((1-(tert-butyl)-5-methyl-1H-pyrazol-3-yl)amino)-3,5-difluoropyridin-2-yl)-methyl)-2-methylpiperidine-4-carboxylate (131 mg, 274.294 μmol) was converted to the title compound (77 mg, Y=45%) as a yellow oil. LCMS (ESI, m/z): 620 [M+H]⁺.

Step 4: (2R,4R)-1-(3-chloro-2-fluorobenzyl)-4-((3,5-difluoro-6-((5-methyl-1H-pyrazol-3-yl) amino) pyridin-2-yl) methyl)-2-methylpiperidine-4-carboxylic acid

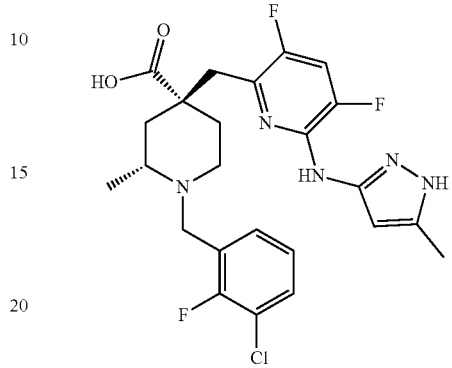

Following the procedure analogous to that described in Step 5 for the synthesis of Example 5, tert-butyl-(2R,4R)-4-((6-((1-(tert-butyl)-5-methyl-1H-pyrazol-3-yl)amino)-3,5-difluoropyridin-2-yl)methyl)-1-(3-chloro-2-fluorobenzyl)-2-methylpiperidine-4-carboxylate (77 mg, 124.164 μmol) was converted to the title compound 48 mg as a white solid. LCMS (ESI, m/z): 508 [M+H]⁺. ¹H NMR (400 MHz, MeOD) δ 7.59 (m, 3H), 7.24 (t, J=8.0 Hz, 1H), 6.10 (s, 1H), 3.44 (s, 2H), 3.22 (d, J=1.6 Hz, 2H), 3.20 (d, J=1.6 Hz, 2H), 2.34 (s, 3H), 2.06 (dd, J=30.2, 18.6 Hz, 5H), 1.52 (d, J=6.2 Hz, 3H).

The following example in Table 11 was synthesized using the above procedure with the corresponding starting materials and intermediates.

TABLE 11

| Example No. | Structure | Chemical Name | ¹HNMR & MS: (M + H)⁺ |
|---|---|---|---|
| 92 | 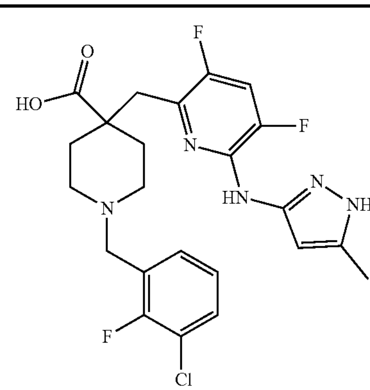 | 1-(3-chloro-2-fluorobenzyl)-4-((3,5-difluoro-6-((5-methyl-1H-pyrazol-3-yl)amino)pyridin-2-yl)methyl)piperidine-4)-carboxylic acid | 1H NMR (400 MHz, MeOD) δ 7.67 (ddd, J = 20.1, 14.1, 8.2 Hz, 3H), 7.32 (t, J = 7.8 Hz, 1H), 6.23 (s, 1H), 4.45 (s, 2H), 3.56 (d, J = 12.9 Hz, 2H), 3.25 (s, 2H), 3.11 (t, J = 12.8 Hz, 2H), 2.43 (d, J = 18.8 Hz, 5H), 2.08 (t, J = 12.3 Hz, 2H). MS: 494 (M + H)⁺ |

Example 93

(2R,4R)-1-(3-chloro-2-fluorobenzyl)-4-((3,5-difluoro-4-methyl-6-((5-methyl-1H-pyrazol-3-yl)amino)pyridin-2-yl)methyl)-2-methylpiperidine-4-carboxylic acid

Step 1: tert-butyl-(2R,4R)-4-((6-chloro-3,5-difluoropyridin-2-yl)methyl)-2-methylpiperidine-4-carboxylate

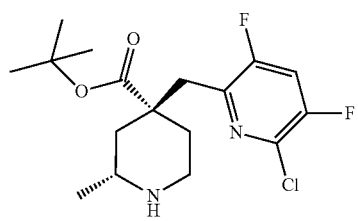 [SMILES: C[C@@H]1C[C@](Cc2nc(Cl)c(F)cc2F)(C(=O)OC(C)(C)C)CCN1]

A solution of INT C6 (1.23 g, 2.668 mmol) in dichloromethane (18 ml) was added trifluoroacetic acid (2 ml) and stirred at room temperature for 1 h. After completion, the reaction was quenched with saturated sodium bicarbonate solution (100 ml) and extracted with DCM. The organic layer was dried over anhydrous sodium sulfate, filtered and concentrated under reduced pressure to afford (0.93 g, 2.577 mmol, Y=97%) of the title compound as a yellow solid. LCMS (ESI, m/z): 361 [M+H]$^+$.

Step 2: tert-butyl-(2R,4R)-1-(3-chloro-2-fluorobenzyl)-4-((6-chloro-3,5-difluoropyridin-2-yl) methyl)-2-methylpiperidine-4-carboxylate

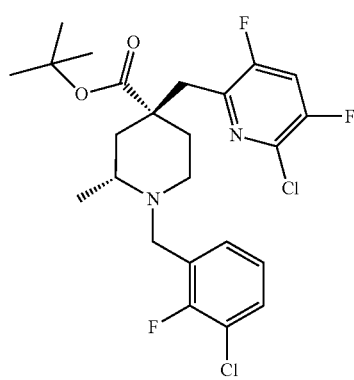 [SMILES: C[C@@H]1C[C@](Cc2nc(Cl)c(F)cc2F)(C(=O)OC(C)(C)C)CCN1Cc1cccc(Cl)c1F]

A mixture of tert-butyl-(2R,4R)-4-((6-chloro-3,5-difluoropyridin-2-yl)methyl)-2-methylpiperidine-4-carboxylate (0.93 g, 2.577 mmol), potassium carbonate (0.91 g, 6.584 mmol) and 1-(bromomethyl)-3-chloro-2-fluorobenzene (0.59 g, 2.640 mmol) in ACN (10 mL) was stirred for 2 h at room temperature. After completion, the resulting mixture was filtered and concentrated under vacuum. The crude product was purified by silica gel column chromatography eluting with EtOAc/hexane (0~30%) to afford (0.91 g, Y=70%) of the title compound as a yellow solid. LCMS (ESI, m/z): 503 [M+H]$^+$.

Step 3: tert-butyl-(2R,4R)-1-(3-chloro-2-fluorobenzyl)-4-((6-chloro-3,5-difluoro-4-methylpyridin-2-yl)methyl)-2-methylpiperidine-4-carboxylate A solution of diisopropylamine (527 mg, 5.208 mmol) in THF (3 ml) was added n-butyllithium 2.5 M in THF (1.5 ml, 3.75 mmol) at −70~−60° C. under nitrogen. The solution was stirred for 1 h at −10° C.~0° C. The resulting solution was slowly added tert-butyl-(2R,4R)-1-(3-chloro-2-fluorobenzyl)-4-((6-chloro-3,5-difluoropyridin-2-yl)methyl)-2-methylpiperidine-4-carboxylate (0.91 g, 1.808 mmol) in THF (5 ml). The solution was stirred at −70° C.~60° C. for 1 h.

A solution of iodomethane (450 mg, 3.170 mmol) in THF (3 ml) was added to the above solution. The resulting solution was stirred at −70° C.~−60° C. for 2 h. After completion, the reaction was quenched with saturated ammonium chloride solution (100 mL) and extracted with EtOAc. The organic layer were combined, dried over anhydrous sodium sulfate and concentrated under vacuum. The residue was purified by C18 reverse phase chromatography eluting with H$_2$O/ACN to afford (0.92 g, 1.778 mmol, Y=98%) of the title compound as a yellow oil. LCMS (ESI, m/z): 517 [M+H]$^+$.

Step 4: tert-butyl-(2R,4R)-4-((6-((1-(tert-butyl)-5-methyl-1H-pyrazol-3-yl)amino)-3,5-difluoro-4-methylpyridin-2-yl)methyl)-1-(3-chloro-2-fluorobenzyl)-2-methylpiperidine-4-carboxylate

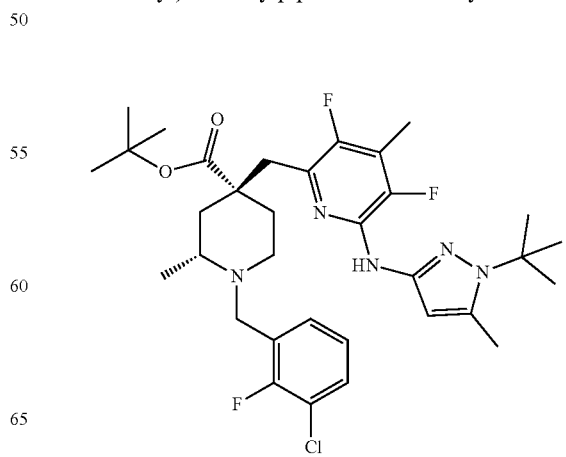

A mixture of tert-butyl-(2R,4R)-1-(3-chloro-2-fluorobenzyl)-4-((6-chloro-3,5-difluoro-4-methylpyridin-2-yl)methyl)-2-methylpiperidine-4-carboxylate (0.92 g, 1.778 mmol), tris(dibenzylideneacetone)dipalladium (488.467 mg, 533.426 μmol), dimethylbwasdiphenylphosphinoxanthene (411.533 mg, 711.235 μmol), 1-tert-butyl-3-methyl-1H-pyrazol-5-amine (354.180 mg, 2.312 mmol) and K₃PO₄ (754.856 mg, 3.556 mmol) in 1,4-dioxane (15 ml) was stirred at 110° C. for 5 h under nitrogen. The resulting solution was cooled to room temperature and diluted with brine and extracted with ethyl acetate. The organic layer was dried over anhydrous sodium sulfate, filtered and concentrated under reduced pressure. The residue was purified by C18 reverse phase chromatography eluting with H₂O/CH₃CN to afford (714 mg, 1.126 mmol, Y=63%) of the title compound as a yellow solid. LCMS (ESI, m/z): 634 [M+H]⁺.

Step 5: (2R,4R)-1-(3-chloro-2-fluorobenzyl)-4-((3,5-difluoro-4-methyl-6-((5-methyl-1H-pyrazol-3-yl)amino)pyridin-2-yl)methyl)-2-methylpiperidine-4-carboxylic acid

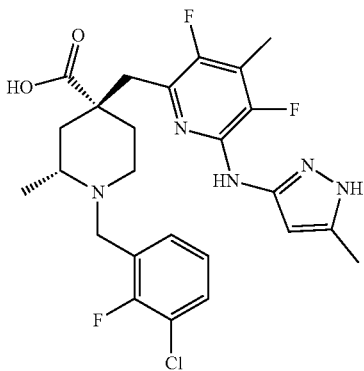

A solution of tert-butyl-(2R,4R)-4-((6-((1-(tert-butyl)-5-methyl-1H-pyrazol-3-yl)amino)-3,5-difluoro-4-methylpyridin-2-yl)methyl)-1-(3-chloro-2-fluorobenzyl)-2-methylpiperidine-4-carboxylat (714 mg, 1.126 mmol) in formic acid (15 mL) was stirred at reflux for 4 h. After completion, the resulting solution was concentrated under reduced pressure. The residue was dissolved in water (40 mL) at 0° C. and adjusted PH=6~7 with sodium hydroxide aqueous solution (5 M). The resulting mixture was extracted with DCM. The organic layer was dried over anhydrous sodium sulfate, filtered and concentrated under reduced pressure. The crude product was purified by C18 reverse phase column chromatography eluting with MeOH/Water to afford (349 mg, 668.632 umol, Y=59%) of the title compound as a white solid. LCMS (ESI, m/z): 522 [M+H]⁺. ¹H NMR (400 MHz, MeOD) δ 7.35 (m, 2H), 7.09 (s, 1H), 5.89 (s, 1H), 4.18 (d, J=13.6 Hz, 1H), 3.53 (m, 1H), 3.06 (s, 2H), 2.95 (s, 1H), 2.80 (d, J=12.4 Hz, 1H), 2.59 (t, J=11.2 Hz, 1H), 2.13 (s, 6H), 1.83 (t, J=11.1 Hz, 2H), 1.73 (s, 2H), 1.19 (d, J=6.1 Hz, 3H).

Example 94

(2R,4R)-1-(3-chloro-2-fluorobenzyl)-4-((3-fluoro-4-(2-fluoropropan-2-yl)-6-((5-methyl-1H-pyrazol-3-yl)amino)pyridin-2-yl)methyl)-2-methylpiperidine-4-carboxylic acid Step 1: di-tert-butyl-(2R,4R)-4-((6-bromo-3-fluoro-4-(2-hydroxypropan-2-yl)pyridin-2-yl) methyl)-2-methylpiperidine-1,4-dicarboxylate

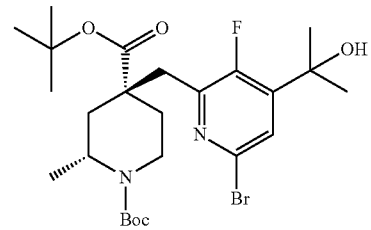 [SMILES: C[C@@H]1C[C@](Cc2nc(Br)cc(C(C)(C)O)c2F)(C(=O)OC(C)(C)C)CCN1C(=O)OC(C)(C)C]

Following the procedure analogous to that described in Step 1 for the synthesis of Example 62, INT C2 (635 mg, 1.303 mmol) was converted to the title compound (431 mg, Y=61%) as a yellow oil. LCMS (ESI, m/z): 545 [M+H]⁺.

Step 2: di-tert-butyl-(2R,4R)-4-((6-bromo-3-fluoro-4-(2-fluoropropan-2-yl)pyridin-2-yl)methyl)-2-methylpiperidine-1,4-dicarboxylate

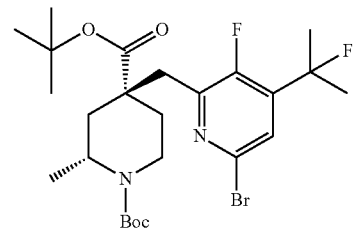 [SMILES: C[C@@H]1C[C@](Cc2nc(Br)cc(C(C)(C)F)c2F)(C(=O)OC(C)(C)C)CCN1C(=O)OC(C)(C)C]

To a solution of di-tert-butyl-(2R,4R)-4-((6-bromo-3-fluoro-4-(2-hydroxypropan-2-yl) pyridin-2-yl)methyl)-2-methylpiperidine-1,4-dicarboxylate (431 mg, 790.128 μmol) in DCM (20 ml) was added DAST (0.5 mL). The reaction mixture was stirred at room temperature for 2 h. The resulting solution was quenched with saturated sodium bicarbonate aqueous solution and extracted with DCM (50 mL). The organic layer was washed with brine (100 mL), dried over anhydrous sodium sulfate, filtered and concentrated under reduced pressure. The resulting residue was purified by C18 reversed phase column chromatography eluting with H₂O/ACN to afford di-tert-butyl-(2R,4R)-4-((6-bromo-3-fluoro-4-(2-fluoropropan-2-yl)pyridin-2-yl)methyl)-2-methyl piperidine-1,4-dicarboxylate (387 mg, Y=89%) as a yellow oil. LCMS (ESI, m/z): 547 [M+H]⁺.

Step 3: tert-butyl-(2R,4R)-4-((6-bromo-3-fluoro-4-(2-fluoropropan-2-yl)pyridin-2-yl)methyl)-2-methylpiperidine-4-carboxylate

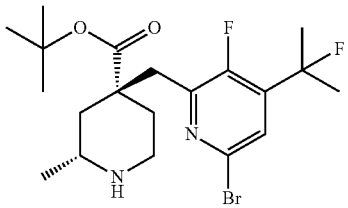 [SMILES: C[C@@H]1C[C@](Cc2nc(Br)cc(C(C)(C)F)c2F)(C(=O)OC(C)(C)C)CCN1]

Following the procedure analogous to that described in Step 3 for the synthesis of Example 5, di-tert-butyl (2R,4R)-4-((6-bromo-3-fluoro-4-(2-fluoropropan-2-yl)pyridin-2-yl)methyl)-2-methyl piperidine-1,4-dicarboxylate (387 mg, 706.885 μmol) was converted to the title compound (268 mg, Y=85%) as a yellow oil. LCMS (ESI, m/z): 447 [M+H]⁺.

Step 4: tert-butyl-(2R,4R)-4-((6-bromo-3-fluoro-4-(2-fluoropropan-2-yl)pyridin-2-yl)methyl)-1-(3-chloro-2-fluorobenzyl)-2-methylpiperidine-4-carboxylate

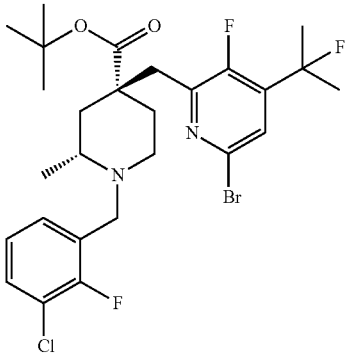 [SMILES: C[C@@H]1C[C@](Cc2nc(Br)cc(C(C)(C)F)c2F)(C(=O)OC(C)(C)C)CCN1Cc1cccc(Cl)c1F]

Following the procedure analogous to that described in Step 4 for the synthesis of Example 5, tert-butyl-(2R,4R)-4-((6-bromo-3-fluoro-4-(2-fluoropropan-2-yl)pyridin-2-yl)methyl)-2-methylpiperidine-4-carboxylate (268 mg, 599.075 μmol) was converted to the title compound (167 mg, Y=47%) as a yellow oil. LCMS (ESI, m/z): 589 [M+H]⁺.

Step 5: tert-butyl-(2R,4R)-4-((6-((1-(tert-butyl)-5-methyl-1H-pyrazol-3-yl)amino)-3-fluoro-4-(2-fluoropropan-2-yl)pyridin-2-yl)methyl)-1-(3-chloro-2-fluorobenzyl)-2-methylpiperidine-4-carboxylate

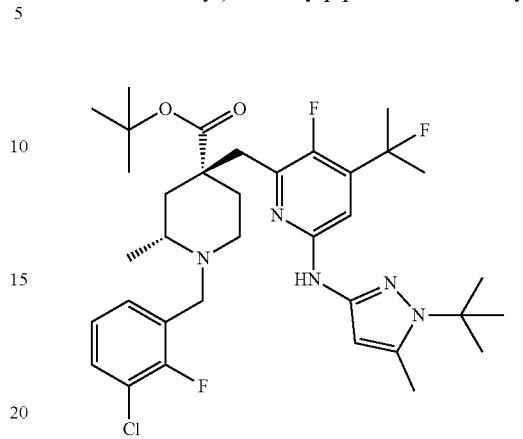

Following the procedure analogous to that described in Step 2 for the synthesis of Example 5, tert-butyl-(2R,4R)-4-((6-bromo-3-fluoro-4-(2-fluoropropan-2-yl)pyridin-2-yl)methyl)-1-(3-chloro-2-fluorobenzyl)-2-methylpiperidine-4-carboxylate (167 mg, 283.092 umol) was converted to the title compound (168 mg, Y=89%) as a yellow oil. LCMS (ESI, m/z): 662 [M+H]⁺.

Step 6: (2R,4R)-1-(3-chloro-2-fluorobenzyl)-4-((3-fluoro-4-(2-fluoropropan-2-yl)-6-((5-methyl-1H-pyrazol-3-yl)amino)pyridin-2-yl)methyl)-2-methylpiperidine-4-carboxylic acid

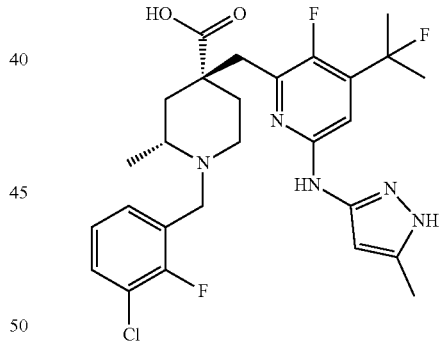

Following the procedure analogous to that described in Step 5 for the synthesis of Example 5, tert-butyl-(2R,4R)-4-((6-((1-(tert-butyl)-5-methyl-1H-pyrazol-3-yl)amino)-3-fluoro-4-(2-fluoropropan-2-yl)pyridin-2-yl)methyl)-1-(3-chloro-2-fluorobenzyl)-2-methylpiperidine-4-carboxylate (168 mg, 253.690 umol) was converted to the title compound (27 mg) as a white solid. LCMS (ESI, m/z): 550 [M+H]⁺. NMR (400 MHz, MeOD) δ 7.70 (t, J=7.6 Hz, 1H), 7.56 (t, J=6.9 Hz, 1H), 7.36 (t, J=7.9 Hz, 1H), 6.96 (d, J=4.6 Hz, 1H), 5.99 (s, 1H), 3.42 (s, 4H), 2.37 (s, 3H), 2.19 (dd, J=43.0, 16.1 Hz, 5H), 1.74 (d, J=22.7 Hz, 6H), 1.58 (d, J=6.1 Hz, 3H).

The following examples in Table 12 were synthesized using the above procedure or modified procedure with the corresponding starting materials.

| Example No. | Structure | Chemical Name | MS: (M + H)⁺ |
|---|---|---|---|
| 95. | 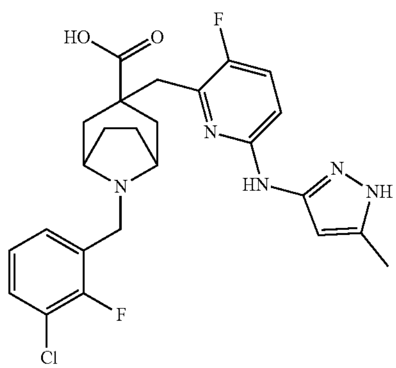 [SMILES: Cc1cc(Nc2ccc(F)c(CC3(C(=O)O)CC4CCC(C3)N4Cc3cccc(Cl)c3F)n2)n[nH]1] | (1R,5S)-8-(3-chloro-2-fluorobenzyl)-3-((3-fluoro-6-((5-methyl-1H-pyrazol-3-yl)amino)pyridin-2-yl)methyl)-8-azabicyclo[3.2.1]-octane-3-carboxylic acid | 502 |
| 96. | 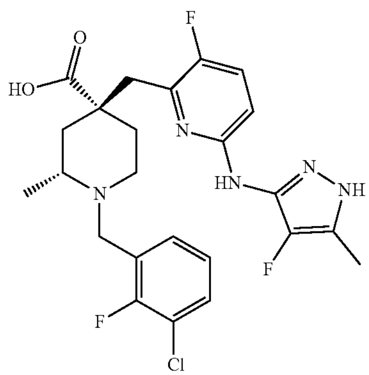 | (2R,4R)-1-(3-chloro-2-fluorobenzyl)-4-((3-fluoro-6-((4-fluoro-5-methyl-1H-pyrazol-3-yl)amino)-pyridin-2-yl)methyl)-2-methyl-piperidine-4-carboxylic acid | 508 |
| 97. | 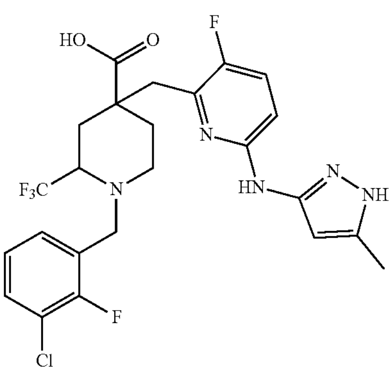 [SMILES: Cc1cc(Nc2ccc(F)c(CC3(C(=O)O)CCN(Cc4cccc(Cl)c4F)C(C(F)(F)F)C3)n2)n[nH]1] | 1-(3-chloro-2-fluorobenzyl)-4-((3-fluoro-6-((5-methyl-1H-pyrazol-3-yl)amino)pyridin-2-yl)methyl)-2-(trifluoromethyl)piperidine-4-carboxylic acid | 544 |
| 98. | 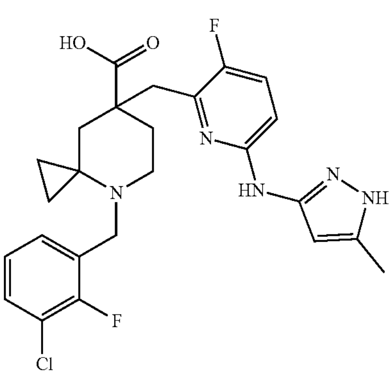 [SMILES: Cc1cc(Nc2ccc(F)c(CC3(C(=O)O)CCN(Cc4cccc(Cl)c4F)C4(CC4)C3)n2)n[nH]1] | 4-(3-chloro-2-fluorobenzyl)-7-((3-fluoro-6-((5-methyl-1H-pyrazol-3-yl)amino)pyridin-2-yl)methyl)-4-azaspiro[2.5]octane-7-carboxylic acid | 502 |

| Example No. | Structure | Chemical Name | MS: (M + H)+ |
|---|---|---|---|
| 99. | 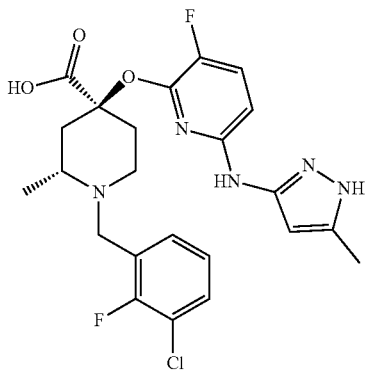 | (2R,4S)-1-(3-chloro-2-fluorobenzyl)-4-((3-fluoro-6-((5-methyl-1H-pyrazol-3-yl)amino)pyridin-2-yl)oxy)-2-methylpiperidine-4-carboxylic acid | 492 |
| 100. | 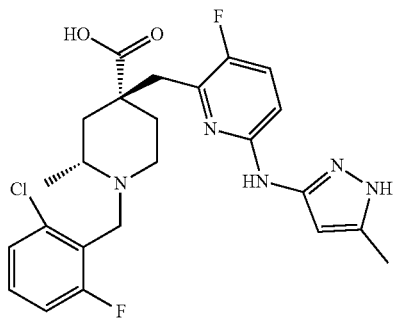 [SMILES: Cc1cc(Nc2ccc(F)c(C[C@@]3(C(=O)O)CCN(Cc4c(F)cccc4Cl)[C@H](C)C3)n2)n[nH]1] | (2R,4R)-1-(2-chloro-6-fluorobenzyl)-4-((3-fluoro-6-((5-methyl-1H-pyrazol-3-yl)amino)pyridin-2-yl)methyl)-2-methylpiperidine-4)-carboxylic acid | 490 |
| 101. | 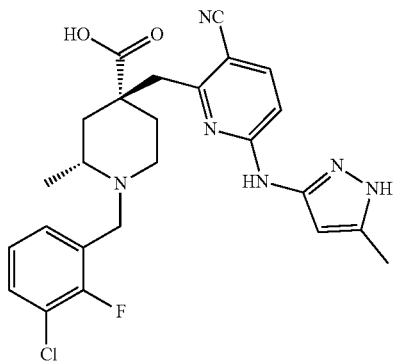 | (2R,4R)-1-(3-chloro-2-fluorobenzyl)-4-((3-cyano-6-((5-methyl-1H-pyrazol-3-yl)amino)pyridin-2-yl)methyl)-2-methylpiperidine-4-carboxylic acid | 497 |
| 102. | 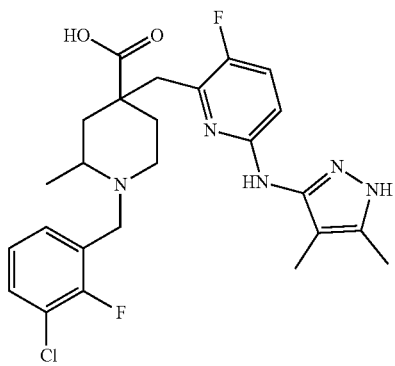 [SMILES: Cc1[nH]nc(Nc2ccc(F)c(CC3(C(=O)O)CCN(Cc4cccc(Cl)c4F)C(C)C3)n2)c1C] | 1-(3-chloro-2-fluorobenzyl)-4-((6-((4,5-dimethyl-1H-pyrazol-3-yl)-amino)-3-fluoropyridin-2-yl)-methyl)-2-methylpiperidine-4-carboxylic acid | 504 |

-continued

| Example No. | Structure | Chemical Name | MS: (M + H)+ |
|---|---|---|---|
| 103. | 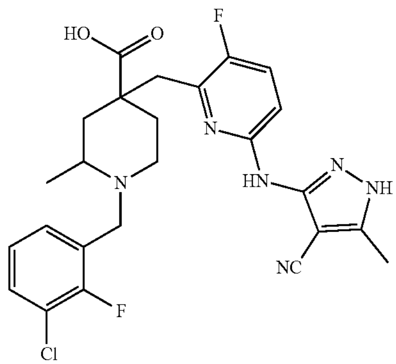 [SMILES: Cc1[nH]nc(Nc2ccc(F)c(CC3(C(=O)O)CCN(Cc4cccc(Cl)c4F)C(C)C3)n2)c1C#N] | 1-(3-chloro-2-fluorobenzyl)-4-((6-((4-cyano-5-methyl-1H-pyrazol-3-yl)amino)-3-fluoropyridin-2-yl)methyl)-2-methylpiperidine-4-carboxylic acid | 515 |
| 104. | 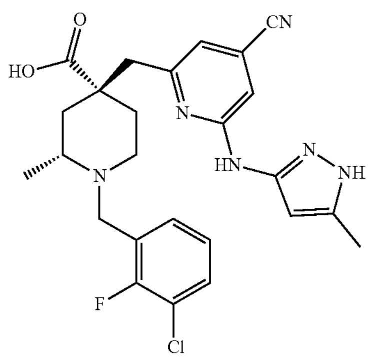 | (2R,4R)-1-(3-chloro-2-fluorobenzyl)-4-((4-cyano-6-((5-methyl-1H-pyrazol-3-yl)amino)pyridin-2-yl)methyl)-2-methylpiperidine-4-carboxylic acid | 497 |
| 105. | 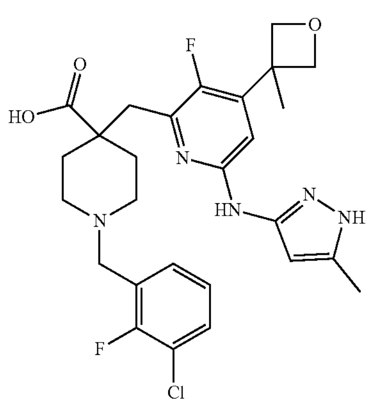 [SMILES: Cc1cc(Nc2cc(C3(C)COC3)c(F)c(CC3(C(=O)O)CCN(Cc4cccc(Cl)c4F)CC3)n2)n[nH]1] | 1-(3-chloro-2-fluorobenzyl)-4-((3-fluoro-6-((5-methyl-1H-pyrazol-3-yl)amino)-4-(3-methyloxetan-3-yl)pyridin-2-yl)methyl)piperidine-4-carboxylic acid | 546 |
| 106. | 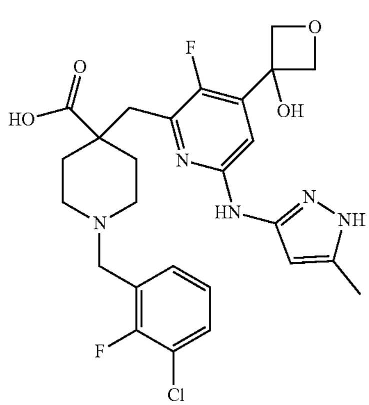 [SMILES: Cc1cc(Nc2cc(C3(O)COC3)c(F)c(CC3(C(=O)O)CCN(Cc4cccc(Cl)c4F)CC3)n2)n[nH]1] | 1-(3-chloro-2-fluorobenzyl)-4-((3-fluoro-4-(3-hydroxyoxetan-3-yl)-6-((5-methyl-1H-pyrazol-3-yl)amino)pyridin-2-yl)methyl)piperidine-4-carboxylic acid | 548 |

-continued

| Example No. | Structure | Chemical Name | MS: (M + H)+ |
|---|---|---|---|
| 107. | 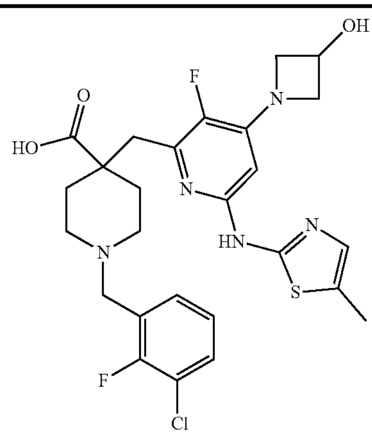 | 1-(3-chloro-2-fluorobenzyl)-4-((3-fluoro-4-(3-hydroxyazetidin-1-yl)-6-((5-methylthiazol-2-yl)amino)pyridin-2-yl)methyl)piperidine-4-carboxylic acid | 564 |
| 108. | 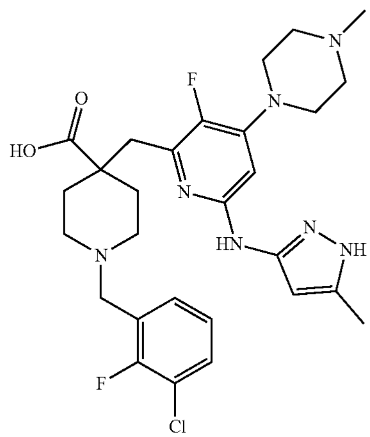 [SMILES: Cc1cc(Nc2cc(N3CCN(C)CC3)c(F)c(CC3(C(=O)O)CCN(Cc4cccc(Cl)c4F)CC3)n2)n[nH]1] | 1-(3-chloro-2-fluorobenzyl)-4-((3-fluoro-6-((5-methyl-1H-pyrazol-3-yl)amino)-4-(4-methylpiperazin-1-yl)pyridin-2-yl)methyl)-piperidine-4-carboxylic acid | 574 |
| 109. | 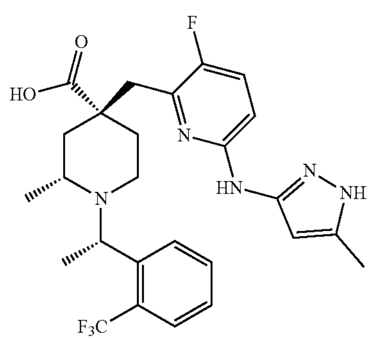 | (2R,4R)-4-((3-fluoro-6-((5-methyl-1H-pyrazol-3-yl)amino)pyridin-2-yl)methyl)-2-methyl-1-((S)-1-(2-(trifluoromethyl)phenyl)ethyl)piperidine-4-carboxylic acid | 520 |
| 110. | 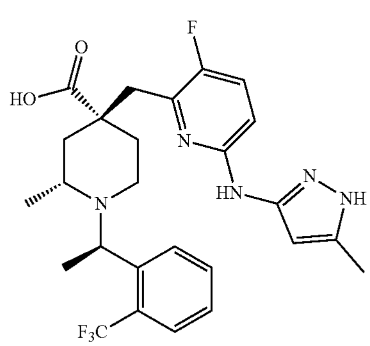 | (2R,4R)-4-((3-fluoro-6-((5-methyl-1H-pyrazol-3-yl)amino)pyridin-2-yl)methyl)-2-methyl-1-((R)-1-(2-(trifluoromethyl)phenyl)ethyl)-piperidine-4-carboxylic acid | 520 |

| Example No. | Structure | Chemical Name | MS: (M + H)+ |
|---|---|---|---|
| 111. | 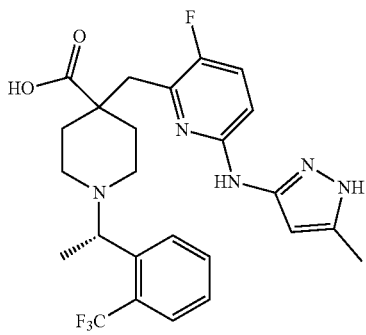 [SMILES: Cc1cc(Nc2ccc(F)c(CC3(C(=O)O)CCN([C@@H](C)c4ccccc4C(F)(F)F)CC3)n2)n[nH]1] | (S)-4-((3-fluoro-6-((5-methyl-1H-pyrazol-3-yl)amino)pyridin-2-yl)methyl)-1-(1-(2-(trifluoromethyl)phenyl)ethyl)piperidine-4-carboxylic acid | 505 |
| 112. | 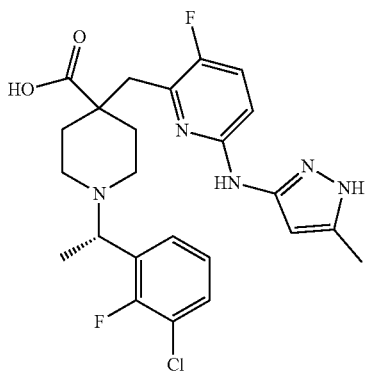 [SMILES: Cc1cc(Nc2ccc(F)c(CC3(C(=O)O)CCN([C@@H](C)c4cccc(Cl)c4F)CC3)n2)n[nH]1] | (S)-1-(1-(3-chloro-2-fluorophenyl)ethyl)-4-((3-fluoro-6-((5-methyl-1H-pyrazol-3-yl)amino)pyridine-2-yl)methyl)piperidine-4-carboxylic acid | 490 |
| 113. | 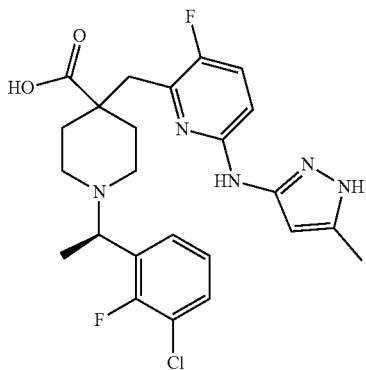 [SMILES: Cc1cc(Nc2ccc(F)c(CC3(C(=O)O)CCN([C@H](C)c4cccc(Cl)c4F)CC3)n2)n[nH]1] | (R)-1-(1-(3-chloro-2-fluorophenyl)ethyl)-4-((3-fluoro-6-((5-methyl-1H-pyrazol-3-yl)amino)pyridin-2-yl)methyl)piperidine-4-carboxylic acid | 490 |
| 114. | 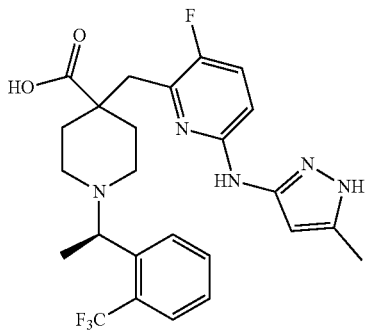 [SMILES: Cc1cc(Nc2ccc(F)c(CC3(C(=O)O)CCN([C@H](C)c4ccccc4C(F)(F)F)CC3)n2)n[nH]1] | (R)-4-((3-fluoro-6-((5-methyl-1H-pyrazol-3-yl)amino)pyridin-2-yl)methyl)-1-(1-(2-(trifluoromethyl)phenyl)ethyl)piperidine-4-carboxylic acid | 506 |

| Example No. | Structure | Chemical Name | MS: (M + H)+ |
|---|---|---|---|
| 115. | 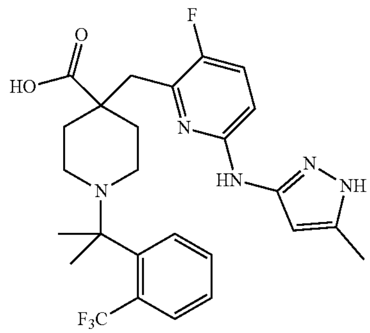 | 4-((3-fluoro-6-((5-methyl-1H-pyrazol-3-yl)amino)pyridin-2-yl)methyl)-1-(2-(2-(trifluoromethyl)phenyl)propan-2-yl)piperidine-4-carboxylic acid | 520 |
| 116. | 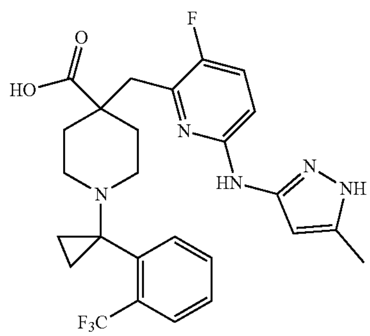 [SMILES: Cc1cc(Nc2ccc(F)c(CC3(C(=O)O)CCN(C4(c5ccccc5C(F)(F)F)CC4)CC3)n2)n[nH]1] | 4-((3-fluoro-6-((5-methyl-1H-pyrazol-3-yl)amino)pyridin-2-yl)methyl)-1-(1-(2-(trifluoromethyl)phenyl)cyclopropyl)piperidine-4-carboxylic acid | 518 |
| 117. | 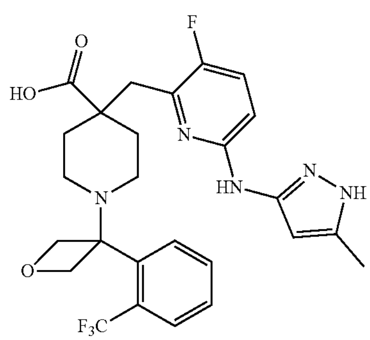 [SMILES: Cc1cc(Nc2ccc(F)c(CC3(C(=O)O)CCN(C4(c5ccccc5C(F)(F)F)COC4)CC3)n2)n[nH]1] | 4-((3-fluoro-6-((5-methyl-1H-pyrazol-3-yl)amino)pyridin-2-yl)methyl)-1-(3-(2-(trifluoromethyl)phenyl)oxetan-3-yl)piperidine-4-carboxylic acid | 534 |
| 118. | 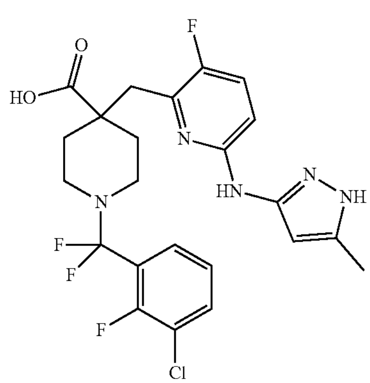 [SMILES: Cc1cc(Nc2ccc(F)c(CC3(C(=O)O)CCN(C(F)(F)c4cccc(Cl)c4F)CC3)n2)n[nH]1] | 1-((3-chloro-2-fluorophenyl)difluoromethyl)-4-((3-fluoro-6-((5-methyl-1H-pyrazol-3-yl)amino)pyridin-2-yl)methyl)piperidine-4-carboxylic acid | 512 |

| Example No. | Structure | Chemical Name | MS: (M + H)+ |
|---|---|---|---|
| 119. | 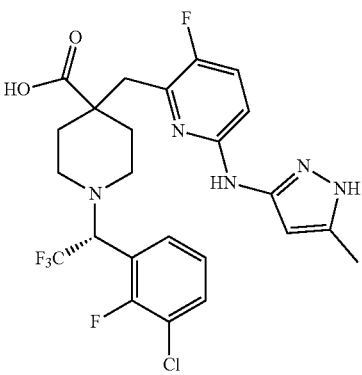 [SMILES: Cc1cc(Nc2ccc(F)c(CC3(C(=O)O)CCN([C@H](c4cccc(Cl)c4F)C(F)(F)F)CC3)n2)n[nH]1] | (R)-1-(1-(3-chloro-2-fluorophenyl)-2,2,2-trifluoroethyl)-4-((3-fluoro-6-((5-methyl-1H-pyrazol-3-yl)amino)pyridin-2-yl)methyl)-piperidine-4-carboxylic acid | 544 |
| 120. | 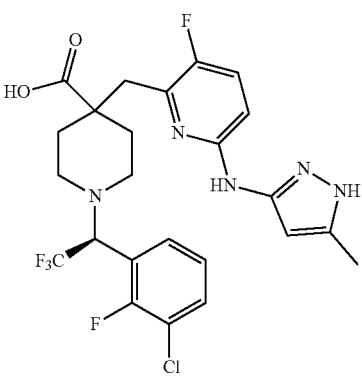 [SMILES: Cc1cc(Nc2ccc(F)c(CC3(C(=O)O)CCN([C@@H](c4cccc(Cl)c4F)C(F)(F)F)CC3)n2)n[nH]1] | (S)-1-(1-(3-chloro-2-fluorophenyl)-2,2,2-trifluoroethyl)-4-((3-fluoro-6-((5-methyl-1H-pyrazol-3-yl)amino)pyridin-2-yl)methyl)-piperidine-4-carboxylic acid | 544 |
| 121. | 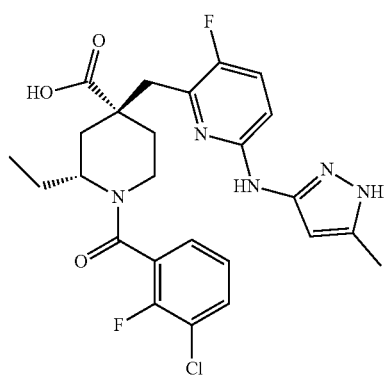 [SMILES: CC[C@@H]1C[C@](Cc2nc(Nc3cc(C)[nH]n3)ccc2F)(C(=O)O)CCN1C(=O)c1cccc(Cl)c1F] | (2R,4R)-1-(3-chloro-2-fluorobenzoyl)-2-ethyl-4-((3-fluoro-6-((5-methyl-1H-pyrazol-3-yl)amino)-pyridin-2-yl)methyl)piperidine-4-carboxylic acid | 518 |
| 122. | 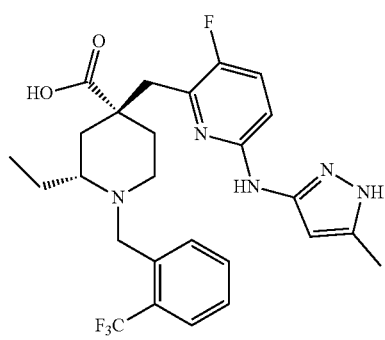 | (2R,4R)-2-ethyl-4-((3-fluoro-6-((5-methyl-1H-pyrazol-3-yl)amino)pyridin-2-yl)methyl)-1-(2-(trifluoromethyl)benzyl)piperidine-4-carboxylic acid | 520 |

-continued

| Example No. | Structure | Chemical Name | MS: (M + H)+ |
|---|---|---|---|
| 123. | 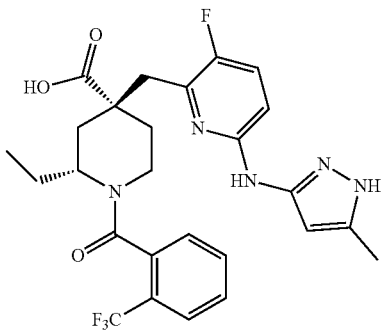 [SMILES: CC[C@@H]1C[C@](Cc2nc(Nc3cc(C)[nH]n3)ccc2F)(C(=O)O)CCN1C(=O)c1ccccc1C(F)(F)F] | (2R,4R)-2-ethyl-4-((3-fluoro-6-((5-methyl-1H-pyrazol-3-yl)amino)pyridin-2-yl)methyl)-1-(2-(trifluoromethyl)benzoyl)piperidine-4-carboxylic acid | 534 |
| 124. | 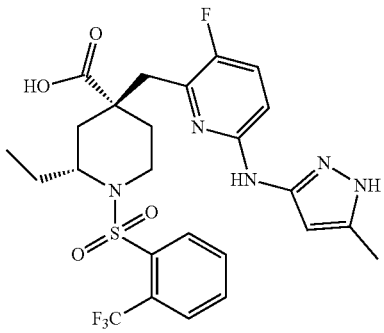 [SMILES: CC[C@@H]1C[C@](Cc2nc(Nc3cc(C)[nH]n3)ccc2F)(C(=O)O)CCN1S(=O)(=O)c1ccccc1C(F)(F)F] | (2R,4R)-2-ethyl-4-((3-fluoro-6-((5-methyl-1H-pyrazol-3-yl)amino)pyridin-2-yl)methyl)-1-((2-(trifluoromethyl)phenyl)sulfonyl)-piperidine-4-carboxylic acid | 570 |
| 125. | 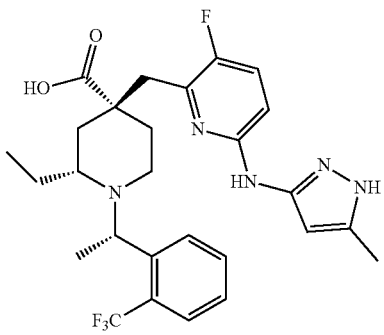 [SMILES: CC[C@@H]1C[C@](Cc2nc(Nc3cc(C)[nH]n3)ccc2F)(C(=O)O)CCN1[C@@H](C)c1ccccc1C(F)(F)F] | (2R,4R)-2-ethyl-4-((3-fluoro-6-((5-methyl-1H-pyrazol-3-yl)amino)pyridin-2-yl)methyl)-1-((S)-1-(2-(trifluoromethyl)phenyl)ethyl)piperidine-4-carboxylic acid | 534 |
| 126. | 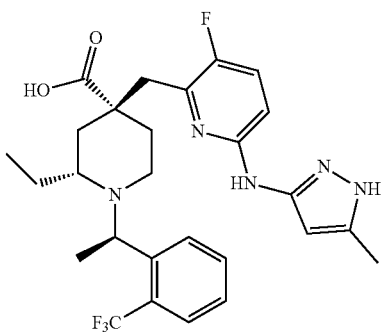 [SMILES: CC[C@@H]1C[C@](Cc2nc(Nc3cc(C)[nH]n3)ccc2F)(C(=O)O)CCN1[C@H](C)c1ccccc1C(F)(F)F] | (2R,4R)-2-ethyl-4-((3-fluoro-6-((5-methyl-1H-pyrazol-3-yl)amino)pyridin-2-yl)methyl)-1-((R)-1-(2-(trifluoromethyl)phenyl)ethyl)piperidine-4-carboxylic acid | 534 |

-continued

| Example No. | Structure | Chemical Name | MS: (M + H)+ |
|---|---|---|---|
| 127. | 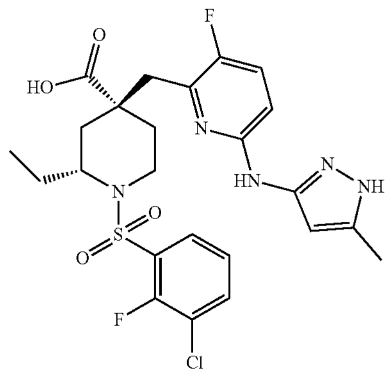 [SMILES: CC[C@@H]1C[C@](Cc2nc(Nc3cc(C)[nH]n3)ccc2F)(C(=O)O)CCN1S(=O)(=O)c1cccc(Cl)c1F] | (2R,4R)-1-((3-chloro-2-fluoro-phenyl)sulfonyl)-2-ethyl-4-((3-fluoro-6-((5-methyl-1H-pyrazol-3-yl)amino)pyridin-2-yl)methyl)piperidine-4-carboxylic acid | 554 |
| 128. | 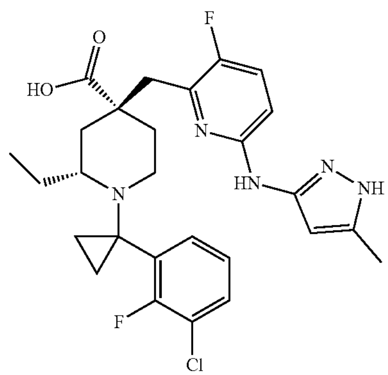 [SMILES: CC[C@@H]1C[C@](Cc2nc(Nc3cc(C)[nH]n3)ccc2F)(C(=O)O)CCN1C1(c2cccc(Cl)c2F)CC1] | (2R,4R)-1-(1-(3-chloro-2-fluoro-phenyl)cyclopropyl)-2-ethyl-4-((3-fluoro-6-((5-methyl-1H-pyrazol-3-yl)amino)pyridin-2-yl)methyl)-piperidine-4-carboxylic acid | 530 |
| 129. | 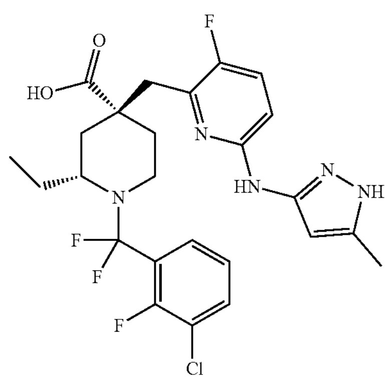 [SMILES: CC[C@@H]1C[C@](Cc2nc(Nc3cc(C)[nH]n3)ccc2F)(C(=O)O)CCN1C(F)(F)c1cccc(Cl)c1F] | (2R,4R)-1-((3-chloro-2-fluoro-phenyl)difluoromethyl)-2-ethyl-4-((3-fluoro-6-((5-methyl-1H-pyrazol-3-yl)amino)pyridin-2-yl)methyl)-piperidine-4-carboxylic acid | 540 |
| 130. | 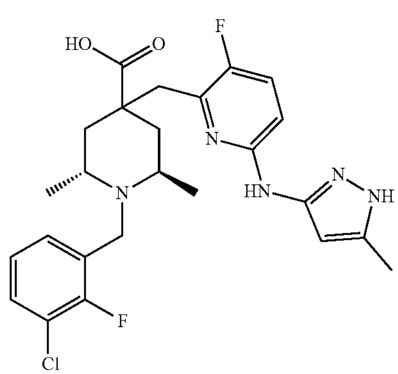 [SMILES: Cc1cc(Nc2ccc(F)c(CC3(C(=O)O)C[C@@H](C)N(Cc4cccc(Cl)c4F)[C@H](C)C3)n2)n[nH]1] | (2R,6R)-1-(3-chloro-2-fluoroben-zyl)-4-((3-fluoro-6-((5-methyl-1H-pyrazol-3-yl)amino)pyridin-2-yl)methyl)-2,6-dimethylpiperidine-4-carboxylic acid | 504 |

-continued

| Example No. | Structure | Chemical Name | MS: (M + H)+ |
|---|---|---|---|
| 131. | 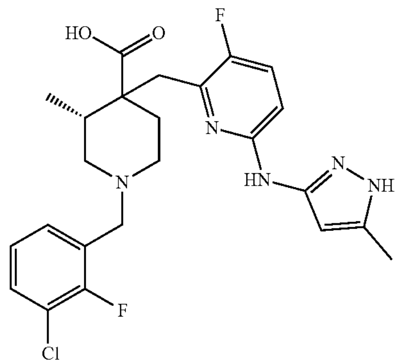 [SMILES: Cc1cc(Nc2ccc(F)c(CC3(C(=O)O)CCN(Cc4cccc(Cl)c4F)C[C@@H]3C)n2)n[nH]1] | (3R)-1-(3-chloro-2-fluorobenzyl)-4-((3-fluoro-6-((5-methyl-1H-pyrazol-3-yl)amino)pyridin-2-yl)methyl)-3-methylpiperidine-4)-carboxylic acid | 490 |
| 132. | 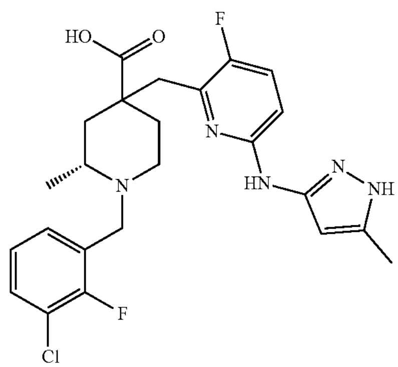 [SMILES: Cc1cc(Nc2ccc(F)c(CC3(C(=O)O)CCN(Cc4cccc(Cl)c4F)[C@H](C)C3)n2)n[nH]1] | (2R)-1-(3-chloro-2-fluorobenzyl)-4-((3-fluoro-6-((5-methyl-1H-pyrazol-3-yl)amino)pyridin-2-yl)methyl)-2-methylpiperidine-4)-carboxylic acid | 490 |
| 133. | 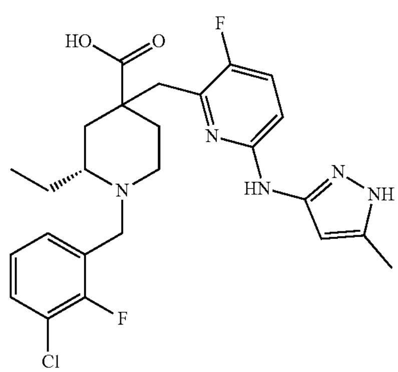 [SMILES: CC[C@@H]1CC(Cc2nc(Nc3cc(C)[nH]n3)ccc2F)(C(=O)O)CCN1Cc1cccc(Cl)c1F] | (2R)-1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid | 504 |
| 134. | 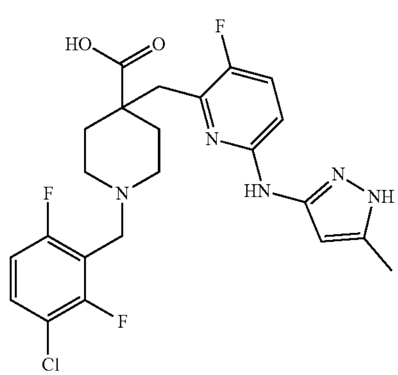 | 1-(3-chloro-2,6-difluorobenzyl)-4-((3-fluoro-6-((5-methyl-1H-pyrazol-3-yl)amino)pyridin-2-yl)methyl)piperidine-4-carboxylic acid | 494 |

-continued

| Example No. | Structure | Chemical Name | MS: (M + H)+ |
|---|---|---|---|
| 135. | 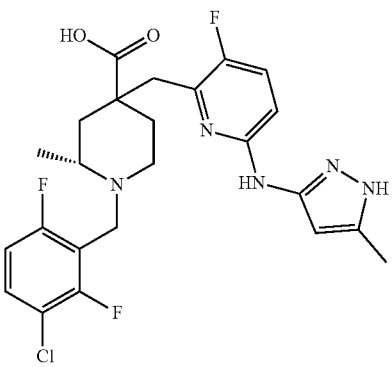 [SMILES: Cc1cc(Nc2ccc(F)c(CC3(C(=O)O)CCN(Cc4c(F)ccc(Cl)c4F)[C@H](C)C3)n2)n[nH]1] | (2R)-1-(3-chloro-2,6-difluorobenzyl)-4-((3-fluoro-6-((5-methyl-1H-pyrazol-3-yl)amino)pyridin-2-yl)methyl)-2-methylpiperidine-4-carboxylic acid | 508 |
| 136. | 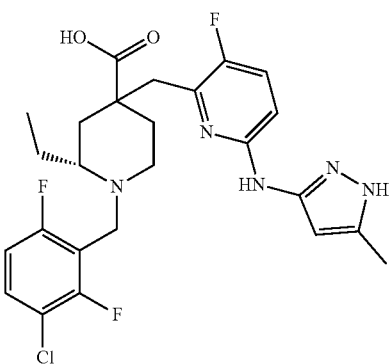 [SMILES: CC[C@@H]1CC(Cc2nc(Nc3cc(C)[nH]n3)ccc2F)(C(=O)O)CCN1Cc1c(F)ccc(Cl)c1F] | (2R)-1-(3-chloro-2,6-difluorobenzyl)-2-ethyl-4-((3-fluoro-6-((5-methyl-1H-pyrazol-3-yl)amino)-pyridin-2-yl)methyl)piperidine-4)-carboxylic acid | 522 |
| 137. | 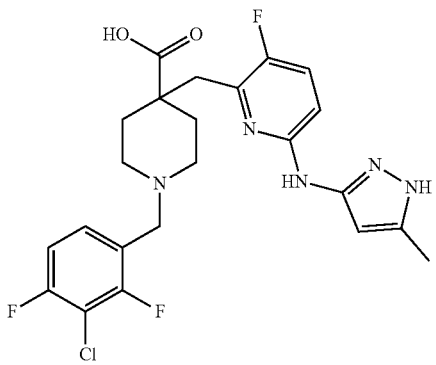 [SMILES: Cc1cc(Nc2ccc(F)c(CC3(C(=O)O)CCN(Cc4ccc(F)c(Cl)c4F)CC3)n2)n[nH]1] | 1-(3-chloro-2,4-difluorobenzyl)-4-((3-fluoro-6-((5-methyl-1H-pyrazol-3-yl)amino)pyridin-2-yl)-methyl)piperidine-4-carboxylic acid | 494 |
| 138. | 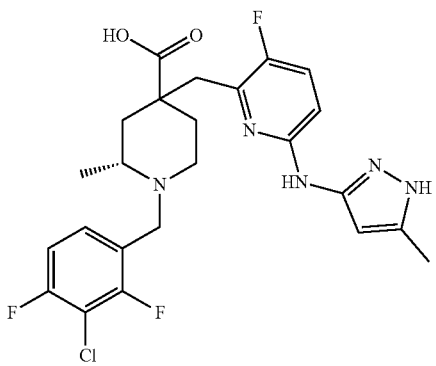 [SMILES: Cc1cc(Nc2ccc(F)c(CC3(C(=O)O)CCN(Cc4ccc(F)c(Cl)c4F)[C@H](C)C3)n2)n[nH]1] | (2R)-1-(3-chloro-2,4-difluorobenzyl)-4-((3-fluoro-6-((5-methyl-1H-pyrazol-3-yl)amino)pyridin-2-yl)methyl)-2-methylpiperidine-4-carboxylic acid | 508 |

-continued

| Example No. | Structure | Chemical Name | MS: (M + H)+ |
|---|---|---|---|
| 139. | 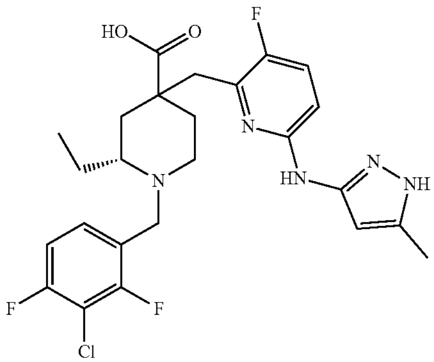 [SMILES: CC[C@@H]1CC(Cc2nc(Nc3cc(C)[nH]n3)ccc2F)(C(=O)O)CCN1Cc1ccc(F)c(Cl)c1F] | (2R)-1-(3-chloro-2,4-difluorobenzyl)-2-ethyl-4-((3-fluoro-6-((5-methyl-1H-pyrazol-3-yl)amino)-pyridin-2-yl)methyl)piperidine-4)-carboxylic acid | 522 |
| 140. | 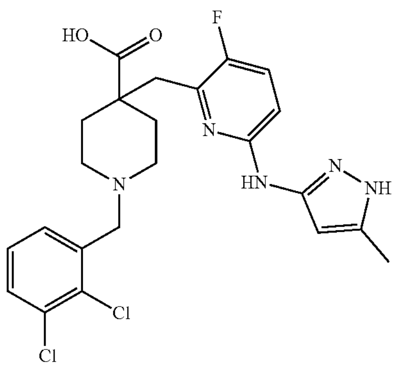 [SMILES: Cc1cc(Nc2ccc(F)c(CC3(C(=O)O)CCN(Cc4cccc(Cl)c4Cl)CC3)n2)n[nH]1] | 1-(2,3-dichlorobenzyl)-4-((3-fluoro-6-((5-methyl-1H-pyrazol-3-yl)amino)pyridin-2-yl)methyl)-piperidine-4-carboxylic acid | 492 |
| 141. | 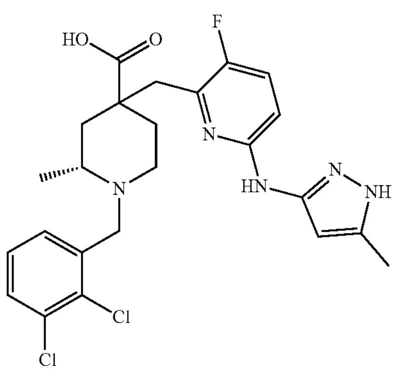 [SMILES: Cc1cc(Nc2ccc(F)c(CC3(C(=O)O)CCN(Cc4cccc(Cl)c4Cl)[C@H](C)C3)n2)n[nH]1] | (2R)-1-(2,3-dichlorobenzyl)-4-((3-fluoro-6-((5-methyl-1H-pyrazol-3-yl)amino)pyridin-2-yl)methyl)-2-methylpiperidine-4-carboxylic acid | 506 |
| 142. | 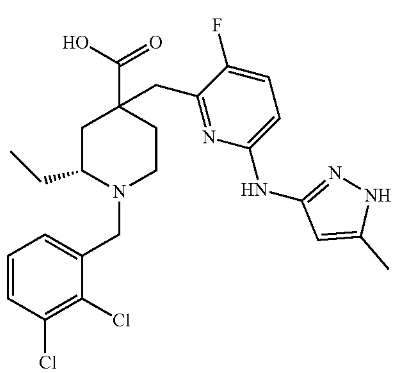 [SMILES: CC[C@@H]1CC(Cc2nc(Nc3cc(C)[nH]n3)ccc2F)(C(=O)O)CCN1Cc1cccc(Cl)c1Cl] | (2R)-1-(2,3-dichlorobenzyl)-2-ethyl-4-((3-fluoro-6-((5-methyl-1H-pyrazol-3-yl)amino)pyridin-2-yl)methyl)piperidine-4-carboxylic acid | 520 |

-continued

| Example No. | Structure | Chemical Name | MS: (M + H)+ |
|---|---|---|---|
| 143. | 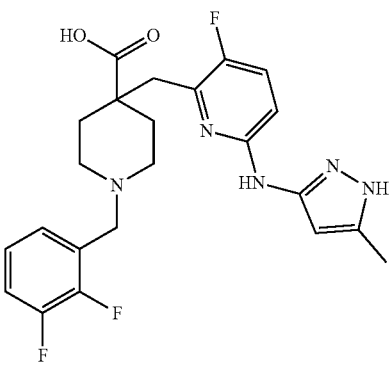 [SMILES: Cc1cc(Nc2ccc(F)c(CC3(C(=O)O)CCN(Cc4cccc(F)c4F)CC3)n2)n[nH]1] | 1-(2,3-difluorobenzyl)-4-((3-fluoro-6-((5-methyl-1H-pyrazol-3-yl)amino)pyridin-2-yl)methyl)-piperidine-4-carboxylic acid | 460 |
| 144. | 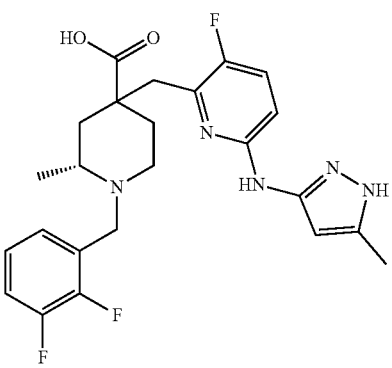 [SMILES: Cc1cc(Nc2ccc(F)c(CC3(C(=O)O)CCN(Cc4cccc(F)c4F)[C@H](C)C3)n2)n[nH]1] | (2R)-1-(2,3-difluorobenzyl)-4-((3-fluoro-6-((5-methyl-1H-pyrazol-3-yl)amino)pyridin-2-yl)-methyl-)-2-methylpiperidine-4-carboxylic acid | 474 |
| 145. | 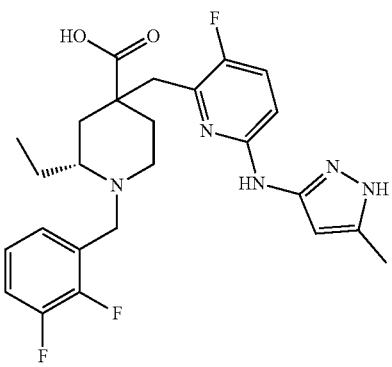 [SMILES: CC[C@@H]1CC(Cc2nc(Nc3cc(C)[nH]n3)ccc2F)(C(=O)O)CCN1Cc1cccc(F)c1F] | (2R)-1-(2,3-difluorobenzyl)-2-ethyl-4-((3-fluoro-6-((5-methyl-1H-pyrazol-3-yl)amino)pyridin-2-yl)methyl)piperidine-4-carboxylic acid | 488 |
| 146. | 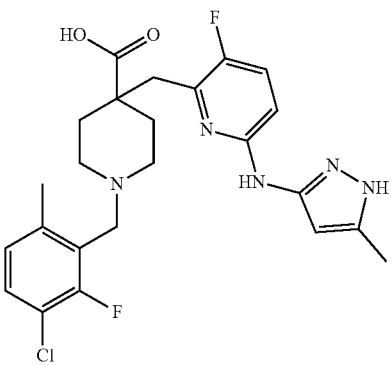 [SMILES: Cc1cc(Nc2ccc(F)c(CC3(C(=O)O)CCN(Cc4c(C)ccc(Cl)c4F)CC3)n2)n[nH]1] | 1-(3-chloro-2-fluoro-6-methyl-benzyl)-4-((3-fluoro-6-((5-methyl-1H-pyrazol-3-yl)amino)pyridin-2-yl)methyl)piperidine-4-carboxylic acid | 490 |

-continued

| Example No. | Structure | Chemical Name | MS: (M + H)+ |
|---|---|---|---|
| 147. | 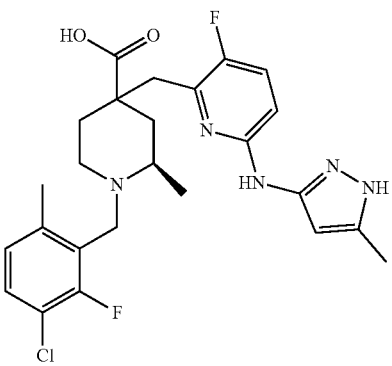 [SMILES: Cc1cc(Nc2ccc(F)c(CC3(C(=O)O)CCN(Cc4c(C)ccc(Cl)c4F)[C@H](C)C3)n2)n[nH]1] | (2 R)-1-(3-chloro-2-fluoro-6-methylbenzyl)-4-((3-fluoro-6-((5-methyl-1H-pyrazol-3-yl)amino)-pyridin-2-yl)methyl)-2-methyl-piperidine-4-carboxylic acid | 504 |
| 148. | 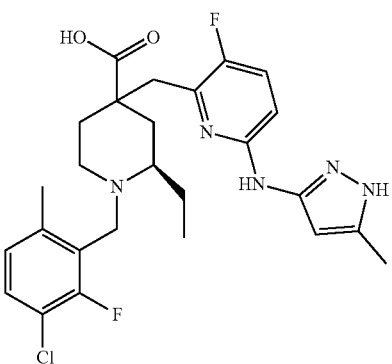 [SMILES: CC[C@@H]1CC(Cc2nc(Nc3cc(C)[nH]n3)ccc2F)(C(=O)O)CCN1Cc1c(C)ccc(Cl)c1F] | (2R)-1-(3-chloro-2-fluoro-6-methylbenzyl)-2-ethyl-4-((3-fluoro-6-((5-methyl-1H-pyrazol-3-yl)-amino)pyridin-2-yl)methyl)piperidine-4-carboxylic acid | 518 |
| 149. | 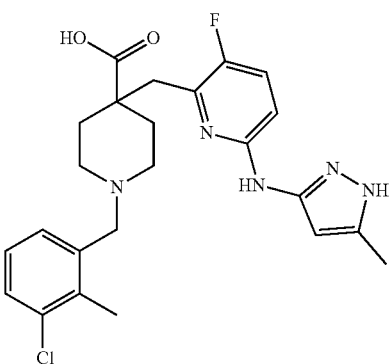 [SMILES: Cc1cc(Nc2ccc(F)c(CC3(C(=O)O)CCN(Cc4cccc(Cl)c4C)CC3)n2)n[nH]1] | 1-(3-chloro-2-methylbenzyl)-4-((3-fluoro-6-((5-methyl-1H-pyrazol-3-yl)amino)pyridin-2-yl)methyl)-piperidine-4-carboxylic acid | 472 |
| 150. | 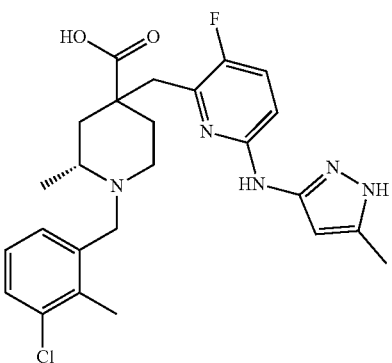 [SMILES: Cc1cc(Nc2ccc(F)c(CC3(C(=O)O)CCN(Cc4cccc(Cl)c4C)[C@H](C)C3)n2)n[nH]1] | (2R)-1-(3-chloro-2-methylbenzyl)-4-((3-fluoro-6-((5-methyl-1H-pyrazol-3-yl)amino)pyridin-2-yl)methyl)-2-methylpiperidine-4)-carboxylic acid | 486 |

| Example No. | Structure | Chemical Name | MS: (M + H)+ |
|---|---|---|---|
| 151. | 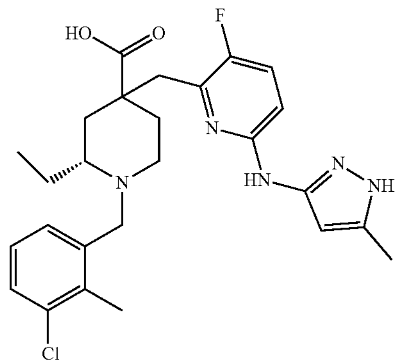 [SMILES: CC[C@@H]1CC(Cc2nc(Nc3cc(C)[nH]n3)ccc2F)(C(=O)O)CCN1Cc1cccc(Cl)c1C] | (2R)-1-(3-chloro-2-methylbenzyl)-2-ethyl-4-((3-fluoro-6-((5-methyl-1H-pyrazol-3-yl)amino)pyridin-2-yl)methyl)piperidine-4-carboxylic acid | 500 |
| 152. | 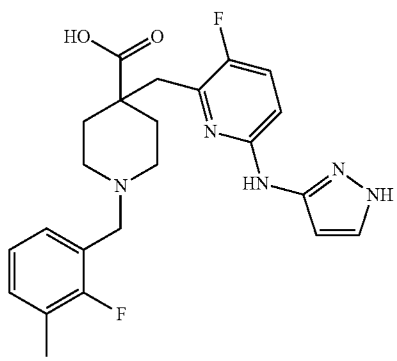 [SMILES: Cc1cccc(CN2CCC(Cc3nc(Nc4cc[nH]n4)ccc3F)(C(=O)O)CC2)c1F] | 4-((6-((1H-pyrazol-3-yl)amino)-3-fluoropyridin-2-yl)methyl)-1-(2-fluoro-3-methylbenzyl)piperidine-4-carboxylic acid | 442 |
| 153. | 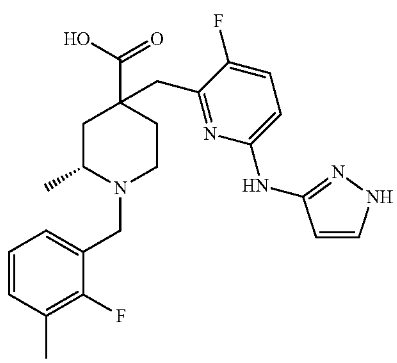 [SMILES: Cc1cccc(CN2CCC(Cc3nc(Nc4cc[nH]n4)ccc3F)(C(=O)O)C[C@H]2C)c1F] | (2R)-4-((6-((1H-pyrazol-3-yl)amino)-3-fluoropyridin-2-yl)methyl)-1-(2-fluoro-3-methylbenzyl)-2-methyl-piperidine-4-carboxylic acid | 456 |
| 154. | 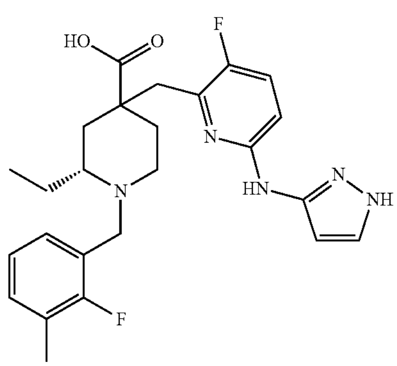 [SMILES: CC[C@@H]1CC(Cc2nc(Nc3cc[nH]n3)ccc2F)(C(=O)O)CCN1Cc1cccc(C)c1F] | (2R)-4-((6-((1H-pyrazol-3-yl)amino)-3-fluoropyridin-2-yl)methyl)-2-ethyl-1-(2-fluoro-3-methylbenzyl)piperidine-4-carboxylic acid | 470 |

| Example No. | Structure | Chemical Name | MS: (M + H)+ |
|---|---|---|---|
| 155. | 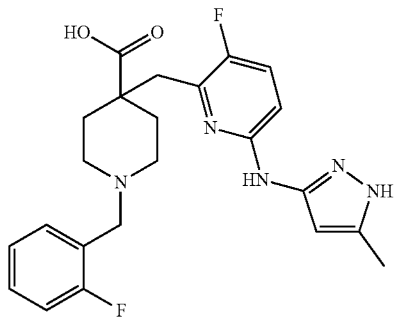 [SMILES: Cc1cc(Nc2ccc(F)c(CC3(C(=O)O)CCN(Cc4ccccc4F)CC3)n2)n[nH]1] | 4-((3-fluoro-6-((5-methy 1-1H-pyrazol-3-yl)amino)pyridin-2-yl)-methyl)-1-(2-fluorobenzyl)piperidine-4-carboxylic acid | 442 |
| 156. | 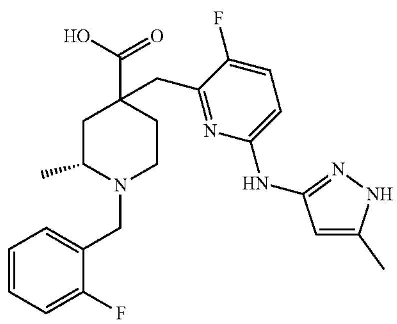 [SMILES: Cc1cc(Nc2ccc(F)c(CC3(C(=O)O)CCN(Cc4ccccc4F)[C@H](C)C3)n2)n[nH]1] | (2R)-4-((3-fluoro-6-((5-methyl-1H-pyrazol-3-yl)amino)pyridin-2-yl)methyl)-1-(2-fluorobenzyl)-2-methylpiperidine-4-carboxylic acid | 456 |
| 157. | 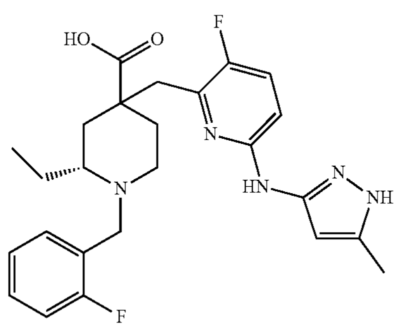 [SMILES: CC[C@@H]1CC(Cc2nc(Nc3cc(C)[nH]n3)ccc2F)(C(=O)O)CCN1Cc1ccccc1F] | (2R)-2-ethyl-4-((3-fluoro-6-((5-methyl-1H-pyrazol-3-yl)amino)-pyridin-2-yl)methyl)-1-(2-fluoro-benzyl)piperidine-4-carboxylic acid | 470 |
| 158. | 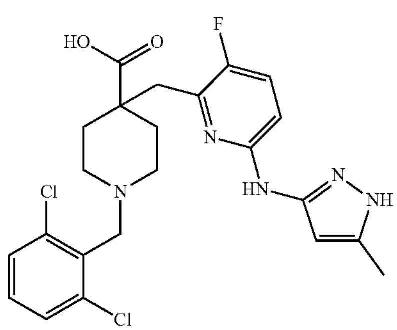 [SMILES: Cc1cc(Nc2ccc(F)c(CC3(C(=O)O)CCN(Cc4c(Cl)cccc4Cl)CC3)n2)n[nH]1] | 1-(2,6-dichlorobenzyl)-4-((3-fluoro-6-((5-methyl-1H-pyrazol-3-yl)amino)pyridin-2-yl)methyl)-piperidine-4-carboxylic acid | 492 |

-continued

| Example No. | Structure | Chemical Name | MS: (M + H)+ |
|---|---|---|---|
| 159. | 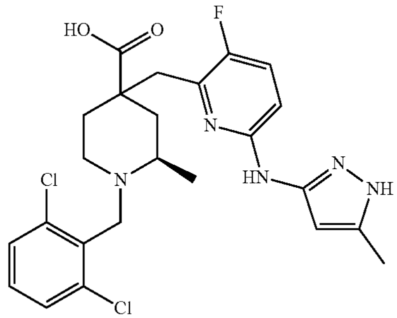 [SMILES: Cc1cc(Nc2ccc(F)c(CC3(C(=O)O)CCN(Cc4c(Cl)cccc4Cl)[C@H](C)C3)n2)n[nH]1] | (2R)-1-(2,6-dichlorobenzyl)-4-((3-fluoro-6-((5-methyl-1H-pyrazol-3-yl)amino)pyridin-2-yl)methyl)-2-methylpiperidine-4-carboxylic acid | 506 |
| 160. | 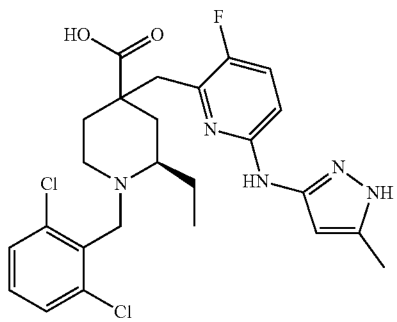 [SMILES: CC[C@@H]1CC(Cc2nc(Nc3cc(C)[nH]n3)ccc2F)(C(=O)O)CCN1Cc1c(Cl)cccc1Cl] | (2R)-1-(2,6-dichlorobenzyl)-2-ethyl-4-((3-fluoro-6-((5-methyl-1H-pyrazol-3-yl)amino)pyridin-2-yl)methyl)piperidine-4-carboxylic acid | 520 |
| 161. | 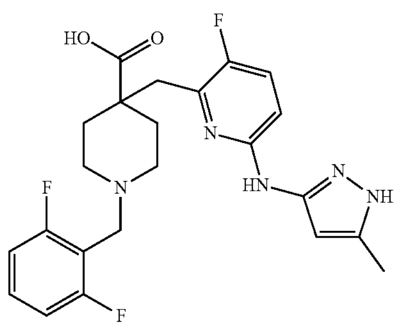 [SMILES: Cc1cc(Nc2ccc(F)c(CC3(C(=O)O)CCN(Cc4c(F)cccc4F)CC3)n2)n[nH]1] | 1-(2,6-difluorobenzyl)-4-((3-fluoro-6-((5-methyl-1H-pyrazol-3-yl)amino)pyridin-2-yl)methyl)-piperidine-4-carboxylic acid | 560 |
| 162. | 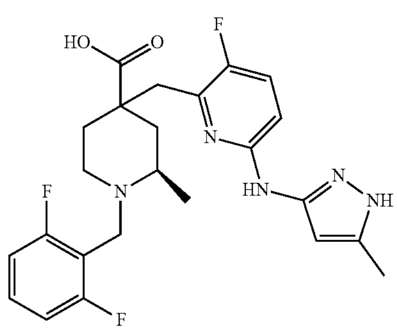 [SMILES: Cc1cc(Nc2ccc(F)c(CC3(C(=O)O)CCN(Cc4c(F)cccc4F)[C@H](C)C3)n2)n[nH]1] | (2R)-1-(2,6-difluorobenzyl)-4-((3-fluoro-6-((5-methyl-1H-pyrazol-3-yl)amino)pyridin-2-yl)methyl)-2-methylpiperidine-4-carboxylic acid | 474 |

-continued

| Example No. | Structure | Chemical Name | MS: (M + H)+ |
|---|---|---|---|
| 163. | 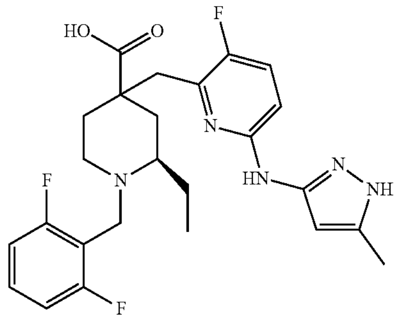 [SMILES: CC[C@@H]1CC(Cc2nc(Nc3cc(C)[nH]n3)ccc2F)(C(=O)O)CCN1Cc1c(F)cccc1F] | (2R)-1-(2,6-difluorobenzyl)-2-ethyl-4-((3-fluoro-6-((5-methyl-1H-pyrazol-3-yl)amino)pyridin-2-yl)methyl)piperidine-4-carboxylic acid | 488 |
| 164. | 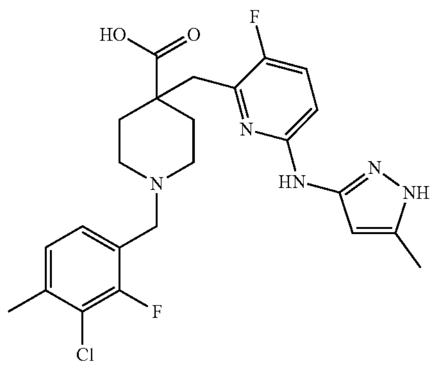 | 1-(3-chloro-2-fluoro-4-methylbenzyl)-4-((3-fluoro-6-((5-methyl-1H-pyrazol-3-yl)amino)pyridin-2-yl)methyl)piperidine-4-carboxylic acid | 490 |
| 165. | 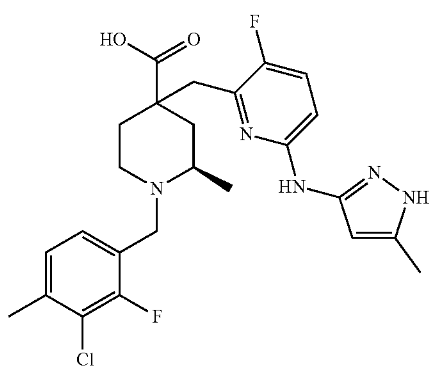 | (2R)-1-(3-chloro-2-fluoro-4-methylbenzyl)-4-((3-fluoro-6-((5-methyl-1H-pyrazol-3-yl)amino)pyridin-2-yl)methyl)-2-methylpiperidine-4-carboxylic acid | 504 |
| 166. | 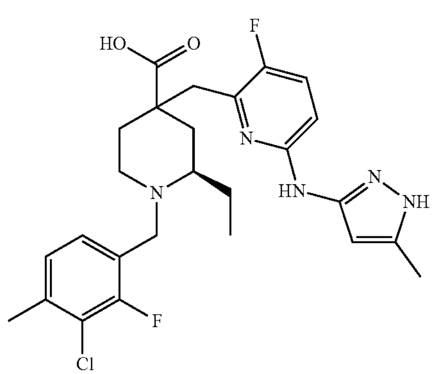 | (2R)-1-(3-chloro-2-fluoro-4-methylbenzyl)-2-ethyl-4-((3-fluoro-6-((5-methyl-1H-pyrazol-3-yl)amino)pyridin-2-yl)methyl)piperidine-4-carboxylic acid | 518 |

| Example No. | Structure | Chemical Name | MS: (M + H)+ |
|---|---|---|---|
| 167. | 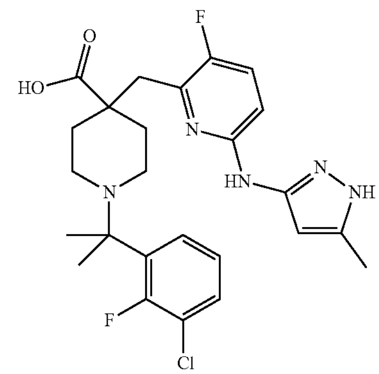 [SMILES: Cc1cc(Nc2ccc(F)c(CC3(C(=O)O)CCN(C(C)(C)c4cccc(Cl)c4F)CC3)n2)n[nH]1] | 1-(2-(3-chloro-2-fluorophenyl)-propan-2-yl)-4-((3-fluoro-6-((5-methyl-1H-pyrazol-3-yl)amino)pyridin-2-yl)methyl)piperidine-4-carboxylic acid | 504 |
| 168. | 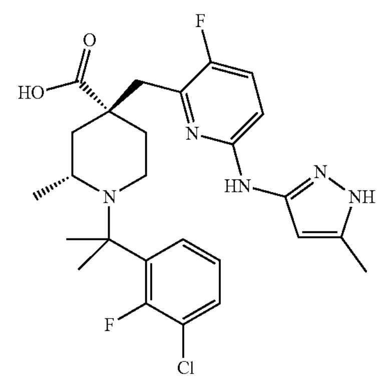 | (2R,4R)-1-(2-(3-chloro-2-fluorophenyl)propan-2-yl)-4-((3-fluoro-6-((5-methyl-1H-pyrazol-3-yl)amino)pyridin-2-yl)methyl)-2-methylpiperidine-4-carboxylic acid | 518 |
| 169. | 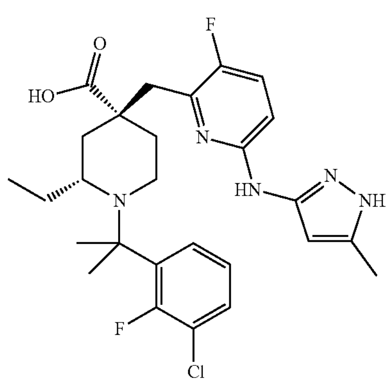 [SMILES: CC[C@@H]1C[C@](Cc2nc(Nc3cc(C)[nH]n3)ccc2F)(C(=O)O)CCN1C(C)(C)c1cccc(Cl)c1F] | (2R,4R)-1-(2-(3-chloro-2-fluorophenyl)propan-2-yl)-2-ethyl-4-((3-fluoro-6-((5-methyl-1H-pyrazol-3-yl)amino)pyridin-2-yl)methyl)-piperidine-4-carboxylic acid | 532 |
| 170. | 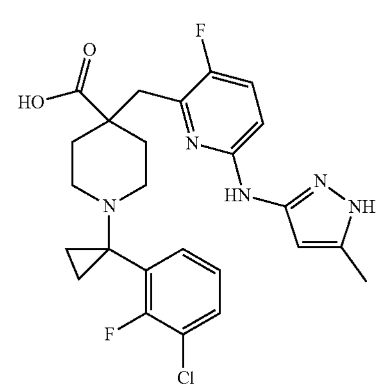 [SMILES: Cc1cc(Nc2ccc(F)c(CC3(C(=O)O)CCN(C4(c5cccc(Cl)c5F)CC4)CC3)n2)n[nH]1] | 1-(1-(3-chloro-2-fluorophenyl)-cyclopropyl)-4-((3-fluoro-6-((5-methyl-1H-pyrazol-3-yl)amino)-pyridin-2-yl)methyl)piperidine-4-carboxylic acid | 502 |

| Example No. | Structure | Chemical Name | MS: (M + H)+ |
|---|---|---|---|
| 171. | 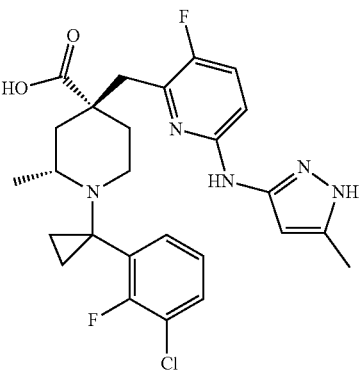 | (2R,4R)-1-(1-(3-chloro-2-fluorophenyl)cyclopropyl)-4-((3-fluoro-6-((5-methyl-1H-pyrazol-3-yl)amino)pyridin-2-yl)methyl)-2-methylpiperidine-4-carboxylic acid | 516 |
| 172. | 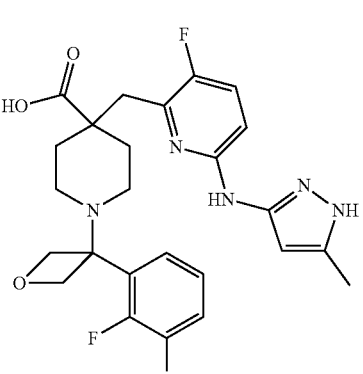 | 1-(3-(3-chloro-2-fluorophenyl)-oxetan-3-yl)-4-((3-fluoro-6-((5-methyl-1H-pyrazol-3-yl)amino)-pyridin-2-yl)methyl)piperidine-4)-xylic acid | 518 |
| 173. | 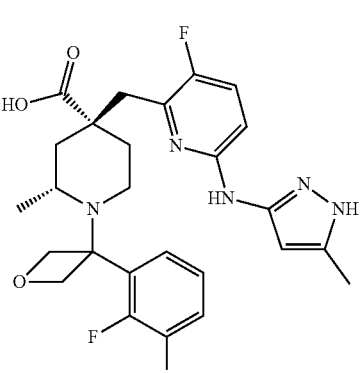 | (2R,4R)-1-(3-(3-chloro-2-fluorophenyl)oxetan-3-yl)-4-((3-fluoro-6-((5-methyl-1H-pyrazol-3-yl)amino)pyridin-2-yl)methyl)-2-methylpiperidine-4-carboxylic acid | 532 |
| 174. | 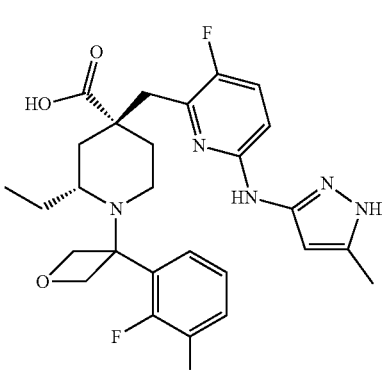 | (2R,4R)-1-(3-(3-chloro-2-fluorophenyl)oxetan-3-yl)-2-ethyl-4-((3-fluoro-6-((5-methyl-1H-pyrazol-3-yl)amino)pyridin-2-yl)methyl)-piperidine-4-carboxylic acid | 545 |

-continued

| Example No. | Structure | Chemical Name | MS: (M + H)+ |
|---|---|---|---|
| 175. | 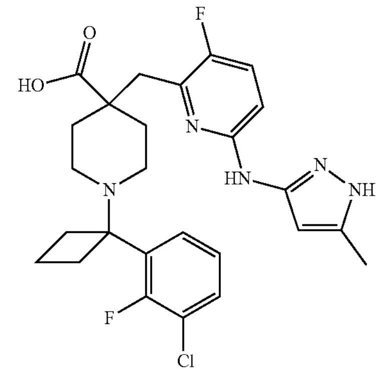 [SMILES: Cc1cc(Nc2ccc(F)c(CC3(C(=O)O)CCN(C4(c5cccc(Cl)c5F)CCC4)CC3)n2)n[nH]1] | 1-(1-(3-chloro-2-fluorophenyl)-cyclobutyl)-4-((3-fluoro-6-((5-methyl-1H-pyrazol-3-yl)amino)py-ridin-2-yl)methyl)piperidine-4-carboxylic acid | 516 |
| 176. | 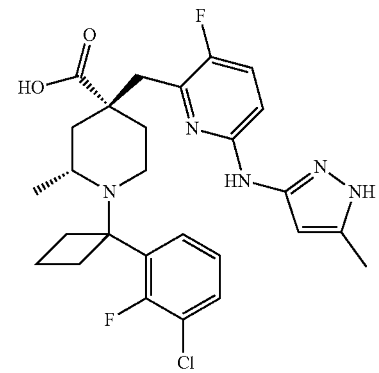 | (2R,4R)-1-(1-(3-chloro-2-fluoro-phenyl)cyclobutyl)-4-((3-fluoro-6-((5-methyl-1H-pyrazol-3-yl)-amino)pyridin-2-yl)methyl)-2-methylpiperidine-4-carboxylic acid | 530 |
| 177. | 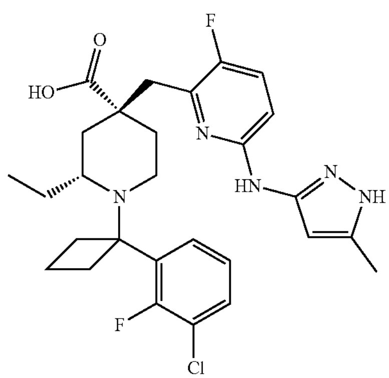 [SMILES: CC[C@@H]1C[C@](Cc2nc(Nc3cc(C)[nH]n3)ccc2F)(C(=O)O)CCN1C1(c2cccc(Cl)c2F)CCC1] | (2R,4R)-1-(1-(3-chloro-2-fluoro-phenyl)cyclobutyl)-2-ethyl-4-((3-fluoro-6-((5-methyl-1H-pyrazol-3-yl)amino)pyridin-2-yl)methyl)piperidine-4-carboxylic acid | 544 |
| 178. | 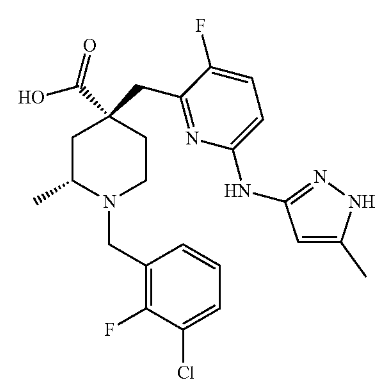 | (2R,4R)-1-(3-chloro-2-fluoroben-zyl)-4-((3-fluoro-6-((5-methyl-1H-pyrazol-3-yl)amino)pyridin-2-yl)methyl)-2-methylpiperidine-4-carboxylic acid | 490 |

-continued

| Example No. | Structure | Chemical Name | MS: (M + H)+ |
|---|---|---|---|
| 179. | 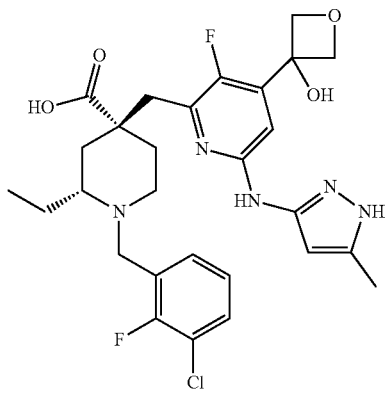 [SMILES: CC[C@@H]1C[C@](Cc2nc(Nc3cc(C)[nH]n3)cc(C3(O)COC3)c2F)(C(=O)O)CCN1Cc1cccc(Cl)c1F] | (2R,4R)-1-(3-chloro-2-fluorobenzyl)-2-ethyl-4-((3-fluoro-4-(3-hydroxyoxetan-3-yl)-6-((5-methyl-1H-pyrazol-3-yl)amino)pyridin-2-yl)methyl)piperidine-4-carboxylic acid | 576 |
| 180. | 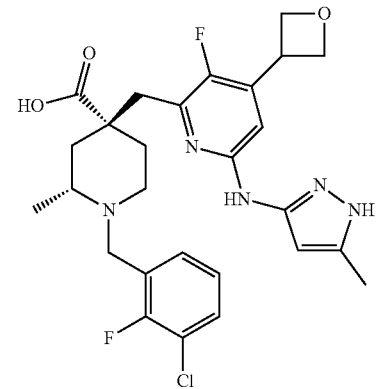 | (2R,4R)-1-(3-chloro-2-fluorobenzyl)-4-((3-fluoro-6-((5-methyl-1H-pyrazol-3-yl)amino)-4-(oxetan-3-yl)pyridin-2-yl)methyl)-2-methylpiperidine-4-carboxylic acid | 546 |
| 181. | 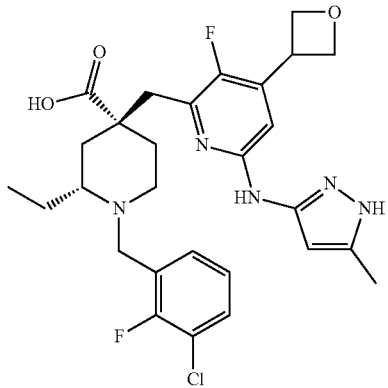 [SMILES: CC[C@@H]1C[C@](Cc2nc(Nc3cc(C)[nH]n3)cc(C3COC3)c2F)(C(=O)O)CCN1Cc1cccc(Cl)c1F] | (2R,4R)-1-(3-chloro-2-fluorobenzyl)-2-ethyl-4-((3-fluoro-6-((5-methyl-1H-pyrazol-3-yl)amino)-4-(oxetan-3-yl)pyridin-2-yl)methyl)piperidine-4-carboxylic acid | 560 |

| Example No. | Structure | Chemical Name | MS: (M + H)+ |
|---|---|---|---|
| 182. | 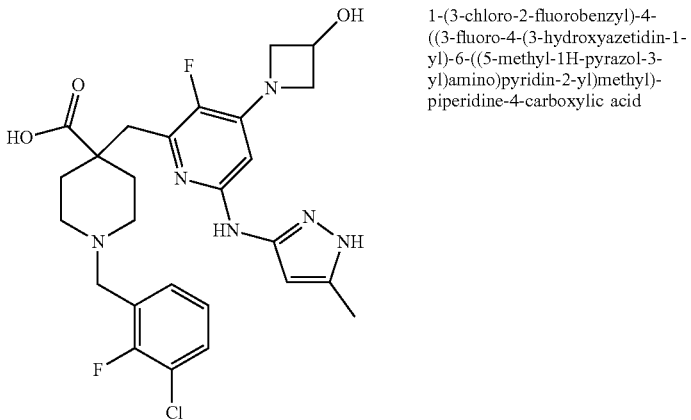 | 1-(3-chloro-2-fluorobenzyl)-4-((3-fluoro-4-(3-hydroxyazetidin-1-yl)-6-((5-methyl-1H-pyrazol-3-yl)amino)pyridin-2-yl)methyl)-piperidine-4-carboxylic acid | 547 |
| 183. | 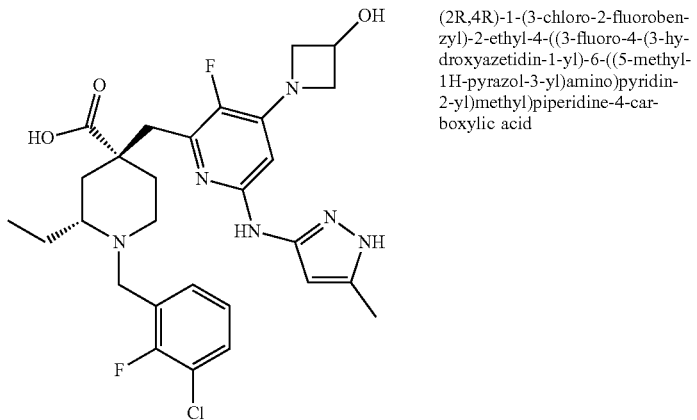 | (2R,4R)-1-(3-chloro-2-fluorobenzyl)-2-ethyl-4-((3-fluoro-4-(3-hydroxyazetidin-1-yl)-6-((5-methyl-1H-pyrazol-3-yl)amino)pyridin-2-yl)methyl)piperidine-4-carboxylic acid | 575 |
| 184. | 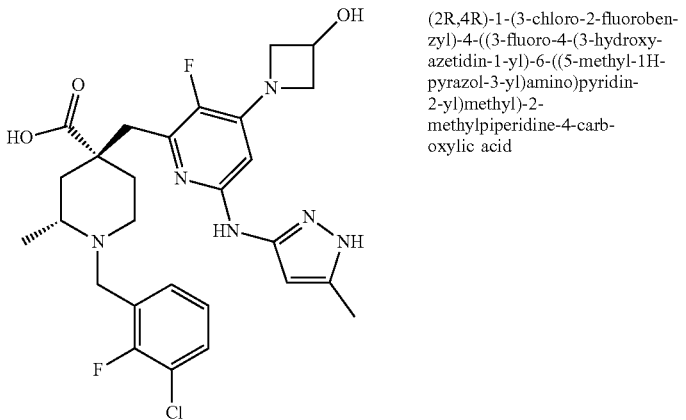 | (2R,4R)-1-(3-chloro-2-fluorobenzyl)-4-((3-fluoro-4-(3-hydroxyazetidin-1-yl)-6-((5-methyl-1H-pyrazol-3-yl)amino)pyridin-2-yl)methyl)-2-methylpiperidine-4-carboxylic acid | 561 |

| Example No. | Structure | Chemical Name | MS: (M + H)+ |
|---|---|---|---|
| 185. | 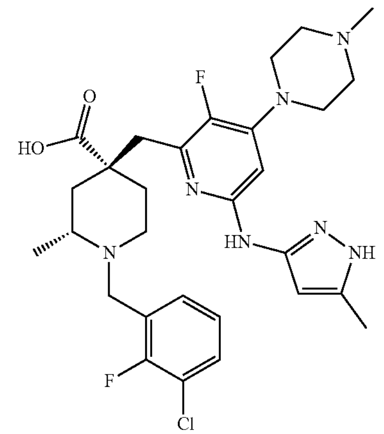 | (2R,4R)-1-(3-chloro-2-fluorobenzyl)-4-((3-fluoro-6-((5-methyl-1H-pyrazol-3-yl)amino)-4-(4-methylpiperazin-1-yl)pyridin-2-yl)methyl)-2-methylpiperidine-4-carboxylic acid | 588 |
| 186. | 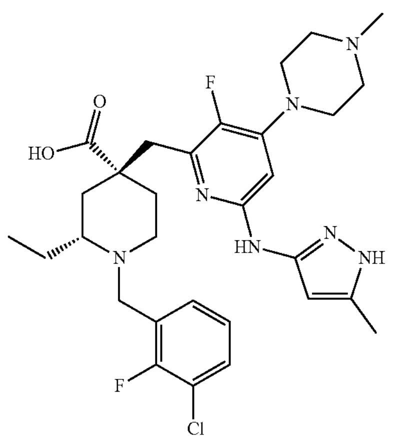 [SMILES: CC[C@@H]1C[C@](Cc2nc(Nc3cc(C)[nH]n3)cc(N3CCN(C)CC3)c2F)(C(=O)O)CCN1Cc1cccc(Cl)c1F] | (2R,4R)-1-(3-chloro-2-fluorobenzyl)-2-ethyl-4-((3-fluoro-6-((5-methyl-1H-pyrazol-3-yl)amino)-4-(4-methylpiperazin-1-yl)pyridin-2-yl)methyl)piperidine-4-carboxylic acid | 602 |
| 187. | 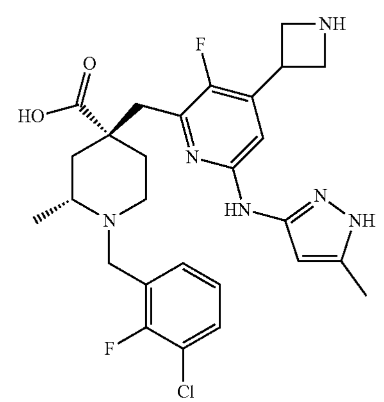 | (2R,4R)-4-((4-(azetidin-3-yl)-3-fluoro-6-((5-methyl-1H-pyrazol-3-yl)amino)pyridin-2-yl)methyl)-1-(3-chloro-2-fluorobenzyl)-2-methylpiperidine-4-carboxylic acid | 545 |

| Example No. | Structure | Chemical Name | MS: (M + H)+ |
|---|---|---|---|
| 188. | 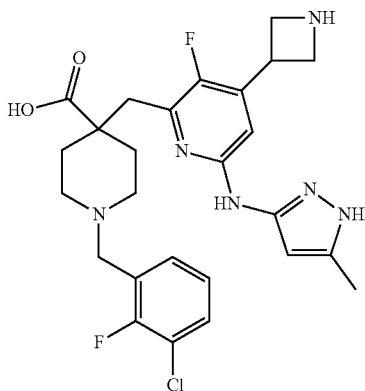 [SMILES: Cc1cc(Nc2cc(C3CNC3)c(F)c(CC3(C(=O)O)CCN(Cc4cccc(Cl)c4F)CC3)n2)n[nH]1] | 4-((4-(azetidin-3-yl)-3-fluoro-6-((5-methyl-1H-pyrazol-3-yl)amino)pyridin-2-yl)methyl)-1-(3-chloro-2-fluorobenzyl)piperidine-4-carboxylic acid | 531 |
| 189. | 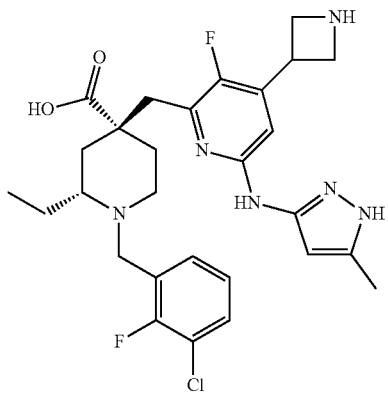 [SMILES: CC[C@@H]1C[C@](Cc2nc(Nc3cc(C)[nH]n3)cc(C3CNC3)c2F)(C(=O)O)CCN1Cc1cccc(Cl)c1F] | (2R,4R)-4-((4-(azetidin-3-yl)-3-fluoro-6-((5-methyl-1H-pyrazol-3-yl)amino)pyridin-2-yl)methyl)-1-(3-chloro-2-fluorobenzyl)-2-ethylpiperidine-4-carboxylic acid | 559 |
| 190. | 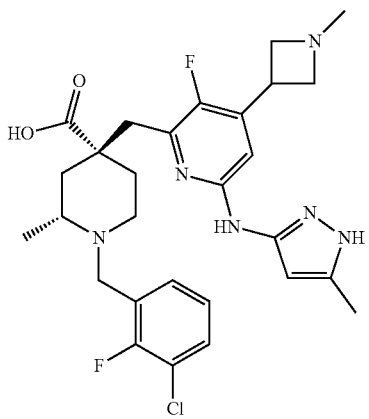 | (2R,4R)-1-(3-chloro-2-fluorobenzyl)-4-((3-fluoro-6-((5-methyl-1H-pyrazol-3-yl)amino)-4-(1-methylazetidin-3-yl)pyridin-2-yl)methyl)-2-methylpiperidine-4-carboxylic acid | 559 |

-continued

| Example No. | Structure | Chemical Name | MS: (M + H)+ |
|---|---|---|---|
| 191. | 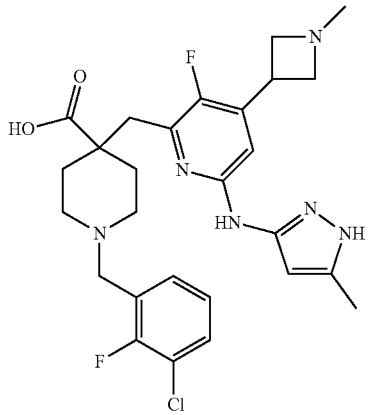 [SMILES: Cc1cc(Nc2cc(C3CN(C)C3)c(F)c(CC3(C(=O)O)CCN(Cc4cccc(Cl)c4F)CC3)n2)n[nH]1] | 1-(3-chloro-2-fluorobenzyl)-4-((3-fluoro-6-((5-methyl-1H-pyrazol-3-yl)amino)-4-(1-methylazetidin-3-yl)pyridin-2-yl)methyl)piperidine-4-carboxylic acid | 545 |
| 192. | 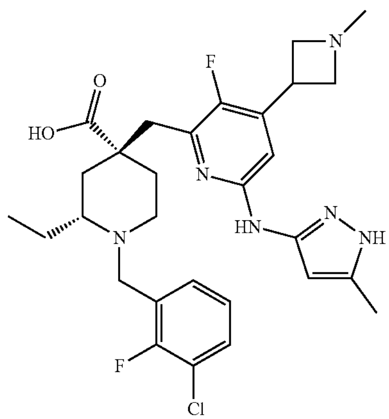 [SMILES: CC[C@@H]1C[C@](Cc2nc(Nc3cc(C)[nH]n3)cc(C3CN(C)C3)c2F)(C(=O)O)CCN1Cc1cccc(Cl)c1F] | (2R,4R)-1-(3-chloro-2-fluorobenzyl)-2-ethyl-4-((3-fluoro-6-((5-methyl-1H-pyrazol-3-yl)amino)-4-(1-methylazetidin-3-yl)pyridin-2-yl)methyl)piperidine-4-carboxylic acid | 573 |
| 193. | 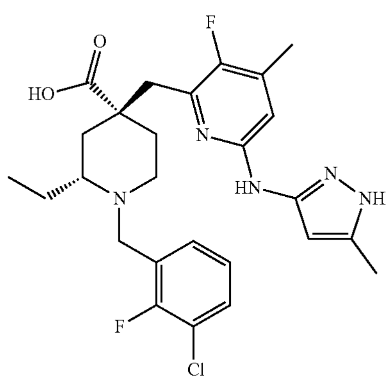 [SMILES: CC[C@@H]1C[C@](Cc2nc(Nc3cc(C)[nH]n3)cc(C)c2F)(C(=O)O)CCN1Cc1cccc(Cl)c1F] | (2R,4R)-1-(3-chloro-2-fluorobenzyl)-2-ethyl-4-((3-fluoro-4-methyl-6-((5-methyl-1H-pyrazol-3-yl)amino)pyridin-2-yl)methyl)piperidine-4-carboxylic acid | 518 |
| 194. | 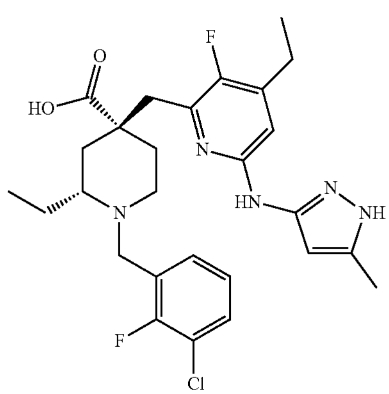 [SMILES: CCc1cc(Nc2cc(C)[nH]n2)nc(C[C@@]2(C(=O)O)CCN(Cc3cccc(Cl)c3F)[C@H](CC)C2)c1F] | (2R,4R)-1-(3-chloro-2-fluorobenzyl)-2-ethyl-4-((4-ethyl-3-fluoro-6-((5-methyl-1H-pyrazol-3-yl)amino)pyridin-2-yl)methyl)piperidine-4-carboxylic acid | 532 |

-continued

| Example No. | Structure | Chemical Name | MS: (M + H)⁺ |
|---|---|---|---|
| 195. | 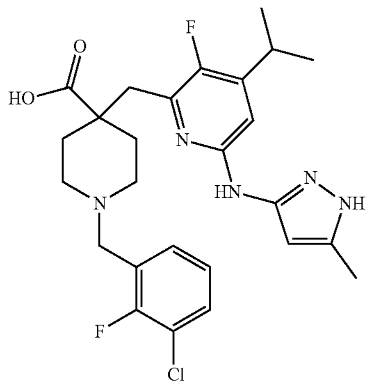 [SMILES: Cc1cc(Nc2cc(C(C)C)c(F)c(CC3(C(=O)O)CCN(Cc4cccc(Cl)c4F)CC3)n2)n[nH]1] | 1-(3-chloro-2-fluorobenzyl)-4-((3-fluoro-4-isopropyl-6-((5-methyl-1H-pyrazol-3-yl)amino)pyridin-2-yl)methyl)piperidine-4-carboxylic acid | 518 |
| 196. | 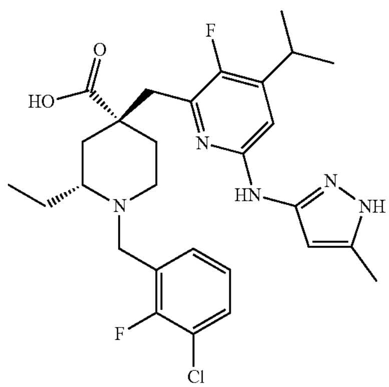 [SMILES: CC[C@@H]1C[C@](Cc2nc(Nc3cc(C)[nH]n3)cc(C(C)C)c2F)(C(=O)O)CCN1Cc1cccc(Cl)c1F] | (2R,4R)-1-(3-chloro-2-fluorobenzyl)-2-ethyl-4-((3-fluoro-4-isopropyl-6-((5-methyl-1H-pyrazol-3-yl)amino)pyridin-2-yl)methyl)piperidine-4-carboxylic acid | 546 |
| 197. | 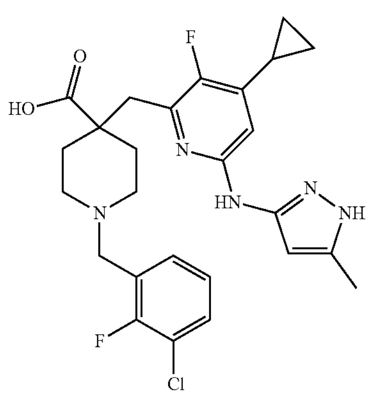 [SMILES: Cc1cc(Nc2cc(C3CC3)c(F)c(CC3(C(=O)O)CCN(Cc4cccc(Cl)c4F)CC3)n2)n[nH]1] | 1-(3-chloro-2-fluorobenzyl)-4-((4-cyclopropyl-3-fluoro-6-((5-methyl-1H-pyrazol-3-yl)amino)py-ridin-2-yl)methyl)piperidine-4-carboxylic acid | 516 |
| 198. | 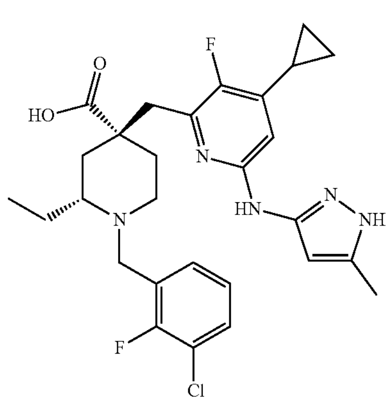 [SMILES: CC[C@@H]1C[C@](Cc2nc(Nc3cc(C)[nH]n3)cc(C3CC3)c2F)(C(=O)O)CCN1Cc1cccc(Cl)c1F] | (2R,4R)-1-(3-chloro-2-fluorobenzyl)-4-((4-cyclopropyl-3-fluoro-6-((5-methyl-1H-pyrazol-3-yl)-amino)pyridin-2-yl)methyl)-2-ethyl-piperidine-4-carboxylic acid | 544 |

| Example No. | Structure | Chemical Name | MS: (M + H)+ |
|---|---|---|---|
| 199. | 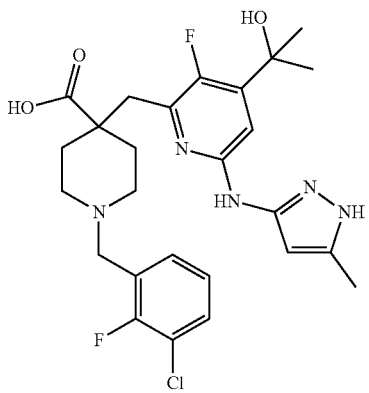 [SMILES: Cc1cc(Nc2cc(C(C)(C)O)c(F)c(CC3(C(=O)O)CCN(Cc4cccc(Cl)c4F)CC3)n2)n[nH]1] | 1-(3-chloro-2-fluorobenzyl)-4-((3-fluoro-4-(2-hydroxypropan-2-yl)-6-((5-methyl-1H-pyrazol-3-yl)amino)pyridin-2-yl)methyl)piperidine-4-carboxylic acid | 534 |
| 200. | 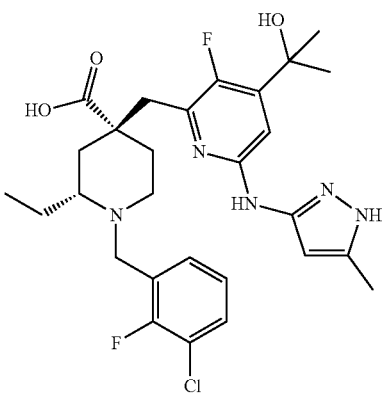 [SMILES: CC[C@@H]1C[C@](Cc2nc(Nc3cc(C)[nH]n3)cc(C(C)(C)O)c2F)(C(=O)O)CCN1Cc1cccc(Cl)c1F] | (2R,4R)-1-(3-chloro-2-fluorobenzyl)-2-ethyl-4-((3-fluoro-4-(2-hydroxypropan-2-yl)-6-((5-methyl-1H-pyrazol-3-yl)amino)pyridin-2-yl)methyl)piperidine-4-carboxylic acid | 562 |
| 201. | 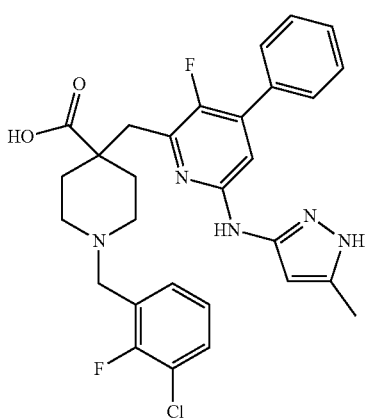 [SMILES: Cc1cc(Nc2cc(-c3ccccc3)c(F)c(CC3(C(=O)O)CCN(Cc4cccc(Cl)c4F)CC3)n2)n[nH]1] | 1-(3-chloro-2-fluorobenzyl)-4-((3-fluoro-6-((5-methyl-1H-pyrazol-3-yl)amino)-4-phenylpyridin-2-yl)methyl)piperidine-4-carboxylic acid | 552 |

| Example No. | Structure | Chemical Name | MS: (M + H)+ |
|---|---|---|---|
| 202. | 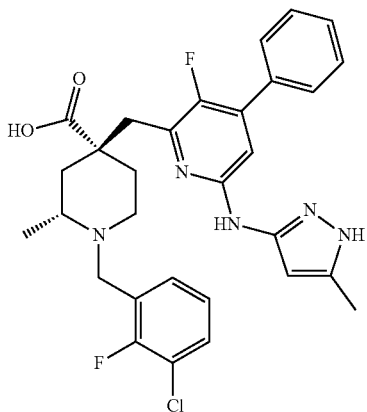 | (2R,4R)-1-(3-chloro-2-fluorobenzyl)-4-((3-fluoro-6-((5-methyl-1H-pyrazol-3-yl)amino)-4-phenyl pyridin-2-yl)methyl)-2-methyl-piperidine-4-carboxylic acid | 566 |
| 203. | 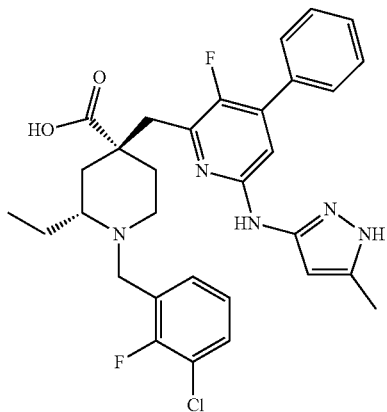 [SMILES: CC[C@@H]1C[C@](Cc2nc(Nc3cc(C)[nH]n3)cc(-c3ccccc3)c2F)(C(=O)O)CCN1Cc1cccc(Cl)c1F] | (2R,4R)-1-(3-chloro-2-fluorobenzyl)-2-ethyl-4-((3-fluoro-6-((5-methyl-1H-pyrazol-3-yl)amino)-4-phenylpyridin-2-yl)methyl)piperidine-4-carboxylic acid | 580 |
| 204. | 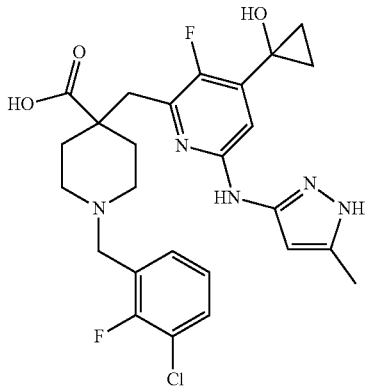 [SMILES: Cc1cc(Nc2cc(C3(O)CC3)c(F)c(CC3(C(=O)O)CCN(Cc4cccc(Cl)c4F)CC3)n2)n[nH]1] | 1-(3-chloro-2-fluorobenzyl)-4-((3-fluoro-4-(1-hydroxycyclopropyl)-6-((5-methyl-1H-pyrazol-3-yl)amino)pyridin-2-yl)methyl)piperidine-4-carboxylic acid | 532 |

| Example No. | Structure | Chemical Name | MS: (M + H)+ |
|---|---|---|---|
| 205. | 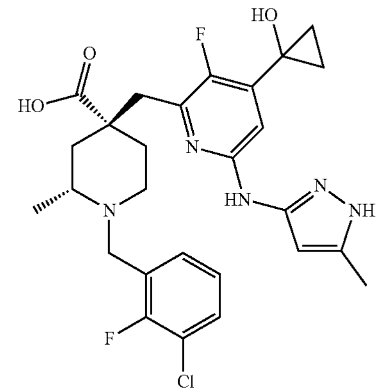 | (2R,4R)-1-(3-chloro-2-fluorobenzyl)-4-((3-fluoro-4-(1-hydroxycyclopropyl)-6-((5-methyl-1H-pyrazol-3-yl)amino)pyridin-2-yl)methyl)-2-methylpiperidine-4-carboxylic acid | 546 |
| 206. | 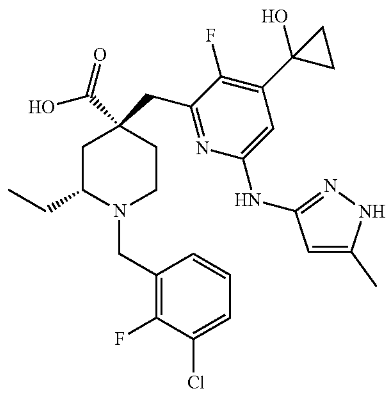 [SMILES: CC[C@@H]1C[C@](Cc2nc(Nc3cc(C)[nH]n3)cc(C3(O)CC3)c2F)(C(=O)O)CCN1Cc1cccc(Cl)c1F] | (2R,4R)-1-(3-chloro-2-fluorobenzyl)-2-ethyl-4-((3-fluoro-4-(1-hydroxycyclopropyl)-6-((5-methyl-1H-pyrazol-3-yl)amino)pyridin-2-yl)methyl)piperidine-4-carboxylic acid | 560 |
| 207. | 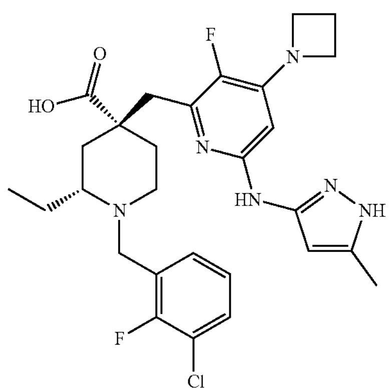 [SMILES: CC[C@@H]1C[C@](Cc2nc(Nc3cc(C)[nH]n3)cc(N3CCC3)c2F)(C(=O)O)CCN1Cc1cccc(Cl)c1F] | (2R,4R)-4-((4-(azetidin-1-yl)-3-fluoro-6-((5-methyl-1H-pyrazol-3-yl)amino)pyridin-2-yl)methyl)-1-(3-chloro-2-fluorobenzyl)-2-ethylpiperidine-4-carboxylic acid | 559 |
| 208. | 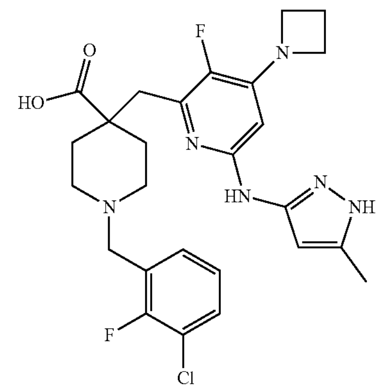 [SMILES: Cc1cc(Nc2cc(N3CCC3)c(F)c(CC3(C(=O)O)CCN(Cc4cccc(Cl)c4F)CC3)n2)n[nH]1] | 4-((4-(azetidin-1-yl)-3-fluoro-6-((5-methyl-1H-pyrazol-3-yl)amino)pyridin-2-yl)methyl)-1-(3-chloro-2-fluorobenzyl)piperidine-4-carboxylic acid | 531 |

-continued

| Example No. | Structure | Chemical Name | MS: (M + H)+ |
|---|---|---|---|
| 209. | 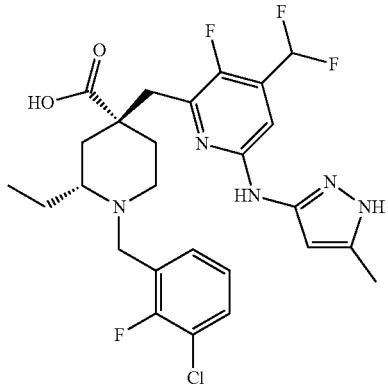 [SMILES: CC[C@@H]1C[C@](Cc2nc(Nc3cc(C)[nH]n3)cc(C(F)F)c2F)(C(=O)O)CCN1Cc1cccc(Cl)c1F] | (2R,4R)-1-(3-chloro-2-fluorobenzyl)-4-((4-(difluoromethyl)-3-fluoro-6-((5-methyl-1H-pyrazol-3-yl)amino)pyridin-2-yl)methyl)-2-ethylpiperidine-4-carboxylic acid | 554 |
| 210. | 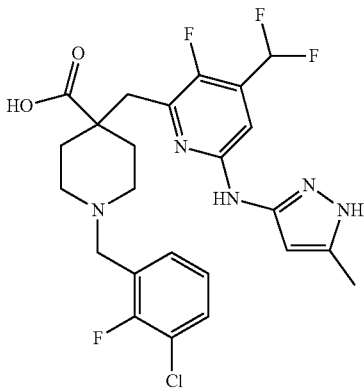 [SMILES: Cc1cc(Nc2cc(C(F)F)c(F)c(CC3(C(=O)O)CCN(Cc4cccc(Cl)c4F)CC3)n2)n[nH]1] | 1-(3-chloro-2-fluorobenzyl)-4-((4-(difluoromethyl)-3-fluoro-6-((5-methyl-1H-pyrazol-3-yl)amino)pyridin-2-yl)methyl)piperidine-4-carboxylic acid | 526 |
| 211. | 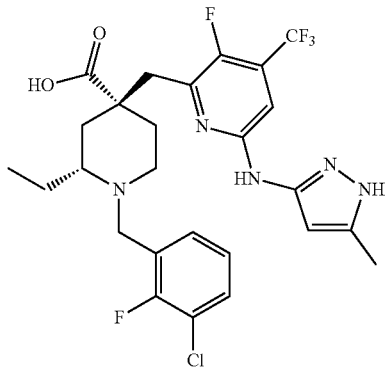 [SMILES: CC[C@@H]1C[C@](Cc2nc(Nc3cc(C)[nH]n3)cc(C(F)(F)F)c2F)(C(=O)O)CCN1Cc1cccc(Cl)c1F] | (2R,4R)-1-(3-chloro-2-fluorobenzyl)-2-ethyl-4-((3-fluoro-6-((5-methyl-1H-pyrazol-3-yl)amino)-4-(trifluoromethyl)pyridin-2-yl)methyl)piperidine-4-carboxylic acid | 572 |
| 212. | 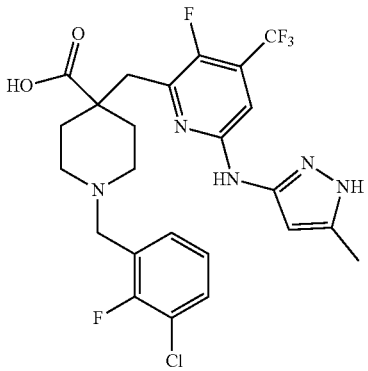 | 1-(3-chloro-2-fluorobenzyl)-4-((3-fluoro-6-((5-methyl-1H-pyrazol-3-yl)amino)-4-(trifluoromethyl)pyridin-2-yl)methyl)piperidine-4-carboxylic acid | 544 |

-continued

| Example No. | Structure | Chemical Name | MS: (M + H)+ |
|---|---|---|---|
| 213. | 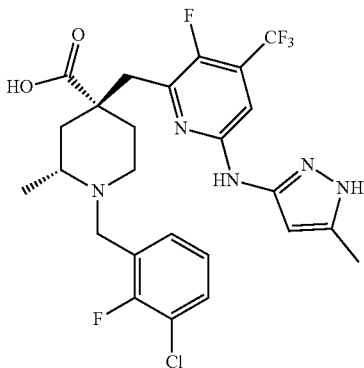 | (2R,4R)-1-(3-chloro-2-fluorobenzyl)-4-((3-fluoro-6-((5-methyl-1H-pyrazol-3-yl)amino)-4-(trifluoromethyl)pyridin-2-yl)methyl)-2-methylpiperidine-4-carboxylic acid | 558 |
| 214. | 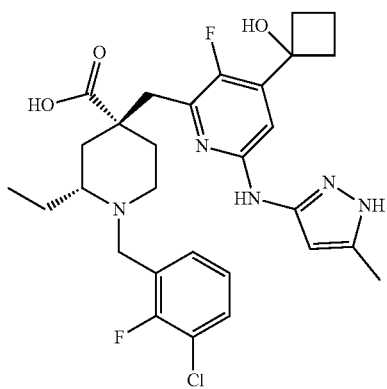 [SMILES: CC[C@@H]1C[C@](Cc2nc(Nc3cc(C)[nH]n3)cc(C3(O)CCC3)c2F)(C(=O)O)CCN1Cc1cccc(Cl)c1F] | (2R,4R)-1-(3-chloro-2-fluorobenzyl)-2-ethyl-4-((3-fluoro-4-(1-hydroxycyclobutyl)-6-((5-methyl-1H-pyrazol-3-yl)amino)pyridin-2-yl)methyl)piperidine-4-carboxylic acid | 574 |
| 215. | 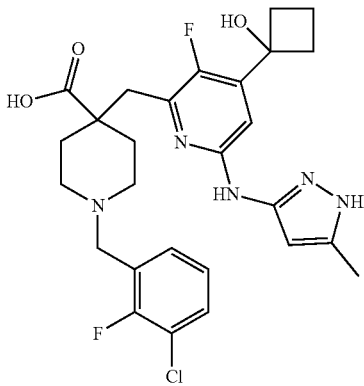 [SMILES: Cc1cc(Nc2cc(C3(O)CCC3)c(F)c(CC3(C(=O)O)CCN(Cc4cccc(Cl)c4F)CC3)n2)n[nH]1] | 1-(3-chloro-2-fluorobenzyl)-4-((3-fluoro-4-(1-hydroxycyclobutyl)-6-((5-methyl-1H-pyrazol-3-yl)amino)pyridin-2-yl)methyl)piperidine-4-carboxylic acid | 546 |
| 216. | 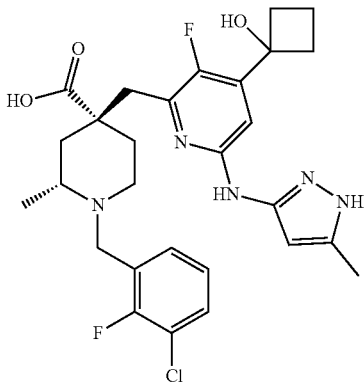 | (2R,4R)-1-(3-chloro-2-fluorobenzyl)-4-((3-fluoro-4-(1-hydroxycyclobutyl)-6-((5-methyl-1H-pyrazol-3-yl)amino)pyridin-2-yl)methyl)-2-methylpiperidine-4-carboxylic acid | 560 |

-continued

| Example No. | Structure | Chemical Name | MS: (M + H)+ |
|---|---|---|---|
| 217. | 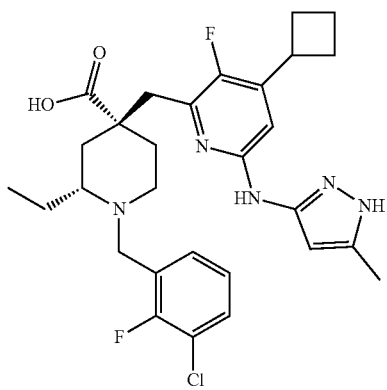 [SMILES: CC[C@@H]1C[C@](Cc2nc(Nc3cc(C)[nH]n3)cc(C3CCC3)c2F)(C(=O)O)CCN1Cc1cccc(Cl)c1F] | (2R,4R)-1-(3-chloro-2-fluorobenzyl)-4-((4-cyclobutyl-3-fluoro-6-((5-methyl-1H-pyrazol-3-yl)amino)-pyridin-2-yl)methyl)-2-ethyl piperidine-4-carboxylic acid | 558 |
| 218. | 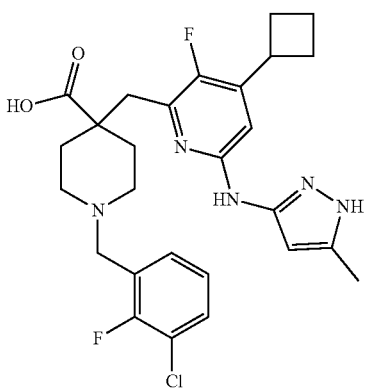 [SMILES: Cc1cc(Nc2cc(C3CCC3)c(F)c(CC3(C(=O)O)CCN(Cc4cccc(Cl)c4F)CC3)n2)n[nH]1] | 1-(3-chloro-2-fluorobenzyl)-4-((4-cyclobutyl-3-fluoro-6-((5-methyl-1H-pyrazol-3-yl)amino)pyridin-2-yl)methyl)piperidine-4-carboxylic acid | 530 |
| 219. | 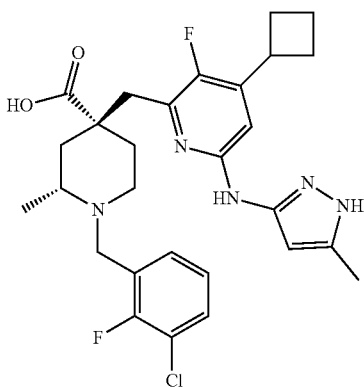 | (2R,4R)-1-(3-chloro-2-fluorobenzyl)-4-((4-cyclobutyl-3-fluoro-6-((5-methyl-1H-pyrazol-3-yl)amino)-pyridin-2-yl)methyl)-2-methyl-piperidine-4-carboxylic acid | 544 |
| 220. | 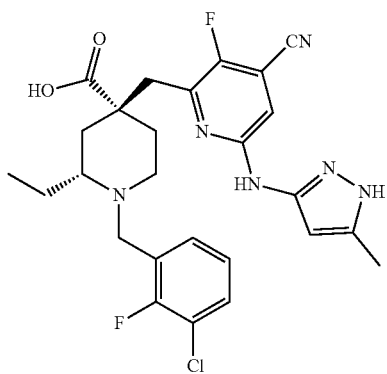 [SMILES: CC[C@@H]1C[C@](Cc2nc(Nc3cc(C)[nH]n3)cc(C#N)c2F)(C(=O)O)CCN1Cc1cccc(Cl)c1F] | (2R,4R)-1-(3-chloro-2-fluorobenzyl)-4-((4-cyano-3-fluoro-6-((5-methyl-1H-pyrazol-3-yl)amino)-pyridin-2-yl)methyl)-2-ethyl piperidine-4-carboxylic acid | 529 |

| Example No. | Structure | Chemical Name | MS: (M + H)+ |
|---|---|---|---|
| 221. | 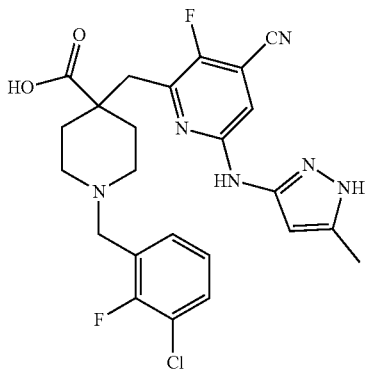 | 1-(3-chloro-2-fluorobenzyl)-4-((4-cyano-3-fluoro-6-((5-methyl-1H-pyrazol-3-yl)amino)pyridin-2-yl)methyl)piperidine-4-carboxylic acid | 501 |
| 222. | 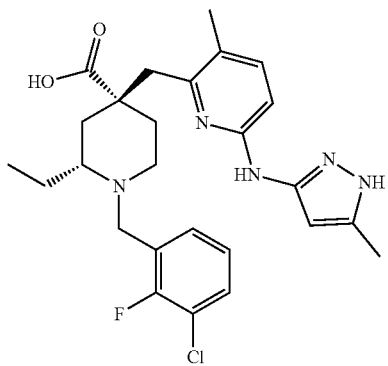 [SMILES: CC[C@@H]1C[C@](Cc2nc(Nc3cc(C)[nH]n3)ccc2C)(C(=O)O)CCN1Cc1cccc(Cl)c1F] | (2R,4R)-1-(3-chloro-2-fluorobenzyl)-2-ethyl-4-((3-methyl-6-((5-methyl-1H-pyrazol-3-yl)amino)-pyridin-2-yl)methyl)piperidine-4)-carboxylic acid | 500 |
| 223. | 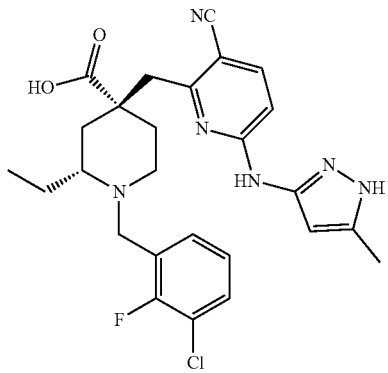 [SMILES: CC[C@@H]1C[C@](Cc2nc(Nc3cc(C)[nH]n3)ccc2C#N)(C(=O)O)CCN1Cc1cccc(Cl)c1F] | (2R,4R)-1-(3-chloro-2-fluorobenzyl)-4-((3-cyano-6-((5-methyl-1H-pyrazol-3-yl)amino)pyridin-2-yl)methyl)-2-ethylpiperidine-4)-carboxylic acid | 511 |
| 224. | 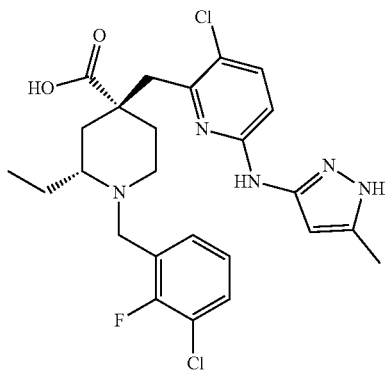 [SMILES: CC[C@@H]1C[C@](Cc2nc(Nc3cc(C)[nH]n3)ccc2Cl)(C(=O)O)CCN1Cc1cccc(Cl)c1F] | (2R,4R)-1-(3-chloro-2-fluorobenzyl)-4-((3-chloro-6-((5-methyl-1H-pyrazol-3-yl)amino)pyridin-2-yl)methyl)-2-ethylpiperidine-4)-carboxylic acid | 520 |

| Example No. | Structure | Chemical Name | MS: (M + H)+ |
|---|---|---|---|
| 225. | 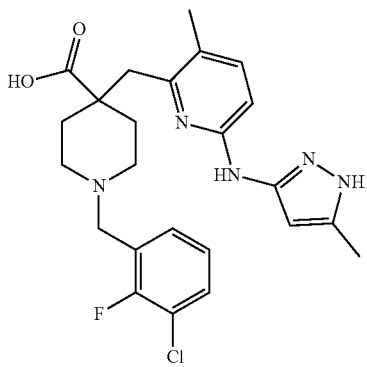 [SMILES: Cc1cc(Nc2ccc(C)c(CC3(C(=O)O)CCN(Cc4cccc(Cl)c4F)CC3)n2)n[nH]1] | 1-(3-chloro-2-fluorobenzyl)-4-((3-methyl-6-((5-methyl-1H-pyrazol-3-yl)amino)pyridin-2-yl)methyl)-piperidine-4-carboxylic acid | 472 |
| 226. | 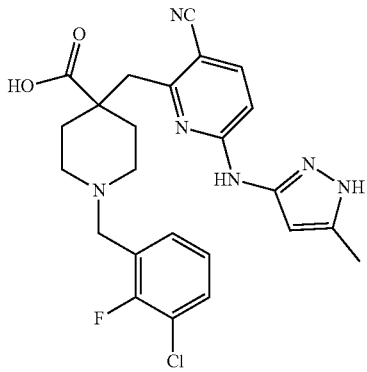 [SMILES: Cc1cc(Nc2ccc(C#N)c(CC3(C(=O)O)CCN(Cc4cccc(Cl)c4F)CC3)n2)n[nH]1] | 1-(3-chloro-2-fluorobenzyl)-4-((3-cyano-6-((5-methyl-1H-pyrazol-3-yl)amino)pyridin-2-yl)methyl)-piperidine-4-carboxylic acid | 483 |
| 227. | 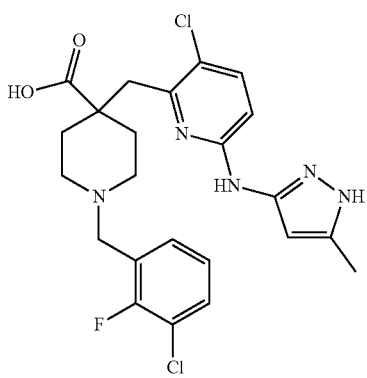 [SMILES: Cc1cc(Nc2ccc(Cl)c(CC3(C(=O)O)CCN(Cc4cccc(Cl)c4F)CC3)n2)n[nH]1] | 1-(3-chloro-2-fluorobenzyl)-4-((3-chloro-6-((5-methyl-1H-pyrazol-3-yl)amino)pyridin-2-yl)methyl)-piperidine-4-carboxylic acid | 492 |
| 228. | 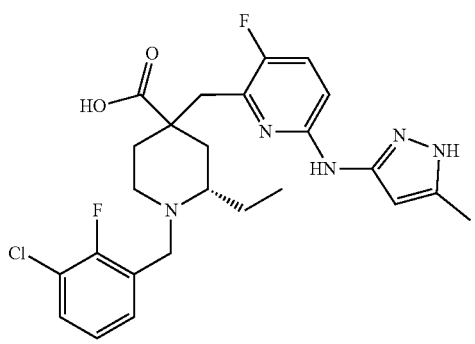 [SMILES: CC[C@H]1CC(Cc2nc(Nc3cc(C)[nH]n3)ccc2F)(C(=O)O)CCN1Cc1cccc(Cl)c1F] | (2S)-1-(3-chloro-2-fluorobenzyl)-2-ethyl-4-((3-fluoro-6-((5-methyl-1H-pyrazol-3-yl)amino)pyridin-2-yl)methyl)piperidine-4-carboxylic acid | 504 |

| Example No. | Structure | Chemical Name | MS: (M + H)+ |
|---|---|---|---|
| 229. | 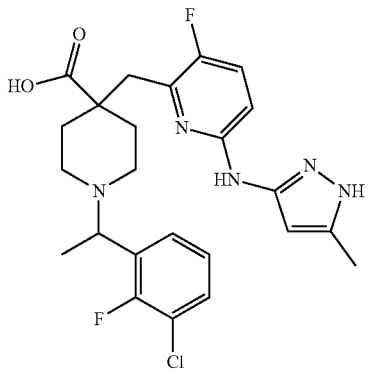 [SMILES: Cc1cc(Nc2ccc(F)c(CC3(C(=O)O)CCN(C(C)c4cccc(Cl)c4F)CC3)n2)n[nH]1] | 1-(1-(3-chloro-2-fluorophenyl)ethyl)-4-((3-fluoro-6-((5-methyl-1H-pyrazol-3-yl)amino)pyridin-2-yl)methyl)piperidine-4-carboxylic acid | 490 |
| 230. | 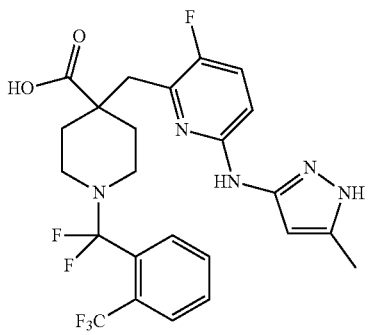 [SMILES: Cc1cc(Nc2ccc(F)c(CC3(C(=O)O)CCN(C(F)(F)c4ccccc4C(F)(F)F)CC3)n2)n[nH]1] | 1-(difluoro(2-(trifluoromethyl)-phenyl)methyl)-4-((3-fluoro-6-((5-methyl-1H-pyrazol-3-yl)amino)-pyridin-2-yl)methyl)piperidine-4-carboxylic acid | 527 |
| 231. | 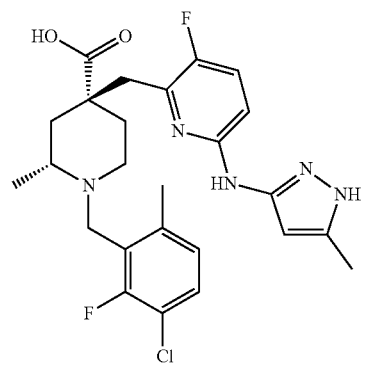 | (2R,4R)-1-(3-chloro-2-fluoro-6-methylbenzyl)-4-((3-fluoro-6-((5-methyl-1H-pyrazol-3-yl)amino)-pyridin-2-yl)methyl)-2-methyl-piperidine-4-carboxylic acid | 504 |
| 232. | 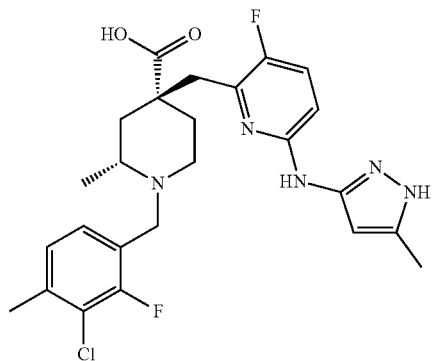 | (2R,4R)-1-(3-chloro-2-fluoro-4-methylbenzyl)-4-((3-fluoro-6-((5-methyl-1H-pyrazol-3-yl)amino)-pyridin-2-yl)methyl)-2-methyl-piperidine-4-carboxylic acid | 504 |

| Example No. | Structure | Chemical Name | MS: (M + H)+ |
|---|---|---|---|
| 233. | 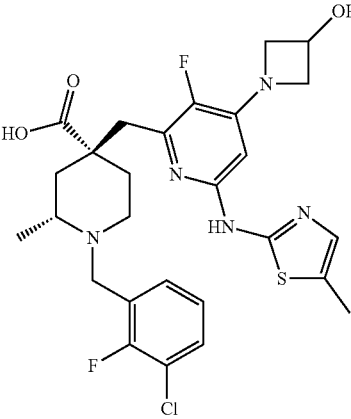 | (2R,4R)-1-(3-chloro-2-fluorobenzyl)-4-((3-fluoro-4-(3-hydroxyazetidin-1-yl)-6-((5-methylthiazol-2-yl)amino)pyridin-2-yl)methyl)-2-methylpiperidine-4-carboxylic acid | 578 |
| 234. | 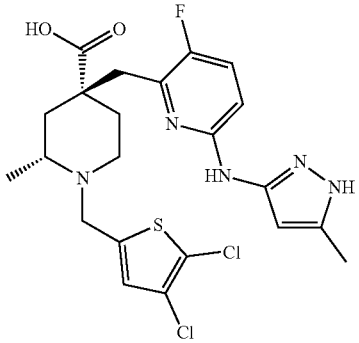 | (2R,4R)-1-((4,5-dichlorothiophen-2-yl)methyl)-4-((3-fluoro-6-((5-methyl-1H-pyrazol-3-yl)amino)pyridin-2-yl)methyl)-2-methyl piperidine-4-carboxylic acid | 512 |
| 235. | 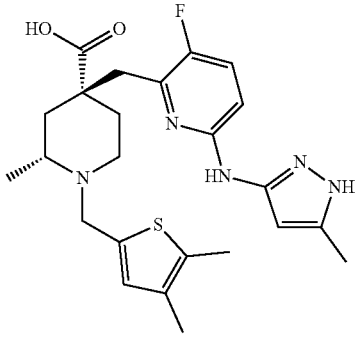 | (2R,4R)-1-((4?5-dimethylthiophen-2-yl)methyl)-4-((3-fluoro-6-((5-methyl-1H-pyrazol-3-yl)amino)pyridin-2-yl)methyl)-2-methyl piperidine-4-carboxylic acid | 472 |
| 236. | 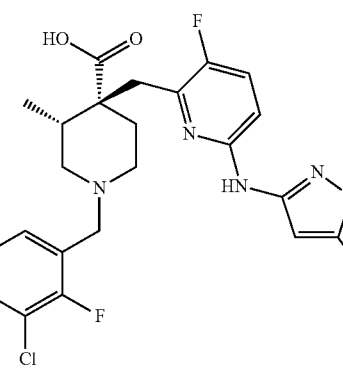 | (3R,4S)-1-(3-chloro-2-fluorobenzyl)-4-((3-fluoro-6-((5-methyl-1H-pyrazol-3-yl)amino)pyridin-2-yl)methyl)-3-methylpiperidine-4)-carboxylic acid | 490 |

-continued

| Example No. | Structure | Chemical Name | MS: (M + H)+ |
|---|---|---|---|
| 237. | 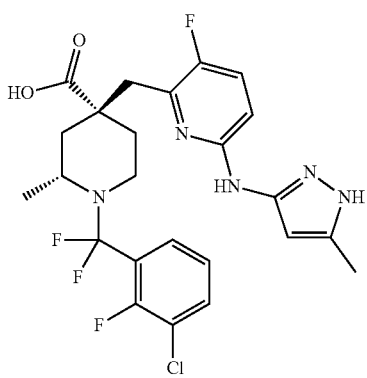 | (2R,4R)-1-((3-chloro-2-fluoro-phenyl)difluoromethyl)-4-((3-fluoro-6-((5-methyl-1H-pyrazol-3-yl)-amino)pyridin-2-yl)methyl)-2-methylpiperidine-4-carboxylic acid | 526 |
| 238. | 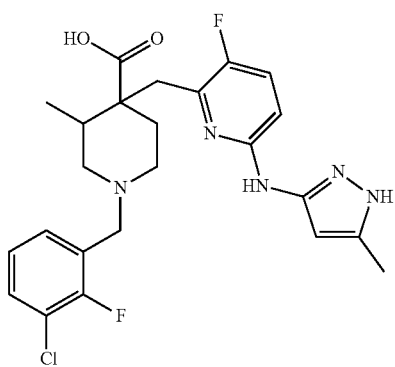 [SMILES: Cc1cc(Nc2ccc(F)c(CC3(C(=O)O)CCN(Cc4cccc(Cl)c4F)CC3C)n2)n[nH]1] | 1-(3-chloro-2-fluorobenzyl)-4-((3-fluoro-6-((5-methyl-1H-pyrazol-3-yl)amino)pyridin-2-yl)methyl)-3-methylpiperidine-4-carboxylic acid | 490 |
| 239. | 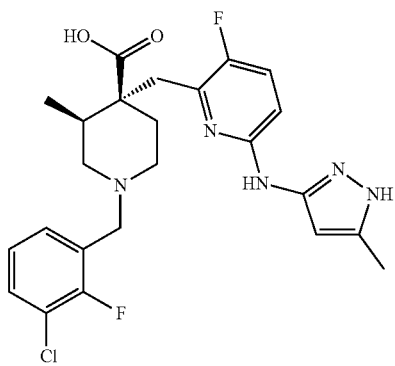 [SMILES: Cc1cc(Nc2ccc(F)c(C[C@]3(C(=O)O)CCN(Cc4cccc(Cl)c4F)C[C@H]3C)n2)n[nH]1] | (3S,4R)-1-(3-chloro-2-fluoroben-zyl)-4-((3-fluoro-6-((5-methyl-1H-pyrazol-3-yl)amino)pyridin-2-yl)methyl)-3-methylpiperidine-4-carboxylic acid | 490 |
| 240. | 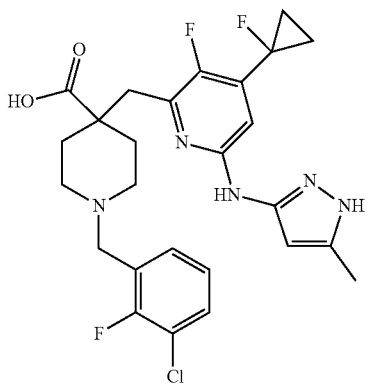 [SMILES: Cc1cc(Nc2cc(C3(F)CC3)c(F)c(CC3(C(=O)O)CCN(Cc4cccc(Cl)c4F)CC3)n2)n[nH]1] | 1-(3-chloro-2-fluorobenzyl)-4-((3-fluoro-4-(1-fluorocyclopropyl)-6-((5-methyl-1H-pyrazol-3-yl)-amino)pyridin-2-yl)methyl)piperi-dine-4-carboxylic acid | 534 |

| Example No. | Structure | Chemical Name | MS: (M + H)+ |
|---|---|---|---|
| 241. | 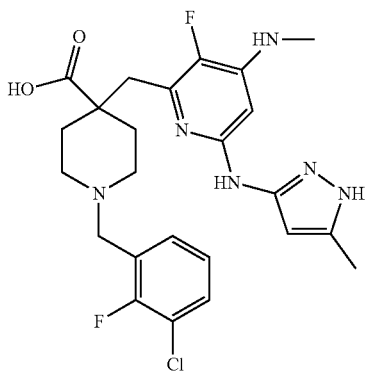 [SMILES: CNc1cc(Nc2cc(C)[nH]n2)nc(CC2(C(=O)O)CCN(Cc3cccc(Cl)c3F)CC2)c1F] | 1-(3-chloro-2-fluorobenzyl)-4-((3-fluoro-6-((5-methyl-1H-pyrazol-3-yl)amino)-4-(methylamino)-pyridin-2-yl)methyl)piperidine-4)-carboxylic acid | 505 |
| 242. | 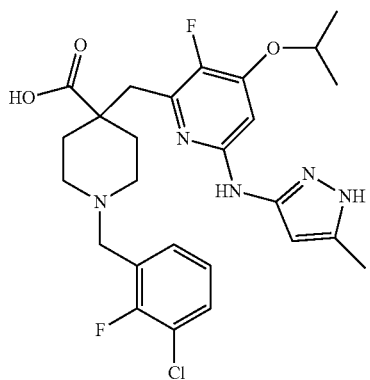 [SMILES: Cc1cc(Nc2cc(OC(C)C)c(F)c(CC3(C(=O)O)CCN(Cc4cccc(Cl)c4F)CC3)n2)n[nH]1] | 1-(3-chloro-2-fluorobenzyl)-4-((3-fluoro-4-isopropoxy-6-((5-methyl-1H-pyrazol-3-yl)amino)pyridin-2-yl)methyl)piperidine-4-carboxylic acid | 534 |
| 243. | 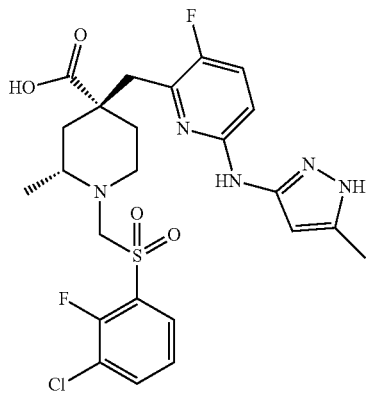 | (2R,4R)-1-(((3-chloro-2-fluorophenyl)sulfonyl)methyl)-4-((3-fluoro-6-((5-methyl-1H-pyrazol-3-yl)amino)pyridin-2-yl)methyl)-2-methylpiperidine-4-carboxylic acid | 554 |
| 244. | 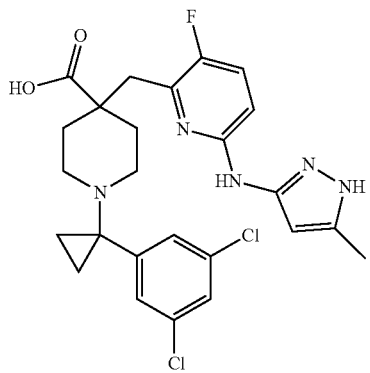 [SMILES: Cc1cc(Nc2ccc(F)c(CC3(C(=O)O)CCN(C4(c5cc(Cl)cc(Cl)c5)CC4)CC3)n2)n[nH]1] | 1-(1-(3,5-dichlorophenyl)cyclopropyl)-4-((3-fluoro-6-((5-methyl-1H-pyrazol-3-yl)amino)pyridin-2-yl)methyl)piperidine-4-carboxylic acid | 518 |

-continued

| Example No. | Structure | Chemical Name | MS: (M + H)+ |
|---|---|---|---|
| 245. | 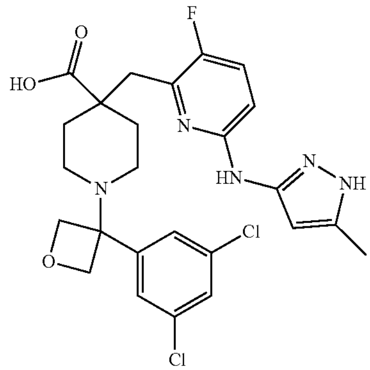 [SMILES: Cc1cc(Nc2ccc(F)c(CC3(C(=O)O)CCN(C4(c5cc(Cl)cc(Cl)c5)COC4)CC3)n2)n[nH]1] | 1-(3-(3,5-dichlorophenyl)oxetan-3-yl)-4-((3-fluoro-6-((5-methyl-1H-pyrazol-3-yl)amino)pyridin-2-yl)methyl)piperidine-4-carboxylic acid | 534 |
| 246. | 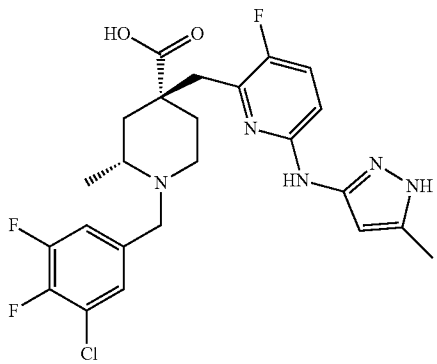 [SMILES: Cc1cc(Nc2ccc(F)c(C[C@@]3(C(=O)O)CCN(Cc4cc(F)c(F)c(Cl)c4)[C@H](C)C3)n2)n[nH]1] | (2R,4R)-1-(3-chloro-4,5-difluorobenzyl)-4-((3-fluoro-6-((5-methyl-1H-pyrazol-3-yl)amino)pyridin-2-yl)methyl)-2-methylpiperidine-4-carboxylic acid | 508 |
| 247. | 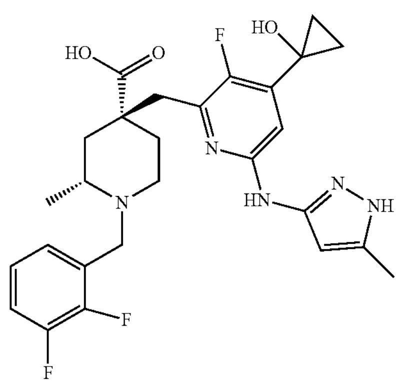 | (2R,4R)-1-(2,3-difluorobenzyl)-4-((3-fluoro-4-(1-hydroxycyclopropyl)-6-((5-methyl-1H-pyrazol-3-yl)amino)pyridin-2-yl)methyl)-2-methylpiperidine-4-carboxylic acid | 530 |
| 248. | 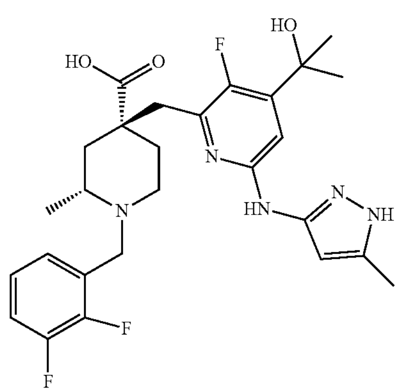 [SMILES: Cc1cc(Nc2cc(C(C)(C)O)c(F)c(C[C@@]3(C(=O)O)CCN(Cc4cccc(F)c4F)[C@H](C)C3)n2)n[nH]1] | (2R,4R)-1-(2,3-difluorobenzyl)-4-((3-fluoro-4-(2-hydroxypropan-2-yl)-6-((5-methyl-1H-pyrazol-3-yl)amino)pyridin-2-yl)methyl)-2-methylpiperidine-4-carboxylic acid | 532 |

-continued

| Example No. | Structure | Chemical Name | MS: (M + H)+ |
|---|---|---|---|
| 249. | 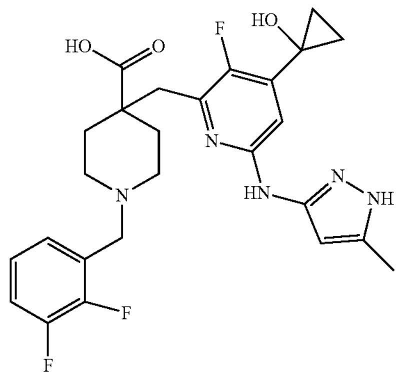 [SMILES: Cc1cc(Nc2cc(C3(O)CC3)c(F)c(CC3(C(=O)O)CCN(Cc4cccc(F)c4F)CC3)n2)n[nH]1] | 1-(2,3-difluorobenzyl)-4-((3-fluoro-4-(1-hydroyycyclopropyl)-6-((5-methyl-1H-pyrazol-3-yl)-amino)pyridin-2-yl)methyl)-piperidine-4-carboxylic acid | 516 |
| 250. | 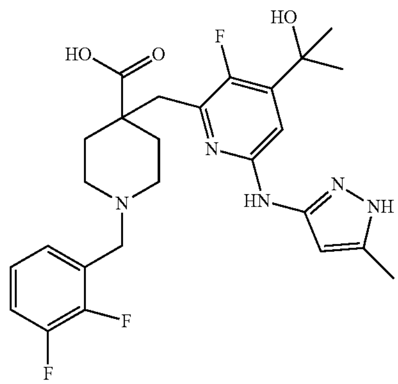 [SMILES: Cc1cc(Nc2cc(C(C)(C)O)c(F)c(CC3(C(=O)O)CCN(Cc4cccc(F)c4F)CC3)n2)n[nH]1] | 1-(2,3-difluorobenzyl)-4-((3-fluoro-4-(2-hydroxypropan-2-yl)-6-((5-methyl-1H-pyrazol-3-yl)amino)-pyridin-2-yl)methyl)piperidine-4-carboxylic acid | 518 |
| 251. | 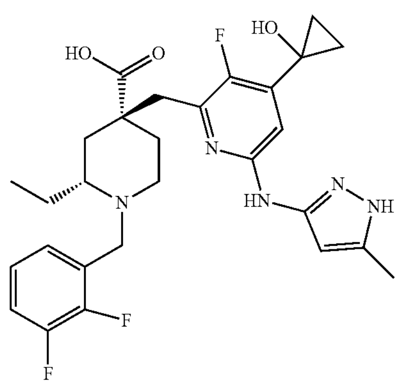 [SMILES: CC[C@@H]1C[C@](Cc2nc(Nc3cc(C)[nH]n3)cc(C3(O)CC3)c2F)(C(=O)O)CCN1Cc1cccc(F)c1F] | (2R,4R)-1-(2,3-difluorobenzyl)-2-ethyl-4-((3-fluoro-4-(1-hydroxy-cyclopropyl)-6-((5-methyl-1H-pyrazol-3-yl)amino)pyridin-2-yl)methyl)piperidine-4-carboxylic acid | 544 |
| 252. | 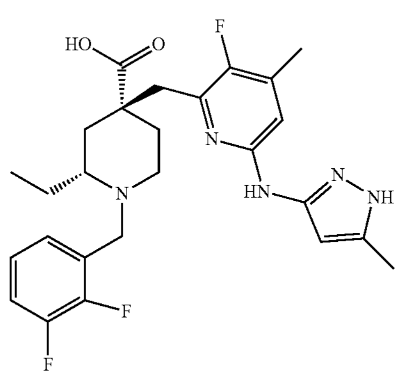 | (2R,4R)-1-(2,3-difluorobenzyl)-2-ethyl-4-((3-fluoro-4-methyl-6-((5-methyl-1H-pyrazol-3-yl)amino)-pyridin-2-yl)methyl)piperidine-4-carboxylic acid | 502 |

-continued

| Example No. | Structure | Chemical Name | MS: (M + H)+ |
|---|---|---|---|
| 253. | 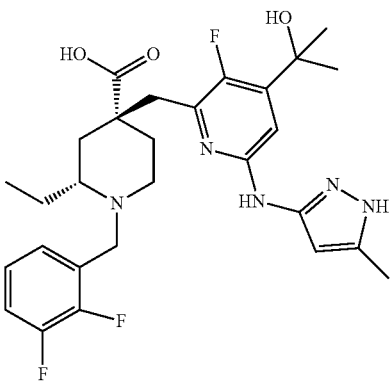 [SMILES: CC[C@@H]1C[C@](Cc2nc(Nc3cc(C)[nH]n3)cc(C(C)(C)O)c2F)(C(=O)O)CCN1Cc1cccc(F)c1F] | (2R,4R)-1-(2,3-difluorobenzyl)-2-ethyl-4-((3-fluoro-4-(2-hydroxy-propan-2-yl)-6-((5-methyl-1H-pyrazol-3-yl)amino)pyridin-2-yl)methyl)piperidine-4-carboxylic acid | 546 |
| 254. | 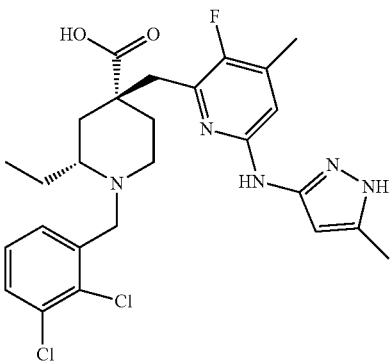 [SMILES: CC[C@@H]1C[C@](Cc2nc(Nc3cc(C)[nH]n3)cc(C)c2F)(C(=O)O)CCN1Cc1cccc(Cl)c1Cl] | (2R,4R)-1-(2,3-dichlorobenzyl)-2-ethyl-4-((3-fluoro-4-methyl-6-((5-methyl-1H-pyrazol-3-yl)amino)-pyridin-2-yl)methyl)piperidine-4-carboxylic acid | 534 |
| 255. | 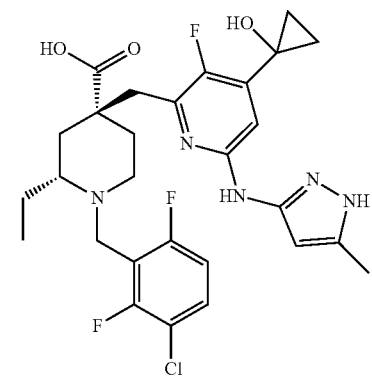 [SMILES: CC[C@@H]1C[C@](Cc2nc(Nc3cc(C)[nH]n3)cc(C3(O)CC3)c2F)(C(=O)O)CCN1Cc1c(F)ccc(Cl)c1F] | (2R,4R)-1-(3-chloro-2,6-difluoro-benzyl)-2-ethyl-4-((3-fluoro-4-(1-hydroxycyclopropyl)-6-((5-methyl-1H-pyrazol-3-yl)amino)py-ridin-2-yl)methyl)piperidine-4)-carboxylic acid | 578 |
| 256. | 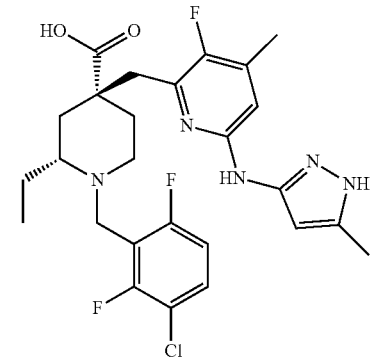 [SMILES: CC[C@@H]1C[C@](Cc2nc(Nc3cc(C)[nH]n3)cc(C)c2F)(C(=O)O)CCN1Cc1c(F)ccc(Cl)c1F] | (2R,4R)-1-(3-chloro-2,6-difluoro-benzyl)-2-ethyl-4-((3-fluoro-4-methyl-6-((5-methyl-1H-pyrazol-3-yl)amino)pyridin-2-yl)methyl)piperidine-4-carboxylic acid | 536 |

| Example No. | Structure | Chemical Name | MS: (M + H)+ |
|---|---|---|---|
| 257. | 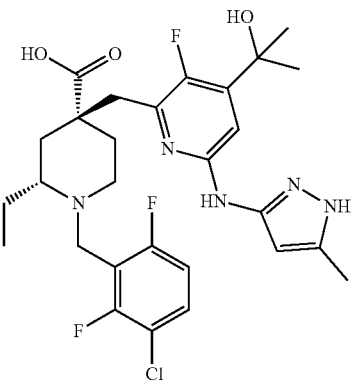 [SMILES: CC[C@@H]1C[C@](Cc2nc(Nc3cc(C)[nH]n3)cc(C(C)(C)O)c2F)(C(=O)O)CCN1Cc1c(F)ccc(Cl)c1F] | (2R,4R)-1-(3-chloro-2,6-difluoro-benzyl)-2-ethyl-4-((3-fluoro-4-(2-hydroxypropan-2-yl)-6-((5-methyl-1H-pyrazol-3-yl)amino)-pyridin-2-yl)methyl)piperidine-4)-carboxylic acid | 580 |
| 258. | 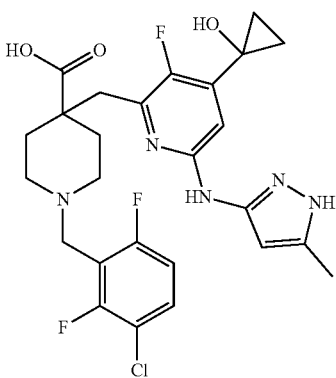 [SMILES: Cc1cc(Nc2cc(C3(O)CC3)c(F)c(CC3(C(=O)O)CCN(Cc4c(F)ccc(Cl)c4F)CC3)n2)n[nH]1] | 1-(3-chloro-2,6-difluorobenzyl)-4-((3-fluoro-4-(1-hydroxycyclo-propyl)-6-((5-methyl-1H-pyrazol-3-yl)amino)pyridin-2-yl)methyl)-piperidine-4-carboxylic acid | 550 |
| 259. | 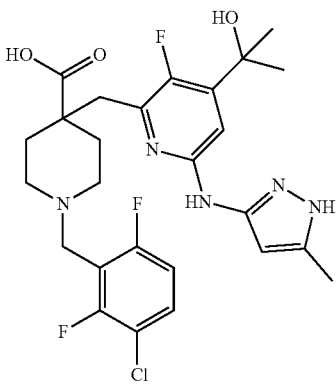 [SMILES: Cc1cc(Nc2cc(C(C)(C)O)c(F)c(CC3(C(=O)O)CCN(Cc4c(F)ccc(Cl)c4F)CC3)n2)n[nH]1] | 1-(3-chloro-2,6-difluorobenzyl)-4-((3-fluoro-4-(2-hydroxypropan-2-yl)-6-((5-methyl-1H-pyrazol-3-yl)amino)pyridin-2-yl)methyl)-piperidine-4-carboxylic acid | 552 |
| 260. | 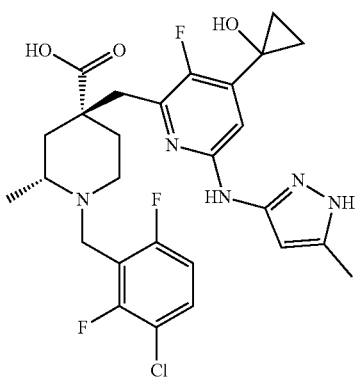 | (2R,4R)-1-(3-chloro-2,6-difluoro-benzyl)-4-((3-fluoro-4-(1-hy-droxycyclopropyl)-6-((5-methyl-1H-pyrazol-3-yl)amino)pyridin-2-yl)methyl)-2-methylpiperidine-4)-carboxylic acid | 564 |

-continued

| Example No. | Structure | Chemical Name | MS: (M + H)+ |
|---|---|---|---|
| 261. | 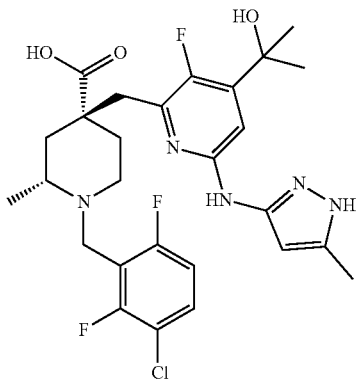 | (2R,4R)-1-(3-chloro-2,6-difluoro-benzyl)-4-((3-fluoro-4-(2-hydroxypropan-2-yl)-6-((5-methyl-1H-pyrazol-3-yl)amino)pyridin-2-yl)methyl)-2-methylpiperidine-4)-carboxylic acid | 566 |
| 262. | 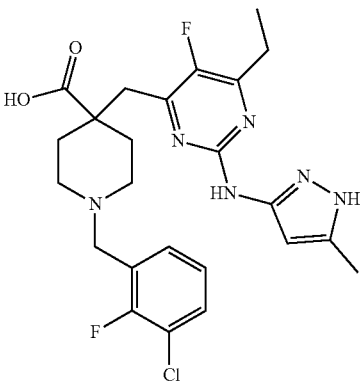 [SMILES: CCc1nc(Nc2cc(C)[nH]n2)nc(CC2(C(=O)O)CCN(Cc3cccc(Cl)c3F)CC2)c1F] | 1-(3-chloro-2-fluorobenzyl)-4-((6-ethyl-5-fluoro-2-((5-methyl-1H-pyrazol-3-yl)amino)pyrimidin-4-yl)methyl)piperidine-4-carboxylic acid | 505 |
| 263. | 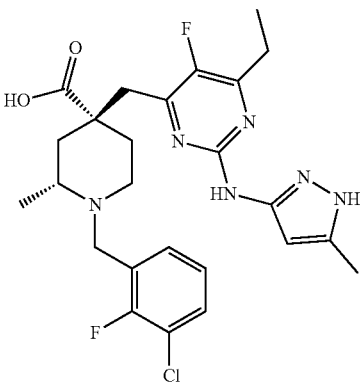 | (2R,4R)-1-(3-chloro-2-fluorobenzyl)-4-((6-ethyl-5-fluoro-2-((5-methyl-1H-pyrazol-3-yl)amino)-pyrimidin-4-yl)methyl)-2-methyl-piperidine-4-carboxylic acid | 519 |
| 264. | 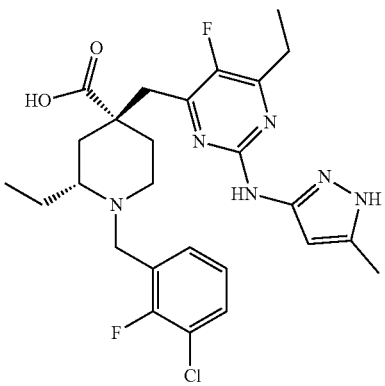 [SMILES: CCc1nc(Nc2cc(C)[nH]n2)nc(C[C@@]2(C(=O)O)CCN(Cc3cccc(Cl)c3F)[C@H](CC)C2)c1F] | (2R,4R)-1-(3-chloro-2-fluorobenzyl)-2-ethyl-4-((6-ethyl-5-fluoro-2-((5-methyl-1H-pyrazol-3-yl)-amino)pyrimidin-4-yl)methyl)piperidine-4-carboxylic acid | 533 |

| Example No. | Structure | Chemical Name | MS: (M + H)+ |
|---|---|---|---|
| 265. | 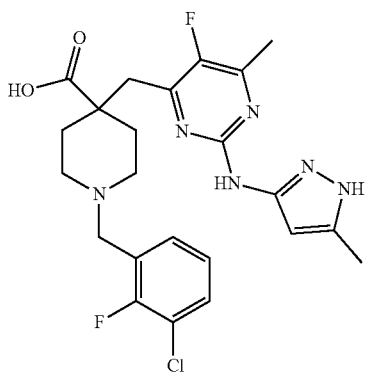 [SMILES: Cc1cc(Nc2nc(C)c(F)c(CC3(C(=O)O)CCN(Cc4cccc(Cl)c4F)CC3)n2)n[nH]1] | 1-(3-chloro-2-fluorobenzyl)-4-((5-fluoro-6-methyl-2-((5-methyl-1H-pyrazol-3-yl)amino)pyrimidin-4-yl)methyl)piperidine-4-carboxylic acid | 491 |
| 266. | 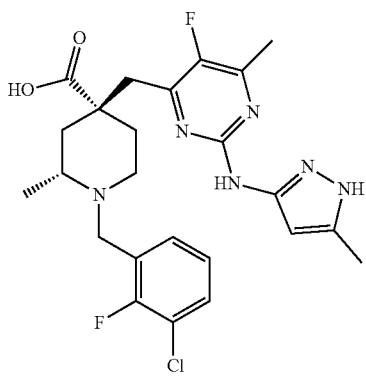 | (2R,4R)-1-(3-chloro-2-fluorobenzyl)-4-((5-fluoro-6-methyl-2-((5-methyl-1H-pyrazol-3-yl)amino)-pyrimidin-4-yl)methyl)-2-methylpiperidine-4-carboxylic acid | 505 |
| 267. | 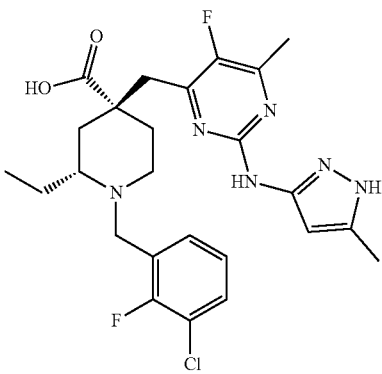 [SMILES: CC[C@@H]1C[C@](Cc2nc(Nc3cc(C)[nH]n3)nc(C)c2F)(C(=O)O)CCN1Cc1cccc(Cl)c1F] | (2R,4R)-1-(3-chloro-2-fluorobenzyl)-2-ethyl-4-((5-fluoro-6-methyl-2-((5-methyl-1H-pyrazol-3-yl)amino)pyrimidin-4-yl)methyl)-piperidine-4-carboxylic acid | 519 |
| 268. | 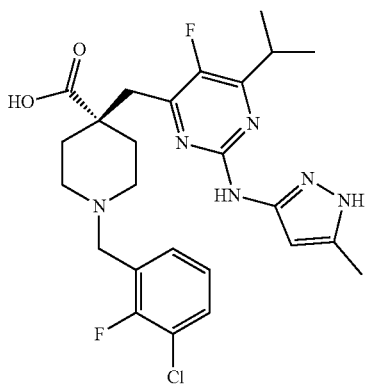 | 1-(3-chloro-2-fluorobenzyl)-4-((5-fluoro-6-isopropyl-2-((5-methyl-1H-pyrazol-3-yl)amino)pyrimidin-4-yl)methyl)piperidine-4-carboxylic acid | 519 |

-continued

| Example No. | Structure | Chemical Name | MS: (M + H)+ |
|---|---|---|---|
| 269. | 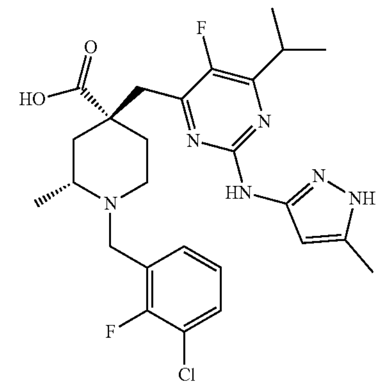 | (2R,4R)-1-(3-chloro-2-fluorobenzyl)-4-((5-fluoro-6-isopropyl-2-((5-methyl-1H-pyrazol-3-yl)amino)pyrimidin-4-yl)methyl)-2-methylpiperidine-4-carboxylic acid | 533 |
| 270. | 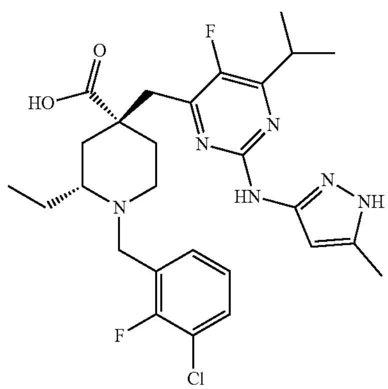 [SMILES: CC[C@@H]1C[C@](Cc2nc(Nc3cc(C)[nH]n3)nc(C(C)C)c2F)(C(=O)O)CCN1Cc1cccc(Cl)c1F] | (2R,4R)-1-(3-chloro-2-fluorobenzyl)-2-ethyl-4-((5-fluoro-6-isopropyl-2-((5-methyl-1H-pyrazol-3-yl)amino)pyrimidin-4-yl)methyl)-piperidine-4-carboxylic acid | 547 |
| 271. | 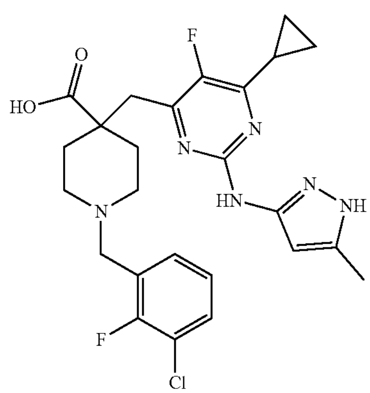 [SMILES: Cc1cc(Nc2nc(CC3(C(=O)O)CCN(Cc4cccc(Cl)c4F)CC3)c(F)c(C3CC3)n2)n[nH]1] | 1-(3-chloro-2-fluorobenzyl)-4-((6-cyclopropyl-5-fluoro-2-((5-methyl-1H-pyrazol-3-yl)amino)pyrimidin-4-yl)methyl)piperidine-4-carboxylic acid | 517 |
| 272. | 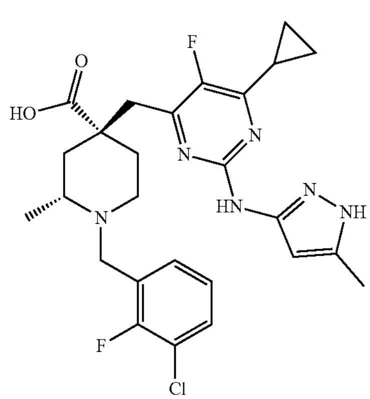 | (2R,4R)-1-(3-chloro-2-fluorobenzyl)-4-((6-cyclopropyl-5-fluoro-2-((5-methyl-1H-pyrazol-3-yl)amino)pyrimidin-4-yl)methyl)-2-methylpiperidine-4-carboxylic acid | 531 |

-continued

| Example No. | Structure | Chemical Name | MS: (M + H)⁺ |
|---|---|---|---|
| 273. | 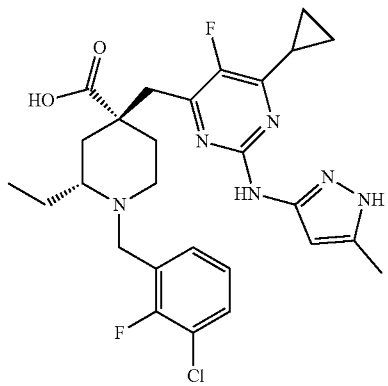 [SMILES: CC[C@@H]1C[C@](Cc2nc(Nc3cc(C)[nH]n3)nc(C3CC3)c2F)(C(=O)O)CCN1Cc1cccc(Cl)c1F] | (2R,4R)-1-(3-chloro-2-fluorobenzyl)-4-((6-cyclopropyl-5-fluoro-2-((5-methyl-1H-pyrazol-3-yl)amino)pyrimidin-4-yl)methyl)-2-ethylpiperidine-4-carboxylic acid | 545 |
| 274. | 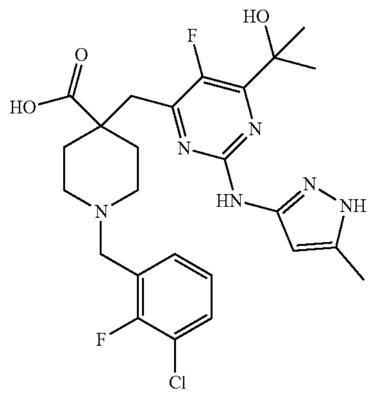 [SMILES: Cc1cc(Nc2nc(CC3(C(=O)O)CCN(Cc4cccc(Cl)c4F)CC3)c(F)c(C(C)(C)O)n2)n[nH]1] | 1-(3-chloro-2-fluorobenzyl)-4-((5-fluoro-6-(2-hydroxypropan-2-yl)-2-((5-methyl-1H-pyrazol-3-yl)amino)pyrimidin-4-yl)methyl)-piperidine-4-carboxylic acid | 535 |
| 275. | 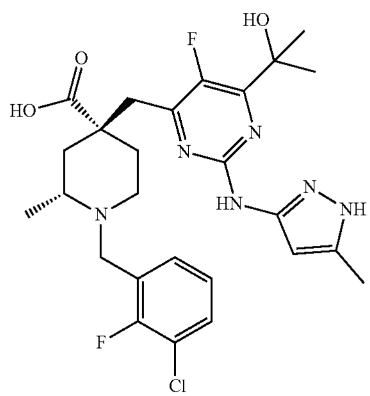 | (2R,4R)-1-(3-chloro-2-fluorobenzyl)-4-((5-fluoro-6-(2-hydroxypropan-2-yl)-2-((5-methyl-1H-pyrazol-3-yl)amino)pyrimidin-4-yl)methyl)-2-methylpiperidine-4-carboxylic acid | 549 |
| 276. | 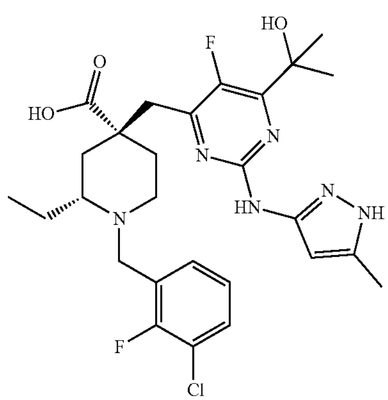 [SMILES: CC[C@@H]1C[C@](Cc2nc(Nc3cc(C)[nH]n3)nc(C(C)(C)O)c2F)(C(=O)O)CCN1Cc1cccc(Cl)c1F] | (2R,4R)-1-(3-chloro-2-fluorobenzyl)-2-ethyl-4-((5-fluoro-6-(2-hydroxypropan-2-yl)-2-((5-methyl-1H-pyrazol-3-yl)amino)pyrimidin-4-yl)methyl)piperidine-4-carboxylic acid | 563 |

| Example No. | Structure | Chemical Name | MS: (M + H)+ |
|---|---|---|---|
| 277. | 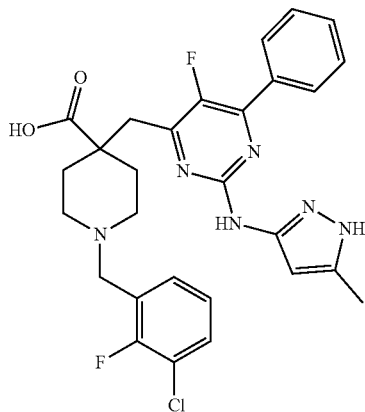 [SMILES: Cc1cc(Nc2nc(CC3(C(=O)O)CCN(Cc4cccc(Cl)c4F)CC3)c(F)c(-c3ccccc3)n2)n[nH]1] | 1-(3-chloro-2-fluorobenzyl)-4-((5-fluoro-2-((5-methyl-1H-pyrazol-3-yl)amino)-6-phenylpyrimidin-4-yl)methyl)piperidine-4-carboxylic acid | 553 |
| 278. | 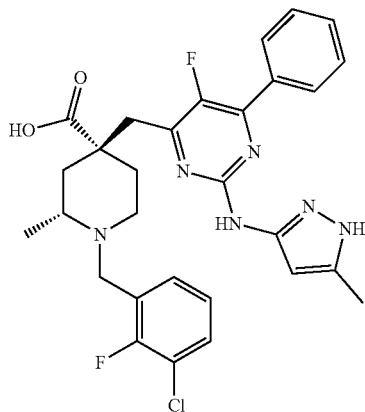 | (2R,4R)-1-(3-chloro-2-fluorobenzyl)-4-((5-fluoro-2-((5-methyl-1H-pyrazol-3-yl)amino)-6-phenylpyrimidin-4-yl)methyl)-2-methyl-piperidine-4-carboxylic acid | 567 |
| 279. | 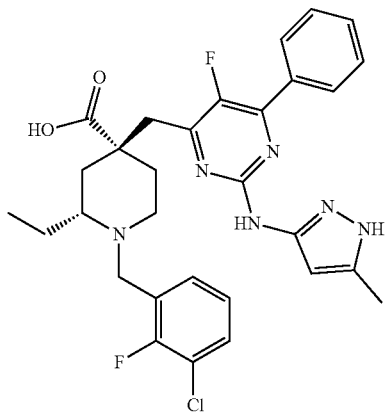 [SMILES: CC[C@@H]1C[C@](Cc2nc(Nc3cc(C)[nH]n3)nc(-c3ccccc3)c2F)(C(=O)O)CCN1Cc1cccc(Cl)c1F] | (2R,4R)-1-(3-chloro-2-fluorobenzyl)-2-ethyl-4-((5-fluoro-2-((5-methyl-1H-pyrazol-3-yl)amino)-6-phenylpyrimidin-4-yl)methyl)-piperidine-4-carboxylic acid | 581 |

-continued

| Example No. | Structure | Chemical Name | MS: (M + H)+ |
|---|---|---|---|
| 280. | 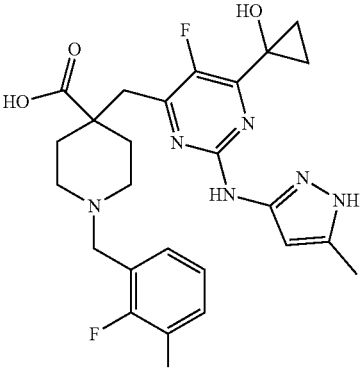 | 1-(3-chloro-2-fluorobenzyl)-4-((5-fluoro-6-(1-hydroxycyclopropyl)-2-((5-methyl-1H-pyrazol-3-yl)amino)pyrimidin-4-yl)methyl)-piperidine-4-carboxylic acid | 533 |
| 281. | 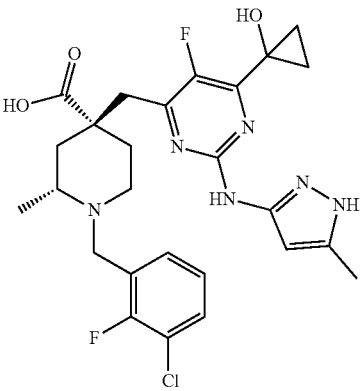 | (2R,4R)-1-(3-chloro-2-fluorobenzyl)-4-((5-fluoro-6-(1-hydroxycyclopropyl)-2-((5-methyl-1H-pyrazol-3-yl)amino)pyrimidin-4-yl)methyl)-2-methylpiperidine-4)-carboxylic acid | 547 |
| 282. | 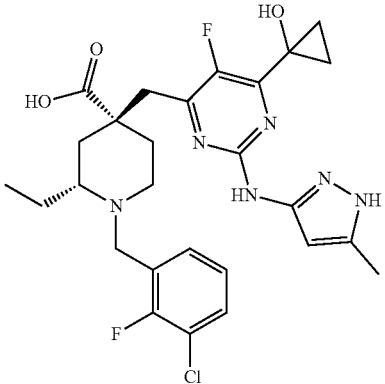 [SMILES: CC[C@@H]1C[C@](Cc2nc(Nc3cc(C)[nH]n3)nc(C3(O)CC3)c2F)(C(=O)O)CCN1Cc1cccc(Cl)c1F] | (2R,4R)-1-(3-chloro-2-fluorobenzyl)-2-ethyl-4-((5-fluoro-6-(1-hydroxycyclopropyl)-2-((5-methyl-1H-pyrazol-3-yl)amino)pyrimidin-4-yl)methyl)piperidine-4-carboxylic acid | 561 |
| 283. | 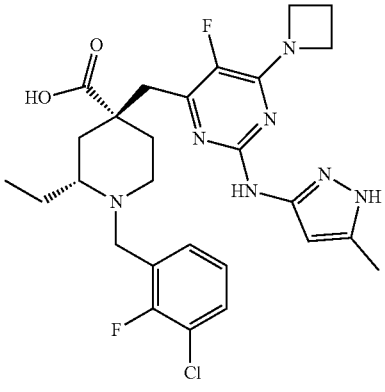 [SMILES: CC[C@@H]1C[C@](Cc2nc(Nc3cc(C)[nH]n3)nc(N3CCC3)c2F)(C(=O)O)CCN1Cc1cccc(Cl)c1F] | (2R,4R)-4-((6-(azetidin-1-yl)-5-fluoro-2-((5-methyl-1H-pyrazol-3-yl)amino)pyrimidin-4-yl)methyl)-1-(3-chloro-2-fluorobenzyl)-2-ethylpiperidine-4-carboxylic acid | 560 |

| Example No. | Structure | Chemical Name | MS: (M + H)⁺ |
|---|---|---|---|
| 284. | 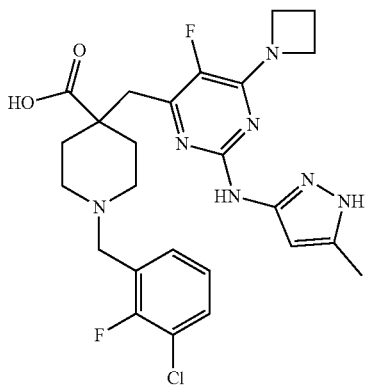 [SMILES: Cc1cc(Nc2nc(CC3(C(=O)O)CCN(Cc4cccc(Cl)c4F)CC3)c(F)c(N3CCC3)n2)n[nH]1] | 4-((6-(azetidin-1-yl)-5-fluoro-2-((5-methyl-1H-pyrazol-3-yl)amino)pyrimidin-4-yl)methyl)-1-(3-chloro-2-fluorobenzyl)piperidine-4-carboxylic acid | 532 |
| 285. | 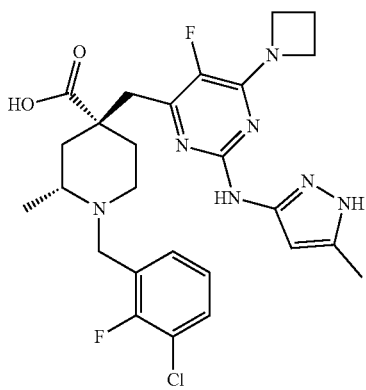 | (2R,4R)-4-((6-(azetidin-1-yl)-5-fluoro-2-((5-methyl-1H-pyrazol-3-yl)amino)pyrimidin-4-yl)methyl)-1-(3-chloro-2-fluorobenzyl)-2-methylpiperidine-4-carboxylic acid | 546 |
| 286. | 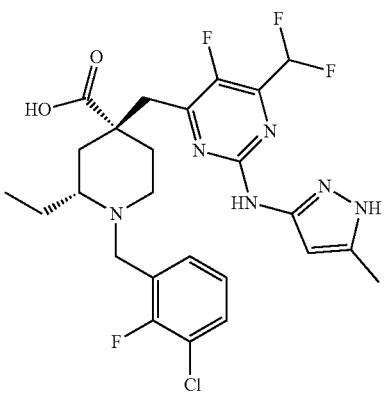 [SMILES: CC[C@@H]1C[C@](Cc2nc(Nc3cc(C)[nH]n3)nc(C(F)F)c2F)(C(=O)O)CCN1Cc1cccc(Cl)c1F] | (2R,4R)-1-(3-chloro-2-fluorobenzyl)-4-((6-(difluoromethyl)-5-fluoro-2-((5-methyl-1H-pyrazol-3-yl)amino)pyrimidin-4-yl)methyl)-2-ethylpiperidine-4-carboxylic acid | 555 |
| 287. | 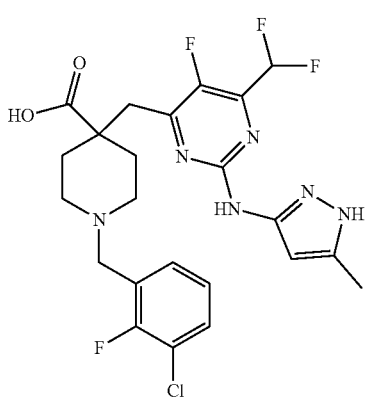 [SMILES: Cc1cc(Nc2nc(CC3(C(=O)O)CCN(Cc4cccc(Cl)c4F)CC3)c(F)c(C(F)F)n2)n[nH]1] | 1-(3-chloro-2-fluorobenzyl)-4-((6-(difluoromethyl)-5-fluoro-2-((5-methyl-1H-pyrazol-3-yl)amino)pyrimidin-4-yl)methyl)piperidine-4-carboxylic acid | 527 |

| Example No. | Structure | Chemical Name | MS: (M + H)+ |
|---|---|---|---|
| 288. | 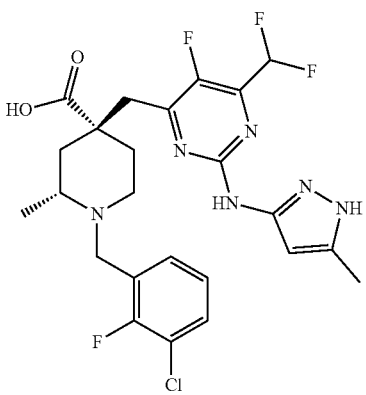 | (2R,4R)-1-(3-chloro-2-fluorobenzyl)-4-((6-(difluoromethyl)-5-fluoro-2-((5-methyl-1H-pyrazol-3-yl)amino)pyrimidin-4-yl)methyl)-2-methylpiperidine-4-carboxylic acid | 541 |
| 289. | 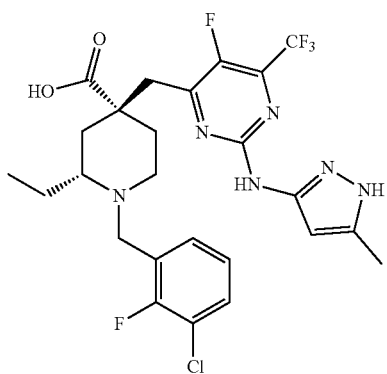 [SMILES: CC[C@@H]1C[C@](Cc2nc(Nc3cc(C)[nH]n3)nc(C(F)(F)F)c2F)(C(=O)O)CCN1Cc1cccc(Cl)c1F] | (2R,4R)-1-(3-chloro-2-fluorobenzyl)-2-ethyl-4-((5-fluoro-2-((5-methyl-1H-pyrazol-3-yl)amino)-6-(trifluoromethyl)pyrimidin-4-yl)methyl)piperidine-4-carboxylic acid | 573 |
| 291. | 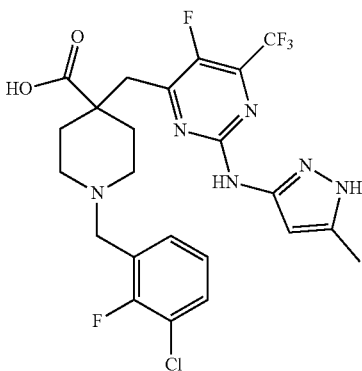 | 1-(3-chloro-2-fluorobenzyl)-4-((5-fluoro-2-((5-methyl-1H-pyrazol-3-yl)amino)-6-(trifluoromethyl)pyrimidin-4-yl)methyl)piperidine-4-carboxylic acid | 545 |
| 292. | 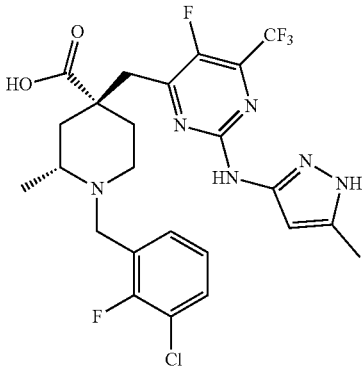 | (2R,4R)-1-(3-chloro-2-fluorobenzyl)-4-((5-fluoro-2-((5-methyl-1H-pyrazol-3-yl)amino)-6-(trifluoromethyl)pyrimidin-4-yl)methyl)-2-methylpiperidine-4-carboxylic acid | 559 |

-continued

| Example No. | Structure | Chemical Name | MS: (M + H)+ |
|---|---|---|---|
| 292. | 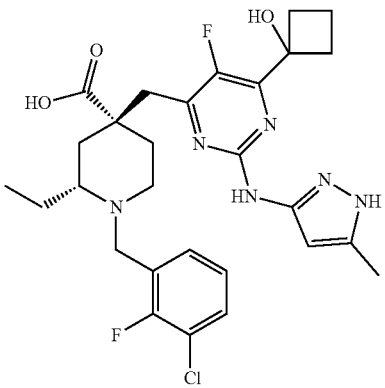 [SMILES: CC[C@@H]1C[C@](Cc2nc(Nc3cc(C)[nH]n3)nc(C3(O)CCC3)c2F)(C(=O)O)CCN1Cc1cccc(Cl)c1F] | (2R,4R)-1-(3-chloro-2-fluorobenzyl)-2-ethyl-4-((5-fluoro-6-(1-hydroxycyclobutyl)-2-((5-methyl-1H-pyrazol-3-yl)amino)pyrimidin-4-yl)methyl)piperidine-4-carboxylic acid | 575 |
| 293. | 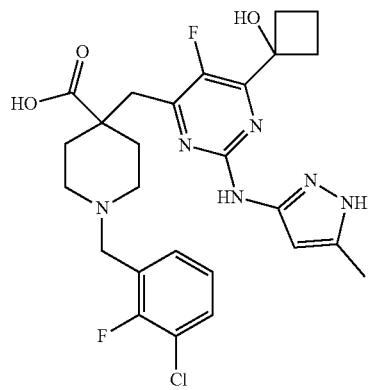 [SMILES: Cc1cc(Nc2nc(CC3(C(=O)O)CCN(Cc4cccc(Cl)c4F)CC3)c(F)c(C3(O)CCC3)n2)n[nH]1] | 1-(3-chloro-2-fluorobenzyl)-4-((5-fluoro-6-(1-hydroxycyclobutyl)-2-((5-methyl-1H-pyrazol-3-yl)amino)pyrimidin-4-yl)methyl)-piperidine-4-carboxylic acid | 547 |
| 294. | 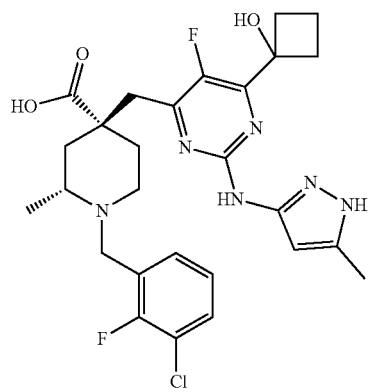 | (2R,4R)-1-(3-chloro-2-fluorobenzyl)-4-((5-fluoro-6-(1-hydroxycyclobutyl)-2-((5-methyl-1H-pyrazol-3-yl)amino)pyrimidin-4-yl)methyl)-2-methylpiperidine-4-carboxylic acid | 561 |
| 295. | 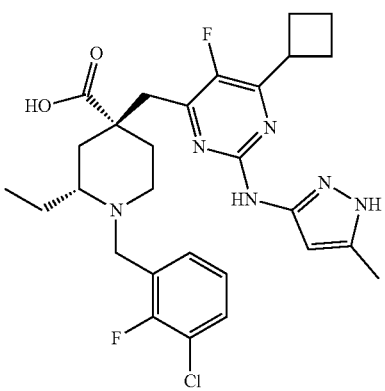 [SMILES: CC[C@@H]1C[C@](Cc2nc(Nc3cc(C)[nH]n3)nc(C3CCC3)c2F)(C(=O)O)CCN1Cc1cccc(Cl)c1F] | (2R,4R)-1-(3-chloro-2-fluorobenzyl)-4-((6-cyclobutyl-5-fluoro-2-((5-methyl-1H-pyrazol-3-yl)amino)pyrimidin-4-yl)methyl)-2-ethylpiperidine-4-carboxylic acid | 559 |

| Example No. | Structure | Chemical Name | MS: (M + H)⁺ |
|---|---|---|---|
| 296. | 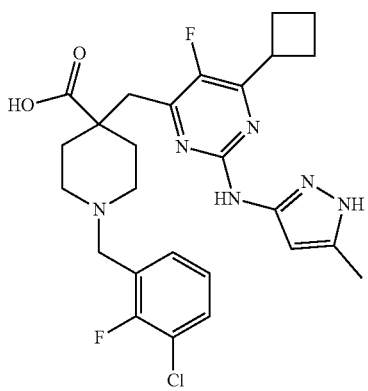 | 1-(3-chloro-2-fluorobenzyl)-4-((6-cyclobutyl-5-fluoro-2-((5-methyl-1H-pyrazol-3-yl)amino)pyrimidin-4-yl)methyl)piperidine-4-carboxylic acid | 531 |
| 297. | 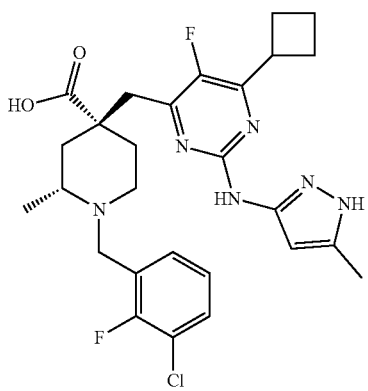 | (2R,4R)-1-(3-chloro-2-fluorobenzyl)-4-((6-cyclobutyl-5-fluoro-2-((5-methyl-1H-pyrazol-3-yl)amino)pyrimidin-4-yl)methyl)-2-methylpiperidine-4-carboxylic acid | 545 |
| 298. | 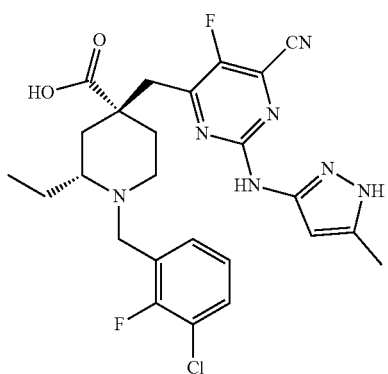 | (2R,4R)-1-(3-chloro-2-fluorobenzyl)-4-((6-cyano-5-fluoro-2-((5-methyl-1H-pyrazol-3-yl)amino)pyrimidin-4-yl)methyl)-2-ethylpiperidine-4-carboxylic acid | 530 |
| 299. | 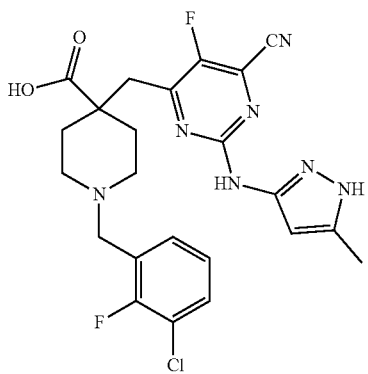 [SMILES: Cc1cc(Nc2nc(C#N)c(F)c(CC3(C(=O)O)CCN(Cc4cccc(Cl)c4F)CC3)n2)n[nH]1] | 1-(3-chloro-2-fluorobenzyl)-4-((6-cyano-5-fluoro-2-((5-methyl-1H-pyrazol-3-yl)amino)pyrimidin-4-yl)methyl)piperidine-4-carboxylic acid | 502 |

-continued

| Example No. | Structure | Chemical Name | MS: (M + H)+ |
|---|---|---|---|
| 300. | 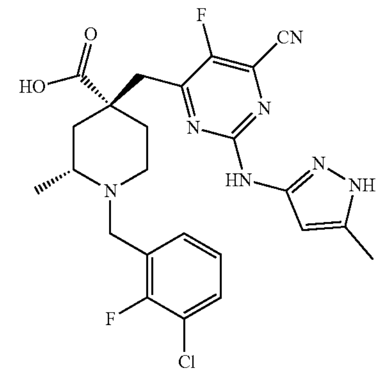 | (2R,4R)-1-(3-chloro-2-fluorobenzyl)-4-((6-cyano-5-fluoro-2-((5-methyl-1H-pyrazol-3-yl)amino)-pyrimidin-4-yl)methyl)-2-methyl piperidine-4-carboxylic acid | 516 |
| 301. | 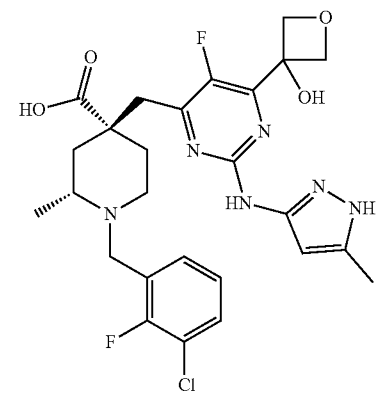 | (2R,4R)-1-(3-chloro-2-fluorobenzyl)-4-((5-fluoro-6-(3-hydroxy-oxetan-3-yl)-2-((5-methyl-1H-pyrazol-3-yl)amino)pyrimidin-4-yl)-methyl)-2-methylpiperidine-4)-carboxylic acid | 563 |
| 302. | 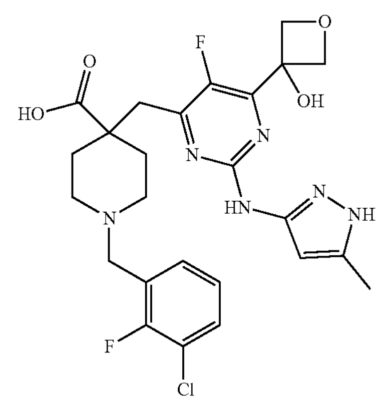 [SMILES: Cc1cc(Nc2nc(CC3(C(=O)O)CCN(Cc4cccc(Cl)c4F)CC3)c(F)c(C3(O)COC3)n2)n[nH]1] | 1-(3-chloro-2-fluorobenzyl)-4-((5-fluoro-6-(3-hydroxyoxetan-3-yl)-2-((5-methyl-1H-pyrazol-3-yl)-arnino)pyrimidin-4-yl)methyl)-piperidine-4-carboxylic acid | 549 |
| 303. | 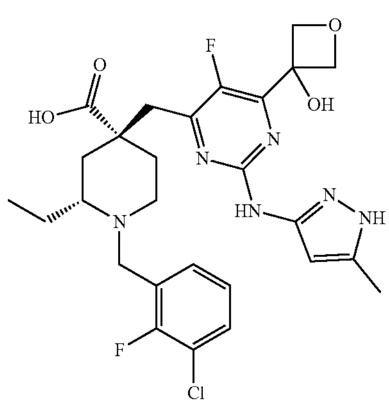 [SMILES: CC[C@@H]1C[C@](Cc2nc(Nc3cc(C)[nH]n3)nc(C3(O)COC3)c2F)(C(=O)O)CCN1Cc1cccc(Cl)c1F] | (2R,4R)-1-(3-chloro-2-fluorobenzyl)-2-ethyl-4-((5-fluoro-6-(3-hydroxyoxetan-3-yl)-2-((5-methyl-1H-pyrazol-3-yl)amino)pyrimidin-4-yl)methyl)piperidine-4-carboxylic acid | 577 |

-continued

| Example No. | Structure | Chemical Name | MS: (M + H)⁺ |
|---|---|---|---|
| 304. | 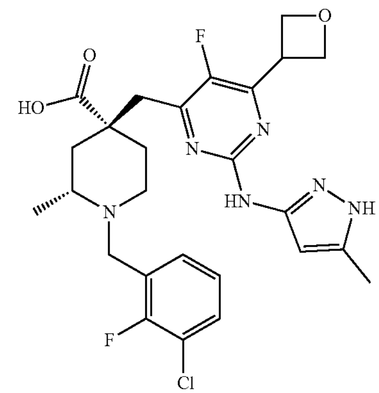 | (2R,4R)-1-(3-chloro-2-fluorobenzyl)-4-((5-fluoro-2-((5-methyl-1H-pyrazol-3-yl)amino)-6-(oxetan-3-yl)pyrimidin-4-yl)methyl)-2-methylpiperidine-4-carboxylic acid | 547 |
| 305. | 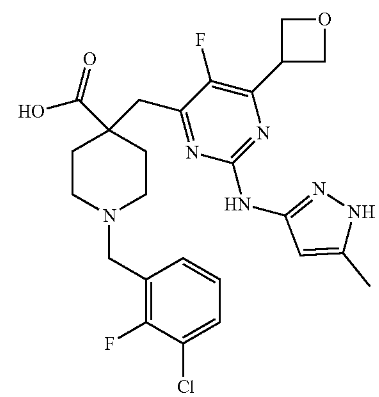 [SMILES: Cc1cc(Nc2nc(CC3(C(=O)O)CCN(Cc4cccc(Cl)c4F)CC3)c(F)c(C3COC3)n2)n[nH]1] | 1-(3-chloro-2-fluorobenzyl)-4-((5-fluoro-2-((5-methyl-1H-pyrazol-3-yl)amino)-6-(oxetan-3-yl)pyrimidin-4-yl)methyl)piperidine-4-carboxylic acid | 533 |
| 306. | 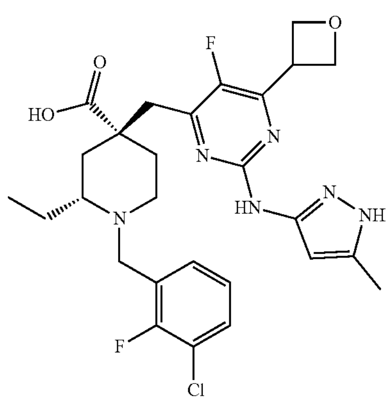 [SMILES: CC[C@@H]1C[C@](Cc2nc(Nc3cc(C)[nH]n3)nc(C3COC3)c2F)(C(=O)O)CCN1Cc1cccc(Cl)c1F] | (2R,4R)-1-(3-chloro-2-fluorobenzyl)-2-ethyl-4-((5-fluoro-2-((5-methyl-1H-pyrazol-3-yl)amino)-6-(oxetan-3-yl)pyrimidin-4-yl)methyl)piperidine-4-carboxylic acid | 561 |
| 307. | 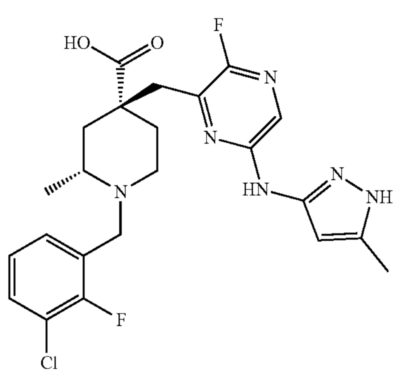 [SMILES: Cc1cc(Nc2cnc(F)c(C[C@@]3(C(=O)O)CCN(Cc4cccc(Cl)c4F)[C@H](C)C3)n2)n[nH]1] | (2R,4R)-1-(3-chloro-2-fluorobenzyl)-4-((3-fluoro-6-((5-methyl-1H-pyrazol-3-yl)amino)pyrazin-2-yl)methyl)-2-methylpiperidine-4-carboxylic acid | 491 |

-continued

| Example No. | Structure | Chemical Name | MS: (M + H)+ |
|---|---|---|---|
| 308. | 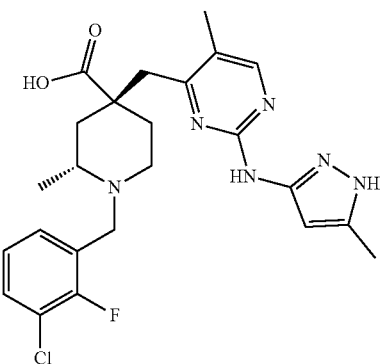 [SMILES: Cc1cc(Nc2ncc(C)c(C[C@@]3(C(=O)O)CCN(Cc4cccc(Cl)c4F)[C@H](C)C3)n2)n[nH]1] | (2R,4R)-1-(3-chloro-2-fluorobenzyl)-2-methyl-4-((5-methyl-2-((5-methyl-1H-pyrazol-3-yl)amino)pyrimidin-4-yl)methyl)piperidine-4-carboxylic acid | 487 |
| 309. | 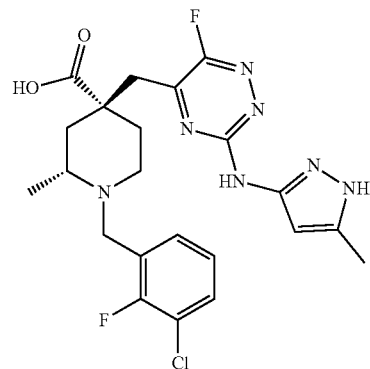 | (2R,4R)-1-(3-chloro-2-fluorobenzyl)-4-((6-fluoro-3-((5-methyl-1H-pyrazol-3-yl)amino)-1,2,4-triazin-5-yl)methyl)-2-methylpiperidine-4-carboxylic acid | 492 |
| 310. | 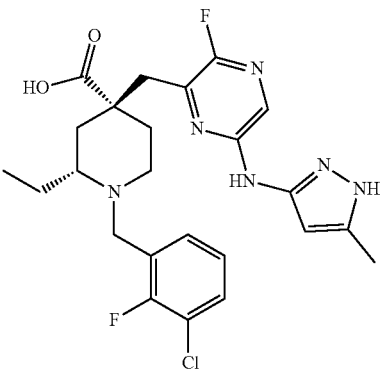 [SMILES: CC[C@@H]1C[C@](Cc2nc(Nc3cc(C)[nH]n3)cnc2F)(C(=O)O)CCN1Cc1cccc(Cl)c1F] | (2R,4R)-1-(3-chloro-2-fluorobenzyl)-2-ethyl-4-((3-fluoro-6-((5-methyl-1H-pyrazol-3-yl)amino)pyrazin-2-yl)methyl)piperidine-4-carboxylic acid | 505 |
| 311. | 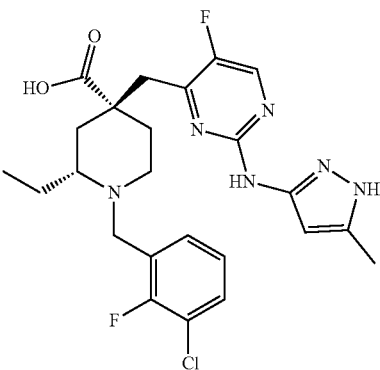 [SMILES: CC[C@@H]1C[C@](Cc2nc(Nc3cc(C)[nH]n3)ncc2F)(C(=O)O)CCN1Cc1cccc(Cl)c1F] | (2R,4R)-1-(3-chloro-2-fluorobenzyl)-2-ethyl-4-((5-fluoro-2-((5-methy1-1H-pyrazol-3-yl)amino)pyrimidin-4-yl)methyl)piperidine-4-carboxylic acid | 505 |

| Example No. | Structure | Chemical Name | MS: (M + H)+ |
|---|---|---|---|
| 312. | 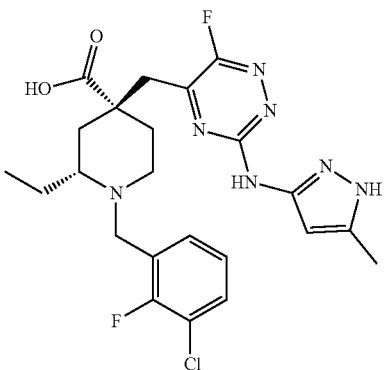 [SMILES: CC[C@@H]1C[C@](Cc2nc(Nc3cc(C)[nH]n3)nnc2F)(C(=O)O)CCN1Cc1cccc(Cl)c1F] | (2R,4R)-1-(3-chloro-2-fluorobenzyl)-2-ethyl-4-((6-fluoro-3-((5-methyl-1H-pyrazol-3-yl)amino)-1,2,4-triazin-5-yl)methyl)piperidine-4-carboxylic acid | 506 |
| 313. | 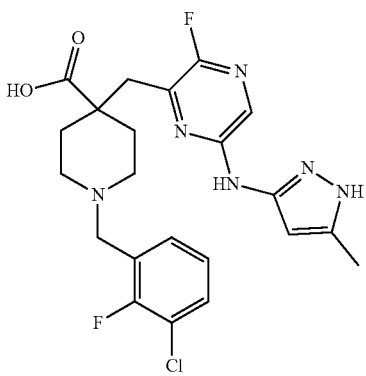 | 1-(3-chloro-2-fluorobenzyl)-4-((3-fluoro-6-((5-methyl-1H-pyrazol-3-yl)amino)pyrazin-2-yl)methyl)-piperidine-4-carboxylic acid | 477 |
| 314. | 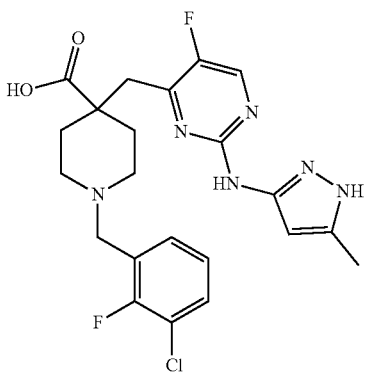 [SMILES: Cc1cc(Nc2ncc(F)c(CC3(C(=O)O)CCN(Cc4cccc(Cl)c4F)CC3)n2)n[nH]1] | 1-(3-chloro-2-fluorobenzyl)-4-((5-fluoro-2-((5-methyl-1H-pyrazol-3-yl)amino)pyrimidin-4-yl)-methyl)piperidine-4-carboxylic acid | 477 |
| 315. | 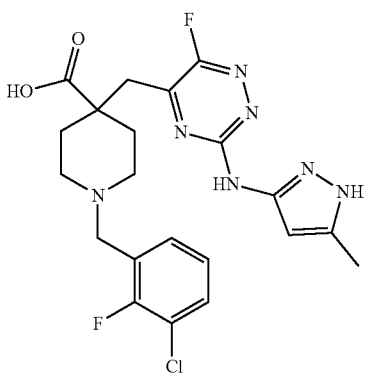 | 1-(3-chloro-2-fluorobenzyl)-4-((6-fluoro-3-((5-methyl-1H-pyrazol-3-yl)amino)-1,2,4-triazin-5-yl)methyl)piperidine-4-carboxylic acid | 478 |

-continued

| Example No. | Structure | Chemical Name | MS: (M + H)+ |
|---|---|---|---|
| 316. | 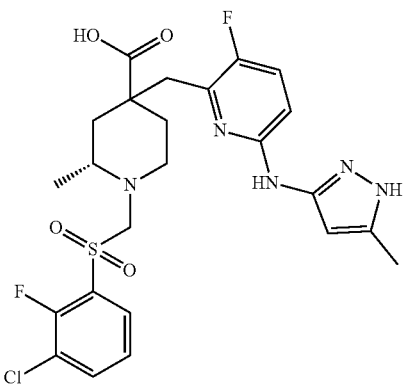 [SMILES: Cc1cc(Nc2ccc(F)c(CC3(C(=O)O)CCN(CS(=O)(=O)c4cccc(Cl)c4F)[C@H](C)C3)n2)n[nH]1] | (2R)-1-(((3-chloro-2-fluorophenyl)-sulfonyl)methyl)-4-((3-fluoro-6-((5-methyl-1H-pyrazol-3-yl)-amino)pyridin-2-yl)methyl)-2-methylpiperidine-4-carboxylic acid | 554 |
| 317. | 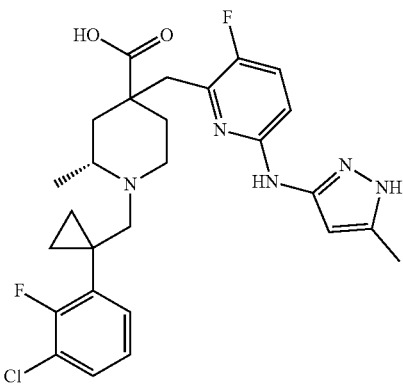 [SMILES: Cc1cc(Nc2ccc(F)c(CC3(C(=O)O)CCN(CC4(c5cccc(Cl)c5F)CC4)[C@H](C)C3)n2)n[nH]1] | (2R)-1-((1-(3-chloro-2-fluoro-phenyl)cyclopropyl)methyl)-4-((3-fluoro-6-((5-methyl-1H-pyrazol-3-yl)amino)pyridin-2-yl)methyl)-2-methylpiperidine-4-carboxylic acid | 530 |
| 318. | 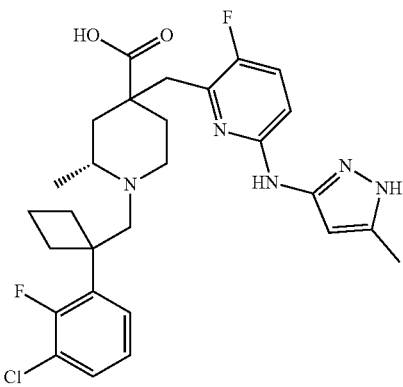 [SMILES: Cc1cc(Nc2ccc(F)c(CC3(C(=O)O)CCN(CC4(c5cccc(Cl)c5F)CCC4)[C@H](C)C3)n2)n[nH]1] | (2R)-1-((1-(3-chloro-2-fluoro-phenyl)cyclobutyl)methyl)-4-((3-fluoro-6-((5-methyl-1H-pyrazol-3-yl)amino)pyridin-2-yl)methyl)-2-methylpiper-idine-4-carboxylic acid | 544 |
| 319. | 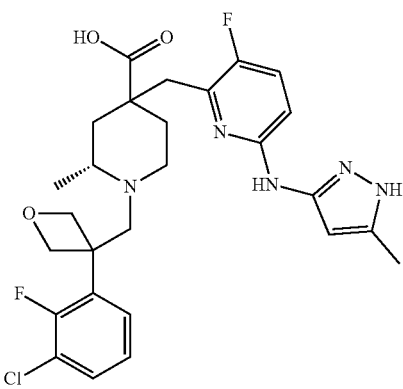 [SMILES: Cc1cc(Nc2ccc(F)c(CC3(C(=O)O)CCN(CC4(c5cccc(Cl)c5F)COC4)[C@H](C)C3)n2)n[nH]1] | (2R)-1-((3-(3-chloro-2-fluoro-phenyl)oxetan-3-yl)methyl)-4-((3-fluoro-6-((5-methyl-1H-pyrazol-3-yl)amino)pyridin-2-yl)methyl)-2-methylpiperidine-4-carboxylic acid | 546 |

-continued

| Example No. | Structure | Chemical Name | MS: (M + H)⁺ |
|---|---|---|---|
| 320. | 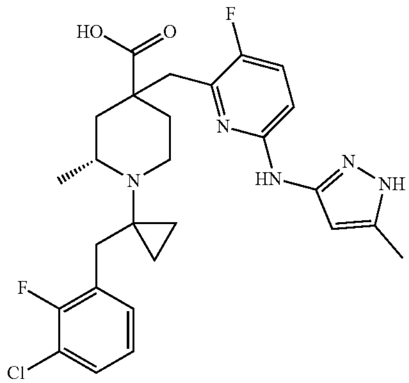 [SMILES: Cc1cc(Nc2ccc(F)c(CC3(C(=O)O)CCN(C4(Cc5cccc(Cl)c5F)CC4)[C@H](C)C3)n2)n[nH]1] | (2R)-1-(1-(3-chloro-2-fluorobenzyl)cyclopropyl)-4-((3-fluoro-6-((5-methyl-1H-pyrazol-3-yl)amino)-pyridin-2-yl)methyl)-2-methyl-piperidine-4-carboxylic acid | 530 |
| 321. | 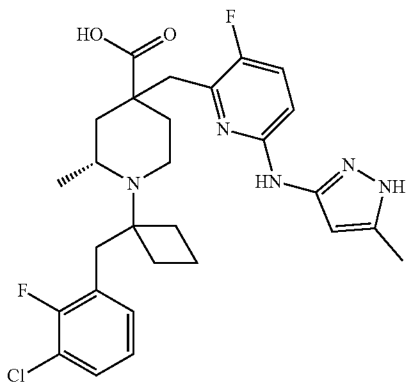 [SMILES: Cc1cc(Nc2ccc(F)c(CC3(C(=O)O)CCN(C4(Cc5cccc(Cl)c5F)CCC4)[C@H](C)C3)n2)n[nH]1] | (2R)-1-(1-(3-chloro-2-fluorobenzyl)cyclobutyl)-4-((3-fluoro-6-((5-methyl-1H-pyrazol-3-yl)amino)pyridin-2-yl)methyl)-2-methyl piperidine-4-carboxylic acid | 544 |
| 322. | 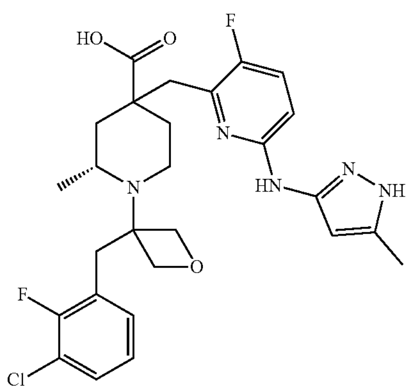 [SMILES: Cc1cc(Nc2ccc(F)c(CC3(C(=O)O)CCN(C4(Cc5cccc(Cl)c5F)COC4)[C@H](C)C3)n2)n[nH]1] | (2R)-1-(3-(3-chloro-2-fluorobenzyl)oxetan-3-yl)-4-((3-fluoro-6-((5-methyl-1H-pyrazol-3-yl)amino)pyridin-2-yl)methyl)-2-methyl piperidine-4-carboxylic acid | 546 |
| 323. | 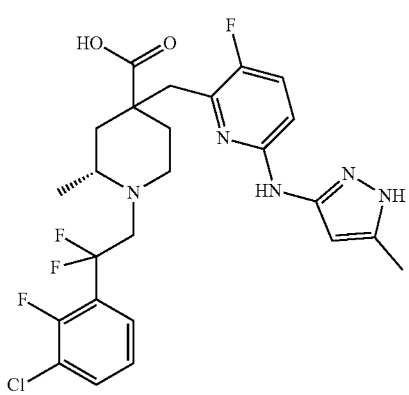 [SMILES: Cc1cc(Nc2ccc(F)c(CC3(C(=O)O)CCN(CC(F)(F)c4cccc(Cl)c4F)[C@H](C)C3)n2)n[nH]1] | (2R)-1-(2-(3-chloro-2-fluorophenyl)-2,2-difluoroethyl)-4-((3-fluoro-6-((5-methyl-1H-pyrazol-3-yl)amino)pyridin-2-yl)methyl)-2-methylpiperidine-4-carboxylic acid | 540 |

| Example No. | Structure | Chemical Name | MS: (M + H)+ |
|---|---|---|---|
| 324. | 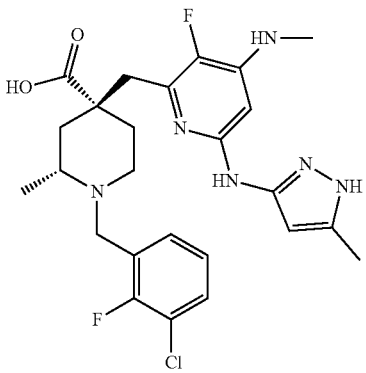 | (2R,4R)-1-(3-chloro-2-fluorobenzyl)-4-((3-fluoro-6-((5-methyl-1H-pyrazol-3-yl)amino)-4-(methylamino)pyridin-2-yl)methyl)-2-methylpiperidine-4-carboxylic acid | 519 |
| 325. | 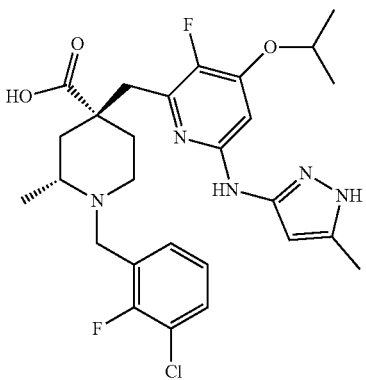 | (2R,4R)-1-(3-chloro-2-fluorobenzyl)-4-((3-fluoro-4-isopropoxy-6-((5-methyl-1H-pyrazol-3-yl)amino)pyridin-2-yl)methyl)-2-methyl-piperidine-4-carboxylic acid | 548 |
| 326. | 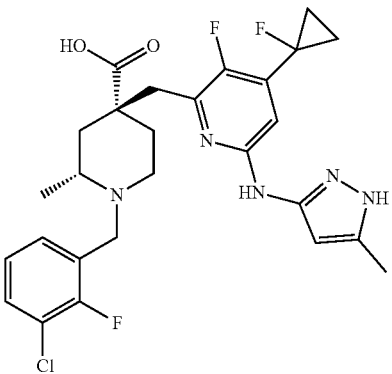 [SMILES: Cc1cc(Nc2cc(C3(F)CC3)c(F)c(C[C@@]3(C(=O)O)CCN(Cc4cccc(Cl)c4F)[C@H](C)C3)n2)n[nH]1] | (2R,4R)-1-(3-chloro-2-fluorobenzyl)-4-((3-fluoro-4-(1-fluorocyclopropyl)-6-((5-methyl-1H-pyrazol-3-yl)amino)pyridin-2-yl)methyl)-2-methylpiperidine-4-carboxylic acid | 548 |
| 327. | 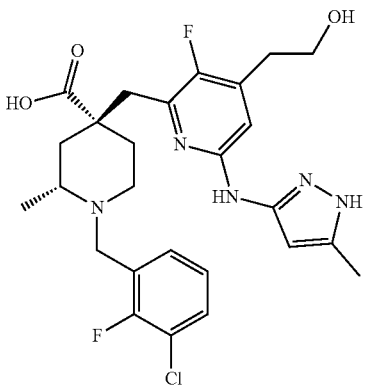 | (2R,4R)-1-(3-chloro-2-fluorobenzyl)-4-((3-fluoro-4-(2-hydroxyethyl)-6-((5-methyl-1H-pyrazol-3-yl)amino)pyridin-2-yl)methyl)-2-methylpiperidine-4-carboxylic acid | 534 |

-continued

| Example No. | Structure | Chemical Name | MS: (M + H)+ |
|---|---|---|---|
| 328. | 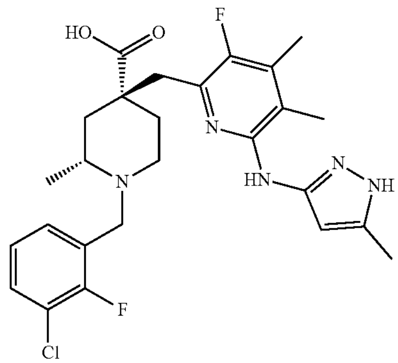 [SMILES: Cc1cc(Nc2nc(C[C@@]3(C(=O)O)CCN(Cc4cccc(Cl)c4F)[C@H](C)C3)c(F)c(C)c2C)n[nH]1] | (2R,4R)-1-(3-chloro-2-fluorobenzyl)-4-((3-fluoro-4,5-dimethyl-6-((5-methyl-1H-pyrazol-3-yl)amino)pyridin-2-yl)methyl)-2-methyl-piperidine-4-carboxylic acid | 518 |
| 329. | 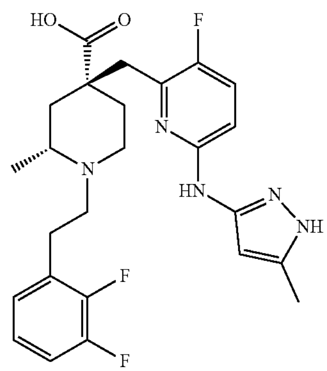 [SMILES: Cc1cc(Nc2ccc(F)c(C[C@@]3(C(=O)O)CCN(CCc4cccc(F)c4F)[C@H](C)C3)n2)n[nH]1] | (2R,4R)-1-(2,3-difluorophenethyl)-4-((3-fluoro-6-((5-methyl-1H-pyrazol-3-yl)amino)pyridin-2-yl)methyl)-2-methylpiperidine-4)-carboxylic acid | 487 |
| 330. | 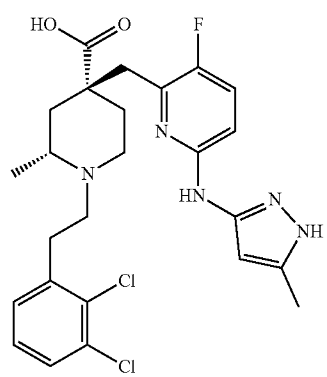 [SMILES: Cc1cc(Nc2ccc(F)c(C[C@@]3(C(=O)O)CCN(CCc4cccc(Cl)c4Cl)[C@H](C)C3)n2)n[nH]1] | (2R,4R)-1-(2,3-dichlorophenethyl)-4-((3-fluoro-6-((5-methyl-1H-pyrazol-3-yl)amino)pyridin-2-yl)-methyl)-2-methylpiperidine-4)-carboxylic acid | 520 |
| 331. | 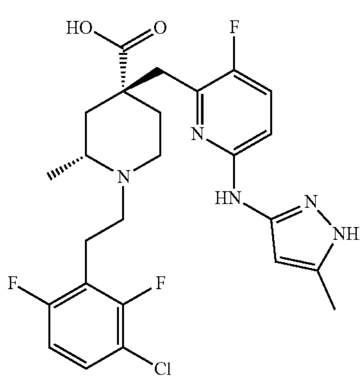 [SMILES: Cc1cc(Nc2ccc(F)c(C[C@@]3(C(=O)O)CCN(CCc4c(F)ccc(Cl)c4F)[C@H](C)C3)n2)n[nH]1] | (2R,4R)-1-(3-chloro-2,6-difluoro-phenethyl)-4-((3-fluoro-6-((5-methyl-1H-pyrazol-3-yl)amino)-pyridin-2-yl)methyl)-2-methyl-piperidine-4-carboxylic acid | 522 |

-continued

| Example No. | Structure | Chemical Name | MS: (M + H)+ |
|---|---|---|---|
| 332. | 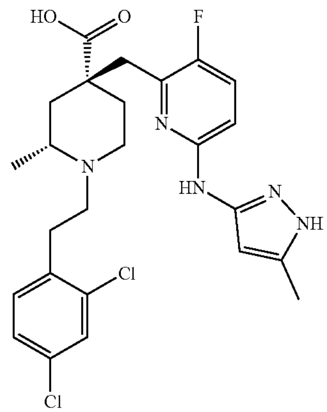 [SMILES: Cc1cc(Nc2ccc(F)c(C[C@@]3(C(=O)O)CCN(CCc4ccc(Cl)cc4Cl)[C@H](C)C3)n2)n[nH]1] | (2R,4R)-1-(2,4-dichlorophenethyl)-4-((3-fluoro-6-((5-methyl-1H-pyrazol-3-yl)amino)pyridin-2-yl)-methyl)-2-methylpiperidine-4)-carboxylic acid | 520 |
| 333. | 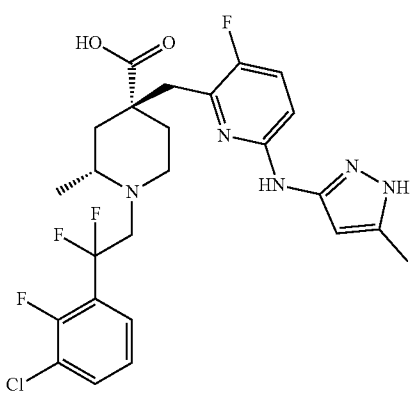 [SMILES: Cc1cc(Nc2ccc(F)c(C[C@@]3(C(=O)O)CCN(CC(F)(F)c4cccc(Cl)c4F)[C@H](C)C3)n2)n[nH]1] | (2R,4R)-1-(2-(3-chloro-2-fluorophenyl)-2,2-difluoroethyl)-4-((3-fluoro-6-((5-methyl-1H-pyrazol-3-yl)amino)pyridin-2-yl)methyl)-2-methylpiperidine-4-carboxylic acid | 540 |
| 334. | 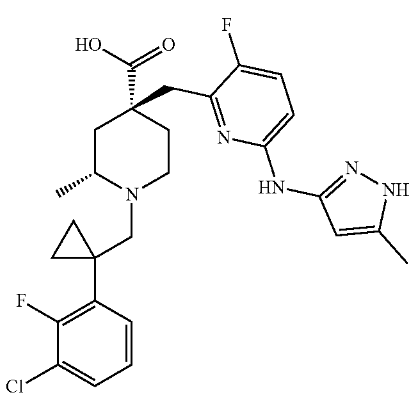 [SMILES: Cc1cc(Nc2ccc(F)c(C[C@@]3(C(=O)O)CCN(CC4(c5cccc(Cl)c5F)CC4)[C@H](C)C3)n2)n[nH]1] | (2R,4R)-1-((1-(3-chloro-2-fluorophenyl)cyclopropyl)methyl)-4-((3-fluoro-6-((5-methyl-1H-pyrazol-3-yl)amino)pyridin-2-yl)methyl)-2-methylpiperidine-4-carboxylic acid | 530 |
| 335. | 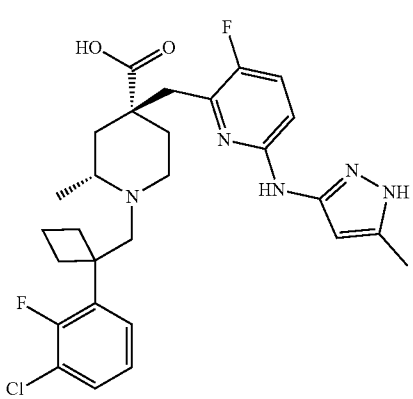 [SMILES: Cc1cc(Nc2ccc(F)c(C[C@@]3(C(=O)O)CCN(CC4(c5cccc(Cl)c5F)CCC4)[C@H](C)C3)n2)n[nH]1] | (2R,4R)-1-((1-(3-chloro-2-fluorophenyl)cyclobutyl)methyl)-4-((3-fluoro-6-((5-methyl-1H-pyrazol-3-yl)amino)pyridin-2-yl)methyl)-2-methylpiperidine-4-carboxylic acid | 544 |

-continued

| Example No. | Structure | Chemical Name | MS: (M + H)+ |
|---|---|---|---|
| 336. | 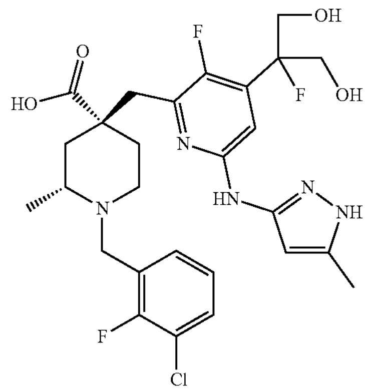 | (2R,4R)-1-(3-chloro-2-fluorobenzyl)-4-((3-fluoro-4-(2-fluoro-1,3-dihydroxypropan-2-yl)-6-((5-methyl-1H-pyrazol-3-yl)amino)pyridin-2-yl)methyl)-2-methylpiperidine-4-carboxylic acid | 582 |
| 337. | 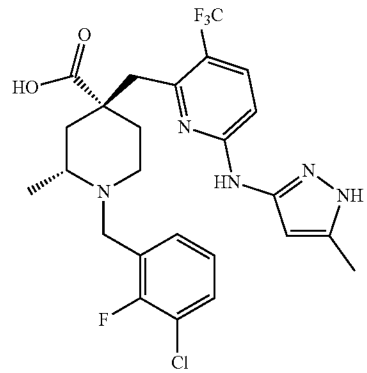 | (2R,4R)-1-(3-chloro-2-fluorobenzyl)-2-methyl-4-((6-((5-methyl-1H-pyrazol-3-yl)amino)-3-(trifluoromethyl)pyridin-2-yl)methyl)piperidine-4-carboxylic acid | 540 |
| 338. | 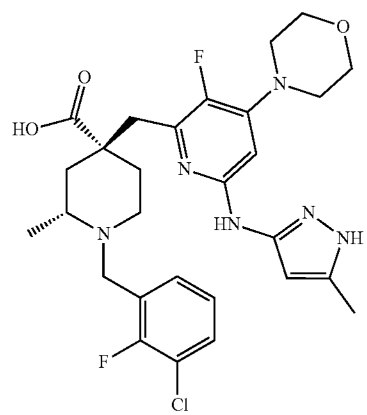 | (2R,4R)-1-(3-chloro-2-fluorobenzyl)-4-((3-fluoro-6-((5-methyl-1H-pyrazol-3-yl)amino)-4-morpholinopyridin-2-yl)methyl)-2-methylpiperidine-4-carboxylic acid | 575 |
| 339. | 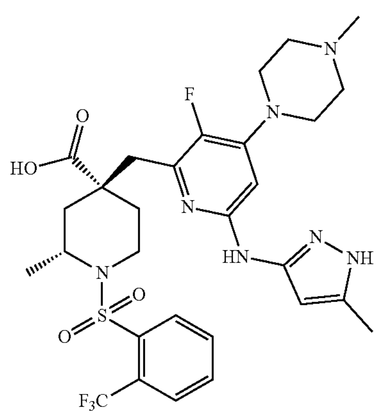 | (2R,4R)-4-((3-fluoro-6-((5-methyl-1H-pyrazol-3-yl)amino)-4-(4-methylpiperazin-1-yl)pyridin-2-yl)methyl)-2-methyl-1-((2-(trifluoromethyl)phenyl)sulfonyl)piperidine-4-carboxylic acid | 654 |

| Example No. | Structure | Chemical Name | MS: (M + H)+ |
|---|---|---|---|
| 340. | 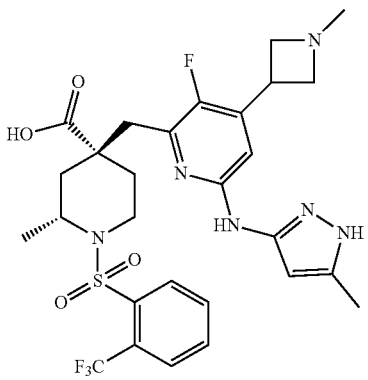 | (2R,4R)-4-((3-fluoro-6-((5-methyl-1H-pyrazol-3-yl)amino)-4-(1-methylazetidin-3-yl)pyridin-2-yl)methyl)-2-methyl-1-((2-(trifluoromethyl)phenyl)sulfonyl)piperidine-4-carboxylic acid | 625 |
| 341. | 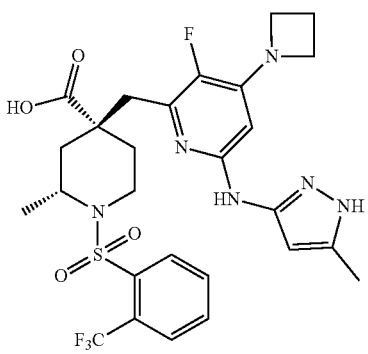 | (2R,4R)-4-((4-(azetidin-1-yl)-3-fluoro-6-((5-methyl-1H-pyrazol-3-yl)amino)pyridin-2-yl)methyl)-2-methyl-1-((2-(trifluoromethyl)phenyl)sulfonyl)piperidine-4-carboxylic acid | 611 |
| 342. | 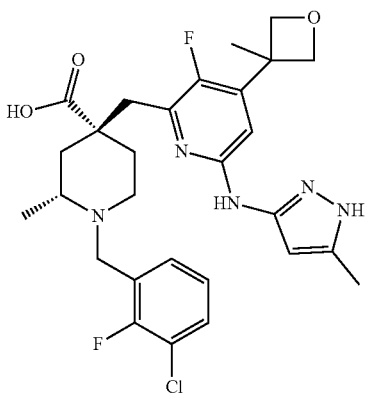 | (2R,4R)-1-(3-chloro-2-fluorobenzyl)-4-((3-fluoro-6-((5-methyl-1H-pyrazol-3-yl)amino)-4-(3-methyloxetan-3-yl)pyridin-2-yl)methyl)-2-methylpiperidine-4-carboxylic acid | 560 |
| 343. | 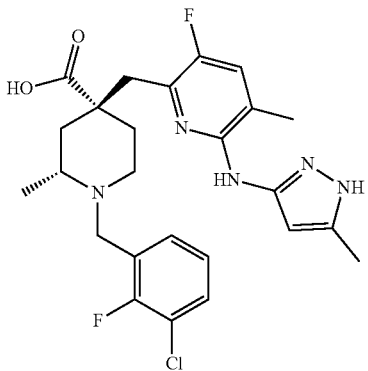 | (2R,4R)-1-(3-chloro-2-fluorobenzyl)-4-((3-fluoro-5-methyl-6-((5-methyl-1H-pyrazol-3-yl)amino)pyridin-2-yl)methyl)-2-methylpiperidine-4-carboxylic acid | 504 |

| Example No. | Structure | Chemical Name | MS: (M + H)+ |
|---|---|---|---|
| 344. | 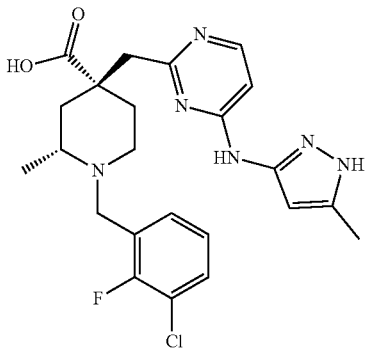 | (2R,4R)-1-(3-chloro-2-fluorobenzyl)-2-methyl-4-((4-((5-methyl-1H-pyrazol-3-yl)amino)pyrimidin-2-yl)methyl)piperidine-4-carboxylic acid | 473 |
| 345. | 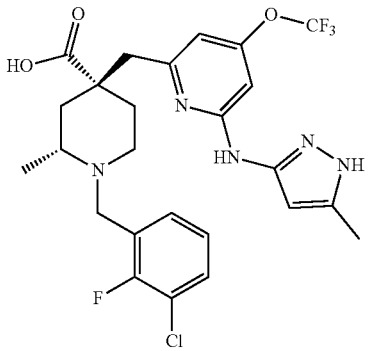 | (2R,4R)-1-(3-chloro-2-fluorobenzyl)-2-methyl-4-((6-((5-methyl-1H-pyrazol-3-yl)amino)-4-(trifluoromethoxy)pyridin-2-yl)methyl)piperidine-4-carboxylic acid | 556 |
| 346. | 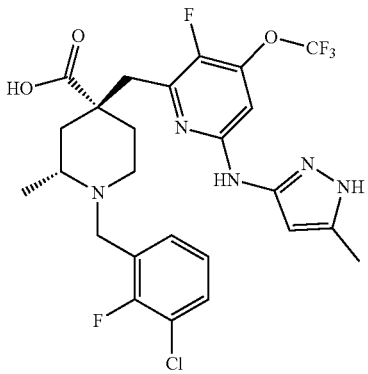 | (2R,4R)-1-(3-chloro-2-fluorobenzyl)-4-((3-fluoro-6-((5-methyl-1H-pyrazol-3-yl)amino)-4-(trifluoromethoxy)pyridin-2-yl)methyl)-2-methylpiperidine-4-carboxylic acid | 574 |
| 347. | 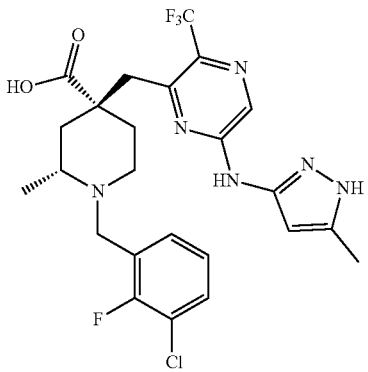 | (2R,4R)-1-(3-chloro-2-fluorobenzyl)-2-methyl-4-((6-((5-methyl-1H-pyrazol-3-yl)amino)-3-(trifluoromethyl)pyrazin-2-yl)methyl)piperidine-4-carboxylic acid | 541 |

-continued

| Example No. | Structure | Chemical Name | MS: (M + H)+ |
|---|---|---|---|
| 348. | 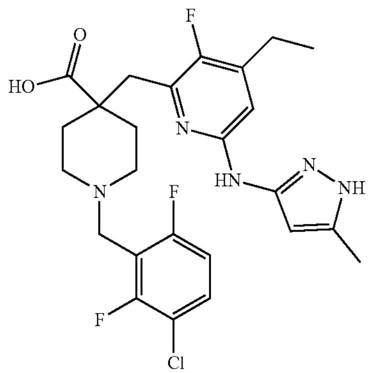 [SMILES: CCc1cc(Nc2cc(C)[nH]n2)nc(CC2(C(=O)O)CCN(Cc3c(F)ccc(Cl)c3F)CC2)c1F] | 1-(3-chloro-2,6-difluorobenzyl)-4-((4-ethyl-3-fluoro-6-((5-methyl-1H-pyrazol-3-yl)amino)pyridin-2-yl)methyl)piperidine-4-carboxylic acid | 522 |
| 349. | 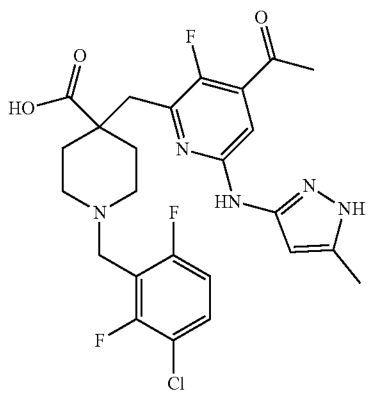 [SMILES: CC(=O)c1cc(Nc2cc(C)[nH]n2)nc(CC2(C(=O)O)CCN(Cc3c(F)ccc(Cl)c3F)CC2)c1F] | 4-((4-acetyl-3-fluoro-6-((5-methyl-1H-pyrazol-3-yl)amino)pyridin-2-yl)methyl)-1-(3-chloro-2,6-difluorobenzyl)piperidine-4-carboxylic acid | 536 |
| 350. | 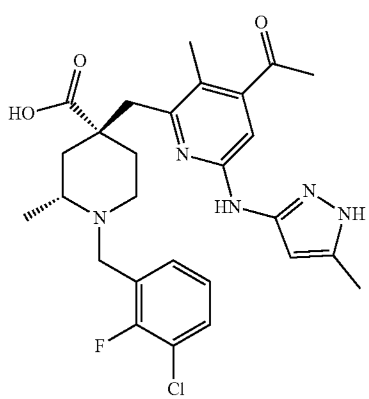 | (2R,4R)-4-((4-acetyl-3-methyl-6-((5-methyl-1H-pyrazol-3-yl)-amino)pyridin-2-yl)methyl)-1-(3-chloro-2-fluorobenzyl)-2-methyl-piperidine-4-carboxylic acid | 528 |
| 351. | 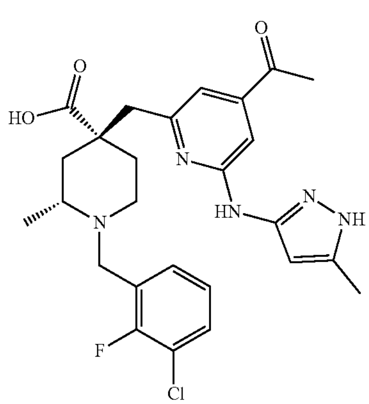 | (2R,4R)-4-((4-acetyl-6-((5-methyl-1H-pyrazol-3-yl)amino)pyridin-2-yl)methyl)-1-(3-chloro-2-fluorobenzyl)-2-methylpiperidine-4)-carboxylic acid | 514 |

| Example No. | Structure | Chemical Name | MS: (M + H)+ |
|---|---|---|---|
| 352. | 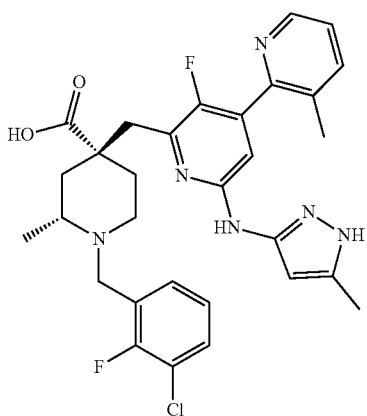 | (2R,4R)-1-(3-chloro-2-fluorobenzyl)-4-((3'-fluoro-3-methyl-6'-((5-methyl-1H-pyrazol-3-yl)amino)-[2,4'-bipyridin]-2'-yl)methyl)-2-methylpiperidine-4-carboxylic acid | 581 |
| 353. | 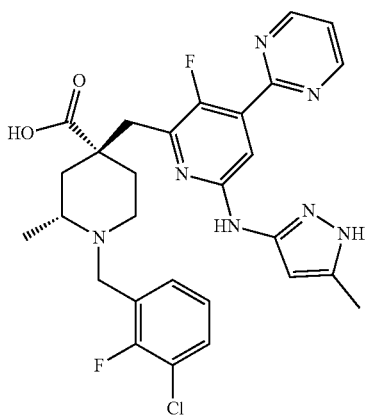 | (2R,4R)-1-(3-chloro-2-fluorobenzyl)-4-((3-fluoro-6-((5-methyl-1H-pyrazol-3-yl)amino)-4-(pyrimidin-2-yl)pyridin-2-yl)methyl)-2-methylpiperidine-4-carboxylic acid | 568 |
| 354. | 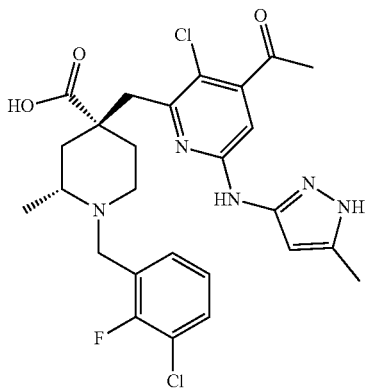 | (2R,4R)-4-((4-acetyl-3-chloro-6-((5-methyl-1H-pyrazol-3-yl)amino)pyridin-2-yl)methyl)-1-(3-chloro-2-fluorobenzyl)-2-methylpiperidine-4-carboxylic acid | 548 |

-continued

| Example No. | Structure | Chemical Name | MS: (M + H)+ |
|---|---|---|---|
| 355. | 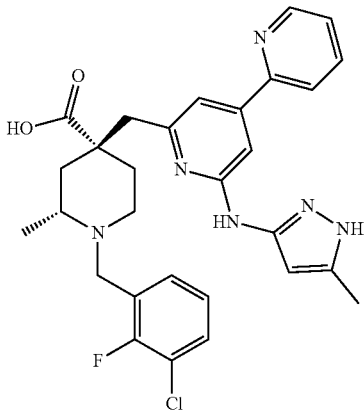 | (2R,4R)-1-(3-chloro-2-fluorobenzyl)-2-methyl-4-((6'-((5-methyl-1H-pyrazol-3-yl)amino)-[2,4'-bipyridin]-2'-yl)methyl)piperidine-4-carboxylic acid | 549 |
| 356. | 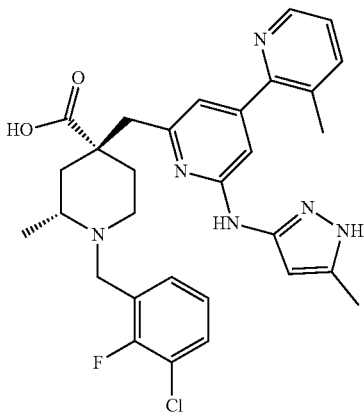 | (2R,4R)-1-(3-chloro-2-fluorobenzyl)-2-methyl-4-((3-methyl-6'-((5-methyl-1H-pyrazol-3-yl)amino)-[2,4'-bipyridin]-2'-yl)methyl)-piperidine-4-carboxylic acid | 563 |
| 357. | 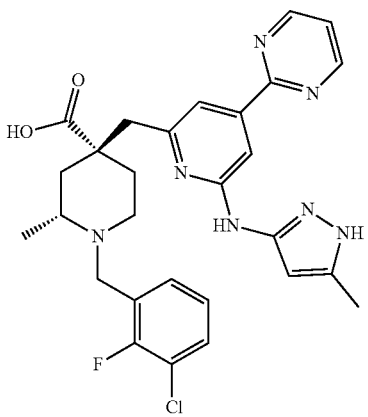 | (2R,4R)-1-(3-chloro-2-fluorobenzyl)-2-methyl-4-((6-((5-methyl-1H-pyrazol-3-yl)amino)-4-(pyrimidin-2-yl)pyridin-2-yl)methyl)-piperidine-4-carboxylic acid | 550 |

| Example No. | Structure | Chemical Name | MS: (M + H)+ |
|---|---|---|---|
| 358. | 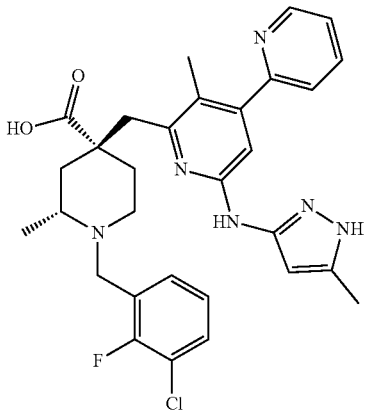 | (2R,4R)-1-(3-chloro-2-fluorobenzyl)-2-methyl-4-((3'-methyl-6'-((5-methyl-1H-pyrazol-3-yl)amino)-[2,4'-bipyridin]-2'-yl)methyl)-piperidine-4-carboxylic acid | 563 |
| 359. | 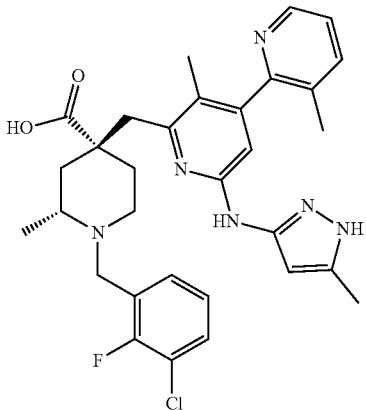 | (2R,4R)-1-(3-chloro-2-fluorobenzyl)-4-((3,3'-dimethyl-6'-((5-methyl-1H-pyrazol-3-yl)amino)-[2,4'-bipyridin]-2'-yl)methyl)-2-methylpiperidine-4-carboxylic acid | 577 |
| 360. | 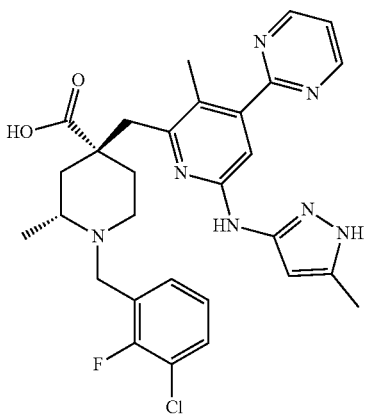 | (2R,4R)-1-(3-chloro-2-fluorobenzyl)-2-methyl-4-((3-methyl-6-((5-methyl-1H-pyrazol-3-yl)amino)-4-(pyrimidin-2-yl)pyridin-2-yl)methyl)piperidine-4-carboxylic acid | 564 |

-continued

| Example No. | Structure | Chemical Name | MS: (M + H)⁺ |
|---|---|---|---|
| 361. | 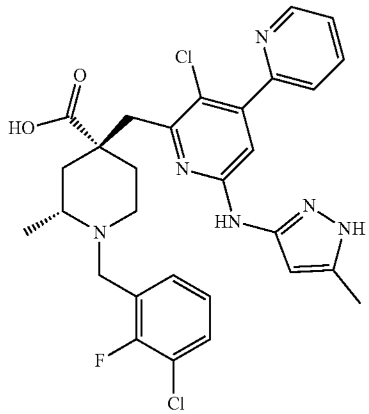 | (2R,4R)-1-(3-chloro-2-fluorobenzyl)-4-((3'-chloro-6'-((5-methyl-1H-pyrazol-3-yl)amino)-[2,4'-bipyridin]-2'-yl)methyl)-2-methylpiperidine-4-carboxylic acid | 583 |
| 362. | 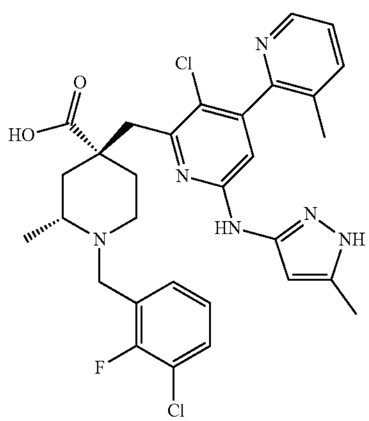 | (2R,4R)-1-(3-chloro-2-fluorobenzyl)-4-((3'-chloro-3-methyl-6'-((5-methyl-1H-pyrazol-3-yl)amino)-[2,4'-bipyridin]-2'-yl)methyl)-2-methylpiperidine-4-carboxylic acid | 598 |
| 363. | 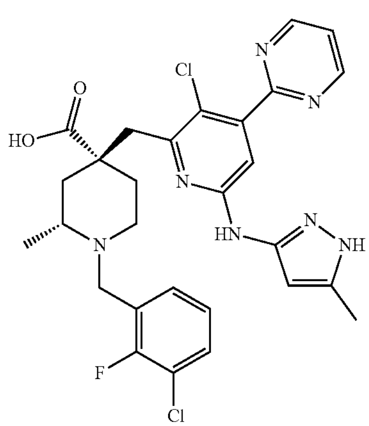 | (2R,4R)-1-(3-chloro-2-fluorobenzyl)-4-((3-chloro-6-((5-methyl-1H-pyrazol-3-yl)amino)-4-(pyrimidin-2-yl)pyridin-2-yl)methyl)-2-methylpiperidine-4-carboxylic acid | 584 |

| Example No. | Structure | Chemical Name | MS: (M + H)+ |
| --- | --- | --- | --- |
| 364. | 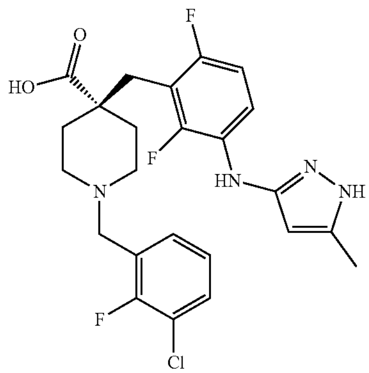 | 1-(3-chloro-2-fluorobenzyl)-4-(2,6-difluoro-3-((5-methyl-1H-pyrazol-3-yl)amino)benzyl)piperidine-4-carboxylic acid | 493 |
| 365. | 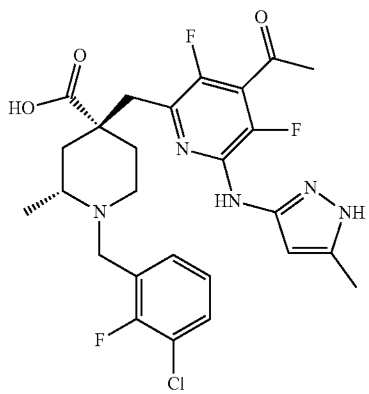 | (2R,4R)-4-((4-acetyl-3,5-difluoro-6-((5-methyl-1H-pyrazol-3-yl)amino)pyridin-2-yl)methyl)-1-(3-chloro-2-fluorobenzyl)-2-methyl-piperidine-4-carboxylic acid | 550 |
| 366. | 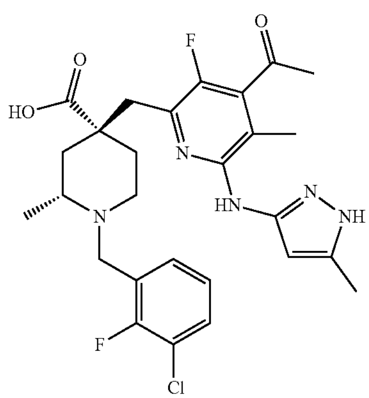 | (2R,4R)-4-((4-acetyl-3-fluoro-5-methyl-6-((5-methyl-1H-pyrazol-3-yl)amino)pyridin-2-yl)methyl)-1-(3-chloro-2-fluorobenzyl)-2-methylpiperidine-4-carboxylic acid | 546 |
| 367. | 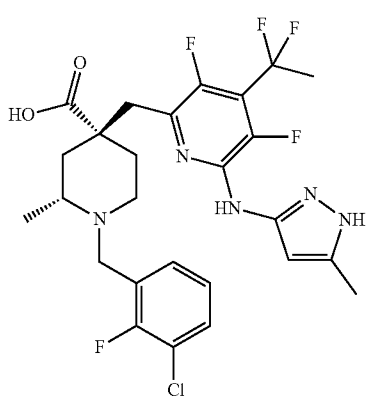 | (2R,4R)-1-(3-chloro-2-fluorobenzyl)-4-((4-(1,1-difluoroethyl)-3,5-difluoro-6-((5-methyl-1H-pyrazol-3-yl)amino)pyridin-2-yl)methyl)-2-methylpiperidine-4-carboxylic acid | 572 |

| Example No. | Structure | Chemical Name | MS: (M + H)+ |
|---|---|---|---|
| 368. | 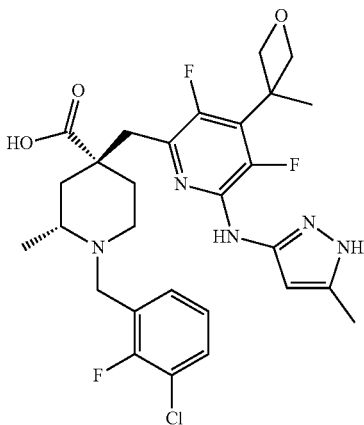 | (2R,4R)-1-(3-chloro-2-fluorobenzyl)-4-((3,5-difluoro-6-((5-methyl-1H-pyrazol-3-yl)amino)-4-(3-methyloxetan-3-yl)pyridin-2-yl)methyl)-2-methylpiperidine-4-carboxylic acid | 578 |
| 369. | 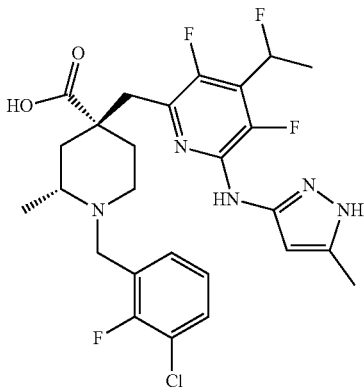 | (2R,4R)-1-(3-chloro-2-fluorobenzyl)-4-((3,5-difluoro-4-(1-fluoroethyl)-6-((5-methyl-1H-pyrazol-3-yl)amino)pyridin-2-yl)methyl)-2-methylpiperidine-4-carboxylic acid | 554 |
| 370. | 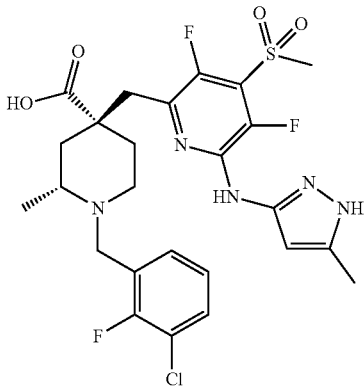 | (2R,4R)-1-(3-chloro-2-fluorobenzyl)-4-((3,5-difluoro-6-((5-methyl-1H-pyrazol-3-yl)amino)-4-(methylsulfonyl)pyridin-2-yl)methyl)-2-methylpiperidine-4-carboxylic acid | 586 |

-continued

| Example No. | Structure | Chemical Name | MS: (M + H)+ |
|---|---|---|---|
| 371. | 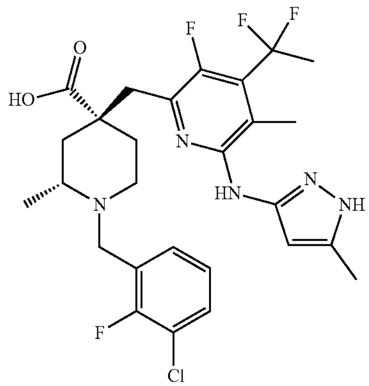 | (2R,4R)-1-(3-chloro-2-fluorobenzyl)-4-((4-(1,1-difluoroethyl)-3-fluoro-5-methyl-6-((5-methyl-1H-pyrazol-3-yl)amino)pyridin-2-yl)methyl)-2-methylpiperidine-4-carboxylic acid | 568 |
| 372. | 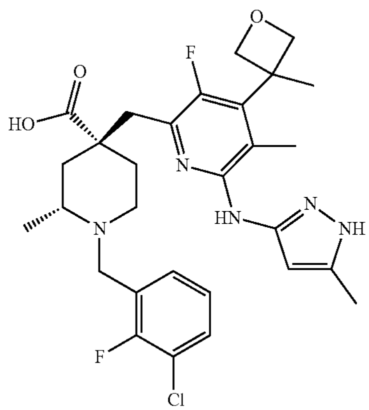 | (2R,4R)-1-(3-chloro-2-fluorobenzyl)-4-((3-fluoro-5-methyl-6-((5-methyl-1H-pyrazol-3-yl)amino)-4-(3-methyloxetan-3-yl)pyridin-2-yl)methyl)-2-methylpiperidine-4-carboxylic acid | 574 |
| 373. | 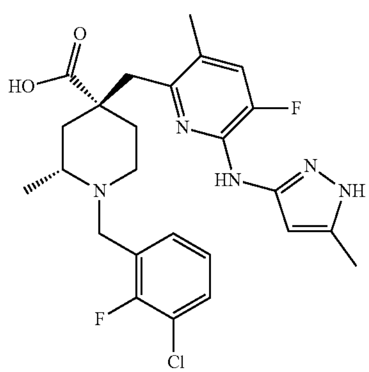 | (2R,4R)-1-(3-chloro-2-fluorobenzyl)-4-((5-fluoro-3-methyl-6-((5-methyl-1H-pyrazol-3-yl)amino)pyridin-2-yl)methyl)-2-methylpiperidine-4-carboxylic acid | 504 |
| 374. | 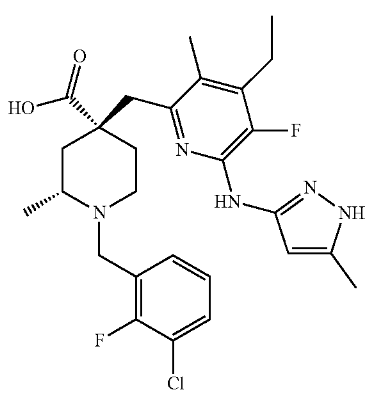 | (2R,4R)-1-(3-chloro-2-fluorobenzyl)-4-((4-ethyl-5-fluoro-3-methyl-6-((5-methyl-1H-pyrazol-3-yl)amino)pyridin-2-yl)methyl)-2-methylpiperidine-4-carboxylic acid | 532 |

| Example No. | Structure | Chemical Name | MS: (M + H)+ |
|---|---|---|---|
| 375. | 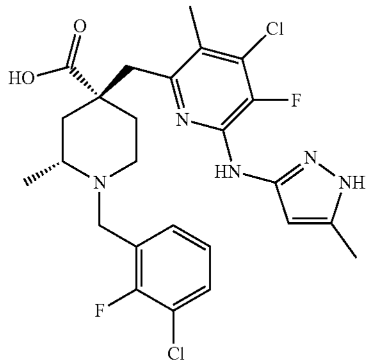 | (2R,4R)-1-(3-chloro-2-fluorobenzyl)-4-((4-chloro-3-methyl-5-fluoro-6-((5-methyl-1H-pyrazol-3-yl)amino)pyridin-2-yl)methyl)-2-methylpiperidine-4-carboxylic acid | 538 |
| 376. | 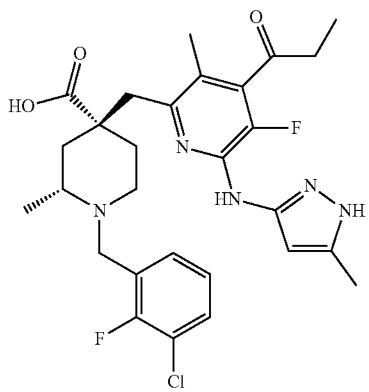 | (2R,4R)-1-(3-chloro-2-fluorobenzyl)-4-((5-fluoro-3-methyl-6-((5-methyl-1H-pyrazol-3-yl)amino)-4-propionylpyridin-2-yl)methyl)-2-methylpiperidine-4-carboxylic acid | 560 |
| 377. | 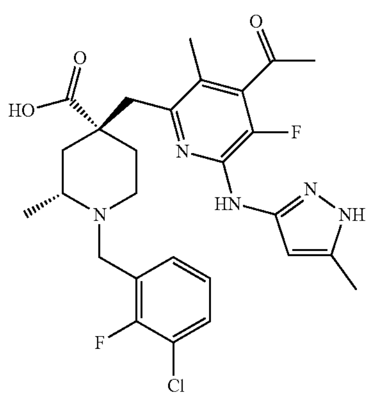 | (2R,4R)-4-((4-acetyl-3-methyl-5-fluoro-6-((5-methyl-1H-pyrazol-3-yl)amino)pyridin-2-yl)methyl)-1-(3-chloro-2-fluorobenzyl)-2-methylpiperidine-4-carboxylic acid | 546 |
| 378. | 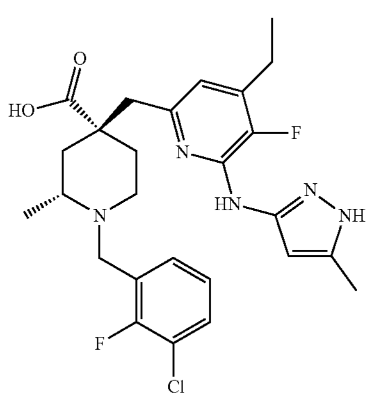 | (2R,4R)-1-(3-chloro-2-fluorobenzyl)-4-((4-ethyl-5-fluoro-6-((5-methyl-1H-pyrazol-3-yl)amino)pyridin-2-yl)methyl)-2-methylpiperidine-4-carboxylic acid | 518 |

-continued

| Example No. | Structure | Chemical Name | MS: (M + H)+ |
|---|---|---|---|
| 379. | 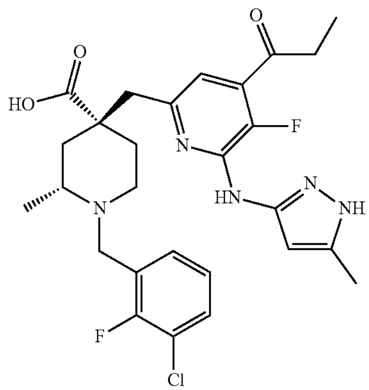 | (2R,4R)-1-(3-chloro-2-fluorobenzyl)-4-((5-fluoro-6-((5-methyl-1H-pyrazol-3-yl)amino)-4-propionyl-pyridin-2-yl)methyl)-2-methyl piperidine-4-carboxylic acid | 546 |
| 380. | 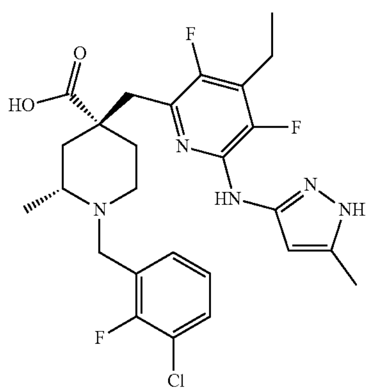 | (2R,4R)-1-(3-chloro-2-fluorobenzyl)-4-((4-ethyl-3,5-difluoro-6-((5-methyl-1H-pyrazol-3-yl)amino)pyridin-2-yl)methyl)-2-methyl piperidine-4-carboxylic acid | 536 |
| 381. | 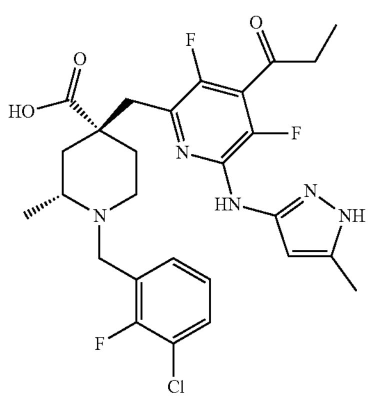 | (2R,4R)-1-(3-chloro-2-fluorobenzyl)-4-((3,5-difluoro-6-((5-methyl-1H-pyrazol-3-yl)amino)-4-propionylpyridin-2-yl)methyl)-2-methylpiperidine-4-carboxylic acid | 564 |
| 382. | 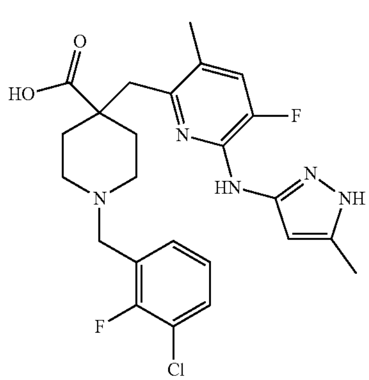 | 1-(3-chloro-2-fluorobenzyl)-4-((3-methyl-5-fluoro-6-((5-methyl-1H-pyrazol-3-yl)amino)pyridin-2-yl)methyl)piperidine-4-carboxylic acid | 490 |

-continued

| Example No. | Structure | Chemical Name | MS: (M + H)+ |
|---|---|---|---|
| 383. | 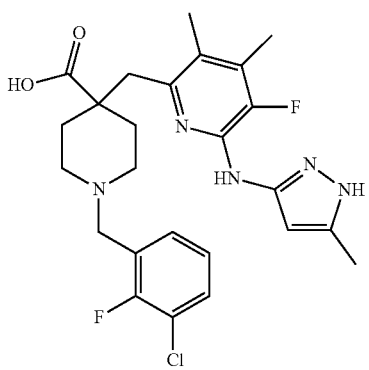 | 1-(3-chloro-2-fluorobenzyl)-4-((3-methyl-5-fluoro-4-methyl-6-((5-methyl-1H-pyrazol-3-yl)amino)pyridin-2-yl)methyl)piperidine-4-carboxylic acid | 504 |
| 384. | 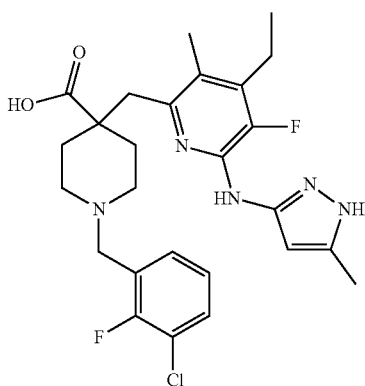 [SMILES: CCc1c(C)c(CC2(C(=O)O)CCN(Cc3cccc(Cl)c3F)CC2)nc(Nc2cc(C)[nH]n2)c1F] | 1-(3-chloro-2-fluorobenzyl)-4-((4-ethyl-5-fluoro-3-methyl-6-((5-methyl-1H-pyrazol-3-yl)amino)-pyridin-2-yl)methyl)piperidine-4)-carboxylic acid | 518 |
| 385. | 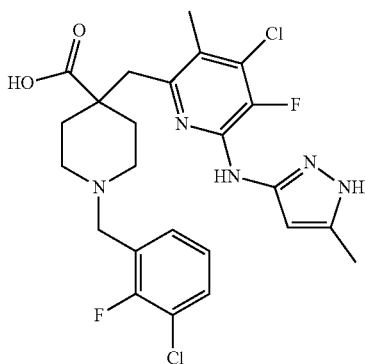 | 1-(3-chloro-2-fluorobenzyl)-4-((4-chloro-3-methyl-5-fluoro-6-((5-methyl-1H-pyrazol-3-yl)amino)pyridin-2-yl)methyl)piperidine-4-carboxylic acid | 524 |
| 386. | 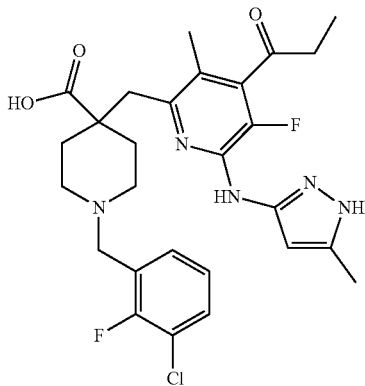 | 1-(3-chloro-2-fluorobenzyl)-4-((3-methyl-5-fluoro-6-((5-methyl-1H-pyrazol-3-yl)amino)-4-propionylpyridin-2-yl)methyl)piperidine-4-carboxylic acid | 546 |

-continued

| Example No. | Structure | Chemical Name | MS: (M + H)+ |
|---|---|---|---|
| 387. | 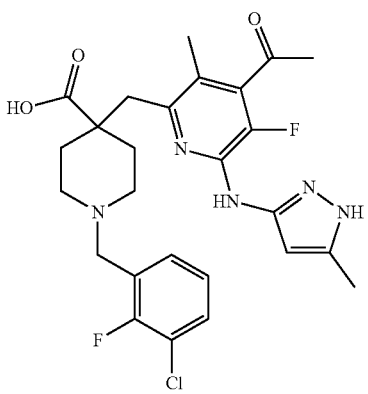 [SMILES: CC(=O)c1c(C)c(CC2(C(=O)O)CCN(Cc3cccc(Cl)c3F)CC2)nc(Nc2cc(C)[nH]n2)c1F] | 4-((4-acetyl-3-methyl-5-fluoro-6-((5-methyl-1H-pyrazol-3-yl)amino)pyridin-2-yl)methyl)-1-(3-chloro-2-fluorobenzyl)piperidine-4-carboxylic acid | 532 |
| 388. | 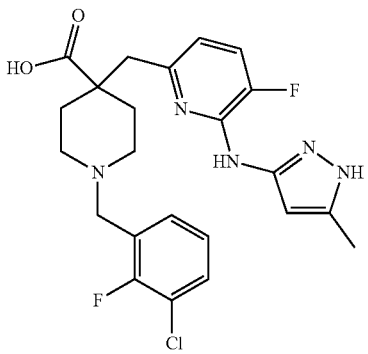 [SMILES: Cc1cc(Nc2nc(CC3(C(=O)O)CCN(Cc4cccc(Cl)c4F)CC3)ccc2F)n[nH]1] | 1-(3-chloro-2-fluorobenzyl)-4-((5-fluoro-6-((5-methyl-1H-pyrazol-3-yl)amino)pyridin-2-yl)methyl)piperidine-4-carboxylic acid | 476 |
| 389. | 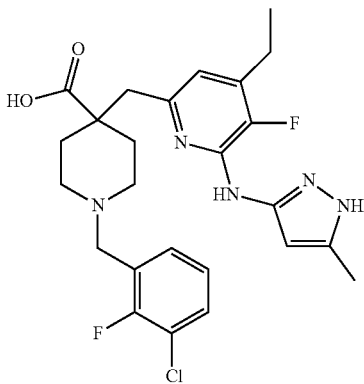 | 1-(3-chloro-2-fluorobenzyl)-4-((4-ethyl-5-fluoro-6-((5-methyl-1H-pyrazol-3-yl)amino)pyridin-2-yl)methyl)piperidine-4-carboxylic acid | 504 |
| 390. | 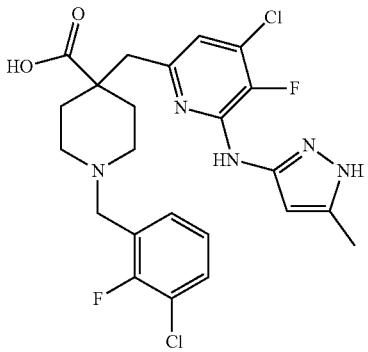 | 1-(3-chloro-2-fluorobenzyl)-4-((4-chloro-5-fluoro-6-((5-methyl-1H-pyrazol-3-yl)amino)pyridin-2-yl)methyl)piperidine-4-carboxylic acid | 510 |

-continued

| Example No. | Structure | Chemical Name | MS: (M + H)+ |
|---|---|---|---|
| 391. | 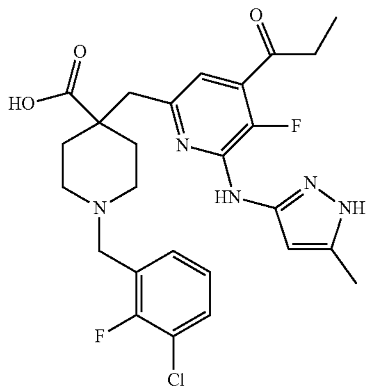 [SMILES: CCC(=O)c1cc(CC2(C(=O)O)CCN(Cc3cccc(Cl)c3F)CC2)nc(Nc2cc(C)[nH]n2)c1F] | 1-(3-chloro-2-fluorobenzyl)-4-((5-fluoro-6-((5-methyl-1H-pyrazol-3-yl)amino)-4-propionylpyridin-2-yl)methyl)piperidine-4-carboxylic acid | 532 |
| 392. | 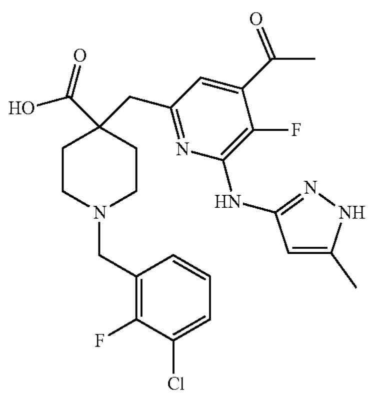 | 4-((4-acetyl-5-fluoro-6-((5-methyl-1H-pyrazol-3-yl)amino)pyridin-2-yl)methyl)-1-(3-chloro-2-fluoobenzyl)piperidine-4-carboxylic acid | 518 |
| 393. | 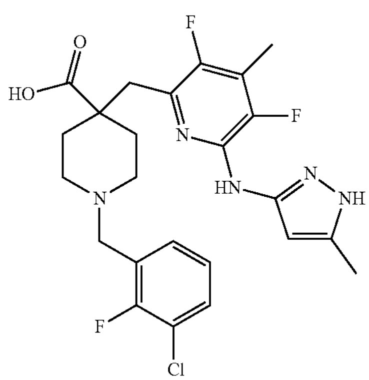 [SMILES: Cc1cc(Nc2nc(CC3(C(=O)O)CCN(Cc4cccc(Cl)c4F)CC3)c(F)c(C)c2F)n[nH]1] | 1-(3-chloro-2-fluorobenzyl)-4-((3,5-difluoro-4-methyl-6-((5-methyl-1H-pyrazol-3-yl)amino)pyridin-2-yl)methyl)piperidine-4-carboxylic acid | 508 |
| 394. | 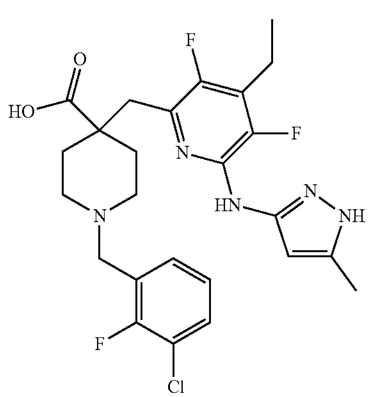 [SMILES: CCc1c(F)c(CC2(C(=O)O)CCN(Cc3cccc(Cl)c3F)CC2)nc(Nc2cc(C)[nH]n2)c1F] | 1-(3-chloro-2-fluorobenzyl)-4-((4-ethyl-3,5-difluoro-6-((5-methyl-1H-pyrazol-3-yl)amino)pyridin-2-yl)methyl)piperidine-4-carboxylic acid | 522 |

-continued

| Example No. | Structure | Chemical Name | MS: (M + H)⁺ |
|---|---|---|---|
| 395. | 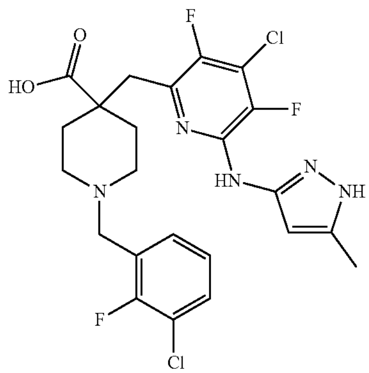 [SMILES: Cc1cc(Nc2nc(CC3(C(=O)O)CCN(Cc4cccc(Cl)c4F)CC3)c(F)c(Cl)c2F)n[nH]1] | 1-(3-chloro-2-fluorobenzyl)-4-((4-chloro-3,5-difluoro-6-((5-methyl-1H-pyrazol-3-yl)amino)pyridin-2-yl)methyl)piperidine-4-carboxylic acid | 528 |
| 396. | 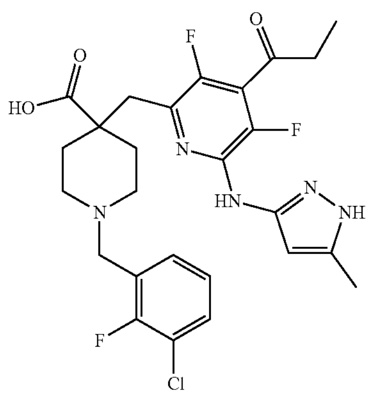 [SMILES: CCC(=O)c1c(F)c(CC2(C(=O)O)CCN(Cc3cccc(Cl)c3F)CC2)nc(Nc2cc(C)[nH]n2)c1F] | 1-(3-chloro-2-fluorobenzyl)-4-((3,5-difluoro-6-((5-methyl-1H-pyrazol-3-yl)amino)-4-propionyl-pyridin-2-yl)methyl)piperidine-4-carboxylic acid | 550 |
| 397. | 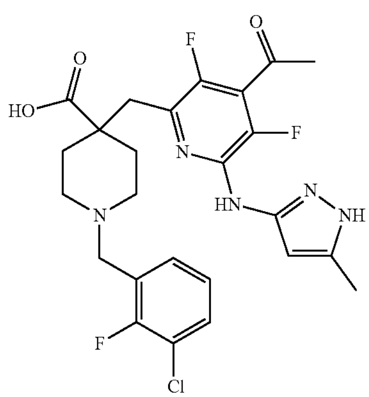 [SMILES: CC(=O)c1c(F)c(CC2(C(=O)O)CCN(Cc3cccc(Cl)c3F)CC2)nc(Nc2cc(C)[nH]n2)c1F] | 4-((4-acetyl-3,5-difluoro-6-((5-methyl-1H-pyrazol-3-yl)amino)-pyridin-2-yl)methyl)-1-(3-chloro-2-fluorobenzyl)piperidine-4-carboxylic acid | 536 |
| 398. | 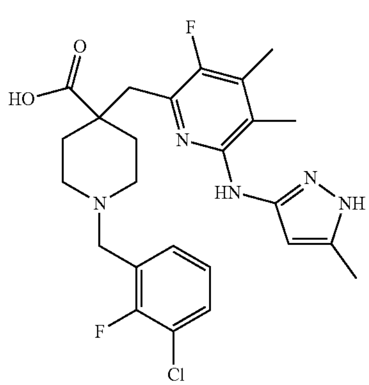 | 1-(3-chloro-2-fluorobenzyl)-4-((3-fluoro-4,5-dimethyl-6-((5-methyl-1H-pyrazol-3-yl)amino)pyridin-2-yl)methyl)piperidine-4-carboxylic acid | 504 |

| Example No. | Structure | Chemical Name | MS: (M + H)+ |
|---|---|---|---|
| 399. | 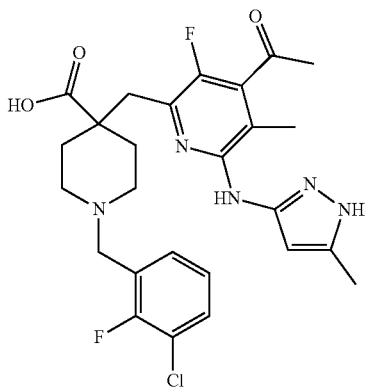 | 4-((4-acetyl-3-fluoro-5-methyl-6-((5-methyl-1H-pyrazol-3-yl)amino)pyridin-2-yl)methyl)-1-(3-chloro-2-fluorobenzyl)piperidine-4-carboxylic acid | 532 |
| 400. | 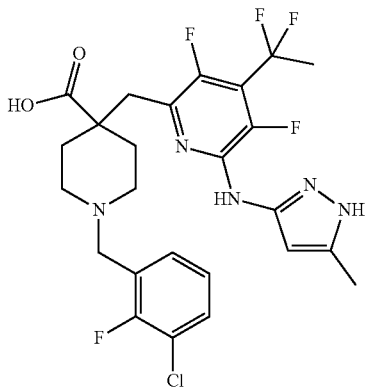 [SMILES: Cc1cc(Nc2nc(CC3(C(=O)O)CCN(Cc4cccc(Cl)c4F)CC3)c(F)c(C(C)(F)F)c2F)n[nH]1] | 1-(3-chloro-2-fluorobenzyl)-4-((4-(1,1-difluoroethyl)-3,5-difluoro-6-((5-methyl-1H-pyrazol-3-yl)amino)pyridin-2-yl)methyl)piperidine-4-carboxylic acid | 558 |
| 401. | 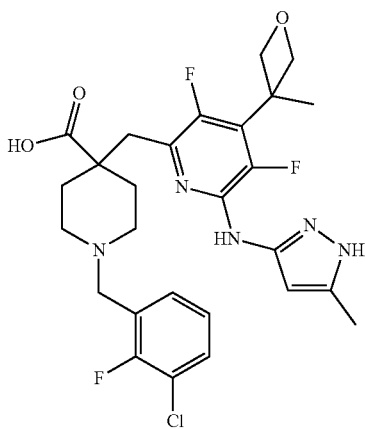 [SMILES: Cc1cc(Nc2nc(CC3(C(=O)O)CCN(Cc4cccc(Cl)c4F)CC3)c(F)c(C3(C)COC3)c2F)n[nH]1] | 1-(3-chloro-2-fluorobenzyl)-4-((3,5-difluoro-6-((5-methyl-1H-pyrazol-3-yl)amino)-4-(3-methyloxetan-3-yl)pyridin-2-yl)methyl)piperidine-4-carboxylic acid | 564 |

-continued

| Example No. | Structure | Chemical Name | MS: (M + H)+ |
|---|---|---|---|
| 402. | 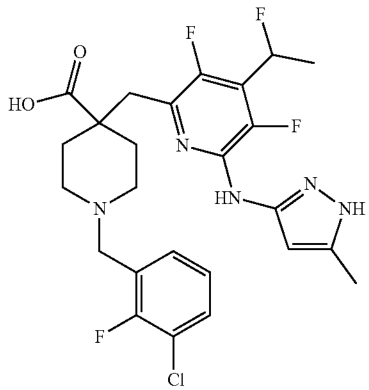 [SMILES: Cc1cc(Nc2nc(CC3(C(=O)O)CCN(Cc4cccc(Cl)c4F)CC3)c(F)c(C(C)F)c2F)n[nH]1] | 1-(3-chloro-2-fluorobenzyl)-4-((3,5-difluoro-4-(1-fluoroethyl)-6-((5-methyl-1H-pyrazol-3-yl)amino)-pyridin-2-yl)methyl)piperidine-4-carboxylic acid | 540 |
| 403. | 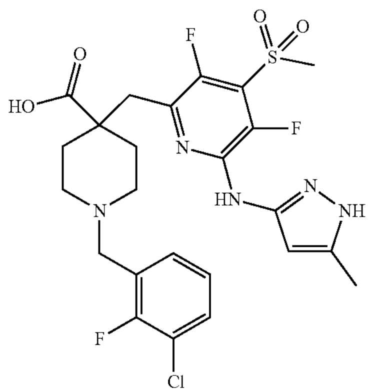 [SMILES: Cc1cc(Nc2nc(CC3(C(=O)O)CCN(Cc4cccc(Cl)c4F)CC3)c(F)c(S(C)(=O)=O)c2F)n[nH]1] | 1-(3-chloro-2-fluorobenzyl)-4-((3,5-difluoro-6-((5-methyl-1H-pyrazol-3-yl)amino)-4-(methylsulfonyl)pyridin-2-yl)methyl)piperidine-4-carboxylic acid | 572 |
| 404. | 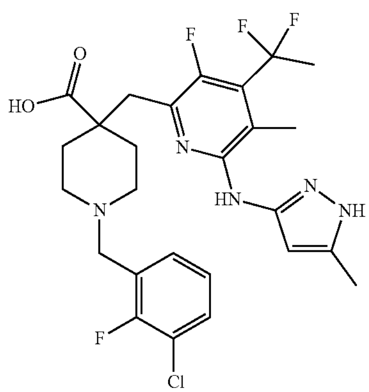 [SMILES: Cc1cc(Nc2nc(CC3(C(=O)O)CCN(Cc4cccc(Cl)c4F)CC3)c(F)c(C(C)(F)F)c2C)n[nH]1] | 1-(3-chloro-2-fluorobenzyl)-4-((4-(1,1-difluoroethyl)-3-fluoro-5-methyl-6-((5-methyl-1H-pyrazol-3-yl)amino)pyridin-2-yl)methyl)piperidine-4-carboxylic acid | 554 |
| 405. | 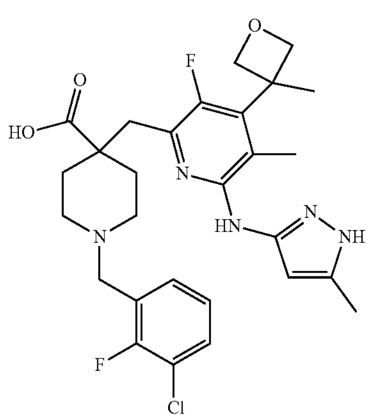 [SMILES: Cc1cc(Nc2nc(CC3(C(=O)O)CCN(Cc4cccc(Cl)c4F)CC3)c(F)c(C3(C)COC3)c2C)n[nH]1] | 1-(3-chloro-2-fluorobenzyl)-4-((3-fluoro-5-methyl-6-((5-methyl-1H-pyrazol-3-yl)amino)-4-(3-methyloxetan-3-yl)pyridin-2-yl)methyl)piperidine-4-carboxylic acid | 560 |

-continued

| Example No. | Structure | Chemical Name | MS: (M + H)+ |
|---|---|---|---|
| 406. | 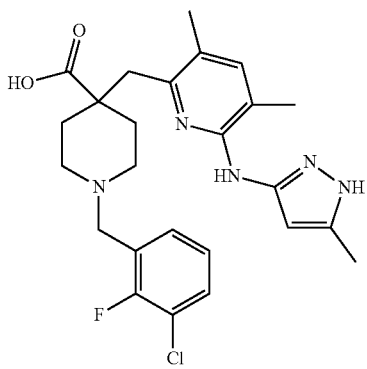 [SMILES: Cc1cc(Nc2nc(CC3(C(=O)O)CCN(Cc4cccc(Cl)c4F)CC3)c(C)cc2C)n[nH]1] | 1-(3-chloro-2-fluorobenzyl)-4-((3,5-dimethyl-6-((5-methyl-1H-pyrazol-3-yl)amino)pyridin-2-yl)-methyl)piperidine-4-carboxylic acid | 486 |
| 407. | 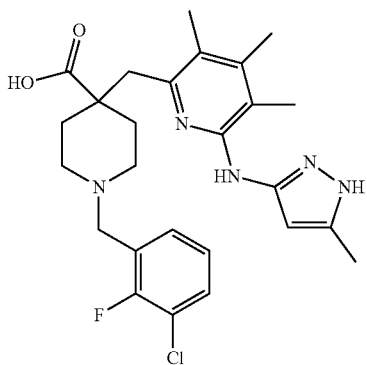 [SMILES: Cc1cc(Nc2nc(CC3(C(=O)O)CCN(Cc4cccc(Cl)c4F)CC3)c(C)c(C)c2C)n[nH]1] | 1-(3-chloro-2-fluorobenzyl)-4-((3,4,5-trimethyl-6-((5-methyl-1H-pyrazol-3-yl)amino)pyridin-2-yl)-methyl)piperidine-4-carboxylic acid | 500 |
| 408. | 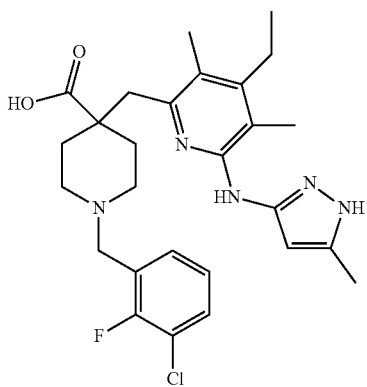 | 1-(3-chloro-2-fluorobenzyl)-4-((4-ethyl-3,5-dimethyl-6-((5-methyl-1H-pyrazol-3-yl)amino)pyridin-2-yl)methyl)piperidine-4-carboxylic acid | 514 |
| 409. | 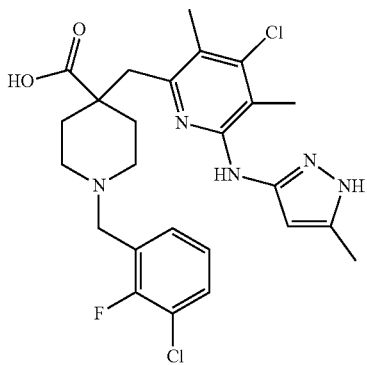 | 1-(3-chloro-2-fluorobenzyl)-4-((4-chloro-3,5-dimethyl-6-((5-methyl-1H-pyrazol-3-yl)amino)pyridin-2-yl)methyl)piperidine-4-carboxylic acid | 520 |

| Example No. | Structure | Chemical Name | MS: (M + H)+ |
|---|---|---|---|
| 410. | 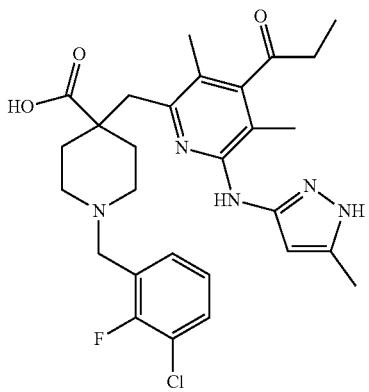 | 1-(3-chloro-2-fluorobenzyl)-4-((3,5-dimethyl-6-((5-methyl-1H-pyrazol-3-yl)amino)-4-propionyl-pyridin-2-yl)methyl)piperidine-4)-carboxylic acid | 542 |
| 411. | 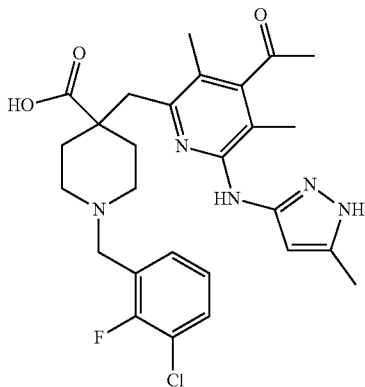 [SMILES: CC(=O)c1c(C)c(CC2(C(=O)O)CCN(Cc3cccc(Cl)c3F)CC2)nc(Nc2cc(C)[nH]n2)c1C] | 4-((4-acetyl-3,5-dimethyl-6-((5-methyl-1H-pyrazol-3-yl)amino)-pyridin-2-yl)methyl)-1-(3-chloro-2-fluorobenzyl)piperidine-4-carboxylic acid | 528 |
| 412. | 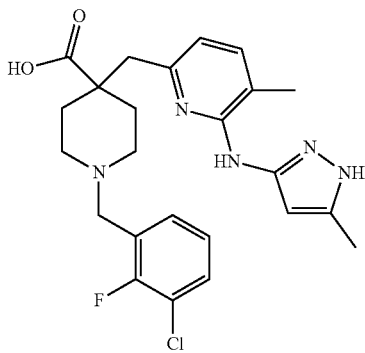 [SMILES: Cc1cc(Nc2nc(CC3(C(=O)O)CCN(Cc4cccc(Cl)c4F)CC3)ccc2C)n[nH]1] | 1-(3-chloro-2-fluorobenzyl)-4-((5-methyl-6-((5-methyl-1H-pyrazol-3-yl)amino)pyridin-2-yl)methyl)-piperidine-4-carboxylic acid | 472 |
| 413. | 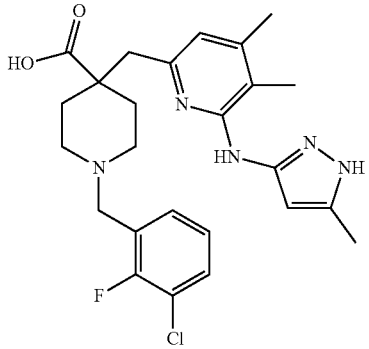 [SMILES: Cc1cc(Nc2nc(CC3(C(=O)O)CCN(Cc4cccc(Cl)c4F)CC3)cc(C)c2C)n[nH]1] | 1-(3-chloro-2-fluorobenzyl)-4-((4,5-dimethyl-6-((5-methyl-1H-pyrazol-3-yl)amino)pyridin-2-yl)-methyl)piperidine-4-carboxylic acid | 486 |

| Example No. | Structure | Chemical Name | MS: (M + H)⁺ |
| --- | --- | --- | --- |
| 414. | 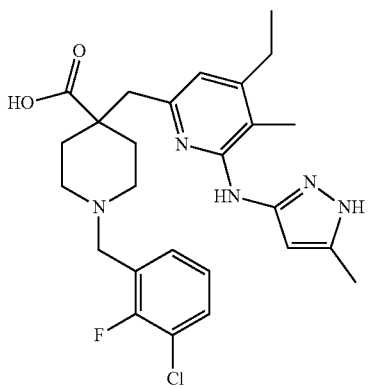 [SMILES: CCc1cc(CC2(C(=O)O)CCN(Cc3cccc(Cl)c3F)CC2)nc(Nc2cc(C)[nH]n2)c1C] | 1-(3-chloro-2-fluorobenzyl)-4-((4-ethyl-5-methyl-6-((5-methyl-1H-pyrazol-3-yl)amino)pyridin-2-yl)methyl)piperidine-4-carboxylic acid | 500 |
| 415. | 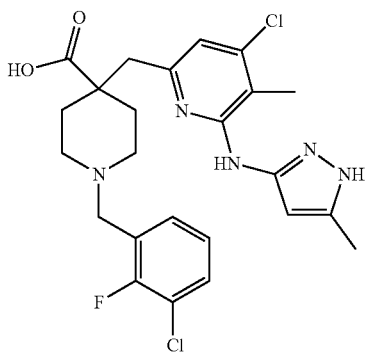 | 1-(3-chloro-2-fluorobenzyl)-4-((4-chloro-5-methyl-6-((5-methyl-1H-pyrazol-3-yl)amino)pyridin-2-yl)methyl)piperidine-4-carboxylic acid | 506 |
| 416. | 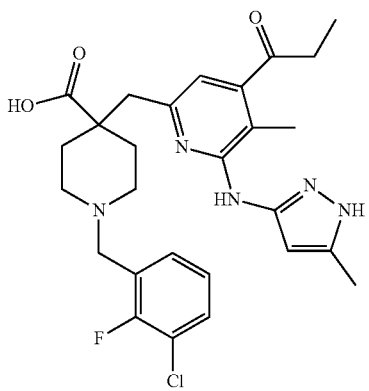 [SMILES: CCC(=O)c1cc(CC2(C(=O)O)CCN(Cc3cccc(Cl)c3F)CC2)nc(Nc2cc(C)[nH]n2)c1C] | 1-(3-chloro-2-fluorobenzyl)-4-((5-methyl-6-((5-methyl-1H-pyrazol-3-yl)amino)-4-propionyl-pyridin-2-yl)methyl)piperidine-4-carboxylic acid | 528 |
| 417. | 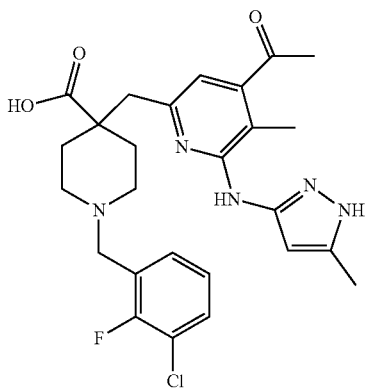 [SMILES: CC(=O)c1cc(CC2(C(=O)O)CCN(Cc3cccc(Cl)c3F)CC2)nc(Nc2cc(C)[nH]n2)c1C] | 4-((4-acetyl-5-methyl-6-((5-methyl-1H-pyrazol-3-yl)amino)pyridin-2-yl)methyl)-1-(3-chloro-2-fluorobenzyl)piperidine-4-carboxylic acid | 514 |

| Example No. | Structure | Chemical Name | MS: (M + H)+ |
|---|---|---|---|
| 418. | 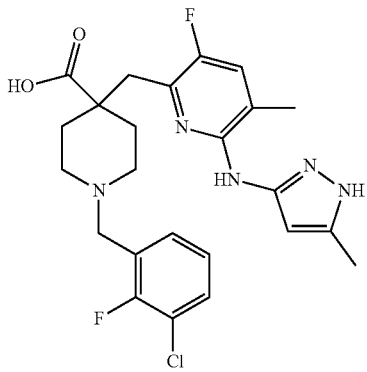 [SMILES: Cc1cc(Nc2nc(CC3(C(=O)O)CCN(Cc4cccc(Cl)c4F)CC3)c(F)cc2C)n[nH]1] | 1-(3-chloro-2-fluorobenzyl)-4-((3-fluoro-5-methyl-6-((5-methyl-1H-pyrazol-3-yl)amino)pyridin-2-yl)methyl)piperidine-4-carboxylic acid | 490 |
| 419. | 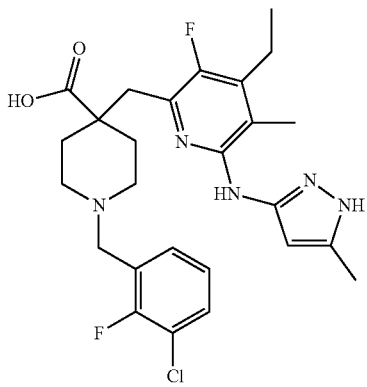 [SMILES: CCc1c(C)c(Nc2cc(C)[nH]n2)nc(CC2(C(=O)O)CCN(Cc3cccc(Cl)c3F)CC2)c1F] | 1-(3-chloro-2-fluorobenzyl)-4-((4-ethyl-3-fluoro-5-methyl-6-((5-methyl-1H-pyrazol-3-yl)amino)-pyridin-2-yl)methyl)piperidine-4)-carboxylic acid | 518 |
| 420. | 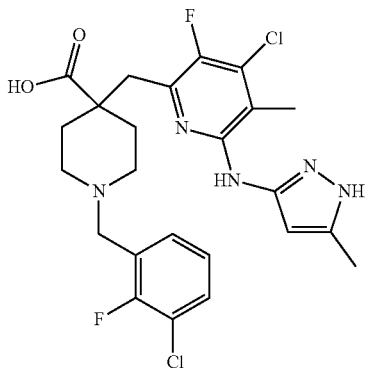 [SMILES: Cc1cc(Nc2nc(CC3(C(=O)O)CCN(Cc4cccc(Cl)c4F)CC3)c(F)c(Cl)c2C)n[nH]1] | 1-(3-chloro-2-fluorobenzyl)-4-((4-chloro-3-fluoro-5-methyl-6-((5-methyl-1H-pyrazol-3-yl)amino)pyridin-2-yl)methyl)piperidine-4-carboxylic acid | 524 |
| 421. | 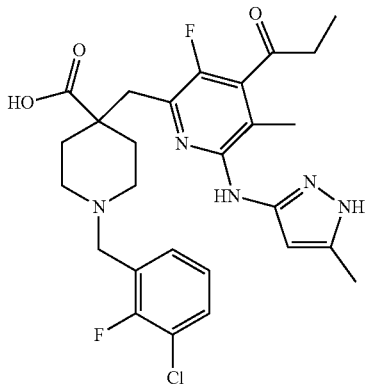 | 1-(3-chloro-2-fluorobenzyl)-4-((3-fluoro-5-methyl-6-((5-methyl-1H-pyrazol-3-yl)amino)-4-propionylpyridin-2-yl)methyl)piperidine-4-carboxylic acid | 546 |

-continued

| Example No. | Structure | Chemical Name | MS: (M + H)+ |
|---|---|---|---|
| 422. | 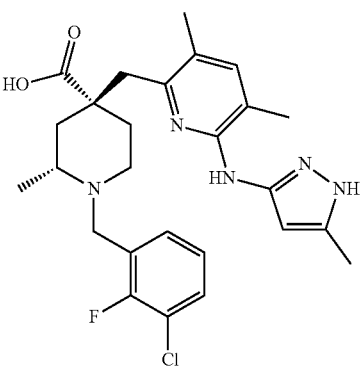 | (2R,4R)-1-(3-chloro-2-fluorobenzyl)-4-((3,5-dimethyl-6-((5-methyl-1H-pyrazol-3-yl)amino)pyridin-2-yl)methyl)-2-methylpiperidine-4-carboxylic acid | 500 |
| 423. | 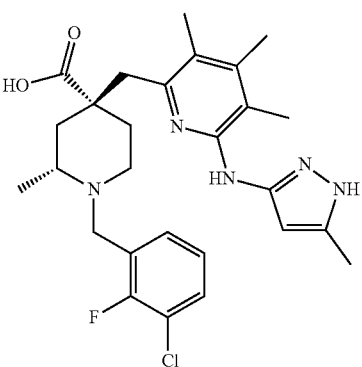 | (2R,4R)-1-(3-chloro-2-fluorobenzyl)-2-methyl-4-((3,4,5-trimethyl-6-((5-methyl-1H-pyrazol-3-yl)amino)pyridin-2-yl)methyl)piperidine-4-carboxylic acid | 514 |
| 424. | 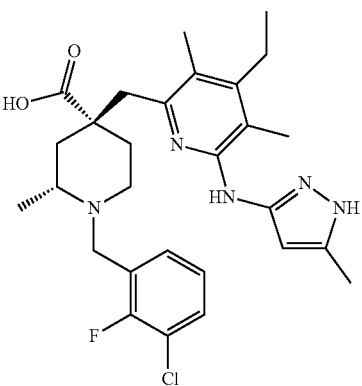 | (2R,4R)-1-(3-chloro-2-fluorobenzyl)-4-((4-ethyl-3,5-dimethyl-6-((5-methyl-1H-pyrazol-3-yl)amino)pyridin-2-yl)methyl)-2-methylpiperidine-4-carboxylic acid | 528 |
| 425. | 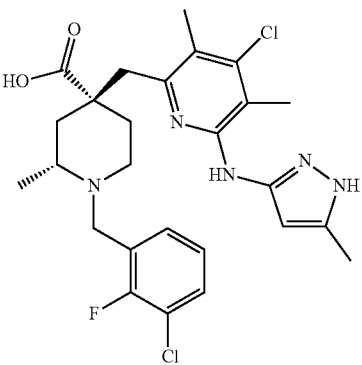 | (2R,4R)-1-(3-chloro-2-fluorobenzyl)-4-((4-chloro-3,5-dimethyl-6-((5-methyl-1H-pyrazol-3-yl)amino)pyridin-2-yl)methyl)-2-methylpiperidine-4-carboxylic acid | 534 |

| Example No. | Structure | Chemical Name | MS: (M + H)+ |
|---|---|---|---|
| 426. | 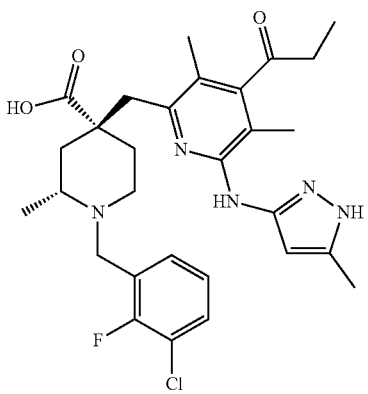 | (2R,4R)-1-(3-chloro-2-fluorobenzyl)-4-((3,5-dimethyl-6-((5-methyl-1H-pyrazol-3-yl)amino)-4-propionylpyridin-2-yl)methyl)-2-methylpiperidine-4-carboxylic acid | 556 |
| 427. | 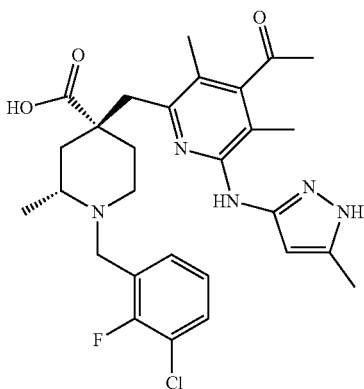 | (2R,4R)-4-((4-acetyl-3,5-dimethyl-6-((5-methyl-1H-pyrazol-3-yl)amino)pyridin-2-yl)methyl)-1-(3-chloro-2-fluorobenzyl)-2-methyl-piperidine-4-carboxylic acid | 542 |
| 428. | 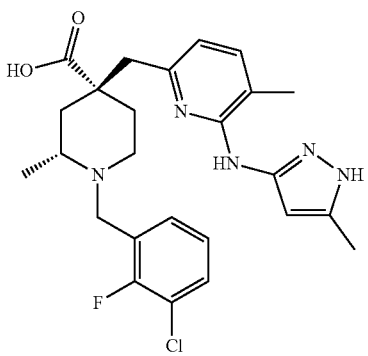 | (2R,4R)-1-(3-chloro-2-fluorobenzyl)-2-methyl-4-((5-methyl-6-((5-methyl-1H-pyrazol-3-yl)amino)pyridin-2-yl)methyl)piperidine-4-carboxylic acid | 486 |
| 429. | 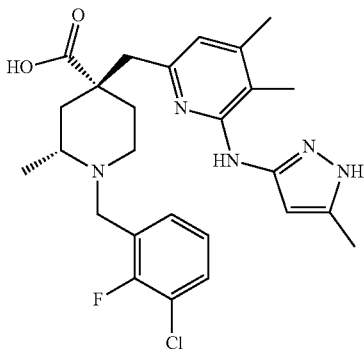 | (2R,4R)-1-(3-chloro-2-fluorobenzyl)-4-((4,5-dimethyl-6-((5-methyl-1H-pyrazol-3-yl)amino)pyridin-2-yl)methyl)-2-methylpiperidine-4-carboxylic acid | 500 |

-continued

| Example No. | Structure | Chemical Name | MS: (M + H)+ |
|---|---|---|---|
| 430. | 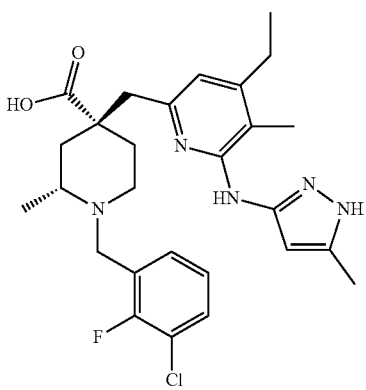 | (2R,4R)-1-(3-chloro-2-fluorobenzyl)-4-((4-ethyl-5-methyl-6-((5-methyl-1H-pyrazol-3-yl)amino)-pyridin-2-yl)methyl)-2-methyl-piperidine-4-carboxylic acid | 514 |
| 431. | 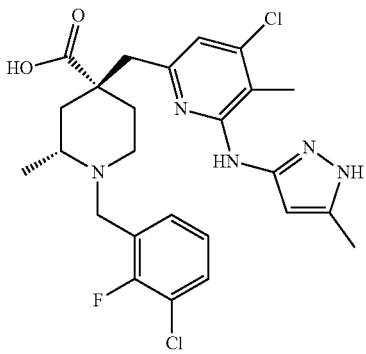 | (2R,4R)-1-(3-chloro-2-fluorobenzyl)-4-((4-chloro-5-methyl-6-((5-methyl-1H-pyrazol-3-yl)amino)-pyridin-2-yl)methyl)-2-methyl-piperidine-4-carboxylic acid | 520 |
| 432. | 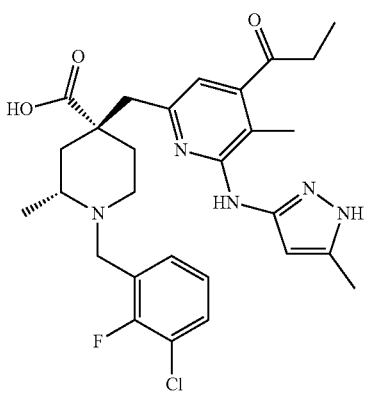 | (2R,4R)-1-(3-chloro-2-fluorobenzyl)-2-methyl-4-((5-methyl-6-((5-methyl-1H-pyrazol-3-yl)amino)-4-propionylpyridin-2-yl)methyl)-piperidine-4-carboxylic acid | 342 |
| 433. | 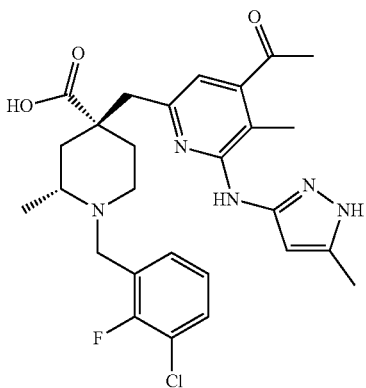 | (2R,4R)-4-((4-acetyl-5-methyl-6-((5-methyl-1H-pyrazol-3-yl)-amino)pyridin-2-yl)methyl)-1-(3-chloro-2-fluorobenzyl)-2-methyl-piperidine-4-carboxylic acid | 528 |

| Example No. | Structure | Chemical Name | MS: (M + H)+ |
|---|---|---|---|
| 434. | 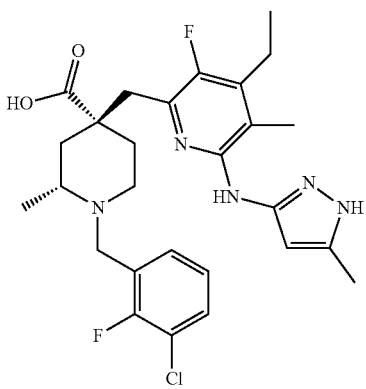 | (2R,4R)-1-(3-chloro-2-fluorobenzyl)-4-((4-ethyl-3-fluoro-5-methyl-6-((5-methyl-1H-pyrazol-3-yl)amino)pyridin-2-yl)methyl)-2-methylpiperidine-4-carboxylic acid | 532 |
| 435. | 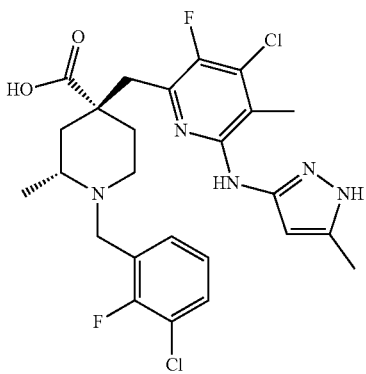 | (2R,4R)-1-(3-chloro-2-fluorobenzyl)-4-((4-chloro-3-fluoro-5-methyl-6-((5-methyl-1H-pyrazol-3-yl)amino)pyridin-2-yl)methyl)-2-methylpiperidine-4-carboxylic acid | 538 |
| 436. | 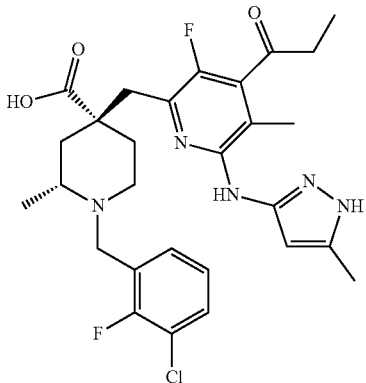 | (2R,4R)-1-(3-chloro-2-fluorobenzyl)-4-((3-fluoro-5-methyl-6-((5-methyl-1H-pyrazol-3-yl)amino)-4-propionylpyridin-2-yl)methyl)-2-methylpiperidine-4-carboxylic acid | 560 |
| 437. | 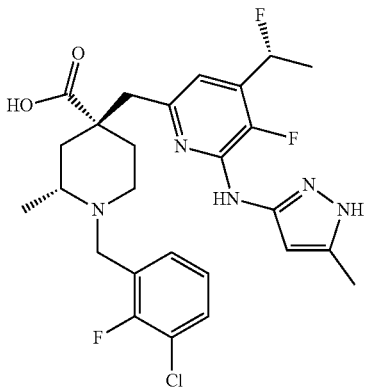 | (2R,4R)-1-(3-chloro-2-fluorobenzyl)-4-((5-fluoro-4-((R)-1-fluoroethyl)-6-((5-methyl-1H-pyrazol-3-yl)amino)pyridin-2-yl)methyl)-2-methylpiperidine-4-carboxylic acid | 536 |

| Example No. | Structure | Chemical Name | MS: (M + H)+ |
|---|---|---|---|
| 438. | 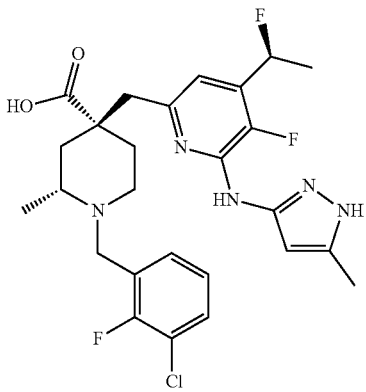 | (2R,4R)-1-(3-chloro-2-fluorobenzyl)-4-((5-fluoro-4-((S)-1-fluoroethyl)-6-((5-methyl-1H-pyrazol-3-yl)amino)pyridin-2-yl)methyl)-2-methylpiperidine-4-carboxylic acid | 536 |
| 439. | 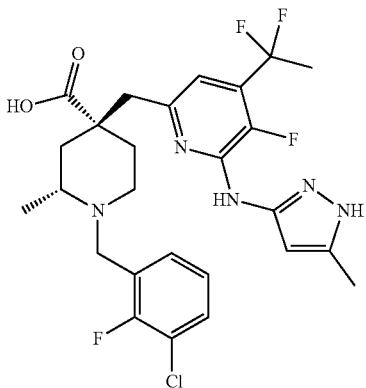 | (2R,4R)-1-(3-chloro-2-fluorobenzyl)-4-((4-(1,1-difluoroethyl)-5-fluoro-6-((5-methyl-1H-pyrazol-3-yl)amino)pyridin-2-yl)methyl)-2-methylpiperidine-4-carboxylic acid | 554 |
| 440. | 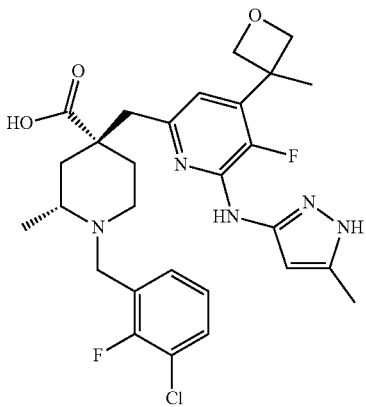 | (2R,4R)-1-(3-chloro-2-fluorobenzyl)-4-((5-fluoro-6-((5-methyl-1H-pyrazol-3-yl)amino)-4-(3-methyloxetan-3-yl)pyridin-2-yl)methyl)-2-methylpiperidine-4-carboxylic acid | 560 |

-continued

| Example No. | Structure | Chemical Name | MS: (M + H)+ |
|---|---|---|---|
| 441. | 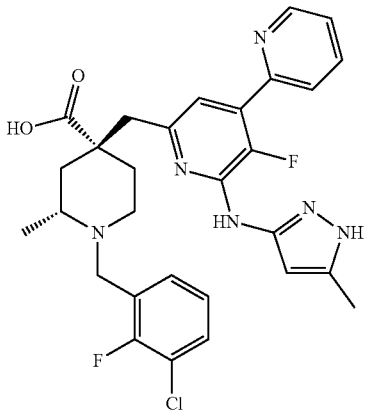 | (2R,4R)-1-(3-chloro-2-fluorobenzyl)-4-((5'-fluoro-6'-((5-methyl-1H-pyrazol-3-yl)amino)-[2,4'-bipyridin]-2'-yl)methyl)-2-methylpiperidine-4-carboxylic acid | 567 |
| 442. | 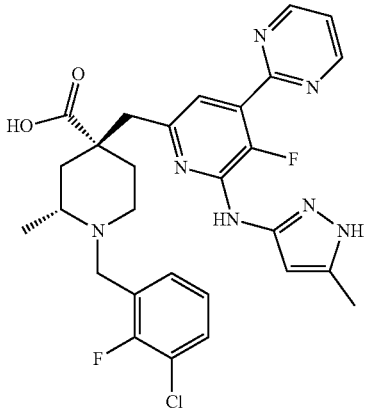 | (2R,4R)-1-(3-chloro-2-fluorobenzyl)-4-((5-fluoro-6-((5-methyl-1H-pyrazol-3-yl)amino)-4-(pyrimidin-2-yl)pyridin-2-yl)methyl)-2-methylpiperidine-4-carboxylic acid | 568 |
| 443. | 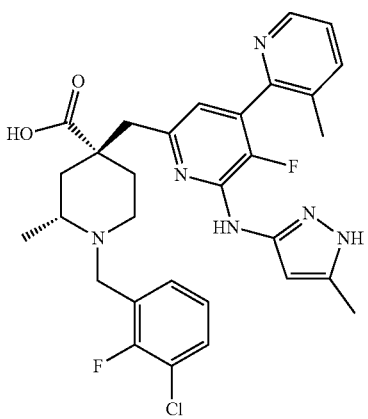 | (2R,4R)-1-(3-chloro-2-fluorobenzyl)-4-((5'-fluoro-3-methyl-6'-((5-methyl-1H-pyrazol-3-yl)amino)-[2,4'-bipyridin]-2'-yl)methyl)-2-methylpiperidine-4-carboxylic acid | 581 |

| Example No. | Structure | Chemical Name | MS: (M + H)+ |
| --- | --- | --- | --- |
| 444. | 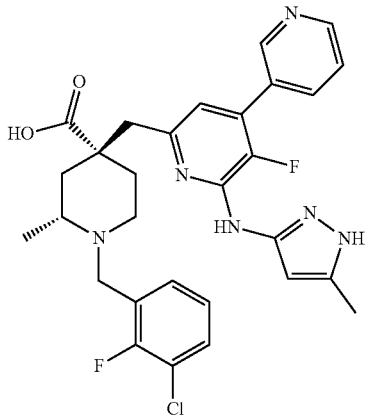 | (2R,4R)-1-(3-chloro-2-fluorobenzyl)-4-((5'-fluoro-6'-((5-methyl-1H-pyrazol-3-yl)amino)-[3,4'-bipyridin]-2'-yl)methyl)-2-methyl-piperidine-4-carboxylic acid | 567 |
| 445. | 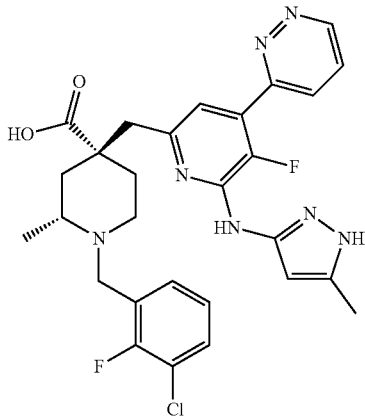 | (2R,4R)-1-(3-chloro-2-fluorobenzyl)-4-((5-fluoro-6-((5-methyl-1H-pyrazol-3-yl)amino)-4-(pyridazin-3-yl)pyridin-2-yl)methyl)-2-methylpiperidine-4-carboxylic acid | 568 |
| 446. | 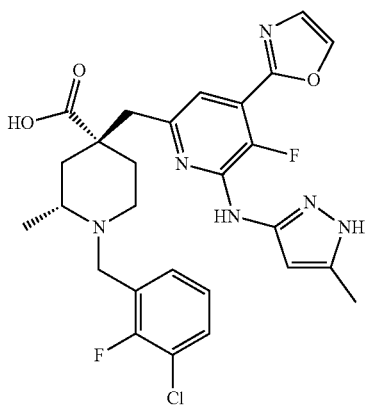 | (2R,4R)-1-(3-chloro-2-fluorobenzyl)-4-((5-fluoro-6-((5-methyl-1H-pyrazol-3-yl)amino)-4-(oxazol-2-yl)pyridin-2-yl)methyl)-2-methylpiperidine-4-carboxylic acid | 557 |

| Example No. | Structure | Chemical Name | MS: (M + H)+ |
|---|---|---|---|
| 447. | 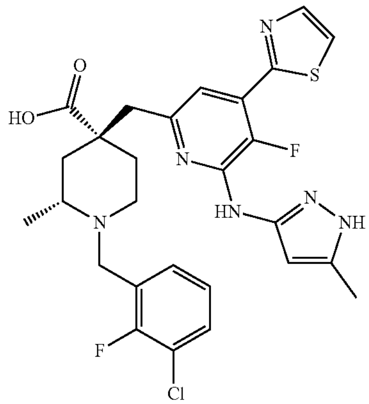 | (2R,4R)-1-(3-chloro-2-fluorobenzyl)-4-((5-fluoro-6-((5-methyl-1H-pyrazol-3-yl)amino)-4-(thiazol-2-yl)pyridin-2-yl)methyl)-2-methylpiperidine-4-carboxylic acid | 573 |
| 448. | 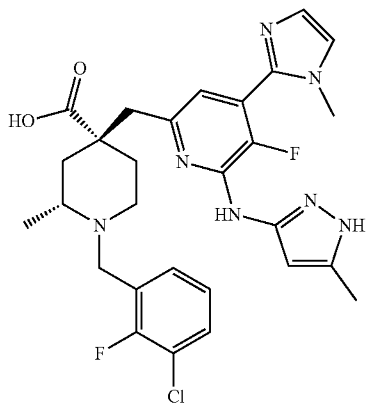 | (2R,4R)-1-(3-chloro-2-fluorobenzyl)-4-((5-fluoro-4-(1-methyl-1H-imidazol-2-yl)-6-((5-methyl-1H-pyrazol-3-yl)amino)pyridin-2-yl)methyl)-2-methylpiperidine-4)-carboxylic acid | 570 |
| 449. | 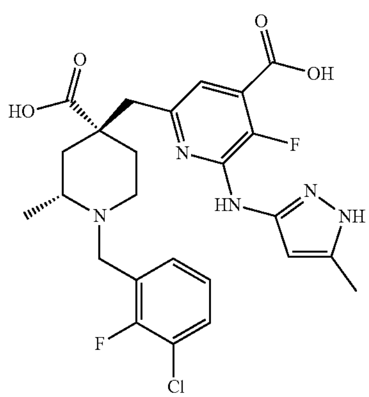 | 6-(((2R,4R)-4-carboxy-1-(3-chloro-2-fluorobenzyl)-2-methylpiperidin-4-yl)methyl)-3-fluoro-2-((5-methyl-1H-pyrazol-3-yl)amino)-isonicotinic acid | 534 |
| 450. | 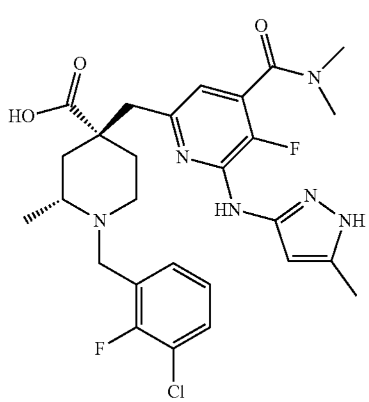 | (2R,4R)-1-(3-chloro-2-fluorobenzyl)-4-((4-(dimethylcarbamoyl)-5-fluoro-6-((5-methyl-1H-pyrazol-3-yl)amino)pyridin-2-yl)methyl)-2-methylpiperidine-4-carboxylic acid | 561 |

| Example No. | Structure | Chemical Name | MS: (M + H)+ |
|---|---|---|---|
| 451. | 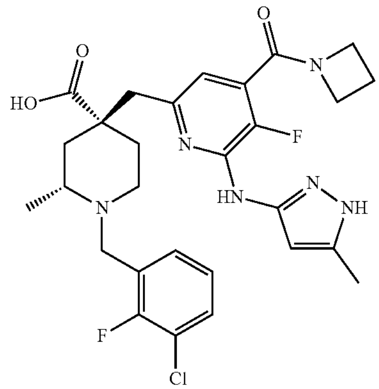 [SMILES: Cc1cc(Nc2nc(C[C@@]3(C(=O)O)CCN(Cc4cccc(Cl)c4F)[C@H](C)C3)cc(C(=O)N3CCC3)c2F)n[nH]1] | (2R,4R)-4-((4-(azetidine-1-carbonyl)-5-fluoro-6-((5-methyl-1H-pyrazol-3-yl)amino)pyridin-2-yl)methyl)-1-(3-chloro-2-fluorobenzyl)-2-methylpiperidine-4-carboxylic acid | 573 |
| 452. | 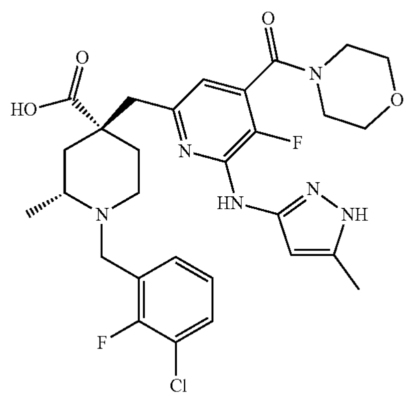 [SMILES: Cc1cc(Nc2nc(C[C@@]3(C(=O)O)CCN(Cc4cccc(Cl)c4F)[C@H](C)C3)cc(C(=O)N3CCOCC3)c2F)n[nH]1] | (2R,4R)-1-(3-chloro-2-fluorobenzyl)-4-((5-fluoro-6-((5-methyl-1H-pyrazol-3-yl)amino)-4-(morpholine-4-carbonyl)pyridin-2-yl)methyl)-2-methylpiperidine-4)-carboxylic acid | 603 |
| 453. | 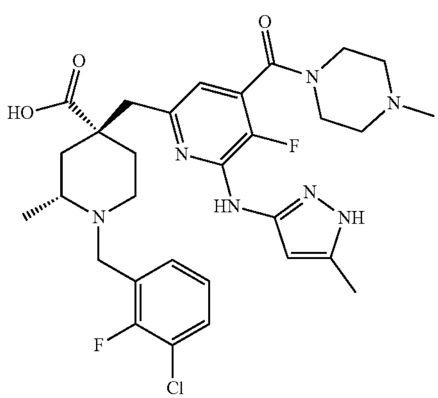 | (2R,4R)-1-(3-chloro-2-fluorobenzyl)-4-((5-fluoro-6-((5-methyl-1H-pyrazol-3-yl)amino)-4-(4-methylpiperazme-1-carbonyl)pyridin-2-yl)methyl)-2-methylpiperidine-4-carboxylic acid | 616 |
| 454. | 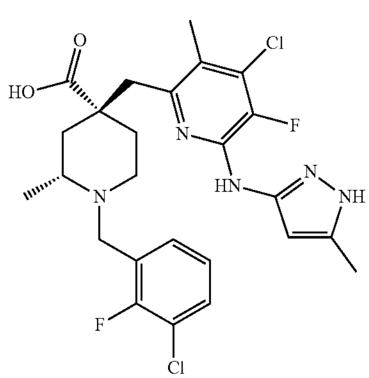 | (2R,4R)-1-(3-chloro-2-fluorobenzyl)-4-((4-chloro-5-fluoro-3-methyl-6-((5-methyl-1H-pyrazol-3-yl)amino)pyridin-2-yl)methyl)-2-methylpiperidine-4-carboxylic acid | 538 |

-continued

| Example No. | Structure | Chemical Name | MS: (M + H)+ |
|---|---|---|---|
| 455. | 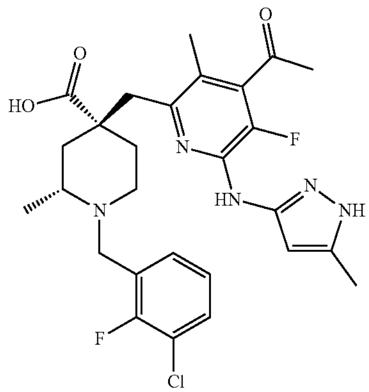 | (2R,4R)-4-((4-acetyl-5-fluoro-3-methyl-6-((5-methyl-1H-pyrazol-3-yl)amino)pyridin-2-yl)methyl)-1-(3-chloro-2-fluorobenzyl)-2-methylpiperidine-4-carboxylic acid | 546 |
| 456. | 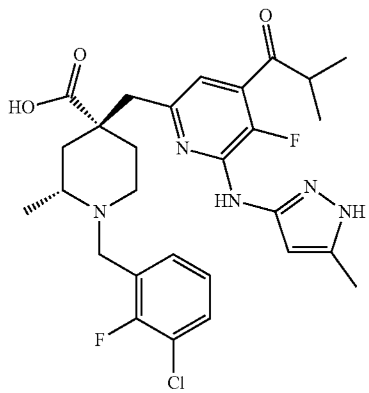 | (2R,4R)-1-(3-chloro-2-fluorobenzyl)-4-((5-fluoro-4-isobutyryl-6-((5-methyl-1H-pyrazol-3-yl)amino)-pyridin-2-yl)methyl)-2-methyl-piperidine-4-carboxylic acid | 560 |
| 457. | 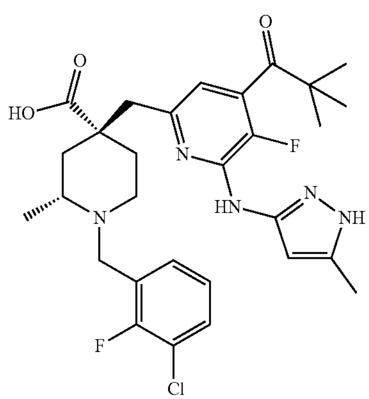 | (2R,4R)-1-(3-chloro-2-fluorobenzyl)-4-((5-fluoro-6-((5-methyl-1H-pyrazol-3-yl)amino)-4-pivalo-ylpyridin-2-yl)methyl)-2-methyl-piperidine-4-carboxylic acid | 574 |
| 458. | 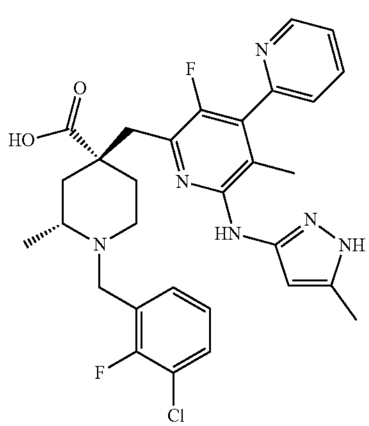 | (2R,4R)-1-(3-chloro-2-fluorobenzyl)-4-((3'-fluoro-5'-methyl-6'-((5-methyl-1H-pyrazol-3-yl)amino)-[2,4'-bipyridin]-2'-yl)methyl)-2-methylpiperidine-4-carboxylic acid | 581 |

| Example No. | Structure | Chemical Name | MS: (M + H)⁺ |
|---|---|---|---|
| 459. | 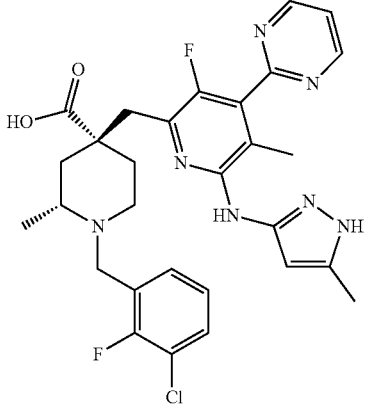 | (2R,4R)-1-(3-chloro-2-fluorobenzyl)-4-((3-fluoro-5-methyl-6-((5-methyl-1H-pyrazol-3-yl)amino)-4-(pyrimidin-2-yl)pyridin-2-yl)methyl)-2-methylpiperidine-4-carboxylic acid | 582 |
| 460. | 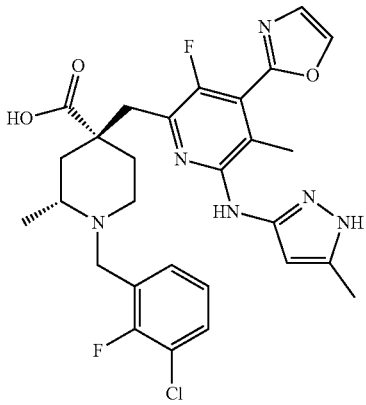 | (2R,4R)-1-(3-chloro-2-fluorobenzyl)-4-((3-fluoro-5-methyl-6-((5-methyl-1H-pyrazol-3-yl)amino)-4-(oxazol-2-yl)pyridin-2-yl)methyl)-2-methylpiperidine-4-carboxylic acid | 571 |
| 461. | 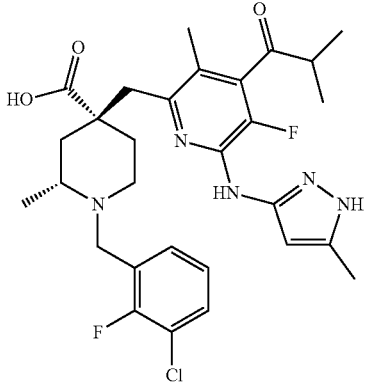 | (2R,4R)-1-(3-chloro-2-fluorobenzyl)-4-((5-fluoro-4-isobutyryl-3-methyl-6-((5-methyl-1H-pyrazol-3-yl)amino)pyridin-2-yl)methyl)-2-methylpiperidine-4-carboxylic acid | 574 |

| Example No. | Structure | Chemical Name | MS: (M + H)+ |
|---|---|---|---|
| 462. | 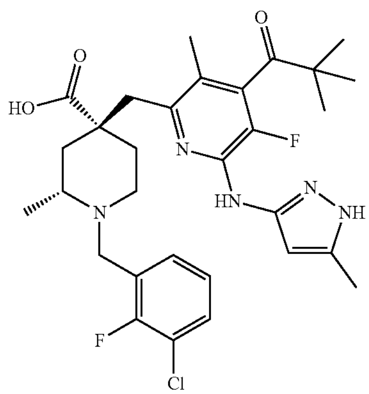 | (2R,4R)-1-(3-chloro-2-fluorobenzyl)-4-((5-fluoro-3-methyl-6-((5-methyl-1H-pyrazol-3-yl)amino)-4-pivaloylpyridin-2-yl)methyl)-2-methylpiperidine-4-carboxylic acid | 588 |
| 463. | 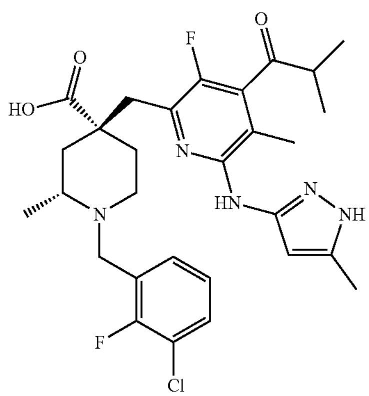 | (2R,4R)-1-(3-chloro-2-fluorobenzyl)-4-((3-fluoro-4-isobutyryl-5-methyl-6-((5-methyl-1H-pyrazol-3-yl)amino)pyridin-2-yl)methyl)-2-methylpiperidine-4-carboxylic acid | 574 |
| 464. | 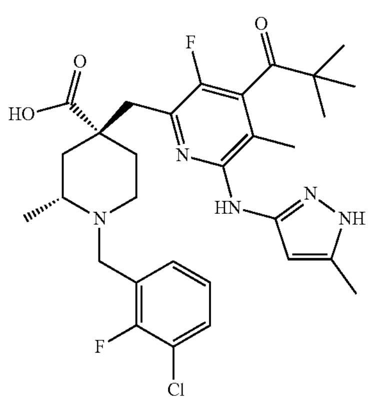 | (2R,4R)-1-(3-chloro-2-fluorobenzyl)-4-((3-fluoro-5-methyl-6-((5-methyl-1H-pyrazol-3-yl)amino)-4-pivaloylpyridin-2-yl)methyl)-2-methylpiperidine-4-carboxylic acid | 588 |
| 465. | 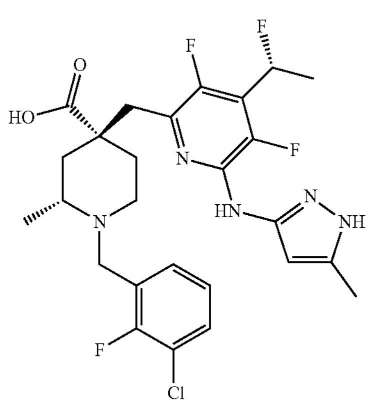 | (2R,4R)-1-(3-chloro-2-fluorobenzyl)-4-((3,5-difluoro-4-((R)-1-fluoroethyl)-6-((5-methyl-1H-pyrazol-3-yl)amino)pyridin-2-yl)methyl)-2-methylpiperidine-4-carboxylic acid | 554 |

| Example No. | Structure | Chemical Name | MS: (M + H)+ |
|---|---|---|---|
| 466. | 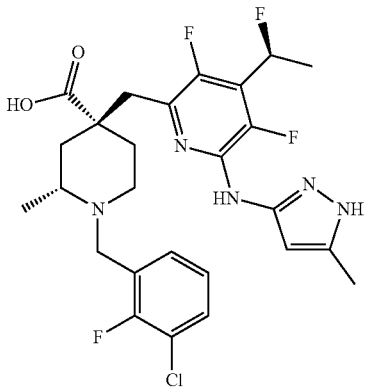 | (2R,4R)-1-(3-chloro-2-fluorobenzyl)-4-((3,5-difluoro-4-((S)-1-fluoroethyl)-6-((5-methyl-1H-pyrazol-3-yl)amino)pyridin-2-yl)methyl)-2-methylpiperidine-4-carboxylic acid | 554 |
| 467. | 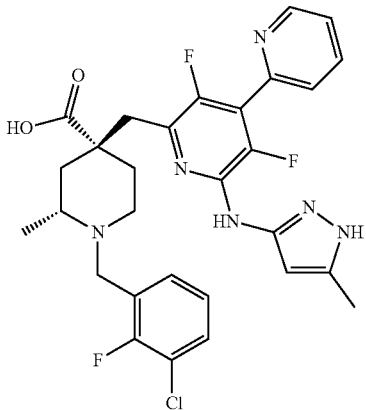 | (2R,4R)-1-(3-chloro-2-fluorobenzyl)-4-((3',5,-difluoro-6'-((5-methyl-1H-pyrazol-3-yl)amino)-[2,4'-bipyridin]-2'-yl)methyl)-2-methylpiperidine-4-carboxylic acid | 585 |
| 468. | 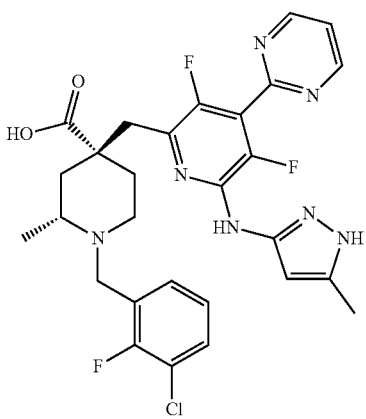 | (2R,4R)-1-(3-chloro-2-fluorobenzyl)-4-((3,5-difluoro-6-((5-methyl-1H-pyrazol-3-yl)amino)-4-(pyrimidin-2-yl)pyridin-2-yl)methyl)-2-methylpiperidine-4-carboxylic acid | 586 |

-continued

| Example No. | Structure | Chemical Name | MS: (M + H)+ |
| --- | --- | --- | --- |
| 469. | 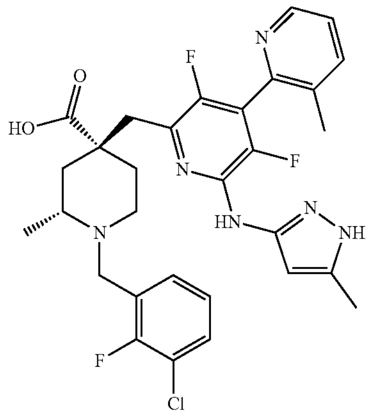 | (2R,4R)-1-(3-chloro-2-fluorobenzyl)-4-((3',5'-difluoro-3-methyl-6'-((5-methyl-1H-pyrazol-3-yl)amino)-[2,4'-bipyridin]-2'-yl)methyl)-2-methylpiperidine-4-carboxylic acid | 599 |
| 470. | 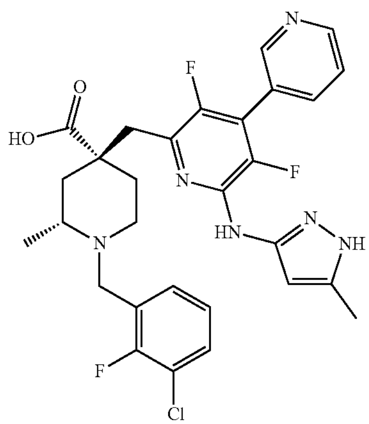 | (2R,4R)-1-(3-chloro-2-fluorobenzyl)-4-((3',5'-difluoro-6'-((5-methyl-1H-pyrazol-3-yl)amino)-[3,4'-bipyridin]-2'-yl)methyl)-2-methylpiperidine-4-carboxylic acid | 585 |
| 471. | 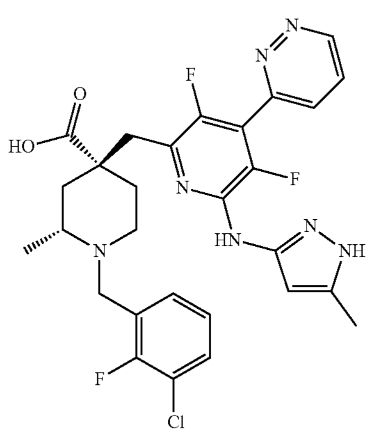 | (2R,4R)-1-(3-chloro-2-fluorobenzyl)-4-((3,5-difluoro-6-((5-methyl-1H-pyrazol-3-yl)amino)-4-(pyridazin-3-yl)pyridin-2-yl)methyl)-2-methylpiperidine-4-carboxylic acid | 586 |

-continued

| Example No. | Structure | Chemical Name | MS: (M + H)+ |
| --- | --- | --- | --- |
| 472. | 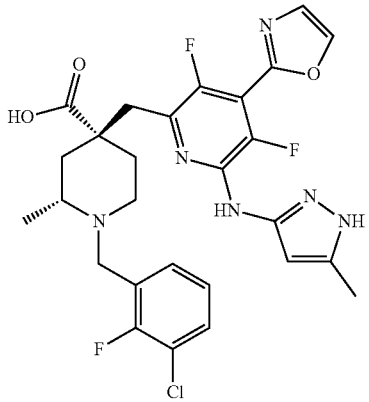 | (2R,4R)-1-(3-chloro-2-fluorobenzyl)-4-((3,5-difluoro-6-((5-methyl-1H-pyrazol-3-yl)amino)-4-(oxazol-2-yl)pyridin-2-yl)methyl)-2-methylpiperidine-4-carboxylic acid | 575 |
| 473. | 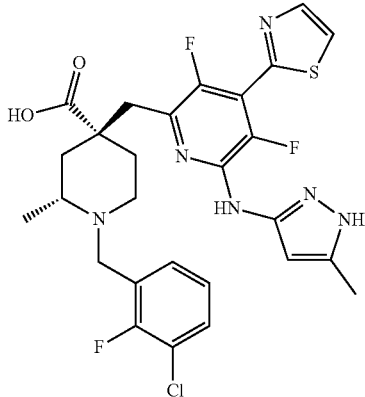 | (2R,4R)-1-(3-chloro-2-fluorobenzyl)-4-((3,5-difluoro-6-((5-methyl-1H-pyrazol-3-yl)amino)-4-(thiazol-2-yl)pyridin-2-yl)methyl)-2-methylpiperidine-4-carboxylic acid | 591 |
| 474. | 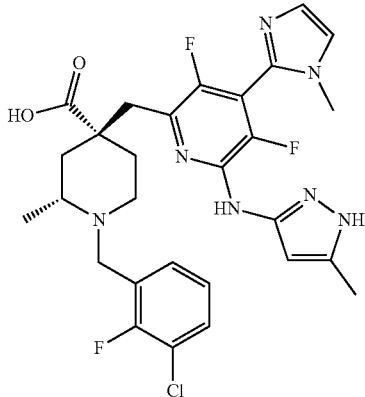 | (2R,4R)-1-(3-chloro-2-fluorobenzyl)-4-((3,5-difluoro-4-(1-methyl-1H-imidazol-2-yl)-6-((5-methyl-1H-pyrazol-3-yl)amino)pyridin-2-yl)methyl)-2-methylpiperidine-4-carboxylic acid | 588 |

-continued

| Example No. | Structure | Chemical Name | MS: (M + H)+ |
|---|---|---|---|
| 475. | 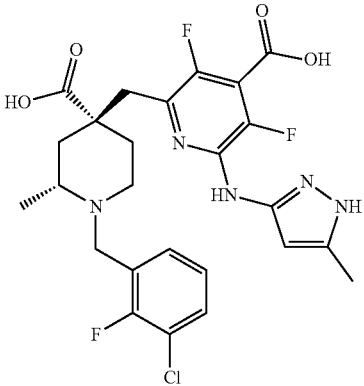 | 2-(((2R,4R)-4-carboxy-1-(3-chloro-2-fluorobenzyl)-2-methylpiperidin-4-yl)methyl)-3,5-difluoro-6-((5-methyl-1H-pyrazol-3-yl)amino)isonicotinic acid | 552 |
| 476. | 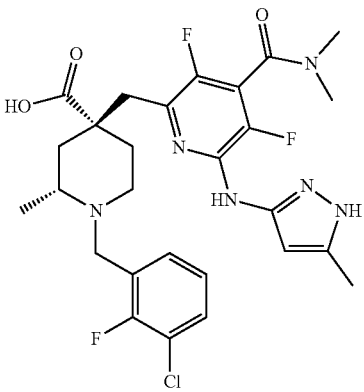 | (2R,4R)-1-(3-chloro-2-fluorobenzyl)-4-((4-(dimethylcarbamoyl)-3,5-difluoro-6-((5-methyl-1H-pyrazol-3-yl)amino)pyridin-2-yl)methyl)-2-methylpiperidine-4-carboxylic acid | 579 |
| 477. | 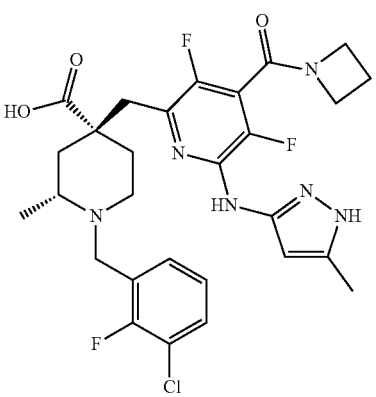 [SMILES: Cc1cc(Nc2nc(C[C@@]3(C(=O)O)CCN(Cc4cccc(Cl)c4F)[C@H](C)C3)c(F)c(C(=O)N3CCC3)c2F)n[nH]1] | (2R,4R)-4-((4-(azetidine-1-carbonyl)-3,5-difluoro-6-((5-methyl-1H-pyrazol-3-yl)amino)pyridin-2-yl)methyl)-1-(3-chloro-2-fluorobenzyl)-2-methylpiperidine-4-carboxylic acid | 591 |
| 478. | 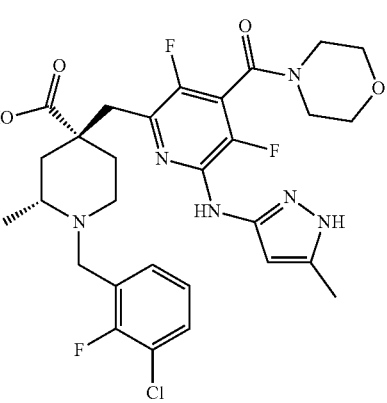 | (2R,4R)-1-(3-chloro-2-fluorobenzyl)-4-((3,5-difluoro-6-((5-methyl-1H-pyrazol-3-yl)amino)-4-(morpholine-4-carbonyl)pyridin-2-yl)methyl)-2-methylpiperidine-4-carboxylic acid | 621 |

-continued

| Example No. | Structure | Chemical Name | MS: (M + H)+ |
|---|---|---|---|
| 479. | 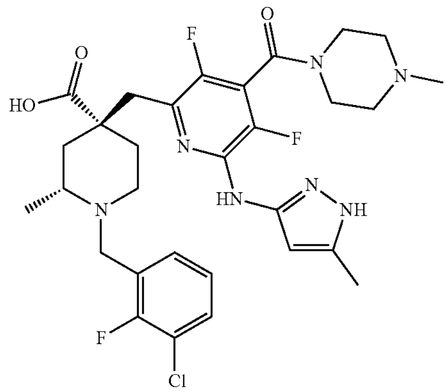 | (2R,4R)-1-(3-chloro-2-fluorobenzyl)-4-((3,5-difluoro-6-((5-methyl-1H-pyrazol-3-yl)amino)-4-(4-methylpiperazine-1-carbonyl)-pyridin-2-yl)methyl)-2-methylpiperidine-4-carboxylic acid | 634 |
| 480. | 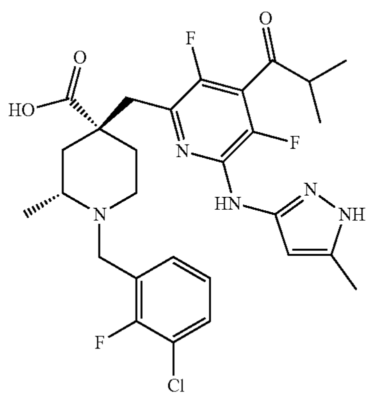 | (2R,4R)-1-(3-chloro-2-fluorobenzyl)-4-((3,5-difluoro-4-isobutyryl-6-((5-methyl-1H-pyrazol-3-yl)amino)pyridin-2-yl)methyl)-2-methylpiperidine-4-carboxylic acid | 578 |
| 481. | 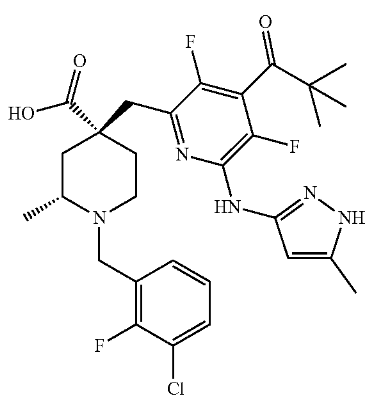 | (2R,4R)-1-(3-chloro-2-fluorobenzyl)-4-((3,5-difluoro-6-((5-methyl-1H-pyrazol-3-yl)amino)-4-pivaloylpyridin-2-yl)methyl)-2-methylpiperidine-4-carboxylic acid | 592 |
| 482. | 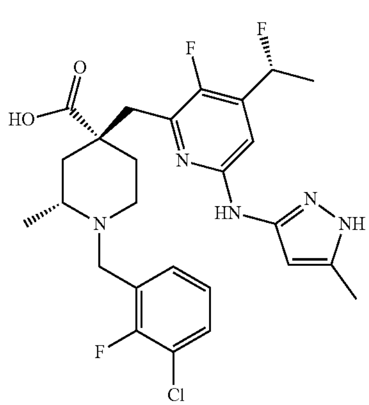 | (2R,4R)-1-(3-chloro-2-fluorobenzyl)-4-((3-fluoro-4-((R)-1-fluoroethyl)-6-((5-methyl-1H-pyrazol-3-yl)amino)pyridin-2-yl)methyl)-2-methylpiperidine-4-carboxylic acid | 536 |

| Example No. | Structure | Chemical Name | MS: (M + H)+ |
|---|---|---|---|
| 483. | 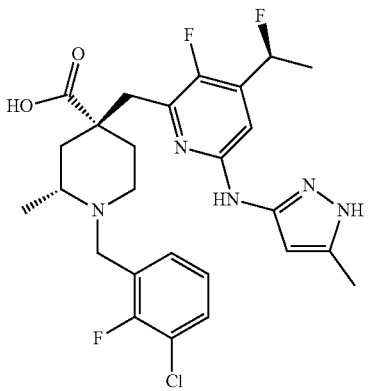 | (2R,4R)-1-(3-chloro-2-fluorobenzyl)-4-((3-fluoro-4-((S)-1-fluoroethyl)-6-((5-methyl-1H-pyrazol-3-yl)amino)pyridin-2-yl)methyl)-2-methylpiperidine-4-carboxylic acid | 536 |
| 484. | 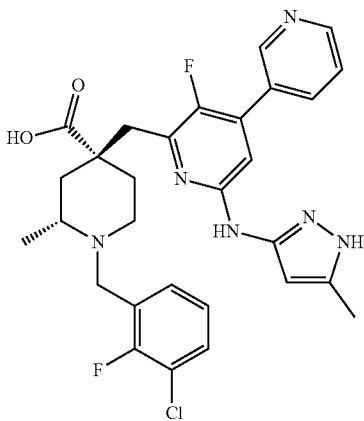 | (2R,4R)-1-(3-chloro-2-fluorobenzyl)-4-((3'-fluoro-6'-((5-methyl-1H-pyrazol-3-yl)amino)-[3,4'-bipyridin]-2'-yl)methyl)-2-methylpiperidine-4-carboxylic acid | 567 |
| 485. | 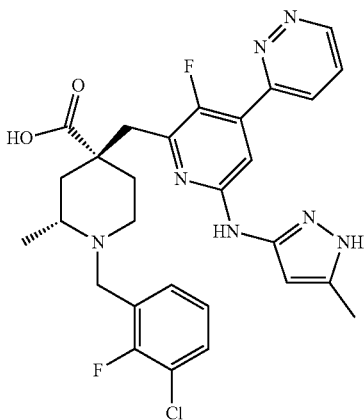 | (2R,4R)-1-(3-chloro-2-fluorobenzyl)-4-((3-fluoro-6-((5-methyl-1H-pyrazol-3-yl)amino)-4-(pyridazin-3-yl)pyridin-2-yl)methyl)-2-methylpiperidine-4-carboxylic acid | 568 |

-continued

| Example No. | Structure | Chemical Name | MS: (M + H)+ |
|---|---|---|---|
| 486. | 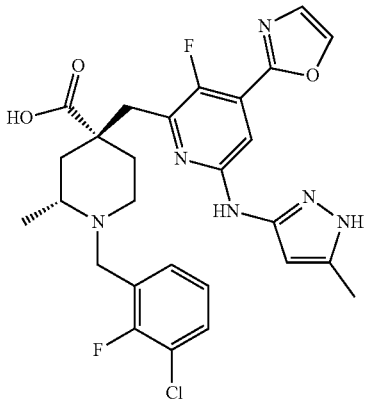 | (2R,4R)-1-(3-chloro-2-fluorobenzyl)-4-((3-fluoro-6-((5-methyl-1H-pyrazol-3-yl)amino)-4-(oxazol-2-yl)pyridin-2-yl)methyl)-2-methylpiperidine-4-carboxylic acid | 557 |
| 487. | 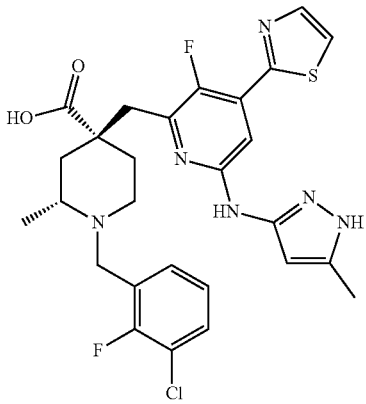 | (2R,4R)-1-(3-chloro-2-fluorobenzyl)-4-((3-fluoro-6-((5-methyl-1H-pyrazol-3-yl)amino)-4-(thiazol-2-yl)pyridin-2-yl)methyl)-2-methylpiperidine-4-carboxylic acid | 573 |
| 488. | 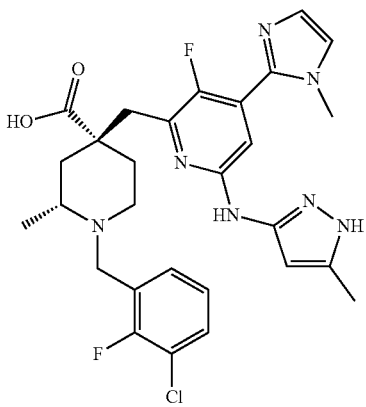 | (2R,4R)-1-(3-chloro-2-fluorobenzyl)-4-((3-fluoro-4-(1-methyl-1H-imidazol-2-yl)-6-((5-methyl-1H-pyrazol-3-yl)amino)pyridin-2-yl)methyl)-2-methylpiperidine-4-carboxylic acid | 570 |

| Example No. | Structure | Chemical Name | MS: (M + H)+ |
|---|---|---|---|
| 489. | 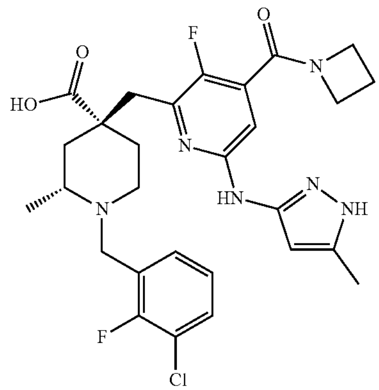 [SMILES: Cc1cc(Nc2cc(C(=O)N3CCC3)c(F)c(C[C@@]3(C(=O)O)CCN(Cc4cccc(Cl)c4F)[C@H](C)C3)n2)n[nH]1] | (2R,4R)-4-((4-(azetidine-1-carbonyl)-3-fluoro-6-((5-methyl-1H-pyrazol-3-yl)amino)pyridin-2-yl)methyl)-1-(3-chloro-2-fluorobenzyl)-2-methylpiperidine-4-carboxylic acid | 573 |
| 490. | 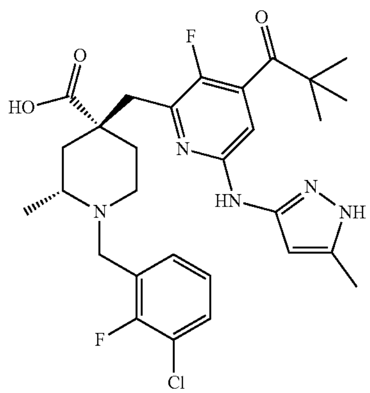 | (2R,4R)-1-(3-chloro-2-fluorobenzyl)-4-((3-fluoro-6-((5-methyl-1H-pyrazol-3-yl)amino)-4-pivaloylpyridin-2-yl)methyl)-2-methylpiperidine-4-carboxylic acid | 574 |
| 491. | 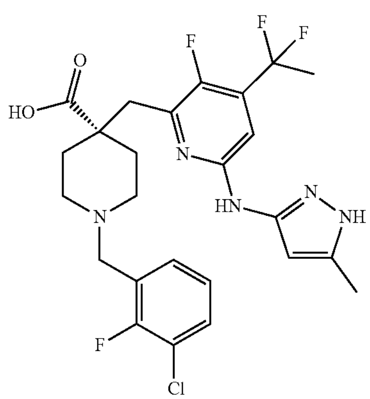 | 1-(3-chloro-2-fluorobenzyl)-4-((4-(1,1-difluoroethyl)-3-fluoro-6-((5-methyl-1H-pyrazol-3-yl)amino)pyridin-2-yl)methyl)piperidine-4-carboxylic acid | 540 |
| 492. | 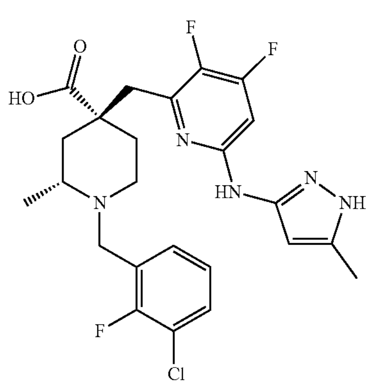 | (2R,4R)-1-(3-chloro-2-fluorobenzyl)-4-((3,4-difluoro-6-((5-methyl-1H-pyrazol-3-yl)amino)pyridin-2-yl)methyl)-2-methylpiperidine-4-carboxylic acid | 508 |

-continued

| Example No. | Structure | Chemical Name | MS: (M + H)+ |
|---|---|---|---|
| 493. | 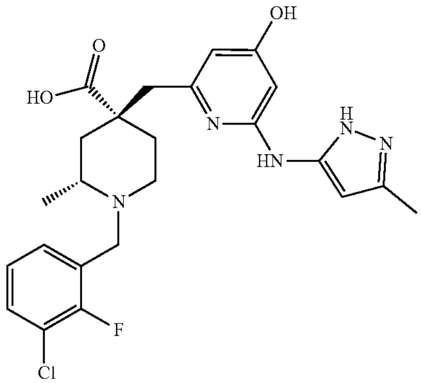 [SMILES: Cc1cc(Nc2cc(O)cc(C[C@@]3(C(=O)O)CCN(Cc4cccc(Cl)c4F)[C@H](C)C3)n2)[nH]n1] | (2R,4R)-1-(3-chloro-2-fluorobenzyl)-4-((4-hydroxy-6-((3-methyl-1H-pyrazol-5-yl)amino)pyridin-2-yl)methyl)-2-methylpiperidine-4-carboxylic acid | 508 |
| 494. | 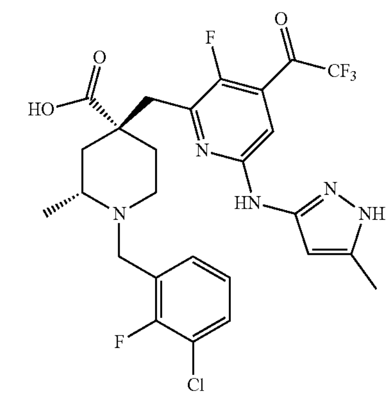 | (2R,4R)-1-(3-chloro-2-fluorobenzyl)-4-((3-fluoro-6-((5-methyl-1H-pyrazol-3-yl)amino)-4-(2,2,2-trifluoroacetyl)pyridin-2-yl)methyl)-2-methylpiperidine-4-carboxylic acid | 586 |
| 495. | 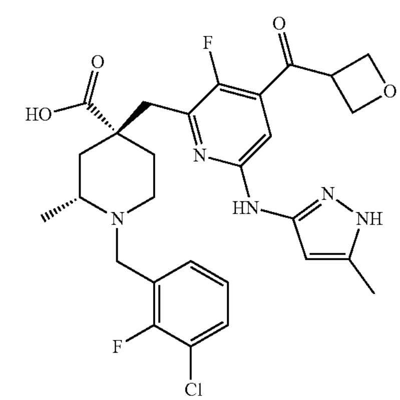 [SMILES: Cc1cc(Nc2cc(C(=O)C3COC3)c(F)c(C[C@@]3(C(=O)O)CCN(Cc4cccc(Cl)c4F)[C@H](C)C3)n2)n[nH]1] | (2R,4R)-1-(3-chloro-2-fluorobenzyl)-4-((3-fluoro-6-((5-methyl-1H-pyrazol-3-yl)amino)-4-(oxetane-3-carbonyl)pyridin-2-yl)methyl)-2-methylpiperidine-4-carboxylic acid | 574 |
| 496. | 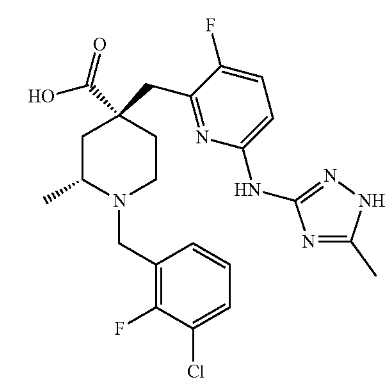 | (2R,4R)-1-(3-chloro-2-fluorobenzyl)-4-(2-fluoro-5-((5-methyl-1H-1,2,4-triazol-3-yl)amino)benzyl)-2-methylpiperidine-4-carboxylic acid | 490 |

Pharmacological Testing

Note that an Aurora A selective inhibitor, LY3295668, presently under clinical development was used as a control compound.

Example A: Evaluation of Aurora a and Aurora B Inhibitory Effect—Kinase Assay

The inhibitory activities of a test compound against Aurora A and Aurora B were measured according to the following method.

The $IC_{50}$ value of Aurora A and Aurora B kinase was performed by Sundia MediTech Co. Ltd. using Mobility shift assay. And the results are shown in Table A.

Experimental Methods:
(1) Prepare a 1× kinase buffer [50 mM 4-(2-hydroxy-ethyl)-1-piperazineethanesulfonic acid (HEPES), PH 7.5, 0.01% Brij-35, 10 mM $MgCl_2$, 2 mM dithiothreitol (DTT)].
(2) Prepare compound:

The testing compound was dissolved with DMSO. The testing compound was diluted up to 100× final concentration in a 384-well plate. Transfer 250 nL of the compound dilution to a 384-well assay plate using Echo 550. 100% DMSO of 250 nL was added to the negative control well and the positive control well.

(3) Prepare a 2.5× enzyme solution using the above 1× kinase buffer.
(4) Add 10 μL of the 2.5× enzyme solution to the compound well and the positive control well of the 384-well assay plate. Add 10 μL of the 1× kinase buffer to the negative control well.
(5) The 384-well plate was centrifuged at 1000 rpm for 30 seconds and incubated at room temperature for 10 min.
(6) A mixture of ATP and Kinase substrate 21 with a final concentration of 25/15× was prepared by the 1× kinase buffer.
(7) Add 15 μL of the mixture of 25/15×ATP and kinase substrate solution 21 to start reaction.
(8) The 384-well plate was centrifuged at 1000 rpm for 30 seconds and incubated at room temperature.
(9) 30 μL of the stop and detection buffer was added to stop the kinase reaction and centrifuged at 1000 rpm for 30 seconds.
(10) Collect data on Caliper EZ ReaderII.

Data Analysis:

$$Inhibition\% = \frac{Conversion\%\_max - Conversion\%\_sample}{Conversion\%_{max} - Conversion\%\_min} \times 100 \quad \text{Formula}$$

Conversion %_sample is conversion rate data of samples. Conversion %_min is mean value of negative control (conversion rate data without enzyme activation). Conversion %_max is mean positive control (conversion rate data without compound).

Curve Fitting:

The log of concentration is on the X axis, and the percentage inhibition is on the Y axis. Fit the Quantitative effect curves with log (inhibitor) vs. response—Variable slope in GraphPad Prism5 obtain $IC_{50}$ values. Equation used is Y=Bottom+(Top−Bottom)/(1+10^((Log $IC_{50}$−X)*Hill-Slope)).

TABLE A

| Example | Aurora A $IC_{50}$/nM | $IC_{50}$ Ratio Aur B/Aur A |
|---|---|---|
| 1 | 1.3 | 2288 |
| 2 | 2.9 | 1236 |
| 5 | 0.59 | 1311 |
| 6 | 0.33 | 6112 |
| 8 | 1.2 | 1288 |
| 10 | 1.0 | 979 |
| 11 | 0.64 | 2264 |
| 12 | 2.4 | 2560 |
| 15 | 0.55 | 1755 |
| 16 | 1.7 | 1812 |
| 17 | 3.2 | 2974 |
| 21 | 3.1 | 1789 |
| 23 | 0.91 | 613 |
| 26 | 2.9 | 1499 |
| 27 | 0.81 | 622 |
| 29 | 1.4 | 586 |
| 30 | 1.1 | 782 |
| 33 | 1.5 | 3757 |
| 35 | 1.9 | 2403 |
| 38 | 0.85 | 986 |
| 39 | 0.57 | 3019 |
| 41 | 2.7 | 3682 |
| 45 | 0.88 | 523 |
| 49 | 0.7 | 443 |
| 50 | 0.52 | 845 |
| 51 | 0.22 | 2833 |
| 52 | 1.3 | 1285 |
| 53 | 0.55 | 562 |
| 54 | 0.43 | 2041 |
| 55 | 0.88 | 3835 |
| 66 | 0.57 | 716 |
| 67 | 1.6 | 759 |
| 69 | 0.91 | 1444 |
| 72 | 0.64 | 582 |
| 73 | 0.76 | 779 |
| 74 | 0.67 | 3358 |
| 78 | 0.37 | 1219 |
| 79 | 0.61 | 2036 |
| 81 | 0.77 | 1353 |
| 84 | 1.4 | 4026 |
| 90 | 0.54 | 1479 |
| 91 | 1.1 | 451 |
| 92 | 0.74 | 4393 |
| 102 | 0.93 | 804 |
| LY3295668 | 1.0 | 741 |

As a result, the compound of the invention exhibited high inhibitory activity against Aurora A and low inhibitory activity Aurora B, compared to a control compound, LY3295668. It was demonstrated that the compound of the invention has selectivity for Aurora A.

Example B: Cell Proliferation Assay

NCI-H2171 and NCI-H446 cell proliferation analysis were conducted by CellTiter-Glo (Promega, Cat #G1111). The cells will be harvested respectively during the logarithmic growth period and counted with hemocytometer. The cell viability is over 90% by trypan blue exclusion. Adjust NCI-H2171 and NCI-H446 cells concentrations to $1.0 \times 10^5$ cells/mL with complete medium (RPMI-1640 medium supplemented with 10% (v/v) fetal bovine serum). 100 μL/cell suspensions were added to 96-well plates, and the final cell densities were $1.0 \times 10^4$ cells/well. The plate will be cultured overnight in 5% $CO_2$ and 95% humidity at 37° C. The next day, the test compound was dissolved in DMSO as stock solution. Then the different concentrations of compound were added into 96-well plates. The plates will be cultured for 5 days, then measured by means of CellTiter- Glo assay. 50 µL/cell CellTiter-Glo reagent was added into 96-well plates. Shock incubation for 5 min and then stand incubation for 10 min at room temperature. Record the Luminosity values using an microplate spectrophotometer (Spark, Tecan). Fit the data using GraphPad 8.0 and obtain $IC_{50}$ values.

Formula:

$$\text{Survival (\%)} = (Lum_{test} - Lum_{media\ control}) / (Lum_{cell\ control} - Lum_{media\ control}) \times 100\%$$

The $IC_{50}$ results of the compounds of the invention are shown by Table B.

TABLE B

| Example | NCI-H2171 $IC_{50}$/nM | NCI-H446 $IC_{50}$/nM |
| --- | --- | --- |
| 5 | 30 | 80 |
| 6 | 55 | 103 |
| 8 | 75 | 119 |
| 30 | 62 | 128 |
| 49 | 18 | 24 |
| 50 | 25 | 73 |
| 53 | 57 | 154 |
| 69 | 41 | 87 |
| 72 | 23 | 56 |
| 73 | 27 | 63 |
| 78 | 13 | 32 |
| LY3295668 | 47 | 67 |

As a result, the compound according to the invention exhibited excellent cell growth inhibitory effect.

Example C: In Vivo Assay

This study is to examine the anti-tumor efficacy of test compounds in NCI-H446 and NCI-H69 human small cell lung cancer xenograft model in BALB/c nude mice. Each mouse was inoculated subcutaneously at the right flank region with NCI-H446 ($3 \times 10^6$) and NCI-H69 cells ($5 \times 10^6$) in 0.1 mL of PBS and Matrigel (1:1) for tumor development. The mouse were randomized according to tumor size and weight, the treatment began when the mean tumor size reached 100-200 mm$^3$. Anti-tumor activity was assessed according to relative tumor inhibition rate (TGI).

Tumor volumes were measured in two dimensions using a caliper, and the volume was expressed in mm$^3$ using the formula: V=0.5 a×b$^2$ where a and b are the long and short diameters of the tumor, respectively. Statistical analysis of difference in tumor volume among the groups were performed using one-way ANOVA. All data was analyzed using SPSS 22.0 software, p<0.05 was considered to be statistically significant.

The results are shown as in Table C.

TABLE C

| Example | Dose mg/kg | Administration | Administration frequency | Treatment/days | TV (mm$^3$)$^a$ | $TGI_{TV}$(%) | p$^b$ |
| --- | --- | --- | --- | --- | --- | --- | --- |
| Vehicle | — | po. | BID × 10days, QD × 19days | 29 | 1551 ± 126 | — | — |
| 5 | 15 | po. | | 29 | 27 ± 5 | 98 | 0.000 |
| 49 | 15 | po. | | 29 | 160 ± 26 | 90 | 0.000 |
| 72 | 15 | po. | | 29 | 176 ± 25 | 89 | 0.000 |
| 78 | 15 | po. | | 29 | 65 ± 14 | 96 | 0.000 |
| LY3295668 | 15 | po. | | 29 | 245 ± 27 | 84 | 0.000 |

Note: a.mean ± sem; b.vs.Vehicle

Example D: PK in Rat

The compounds were dissolved into 10% DMSO, 30% PEG400, and 60% saline to obtain a solution. SD male rats were given the compound orally and intravenously. Then plasma samples were collected at 0 hour (pre-dose), 0.25, 0.5, 1, 2, 4, 7, 24 hours post-dose. Plasma drug concentration was detected by LC-MS/MS. Pharmacokinetic parameters were calculated using WinNonlin's software with non-compartmental model.

The results are shown in Table D.

TABLE D

| | IV: 3 mg/kg | | PO: 10 mg/kg | | | |
| --- | --- | --- | --- | --- | --- | --- |
| Example | CL (mL/min/kg) | Vss (L/kg) | $C_{max}$ (ng/mL) | $AUC_{last}$ (h * ng/mL) | F% | $t_{1/2}$ (h) |
| 5 | 2.74 | 0.56 | 26600 | 179482 | 168 | 4.25 |
| 6 | 0.67 | 0.18 | 34900 | 215445 | 86 | 6.3 |
| 49 | 1.05 | 0.22 | 21033 | 201715 | 127 | 2.95 |
| 50 | 1.45 | 0.26 | 16100 | 172609 | 140 | 3.62 |
| 78 | 0.585 | 0.22 | 28900 | 235572 | 85.8 | 4.61 |
| LY3295668 | 1.52 | 0.29 | 15033 | 91211 | 81 | 3.37 |

From the above, the compound according to the invention is believed to be useful as an antitumor agent since it exhibits not only excellent cell growth inhibitory action based on Aurora A selective inhibitory activity. They also showed a great anti-tumor efficacy in vivo models.

The compounds of the present invention are preferably formulated as pharmaceutical compositions administered by a variety of routes. Most preferably, such compositions are for oral administration. Such pharmaceutical compositions and processes for preparing the same are well known in the art. See, e.g., REMINGTON: THE SCIENCE AND PRACTICE OF PHARMACY (A. Gennaro, et al, eds., 19$^{th}$ ed., Mack Publishing Co., 1995). The compounds of Formula I, II, III, IV, V, VI or VII are generally effective over a wide dosage range.

For example, dosages per day normally fall within the range of about 1 mg to about 200 mg total daily dose, preferably 0.2 mg to 50 mg total daily dose, more preferably 0.2 mg to 20 mg total daily dose. In some instances dosage levels below the lower limit of the aforesaid range may be more than adequate, while in other cases still larger doses may be employed. The above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

What is claimed is:

1. A compound which is

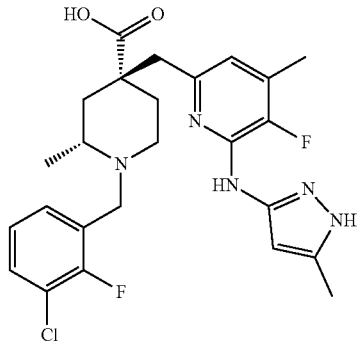 [SMILES: Cc1cc(Nc2nc(C[C@@]3(C(=O)O)CCN(Cc4cccc(Cl)c4F)[C@H](C)C3)cc(C)c2F)n[nH]1]

or a pharmaceutically acceptable salt thereof.

2. A compound which is

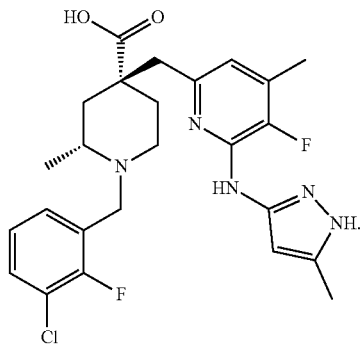 [SMILES: Cc1cc(Nc2nc(C[C@@]3(C(=O)O)CCN(Cc4cccc(Cl)c4F)[C@H](C)C3)cc(C)c2F)n[nH]1]

3. A pharmaceutical composition comprising a therapeutically effective amount of the compound or pharmaceutically acceptable salt thereof of claim 1 and at least one pharmaceutically acceptable excipient.

4. A pharmaceutical composition comprising a therapeutically effective amount of the compound of claim 2 and at least one pharmaceutically acceptable excipient.

* * * * *